US008431345B2

(12) United States Patent
Kinoshita et al.

(10) Patent No.: US 8,431,345 B2
(45) Date of Patent: Apr. 30, 2013

(54) METHOD FOR DETERMINATION OF PROGRESSION RISK OF GLAUCOMA

(75) Inventors: Shigeru Kinoshita, Osaka (JP); Kei Tashiro, Kyoto (JP); Masakazu Nakano, Kyoto (JP); Tomohito Yagi, Kyoto (JP); Kazuhiko Mori, Kyoto (JP); Yoko Ikeda, Kyoto (JP); Takazumi Taniguchi, Ikoma (JP); Masaaki Kageyama, Ikoma (JP)

(73) Assignees: Shigeru Kinoshita, Osaka-shi (JP); Kei Tashiro, Kyoto-shi (JP); Santen Pharmaceutical Co., Ltd., Osaka-shi (JP)

( * ) Notice: Subject to any disclaimer, the term of this patent is extended or adjusted under 35 U.S.C. 154(b) by 313 days.

(21) Appl. No.: 12/596,462

(22) PCT Filed: Apr. 17, 2008

(86) PCT No.: PCT/JP2008/057533
§ 371 (c)(1),
(2), (4) Date: Oct. 19, 2009

(87) PCT Pub. No.: WO2008/130009
PCT Pub. Date: Oct. 30, 2008

(65) Prior Publication Data
US 2011/0207122 A1 Aug. 25, 2011

(30) Foreign Application Priority Data
Apr. 17, 2007 (JP) ................... 2007-108688

(51) Int. Cl.
C12Q 1/68 (2006.01)
C07H 21/02 (2006.01)
C07H 21/04 (2006.01)

(52) U.S. Cl.
USPC ........ 435/6.11; 435/6.1; 536/23.5; 536/24.31

(58) Field of Classification Search ........................ None
See application file for complete search history.

(56) References Cited

U.S. PATENT DOCUMENTS
2006/0073506 A1 4/2006 Christians et al.

FOREIGN PATENT DOCUMENTS
| CN | 1250484 A | 4/2000 |
| JP | 2002 306165 | 10/2002 |
| WO | 2005 090602 | 9/2005 |
| WO | 2008 050356 | 5/2008 |

OTHER PUBLICATIONS

Hirschhorn et al. Genetics in Medicine. vol. 4, No. 2, pp. 45-61, Mar. 2002.*
Lucentini et al. The Scientist (2004) vol. 18, p. 20.*
Liu et al. Invest Ophthalmol Vis Sci. 2008. 49: 3465-3468.*
Wacholder et al. J. Natl. Cancer Institute (2004) 96(6):434-442.*
Halushka et al. Nature. Jul. 1999. 22: 239-247.*
NCBI SNP Database, National Center for Biotechnology Information, National Library of Medicine (Bethesda, MD, USA), rs1187626, printed on May 30, 2012.*
NCBI SNP Database for ss66159951. National Center for Biotechnology Information, National Library of Medicine (Bethesda, MD, USA) rs1187626, Oct. 27, 2006.*
Kim et al. Molecular Vision. 2011. 17: 1136-1143.*
Mashima, Y. "Koreika ni Tomonau Shitsumei Shikkan Kanren Idenshi Takei to O-da-Me-do Iryo heno Katsuyo (Vision Loss Disease-Associated Genetic Polymorphism Accompanying Aging and Utilization to Order-Made Therapy)", Kosei Rodo Kagaku Kenkyuhi Hojokin (Kankakuki Shogai Kenkyu Jigyo) Heisei-14 Nendo Sokatsu Kenkyu Hokokusho (Heisei-14 (2002) Comprehensive Research Report, Public Welfare and Labor Bureau, Science Research Fee Subsidization (Sensory Organ Disorder Study Enterprise), pp. 10-14, 2005, (with Partial English translation).
Mashima, Y. "Koreika ni Tomonau Shitsumei Shikkan Kanren Idenshi Takei to O-da-Me-do Iryo heno Katsuyo (Vision Loss Disease-Associated Genetic Polymorphism Accompanying Aging and Utilization to Order-Made Therapy)", Kosei Rodo Kagaku Kenkyuhi Hojokin (Kankauki Shogai Kenkyu Jigyo) Heisei-15 Nendo Sokatsu Kenkyu Hokokusho (Heisei-15 (2003) Comprehensive Research Report, Public Welfare and Labor Bureau, Science Research Fee Subsidization (Sensory Organ Disorder Study Enterpris), pp. 15-19, 2005, (with partial English translation).
Mashima, Y. "Koreika ni Tomonau Shitsumei Shikkan Kanren Idenshi Takei to O-da-Me-do Iryo heno Katsuyo (Vision Loss Disease-Associated Genetic Polymorphism Accompanying Aging and Utilization to Order-Made Therapy)", Kosei Rodo Kagaku Kenkyuhi Hojokin (Kankakuki Shogai Kenkyu Jigyo) Heisei-16 Nendo Sokatsu Kenkyu Hokokusho (Heisei-16 (2004) Comprehensive Research Report, Public Welfare and Labor Bureau, Science Research Fee Subsidization (Sensory Organ Disorder Study Enterpris), pp. 20-23, 2004 (with partial English translation), 2005.
Mashima, Y. "Ganka Kensa Shindanho (Ophthalmolgic Examination and Dagnostic Methods), DAI-108-Kai Nippon Ganka Gakkai Sokai Shukudai Hokoku IV (108th ANNUAL General Assembly Meeting of Society of Japanese Ophthalmologists Homework Report IV", vol. 108, No. 12, pp. 863-886, (2004).
Zenkel, Matthias et al., "Differential Gene Expression in Pseudoexfoliation Syndrome", Investigative Ophthalmology & Visual Science, vol. 46, No. 10, pp. 3742-3752, (2005).

(Continued)

Primary Examiner — Carla Myers
(74) Attorney, Agent, or Firm — Oblon, Spivak, McClelland, Maier & Neustadt, L.L.P.

(57) ABSTRACT

A method of determining the presence or the absence of a glaucoma risk, including the steps of detecting in vitro an allele and/or a genotype of a single nucleotide polymorphism which is located on a 31st base of a base sequence, in a sample from a subject, wherein the base sequence is at least one base sequence selected from the group consisting of base sequences shown in SEQ ID NOs: 203 to 752 or a complementary sequence thereto (step A), and comparing the allele and/or the genotype detected in the step A with at least one of an allele and/or a genotype, containing a high-risk allele, in the base sequences shown in SEQ ID NOs: 203 to 752 (step B). According to the method of the present invention, the level of a progressive risk of glaucoma in a sample donor can be determined by analyzing an allele or a genotype of a single nucleotide polymorphism in the present invention in the sample, so that the sample donor can take a preventive measure of glaucoma, or can receive appropriate treatments, on the basis of this risk.

11 Claims, No Drawings

OTHER PUBLICATIONS

Inagaki, Y. et al., "Polymorphism of Beta-adrenergic receptors and susceptibility to open-angle Glaucoma", Molecular Vision, vol. 12, pp. 673-680, (2006).

Ishikawa, Karin et al., "Association between glaucoma and gene polymorphism of Endothelin type A receptor", Molecular Vision, vol. 11, pp. 431-437, 2005

Funayama, Tomoyo et al., "SNPs and Interaction Analyses of Noelin 2, Myocilin, and Optineurin Genes in Japanese Patients with Open-Angle Glaucoma", Investigative Ophthalmology & Visual Science, vol. 47, No. 12, pp. 5368-5375, Dec. 2006.

Kim, Seok Hwan et al., "Investigations on the association between normal tension glaucoma and single nucleotide polymorphisms of the Endothelin-1 and Endothelin receptor genes", Molecular Vision, vol. 12, pp. 1016-1021, (2006).

Fan, Bao Jian, et al., "SNPs and interaction analyses of myocilin, optineurin, and apolipoprotein E in primary open angle glaucoma patients", Molecular Vision, vol. 11, pp. 625-631, (2005).

Wang, I-Jong et al., "The association of single nucleotide polymorphisms in the MMP-9 genes with susceptibility to acute primay angle closure glaucoma in Taiwanese patients", Molecular Vision, vol. 12, pp. 1223-1232, (2006).

Tsai, Fuu-jen et al., "A codon 31$^{ser-arg}$ polymorphism of the WAF-1/CIP-1/p21/tumour suppressor gene in Chinese primary open-angle glaucoma", Acta Ophthalmologica Scandinavica, vol. 82, pp. 76-80, (2004).

Fan Bao Jian et al., "Gene mapping for prmary open angle glaucoma", Clinical Biochemistry, Elsevier, vol. 39, pp. 249-258, (2006).

Ray, Kunal et al., "Recent advances in molecular genetics of glaucoma", Molecular and Cellular Biochemistry, vol. 253, pp. 223-231, (2003).

Higashide, Tomomi "Gankai notameno Sentan Iryo (series: High-Technology Therapy for Ophthalmologists), SNP to Ryokunaisho (SNP and Glaucoma)", Journal of the Eye, vol. 18, No. 6, pp. 745-746, 2001, (with partial English translation).

Okada, Y. "Seijo Gan-atsu Ryokunaisho to Idenshi Takei: OPA1 deno Kento (Normal Tesnsion Glaucoma and Gene Polymorphism Studies on OPTA1", Journal of the Japan Ophthalmologists Association, vol. 73, No. 8, pp. 867-870, 2002, (with partial English transition).

Rezaie, Tayebeh et al., "Adult-Onset Primay Open-Angle Glaucoma Caused by Mutations in Optimeurin", Science, vol. 295, pp. 1077-1079, (Feb. 8, 2002).

Wiggs, J. L. et al., "Genome-wide scan for adult onset primary open angle glaucoma", Human Molecular Gentics, vol. 9, No. 7, pp. 1109-1117, (2000).

Nemesure, Barbara et al., "A genome-wide scan for primary open-angle glaucoma (POAG): The Barbados Family Study of Open-Angle Glaucoma", Original Investigation, Hum Genet, vol. 112, pp. 600-609, (2003).

Wiggs, J. L. et al., "A genomewide Scan Identifies Novel Early-Onset Primary Open-Angle Glaucoma Loci on 9q22 and 20p12", Am. J. Hum. Genet., vol. 74, pp. 1314-1320, (2004).

Kouichi Ozaki, et al., "Functional SNPs in the lymphotoxin-α gene that are associated with susceptibility to myocardial infarction", Nature Genetics, Nature Publishing Group, vol. 32, XP-002964781, Dec. 1, 2002, pp. 650-654.

Robert J. Klein, et al, "Complement Factor H Polymorphism in Age-Related Macular Degeneration", Science, vol. 308, No. 5720, XP-002544688, Apr. 15, 2005, pp. 385-389.

Stefan Kammerer, et al., "Association of the NuMA region on Chromosome 11q13 with breast cancer susceptibility", PNAS, vol. 102, No. 6, XP002988652, Feb. 8, 2005, pp. 2004-2009.

Extended European Search Report issued Oct. 8, 2010, in European Patent Application No. 08751865.0.

Extended European Search Report issued Oct. 8, 2010, in European Patent Application No. 08740595.7.

European Office Action issued Dec. 23, 2011, in Patent Application No. 08 740 595.7.

James C. Vickers, et al., "The apolipoprotein ϵ4 gene is associated with elevated risk of normal tension glaucoma", Molecular Vision, vol. 8, XP 55014422, Oct. 14, 2002, pp. 389-393.

Erkki Juronen, et al., "Polymorphic Glutathione S-transferase M1 is a Risk Factor of Primary Open-angle Glaucoma among Estonians", Experimental Eye Research, vol. 71, No. 5, XP 55014423, Nov. 1, 2000, pp. 447-452.

Combined Chinese Office Action and Search Report issued Aug. 2, 2012, in Patent Application No. 200880020582.2.

Japanese Office Action issued Oct. 9, 2012, in Patent Application No. 2009-510856.

Japanese Office Action issued Oct. 4, 2012, in Patent Application No. 2009-510857.

Xiao-Hong Jin et al., "Primary open-angle glaucoma progress in genetics," *Chinese Journal of Practical Ophthalmology*, vol. 20, No. 1, Jan. 31, 2002, pp. 7-11.

Jian-Wen Wang, et al., "Relevant gene study of primary open-angle glaucoma", International Journal of Ophthalmology, vol. 5, No. 4, Aug. 2005, pp. 711-714 (with English Abstract).

Dan-Ning Hu, et al., "Hepatocyte Growth Factor is Increased in the Aqueous Humor of Glaucomatous Eyes", Journal of Glaucoma, vol. 10, No. 3, Jun. 2001, pp. 152-157.

Frank W. Rozsa, et al., "Gene expression profile of human trabecular meshwork cells in response to long-term dexamethasone exposure", Molecular Vision, vol. 12, 2006, pp. 125-141.

Frank W. Rozsa, et al., "Differential Expression Profile Prioritization of Positional Candidate Glaucoma Genes", Arch. Ophthalmol., vol. 125, Jan. 2007, pp. 117-127.

Xiao-Hong Jin, "Prima open-angle glaucoma progress in genetics", Jan. 31, 2002, pp. 7-11, Chinese J Practical Opthalm. vol. 20, No. 1.

U.S. Appl. No. 12/596,258, filed Oct. 16, 2009, Kinoshita, et al.

U.S. Appl. No. 13/546,674, filed Jul. 11, 2012, Kinoshita, et al.

\* cited by examiner

SEQUENCE LISTING

```
<160> NUMBER OF SEQ ID NOS: 1061

<210> SEQ ID NO 1
<211> LENGTH: 61
<212> TYPE: DNA
<213> ORGANISM: Homo sapiens

<400> SEQUENCE: 1
cggtgctgca ccgtggatgt gagtccttgc acagtggtga aatgtagtag aggagtgatc    60
t                                                                    61

<210> SEQ ID NO 2
<211> LENGTH: 61
<212> TYPE: DNA
<213> ORGANISM: Homo sapiens

<400> SEQUENCE: 2
cggtgctgca ccgtggatgt gagtccttgc gcagtggtga aatgtagtag aggagtgatc    60
t                                                                    61

<210> SEQ ID NO 3
<211> LENGTH: 61
<212> TYPE: DNA
<213> ORGANISM: Homo sapiens

<400> SEQUENCE: 3
ccggagtatc ccgctttctt tggaggaaac aaccgcatca gatctgcgct gcggcagagg    60
c                                                                    61

<210> SEQ ID NO 4
<211> LENGTH: 61
<212> TYPE: DNA
<213> ORGANISM: Homo sapiens

<400> SEQUENCE: 4
```

```
ccggagtatc cgctttctt tggaggaaac caccgcatca gatctgcgct gcggcagagg    60
c                                                                  61

<210> SEQ ID NO 5
<211> LENGTH: 61
<212> TYPE: DNA
<213> ORGANISM: Homo sapiens

<400> SEQUENCE: 5
tcagcaccct gcaccagtcc aagtacatga cagataccac agggaaggag ttcagaactg    60
t                                                                   61

<210> SEQ ID NO 6
<211> LENGTH: 61
<212> TYPE: DNA
<213> ORGANISM: Homo sapiens

<400> SEQUENCE: 6
tcagcaccct gcaccagtcc aagtacatga tagataccac agggaaggag ttcagaactg    60
t                                                                   61

<210> SEQ ID NO 7
<211> LENGTH: 61
<212> TYPE: DNA
<213> ORGANISM: Homo sapiens

<400> SEQUENCE: 7
ttctccatca tcctctttct ctattctcca gacattaggc acccactgtg tgcccagcac    60
a                                                                   61

<210> SEQ ID NO 8
<211> LENGTH: 61
<212> TYPE: DNA
<213> ORGANISM: Homo sapiens

<400> SEQUENCE: 8
ttctccatca tcctctttct ctattctcca tacattaggc acccactgtg tgcccagcac    60
a                                                                   61

<210> SEQ ID NO 9
<211> LENGTH: 61
<212> TYPE: DNA
<213> ORGANISM: Homo sapiens

<400> SEQUENCE: 9
gtttccagaa ctcttttttgg ccaggctcca agctaagctc tgtaggaagc ttgatgatgg    60
g                                                                    61

<210> SEQ ID NO 10
<211> LENGTH: 61
<212> TYPE: DNA
<213> ORGANISM: Homo sapiens

<400> SEQUENCE: 10
gtttccagaa ctcttttttgg ccaggctcca ggctaagctc tgtaggaagc ttgatgatgg    60
g                                                                    61

<210> SEQ ID NO 11
<211> LENGTH: 61
```

<212> TYPE: DNA
<213> ORGANISM: Homo sapiens

<400> SEQUENCE: 11
cctgcagagg ggatttgctt tgctaaagga gtcaccacag agcacccgag agtaacaggt    60
t                                                                   61

<210> SEQ ID NO 12
<211> LENGTH: 61
<212> TYPE: DNA
<213> ORGANISM: Homo sapiens

<400> SEQUENCE: 12
cctgcagagg ggatttgctt tgctaaagga ttcaccacag agcacccgag agtaacaggt    60
t                                                                   61

<210> SEQ ID NO 13
<211> LENGTH: 61
<212> TYPE: DNA
<213> ORGANISM: Homo sapiens

<400> SEQUENCE: 13
gagtgggcag ttggaaacag ctatgaaacc agcatttagt gatggggcag tagggctggg    60
g                                                                   61

<210> SEQ ID NO 14
<211> LENGTH: 61
<212> TYPE: DNA
<213> ORGANISM: Homo sapiens

<400> SEQUENCE: 14
gagtgggcag ttggaaacag ctatgaaacc ggcatttagt gatggggcag tagggctggg    60
g                                                                   61

<210> SEQ ID NO 15
<211> LENGTH: 61
<212> TYPE: DNA
<213> ORGANISM: Homo sapiens

<400> SEQUENCE: 15
aaccccatgc ctacatccat tatcaaccta cgcctatgct aaagcttgtt acaatgagca    60
g                                                                   61

<210> SEQ ID NO 16
<211> LENGTH: 61
<212> TYPE: DNA
<213> ORGANISM: Homo sapiens

<400> SEQUENCE: 16
aaccccatgc ctacatccat tatcaaccta tgcctatgct aaagcttgtt acaatgagca    60
g                                                                   61

<210> SEQ ID NO 17
<211> LENGTH: 61
<212> TYPE: DNA
<213> ORGANISM: Homo sapiens

<400> SEQUENCE: 17
ttccctgact cttgaagagg acagtggaca atgctgttta atggtggaca cagaaggatc    60
a                                                                   61

<210> SEQ ID NO 18
<211> LENGTH: 61
<212> TYPE: DNA
<213> ORGANISM: Homo sapiens

<400> SEQUENCE: 18
ttccctgact cttgaagagg acagtggaca gtgctgttta atggtggaca cagaaggatc    60
a                                                                   61

<210> SEQ ID NO 19
<211> LENGTH: 61
<212> TYPE: DNA
<213> ORGANISM: Homo sapiens

<400> SEQUENCE: 19
tatggaagca ctgtgaaaga caaactactc cgaatactga aagtttcttt tacaaaaaca    60
t                                                                   61

<210> SEQ ID NO 20
<211> LENGTH: 61
<212> TYPE: DNA
<213> ORGANISM: Homo sapiens

<400> SEQUENCE: 20
tatggaagca ctgtgaaaga caaactactc tgaatactga aagtttcttt tacaaaaaca    60
t                                                                   61

<210> SEQ ID NO 21
<211> LENGTH: 61
<212> TYPE: DNA
<213> ORGANISM: Homo sapiens

<400> SEQUENCE: 21
ataacacctg ccactgacct tccatgagca gtgactatgt ggtttcaaca ttggtcccac    60
c                                                                   61

<210> SEQ ID NO 22
<211> LENGTH: 61
<212> TYPE: DNA
<213> ORGANISM: Homo sapiens

<400> SEQUENCE: 22
ataacacctg ccactgacct tccatgagca ttgactatgt ggtttcaaca ttggtcccac    60
c                                                                   61

<210> SEQ ID NO 23
<211> LENGTH: 61
<212> TYPE: DNA
<213> ORGANISM: Homo sapiens

<400> SEQUENCE: 23
gccactgcca ccactcctgc agattgttcc agctgtgtta ctaaatacag gttgcttttc    60
t                                                                   61

<210> SEQ ID NO 24
<211> LENGTH: 61
<212> TYPE: DNA
<213> ORGANISM: Homo sapiens

<400> SEQUENCE: 24

```
gccactgcca ccactcctgc agattgttcc cgctgtgtta ctaaatacag gttgcttttc    60
t                                                                    61

<210> SEQ ID NO 25
<211> LENGTH: 61
<212> TYPE: DNA
<213> ORGANISM: Homo sapiens

<400> SEQUENCE: 25
gtgagccacc atgcccagcc ctgtcatcta cctttctgag agcagcttct acccatctga    60
a                                                                    61

<210> SEQ ID NO 26
<211> LENGTH: 61
<212> TYPE: DNA
<213> ORGANISM: Homo sapiens

<400> SEQUENCE: 26
gtgagccacc atgcccagcc ctgtcatcta tctttctgag agcagcttct acccatctga    60
a                                                                    61

<210> SEQ ID NO 27
<211> LENGTH: 61
<212> TYPE: DNA
<213> ORGANISM: Homo sapiens

<400> SEQUENCE: 27
cttgtcttca agagcagatg cagattatcc cgagcccagg ggacctatgt gagggagctt    60
c                                                                    61

<210> SEQ ID NO 28
<211> LENGTH: 61
<212> TYPE: DNA
<213> ORGANISM: Homo sapiens

<400> SEQUENCE: 28
cttgtcttca agagcagatg cagattatcc tgagcccagg ggacctatgt gagggagctt    60
c                                                                    61

<210> SEQ ID NO 29
<211> LENGTH: 61
<212> TYPE: DNA
<213> ORGANISM: Homo sapiens

<400> SEQUENCE: 29
agtgggaccc tgtgaggcaa acatcaccac aaggctggga acagcaggac tcaggcactg    60
c                                                                    61

<210> SEQ ID NO 30
<211> LENGTH: 61
<212> TYPE: DNA
<213> ORGANISM: Homo sapiens

<400> SEQUENCE: 30
agtgggaccc tgtgaggcaa acatcaccac gaggctggga acagcaggac tcaggcactg    60
c                                                                    61

<210> SEQ ID NO 31
<211> LENGTH: 61
```

```
<212> TYPE: DNA
<213> ORGANISM: Homo sapiens

<400> SEQUENCE: 31
tatataataa agacatctga taacatgaca gctaaggctc cttctaggta taaaacgtta      60
t                                                                    61

<210> SEQ ID NO 32
<211> LENGTH: 61
<212> TYPE: DNA
<213> ORGANISM: Homo sapiens

<400> SEQUENCE: 32
tatataataa agacatctga taacatgaca tctaaggctc cttctaggta taaaacgtta      60
t                                                                    61

<210> SEQ ID NO 33
<211> LENGTH: 61
<212> TYPE: DNA
<213> ORGANISM: Homo sapiens

<400> SEQUENCE: 33
atggcagggg ccagggtgag tggagaatac cgcttgatga gagaacccca aggcggagag      60
g                                                                    61

<210> SEQ ID NO 34
<211> LENGTH: 61
<212> TYPE: DNA
<213> ORGANISM: Homo sapiens

<400> SEQUENCE: 34
atggcagggg ccagggtgag tggagaatac tgcttgatga gagaacccca aggcggagag      60
g                                                                    61

<210> SEQ ID NO 35
<211> LENGTH: 61
<212> TYPE: DNA
<213> ORGANISM: Homo sapiens

<400> SEQUENCE: 35 ccctttctt tcttgttctt tttaagactc aatctcaaat ctgcaaccta cctaccataa       60
g                                                                    61

<210> SEQ ID NO 36
<211> LENGTH: 61
<212> TYPE: DNA
<213> ORGANISM: Homo sapiens

<400> SEQUENCE: 36 ccctttctt tcttgttctt tttaagactc gatctcaaat ctgcaaccta cctaccataa       60
g                                                                    61

<210> SEQ ID NO 37
<211> LENGTH: 61
<212> TYPE: DNA
<213> ORGANISM: Homo sapiens

<400> SEQUENCE: 37
tttctggctt agaattattc ataggtacaa cgctgatggc tcttctgaaa ttgcccctgc      60
a                                                                    61
```

<210> SEQ ID NO 38
<211> LENGTH: 61
<212> TYPE: DNA
<213> ORGANISM: Homo sapiens

<400> SEQUENCE: 38
tttctggctt agaattattc ataggtacaa ggctgatggc tcttctgaaa ttgcccctgc      60
a                                                                    61

<210> SEQ ID NO 39
<211> LENGTH: 61
<212> TYPE: DNA
<213> ORGANISM: Homo sapiens

<400> SEQUENCE: 39
acaaagcagc tatgatcata ggcacatgaa agcaaaatgt actggtgatt tcatgttcct      60
c                                                                    61

<210> SEQ ID NO 40
<211> LENGTH: 61
<212> TYPE: DNA
<213> ORGANISM: Homo sapiens

<400> SEQUENCE: 40
acaaagcagc tatgatcata ggcacatgaa cgcaaaatgt actggtgatt tcatgttcct      60
c                                                                    61

<210> SEQ ID NO 41
<211> LENGTH: 61
<212> TYPE: DNA
<213> ORGANISM: Homo sapiens

<400> SEQUENCE: 41
aagagatagg aaaagacaca gagacacaga cgggaatgcc gggtgaagac agaggaaaat      60
a                                                                    61

<210> SEQ ID NO 42
<211> LENGTH: 61
<212> TYPE: DNA
<213> ORGANISM: Homo sapiens

<400> SEQUENCE: 42
aagagatagg aaaagacaca gagacacaga ggggaatgcc gggtgaagac agaggaaaat      60
a                                                                    61

<210> SEQ ID NO 43
<211> LENGTH: 61
<212> TYPE: DNA
<213> ORGANISM: Homo sapiens

<400> SEQUENCE: 43
taatatactg caaccacatg agatttatct aagaagtgca gttttgttt aacatgcaga       60
a                                                                    61

<210> SEQ ID NO 44
<211> LENGTH: 61
<212> TYPE: DNA
<213> ORGANISM: Homo sapiens

<400> SEQUENCE: 44

```
taatatactg caaccacatg agatttatct gagaagtgca agttttgttt aacatgcaga    60
a                                                                   61

<210> SEQ ID NO 45
<211> LENGTH: 61
<212> TYPE: DNA
<213> ORGANISM: Homo sapiens

<400> SEQUENCE: 45
tgcaaagaaa atgaatcact catgggtata caaaatgtta cagcctcttt ggaaaacagt    60
t                                                                   61

<210> SEQ ID NO 46
<211> LENGTH: 61
<212> TYPE: DNA
<213> ORGANISM: Homo sapiens

<400> SEQUENCE: 46
tgcaaagaaa atgaatcact catgggtata taaaatgtta cagcctcttt ggaaaacagt    60
t                                                                   61

<210> SEQ ID NO 47
<211> LENGTH: 61
<212> TYPE: DNA
<213> ORGANISM: Homo sapiens

<400> SEQUENCE: 47
ccggagtatc ccgctttctt tggaggaaac aaccgcatca gatctgcgct gcggcagagg    60
c                                                                   61

<210> SEQ ID NO 48
<211> LENGTH: 61
<212> TYPE: DNA
<213> ORGANISM: Homo sapiens

<400> SEQUENCE: 48
ccggagtatc ccgctttctt tggaggaaac caccgcatca gatctgcgct gcggcagagg    60
c                                                                   61

<210> SEQ ID NO 49
<211> LENGTH: 61
<212> TYPE: DNA
<213> ORGANISM: Homo sapiens

<400> SEQUENCE: 49
tcagcaccct gcaccagtcc aagtacatga cagataccac agggaaggag ttcagaactg    60
t                                                                   61

<210> SEQ ID NO 50
<211> LENGTH: 61
<212> TYPE: DNA
<213> ORGANISM: Homo sapiens

<400> SEQUENCE: 50
tcagcaccct gcaccagtcc aagtacatga tagataccac agggaaggag ttcagaactg    60
t                                                                   61

<210> SEQ ID NO 51
<211> LENGTH: 61
```

```
<212> TYPE: DNA
<213> ORGANISM: Homo sapiens

<400> SEQUENCE: 51
ttctccatca tcctctttct ctattctcca gacattaggc acccactgtg tgcccagcac        60
a                                                                         61

<210> SEQ ID NO 52
<211> LENGTH: 61
<212> TYPE: DNA
<213> ORGANISM: Homo sapiens

<400> SEQUENCE: 52
ttctccatca tcctctttct ctattctcca tacattaggc acccactgtg tgcccagcac        60
a                                                                         61

<210> SEQ ID NO 53
<211> LENGTH: 61
<212> TYPE: DNA
<213> ORGANISM: Homo sapiens

<400> SEQUENCE: 53
tagggagcaa caccatggtg gtagagaacc aaagtttatt agcatctcta aactcatata        60
g                                                                         61

<210> SEQ ID NO 54
<211> LENGTH: 61
<212> TYPE: DNA
<213> ORGANISM: Homo sapiens

<400> SEQUENCE: 54
tagggagcaa caccatggtg gtagagaacc gaagtttatt agcatctcta aactcatata        60
g                                                                         61

<210> SEQ ID NO 55
<211> LENGTH: 61
<212> TYPE: DNA
<213> ORGANISM: Homo sapiens

<400> SEQUENCE: 55
aatgatatat caatgatata ttgaggagcc cagtaagatc ttaaatctag agggaaggta        60
g                                                                         61

<210> SEQ ID NO 56
<211> LENGTH: 61
<212> TYPE: DNA
<213> ORGANISM: Homo sapiens

<400> SEQUENCE: 56
aatgatatat caatgatata ttgaggagcc tagtaagatc ttaaatctag agggaaggta        60
g                                                                         61

<210> SEQ ID NO 57
<211> LENGTH: 61
<212> TYPE: DNA
<213> ORGANISM: Homo sapiens

<400> SEQUENCE: 57
aattgtgtgt gtgtgttttt aagtttgata cgtctaatgc ttatgaaaat ttttaccaga        60
t                                                                         61
```

<210> SEQ ID NO 58
<211> LENGTH: 61
<212> TYPE: DNA
<213> ORGANISM: Homo sapiens

<400> SEQUENCE: 58
aattgtgtgt gtgtgttttt aagtttgata tgtctaatgc ttatgaaaat ttttaccaga     60
t                                                                    61

<210> SEQ ID NO 59
<211> LENGTH: 61
<212> TYPE: DNA
<213> ORGANISM: Homo sapiens

<400> SEQUENCE: 59
catatacttg ttctcaaacc attcactagc aagaaaaagt ggcctagagc aggggtcagc     60
a                                                                    61

<210> SEQ ID NO 60
<211> LENGTH: 61
<212> TYPE: DNA
<213> ORGANISM: Homo sapiens

<400> SEQUENCE: 60
catatacttg ttctcaaacc attcactagc cagaaaaagt ggcctagagc aggggtcagc     60
a                                                                    61

<210> SEQ ID NO 61
<211> LENGTH: 61
<212> TYPE: DNA
<213> ORGANISM: Homo sapiens

<400> SEQUENCE: 61
ggaagggaac ctgagtatga aaggacaga cgaggagaag ttggttaatg tttacaaact      60
t                                                                    61

<210> SEQ ID NO 62
<211> LENGTH: 61
<212> TYPE: DNA
<213> ORGANISM: Homo sapiens

<400> SEQUENCE: 62
ggaagggaac ctgagtatga aaggacaga tgaggagaag ttggttaatg tttacaaact      60
t                                                                    61

<210> SEQ ID NO 63
<211> LENGTH: 61
<212> TYPE: DNA
<213> ORGANISM: Homo sapiens

<400> SEQUENCE: 63
cttgatttta ttgctaggga ttgtggtaaa acacccaaag aatgtgggta tgtgcctact     60
t                                                                    61

<210> SEQ ID NO 64
<211> LENGTH: 61
<212> TYPE: DNA
<213> ORGANISM: Homo sapiens

<400> SEQUENCE: 64

```
cttgatttta ttgctaggga ttgtggtaaa gcacccaaag aatgtgggta tgtgcctact    60
t                                                                  61

<210> SEQ ID NO 65
<211> LENGTH: 61
<212> TYPE: DNA
<213> ORGANISM: Homo sapiens

<400> SEQUENCE: 65
caacattatc tttctgaggg atacaactca accctgaaca cctgcttaca caggaaacgc    60
a                                                                  61

<210> SEQ ID NO 66
<211> LENGTH: 61
<212> TYPE: DNA
<213> ORGANISM: Homo sapiens

<400> SEQUENCE: 66
caacattatc tttctgaggg atacaactca cccctgaaca cctgcttaca caggaaacgc    60
a                                                                  61

<210> SEQ ID NO 67
<211> LENGTH: 61
<212> TYPE: DNA
<213> ORGANISM: Homo sapiens

<400> SEQUENCE: 67
ccatacagcc aaaagcccac atcctacatc cgagtaacag cccaggctga catgacccca    60
g                                                                  61

<210> SEQ ID NO 68
<211> LENGTH: 61
<212> TYPE: DNA
<213> ORGANISM: Homo sapiens

<400> SEQUENCE: 68
ccatacagcc aaaagcccac atcctacatc tgagtaacag cccaggctga catgacccca    60
g                                                                  61

<210> SEQ ID NO 69
<211> LENGTH: 61
<212> TYPE: DNA
<213> ORGANISM: Homo sapiens

<400> SEQUENCE: 69
gtttgtccct ttttaaagtt gttggtttaa aatttctctg atacaaaaat agtgacccag    60
g                                                                  61

<210> SEQ ID NO 70
<211> LENGTH: 61
<212> TYPE: DNA
<213> ORGANISM: Homo sapiens

<400> SEQUENCE: 70
gtttgtccct ttttaaagtt gttggtttaa catttctctg atacaaaaat agtgacccag    60
g                                                                  61

<210> SEQ ID NO 71
<211> LENGTH: 61
```

```
<212> TYPE: DNA
<213> ORGANISM: Homo sapiens

<400> SEQUENCE: 71
acaaagcagc tatgatcata ggcacatgaa agcaaaatgt actggtgatt tcatgttcct      60
c                                                                      61

<210> SEQ ID NO 72
<211> LENGTH: 61
<212> TYPE: DNA
<213> ORGANISM: Homo sapiens

<400> SEQUENCE: 72
acaaagcagc tatgatcata ggcacatgaa cgcaaaatgt actggtgatt tcatgttcct      60
c                                                                      61

<210> SEQ ID NO 73
<211> LENGTH: 61
<212> TYPE: DNA
<213> ORGANISM: Homo sapiens

<400> SEQUENCE: 73
gagctctctg gatagatatt tccattccac cgtcgcatct tcccagcaga gtgtgggtga      60
a                                                                      61

<210> SEQ ID NO 74
<211> LENGTH: 61
<212> TYPE: DNA
<213> ORGANISM: Homo sapiens

<400> SEQUENCE: 74
gagctctctg gatagatatt tccattccac tgtcgcatct tcccagcaga gtgtgggtga      60
a                                                                      61

<210> SEQ ID NO 75
<211> LENGTH: 61
<212> TYPE: DNA
<213> ORGANISM: Homo sapiens

<400> SEQUENCE: 75
cttaggaagt ggtatcctaa ggtgagatgt aaaggaagac taggagttag gtcagcaaga      60
g                                                                      61

<210> SEQ ID NO 76
<211> LENGTH: 61
<212> TYPE: DNA
<213> ORGANISM: Homo sapiens

<400> SEQUENCE: 76
cttaggaagt ggtatcctaa ggtgagatgt gaaggaagac taggagttag gtcagcaaga      60
g                                                                      61

<210> SEQ ID NO 77
<211> LENGTH: 61
<212> TYPE: DNA
<213> ORGANISM: Homo sapiens

<400> SEQUENCE: 77
gttgaacttt tatttctcaa ggagcagata ctagatatac ataccatgtt gactcaagcc      60
c                                                                      61
```

<210> SEQ ID NO 78
<211> LENGTH: 61
<212> TYPE: DNA
<213> ORGANISM: Homo sapiens

<400> SEQUENCE: 78
gttgaacttt tatttctcaa ggagcagata gtagatatac ataccatgtt gactcaagcc    60
c                                                                   61

<210> SEQ ID NO 79
<211> LENGTH: 61
<212> TYPE: DNA
<213> ORGANISM: Homo sapiens

<400> SEQUENCE: 79
ggtgctttga aagaacaatt gctcctacaa acatcaaatc aaacttttag aagctgataa    60
a                                                                   61

<210> SEQ ID NO 80
<211> LENGTH: 61
<212> TYPE: DNA
<213> ORGANISM: Homo sapiens

<400> SEQUENCE: 80
ggtgctttga aagaacaatt gctcctacaa ccatcaaatc aaacttttag aagctgataa    60
a                                                                   61

<210> SEQ ID NO 81
<211> LENGTH: 61
<212> TYPE: DNA
<213> ORGANISM: Homo sapiens

<400> SEQUENCE: 81
tatgccaatg aaatccccat gctggagaca acttattaga aagactgagc atatgtacta    60
t                                                                   61

<210> SEQ ID NO 82
<211> LENGTH: 61
<212> TYPE: DNA
<213> ORGANISM: Homo sapiens

<400> SEQUENCE: 82
tatgccaatg aaatccccat gctggagaca gcttattaga aagactgagc atatgtacta    60
t                                                                   61

<210> SEQ ID NO 83
<211> LENGTH: 61
<212> TYPE: DNA
<213> ORGANISM: Homo sapiens

<400> SEQUENCE: 83
attcccctta ggattcaagg cagactgcac cgtgagaaat catttgtcct ttgcacacag    60
t                                                                   61

<210> SEQ ID NO 84
<211> LENGTH: 61
<212> TYPE: DNA
<213> ORGANISM: Homo sapiens

<400> SEQUENCE: 84

```
attcccctta ggattcaagg cagactgcac tgtgagaaat catttgtcct ttgcacacag    60
t                                                                   61
```

<210> SEQ ID NO 85
<211> LENGTH: 61
<212> TYPE: DNA
<213> ORGANISM: Homo sapiens

<400> SEQUENCE: 85

```
gtcaatactt tagagtaatg ttatagacca gggctaaaat ttacatgaga atagaagagg    60
c                                                                   61
```

<210> SEQ ID NO 86
<211> LENGTH: 61
<212> TYPE: DNA
<213> ORGANISM: Homo sapiens

<400> SEQUENCE: 86

```
gtcaatactt tagagtaatg ttatagacca tggctaaaat ttacatgaga atagaagagg    60
c                                                                   61
```

<210> SEQ ID NO 87
<211> LENGTH: 61
<212> TYPE: DNA
<213> ORGANISM: Homo sapiens

<400> SEQUENCE: 87

```
tgtgagattt gtaacaaata aattagctct gaactcttca tgtaacaaga tgtctagttt    60
c                                                                   61
```

<210> SEQ ID NO 88
<211> LENGTH: 61
<212> TYPE: DNA
<213> ORGANISM: Homo sapiens

<400> SEQUENCE: 88

```
tgtgagattt gtaacaaata aattagctct taactcttca tgtaacaaga tgtctagttt    60
c                                                                   61
```

<210> SEQ ID NO 89
<211> LENGTH: 61
<212> TYPE: DNA
<213> ORGANISM: Homo sapiens

<400> SEQUENCE: 89

```
cgattactta attattccat ctggaattta cggactaaaa cagaagtcta tttttatttt    60
a                                                                   61
```

<210> SEQ ID NO 90
<211> LENGTH: 61
<212> TYPE: DNA
<213> ORGANISM: Homo sapiens

<400> SEQUENCE: 90

```
cgattactta attattccat ctggaattta tggactaaaa cagaagtcta tttttatttt    60
a                                                                   61
```

<210> SEQ ID NO 91
<211> LENGTH: 61

```
<212> TYPE: DNA
<213> ORGANISM: Homo sapiens

<400> SEQUENCE: 91
tttttttttt ttacagattt tgataacata cgtgcttgtt agaagacaaa ttatatgaca      60
g                                                                     61

<210> SEQ ID NO 92
<211> LENGTH: 61
<212> TYPE: DNA
<213> ORGANISM: Homo sapiens

<400> SEQUENCE: 92
tttttttttt ttacagattt tgataacata tgtgcttgtt agaagacaaa ttatatgaca      60
g                                                                     61

<210> SEQ ID NO 93
<211> LENGTH: 61
<212> TYPE: DNA
<213> ORGANISM: Homo sapiens

<400> SEQUENCE: 93
caagaccgaa aactttgtgg caaagataag cagtgagtga gctcctgaag tctttatctt      60
t                                                                     61

<210> SEQ ID NO 94
<211> LENGTH: 61
<212> TYPE: DNA
<213> ORGANISM: Homo sapiens

<400> SEQUENCE: 94
caagaccgaa aactttgtgg caaagataag gagtgagtga gctcctgaag tctttatctt      60
t                                                                     61

<210> SEQ ID NO 95
<211> LENGTH: 61
<212> TYPE: DNA
<213> ORGANISM: Homo sapiens

<400> SEQUENCE: 95
acctcttagg taagctttga gtgtctgtca agaaatgtgt ccatttgatt tatcaaattt      60
a                                                                     61

<210> SEQ ID NO 96
<211> LENGTH: 61
<212> TYPE: DNA
<213> ORGANISM: Homo sapiens

<400> SEQUENCE: 96
acctcttagg taagctttga gtgtctgtca cgaaatgtgt ccatttgatt tatcaaattt      60
a                                                                     61

<210> SEQ ID NO 97
<211> LENGTH: 61
<212> TYPE: DNA
<213> ORGANISM: Homo sapiens

<400> SEQUENCE: 97
aacatacttt taataacttt gtaagtcaaa gaggaaggca taaggaaatt aaaaactatt      60
t                                                                     61
```

<210> SEQ ID NO 98
<211> LENGTH: 61
<212> TYPE: DNA
<213> ORGANISM: Homo sapiens

<400> SEQUENCE: 98
aacatacttt taaataactt gtaagtcaaa taggaaggca taaggaaatt aaaaactatt    60
t                                                                   61

<210> SEQ ID NO 99
<211> LENGTH: 61
<212> TYPE: DNA
<213> ORGANISM: Homo sapiens

<400> SEQUENCE: 99
ttaaaaatat tgttgggtgt gaattttgaa aagggaagag ttttatgaaa tgcttctaat    60
g                                                                   61

<210> SEQ ID NO 100
<211> LENGTH: 61
<212> TYPE: DNA
<213> ORGANISM: Homo sapiens

<400> SEQUENCE: 100
ttaaaaatat tgttgggtgt gaattttgaa gagggaagag ttttatgaaa tgcttctaat    60
g                                                                   61

<210> SEQ ID NO 101
<211> LENGTH: 61
<212> TYPE: DNA
<213> ORGANISM: Homo sapiens

<400> SEQUENCE: 101
tagaaataat gtaaatcgat actgctctga cgttttcctt tgtatttact gatcagatat    60
c                                                                   61

<210> SEQ ID NO 102
<211> LENGTH: 61
<212> TYPE: DNA
<213> ORGANISM: Homo sapiens

<400> SEQUENCE: 102
tagaaataat gtaaatcgat actgctctga tgttttcctt tgtatttact gatcagatat    60
c                                                                   61

<210> SEQ ID NO 103
<211> LENGTH: 61
<212> TYPE: DNA
<213> ORGANISM: Homo sapiens

<400> SEQUENCE: 103
gtcaatagag gtcagaactt caaggacata agttgggaat gctacagccg agaaaggcag    60
t                                                                   61

<210> SEQ ID NO 104
<211> LENGTH: 61
<212> TYPE: DNA
<213> ORGANISM: Homo sapiens

<400> SEQUENCE: 104

```
gtcaatagag gtcagaactt caaggacata ggttgggaat gctacagccg agaaaggcag    60
t                                                                    61

<210> SEQ ID NO 105
<211> LENGTH: 61
<212> TYPE: DNA
<213> ORGANISM: Homo sapiens

<400> SEQUENCE: 105
tatttatgaa gtcaactata ttctagtaga acgatgctta atgaattatt acacatccag    60
a                                                                    61

<210> SEQ ID NO 106
<211> LENGTH: 61
<212> TYPE: DNA
<213> ORGANISM: Homo sapiens

<400> SEQUENCE: 106
tatttatgaa gtcaactata ttctagtaga ccgatgctta atgaattatt acacatccag    60
a                                                                    61

<210> SEQ ID NO 107
<211> LENGTH: 61
<212> TYPE: DNA
<213> ORGANISM: Homo sapiens

<400> SEQUENCE: 107 cacattttt cttagatgaa ttttatgta aatcaaggca taatcaaaat aaattttgt      60 c                                                                    61

<210> SEQ ID NO 108
<211> LENGTH: 61
<212> TYPE: DNA
<213> ORGANISM: Homo sapiens

<400> SEQUENCE: 108 cacattttt cttagatgaa ttttatgta gatcaaggca taatcaaaat aaattttgt      60 c                                                                    61

<210> SEQ ID NO 109
<211> LENGTH: 61
<212> TYPE: DNA
<213> ORGANISM: Homo sapiens

<400> SEQUENCE: 109 aactccttt gaagagtctc tgagctaaca agtcaacatc agcataaagt aatgcagcct    60
g                                                                    61

<210> SEQ ID NO 110
<211> LENGTH: 61
<212> TYPE: DNA
<213> ORGANISM: Homo sapiens

<400> SEQUENCE: 110 aactccttt gaagagtctc tgagctaaca cgtcaacatc agcataaagt aatgcagcct    60
g                                                                    61

<210> SEQ ID NO 111
<211> LENGTH: 61
```

```
<212> TYPE: DNA
<213> ORGANISM: Homo sapiens

<400> SEQUENCE: 111
agagatgcta taaattgtac ttggtttcaa cgtagggtga tcaccttttc tttcatgact    60
a                                                                    61

<210> SEQ ID NO 112
<211> LENGTH: 61
<212> TYPE: DNA
<213> ORGANISM: Homo sapiens

<400> SEQUENCE: 112
agagatgcta taaattgtac ttggtttcaa tgtagggtga tcaccttttc tttcatgact    60
a                                                                    61

<210> SEQ ID NO 113
<211> LENGTH: 61
<212> TYPE: DNA
<213> ORGANISM: Homo sapiens

<400> SEQUENCE: 113
ttacatctat ccaggggcaa tttctgatga ctattttat taatgatcta ataaaatgtc     60
t                                                                    61

<210> SEQ ID NO 114
<211> LENGTH: 61
<212> TYPE: DNA
<213> ORGANISM: Homo sapiens

<400> SEQUENCE: 114
ttacatctat ccaggggcaa tttctgatga gtattttat taatgatcta ataaaatgtc     60
t                                                                    61

<210> SEQ ID NO 115
<211> LENGTH: 61
<212> TYPE: DNA
<213> ORGANISM: Homo sapiens

<400> SEQUENCE: 115
cgcagaccaa cacctggaat cctgtagcaa atgccttcat aagaactgaa aaggactctt    60
a                                                                    61

<210> SEQ ID NO 116
<211> LENGTH: 61
<212> TYPE: DNA
<213> ORGANISM: Homo sapiens

<400> SEQUENCE: 116
cgcagaccaa cacctggaat cctgtagcaa ctgccttcat aagaactgaa aaggactctt    60
a                                                                    61

<210> SEQ ID NO 117
<211> LENGTH: 61
<212> TYPE: DNA
<213> ORGANISM: Homo sapiens

<400> SEQUENCE: 117
tcagggcaaa tgacctcact ccatgatgga cgctttgagg aagggaataa atgaataaat    60
a                                                                    61
```

<210> SEQ ID NO 118
<211> LENGTH: 61
<212> TYPE: DNA
<213> ORGANISM: Homo sapiens

<400> SEQUENCE: 118
tcagggcaaa tgacctcact ccatgatgga tgctttgagg aagggaataa atgaataaat    60
a                                                                   61

<210> SEQ ID NO 119
<211> LENGTH: 61
<212> TYPE: DNA
<213> ORGANISM: Homo sapiens

<400> SEQUENCE: 119
gctgtgcggt ttgaaatatg aactctgtaa cctcttcagt ggctcccaca tcccagggct    60
g                                                                   61

<210> SEQ ID NO 120
<211> LENGTH: 61
<212> TYPE: DNA
<213> ORGANISM: Homo sapiens

<400> SEQUENCE: 120
gctgtgcggt ttgaaatatg aactctgtaa tctcttcagt ggctcccaca tcccagggct    60
g                                                                   61

<210> SEQ ID NO 121
<211> LENGTH: 61
<212> TYPE: DNA
<213> ORGANISM: Homo sapiens

<400> SEQUENCE: 121
tccctgaggg cctcacttgc tccatgagac aaactcacta cagcgttcat cttgtttaaa    60
a                                                                   61

<210> SEQ ID NO 122
<211> LENGTH: 61
<212> TYPE: DNA
<213> ORGANISM: Homo sapiens

<400> SEQUENCE: 122
tccctgaggg cctcacttgc tccatgagac gaactcacta cagcgttcat cttgtttaaa    60
a                                                                   61

<210> SEQ ID NO 123
<211> LENGTH: 61
<212> TYPE: DNA
<213> ORGANISM: Homo sapiens

<400> SEQUENCE: 123
tcatgttact tactgagttc taatttctac agtaccacta aaaactctgg agtgaccgtc    60
t                                                                   61

<210> SEQ ID NO 124
<211> LENGTH: 61
<212> TYPE: DNA
<213> ORGANISM: Homo sapiens

<400> SEQUENCE: 124

```
tcatgttact tactgagttc taatttctac ggtaccacta aaaactctgg agtgaccgtc    60
t                                                                   61

<210> SEQ ID NO 125
<211> LENGTH: 61
<212> TYPE: DNA
<213> ORGANISM: Homo sapiens

<400> SEQUENCE: 125
atcaatccac tcaaaaattg ccccatataa agttgaaatt taatgttgca tgtaaatgat    60
c                                                                   61

<210> SEQ ID NO 126
<211> LENGTH: 61
<212> TYPE: DNA
<213> ORGANISM: Homo sapiens

<400> SEQUENCE: 126
atcaatccac tcaaaaattg ccccatataa ggttgaaatt taatgttgca tgtaaatgat    60
c                                                                   61

<210> SEQ ID NO 127
<211> LENGTH: 61
<212> TYPE: DNA
<213> ORGANISM: Homo sapiens

<400> SEQUENCE: 127
tggctggaag actcccagcc tgagtcattc agaaacagat ttacaaagca ctcgggagga    60
t                                                                   61

<210> SEQ ID NO 128
<211> LENGTH: 61
<212> TYPE: DNA
<213> ORGANISM: Homo sapiens

<400> SEQUENCE: 128
tggctggaag actcccagcc tgagtcattc ggaaacagat ttacaaagca ctcgggagga    60
t                                                                   61

<210> SEQ ID NO 129
<211> LENGTH: 61
<212> TYPE: DNA
<213> ORGANISM: Homo sapiens

<400> SEQUENCE: 129
gaggatcccg agggaatgat caggccgaga cggaggaaga gccttcatga ccaagtgggt    60
c                                                                   61

<210> SEQ ID NO 130
<211> LENGTH: 61
<212> TYPE: DNA
<213> ORGANISM: Homo sapiens

<400> SEQUENCE: 130
gaggatcccg agggaatgat caggccgaga tggaggaaga gccttcatga ccaagtgggt    60
c                                                                   61

<210> SEQ ID NO 131
<211> LENGTH: 61
```

```
<212> TYPE: DNA
<213> ORGANISM: Homo sapiens

<400> SEQUENCE: 131
ccacaaaggc ttccttcacg tgtctggtca cgaatgctgc ctgccaacag gggaaccttg      60
g                                                                    61

<210> SEQ ID NO 132
<211> LENGTH: 61
<212> TYPE: DNA
<213> ORGANISM: Homo sapiens

<400> SEQUENCE: 132
ccacaaaggc ttccttcacg tgtctggtca tgaatgctgc ctgccaacag gggaaccttg      60
g                                                                    61

<210> SEQ ID NO 133
<211> LENGTH: 61
<212> TYPE: DNA
<213> ORGANISM: Homo sapiens

<400> SEQUENCE: 133
taaacaggaa ttgtaaatac ttgtgtgtta cgaaattatt tgagcagaat tccttctcat      60
a                                                                    61

<210> SEQ ID NO 134
<211> LENGTH: 61
<212> TYPE: DNA
<213> ORGANISM: Homo sapiens

<400> SEQUENCE: 134
taaacaggaa ttgtaaatac ttgtgtgtta tgaaattatt tgagcagaat tccttctcat      60
a                                                                    61

<210> SEQ ID NO 135
<211> LENGTH: 61
<212> TYPE: DNA
<213> ORGANISM: Homo sapiens

<400> SEQUENCE: 135
gaaaagccaa cagtggcaca aaggccacta cctaaaaacg tcattttagt ttagtaataa      60
a                                                                    61

<210> SEQ ID NO 136
<211> LENGTH: 61
<212> TYPE: DNA
<213> ORGANISM: Homo sapiens

<400> SEQUENCE: 136
gaaaagccaa cagtggcaca aaggccacta tctaaaaacg tcattttagt ttagtaataa      60
a                                                                    61

<210> SEQ ID NO 137
<211> LENGTH: 61
<212> TYPE: DNA
<213> ORGANISM: Homo sapiens

<400> SEQUENCE: 137
ctgggttcaa gttaataatc cctgttagac cgaatgtacc tccccagaag ggcctacctc      60
a                                                                    61
```

<210> SEQ ID NO 138
<211> LENGTH: 61
<212> TYPE: DNA
<213> ORGANISM: Homo sapiens

<400> SEQUENCE: 138
ctgggttcaa gttaataatc cctgttagac ggaatgtacc tccccagaag ggcctacctc    60
a                                                                    61

<210> SEQ ID NO 139
<211> LENGTH: 61
<212> TYPE: DNA
<213> ORGANISM: Homo sapiens

<400> SEQUENCE: 139
ctattagcta ttcactgtat ctgtaatata cgctgtctaa tgtatctgta agggttaaat    60
c                                                                    61

<210> SEQ ID NO 140
<211> LENGTH: 61
<212> TYPE: DNA
<213> ORGANISM: Homo sapiens

<400> SEQUENCE: 140
ctattagcta ttcactgtat ctgtaatata tgctgtctaa tgtatctgta agggttaaat    60
c                                                                    61

<210> SEQ ID NO 141
<211> LENGTH: 61
<212> TYPE: DNA
<213> ORGANISM: Homo sapiens

<400> SEQUENCE: 141
taaaattaag atttcacgtt tcatgtattc cccgagaaaa ttaagctgag tgatggaata    60
c                                                                    61

<210> SEQ ID NO 142
<211> LENGTH: 61
<212> TYPE: DNA
<213> ORGANISM: Homo sapiens

<400> SEQUENCE: 142
taaaattaag atttcacgtt tcatgtattc tccgagaaaa ttaagctgag tgatggaata    60
c                                                                    61

<210> SEQ ID NO 143
<211> LENGTH: 61
<212> TYPE: DNA
<213> ORGANISM: Homo sapiens

<400> SEQUENCE: 143
agaagctccc gcatttctca ccttttacaa ctataatgac agaactagac gctgtcctct    60
a                                                                    61

<210> SEQ ID NO 144
<211> LENGTH: 61
<212> TYPE: DNA
<213> ORGANISM: Homo sapiens

<400> SEQUENCE: 144

-continued

```
agaagctccc gcatttctca cctttttacaa gtataatgac agaactagac gctgtcctct    60
a                                                                    61

<210> SEQ ID NO 145
<211> LENGTH: 61
<212> TYPE: DNA
<213> ORGANISM: Homo sapiens

<400> SEQUENCE: 145
accttaatca gaaatttcca gtttccaaaa attgtattat actcaggttg gccctaggtt    60
t                                                                    61

<210> SEQ ID NO 146
<211> LENGTH: 61
<212> TYPE: DNA
<213> ORGANISM: Homo sapiens

<400> SEQUENCE: 146
accttaatca gaaatttcca gtttccaaaa gttgtattat actcaggttg gccctaggtt    60
t                                                                    61

<210> SEQ ID NO 147
<211> LENGTH: 61
<212> TYPE: DNA
<213> ORGANISM: Homo sapiens

<400> SEQUENCE: 147
accaaagtgg gtaggatttg ttttcagtgg ccacatatca agcccatttt taaattattg    60
a                                                                    61

<210> SEQ ID NO 148
<211> LENGTH: 61
<212> TYPE: DNA
<213> ORGANISM: Homo sapiens

<400> SEQUENCE: 148
accaaagtgg gtaggatttg ttttcagtgg gcacatatca agcccatttt taaattattg    60
a                                                                    61

<210> SEQ ID NO 149
<211> LENGTH: 61
<212> TYPE: DNA
<213> ORGANISM: Homo sapiens

<400> SEQUENCE: 149
ctagctaaag gactaagaac ggggcagcct aacaaaatga aggcttttag acaataacca    60
c                                                                    61

<210> SEQ ID NO 150
<211> LENGTH: 61
<212> TYPE: DNA
<213> ORGANISM: Homo sapiens

<400> SEQUENCE: 150
ctagctaaag gactaagaac ggggcagcct cacaaaatga aggcttttag acaataacca    60
c                                                                    61

<210> SEQ ID NO 151
<211> LENGTH: 61
```

```
<212> TYPE: DNA
<213> ORGANISM: Homo sapiens

<400> SEQUENCE: 151
cccttctctg taataacact acgctaggtc acgatagatc tttaggggt gtatatttgg      60 a                                                                     61

<210> SEQ ID NO 152
<211> LENGTH: 61
<212> TYPE: DNA
<213> ORGANISM: Homo sapiens

<400> SEQUENCE: 152
cccttctctg taataacact acgctaggtc gcgatagatc tttaggggt gtatatttgg      60 a                                                                     61

<210> SEQ ID NO 153
<211> LENGTH: 61
<212> TYPE: DNA
<213> ORGANISM: Homo sapiens

<400> SEQUENCE: 153
ggaactagag tttctgagag caaggtgaga agattatgca tgaagacact gggctgtcat    60
c                                                                     61

<210> SEQ ID NO 154
<211> LENGTH: 61
<212> TYPE: DNA
<213> ORGANISM: Homo sapiens

<400> SEQUENCE: 154
ggaactagag tttctgagag caaggtgaga ggattatgca tgaagacact gggctgtcat    60
c                                                                     61

<210> SEQ ID NO 155
<211> LENGTH: 61
<212> TYPE: DNA
<213> ORGANISM: Homo sapiens

<400> SEQUENCE: 155
ttagaaaata actgagaagt aaagtgtaga cgaaggaaag tgtatattgg taaaagcata    60
t                                                                     61

<210> SEQ ID NO 156
<211> LENGTH: 61
<212> TYPE: DNA
<213> ORGANISM: Homo sapiens

<400> SEQUENCE: 156
ttagaaaata actgagaagt aaagtgtaga tgaaggaaag tgtatattgg taaaagcata    60
t                                                                     61

<210> SEQ ID NO 157
<211> LENGTH: 61
<212> TYPE: DNA
<213> ORGANISM: Homo sapiens

<400> SEQUENCE: 157
tgctattacc ctcctcggtt ggctccagca ataagcctaa tgacctctac aaagctgttc    60
t                                                                     61
```

<210> SEQ ID NO 158
<211> LENGTH: 61
<212> TYPE: DNA
<213> ORGANISM: Homo sapiens

<400> SEQUENCE: 158
tgctattacc ctcctcggtt ggctccagca gtaagcctaa tgacctctac aaagctgttc    60
t                                                                   61

<210> SEQ ID NO 159
<211> LENGTH: 61
<212> TYPE: DNA
<213> ORGANISM: Homo sapiens

<400> SEQUENCE: 159
attctcgttt gaggaagatt ttctaagtca ctaacctgta atcttcctat tacaaccaat    60
t                                                                   61

<210> SEQ ID NO 160
<211> LENGTH: 61
<212> TYPE: DNA
<213> ORGANISM: Homo sapiens

<400> SEQUENCE: 160
attctcgttt gaggaagatt ttctaagtca ttaacctgta atcttcctat tacaaccaat    60
t                                                                   61

<210> SEQ ID NO 161
<211> LENGTH: 61
<212> TYPE: DNA
<213> ORGANISM: Homo sapiens

<400> SEQUENCE: 161
ttctgtttaa caattaatat tttatctgag actattgtgc actgtaattt ttatgaactt    60
a                                                                   61

<210> SEQ ID NO 162
<211> LENGTH: 61
<212> TYPE: DNA
<213> ORGANISM: Homo sapiens

<400> SEQUENCE: 162
ttctgtttaa caattaatat tttatctgag cctattgtgc actgtaattt ttatgaactt    60
a                                                                   61

<210> SEQ ID NO 163
<211> LENGTH: 61
<212> TYPE: DNA
<213> ORGANISM: Homo sapiens

<400> SEQUENCE: 163
ctaagcagga gtctttcagg actgaaaaaa cgttatgagg ctgttggtga aacttgaatg    60
g                                                                   61

<210> SEQ ID NO 164
<211> LENGTH: 61
<212> TYPE: DNA
<213> ORGANISM: Homo sapiens

<400> SEQUENCE: 164

```
ctaagcagga gtctttcagg actgaaaaaa tgttatgagg ctgttggtga aacttgaatg    60
g                                                                   61

<210> SEQ ID NO 165
<211> LENGTH: 61
<212> TYPE: DNA
<213> ORGANISM: Homo sapiens

<400> SEQUENCE: 165
taagcctagc tgggggagta gaacacatta caattgaaca caaattataa taatgcaagg    60
c                                                                   61

<210> SEQ ID NO 166
<211> LENGTH: 61
<212> TYPE: DNA
<213> ORGANISM: Homo sapiens

<400> SEQUENCE: 166
taagcctagc tgggggagta gaacacatta gaattgaaca caaattataa taatgcaagg    60
c                                                                   61

<210> SEQ ID NO 167
<211> LENGTH: 61
<212> TYPE: DNA
<213> ORGANISM: Homo sapiens

<400> SEQUENCE: 167
agttttaggt gacttcctca aattccccaa acctaaattc tatttgctta ttttacttct    60
g                                                                   61

<210> SEQ ID NO 168
<211> LENGTH: 61
<212> TYPE: DNA
<213> ORGANISM: Homo sapiens

<400> SEQUENCE: 168
agttttaggt gacttcctca aattccccaa tcctaaattc tatttgctta ttttacttct    60
g                                                                   61

<210> SEQ ID NO 169
<211> LENGTH: 61
<212> TYPE: DNA
<213> ORGANISM: Homo sapiens

<400> SEQUENCE: 169
acagtggaga cttcgtgctc agagaagaga agggaagttt tcttggtccg ccctagtgtt    60
t                                                                   61

<210> SEQ ID NO 170
<211> LENGTH: 61
<212> TYPE: DNA
<213> ORGANISM: Homo sapiens

<400> SEQUENCE: 170
acagtggaga cttcgtgctc agagaagaga cgggaagttt tcttggtccg ccctagtgtt    60
t                                                                   61

<210> SEQ ID NO 171
<211> LENGTH: 61
```

```
<212> TYPE: DNA
<213> ORGANISM: Homo sapiens

<400> SEQUENCE: 171
agcaaaggag gtaaatggtg tccttgaaaa cacttgcctg tgagtttctg gatctccatg    60
c                                                                    61

<210> SEQ ID NO 172
<211> LENGTH: 61
<212> TYPE: DNA
<213> ORGANISM: Homo sapiens

<400> SEQUENCE: 172
agcaaaggag gtaaatggtg tccttgaaaa tacttgcctg tgagtttctg gatctccatg    60
c                                                                    61

<210> SEQ ID NO 173
<211> LENGTH: 61
<212> TYPE: DNA
<213> ORGANISM: Homo sapiens

<400> SEQUENCE: 173
agcagcacag aattgcaggt ggactcttta aagctattct gttctgctaa caaggagcaa    60
g                                                                    61

<210> SEQ ID NO 174
<211> LENGTH: 61
<212> TYPE: DNA
<213> ORGANISM: Homo sapiens

<400> SEQUENCE: 174
agcagcacag aattgcaggt ggactcttta cagctattct gttctgctaa caaggagcaa    60
g                                                                    61

<210> SEQ ID NO 175
<211> LENGTH: 61
<212> TYPE: DNA
<213> ORGANISM: Homo sapiens

<400> SEQUENCE: 175
gtccctcact ggaacaagat ctgtgagtga cgtaaagctt tctggtaaag gcaaaggaag    60
t                                                                    61

<210> SEQ ID NO 176
<211> LENGTH: 61
<212> TYPE: DNA
<213> ORGANISM: Homo sapiens

<400> SEQUENCE: 176
gtccctcact ggaacaagat ctgtgagtga tgtaaagctt tctggtaaag gcaaaggaag    60
t                                                                    61

<210> SEQ ID NO 177
<211> LENGTH: 61
<212> TYPE: DNA
<213> ORGANISM: Homo sapiens

<400> SEQUENCE: 177
cacatgtgta gaccctggtc tatgcaagca acatatattt tctcatttat ttcttaccac    60
a                                                                    61
```

<210> SEQ ID NO 178
<211> LENGTH: 61
<212> TYPE: DNA
<213> ORGANISM: Homo sapiens

<400> SEQUENCE: 178
cacatgtgta gaccctggtc tatgcaagca gcatatattt tctcatttat ttcttaccac    60
a                                                                   61

<210> SEQ ID NO 179
<211> LENGTH: 61
<212> TYPE: DNA
<213> ORGANISM: Homo sapiens

<400> SEQUENCE: 179
ttggtctatt ttggtgaaaa gcagatatta agcctatttg tccccttcca cagtgtgacc    60
t                                                                   61

<210> SEQ ID NO 180
<211> LENGTH: 61
<212> TYPE: DNA
<213> ORGANISM: Homo sapiens

<400> SEQUENCE: 180
ttggtctatt ttggtgaaaa gcagatatta ggcctatttg tccccttcca cagtgtgacc    60
t                                                                   61

<210> SEQ ID NO 181
<211> LENGTH: 61
<212> TYPE: DNA
<213> ORGANISM: Homo sapiens

<400> SEQUENCE: 181
ccactgggcc atttctgtgt gtaagttccc cataataaaa ccttgtgcct tgtttgttgg    60
c                                                                   61

<210> SEQ ID NO 182
<211> LENGTH: 61
<212> TYPE: DNA
<213> ORGANISM: Homo sapiens

<400> SEQUENCE: 182
ccactgggcc atttctgtgt gtaagttccc tataataaaa ccttgtgcct tgtttgttgg    60
c                                                                   61

<210> SEQ ID NO 183
<211> LENGTH: 61
<212> TYPE: DNA
<213> ORGANISM: Homo sapiens

<400> SEQUENCE: 183
tttgatgaca tattctgaga gatgttctga atattaaata cttggttttg aaaacaagtt    60
t                                                                   61

<210> SEQ ID NO 184
<211> LENGTH: 61
<212> TYPE: DNA
<213> ORGANISM: Homo sapiens

<400> SEQUENCE: 184

```
tttgatgaca tattctgaga gatgttctga gtattaaata cttggttttg aaaacaagtt    60
t                                                                   61

<210> SEQ ID NO 185
<211> LENGTH: 61
<212> TYPE: DNA
<213> ORGANISM: Homo sapiens

<400> SEQUENCE: 185
tagcaattag gaatgctact agtaatacca atatctgcac tgagtagttt caaagagctg    60
a                                                                   61

<210> SEQ ID NO 186
<211> LENGTH: 61
<212> TYPE: DNA
<213> ORGANISM: Homo sapiens

<400> SEQUENCE: 186
tagcaattag gaatgctact agtaatacca gtatctgcac tgagtagttt caaagagctg    60
a                                                                   61

<210> SEQ ID NO 187
<211> LENGTH: 61
<212> TYPE: DNA
<213> ORGANISM: Homo sapiens

<400> SEQUENCE: 187
gttatagaag aggtgaaagg tgaatcaata aaatcaataa agagtttata atgtcagtac    60
a                                                                   61

<210> SEQ ID NO 188
<211> LENGTH: 61
<212> TYPE: DNA
<213> ORGANISM: Homo sapiens

<400> SEQUENCE: 188
gttatagaag aggtgaaagg tgaatcaata gaatcaataa agagtttata atgtcagtac    60
a                                                                   61

<210> SEQ ID NO 189
<211> LENGTH: 61
<212> TYPE: DNA
<213> ORGANISM: Homo sapiens

<400> SEQUENCE: 189
ttccttattc ctcttctaca cagtcttcat gaaatcaatc actggagccc acattgctgc    60
c                                                                   61

<210> SEQ ID NO 190
<211> LENGTH: 61
<212> TYPE: DNA
<213> ORGANISM: Homo sapiens

<400> SEQUENCE: 190
ttccttattc ctcttctaca cagtcttcat taaatcaatc actggagccc acattgctgc    60
c                                                                   61

<210> SEQ ID NO 191
<211> LENGTH: 61
```

```
<212> TYPE: DNA
<213> ORGANISM: Homo sapiens

<400> SEQUENCE: 191
cgttctgatc aagggctgta agtactagaa cggaagaaca gtgtgctgtg ggaagaaatg      60
g                                                                     61

<210> SEQ ID NO 192
<211> LENGTH: 61
<212> TYPE: DNA
<213> ORGANISM: Homo sapiens

<400> SEQUENCE: 192
cgttctgatc aagggctgta agtactagaa tggaagaaca gtgtgctgtg ggaagaaatg      60
g                                                                     61

<210> SEQ ID NO 193
<211> LENGTH: 61
<212> TYPE: DNA
<213> ORGANISM: Homo sapiens

<400> SEQUENCE: 193
ggaagaattc atcaccagca tacctgtata caaaaaaagt gttgataagt cctttaggca      60
a                                                                     61

<210> SEQ ID NO 194
<211> LENGTH: 61
<212> TYPE: DNA
<213> ORGANISM: Homo sapiens

<400> SEQUENCE: 194
ggaagaattc atcaccagca tacctgtata gaaaaaaagt gttgataagt cctttaggca      60
a                                                                     61

<210> SEQ ID NO 195
<211> LENGTH: 61
<212> TYPE: DNA
<213> ORGANISM: Homo sapiens

<400> SEQUENCE: 195
tgaaggatct cctgccaggt aaagcaaatg aaacttaaca tatcaacgtt aaagaattga      60
c                                                                     61

<210> SEQ ID NO 196
<211> LENGTH: 61
<212> TYPE: DNA
<213> ORGANISM: Homo sapiens

<400> SEQUENCE: 196
tgaaggatct cctgccaggt aaagcaaatg gaacttaaca tatcaacgtt aaagaattga      60
c                                                                     61

<210> SEQ ID NO 197
<211> LENGTH: 61
<212> TYPE: DNA
<213> ORGANISM: Homo sapiens

<400> SEQUENCE: 197
ccctagaggg tatcaagggt tgagcaagaa cgtttacttg tgtcaagcca tttatattta      60
t                                                                     61
```

<210> SEQ ID NO 198
<211> LENGTH: 61
<212> TYPE: DNA
<213> ORGANISM: Homo sapiens

<400> SEQUENCE: 198
ccctagaggg tatcaagggt tgagcaagaa tgtttacttg tgtcaagcca tttatattta    60
t                                                                    61

<210> SEQ ID NO 199
<211> LENGTH: 61
<212> TYPE: DNA
<213> ORGANISM: Homo sapiens

<400> SEQUENCE: 199
atcatgttaa cacaggaagg aactatatag aagaagcaac tttggaggaa gagatttcat    60
c                                                                    61

<210> SEQ ID NO 200
<211> LENGTH: 61
<212> TYPE: DNA
<213> ORGANISM: Homo sapiens

<400> SEQUENCE: 200
atcatgttaa cacaggaagg aactatatag gagaagcaac tttggaggaa gagatttcat    60
c                                                                    61

<210> SEQ ID NO 201
<211> LENGTH: 61
<212> TYPE: DNA
<213> ORGANISM: Homo sapiens

<400> SEQUENCE: 201
tgtatttaaa aatggggcta attatgccca aatcatgatg ggatgaagtg ttgtaaggct    60
t                                                                    61

<210> SEQ ID NO 202
<211> LENGTH: 61
<212> TYPE: DNA
<213> ORGANISM: Homo sapiens

<400> SEQUENCE: 202
tgtatttaaa aatggggcta attatgccca catcatgatg ggatgaagtg ttgtaaggct    60
t                                                                    61

<210> SEQ ID NO 203
<211> LENGTH: 61
<212> TYPE: DNA
<213> ORGANISM: Homo sapiens

<400> SEQUENCE: 203
attgtaaatt cagaaaactt tacagctact acgaggatga cctagcctga gtcccaacta    60
a                                                                    61

<210> SEQ ID NO 204
<211> LENGTH: 61
<212> TYPE: DNA
<213> ORGANISM: Homo sapiens

<400> SEQUENCE: 204

-continued attgtaaatt cagaaaactt tacagctact gcgaggatga cctagcctga gtcccaacta    60
a    61

<210> SEQ ID NO 205
<211> LENGTH: 61
<212> TYPE: DNA
<213> ORGANISM: Homo sapiens

<400> SEQUENCE: 205
gttttattct gaaacgcttc tctgctcaaa actttcaaac cattgttctt tgtctcatga    60
t    61

<210> SEQ ID NO 206
<211> LENGTH: 61
<212> TYPE: DNA
<213> ORGANISM: Homo sapiens

<400> SEQUENCE: 206
gttttattct gaaacgcttc tctgctcaaa tctttcaaac cattgttctt tgtctcatga    60
t    61

<210> SEQ ID NO 207
<211> LENGTH: 61
<212> TYPE: DNA
<213> ORGANISM: Homo sapiens

<400> SEQUENCE: 207
gtgtcaccaa cctgaggctt ctctgttgta actcagttgt ctcaggaact tccatggtta    60
c    61

<210> SEQ ID NO 208
<211> LENGTH: 61
<212> TYPE: DNA
<213> ORGANISM: Homo sapiens

<400> SEQUENCE: 208
gtgtcaccaa cctgaggctt ctctgttgta cctcagttgt ctcaggaact tccatggtta    60
c    61

<210> SEQ ID NO 209
<211> LENGTH: 61
<212> TYPE: DNA
<213> ORGANISM: Homo sapiens

<400> SEQUENCE: 209
tataagagta ctatcaaata taagttttta atatgtatgc agcatttca tttcattgtc    60 a    61

<210> SEQ ID NO 210
<211> LENGTH: 61
<212> TYPE: DNA
<213> ORGANISM: Homo sapiens

<400> SEQUENCE: 210
tataagagta ctatcaaata taagttttta gtatgtatgc agcatttca tttcattgtc    60 a    61

<210> SEQ ID NO 211
<211> LENGTH: 61

<210> SEQ ID NO 211
<211> LENGTH: 61
<212> TYPE: DNA
<213> ORGANISM: Homo sapiens

<400> SEQUENCE: 211
tcctaccgat tttagtgaga gatgcacttc atgacctgac aatgtctcta gctttggacc   60
t                                                                  61

<210> SEQ ID NO 212
<211> LENGTH: 61
<212> TYPE: DNA
<213> ORGANISM: Homo sapiens

<400> SEQUENCE: 212
tcctaccgat tttagtgaga gatgcacttc gtgacctgac aatgtctcta gctttggacc   60
t                                                                  61

<210> SEQ ID NO 213
<211> LENGTH: 61
<212> TYPE: DNA
<213> ORGANISM: Homo sapiens

<400> SEQUENCE: 213
ggaggtgcaa cggtgagggt gtgttggtat atctaaggac aagcgaggag gccagtgaca   60
a                                                                  61

<210> SEQ ID NO 214
<211> LENGTH: 61
<212> TYPE: DNA
<213> ORGANISM: Homo sapiens

<400> SEQUENCE: 214
ggaggtgcaa cggtgagggt gtgttggtat gtctaaggac aagcgaggag gccagtgaca   60
a                                                                  61

<210> SEQ ID NO 215
<211> LENGTH: 61
<212> TYPE: DNA
<213> ORGANISM: Homo sapiens

<400> SEQUENCE: 215
attatccatg gccagggaaa gaaccactca ataggagaaa aggaaaaaaa tccttaaagc   60
t                                                                  61

<210> SEQ ID NO 216
<211> LENGTH: 61
<212> TYPE: DNA
<213> ORGANISM: Homo sapiens

<400> SEQUENCE: 216
attatccatg gccagggaaa gaaccactca gtaggagaaa aggaaaaaaa tccttaaagc   60
t                                                                  61

<210> SEQ ID NO 217
<211> LENGTH: 61
<212> TYPE: DNA
<213> ORGANISM: Homo sapiens

<400> SEQUENCE: 217
cattcacgat aaaaaaaagg tttggcaaat agaggtcaga agaactcatc tttaatctga   60
t                                                                  61

<210> SEQ ID NO 218
<211> LENGTH: 61
<212> TYPE: DNA
<213> ORGANISM: Homo sapiens

<400> SEQUENCE: 218
cattcacgat aaaaaaaagg tttggcaaat tgaggtcaga agaactcatc tttaatctga    60
t                                                                  61

<210> SEQ ID NO 219
<211> LENGTH: 61
<212> TYPE: DNA
<213> ORGANISM: Homo sapiens

<400> SEQUENCE: 219
gccttgcatt attataattt gtgttcaatt ctaatgtgtt ctactccccc agctaggctt    60
a                                                                  61

<210> SEQ ID NO 220
<211> LENGTH: 61
<212> TYPE: DNA
<213> ORGANISM: Homo sapiens

<400> SEQUENCE: 220
gccttgcatt attataattt gtgttcaatt gtaatgtgtt ctactccccc agctaggctt    60
a                                                                  61

<210> SEQ ID NO 221
<211> LENGTH: 61
<212> TYPE: DNA
<213> ORGANISM: Homo sapiens

<400> SEQUENCE: 221
agttttaggt gacttcctca aattccccaa acctaaattc tatttgctta ttttacttct    60
g                                                                  61

<210> SEQ ID NO 222
<211> LENGTH: 61
<212> TYPE: DNA
<213> ORGANISM: Homo sapiens

<400> SEQUENCE: 222
agttttaggt gacttcctca aattccccaa tcctaaattc tatttgctta ttttacttct    60
g                                                                  61

<210> SEQ ID NO 223
<211> LENGTH: 61
<212> TYPE: DNA
<213> ORGANISM: Homo sapiens

<400> SEQUENCE: 223
atatgctttt accaatatac actttccttc atctacactt tacttctcag ttattttcta    60
a                                                                  61

<210> SEQ ID NO 224
<211> LENGTH: 61
<212> TYPE: DNA
<213> ORGANISM: Homo sapiens

<400> SEQUENCE: 224

```
atatgctttt accaatatac actttccttc gtctacactt tacttctcag ttattttcta    60
a                                                                    61

<210> SEQ ID NO 225
<211> LENGTH: 61
<212> TYPE: DNA
<213> ORGANISM: Homo sapiens

<400> SEQUENCE: 225
gctggatgaa atagcattgg atcagaggac aaacaagatc ttccttgtac ctataatact    60
c                                                                    61

<210> SEQ ID NO 226
<211> LENGTH: 61
<212> TYPE: DNA
<213> ORGANISM: Homo sapiens

<400> SEQUENCE: 226
gctggatgaa atagcattgg atcagaggac gaacaagatc ttccttgtac ctataatact    60
c                                                                    61

<210> SEQ ID NO 227
<211> LENGTH: 61
<212> TYPE: DNA
<213> ORGANISM: Homo sapiens

<400> SEQUENCE: 227
ccaaggatga tgggaaaagc aaactgataa acctgttaat ttcccatatg tgactagtag    60
g                                                                    61

<210> SEQ ID NO 228
<211> LENGTH: 61
<212> TYPE: DNA
<213> ORGANISM: Homo sapiens

<400> SEQUENCE: 228
ccaaggatga tgggaaaagc aaactgataa gcctgttaat ttcccatatg tgactagtag    60
g                                                                    61

<210> SEQ ID NO 229
<211> LENGTH: 61
<212> TYPE: DNA
<213> ORGANISM: Homo sapiens

<400> SEQUENCE: 229
atggggttta ggctgcactt aacattattt ctctggagac tgatcttagt ccttaatttc    60
a                                                                    61

<210> SEQ ID NO 230
<211> LENGTH: 61
<212> TYPE: DNA
<213> ORGANISM: Homo sapiens

<400> SEQUENCE: 230
atggggttta ggctgcactt aacattattt gtctggagac tgatcttagt ccttaatttc    60
a                                                                    61

<210> SEQ ID NO 231
<211> LENGTH: 61
```

```
<212> TYPE: DNA
<213> ORGANISM: Homo sapiens

<400> SEQUENCE: 231
gcctcttcta ttctcatgta aattttagcc atggtctata acattactct aaagtattga      60
c                                                                      61

<210> SEQ ID NO 232
<211> LENGTH: 61
<212> TYPE: DNA
<213> ORGANISM: Homo sapiens

<400> SEQUENCE: 232
gcctcttcta ttctcatgta aattttagcc ctggtctata acattactct aaagtattga      60
c                                                                      61

<210> SEQ ID NO 233
<211> LENGTH: 61
<212> TYPE: DNA
<213> ORGANISM: Homo sapiens

<400> SEQUENCE: 233
caggctgcat gtgagccaaa gagagaaaaa aggacttact atgtgctata tctagtaact      60
g                                                                      61

<210> SEQ ID NO 234
<211> LENGTH: 61
<212> TYPE: DNA
<213> ORGANISM: Homo sapiens

<400> SEQUENCE: 234
caggctgcat gtgagccaaa gagagaaaaa gggacttact atgtgctata tctagtaact      60
g                                                                      61

<210> SEQ ID NO 235
<211> LENGTH: 61
<212> TYPE: DNA
<213> ORGANISM: Homo sapiens

<400> SEQUENCE: 235
aagatctata agctttgaag gacctatgaa atgcttgcaa gaaaccagga aaaataatcc      60
t                                                                      61

<210> SEQ ID NO 236
<211> LENGTH: 61
<212> TYPE: DNA
<213> ORGANISM: Homo sapiens

<400> SEQUENCE: 236
aagatctata agctttgaag gacctatgaa gtgcttgcaa gaaaccagga aaaataatcc      60
t                                                                      61

<210> SEQ ID NO 237
<211> LENGTH: 61
<212> TYPE: DNA
<213> ORGANISM: Homo sapiens

<400> SEQUENCE: 237
tttgtcgtca tccatcctgt cgatcaaata atcacagtta agatggaaat atattttcaa      60
a                                                                      61
```

<210> SEQ ID NO 238
<211> LENGTH: 61
<212> TYPE: DNA
<213> ORGANISM: Homo sapiens

<400> SEQUENCE: 238
tttgtcgtca tccatcctgt cgatcaaata gtcacagtta agatggaaat atattttcaa    60
a                                                                   61

<210> SEQ ID NO 239
<211> LENGTH: 61
<212> TYPE: DNA
<213> ORGANISM: Homo sapiens

<400> SEQUENCE: 239
actgtgtgca aaggacaaat gatttctcac agtgcagtct gccttgaatc ctaaggggaa    60
t                                                                   61

<210> SEQ ID NO 240
<211> LENGTH: 61
<212> TYPE: DNA
<213> ORGANISM: Homo sapiens

<400> SEQUENCE: 240
actgtgtgca aaggacaaat gatttctcac ggtgcagtct gccttgaatc ctaaggggaa    60
t                                                                   61

<210> SEQ ID NO 241
<211> LENGTH: 61
<212> TYPE: DNA
<213> ORGANISM: Homo sapiens

<400> SEQUENCE: 241
acaacatgag ggtaactgcc cccatgtttg aattacctct caccgggtcc tttccagcac    60
a                                                                   61

<210> SEQ ID NO 242
<211> LENGTH: 61
<212> TYPE: DNA
<213> ORGANISM: Homo sapiens

<400> SEQUENCE: 242
acaacatgag ggtaactgcc cccatgtttg cattacctct caccgggtcc tttccagcac    60
a                                                                   61

<210> SEQ ID NO 243
<211> LENGTH: 61
<212> TYPE: DNA
<213> ORGANISM: Homo sapiens

<400> SEQUENCE: 243
agcctcctag ggttctaata atcaggacct atggttcagg aatgcacagt agcactcagc    60
t                                                                   61

<210> SEQ ID NO 244
<211> LENGTH: 61
<212> TYPE: DNA
<213> ORGANISM: Homo sapiens

<400> SEQUENCE: 244

```
agcctcctag ggttctaata atcaggacct gtggttcagg aatgcacagt agcactcagc    60
t                                                                   61

<210> SEQ ID NO 245
<211> LENGTH: 61
<212> TYPE: DNA
<213> ORGANISM: Homo sapiens

<400> SEQUENCE: 245
catgggtcca ccctgaggat ctccagtgac atttgcagca ccgaggccca gcacccgaga    60
a                                                                   61

<210> SEQ ID NO 246
<211> LENGTH: 61
<212> TYPE: DNA
<213> ORGANISM: Homo sapiens

<400> SEQUENCE: 246
catgggtcca ccctgaggat ctccagtgac gtttgcagca ccgaggccca gcacccgaga    60
a                                                                   61

<210> SEQ ID NO 247
<211> LENGTH: 61
<212> TYPE: DNA
<213> ORGANISM: Homo sapiens

<400> SEQUENCE: 247
tagaggacag cgtctagttc tgtcattata cttgtaaaag gtgagaaatg cgggagcttc    60
t                                                                   61

<210> SEQ ID NO 248
<211> LENGTH: 61
<212> TYPE: DNA
<213> ORGANISM: Homo sapiens

<400> SEQUENCE: 248
tagaggacag cgtctagttc tgtcattata gttgtaaaag gtgagaaatg cgggagcttc    60
t                                                                   61

<210> SEQ ID NO 249
<211> LENGTH: 61
<212> TYPE: DNA
<213> ORGANISM: Homo sapiens

<400> SEQUENCE: 249
ttgcagtaaa tatggctagt tatctatagg attcaatttt cctcttcttc tgtaataaaa    60
t                                                                   61

<210> SEQ ID NO 250
<211> LENGTH: 61
<212> TYPE: DNA
<213> ORGANISM: Homo sapiens

<400> SEQUENCE: 250
ttgcagtaaa tatggctagt tatctatagg gttcaatttt cctcttcttc tgtaataaaa    60
t                                                                   61

<210> SEQ ID NO 251
<211> LENGTH: 61
```

```
<212> TYPE: DNA
<213> ORGANISM: Homo sapiens

<400> SEQUENCE: 251
ctttctgtct cattcactcc tatgcattgt ctgcaacaga agcacaatga gtagttttta    60
g                                                                   61

<210> SEQ ID NO 252
<211> LENGTH: 61
<212> TYPE: DNA
<213> ORGANISM: Homo sapiens

<400> SEQUENCE: 252
ctttctgtct cattcactcc tatgcattgt gtgcaacaga agcacaatga gtagttttta    60
g                                                                   61

<210> SEQ ID NO 253
<211> LENGTH: 61
<212> TYPE: DNA
<213> ORGANISM: Homo sapiens

<400> SEQUENCE: 253
actggctagt attccatctc actttcatta ctggagaact gaagagccag ctagcctaca    60
a                                                                   61

<210> SEQ ID NO 254
<211> LENGTH: 61
<212> TYPE: DNA
<213> ORGANISM: Homo sapiens

<400> SEQUENCE: 254
actggctagt attccatctc actttcatta gtggagaact gaagagccag ctagcctaca    60
a                                                                   61

<210> SEQ ID NO 255
<211> LENGTH: 61
<212> TYPE: DNA
<213> ORGANISM: Homo sapiens

<400> SEQUENCE: 255
accttcatgg catgccatga gcatatcact atccttaaaa gcacattcat ggtgctggct    60
t                                                                   61

<210> SEQ ID NO 256
<211> LENGTH: 61
<212> TYPE: DNA
<213> ORGANISM: Homo sapiens

<400> SEQUENCE: 256
accttcatgg catgccatga gcatatcact gtccttaaaa gcacattcat ggtgctggct    60
t                                                                   61

<210> SEQ ID NO 257
<211> LENGTH: 61
<212> TYPE: DNA
<213> ORGANISM: Homo sapiens

<400> SEQUENCE: 257
ataaatataa atggcttgac acaagtaaac attcttgctc aaccccttgat accctctagg   60
g                                                                   61
```

<210> SEQ ID NO 258
<211> LENGTH: 61
<212> TYPE: DNA
<213> ORGANISM: Homo sapiens

<400> SEQUENCE: 258
ataaatataa atggcttgac acaagtaaac gttcttgctc aacccttgat accctctagg    60
g                                                                    61

<210> SEQ ID NO 259
<211> LENGTH: 61
<212> TYPE: DNA
<213> ORGANISM: Homo sapiens

<400> SEQUENCE: 259
ccgtattatt taatctaccc cctaattacc aaaatctgtg taaaactatt catgtcccaa    60
t                                                                    61

<210> SEQ ID NO 260
<211> LENGTH: 61
<212> TYPE: DNA
<213> ORGANISM: Homo sapiens

<400> SEQUENCE: 260
ccgtattatt taatctaccc cctaattacc gaaatctgtg taaaactatt catgtcccaa    60
t                                                                    61

<210> SEQ ID NO 261
<211> LENGTH: 61
<212> TYPE: DNA
<213> ORGANISM: Homo sapiens

<400> SEQUENCE: 261
ttgtgttggc tgtaatttgc tttaaaatat attagcacag gctatcaaat gacatatatg    60
t                                                                    61

<210> SEQ ID NO 262
<211> LENGTH: 61
<212> TYPE: DNA
<213> ORGANISM: Homo sapiens

<400> SEQUENCE: 262
ttgtgttggc tgtaatttgc tttaaaatat gttagcacag gctatcaaat gacatatatg    60
t                                                                    61

<210> SEQ ID NO 263
<211> LENGTH: 61
<212> TYPE: DNA
<213> ORGANISM: Homo sapiens

<400> SEQUENCE: 263
aaaacacacc tcctcaggga gatagctgaa agtctcatta ttcattccga ttgagggtca    60
g                                                                    61

<210> SEQ ID NO 264
<211> LENGTH: 61
<212> TYPE: DNA
<213> ORGANISM: Homo sapiens

<400> SEQUENCE: 264

```
aaaacacacc tcctcaggga gatagctgaa cgtctcatta ttcattccga ttgagggtca    60
g                                                                   61

<210> SEQ ID NO 265
<211> LENGTH: 61
<212> TYPE: DNA
<213> ORGANISM: Homo sapiens

<400> SEQUENCE: 265
gtggtccttc gtccaataca attggtatcc atataagcag aggagatttg gacacagaag    60
c                                                                   61

<210> SEQ ID NO 266
<211> LENGTH: 61
<212> TYPE: DNA
<213> ORGANISM: Homo sapiens

<400> SEQUENCE: 266
gtggtccttc gtccaataca attggtatcc gtataagcag aggagatttg gacacagaag    60
c                                                                   61

<210> SEQ ID NO 267
<211> LENGTH: 61
<212> TYPE: DNA
<213> ORGANISM: Homo sapiens

<400> SEQUENCE: 267
tggggactgc agagtattca tatttacaaa actgtagtat tgcatatcta caggtttatg    60
t                                                                   61

<210> SEQ ID NO 268
<211> LENGTH: 61
<212> TYPE: DNA
<213> ORGANISM: Homo sapiens

<400> SEQUENCE: 268
tggggactgc agagtattca tatttacaaa cctgtagtat tgcatatcta caggtttatg    60
t                                                                   61

<210> SEQ ID NO 269
<211> LENGTH: 61
<212> TYPE: DNA
<213> ORGANISM: Homo sapiens

<400> SEQUENCE: 269
tgaaactccc tctgcttatg agataaaaga actagctgaa atcagttgga accaatgtgg    60
c                                                                   61

<210> SEQ ID NO 270
<211> LENGTH: 61
<212> TYPE: DNA
<213> ORGANISM: Homo sapiens

<400> SEQUENCE: 270
tgaaactccc tctgcttatg agataaaaga cctagctgaa atcagttgga accaatgtgg    60
c                                                                   61

<210> SEQ ID NO 271
<211> LENGTH: 61
```

```
<212> TYPE: DNA
<213> ORGANISM: Homo sapiens

<400> SEQUENCE: 271
aagctgtcaa acttcttgga ttttctggat aggccaatag atctatttaa ctataaacct    60
g                                                                    61

<210> SEQ ID NO 272
<211> LENGTH: 61
<212> TYPE: DNA
<213> ORGANISM: Homo sapiens

<400> SEQUENCE: 272
aagctgtcaa acttcttgga ttttctggat gggccaatag atctatttaa ctataaacct    60
g                                                                    61

<210> SEQ ID NO 273
<211> LENGTH: 61
<212> TYPE: DNA
<213> ORGANISM: Homo sapiens

<400> SEQUENCE: 273
tttgcagctc agcaaattaa aattgtaatt cattgtggta attccttgaa ccctgtcttt    60
g                                                                    61

<210> SEQ ID NO 274
<211> LENGTH: 61
<212> TYPE: DNA
<213> ORGANISM: Homo sapiens

<400> SEQUENCE: 274
tttgcagctc agcaaattaa aattgtaatt gattgtggta attccttgaa ccctgtcttt    60
g                                                                    61

<210> SEQ ID NO 275
<211> LENGTH: 61
<212> TYPE: DNA
<213> ORGANISM: Homo sapiens

<400> SEQUENCE: 275
gcaagatagc tgccacagct ccaggcatca aacctaattt taggaccaaa gaagggaggt    60
g                                                                    61

<210> SEQ ID NO 276
<211> LENGTH: 61
<212> TYPE: DNA
<213> ORGANISM: Homo sapiens

<400> SEQUENCE: 276
gcaagatagc tgccacagct ccaggcatca gacctaattt taggaccaaa gaagggaggt    60
g                                                                    61

<210> SEQ ID NO 277
<211> LENGTH: 61
<212> TYPE: DNA
<213> ORGANISM: Homo sapiens

<400> SEQUENCE: 277
atctcagagc tattatgaag tggtgtcaag attgaaaacc agatcagcct ggatttggac    60
t                                                                    61
```

<210> SEQ ID NO 278
<211> LENGTH: 61
<212> TYPE: DNA
<213> ORGANISM: Homo sapiens

<400> SEQUENCE: 278

```
atctcagagc tattatgaag tggtgtcaag gttgaaaacc agatcagcct ggatttggac      60
t                                                                     61
```

<210> SEQ ID NO 279
<211> LENGTH: 61
<212> TYPE: DNA
<213> ORGANISM: Homo sapiens

<400> SEQUENCE: 279

```
aggcagccgt gttaggtatg atgtccccga aagagtacac attaacatga caaagtttga      60
g                                                                     61
```

<210> SEQ ID NO 280
<211> LENGTH: 61
<212> TYPE: DNA
<213> ORGANISM: Homo sapiens

<400> SEQUENCE: 280

```
aggcagccgt gttaggtatg atgtccccga gagagtacac attaacatga caaagtttga      60
g                                                                     61
```

<210> SEQ ID NO 281
<211> LENGTH: 61
<212> TYPE: DNA
<213> ORGANISM: Homo sapiens

<400> SEQUENCE: 281

```
gcgtttctag aagggatgc agagagtgtc agttgtaatt tttaaaccag cccataagct       60
c                                                                     61
```

<210> SEQ ID NO 282
<211> LENGTH: 61
<212> TYPE: DNA
<213> ORGANISM: Homo sapiens

<400> SEQUENCE: 282

```
gcgtttctag aagggatgc agagagtgtc ggttgtaatt tttaaaccag cccataagct       60
c                                                                     61
```

<210> SEQ ID NO 283
<211> LENGTH: 61
<212> TYPE: DNA
<213> ORGANISM: Homo sapiens

<400> SEQUENCE: 283

```
tccaggaaaa ttttcattat tctcaccttt acgggctcat tgatgtttag ggataaaatt      60
c                                                                     61
```

<210> SEQ ID NO 284
<211> LENGTH: 61
<212> TYPE: DNA
<213> ORGANISM: Homo sapiens

<400> SEQUENCE: 284
```

-continued

```
tccaggaaaa ttttcattat tctcaccttt gcgggctcat tgatgtttag ggataaaatt    60
c                                                                   61

<210> SEQ ID NO 285
<211> LENGTH: 61
<212> TYPE: DNA
<213> ORGANISM: Homo sapiens

<400> SEQUENCE: 285
ttcagcaaat attaatatat tagaatttac atgtaccata tcccacaatg ctggtagccc    60
a                                                                   61

<210> SEQ ID NO 286
<211> LENGTH: 61
<212> TYPE: DNA
<213> ORGANISM: Homo sapiens

<400> SEQUENCE: 286
ttcagcaaat attaatatat tagaatttac ctgtaccata tcccacaatg ctggtagccc    60
a                                                                   61

<210> SEQ ID NO 287
<211> LENGTH: 61
<212> TYPE: DNA
<213> ORGANISM: Homo sapiens

<400> SEQUENCE: 287
gctcagagcc tgctactctg aagtctggca atggcaccca cctccctgca gaagaggcag    60
a                                                                   61

<210> SEQ ID NO 288
<211> LENGTH: 61
<212> TYPE: DNA
<213> ORGANISM: Homo sapiens

<400> SEQUENCE: 288
gctcagagcc tgctactctg aagtctggca gtggcaccca cctccctgca gaagaggcag    60
a                                                                   61

<210> SEQ ID NO 289
<211> LENGTH: 61
<212> TYPE: DNA
<213> ORGANISM: Homo sapiens

<400> SEQUENCE: 289
gcctcagaga acacctgcca cacataggcc agacctgatg gcgcatcaca ccagggtaca    60
g                                                                   61

<210> SEQ ID NO 290
<211> LENGTH: 61
<212> TYPE: DNA
<213> ORGANISM: Homo sapiens

<400> SEQUENCE: 290
gcctcagaga acacctgcca cacataggcc ggacctgatg gcgcatcaca ccagggtaca    60
g                                                                   61

<210> SEQ ID NO 291
<211> LENGTH: 61
```

```
<212> TYPE: DNA
<213> ORGANISM: Homo sapiens

<400> SEQUENCE: 291
ttcacaacac agctaaggtt ggtgatagtc agtaacaatg tgggtgttag tttcaaggaa    60
c                                                                    61

<210> SEQ ID NO 292
<211> LENGTH: 61
<212> TYPE: DNA
<213> ORGANISM: Homo sapiens

<400> SEQUENCE: 292
ttcacaacac agctaaggtt ggtgatagtc ggtaacaatg tgggtgttag tttcaaggaa    60
c                                                                    61

<210> SEQ ID NO 293
<211> LENGTH: 61
<212> TYPE: DNA
<213> ORGANISM: Homo sapiens

<400> SEQUENCE: 293
tgaaggatct cctgccaggt aaagcaaatg aaacttaaca tatcaacgtt aaagaattga    60
c                                                                    61

<210> SEQ ID NO 294
<211> LENGTH: 61
<212> TYPE: DNA
<213> ORGANISM: Homo sapiens

<400> SEQUENCE: 294
tgaaggatct cctgccaggt aaagcaaatg gaacttaaca tatcaacgtt aaagaattga    60
c                                                                    61

<210> SEQ ID NO 295
<211> LENGTH: 61
<212> TYPE: DNA
<213> ORGANISM: Homo sapiens

<400> SEQUENCE: 295
tccttccctc ttttactagc tgatattctg agcatccttc taggtccagc tcaaatgtgg    60
c                                                                    61

<210> SEQ ID NO 296
<211> LENGTH: 61
<212> TYPE: DNA
<213> ORGANISM: Homo sapiens

<400> SEQUENCE: 296
tccttccctc ttttactagc tgatattctg cgcatccttc taggtccagc tcaaatgtgg    60
c                                                                    61

<210> SEQ ID NO 297
<211> LENGTH: 61
<212> TYPE: DNA
<213> ORGANISM: Homo sapiens

<400> SEQUENCE: 297
cccaccttgt tttccctcct actctccctt cgtgcttcac accccggct gctcactggc     60
c                                                                    61
```

<210> SEQ ID NO 298
<211> LENGTH: 61
<212> TYPE: DNA
<213> ORGANISM: Homo sapiens

<400> SEQUENCE: 298
cccaccttgt tttccctcct actctccctt ggtgcttcac accccggct gctcactggc      60
c                                                                     61

<210> SEQ ID NO 299
<211> LENGTH: 61
<212> TYPE: DNA
<213> ORGANISM: Homo sapiens

<400> SEQUENCE: 299
tccgatcgga tatccggttt gggcaataag agatgtaaat aaagtgagga ttttaaagcc      60
c                                                                     61

<210> SEQ ID NO 300
<211> LENGTH: 61
<212> TYPE: DNA
<213> ORGANISM: Homo sapiens

<400> SEQUENCE: 300
tccgatcgga tatccggttt gggcaataag ggatgtaaat aaagtgagga ttttaaagcc      60
c                                                                     61

<210> SEQ ID NO 301
<211> LENGTH: 61
<212> TYPE: DNA
<213> ORGANISM: Homo sapiens

<400> SEQUENCE: 301
tgtccattct ctgttgccac tgcaggtaca atactcagaa gcttactgag ctgattttac      60
a                                                                     61

<210> SEQ ID NO 302
<211> LENGTH: 61
<212> TYPE: DNA
<213> ORGANISM: Homo sapiens

<400> SEQUENCE: 302
tgtccattct ctgttgccac tgcaggtaca gtactcagaa gcttactgag ctgattttac      60
a                                                                     61

<210> SEQ ID NO 303
<211> LENGTH: 61
<212> TYPE: DNA
<213> ORGANISM: Homo sapiens

<400> SEQUENCE: 303
accctatacc actaaaccac cctatactct ataccactca tttaaacaca gctgcaggct      60
c                                                                     61

<210> SEQ ID NO 304
<211> LENGTH: 61
<212> TYPE: DNA
<213> ORGANISM: Homo sapiens

<400> SEQUENCE: 304

```
accctatacc actaaaccac cctatactct gtaccactca tttaaacaca gctgcaggct    60
c                                                                   61
```

<210> SEQ ID NO 305
<211> LENGTH: 61
<212> TYPE: DNA
<213> ORGANISM: Homo sapiens

<400> SEQUENCE: 305

```
tgggtcctgg cagacaagga gatgggatga agcatttctc tgataccttg ccttcccttta   60
a                                                                    61
```

<210> SEQ ID NO 306
<211> LENGTH: 61
<212> TYPE: DNA
<213> ORGANISM: Homo sapiens

<400> SEQUENCE: 306

```
tgggtcctgg cagacaagga gatgggatga ggcatttctc tgataccttg ccttccttta    60
a                                                                    61
```

<210> SEQ ID NO 307
<211> LENGTH: 61
<212> TYPE: DNA
<213> ORGANISM: Homo sapiens

<400> SEQUENCE: 307

```
ggggacaaag gtttattaca cgatggtttc aggggcatac agcaaatgga aggtaaatga    60
a                                                                    61
```

<210> SEQ ID NO 308
<211> LENGTH: 61
<212> TYPE: DNA
<213> ORGANISM: Homo sapiens

<400> SEQUENCE: 308

```
ggggacaaag gtttattaca cgatggtttc gggggcatac agcaaatgga aggtaaatga    60
a                                                                    61
```

<210> SEQ ID NO 309
<211> LENGTH: 61
<212> TYPE: DNA
<213> ORGANISM: Homo sapiens

<400> SEQUENCE: 309

```
agagtaaagc accagcataa ccaaaatgac atctataaat aaataggaaa gaacggcact    60
t                                                                    61
```

<210> SEQ ID NO 310
<211> LENGTH: 61
<212> TYPE: DNA
<213> ORGANISM: Homo sapiens

<400> SEQUENCE: 310

```
agagtaaagc accagcataa ccaaaatgac gtctataaat aaataggaaa gaacggcact    60
t                                                                    61
```

<210> SEQ ID NO 311
<211> LENGTH: 61

```
<212> TYPE: DNA
<213> ORGANISM: Homo sapiens

<400> SEQUENCE: 311
tatttattca ccccttctgt ttctgcccat aagagccatg cacactagct gcttctagtt      60
g                                                                     61

<210> SEQ ID NO 312
<211> LENGTH: 61
<212> TYPE: DNA
<213> ORGANISM: Homo sapiens

<400> SEQUENCE: 312
tatttattca ccccttctgt ttctgcccat gagagccatg cacactagct gcttctagtt      60
g                                                                     61

<210> SEQ ID NO 313
<211> LENGTH: 61
<212> TYPE: DNA
<213> ORGANISM: Homo sapiens

<400> SEQUENCE: 313
catctgatcc ttaaagtcaa taggaagtaa ccgactgatt ctggataaac cttttcaggc      60
t                                                                     61

<210> SEQ ID NO 314
<211> LENGTH: 61
<212> TYPE: DNA
<213> ORGANISM: Homo sapiens

<400> SEQUENCE: 314
catctgatcc ttaaagtcaa taggaagtaa gcgactgatt ctggataaac cttttcaggc      60
t                                                                     61

<210> SEQ ID NO 315
<211> LENGTH: 61
<212> TYPE: DNA
<213> ORGANISM: Homo sapiens

<400> SEQUENCE: 315
tagcaattag gaatgctact agtaatacca atatctgcac tgagtagttt caaagagctg      60
a                                                                     61

<210> SEQ ID NO 316
<211> LENGTH: 61
<212> TYPE: DNA
<213> ORGANISM: Homo sapiens

<400> SEQUENCE: 316
tagcaattag gaatgctact agtaatacca gtatctgcac tgagtagttt caaagagctg      60
a                                                                     61

<210> SEQ ID NO 317
<211> LENGTH: 61
<212> TYPE: DNA
<213> ORGANISM: Homo sapiens

<400> SEQUENCE: 317
gacccgagaa tcctctgcac aatggcccca agactatttc cagagcagta agggcctcta      60
c                                                                     61
```

<210> SEQ ID NO 318
<211> LENGTH: 61
<212> TYPE: DNA
<213> ORGANISM: Homo sapiens

<400> SEQUENCE: 318
gacccgagaa tcctctgcac aatggcccca ggactatttc cagagcagta agggcctcta    60
c                                                                   61

<210> SEQ ID NO 319
<211> LENGTH: 61
<212> TYPE: DNA
<213> ORGANISM: Homo sapiens

<400> SEQUENCE: 319
gggagtcaaa gggttttcca ctggagcctg actttctggg ttgttatgca ggcatagtgt    60
c                                                                   61

<210> SEQ ID NO 320
<211> LENGTH: 61
<212> TYPE: DNA
<213> ORGANISM: Homo sapiens

<400> SEQUENCE: 320
gggagtcaaa gggttttcca ctggagcctg gctttctggg ttgttatgca ggcatagtgt    60
c                                                                   61

<210> SEQ ID NO 321
<211> LENGTH: 61
<212> TYPE: DNA
<213> ORGANISM: Homo sapiens

<400> SEQUENCE: 321
gaccctctgt tttgggtaga tgtcgatgaa agtattgata aacttgtttc tgaaataggc    60
a                                                                   61

<210> SEQ ID NO 322
<211> LENGTH: 61
<212> TYPE: DNA
<213> ORGANISM: Homo sapiens

<400> SEQUENCE: 322
gaccctctgt tttgggtaga tgtcgatgaa ggtattgata aacttgtttc tgaaataggc    60
a                                                                   61

<210> SEQ ID NO 323
<211> LENGTH: 61
<212> TYPE: DNA
<213> ORGANISM: Homo sapiens

<400> SEQUENCE: 323
cccaaaatag aaatgttgag ttattaccaa acagacataa tttaattcaa agcattcttt    60
c                                                                   61

<210> SEQ ID NO 324
<211> LENGTH: 61
<212> TYPE: DNA
<213> ORGANISM: Homo sapiens

<400> SEQUENCE: 324

```
cccaaaatag aaatgttgag ttattaccaa gcagacataa tttaattcaa agcattcttt    60
c                                                                   61

<210> SEQ ID NO 325
<211> LENGTH: 61
<212> TYPE: DNA
<213> ORGANISM: Homo sapiens

<400> SEQUENCE: 325
ctcctcactg cctctgctgt tctgtttgat acaaaggaaa gatatttgat caaattccca    60
a                                                                   61

<210> SEQ ID NO 326
<211> LENGTH: 61
<212> TYPE: DNA
<213> ORGANISM: Homo sapiens

<400> SEQUENCE: 326
ctcctcactg cctctgctgt tctgtttgat gcaaaggaaa gatatttgat caaattccca    60
a                                                                   61

<210> SEQ ID NO 327
<211> LENGTH: 61
<212> TYPE: DNA
<213> ORGANISM: Homo sapiens

<400> SEQUENCE: 327
acagaaaatt ctatcaccat acaaaattta atgcagtatt tatgttttaa agcacaggtg    60
t                                                                   61

<210> SEQ ID NO 328
<211> LENGTH: 61
<212> TYPE: DNA
<213> ORGANISM: Homo sapiens

<400> SEQUENCE: 328
acagaaaatt ctatcaccat acaaaattta ttgcagtatt tatgttttaa agcacaggtg    60
t                                                                   61

<210> SEQ ID NO 329
<211> LENGTH: 61
<212> TYPE: DNA
<213> ORGANISM: Homo sapiens

<400> SEQUENCE: 329
agtctatttg tcacaaaagt gcctcctgtt aatttcactg gatgcctcct ctggcgtcct    60
a                                                                   61

<210> SEQ ID NO 330
<211> LENGTH: 61
<212> TYPE: DNA
<213> ORGANISM: Homo sapiens

<400> SEQUENCE: 330
agtctatttg tcacaaaagt gcctcctgtt catttcactg gatgcctcct ctggcgtcct    60
a                                                                   61

<210> SEQ ID NO 331
<211> LENGTH: 61
```

```
<212> TYPE: DNA
<213> ORGANISM: Homo sapiens

<400> SEQUENCE: 331
agaaacagag ccacttcagt gaccatctac aacaaggaat gcagtctttg caaaaatagt    60
t                                                                   61

<210> SEQ ID NO 332
<211> LENGTH: 61
<212> TYPE: DNA
<213> ORGANISM: Homo sapiens

<400> SEQUENCE: 332
agaaacagag ccacttcagt gaccatctac cacaaggaat gcagtctttg caaaaatagt    60
t                                                                   61

<210> SEQ ID NO 333
<211> LENGTH: 61
<212> TYPE: DNA
<213> ORGANISM: Homo sapiens

<400> SEQUENCE: 333
tgttctgctc ccaaccctgt gtcaggtttt acacttctac cttcctgacc ttaatataag    60
c                                                                   61

<210> SEQ ID NO 334
<211> LENGTH: 61
<212> TYPE: DNA
<213> ORGANISM: Homo sapiens

<400> SEQUENCE: 334
tgttctgctc ccaaccctgt gtcaggtttt gcacttctac cttcctgacc ttaatataag    60
c                                                                   61

<210> SEQ ID NO 335
<211> LENGTH: 61
<212> TYPE: DNA
<213> ORGANISM: Homo sapiens

<400> SEQUENCE: 335
ggcatttcag agatcttcaa gacatagcta agaccttgag ggcaaggttt ccagagtagc    60
a                                                                   61

<210> SEQ ID NO 336
<211> LENGTH: 61
<212> TYPE: DNA
<213> ORGANISM: Homo sapiens

<400> SEQUENCE: 336
ggcatttcag agatcttcaa gacatagcta ggaccttgag ggcaaggttt ccagagtagc    60
a                                                                   61

<210> SEQ ID NO 337
<211> LENGTH: 61
<212> TYPE: DNA
<213> ORGANISM: Homo sapiens

<400> SEQUENCE: 337
gaagacagtc cattaacagc tactctaaat aggacaatct gttcacacca gtctccccct    60
a                                                                   61
```

<210> SEQ ID NO 338
<211> LENGTH: 61
<212> TYPE: DNA
<213> ORGANISM: Homo sapiens

<400> SEQUENCE: 338
gaagacagtc cattaacagc tactctaaat gggacaatct gttcacacca gtctccccct       60
a                                                                      61

<210> SEQ ID NO 339
<211> LENGTH: 61
<212> TYPE: DNA
<213> ORGANISM: Homo sapiens

<400> SEQUENCE: 339
agtctctctt tctcctctag atcacaaagg acaagcagtt tccaggatgt cctcatgctc       60
t                                                                      61

<210> SEQ ID NO 340
<211> LENGTH: 61
<212> TYPE: DNA
<213> ORGANISM: Homo sapiens

<400> SEQUENCE: 340
agtctctctt tctcctctag atcacaaagg gcaagcagtt tccaggatgt cctcatgctc       60
t                                                                      61

<210> SEQ ID NO 341
<211> LENGTH: 61
<212> TYPE: DNA
<213> ORGANISM: Homo sapiens

<400> SEQUENCE: 341
catctctgta aatagcctca tatttgagta atttgctgaa tgatccagat ttgagtgtat       60
c                                                                      61

<210> SEQ ID NO 342
<211> LENGTH: 61
<212> TYPE: DNA
<213> ORGANISM: Homo sapiens

<400> SEQUENCE: 342
catctctgta aatagcctca tatttgagta gtttgctgaa tgatccagat ttgagtgtat       60
c                                                                      61

<210> SEQ ID NO 343
<211> LENGTH: 61
<212> TYPE: DNA
<213> ORGANISM: Homo sapiens

<400> SEQUENCE: 343
taaaataaaa atagacttct gttttagtcc ataaattcca gatggaataa ttaagtaatc       60
g                                                                      61

<210> SEQ ID NO 344
<211> LENGTH: 61
<212> TYPE: DNA
<213> ORGANISM: Homo sapiens

<400> SEQUENCE: 344

```
taaaataaaa atagacttct gttttagtcc gtaaattcca gatggaataa ttaagtaatc      60
g                                                                     61

<210> SEQ ID NO 345
<211> LENGTH: 61
<212> TYPE: DNA
<213> ORGANISM: Homo sapiens

<400> SEQUENCE: 345
aaatatgtga gacaaaggtc tgacatatgt atagttgaag ttccagaaga agaaagagaa      60
t                                                                     61

<210> SEQ ID NO 346
<211> LENGTH: 61
<212> TYPE: DNA
<213> ORGANISM: Homo sapiens

<400> SEQUENCE: 346
aaatatgtga gacaaaggtc tgacatatgt gtagttgaag ttccagaaga agaaagagaa      60
t                                                                     61

<210> SEQ ID NO 347
<211> LENGTH: 61
<212> TYPE: DNA
<213> ORGANISM: Homo sapiens

<400> SEQUENCE: 347
acaaaaaact gttaaaaagt tcagagcaag actagaaata agagttagag taataatgtt      60
a                                                                     61

<210> SEQ ID NO 348
<211> LENGTH: 61
<212> TYPE: DNA
<213> ORGANISM: Homo sapiens

<400> SEQUENCE: 348
acaaaaaact gttaaaaagt tcagagcaag gctagaaata agagttagag taataatgtt      60
a                                                                     61

<210> SEQ ID NO 349
<211> LENGTH: 61
<212> TYPE: DNA
<213> ORGANISM: Homo sapiens

<400> SEQUENCE: 349
tctaactctg agacagtttg ttgggtgtga ataaatcagt tacaacagca tggtatagga      60
t                                                                     61

<210> SEQ ID NO 350
<211> LENGTH: 61
<212> TYPE: DNA
<213> ORGANISM: Homo sapiens

<400> SEQUENCE: 350
tctaactctg agacagtttg ttgggtgtga ctaaatcagt tacaacagca tggtatagga      60
t                                                                     61

<210> SEQ ID NO 351
<211> LENGTH: 61
```

```
<212> TYPE: DNA
<213> ORGANISM: Homo sapiens

<400> SEQUENCE: 351
tcacctcagg aatgaatata gatagggaag aaaaaagacc tgagaactaa accatggaat    60
a                                                                   61

<210> SEQ ID NO 352
<211> LENGTH: 61
<212> TYPE: DNA
<213> ORGANISM: Homo sapiens

<400> SEQUENCE: 352
tcacctcagg aatgaatata gatagggaag gaaaaagacc tgagaactaa accatggaat    60
a                                                                   61

<210> SEQ ID NO 353
<211> LENGTH: 61
<212> TYPE: DNA
<213> ORGANISM: Homo sapiens

<400> SEQUENCE: 353
atggcatagc tggcatctga atatttgttc atggatttaa cagattctcc ccaacttgga    60
g                                                                   61

<210> SEQ ID NO 354
<211> LENGTH: 61
<212> TYPE: DNA
<213> ORGANISM: Homo sapiens

<400> SEQUENCE: 354
atggcatagc tggcatctga atatttgttc gtggatttaa cagattctcc ccaacttgga    60
g                                                                   61

<210> SEQ ID NO 355
<211> LENGTH: 61
<212> TYPE: DNA
<213> ORGANISM: Homo sapiens

<400> SEQUENCE: 355 cttttttttcc attttctata ttacagatga attgacatgg tcagtggata aataaatgtg    60
t                                                                    61

<210> SEQ ID NO 356
<211> LENGTH: 61
<212> TYPE: DNA
<213> ORGANISM: Homo sapiens

<400> SEQUENCE: 356 cttttttttcc attttctata ttacagatga gttgacatgg tcagtggata aataaatgtg    60
t                                                                    61

<210> SEQ ID NO 357
<211> LENGTH: 61
<212> TYPE: DNA
<213> ORGANISM: Homo sapiens

<400> SEQUENCE: 357
acttatacat tacatataat tagactccca aataaattct tcctatcctt agctgcatgt    60
g                                                                   61
```

```
<210> SEQ ID NO 358
<211> LENGTH: 61
<212> TYPE: DNA
<213> ORGANISM: Homo sapiens

<400> SEQUENCE: 358
acttatacat tacatataat tagactccca gataaattct tcctatcctt agctgcatgt    60
g                                                                   61

<210> SEQ ID NO 359
<211> LENGTH: 61
<212> TYPE: DNA
<213> ORGANISM: Homo sapiens

<400> SEQUENCE: 359
ctatgagttc agtgctacat aactctctct ctggacagac agctctgcca aagctattac    60
a                                                                   61

<210> SEQ ID NO 360
<211> LENGTH: 61
<212> TYPE: DNA
<213> ORGANISM: Homo sapiens

<400> SEQUENCE: 360
ctatgagttc agtgctacat aactctctct gtggacagac agctctgcca aagctattac    60
a                                                                   61

<210> SEQ ID NO 361
<211> LENGTH: 61
<212> TYPE: DNA
<213> ORGANISM: Homo sapiens

<400> SEQUENCE: 361
acataccaca gagaaatctt tcatgaaagc aaaagtcaat tgataagcaa acttcattgt    60
t                                                                   61

<210> SEQ ID NO 362
<211> LENGTH: 61
<212> TYPE: DNA
<213> ORGANISM: Homo sapiens

<400> SEQUENCE: 362
acataccaca gagaaatctt tcatgaaagc gaaagtcaat tgataagcaa acttcattgt    60
t                                                                   61

<210> SEQ ID NO 363
<211> LENGTH: 61
<212> TYPE: DNA
<213> ORGANISM: Homo sapiens

<400> SEQUENCE: 363
ttggtctatt ttggtgaaaa gcagatatta agcctatttg tccccttcca cagtgtgacc    60
t                                                                   61

<210> SEQ ID NO 364
<211> LENGTH: 61
<212> TYPE: DNA
<213> ORGANISM: Homo sapiens

<400> SEQUENCE: 364
```

```
ttggtctatt ttggtgaaaa gcagatatta ggcctatttg tccccttcca cagtgtgacc    60
t                                                                   61
```

<210> SEQ ID NO 365
<211> LENGTH: 61
<212> TYPE: DNA
<213> ORGANISM: Homo sapiens

<400> SEQUENCE: 365

```
atctgagaga ctgaatgtag aagagtcccc atcaatctgg agcaaataaa cttttgcttt    60
c                                                                   61
```

<210> SEQ ID NO 366
<211> LENGTH: 61
<212> TYPE: DNA
<213> ORGANISM: Homo sapiens

<400> SEQUENCE: 366

```
atctgagaga ctgaatgtag aagagtcccc gtcaatctgg agcaaataaa cttttgcttt    60
c                                                                   61
```

<210> SEQ ID NO 367
<211> LENGTH: 61
<212> TYPE: DNA
<213> ORGANISM: Homo sapiens

<400> SEQUENCE: 367

```
gcaagtgcaa ggaactgaaa gaagatgact atggggtcag agaagattca gataagacta    60
t                                                                   61
```

<210> SEQ ID NO 368
<211> LENGTH: 61
<212> TYPE: DNA
<213> ORGANISM: Homo sapiens

<400> SEQUENCE: 368

```
gcaagtgcaa ggaactgaaa gaagatgact gtggggtcag agaagattca gataagacta    60
t                                                                   61
```

<210> SEQ ID NO 369
<211> LENGTH: 61
<212> TYPE: DNA
<213> ORGANISM: Homo sapiens

<400> SEQUENCE: 369

```
cacatgtgta gaccctggtc tatgcaagca acatatattt tctcatttat ttcttaccac    60
a                                                                   61
```

<210> SEQ ID NO 370
<211> LENGTH: 61
<212> TYPE: DNA
<213> ORGANISM: Homo sapiens

<400> SEQUENCE: 370

```
cacatgtgta gaccctggtc tatgcaagca gcatatattt tctcatttat ttcttaccac    60
a                                                                   61
```

<210> SEQ ID NO 371
<211> LENGTH: 61

```
<212> TYPE: DNA
<213> ORGANISM: Homo sapiens

<400> SEQUENCE: 371 agacccatg tgttcttctt tgtatcttcc atcacatcta gcaacatcca ggtactgggc    60
t                                                                   61

<210> SEQ ID NO 372
<211> LENGTH: 61
<212> TYPE: DNA
<213> ORGANISM: Homo sapiens

<400> SEQUENCE: 372 agacccatg tgttcttctt tgtatcttcc gtcacatcta gcaacatcca ggtactgggc    60
t                                                                   61

<210> SEQ ID NO 373
<211> LENGTH: 61
<212> TYPE: DNA
<213> ORGANISM: Homo sapiens

<400> SEQUENCE: 373
cttcttaaac attcagcttc tgtttcccaa agaagtgcca tcaaagctcc aagggagcca    60
t                                                                   61

<210> SEQ ID NO 374
<211> LENGTH: 61
<212> TYPE: DNA
<213> ORGANISM: Homo sapiens

<400> SEQUENCE: 374
cttcttaaac attcagcttc tgtttcccaa ggaagtgcca tcaaagctcc aagggagcca    60
t                                                                   61

<210> SEQ ID NO 375
<211> LENGTH: 61
<212> TYPE: DNA
<213> ORGANISM: Homo sapiens

<400> SEQUENCE: 375
cctaaagggg atccttaatc aacagtgttc agttgcaaag aatagaaccc gtcaggcttt    60
c                                                                   61

<210> SEQ ID NO 376
<211> LENGTH: 61
<212> TYPE: DNA
<213> ORGANISM: Homo sapiens

<400> SEQUENCE: 376
cctaaagggg atccttaatc aacagtgttc ggttgcaaag aatagaaccc gtcaggcttt    60
c                                                                   61

<210> SEQ ID NO 377
<211> LENGTH: 61
<212> TYPE: DNA
<213> ORGANISM: Homo sapiens

<400> SEQUENCE: 377
tggctactca cctcctccca accttgaaca atataaggac tcaggtttcc aaggaaactc    60
a                                                                   61
```

<210> SEQ ID NO 378
<211> LENGTH: 61
<212> TYPE: DNA
<213> ORGANISM: Homo sapiens

<400> SEQUENCE: 378
tggctactca cctcctccca accttgaaca gtataaggac tcaggtttcc aaggaaactc    60
a                                                                   61

<210> SEQ ID NO 379
<211> LENGTH: 61
<212> TYPE: DNA
<213> ORGANISM: Homo sapiens

<400> SEQUENCE: 379
ctttgattag ccggctataa attcccttcc agaagccagc attgcccttg agggcccca     60
g                                                                   61

<210> SEQ ID NO 380
<211> LENGTH: 61
<212> TYPE: DNA
<213> ORGANISM: Homo sapiens

<400> SEQUENCE: 380
ctttgattag ccggctataa attcccttcc ggaagccagc attgcccttg agggcccca     60
g                                                                   61

<210> SEQ ID NO 381
<211> LENGTH: 61
<212> TYPE: DNA
<213> ORGANISM: Homo sapiens

<400> SEQUENCE: 381
tggtggagtc aaaatgcaaa gacgtgttgg agtgaaatca gcccaaaaca ctgaggtggg    60
g                                                                   61

<210> SEQ ID NO 382
<211> LENGTH: 61
<212> TYPE: DNA
<213> ORGANISM: Homo sapiens

<400> SEQUENCE: 382
tggtggagtc aaaatgcaaa gacgtgttgg cgtgaaatca gcccaaaaca ctgaggtggg    60
g                                                                   61

<210> SEQ ID NO 383
<211> LENGTH: 61
<212> TYPE: DNA
<213> ORGANISM: Homo sapiens

<400> SEQUENCE: 383
tctgcccggg cgaggcagat ctgcagttcc agggaggagg ttctgtgttc tcctgtgcac    60
c                                                                   61

<210> SEQ ID NO 384
<211> LENGTH: 61
<212> TYPE: DNA
<213> ORGANISM: Homo sapiens

<400> SEQUENCE: 384

```
tctgcccggg cgaggcagat ctgcagttcc ggggaggagg ttctgtgttc tcctgtgcac    60
c                                                                   61

<210> SEQ ID NO 385
<211> LENGTH: 61
<212> TYPE: DNA
<213> ORGANISM: Homo sapiens

<400> SEQUENCE: 385
gcatgtgggt tgatgtatga ggttccttgg aagagcagat ttgcagaaat tctggcatct    60
c                                                                   61

<210> SEQ ID NO 386
<211> LENGTH: 61
<212> TYPE: DNA
<213> ORGANISM: Homo sapiens

<400> SEQUENCE: 386
gcatgtgggt tgatgtatga ggttccttgg gagagcagat ttgcagaaat tctggcatct    60
c                                                                   61

<210> SEQ ID NO 387
<211> LENGTH: 61
<212> TYPE: DNA
<213> ORGANISM: Homo sapiens

<400> SEQUENCE: 387
cccttctctg taataacact acgctaggtc acgatagatc tttaggggt gtatatttgg     60
a                                                                   61

<210> SEQ ID NO 388
<211> LENGTH: 61
<212> TYPE: DNA
<213> ORGANISM: Homo sapiens

<400> SEQUENCE: 388
cccttctctg taataacact acgctaggtc gcgatagatc tttaggggt gtatatttgg     60
a                                                                   61

<210> SEQ ID NO 389
<211> LENGTH: 61
<212> TYPE: DNA
<213> ORGANISM: Homo sapiens

<400> SEQUENCE: 389
tggtggcaca cctacctctg tttctggccg aggaataaac actgggggca ccatccttag    60
g                                                                   61

<210> SEQ ID NO 390
<211> LENGTH: 61
<212> TYPE: DNA
<213> ORGANISM: Homo sapiens

<400> SEQUENCE: 390
tggtggcaca cctacctctg tttctggccg cggaataaac actgggggca ccatccttag    60
g                                                                   61

<210> SEQ ID NO 391
<211> LENGTH: 61
```

```
<212> TYPE: DNA
<213> ORGANISM: Homo sapiens

<400> SEQUENCE: 391
tgtaaggttt aaaaaatatc tctatgctgt agtcacgagt gttgctgttc atggtaagag    60
a                                                                   61

<210> SEQ ID NO 392
<211> LENGTH: 61
<212> TYPE: DNA
<213> ORGANISM: Homo sapiens

<400> SEQUENCE: 392
tgtaaggttt aaaaaatatc tctatgctgt cgtcacgagt gttgctgttc atggtaagag    60
a                                                                   61

<210> SEQ ID NO 393
<211> LENGTH: 61
<212> TYPE: DNA
<213> ORGANISM: Homo sapiens

<400> SEQUENCE: 393
ggaagtctcg ctgtgagttg acttctgtat atagggattc atctgtctct tactagttca    60
g                                                                   61

<210> SEQ ID NO 394
<211> LENGTH: 61
<212> TYPE: DNA
<213> ORGANISM: Homo sapiens

<400> SEQUENCE: 394
ggaagtctcg ctgtgagttg acttctgtat ctagggattc atctgtctct tactagttca    60
g                                                                   61

<210> SEQ ID NO 395
<211> LENGTH: 61
<212> TYPE: DNA
<213> ORGANISM: Homo sapiens

<400> SEQUENCE: 395
ctggaaagct agataataat cacagatttt atgcttccaa aagtgttctt cagtctctgg    60
t                                                                   61

<210> SEQ ID NO 396
<211> LENGTH: 61
<212> TYPE: DNA
<213> ORGANISM: Homo sapiens

<400> SEQUENCE: 396
ctggaaagct agataataat cacagatttt gtgcttccaa aagtgttctt cagtctctgg    60
t                                                                   61

<210> SEQ ID NO 397
<211> LENGTH: 61
<212> TYPE: DNA
<213> ORGANISM: Homo sapiens

<400> SEQUENCE: 397
tgctttggct gtgcatcaca tctaatatgg agaggcaccc ttccccatga gtcctgccag    60
g                                                                   61
```

<210> SEQ ID NO 398
<211> LENGTH: 61
<212> TYPE: DNA
<213> ORGANISM: Homo sapiens

<400> SEQUENCE: 398
tgctttggct gtgcatcaca tctaatatgg cgaggcaccc ttccccatga gtcctgccag    60
g                                                                  61

<210> SEQ ID NO 399
<211> LENGTH: 61
<212> TYPE: DNA
<213> ORGANISM: Homo sapiens

<400> SEQUENCE: 399
gcacccttcc ccatgagtcc tgccaggcaa atccttgaaa ttgcctatgg ttgggcctga    60
a                                                                  61

<210> SEQ ID NO 400
<211> LENGTH: 61
<212> TYPE: DNA
<213> ORGANISM: Homo sapiens

<400> SEQUENCE: 400
gcacccttcc ccatgagtcc tgccaggcaa gtccttgaaa ttgcctatgg ttgggcctga    60
a                                                                  61

<210> SEQ ID NO 401
<211> LENGTH: 61
<212> TYPE: DNA
<213> ORGANISM: Homo sapiens

<400> SEQUENCE: 401
ttgggatttt aaaagaaga gtggagtagt attttacagc actggtggtc tgagaattga     60
t                                                                  61

<210> SEQ ID NO 402
<211> LENGTH: 61
<212> TYPE: DNA
<213> ORGANISM: Homo sapiens

<400> SEQUENCE: 402
ttgggatttt aaaagaaga gtggagtagt cttttacagc actggtggtc tgagaattga     60
t                                                                  61

<210> SEQ ID NO 403
<211> LENGTH: 61
<212> TYPE: DNA
<213> ORGANISM: Homo sapiens

<400> SEQUENCE: 403
attaaatctc ataactttt tggaattaga atgggcttcc catcagctga atgggctaca     60
c                                                                  61

<210> SEQ ID NO 404
<211> LENGTH: 61
<212> TYPE: DNA
<213> ORGANISM: Homo sapiens

<400> SEQUENCE: 404

```
attaaatctc aataactttt tggaattaga gtgggcttcc catcagctga atgggctaca    60
c                                                                   61

<210> SEQ ID NO 405
<211> LENGTH: 61
<212> TYPE: DNA
<213> ORGANISM: Homo sapiens

<400> SEQUENCE: 405
tttttcatgt attagtttta aagcctgttc atctgagtct ccattttctc ccatcttccc    60
a                                                                   61

<210> SEQ ID NO 406
<211> LENGTH: 61
<212> TYPE: DNA
<213> ORGANISM: Homo sapiens

<400> SEQUENCE: 406
tttttcatgt attagtttta aagcctgttc gtctgagtct ccattttctc ccatcttccc    60
a                                                                   61

<210> SEQ ID NO 407
<211> LENGTH: 61
<212> TYPE: DNA
<213> ORGANISM: Homo sapiens

<400> SEQUENCE: 407
tccccaattt ccaatttgca aaatggtacc aatgagctct ccttggtaaa gctggattga    60
g                                                                   61

<210> SEQ ID NO 408
<211> LENGTH: 61
<212> TYPE: DNA
<213> ORGANISM: Homo sapiens

<400> SEQUENCE: 408
tccccaattt ccaatttgca aaatggtacc gatgagctct ccttggtaaa gctggattga    60
g                                                                   61

<210> SEQ ID NO 409
<211> LENGTH: 61
<212> TYPE: DNA
<213> ORGANISM: Homo sapiens

<400> SEQUENCE: 409
gataaaaccg gtttggttca attttagtaa catcagcaac aatggtaata atgatacttt    60
g                                                                   61

<210> SEQ ID NO 410
<211> LENGTH: 61
<212> TYPE: DNA
<213> ORGANISM: Homo sapiens

<400> SEQUENCE: 410
gataaaaccg gtttggttca attttagtaa gatcagcaac aatggtaata atgatacttt    60
g                                                                   61

<210> SEQ ID NO 411
<211> LENGTH: 61
```

```
<212> TYPE: DNA
<213> ORGANISM: Homo sapiens

<400> SEQUENCE: 411
gcctattctt gcctttgaaa tggctcgtgc agtggagaaa gagagaacat tccaggagtc    60
c                                                                    61

<210> SEQ ID NO 412
<211> LENGTH: 61
<212> TYPE: DNA
<213> ORGANISM: Homo sapiens

<400> SEQUENCE: 412
gcctattctt gcctttgaaa tggctcgtgc ggtggagaaa gagagaacat tccaggagtc    60
c                                                                    61

<210> SEQ ID NO 413
<211> LENGTH: 61
<212> TYPE: DNA
<213> ORGANISM: Homo sapiens

<400> SEQUENCE: 413
tgcaaatgca gagcagtaaa aagcggagac agcctgtccc attccatact cacagcaaca    60
g                                                                    61

<210> SEQ ID NO 414
<211> LENGTH: 61
<212> TYPE: DNA
<213> ORGANISM: Homo sapiens

<400> SEQUENCE: 414
tgcaaatgca gagcagtaaa aagcggagac ggcctgtccc attccatact cacagcaaca    60
g                                                                    61

<210> SEQ ID NO 415
<211> LENGTH: 61
<212> TYPE: DNA
<213> ORGANISM: Homo sapiens

<400> SEQUENCE: 415
tgctaaggtt ggtcatgggg tatttgagag attacggaaa gacgctttgc ccctcttcct    60
g                                                                    61

<210> SEQ ID NO 416
<211> LENGTH: 61
<212> TYPE: DNA
<213> ORGANISM: Homo sapiens

<400> SEQUENCE: 416
tgctaaggtt ggtcatgggg tatttgagag gttacggaaa gacgctttgc ccctcttcct    60
g                                                                    61

<210> SEQ ID NO 417
<211> LENGTH: 61
<212> TYPE: DNA
<213> ORGANISM: Homo sapiens

<400> SEQUENCE: 417
aaaaggaaat tgctttgctc ttaggtaagc atgaccgcct tatccttacc cctaactgct    60
t                                                                    61
```

<210> SEQ ID NO 418
<211> LENGTH: 61
<212> TYPE: DNA
<213> ORGANISM: Homo sapiens

<400> SEQUENCE: 418
aaaaggaaat tgctttgctc ttaggtaagc gtgaccgcct tatccttacc cctaactgct    60
t    61

<210> SEQ ID NO 419
<211> LENGTH: 61
<212> TYPE: DNA
<213> ORGANISM: Homo sapiens

<400> SEQUENCE: 419
acagtggaga cttcgtgctc agagaagaga agggaagttt tcttggtccg ccctagtgtt    60
t    61

<210> SEQ ID NO 420
<211> LENGTH: 61
<212> TYPE: DNA
<213> ORGANISM: Homo sapiens

<400> SEQUENCE: 420
acagtggaga cttcgtgctc agagaagaga cgggaagttt tcttggtccg ccctagtgtt    60
t    61

<210> SEQ ID NO 421
<211> LENGTH: 61
<212> TYPE: DNA
<213> ORGANISM: Homo sapiens

<400> SEQUENCE: 421
aatgaatttt aggaactggg tctccagcct aacaaccttt gattcttttt aatttcagat    60
a    61

<210> SEQ ID NO 422
<211> LENGTH: 61
<212> TYPE: DNA
<213> ORGANISM: Homo sapiens

<400> SEQUENCE: 422
aatgaatttt aggaactggg tctccagcct gacaaccttt gattcttttt aatttcagat    60
a    61

<210> SEQ ID NO 423
<211> LENGTH: 61
<212> TYPE: DNA
<213> ORGANISM: Homo sapiens

<400> SEQUENCE: 423
taactgtatt ctaacctgtt tctctagcca attgaaatgt ttaacccatg tatatttgaa    60
a    61

<210> SEQ ID NO 424
<211> LENGTH: 61
<212> TYPE: DNA
<213> ORGANISM: Homo sapiens

<400> SEQUENCE: 424

```
taactgtatt ctaacctgtt tctctagcca gttgaaatgt ttaacccatg tatatttgaa    60
a                                                                   61

<210> SEQ ID NO 425
<211> LENGTH: 61
<212> TYPE: DNA
<213> ORGANISM: Homo sapiens

<400> SEQUENCE: 425
tttacagatg agaagactat ggcttaagga aattatgtaa cttgtctgag gtaatacaga    60
g                                                                   61

<210> SEQ ID NO 426
<211> LENGTH: 61
<212> TYPE: DNA
<213> ORGANISM: Homo sapiens

<400> SEQUENCE: 426
tttacagatg agaagactat ggcttaagga gattatgtaa cttgtctgag gtaatacaga    60
g                                                                   61

<210> SEQ ID NO 427
<211> LENGTH: 61
<212> TYPE: DNA
<213> ORGANISM: Homo sapiens

<400> SEQUENCE: 427
aatagtcacc accctaggga catctgagaa actacattca ctgaggtcca gtgatctgtt    60
t                                                                   61

<210> SEQ ID NO 428
<211> LENGTH: 61
<212> TYPE: DNA
<213> ORGANISM: Homo sapiens

<400> SEQUENCE: 428
aatagtcacc accctaggga catctgagaa cctacattca ctgaggtcca gtgatctgtt    60
t                                                                   61

<210> SEQ ID NO 429
<211> LENGTH: 61
<212> TYPE: DNA
<213> ORGANISM: Homo sapiens

<400> SEQUENCE: 429
gaaacctgtc acgaacttgt gatatacgtt accgtcaaac aagaatattc tagattttag    60
a                                                                   61

<210> SEQ ID NO 430
<211> LENGTH: 61
<212> TYPE: DNA
<213> ORGANISM: Homo sapiens

<400> SEQUENCE: 430
gaaacctgtc acgaacttgt gatatacgtt gccgtcaaac aagaatattc tagattttag    60
a                                                                   61

<210> SEQ ID NO 431
<211> LENGTH: 61
```

```
<212> TYPE: DNA
<213> ORGANISM: Homo sapiens

<400> SEQUENCE: 431
ttagaacctg taactattac tttacatgac aaaagagact gtgcagatgt aattaaggta     60
a                                                                    61

<210> SEQ ID NO 432
<211> LENGTH: 61
<212> TYPE: DNA
<213> ORGANISM: Homo sapiens

<400> SEQUENCE: 432
ttagaacctg taactattac tttacatgac gaaagagact gtgcagatgt aattaaggta     60
a                                                                    61

<210> SEQ ID NO 433
<211> LENGTH: 61
<212> TYPE: DNA
<213> ORGANISM: Homo sapiens

<400> SEQUENCE: 433
ctgatggtgc aactttgggc aagtcagcaa acttcagggc tcagttttct cacctgtaaa     60
g                                                                    61

<210> SEQ ID NO 434
<211> LENGTH: 61
<212> TYPE: DNA
<213> ORGANISM: Homo sapiens

<400> SEQUENCE: 434
ctgatggtgc aactttgggc aagtcagcaa ccttcagggc tcagttttct cacctgtaaa     60
g                                                                    61

<210> SEQ ID NO 435
<211> LENGTH: 61
<212> TYPE: DNA
<213> ORGANISM: Homo sapiens

<400> SEQUENCE: 435
gaaaacttgt tatatatgca aacttcagtt agtaagagtc cgttaaactg gaaataggat     60
g                                                                    61

<210> SEQ ID NO 436
<211> LENGTH: 61
<212> TYPE: DNA
<213> ORGANISM: Homo sapiens

<400> SEQUENCE: 436
gaaaacttgt tatatatgca aacttcagtt cgtaagagtc cgttaaactg gaaataggat     60
g                                                                    61

<210> SEQ ID NO 437
<211> LENGTH: 61
<212> TYPE: DNA
<213> ORGANISM: Homo sapiens

<400> SEQUENCE: 437
tgcattcagt taaagaccc aaactctgac aaaaatggaa ctggtattag gaaccacatc      60
a                                                                    61
```

<210> SEQ ID NO 438
<211> LENGTH: 61
<212> TYPE: DNA
<213> ORGANISM: Homo sapiens

<400> SEQUENCE: 438
tgcattcagt taaaagaccc aaactctgac caaaatggaa ctggtattag gaaccacatc    60
a                                                                    61

<210> SEQ ID NO 439
<211> LENGTH: 61
<212> TYPE: DNA
<213> ORGANISM: Homo sapiens

<400> SEQUENCE: 439
tcttttgcat tttactttt ttcccttaca atatatcctg gaaatcaatc catgtcagtt    60
c                                                                    61

<210> SEQ ID NO 440
<211> LENGTH: 61
<212> TYPE: DNA
<213> ORGANISM: Homo sapiens

<400> SEQUENCE: 440
tcttttgcat tttactttt ttcccttaca gtatatcctg gaaatcaatc catgtcagtt    60
c                                                                    61

<210> SEQ ID NO 441
<211> LENGTH: 61
<212> TYPE: DNA
<213> ORGANISM: Homo sapiens

<400> SEQUENCE: 441
ctgcttggtg gtgtcctctc tccaaacttc acaattgcca ggggtcagag ggagaaggga    60
t                                                                    61

<210> SEQ ID NO 442
<211> LENGTH: 61
<212> TYPE: DNA
<213> ORGANISM: Homo sapiens

<400> SEQUENCE: 442
ctgcttggtg gtgtcctctc tccaaacttc gcaattgcca ggggtcagag ggagaaggga    60
t                                                                    61

<210> SEQ ID NO 443
<211> LENGTH: 61
<212> TYPE: DNA
<213> ORGANISM: Homo sapiens

<400> SEQUENCE: 443
ggcatgttgc ctttcctccc ctccatatca actggtcagc atggagagat ggggctgaga    60
c                                                                    61

<210> SEQ ID NO 444
<211> LENGTH: 61
<212> TYPE: DNA
<213> ORGANISM: Homo sapiens

<400> SEQUENCE: 444

-continued ggcatgttgc ctttcctccc ctccatatca gctggtcagc atggagagat ggggctgaga    60
c                                                                   61

<210> SEQ ID NO 445
<211> LENGTH: 61
<212> TYPE: DNA
<213> ORGANISM: Homo sapiens

<400> SEQUENCE: 445
agatgggtcc taaagcacat tgcattcaac ataaatgaaa aaatagaaac ctagactgta    60
g                                                                   61

<210> SEQ ID NO 446
<211> LENGTH: 61
<212> TYPE: DNA
<213> ORGANISM: Homo sapiens

<400> SEQUENCE: 446
agatgggtcc taaagcacat tgcattcaac gtaaatgaaa aaatagaaac ctagactgta    60
g                                                                   61

<210> SEQ ID NO 447
<211> LENGTH: 61
<212> TYPE: DNA
<213> ORGANISM: Homo sapiens

<400> SEQUENCE: 447
attactcgaa taggccagat gattgaaaag attatttaga tagaactatc tcatgactta    60
c                                                                   61

<210> SEQ ID NO 448
<211> LENGTH: 61
<212> TYPE: DNA
<213> ORGANISM: Homo sapiens

<400> SEQUENCE: 448
attactcgaa taggccagat gattgaaaag gttatttaga tagaactatc tcatgactta    60
c                                                                   61

<210> SEQ ID NO 449
<211> LENGTH: 61
<212> TYPE: DNA
<213> ORGANISM: Homo sapiens

<400> SEQUENCE: 449
aggacccttt gtgtccacag tgctgacaca atattatgca gaaagtagga ataaaatgca    60
c                                                                   61

<210> SEQ ID NO 450
<211> LENGTH: 61
<212> TYPE: DNA
<213> ORGANISM: Homo sapiens

<400> SEQUENCE: 450
aggacccttt gtgtccacag tgctgacaca gtattatgca gaaagtagga ataaaatgca    60
c                                                                   61

<210> SEQ ID NO 451
<211> LENGTH: 61

```
<212> TYPE: DNA
<213> ORGANISM: Homo sapiens

<400> SEQUENCE: 451
cctcagagga agggtgaccg aaggagagct agagaaacgg aaagagaatg agaacagaga      60
g                                                                     61

<210> SEQ ID NO 452
<211> LENGTH: 61
<212> TYPE: DNA
<213> ORGANISM: Homo sapiens

<400> SEQUENCE: 452
cctcagagga agggtgaccg aaggagagct cgagaaacgg aaagagaatg agaacagaga      60
g                                                                     61

<210> SEQ ID NO 453
<211> LENGTH: 61
<212> TYPE: DNA
<213> ORGANISM: Homo sapiens

<400> SEQUENCE: 453
taaattagta aataaataca gaacttgaac aaattatcaa ctaccttggc taatatttat      60
a                                                                     61

<210> SEQ ID NO 454
<211> LENGTH: 61
<212> TYPE: DNA
<213> ORGANISM: Homo sapiens

<400> SEQUENCE: 454
taaattagta aataaataca gaacttgaac caattatcaa ctaccttggc taatatttat      60
a                                                                     61

<210> SEQ ID NO 455
<211> LENGTH: 61
<212> TYPE: DNA
<213> ORGANISM: Homo sapiens

<400> SEQUENCE: 455
tgaggtgatc aagagtttgc tagcacaaga aatgaaggta tgtcatctta tttcccttga      60
t                                                                     61

<210> SEQ ID NO 456
<211> LENGTH: 61
<212> TYPE: DNA
<213> ORGANISM: Homo sapiens

<400> SEQUENCE: 456
tgaggtgatc aagagtttgc tagcacaaga gatgaaggta tgtcatctta tttcccttga      60
t                                                                     61

<210> SEQ ID NO 457
<211> LENGTH: 61
<212> TYPE: DNA
<213> ORGANISM: Homo sapiens

<400> SEQUENCE: 457
aaacaaatgc atgtctccta aatacccata acaggcatta atcggccaga gttccagaag      60
t                                                                     61
```

```
<210> SEQ ID NO 458
<211> LENGTH: 61
<212> TYPE: DNA
<213> ORGANISM: Homo sapiens

<400> SEQUENCE: 458
aaacaaatgc atgtctccta aatacccata ccaggcatta atcggccaga gttccagaag      60
t                                                                      61

<210> SEQ ID NO 459
<211> LENGTH: 61
<212> TYPE: DNA
<213> ORGANISM: Homo sapiens

<400> SEQUENCE: 459
ctaaatcgca taacaagagt tatcttctta aacccaccaa cattatcaag aaggtagtaa      60
t                                                                      61

<210> SEQ ID NO 460
<211> LENGTH: 61
<212> TYPE: DNA
<213> ORGANISM: Homo sapiens

<400> SEQUENCE: 460
ctaaatcgca taacaagagt tatcttctta tacccaccaa cattatcaag aaggtagtaa      60
t                                                                      61

<210> SEQ ID NO 461
<211> LENGTH: 61
<212> TYPE: DNA
<213> ORGANISM: Homo sapiens

<400> SEQUENCE: 461
gaactgcatt ccagtaaaac tttaagtaaa agtgcccttg gccaggcgcg ttggctcacg      60
c                                                                      61

<210> SEQ ID NO 462
<211> LENGTH: 61
<212> TYPE: DNA
<213> ORGANISM: Homo sapiens

<400> SEQUENCE: 462
gaactgcatt ccagtaaaac tttaagtaaa ggtgcccttg gccaggcgcg ttggctcacg      60
c                                                                      61

<210> SEQ ID NO 463
<211> LENGTH: 61
<212> TYPE: DNA
<213> ORGANISM: Homo sapiens

<400> SEQUENCE: 463
ttttctgttg agagggatga gtctgaaggc acatgattgg gataaagaaa aggcaggagg      60
g                                                                      61

<210> SEQ ID NO 464
<211> LENGTH: 61
<212> TYPE: DNA
<213> ORGANISM: Homo sapiens

<400> SEQUENCE: 464
```

```
ttttctgttg agagggatga gtctgaaggc gcatgattgg gataaagaaa aggcaggagg    60
g                                                                   61

<210> SEQ ID NO 465
<211> LENGTH: 61
<212> TYPE: DNA
<213> ORGANISM: Homo sapiens

<400> SEQUENCE: 465
cggtgcacgg ggcacagggc agcctctgag aacacatggg ccggtgctac cgcagagggg    60
c                                                                   61

<210> SEQ ID NO 466
<211> LENGTH: 61
<212> TYPE: DNA
<213> ORGANISM: Homo sapiens

<400> SEQUENCE: 466
cggtgcacgg ggcacagggc agcctctgag gacacatggg ccggtgctac cgcagagggg    60
c                                                                   61

<210> SEQ ID NO 467
<211> LENGTH: 61
<212> TYPE: DNA
<213> ORGANISM: Homo sapiens

<400> SEQUENCE: 467
gtatctctgc ctttagagaa ttcactatgc attactttag acaataggtc atcgataaga    60
t                                                                   61

<210> SEQ ID NO 468
<211> LENGTH: 61
<212> TYPE: DNA
<213> ORGANISM: Homo sapiens

<400> SEQUENCE: 468
gtatctctgc ctttagagaa ttcactatgc gttactttag acaataggtc atcgataaga    60
t                                                                   61

<210> SEQ ID NO 469
<211> LENGTH: 61
<212> TYPE: DNA
<213> ORGANISM: Homo sapiens

<400> SEQUENCE: 469
aattggttgt aataggaaga ttacaggtta atgacttaga aaatcttcct caaacgagaa    60
t                                                                   61

<210> SEQ ID NO 470
<211> LENGTH: 61
<212> TYPE: DNA
<213> ORGANISM: Homo sapiens

<400> SEQUENCE: 470
aattggttgt aataggaaga ttacaggtta gtgacttaga aaatcttcct caaacgagaa    60
t                                                                   61

<210> SEQ ID NO 471
<211> LENGTH: 61
```

```
<212> TYPE: DNA
<213> ORGANISM: Homo sapiens

<400> SEQUENCE: 471
aagatttttg taaagtgtat ataggtacca cgatactatg ctgaattctt tttcttctat    60
t                                                                   61

<210> SEQ ID NO 472
<211> LENGTH: 61
<212> TYPE: DNA
<213> ORGANISM: Homo sapiens

<400> SEQUENCE: 472
aagatttttg taaagtgtat ataggtacca ggatactatg ctgaattctt tttcttctat    60
t                                                                   61

<210> SEQ ID NO 473
<211> LENGTH: 61
<212> TYPE: DNA
<213> ORGANISM: Homo sapiens

<400> SEQUENCE: 473
ctagctaaag gactaagaac ggggcagcct aacaaaatga aggcttttag acaataacca    60
c                                                                   61

<210> SEQ ID NO 474
<211> LENGTH: 61
<212> TYPE: DNA
<213> ORGANISM: Homo sapiens

<400> SEQUENCE: 474
ctagctaaag gactaagaac ggggcagcct cacaaaatga aggcttttag acaataacca    60
c                                                                   61

<210> SEQ ID NO 475
<211> LENGTH: 61
<212> TYPE: DNA
<213> ORGANISM: Homo sapiens

<400> SEQUENCE: 475
gtgacctcta ttggacaggg atgaaagccc agtctctcca tgaagttttc tgactccacc    60
c                                                                   61

<210> SEQ ID NO 476
<211> LENGTH: 61
<212> TYPE: DNA
<213> ORGANISM: Homo sapiens

<400> SEQUENCE: 476
gtgacctcta ttggacaggg atgaaagccc ggtctctcca tgaagttttc tgactccacc    60
c                                                                   61

<210> SEQ ID NO 477
<211> LENGTH: 61
<212> TYPE: DNA
<213> ORGANISM: Homo sapiens

<400> SEQUENCE: 477
tcaataattt aaaaatgggc ttgatatgtg cccactgaaa acaaatccta cccactttgg    60
t                                                                   61
```

<210> SEQ ID NO 478
<211> LENGTH: 61
<212> TYPE: DNA
<213> ORGANISM: Homo sapiens

<400> SEQUENCE: 478
tcaataattt aaaaatgggc ttgatatgtg gccactgaaa acaaatccta cccactttgg    60
t                                                                  61

<210> SEQ ID NO 479
<211> LENGTH: 61
<212> TYPE: DNA
<213> ORGANISM: Homo sapiens

<400> SEQUENCE: 479
agttcactga ttcttagttg tgttgagtcc actgatgaac ccatgataac attctttatc    60
t                                                                  61

<210> SEQ ID NO 480
<211> LENGTH: 61
<212> TYPE: DNA
<213> ORGANISM: Homo sapiens

<400> SEQUENCE: 480
agttcactga ttcttagttg tgttgagtcc gctgatgaac ccatgataac attctttatc    60
t                                                                  61

<210> SEQ ID NO 481
<211> LENGTH: 61
<212> TYPE: DNA
<213> ORGANISM: Homo sapiens

<400> SEQUENCE: 481
acagacagag cagctgtgtt gatcacctag aaagtacaaa ctaaatgtgg atcatgggat    60
t                                                                  61

<210> SEQ ID NO 482
<211> LENGTH: 61
<212> TYPE: DNA
<213> ORGANISM: Homo sapiens

<400> SEQUENCE: 482
acagacagag cagctgtgtt gatcacctag gaagtacaaa ctaaatgtgg atcatgggat    60
t                                                                  61

<210> SEQ ID NO 483
<211> LENGTH: 61
<212> TYPE: DNA
<213> ORGANISM: Homo sapiens

<400> SEQUENCE: 483
tcagagatgt acttatttcc tggaagatca agttgcaact gtcagttaac ctataaggat    60
c                                                                  61

<210> SEQ ID NO 484
<211> LENGTH: 61
<212> TYPE: DNA
<213> ORGANISM: Homo sapiens

<400> SEQUENCE: 484

```
tcagagatgt acttatttcc tggaagatca cgttgcaact gtcagttaac ctataaggat    60
c                                                                   61

<210> SEQ ID NO 485
<211> LENGTH: 61
<212> TYPE: DNA
<213> ORGANISM: Homo sapiens

<400> SEQUENCE: 485
ctttatagct agtgtagctg cttcttaaaa caggtgtttc aaacaacgga agggagagcc    60
a                                                                   61

<210> SEQ ID NO 486
<211> LENGTH: 61
<212> TYPE: DNA
<213> ORGANISM: Homo sapiens

<400> SEQUENCE: 486
ctttatagct agtgtagctg cttcttaaaa gaggtgtttc aaacaacgga agggagagcc    60
a                                                                   61

<210> SEQ ID NO 487
<211> LENGTH: 61
<212> TYPE: DNA
<213> ORGANISM: Homo sapiens

<400> SEQUENCE: 487
tttacatttt atccatttat aatcagaatc atggcaatcc aaatgtttac ttttaatatg    60
a                                                                   61

<210> SEQ ID NO 488
<211> LENGTH: 61
<212> TYPE: DNA
<213> ORGANISM: Homo sapiens

<400> SEQUENCE: 488
tttacatttt atccatttat aatcagaatc gtggcaatcc aaatgtttac ttttaatatg    60
a                                                                   61

<210> SEQ ID NO 489
<211> LENGTH: 61
<212> TYPE: DNA
<213> ORGANISM: Homo sapiens

<400> SEQUENCE: 489
tccttcacta gacctcaagt tcaaccagac agcacatgct accccttacc tgtgtgtagg    60
g                                                                   61

<210> SEQ ID NO 490
<211> LENGTH: 61
<212> TYPE: DNA
<213> ORGANISM: Homo sapiens

<400> SEQUENCE: 490
tccttcacta gacctcaagt tcaaccagac ggcacatgct accccttacc tgtgtgtagg    60
g                                                                   61

<210> SEQ ID NO 491
<211> LENGTH: 61
```

```
<212> TYPE: DNA
<213> ORGANISM: Homo sapiens

<400> SEQUENCE: 491
ccatttcttc ccacagcaca ctgttcttcc attctagtac ttacagccct tgatcagaac    60
g                                                                    61

<210> SEQ ID NO 492
<211> LENGTH: 61
<212> TYPE: DNA
<213> ORGANISM: Homo sapiens

<400> SEQUENCE: 492
ccatttcttc ccacagcaca ctgttcttcc gttctagtac ttacagccct tgatcagaac    60
g                                                                    61

<210> SEQ ID NO 493
<211> LENGTH: 61
<212> TYPE: DNA
<213> ORGANISM: Homo sapiens

<400> SEQUENCE: 493
aaaattttag tctcattttt ataaatgcca ataattcaga gaaagtatct tgcagtaaca    60
c                                                                    61

<210> SEQ ID NO 494
<211> LENGTH: 61
<212> TYPE: DNA
<213> ORGANISM: Homo sapiens

<400> SEQUENCE: 494
aaaattttag tctcattttt ataaatgcca gtaattcaga gaaagtatct tgcagtaaca    60
c                                                                    61

<210> SEQ ID NO 495
<211> LENGTH: 61
<212> TYPE: DNA
<213> ORGANISM: Homo sapiens

<400> SEQUENCE: 495
ataagacatt tagaaatttg gcacctcttt actcttattc tgtaatgtag gatattttg     60
c                                                                    61

<210> SEQ ID NO 496
<211> LENGTH: 61
<212> TYPE: DNA
<213> ORGANISM: Homo sapiens

<400> SEQUENCE: 496
ataagacatt tagaaatttg gcacctcttt gctcttattc tgtaatgtag gatattttg     60
c                                                                    61

<210> SEQ ID NO 497
<211> LENGTH: 61
<212> TYPE: DNA
<213> ORGANISM: Homo sapiens

<400> SEQUENCE: 497
aatatgtttt caattcttag gtgcggatag aagtagaatt gtgggctcat atggtgctgt    60
g                                                                    61
```

<210> SEQ ID NO 498
<211> LENGTH: 61
<212> TYPE: DNA
<213> ORGANISM: Homo sapiens

<400> SEQUENCE: 498
aatatgtttt caattcttag gtgcggatag gagtagaatt gtgggctcat atggtgctgt    60
g                                                                  61

<210> SEQ ID NO 499
<211> LENGTH: 61
<212> TYPE: DNA
<213> ORGANISM: Homo sapiens

<400> SEQUENCE: 499
accagtcggt tttctacact gctttatttc atggtatcaa atctgtatt agttgaaatg    60
c                                                                  61

<210> SEQ ID NO 500
<211> LENGTH: 61
<212> TYPE: DNA
<213> ORGANISM: Homo sapiens

<400> SEQUENCE: 500
accagtcggt tttctacact gctttatttc ctggtatcaa atctgtatt agttgaaatg    60
c                                                                  61

<210> SEQ ID NO 501
<211> LENGTH: 61
<212> TYPE: DNA
<213> ORGANISM: Homo sapiens

<400> SEQUENCE: 501
gctttgatgt ctaccaacta attgagctac cccaacagga ggcattcctt ccttcatcag    60
t                                                                   61

<210> SEQ ID NO 502
<211> LENGTH: 61
<212> TYPE: DNA
<213> ORGANISM: Homo sapiens

<400> SEQUENCE: 502
gctttgatgt ctaccaacta attgagctac gccaacagga ggcattcctt ccttcatcag    60
t                                                                   61

<210> SEQ ID NO 503
<211> LENGTH: 61
<212> TYPE: DNA
<213> ORGANISM: Homo sapiens

<400> SEQUENCE: 503
gttctttgtg tcactgactt tggtcaatac aaatgcagac aattcatcca tgctgtgtca    60
t                                                                   61

<210> SEQ ID NO 504
<211> LENGTH: 61
<212> TYPE: DNA
<213> ORGANISM: Homo sapiens

<400> SEQUENCE: 504

```
gttctttgtg tcactgactt tggtcaatac caatgcagac aattcatcca tgctgtgtca    60
t                                                                    61
```

<210> SEQ ID NO 505
<211> LENGTH: 61
<212> TYPE: DNA
<213> ORGANISM: Homo sapiens

<400> SEQUENCE: 505

```
gtcatccgtc caggtcccat aggcgtaagt agtgccaacc caggtccact ggaccccaga    60
t                                                                    61
```

<210> SEQ ID NO 506
<211> LENGTH: 61
<212> TYPE: DNA
<213> ORGANISM: Homo sapiens

<400> SEQUENCE: 506

```
gtcatccgtc caggtcccat aggcgtaagt ggtgccaacc caggtccact ggaccccaga    60
t                                                                    61
```

<210> SEQ ID NO 507
<211> LENGTH: 61
<212> TYPE: DNA
<213> ORGANISM: Homo sapiens

<400> SEQUENCE: 507

```
cccttctcat ttaagagggg aaatggagct atagtagtcg aaagagaccc tcaagttaaa    60
a                                                                    61
```

<210> SEQ ID NO 508
<211> LENGTH: 61
<212> TYPE: DNA
<213> ORGANISM: Homo sapiens

<400> SEQUENCE: 508

```
cccttctcat ttaagagggg aaatggagct gtagtagtcg aaagagaccc tcaagttaaa    60
a                                                                    61
```

<210> SEQ ID NO 509
<211> LENGTH: 61
<212> TYPE: DNA
<213> ORGANISM: Homo sapiens

<400> SEQUENCE: 509

```
cttcattgtc tccaaagtgc tagagtgcat acaataaata cttgatgatt gatattctga    60
g                                                                    61
```

<210> SEQ ID NO 510
<211> LENGTH: 61
<212> TYPE: DNA
<213> ORGANISM: Homo sapiens

<400> SEQUENCE: 510

```
cttcattgtc tccaaagtgc tagagtgcat tcaataaata cttgatgatt gatattctga    60
g                                                                    61
```

<210> SEQ ID NO 511
<211> LENGTH: 61

```
<212> TYPE: DNA
<213> ORGANISM: Homo sapiens

<400> SEQUENCE: 511
ggactggtaa gagtctcaca ctgtccttaa actgtacaac catgtggttt atgctgaaca    60
g                                                                  61

<210> SEQ ID NO 512
<211> LENGTH: 61
<212> TYPE: DNA
<213> ORGANISM: Homo sapiens

<400> SEQUENCE: 512
ggactggtaa gagtctcaca ctgtccttaa gctgtacaac catgtggttt atgctgaaca    60
g                                                                  61

<210> SEQ ID NO 513
<211> LENGTH: 61
<212> TYPE: DNA
<213> ORGANISM: Homo sapiens

<400> SEQUENCE: 513
cccttggctt attttgcttt gcatctttga accataataa atcatagcca tgagtacaac    60
t                                                                  61

<210> SEQ ID NO 514
<211> LENGTH: 61
<212> TYPE: DNA
<213> ORGANISM: Homo sapiens

<400> SEQUENCE: 514
cccttggctt attttgcttt gcatctttga gccataataa atcatagcca tgagtacaac    60
t                                                                  61

<210> SEQ ID NO 515
<211> LENGTH: 61
<212> TYPE: DNA
<213> ORGANISM: Homo sapiens

<400> SEQUENCE: 515
gggtgctgac atatggaagt gttttgaca atccacgttg tgaaggtcag gaggtttgct    60
a                                                                  61

<210> SEQ ID NO 516
<211> LENGTH: 61
<212> TYPE: DNA
<213> ORGANISM: Homo sapiens

<400> SEQUENCE: 516
gggtgctgac atatggaagt gttttgaca gtccacgttg tgaaggtcag gaggtttgct    60
a                                                                  61

<210> SEQ ID NO 517
<211> LENGTH: 61
<212> TYPE: DNA
<213> ORGANISM: Homo sapiens

<400> SEQUENCE: 517
ggcatcagct gagagccacc ttgtaagtgg atctttcaaa ggataacagt caggcttgct    60
a                                                                  61
```

<210> SEQ ID NO 518
<211> LENGTH: 61
<212> TYPE: DNA
<213> ORGANISM: Homo sapiens

<400> SEQUENCE: 518
ggcatcagct gagagccacc ttgtaagtgg gtctttcaaa ggataacagt caggcttgct    60
a                                                                   61

<210> SEQ ID NO 519
<211> LENGTH: 61
<212> TYPE: DNA
<213> ORGANISM: Homo sapiens

<400> SEQUENCE: 519
tgattactca ggattctaca gttcaactgc atggttcttc tgcttttagc tgggctcctt    60
c                                                                   61

<210> SEQ ID NO 520
<211> LENGTH: 61
<212> TYPE: DNA
<213> ORGANISM: Homo sapiens

<400> SEQUENCE: 520
tgattactca ggattctaca gttcaactgc gtggttcttc tgcttttagc tgggctcctt    60
c                                                                   61

<210> SEQ ID NO 521
<211> LENGTH: 61
<212> TYPE: DNA
<213> ORGANISM: Homo sapiens

<400> SEQUENCE: 521
actagtaaat ctgagtcttc atgaataggg acataattta atacattgga gtatacaatt    60
a                                                                   61

<210> SEQ ID NO 522
<211> LENGTH: 61
<212> TYPE: DNA
<213> ORGANISM: Homo sapiens

<400> SEQUENCE: 522
actagtaaat ctgagtcttc atgaataggg gcataattta atacattgga gtatacaatt    60
a                                                                   61

<210> SEQ ID NO 523
<211> LENGTH: 61
<212> TYPE: DNA
<213> ORGANISM: Homo sapiens

<400> SEQUENCE: 523
gtccccacat atctaagttt taggagttca actgaaaatt gtgctaaact ttttgaaaag    60
t                                                                   61

<210> SEQ ID NO 524
<211> LENGTH: 61
<212> TYPE: DNA
<213> ORGANISM: Homo sapiens

<400> SEQUENCE: 524

```
gtccccacat atctaagttt taggagttca cctgaaaatt gtgctaaact ttttgaaaag    60
t                                                                    61

<210> SEQ ID NO 525
<211> LENGTH: 61
<212> TYPE: DNA
<213> ORGANISM: Homo sapiens

<400> SEQUENCE: 525
ggcagcaatg tgggctccag tgattgattt aatgaagact gtgtagaaga ggaataagga    60
a                                                                    61

<210> SEQ ID NO 526
<211> LENGTH: 61
<212> TYPE: DNA
<213> ORGANISM: Homo sapiens

<400> SEQUENCE: 526
ggcagcaatg tgggctccag tgattgattt catgaagact gtgtagaaga ggaataagga    60
a                                                                    61

<210> SEQ ID NO 527
<211> LENGTH: 61
<212> TYPE: DNA
<213> ORGANISM: Homo sapiens

<400> SEQUENCE: 527
cacccatact aaagagggca attgaaactc actccattct tttcaaaccc ccaaatctgt    60
c                                                                    61

<210> SEQ ID NO 528
<211> LENGTH: 61
<212> TYPE: DNA
<213> ORGANISM: Homo sapiens

<400> SEQUENCE: 528
cacccatact aaagagggca attgaaactc gctccattct tttcaaaccc ccaaatctgt    60
c                                                                    61

<210> SEQ ID NO 529
<211> LENGTH: 61
<212> TYPE: DNA
<213> ORGANISM: Homo sapiens

<400> SEQUENCE: 529
atatacacat taaagtttgt ttgagaatta ctgcattaga gaaaaattaa ttctagagct    60
t                                                                    61

<210> SEQ ID NO 530
<211> LENGTH: 61
<212> TYPE: DNA
<213> ORGANISM: Homo sapiens

<400> SEQUENCE: 530
atatacacat taaagtttgt ttgagaatta gtgcattaga gaaaaattaa ttctagagct    60
t                                                                    61

<210> SEQ ID NO 531
<211> LENGTH: 61
```

```
<212> TYPE: DNA
<213> ORGANISM: Homo sapiens

<400> SEQUENCE: 531
ggaactagag tttctgagag caaggtgaga agattatgca tgaagacact gggctgtcat    60
c                                                                    61

<210> SEQ ID NO 532
<211> LENGTH: 61
<212> TYPE: DNA
<213> ORGANISM: Homo sapiens

<400> SEQUENCE: 532
ggaactagag tttctgagag caaggtgaga ggattatgca tgaagacact gggctgtcat    60
c                                                                    61

<210> SEQ ID NO 533
<211> LENGTH: 61
<212> TYPE: DNA
<213> ORGANISM: Homo sapiens

<400> SEQUENCE: 533
aaataggtat agaaaattct caatgaaatc aaatataccg ccactattaa taacttcaaa    60
g                                                                    61

<210> SEQ ID NO 534
<211> LENGTH: 61
<212> TYPE: DNA
<213> ORGANISM: Homo sapiens

<400> SEQUENCE: 534
aaataggtat agaaaattct caatgaaatc gaatataccg ccactattaa taacttcaaa    60
g                                                                    61

<210> SEQ ID NO 535
<211> LENGTH: 61
<212> TYPE: DNA
<213> ORGANISM: Homo sapiens

<400> SEQUENCE: 535
agcccagccc aaatgccaac tcacagagtc atgagctaca taaatggcta ttgttttaag    60
t                                                                    61

<210> SEQ ID NO 536
<211> LENGTH: 61
<212> TYPE: DNA
<213> ORGANISM: Homo sapiens

<400> SEQUENCE: 536
agcccagccc aaatgccaac tcacagagtc gtgagctaca taaatggcta ttgttttaag    60
t                                                                    61

<210> SEQ ID NO 537
<211> LENGTH: 61
<212> TYPE: DNA
<213> ORGANISM: Homo sapiens

<400> SEQUENCE: 537
agcagcacag aattgcaggt ggactcttta aagctattct gttctgctaa caaggagcaa    60
g                                                                    61
```

<210> SEQ ID NO 538
<211> LENGTH: 61
<212> TYPE: DNA
<213> ORGANISM: Homo sapiens

<400> SEQUENCE: 538
agcagcacag aattgcaggt ggactcttta cagctattct gttctgctaa caaggagcaa    60
g                                                                   61

<210> SEQ ID NO 539
<211> LENGTH: 61
<212> TYPE: DNA
<213> ORGANISM: Homo sapiens

<400> SEQUENCE: 539
acttcctttg cctttaccag aaagctttac atcactcaca gatcttgttc cagtgaggga    60
c                                                                   61

<210> SEQ ID NO 540
<211> LENGTH: 61
<212> TYPE: DNA
<213> ORGANISM: Homo sapiens

<400> SEQUENCE: 540
acttcctttg cctttaccag aaagctttac gtcactcaca gatcttgttc cagtgaggga    60
c                                                                   61

<210> SEQ ID NO 541
<211> LENGTH: 61
<212> TYPE: DNA
<213> ORGANISM: Homo sapiens

<400> SEQUENCE: 541
ctcccatgca ggccctgttc caagcatttt aggcagcata ctgactcatt caatcctcag    60
g                                                                   61

<210> SEQ ID NO 542
<211> LENGTH: 61
<212> TYPE: DNA
<213> ORGANISM: Homo sapiens

<400> SEQUENCE: 542
ctcccatgca ggccctgttc caagcatttt gggcagcata ctgactcatt caatcctcag    60
g                                                                   61

<210> SEQ ID NO 543
<211> LENGTH: 61
<212> TYPE: DNA
<213> ORGANISM: Homo sapiens

<400> SEQUENCE: 543
agtccattaa aggtgttgtg tatctaatct atggtgtact ttctcttctc atagagtttt    60
t                                                                   61

<210> SEQ ID NO 544
<211> LENGTH: 61
<212> TYPE: DNA
<213> ORGANISM: Homo sapiens

<400> SEQUENCE: 544

```
agtccattaa aggtgttgtg tatctaatct gtggtgtact ttctcttctc atagagtttt    60
t                                                                   61

<210> SEQ ID NO 545
<211> LENGTH: 61
<212> TYPE: DNA
<213> ORGANISM: Homo sapiens

<400> SEQUENCE: 545
ttttaggtca tatttgtaaa gattgcctac atagctgtca gattcccacc tacaaaataa    60
a                                                                   61

<210> SEQ ID NO 546
<211> LENGTH: 61
<212> TYPE: DNA
<213> ORGANISM: Homo sapiens

<400> SEQUENCE: 546
ttttaggtca tatttgtaaa gattgcctac gtagctgtca gattcccacc tacaaaataa    60
a                                                                   61

<210> SEQ ID NO 547
<211> LENGTH: 61
<212> TYPE: DNA
<213> ORGANISM: Homo sapiens

<400> SEQUENCE: 547
aaaattaaaa caaaaaacca acaacctgga atctgagaaa caacttccaa tcataaatga    60
a                                                                   61

<210> SEQ ID NO 548
<211> LENGTH: 61
<212> TYPE: DNA
<213> ORGANISM: Homo sapiens

<400> SEQUENCE: 548
aaaattaaaa caaaaaacca acaacctgga gtctgagaaa caacttccaa tcataaatga    60
a                                                                   61

<210> SEQ ID NO 549
<211> LENGTH: 61
<212> TYPE: DNA
<213> ORGANISM: Homo sapiens

<400> SEQUENCE: 549
aaggtgattc taggtactta attctcacac atgtggtttg ttatagtaca tttcctaatt    60
t                                                                   61

<210> SEQ ID NO 550
<211> LENGTH: 61
<212> TYPE: DNA
<213> ORGANISM: Homo sapiens

<400> SEQUENCE: 550
aaggtgattc taggtactta attctcacac gtgtggtttg ttatagtaca tttcctaatt    60
t                                                                   61

<210> SEQ ID NO 551
<211> LENGTH: 61
```

```
<212> TYPE: DNA
<213> ORGANISM: Homo sapiens

<400> SEQUENCE: 551
accttaatca gaaatttcca gtttccaaaa attgtattat actcaggttg gccctaggtt    60
t                                                                    61

<210> SEQ ID NO 552
<211> LENGTH: 61
<212> TYPE: DNA
<213> ORGANISM: Homo sapiens

<400> SEQUENCE: 552
accttaatca gaaatttcca gtttccaaaa gttgtattat actcaggttg gccctaggtt    60
t                                                                    61

<210> SEQ ID NO 553
<211> LENGTH: 61
<212> TYPE: DNA
<213> ORGANISM: Homo sapiens

<400> SEQUENCE: 553
gaaattgtca ttacattaat atgcttaatc agttttttgta attaatttct attcaatttt   60
a                                                                    61

<210> SEQ ID NO 554
<211> LENGTH: 61
<212> TYPE: DNA
<213> ORGANISM: Homo sapiens

<400> SEQUENCE: 554
gaaattgtca ttacattaat atgcttaatc ggttttgta attaatttct attcaatttt     60
a                                                                    61

<210> SEQ ID NO 555
<211> LENGTH: 61
<212> TYPE: DNA
<213> ORGANISM: Homo sapiens

<400> SEQUENCE: 555
ttgctaatat acttactaaa atcagcacta agccgtatat taaagcaaaa taacattagt    60
t                                                                    61

<210> SEQ ID NO 556
<211> LENGTH: 61
<212> TYPE: DNA
<213> ORGANISM: Homo sapiens

<400> SEQUENCE: 556
ttgctaatat acttactaaa atcagcacta ggccgtatat taaagcaaaa taacattagt    60
t                                                                    61

<210> SEQ ID NO 557
<211> LENGTH: 61
<212> TYPE: DNA
<213> ORGANISM: Homo sapiens

<400> SEQUENCE: 557
cagctaagtc accagatctg taatgaaga agtcaccttg gatgtccagt tccataaact     60
c                                                                    61
```

<210> SEQ ID NO 558
<211> LENGTH: 61
<212> TYPE: DNA
<213> ORGANISM: Homo sapiens

<400> SEQUENCE: 558
cagctaagtc accagatctg taaatgaaga tgtcaccttg gatgtccagt tccataaact    60
c                                                                   61

<210> SEQ ID NO 559
<211> LENGTH: 61
<212> TYPE: DNA
<213> ORGANISM: Homo sapiens

<400> SEQUENCE: 559
cttatgcctc ttgtctaatt actgtgacta atccccccat cacaatgtta caaagtagtg    60
a                                                                   61

<210> SEQ ID NO 560
<211> LENGTH: 61
<212> TYPE: DNA
<213> ORGANISM: Homo sapiens

<400> SEQUENCE: 560
cttatgcctc ttgtctaatt actgtgacta ctccccccat cacaatgtta caaagtagtg    60
a                                                                   61

<210> SEQ ID NO 561
<211> LENGTH: 61
<212> TYPE: DNA
<213> ORGANISM: Homo sapiens

<400> SEQUENCE: 561
gagaacaaag ccagagtccc aatatcaacc atccagaaat agagcatgca gcccaagatg    60
g                                                                   61

<210> SEQ ID NO 562
<211> LENGTH: 61
<212> TYPE: DNA
<213> ORGANISM: Homo sapiens

<400> SEQUENCE: 562
gagaacaaag ccagagtccc aatatcaacc gtccagaaat agagcatgca gcccaagatg    60
g                                                                   61

<210> SEQ ID NO 563
<211> LENGTH: 61
<212> TYPE: DNA
<213> ORGANISM: Homo sapiens

<400> SEQUENCE: 563
aagccagtga atgcttttaa ttgatgacct acttattctg atggtttata atattaaatg    60
a                                                                   61

<210> SEQ ID NO 564
<211> LENGTH: 61
<212> TYPE: DNA
<213> ORGANISM: Homo sapiens

<400> SEQUENCE: 564

```
aagccagtga atgctttta ttgatgacct gcttattctg atggtttata atattaaatg    60
a                                                                   61

<210> SEQ ID NO 565
<211> LENGTH: 61
<212> TYPE: DNA
<213> ORGANISM: Homo sapiens

<400> SEQUENCE: 565
aatcaaaacc acaatgagat aacatctcac atcggtcata atgactatta ttaatgtcaa    60
a                                                                   61

<210> SEQ ID NO 566
<211> LENGTH: 61
<212> TYPE: DNA
<213> ORGANISM: Homo sapiens

<400> SEQUENCE: 566
aatcaaaacc acaatgagat aacatctcac gtcggtcata atgactatta ttaatgtcaa    60
a                                                                   61

<210> SEQ ID NO 567
<211> LENGTH: 61
<212> TYPE: DNA
<213> ORGANISM: Homo sapiens

<400> SEQUENCE: 567
actcaatgtt tagttcccac ttataattga agacaagcag tatttggttt tctgttcact    60
t                                                                   61

<210> SEQ ID NO 568
<211> LENGTH: 61
<212> TYPE: DNA
<213> ORGANISM: Homo sapiens

<400> SEQUENCE: 568
actcaatgtt tagttcccac ttataattga ggacaagcag tatttggttt tctgttcact    60
t                                                                   61

<210> SEQ ID NO 569
<211> LENGTH: 61
<212> TYPE: DNA
<213> ORGANISM: Homo sapiens

<400> SEQUENCE: 569
acatacacac agtttgcagg agccaaagta cgcaaaaaga actctgctcc aaatagccaa    60
g                                                                   61

<210> SEQ ID NO 570
<211> LENGTH: 61
<212> TYPE: DNA
<213> ORGANISM: Homo sapiens

<400> SEQUENCE: 570
acatacacac agtttgcagg agccaaagta ggcaaaaaga actctgctcc aaatagccaa    60
g                                                                   61

<210> SEQ ID NO 571
<211> LENGTH: 61
```

```
<212> TYPE: DNA
<213> ORGANISM: Homo sapiens

<400> SEQUENCE: 571
ccattcaagt tcaccaaca gcctcataac attttttcag tcctgaaaga ctcctgctta    60
g                                                                  61

<210> SEQ ID NO 572
<211> LENGTH: 61
<212> TYPE: DNA
<213> ORGANISM: Homo sapiens

<400> SEQUENCE: 572
ccattcaagt tcaccaaca gcctcataac gttttttcag tcctgaaaga ctcctgctta    60
g                                                                  61

<210> SEQ ID NO 573
<211> LENGTH: 61
<212> TYPE: DNA
<213> ORGANISM: Homo sapiens

<400> SEQUENCE: 573
atgggagatg ggaaaaggcc taagatataa acctcaggaa cctcaatttt aagggtttgg    60
a                                                                   61

<210> SEQ ID NO 574
<211> LENGTH: 61
<212> TYPE: DNA
<213> ORGANISM: Homo sapiens

<400> SEQUENCE: 574
atgggagatg ggaaaaggcc taagatataa ccctcaggaa cctcaatttt aagggtttgg    60
a                                                                   61

<210> SEQ ID NO 575
<211> LENGTH: 61
<212> TYPE: DNA
<213> ORGANISM: Homo sapiens

<400> SEQUENCE: 575
gtttagaagg tggaatgaac acagatcatt aactgaacat tggaggtggg gaaagaggag    60
a                                                                   61

<210> SEQ ID NO 576
<211> LENGTH: 61
<212> TYPE: DNA
<213> ORGANISM: Homo sapiens

<400> SEQUENCE: 576
gtttagaagg tggaatgaac acagatcatt gactgaacat tggaggtggg gaaagaggag    60
a                                                                   61

<210> SEQ ID NO 577
<211> LENGTH: 61
<212> TYPE: DNA
<213> ORGANISM: Homo sapiens

<400> SEQUENCE: 577
gaataactgg atatattgga ctctattaac attaaaagct ttgtccatta aaaggcacca    60
t                                                                   61
```

<210> SEQ ID NO 578
<211> LENGTH: 61
<212> TYPE: DNA
<213> ORGANISM: Homo sapiens

<400> SEQUENCE: 578
gaataactgg atatattgga ctctattaac gttaaaagct ttgtccatta aaaggcacca    60
t                                                                  61

<210> SEQ ID NO 579
<211> LENGTH: 61
<212> TYPE: DNA
<213> ORGANISM: Homo sapiens

<400> SEQUENCE: 579
aatgaataca ttaaaaatag gtctatttag aaaaacacaa tgtaaaaata aatttttca    60
t                                                                  61

<210> SEQ ID NO 580
<211> LENGTH: 61
<212> TYPE: DNA
<213> ORGANISM: Homo sapiens

<400> SEQUENCE: 580
aatgaataca ttaaaaatag gtctatttag gaaaacacaa tgtaaaaata aatttttca    60
t                                                                  61

<210> SEQ ID NO 581
<211> LENGTH: 61
<212> TYPE: DNA
<213> ORGANISM: Homo sapiens

<400> SEQUENCE: 581
taggttcagt tgcactgcag taagaatccc ataatgtcct gaacagaaaa cacatagatt    60
t                                                                  61

<210> SEQ ID NO 582
<211> LENGTH: 61
<212> TYPE: DNA
<213> ORGANISM: Homo sapiens

<400> SEQUENCE: 582
taggttcagt tgcactgcag taagaatccc gtaatgtcct gaacagaaaa cacatagatt    60
t                                                                  61

<210> SEQ ID NO 583
<211> LENGTH: 61
<212> TYPE: DNA
<213> ORGANISM: Homo sapiens

<400> SEQUENCE: 583
actgcgccca gccggtattg aaggatttta agaaaggctt tggccaaatg tttatgtgca    60
c                                                                  61

<210> SEQ ID NO 584
<211> LENGTH: 61
<212> TYPE: DNA
<213> ORGANISM: Homo sapiens

<400> SEQUENCE: 584

```
actgcgccca gccggtattg aaggatttta ggaaaggctt tggccaaatg tttatgtgca    60
c                                                                    61

<210> SEQ ID NO 585
<211> LENGTH: 61
<212> TYPE: DNA
<213> ORGANISM: Homo sapiens

<400> SEQUENCE: 585
agagttggat atgtgtgcct tggcattagt aagatgcagt tagtggtatc agagttaccc    60
c                                                                    61

<210> SEQ ID NO 586
<211> LENGTH: 61
<212> TYPE: DNA
<213> ORGANISM: Homo sapiens

<400> SEQUENCE: 586
agagttggat atgtgtgcct tggcattagt gagatgcagt tagtggtatc agagttaccc    60
c                                                                    61

<210> SEQ ID NO 587
<211> LENGTH: 61
<212> TYPE: DNA
<213> ORGANISM: Homo sapiens

<400> SEQUENCE: 587
tgacatttag aatgttagcg ttgaatacgc atcaaggaag aaaatcccat tttgaatgac    60
a                                                                    61

<210> SEQ ID NO 588
<211> LENGTH: 61
<212> TYPE: DNA
<213> ORGANISM: Homo sapiens

<400> SEQUENCE: 588
tgacatttag aatgttagcg ttgaatacgc gtcaaggaag aaaatcccat tttgaatgac    60
a                                                                    61

<210> SEQ ID NO 589
<211> LENGTH: 61
<212> TYPE: DNA
<213> ORGANISM: Homo sapiens

<400> SEQUENCE: 589
tcttcttttc tgactaagct atatatttac actgtgaaat tgactgtcat taatcttttt    60
c                                                                    61

<210> SEQ ID NO 590
<211> LENGTH: 61
<212> TYPE: DNA
<213> ORGANISM: Homo sapiens

<400> SEQUENCE: 590
tcttcttttc tgactaagct atatatttac gctgtgaaat tgactgtcat taatcttttt    60
c                                                                    61

<210> SEQ ID NO 591
<211> LENGTH: 61
```

```
<212> TYPE: DNA
<213> ORGANISM: Homo sapiens

<400> SEQUENCE: 591
gtattccatc actcagctta attttctcgg agaatacatg aaacgtgaaa tcttaatttt      60
a                                                                     61

<210> SEQ ID NO 592
<211> LENGTH: 61
<212> TYPE: DNA
<213> ORGANISM: Homo sapiens

<400> SEQUENCE: 592
gtattccatc actcagctta attttctcgg ggaatacatg aaacgtgaaa tcttaatttt      60
a                                                                     61

<210> SEQ ID NO 593
<211> LENGTH: 61
<212> TYPE: DNA
<213> ORGANISM: Homo sapiens

<400> SEQUENCE: 593
gcaatgcttc tttttgagct ctgtcttttt ctaagtattt gtaacaaaaa ctcttcttta      60
t                                                                     61

<210> SEQ ID NO 594
<211> LENGTH: 61
<212> TYPE: DNA
<213> ORGANISM: Homo sapiens

<400> SEQUENCE: 594
gcaatgcttc tttttgagct ctgtcttttt gtaagtattt gtaacaaaaa ctcttcttta      60
t                                                                     61

<210> SEQ ID NO 595
<211> LENGTH: 61
<212> TYPE: DNA
<213> ORGANISM: Homo sapiens

<400> SEQUENCE: 595
aagatttctg ttgatgcaga agctactgac actaggccag atggaaacaa gtaattggga      60
g                                                                     61

<210> SEQ ID NO 596
<211> LENGTH: 61
<212> TYPE: DNA
<213> ORGANISM: Homo sapiens

<400> SEQUENCE: 596
aagatttctg ttgatgcaga agctactgac gctaggccag atggaaacaa gtaattggga      60
g                                                                     61

<210> SEQ ID NO 597
<211> LENGTH: 61
<212> TYPE: DNA
<213> ORGANISM: Homo sapiens

<400> SEQUENCE: 597
tcagttatct ctggctcatg cacctcatcc atcagcaaat taaaacttgg atgtgagatg      60
t                                                                     61
```

<210> SEQ ID NO 598
<211> LENGTH: 61
<212> TYPE: DNA
<213> ORGANISM: Homo sapiens

<400> SEQUENCE: 598

```
tcagttatct ctggctcatg cacctcatcc gtcagcaaat taaaacttgg atgtgagatg    60
t                                                                    61
```

<210> SEQ ID NO 599
<211> LENGTH: 61
<212> TYPE: DNA
<213> ORGANISM: Homo sapiens

<400> SEQUENCE: 599

```
cacagatgca tattcatcca gcaagtattc actgatggcc ctctacaggt caggaagtgt    60
g                                                                    61
```

<210> SEQ ID NO 600
<211> LENGTH: 61
<212> TYPE: DNA
<213> ORGANISM: Homo sapiens

<400> SEQUENCE: 600

```
cacagatgca tattcatcca gcaagtattc gctgatggcc ctctacaggt caggaagtgt    60
g                                                                    61
```

<210> SEQ ID NO 601
<211> LENGTH: 61
<212> TYPE: DNA
<213> ORGANISM: Homo sapiens

<400> SEQUENCE: 601

```
taggtgagtc atttttaac acttgcttac agacccttag ccagctgaac tggtttcagc     60
a                                                                    61
```

<210> SEQ ID NO 602
<211> LENGTH: 61
<212> TYPE: DNA
<213> ORGANISM: Homo sapiens

<400> SEQUENCE: 602

```
taggtgagtc atttttaac acttgcttac ggacccttag ccagctgaac tggtttcagc     60
a                                                                    61
```

<210> SEQ ID NO 603
<211> LENGTH: 61
<212> TYPE: DNA
<213> ORGANISM: Homo sapiens

<400> SEQUENCE: 603

```
attcgacttc ttttcctaaa agttgttttg aatacacagc aatagaaaac atattaatta    60
c                                                                    61
```

<210> SEQ ID NO 604
<211> LENGTH: 61
<212> TYPE: DNA
<213> ORGANISM: Homo sapiens

<400> SEQUENCE: 604
```

```
attcgacttc ttttcctaaa agttgttttg gatacacagc aatagaaaac atattaatta    60
c                                                                   61
```

<210> SEQ ID NO 605
<211> LENGTH: 61
<212> TYPE: DNA
<213> ORGANISM: Homo sapiens

<400> SEQUENCE: 605

```
ctgaagccca ggtctaatta tgcaacatta ctgaccttct taccctccaa tcatcctgta    60
a                                                                   61
```

<210> SEQ ID NO 606
<211> LENGTH: 61
<212> TYPE: DNA
<213> ORGANISM: Homo sapiens

<400> SEQUENCE: 606

```
ctgaagccca ggtctaatta tgcaacatta gtgaccttct taccctccaa tcatcctgta    60
a                                                                   61
```

<210> SEQ ID NO 607
<211> LENGTH: 61
<212> TYPE: DNA
<213> ORGANISM: Homo sapiens

<400> SEQUENCE: 607

```
gtctggctat gggccaccat gcccacagat agtgcagaca agcaggaaga agtgcatgct    60
g                                                                   61
```

<210> SEQ ID NO 608
<211> LENGTH: 61
<212> TYPE: DNA
<213> ORGANISM: Homo sapiens

<400> SEQUENCE: 608

```
gtctggctat gggccaccat gcccacagat tgtgcagaca agcaggaaga agtgcatgct    60
g                                                                   61
```

<210> SEQ ID NO 609
<211> LENGTH: 61
<212> TYPE: DNA
<213> ORGANISM: Homo sapiens

<400> SEQUENCE: 609

```
aactcccttt tctcaaggga catctcctat actggaggaa cagtaagtac agttcccagc    60
a                                                                   61
```

<210> SEQ ID NO 610
<211> LENGTH: 61
<212> TYPE: DNA
<213> ORGANISM: Homo sapiens

<400> SEQUENCE: 610

```
aactcccttt tctcaaggga catctcctat cctggaggaa cagtaagtac agttcccagc    60
a                                                                   61
```

<210> SEQ ID NO 611
<211> LENGTH: 61

```
<212> TYPE: DNA
<213> ORGANISM: Homo sapiens

<400> SEQUENCE: 611
ctgtgtccca ttgatacctg gctttgtcac ataatttgct ttggccaatg aaatgtaagt    60
a                                                                   61

<210> SEQ ID NO 612
<211> LENGTH: 61
<212> TYPE: DNA
<213> ORGANISM: Homo sapiens

<400> SEQUENCE: 612
ctgtgtccca ttgatacctg gctttgtcac gtaatttgct ttggccaatg aaatgtaagt    60
a                                                                   61

<210> SEQ ID NO 613
<211> LENGTH: 61
<212> TYPE: DNA
<213> ORGANISM: Homo sapiens

<400> SEQUENCE: 613
tactcaaaac aaacaaaaaa gacaagacac atttgcaagt tgtttgacaa gggattaata    60
t                                                                   61

<210> SEQ ID NO 614
<211> LENGTH: 61
<212> TYPE: DNA
<213> ORGANISM: Homo sapiens

<400> SEQUENCE: 614
tactcaaaac aaacaaaaaa gacaagacac gtttgcaagt tgtttgacaa gggattaata    60
t                                                                   61

<210> SEQ ID NO 615
<211> LENGTH: 61
<212> TYPE: DNA
<213> ORGANISM: Homo sapiens

<400> SEQUENCE: 615
gtgtgtgtgt gtttatatcc tccactggca aagacttatt tatttattca tttatttatt    60
t                                                                   61

<210> SEQ ID NO 616
<211> LENGTH: 61
<212> TYPE: DNA
<213> ORGANISM: Homo sapiens

<400> SEQUENCE: 616
gtgtgtgtgt gtttatatcc tccactggca gagacttatt tatttattca tttatttatt    60
t                                                                   61

<210> SEQ ID NO 617
<211> LENGTH: 61
<212> TYPE: DNA
<213> ORGANISM: Homo sapiens

<400> SEQUENCE: 617
agaatatcaa aatggactaa tgaaagatct caggcattct gattttccag ggataaacat    60
t                                                                   61
```

<210> SEQ ID NO 618
<211> LENGTH: 61
<212> TYPE: DNA
<213> ORGANISM: Homo sapiens

<400> SEQUENCE: 618
agaatatcaa aatggactaa tgaaagatct gaggcattct gattttccag ggataaacat    60
t                                                                   61

<210> SEQ ID NO 619
<211> LENGTH: 61
<212> TYPE: DNA
<213> ORGANISM: Homo sapiens

<400> SEQUENCE: 619
acagcagctg ggaaacagcc atgtttatcc agaaaagaaa accataagcc tcgagaaact    60
g                                                                   61

<210> SEQ ID NO 620
<211> LENGTH: 61
<212> TYPE: DNA
<213> ORGANISM: Homo sapiens

<400> SEQUENCE: 620
acagcagctg ggaaacagcc atgtttatcc ggaaaagaaa accataagcc tcgagaaact    60
g                                                                   61

<210> SEQ ID NO 621
<211> LENGTH: 61
<212> TYPE: DNA
<213> ORGANISM: Homo sapiens

<400> SEQUENCE: 621
atcatgttaa cacaggaagg aactatatag aagaagcaac tttggaggaa gagatttcat    60
c                                                                   61

<210> SEQ ID NO 622
<211> LENGTH: 61
<212> TYPE: DNA
<213> ORGANISM: Homo sapiens

<400> SEQUENCE: 622
atcatgttaa cacaggaagg aactatatag gagaagcaac tttggaggaa gagatttcat    60
c                                                                   61

<210> SEQ ID NO 623
<211> LENGTH: 61
<212> TYPE: DNA
<213> ORGANISM: Homo sapiens

<400> SEQUENCE: 623
tactacacaa ataactcatg aaggctctac aatgatatct caagatcggg acacttcctc    60
g                                                                   61

<210> SEQ ID NO 624
<211> LENGTH: 61
<212> TYPE: DNA
<213> ORGANISM: Homo sapiens

<400> SEQUENCE: 624

```
tactacacaa ataactcatg aaggctctac gatgatatct caagatcggg acacttcctc    60
g                                                                    61

<210> SEQ ID NO 625
<211> LENGTH: 61
<212> TYPE: DNA
<213> ORGANISM: Homo sapiens

<400> SEQUENCE: 625
tagtggcata tttatcacta ctaagcgacc aatactgaca tgattgttaa ctaaagtcca    60
t                                                                    61

<210> SEQ ID NO 626
<211> LENGTH: 61
<212> TYPE: DNA
<213> ORGANISM: Homo sapiens

<400> SEQUENCE: 626
tagtggcata tttatcacta ctaagcgacc catactgaca tgattgttaa ctaaagtcca    60
t                                                                    61

<210> SEQ ID NO 627
<211> LENGTH: 61
<212> TYPE: DNA
<213> ORGANISM: Homo sapiens

<400> SEQUENCE: 627
tgctattacc ctcctcggtt ggctccagca ataagcctaa tgacctctac aaagctgttc    60
t                                                                    61

<210> SEQ ID NO 628
<211> LENGTH: 61
<212> TYPE: DNA
<213> ORGANISM: Homo sapiens

<400> SEQUENCE: 628
tgctattacc ctcctcggtt ggctccagca gtaagcctaa tgacctctac aaagctgttc    60
t                                                                    61

<210> SEQ ID NO 629
<211> LENGTH: 61
<212> TYPE: DNA
<213> ORGANISM: Homo sapiens

<400> SEQUENCE: 629
tgactgtctc ttcccctagc accagagatc atcttaggct acagctgtgg agtagatgct    60
g                                                                    61

<210> SEQ ID NO 630
<211> LENGTH: 61
<212> TYPE: DNA
<213> ORGANISM: Homo sapiens

<400> SEQUENCE: 630
tgactgtctc ttcccctagc accagagatc gtcttaggct acagctgtgg agtagatgct    60
g                                                                    61

<210> SEQ ID NO 631
<211> LENGTH: 61
```

```
<212> TYPE: DNA
<213> ORGANISM: Homo sapiens

<400> SEQUENCE: 631
taagagtgaa aatcagcatt gtggaaaaac acatgagcag ggtggtctac cactgacaca    60
c                                                                    61

<210> SEQ ID NO 632
<211> LENGTH: 61
<212> TYPE: DNA
<213> ORGANISM: Homo sapiens

<400> SEQUENCE: 632
taagagtgaa aatcagcatt gtggaaaaac gcatgagcag ggtggtctac cactgacaca    60
c                                                                    61

<210> SEQ ID NO 633
<211> LENGTH: 61
<212> TYPE: DNA
<213> ORGANISM: Homo sapiens

<400> SEQUENCE: 633
gatatctgat cagtaaatac aagaaaaac atcagagcag tatcgattta cattatttct     60
a                                                                    61

<210> SEQ ID NO 634
<211> LENGTH: 61
<212> TYPE: DNA
<213> ORGANISM: Homo sapiens

<400> SEQUENCE: 634
gatatctgat cagtaaatac aaagaaaaac gtcagagcag tatcgattta cattatttct    60
a                                                                    61

<210> SEQ ID NO 635
<211> LENGTH: 61
<212> TYPE: DNA
<213> ORGANISM: Homo sapiens

<400> SEQUENCE: 635
ctactctaag ccccaacatg tcagtgataa actcctactt tgaactctta gagcacttcc    60
c                                                                    61

<210> SEQ ID NO 636
<211> LENGTH: 61
<212> TYPE: DNA
<213> ORGANISM: Homo sapiens

<400> SEQUENCE: 636
ctactctaag ccccaacatg tcagtgataa cctcctactt tgaactctta gagcacttcc    60
c                                                                    61

<210> SEQ ID NO 637
<211> LENGTH: 61
<212> TYPE: DNA
<213> ORGANISM: Homo sapiens

<400> SEQUENCE: 637
aaaaaaaaaa ttaaaaggat tcaccctcag atctttgaat gcaaggagtc taattgacca    60
a                                                                    61
```

<210> SEQ ID NO 638
<211> LENGTH: 61
<212> TYPE: DNA
<213> ORGANISM: Homo sapiens

<400> SEQUENCE: 638
aaaaaaaaaa ttaaaaggat tcaccctcag gtctttgaat gcaaggagtc taattgacca    60
a                                                                   61

<210> SEQ ID NO 639
<211> LENGTH: 61
<212> TYPE: DNA
<213> ORGANISM: Homo sapiens

<400> SEQUENCE: 639
taagcacatg gttttactg agcgcctatc attttgctat ctatggtcta acgatacact    60
t                                                                   61

<210> SEQ ID NO 640
<211> LENGTH: 61
<212> TYPE: DNA
<213> ORGANISM: Homo sapiens

<400> SEQUENCE: 640
taagcacatg gttttactg agcgcctatc gttttgctat ctatggtcta acgatacact    60
t                                                                   61

<210> SEQ ID NO 641
<211> LENGTH: 61
<212> TYPE: DNA
<213> ORGANISM: Homo sapiens

<400> SEQUENCE: 641
cagtctggtc gcctctggcc accgaattgt atactcaggt cttagggtac cgaaaaaggg    60
a                                                                   61

<210> SEQ ID NO 642
<211> LENGTH: 61
<212> TYPE: DNA
<213> ORGANISM: Homo sapiens

<400> SEQUENCE: 642
cagtctggtc gcctctggcc accgaattgt gtactcaggt cttagggtac cgaaaaaggg    60
a                                                                   61

<210> SEQ ID NO 643
<211> LENGTH: 61
<212> TYPE: DNA
<213> ORGANISM: Homo sapiens

<400> SEQUENCE: 643
taaaaggctg gtgtgtctag gacatagaag accaataaat gtatggtatg agatggactg    60
g                                                                   61

<210> SEQ ID NO 644
<211> LENGTH: 61
<212> TYPE: DNA
<213> ORGANISM: Homo sapiens

<400> SEQUENCE: 644

```
taaaaggctg gtgtgtctag gacatagaag gccaataaat gtatggtatg agatggactg    60
g                                                                    61

<210> SEQ ID NO 645
<211> LENGTH: 61
<212> TYPE: DNA
<213> ORGANISM: Homo sapiens

<400> SEQUENCE: 645
tgtatttaaa aatggggcta attatgccca aatcatgatg ggatgaagtg ttgtaaggct    60
t                                                                    61

<210> SEQ ID NO 646
<211> LENGTH: 61
<212> TYPE: DNA
<213> ORGANISM: Homo sapiens

<400> SEQUENCE: 646
tgtatttaaa aatggggcta attatgccca catcatgatg ggatgaagtg ttgtaaggct    60
t                                                                    61

<210> SEQ ID NO 647
<211> LENGTH: 61
<212> TYPE: DNA
<213> ORGANISM: Homo sapiens

<400> SEQUENCE: 647
agtggaatcc aatcactcag ccttcaataa atcccaacag acgagggcgg tactttgctt    60
c                                                                    61

<210> SEQ ID NO 648
<211> LENGTH: 61
<212> TYPE: DNA
<213> ORGANISM: Homo sapiens

<400> SEQUENCE: 648
agtggaatcc aatcactcag ccttcaataa gtcccaacag acgagggcgg tactttgctt    60
c                                                                    61

<210> SEQ ID NO 649
<211> LENGTH: 61
<212> TYPE: DNA
<213> ORGANISM: Homo sapiens

<400> SEQUENCE: 649
agtagatttc tgttgcttcc aaacaaagaa acctaaagta cagtgataaa gtaactagca    60
a                                                                    61

<210> SEQ ID NO 650
<211> LENGTH: 61
<212> TYPE: DNA
<213> ORGANISM: Homo sapiens

<400> SEQUENCE: 650
agtagatttc tgttgcttcc aaacaaagaa ccctaaagta cagtgataaa gtaactagca    60
a                                                                    61

<210> SEQ ID NO 651
<211> LENGTH: 61
```

```
<212> TYPE: DNA
<213> ORGANISM: Homo sapiens

<400> SEQUENCE: 651
tggggttcac tgggtttctt cagtctgtga attttgttta catcaaattt ggcaaatttt    60
c                                                                   61

<210> SEQ ID NO 652
<211> LENGTH: 61
<212> TYPE: DNA
<213> ORGANISM: Homo sapiens

<400> SEQUENCE: 652
tggggttcac tgggtttctt cagtctgtga gttttgttta catcaaattt ggcaaatttt    60
c                                                                   61

<210> SEQ ID NO 653
<211> LENGTH: 61
<212> TYPE: DNA
<213> ORGANISM: Homo sapiens

<400> SEQUENCE: 653
attcaagtct ttcaggagtg atgctgatca atagaacata gaccatgtct ataaacccca    60
g                                                                   61

<210> SEQ ID NO 654
<211> LENGTH: 61
<212> TYPE: DNA
<213> ORGANISM: Homo sapiens

<400> SEQUENCE: 654
attcaagtct ttcaggagtg atgctgatca gtagaacata gaccatgtct ataaacccca    60
g                                                                   61

<210> SEQ ID NO 655
<211> LENGTH: 61
<212> TYPE: DNA
<213> ORGANISM: Homo sapiens

<400> SEQUENCE: 655
ccactataat ttatatccat tctacttgat agacatctgc ttgagtgtaa gggatacttg    60
t                                                                   61

<210> SEQ ID NO 656
<211> LENGTH: 61
<212> TYPE: DNA
<213> ORGANISM: Homo sapiens

<400> SEQUENCE: 656
ccactataat ttatatccat tctacttgat ggacatctgc ttgagtgtaa gggatacttg    60
t                                                                   61

<210> SEQ ID NO 657
<211> LENGTH: 61
<212> TYPE: DNA
<213> ORGANISM: Homo sapiens

<400> SEQUENCE: 657
atggagaagc agtgtagtgt agtatcaaca ataagccttg aaaccaagcc aacttatctc    60
t                                                                   61
```

<210> SEQ ID NO 658
<211> LENGTH: 61
<212> TYPE: DNA
<213> ORGANISM: Homo sapiens

<400> SEQUENCE: 658
atggagaagc agtgtagtgt agtatcaaca gtaagccttg aaaccaagcc aacttatctc    60
t                                                                   61

<210> SEQ ID NO 659
<211> LENGTH: 61
<212> TYPE: DNA
<213> ORGANISM: Homo sapiens

<400> SEQUENCE: 659
aaaacatata atctgtttac ctcagatctt acttatcagg aatcacagta tgaatatttt    60
t                                                                   61

<210> SEQ ID NO 660
<211> LENGTH: 61
<212> TYPE: DNA
<213> ORGANISM: Homo sapiens

<400> SEQUENCE: 660
aaaacatata atctgtttac ctcagatctt tcttatcagg aatcacagta tgaatatttt    60
t                                                                   61

<210> SEQ ID NO 661
<211> LENGTH: 61
<212> TYPE: DNA
<213> ORGANISM: Homo sapiens

<400> SEQUENCE: 661
agagggtcac ttgaatcttc attttaggca cctattttgg aaatgtgagg aaaaaagtca    60
g                                                                   61

<210> SEQ ID NO 662
<211> LENGTH: 61
<212> TYPE: DNA
<213> ORGANISM: Homo sapiens

<400> SEQUENCE: 662
agagggtcac ttgaatcttc attttaggca gctattttgg aaatgtgagg aaaaaagtca    60
g                                                                   61

<210> SEQ ID NO 663
<211> LENGTH: 61
<212> TYPE: DNA
<213> ORGANISM: Homo sapiens

<400> SEQUENCE: 663
atatctgaat tctacccact tggataatca ataagcacca caatatgaac aattccatga    60
a                                                                   61

<210> SEQ ID NO 664
<211> LENGTH: 61
<212> TYPE: DNA
<213> ORGANISM: Homo sapiens

<400> SEQUENCE: 664

```
atatctgaat ctacccact tggataatca gtaagcacca caatatgaac aattccatga    60
a                                                                   61

<210> SEQ ID NO 665
<211> LENGTH: 61
<212> TYPE: DNA
<213> ORGANISM: Homo sapiens

<400> SEQUENCE: 665
catgtcaatt caagagggtt aaagattgct attactttcc aaggatcttc attgttcctc    60
t                                                                   61

<210> SEQ ID NO 666
<211> LENGTH: 61
<212> TYPE: DNA
<213> ORGANISM: Homo sapiens

<400> SEQUENCE: 666
catgtcaatt caagagggtt aaagattgct gttactttcc aaggatcttc attgttcctc    60
t                                                                   61

<210> SEQ ID NO 667
<211> LENGTH: 61
<212> TYPE: DNA
<213> ORGANISM: Homo sapiens

<400> SEQUENCE: 667
tttagaaaat ttccaggtgg ataactgcct aaatacagaa atcagaatg ttaatgcatt     60
t                                                                   61

<210> SEQ ID NO 668
<211> LENGTH: 61
<212> TYPE: DNA
<213> ORGANISM: Homo sapiens

<400> SEQUENCE: 668
tttagaaaat ttccaggtgg ataactgcct gaatacagaa atcagaatg ttaatgcatt     60
t                                                                   61

<210> SEQ ID NO 669
<211> LENGTH: 61
<212> TYPE: DNA
<213> ORGANISM: Homo sapiens

<400> SEQUENCE: 669
aagcaccctc aagcttgaga tactaggaga aataaacagc agagcaaatg tgctcagagt    60
g                                                                   61

<210> SEQ ID NO 670
<211> LENGTH: 61
<212> TYPE: DNA
<213> ORGANISM: Homo sapiens

<400> SEQUENCE: 670
aagcaccctc aagcttgaga tactaggaga gataaacagc agagcaaatg tgctcagagt    60
g                                                                   61

<210> SEQ ID NO 671
<211> LENGTH: 61
```

```
<212> TYPE: DNA
<213> ORGANISM: Homo sapiens

<400> SEQUENCE: 671
tcttgtccag aacttttttg atgttaacct aatcacagcc agattttttt tttctgagac    60
a                                                                    61

<210> SEQ ID NO 672
<211> LENGTH: 61
<212> TYPE: DNA
<213> ORGANISM: Homo sapiens

<400> SEQUENCE: 672
tcttgtccag aacttttttg atgttaacct gatcacagcc agattttttt tttctgagac    60
a                                                                    61

<210> SEQ ID NO 673
<211> LENGTH: 61
<212> TYPE: DNA
<213> ORGANISM: Homo sapiens

<400> SEQUENCE: 673
tataccaata agttcaattc catgctaaga aataaactat ggatatgatt actaagttga    60
a                                                                    61

<210> SEQ ID NO 674
<211> LENGTH: 61
<212> TYPE: DNA
<213> ORGANISM: Homo sapiens

<400> SEQUENCE: 674
tataccaata agttcaattc catgctaaga gataaactat ggatatgatt actaagttga    60
a                                                                    61

<210> SEQ ID NO 675
<211> LENGTH: 61
<212> TYPE: DNA
<213> ORGANISM: Homo sapiens

<400> SEQUENCE: 675
tgagcctcgg gtcctccctg aaaggtaagg ataacaggaa gcctctccca aagatgggtc    60
a                                                                    61

<210> SEQ ID NO 676
<211> LENGTH: 61
<212> TYPE: DNA
<213> ORGANISM: Homo sapiens

<400> SEQUENCE: 676
tgagcctcgg gtcctccctg aaaggtaagg gtaacaggaa gcctctccca aagatgggtc    60
a                                                                    61

<210> SEQ ID NO 677
<211> LENGTH: 61
<212> TYPE: DNA
<213> ORGANISM: Homo sapiens

<400> SEQUENCE: 677
taggagtaag tgactttta ggggaaatga atgatcctaa agaacaactg cctgagacaa     60
a                                                                    61
```

<210> SEQ ID NO 678
<211> LENGTH: 61
<212> TYPE: DNA
<213> ORGANISM: Homo sapiens

<400> SEQUENCE: 678
taggagtaag tgactttta ggggaaatga gtgatcctaa agaacaactg cctgagacaa    60
a                                                                  61

<210> SEQ ID NO 679
<211> LENGTH: 61
<212> TYPE: DNA
<213> ORGANISM: Homo sapiens

<400> SEQUENCE: 679
cacctcctca caagggatgg caagctagca atatcgttac agggcacaaa acagcgttta    60
g                                                                  61

<210> SEQ ID NO 680
<211> LENGTH: 61
<212> TYPE: DNA
<213> ORGANISM: Homo sapiens

<400> SEQUENCE: 680
cacctcctca caagggatgg caagctagca gtatcgttac agggcacaaa acagcgttta    60
g                                                                  61

<210> SEQ ID NO 681
<211> LENGTH: 61
<212> TYPE: DNA
<213> ORGANISM: Homo sapiens

<400> SEQUENCE: 681
caatacatgg tccattgtgg gagacagccc aacacacagc atgcaggggc tcagtactca    60
c                                                                  61

<210> SEQ ID NO 682
<211> LENGTH: 61
<212> TYPE: DNA
<213> ORGANISM: Homo sapiens

<400> SEQUENCE: 682
caatacatgg tccattgtgg gagacagccc gacacacagc atgcaggggc tcagtactca    60
c                                                                  61

<210> SEQ ID NO 683
<211> LENGTH: 61
<212> TYPE: DNA
<213> ORGANISM: Homo sapiens

<400> SEQUENCE: 683
gatggagttg ctctgacaaa tgcctctgac aaaaggactc ttgaactcat tgaagtctac    60
c                                                                  61

<210> SEQ ID NO 684
<211> LENGTH: 61
<212> TYPE: DNA
<213> ORGANISM: Homo sapiens

<400> SEQUENCE: 684

-continued gatggagttg ctctgacaaa tgcctctgac gaaaggactc ttgaactcat tgaagtctac    60
c                                                                    61

<210> SEQ ID NO 685
<211> LENGTH: 61
<212> TYPE: DNA
<213> ORGANISM: Homo sapiens

<400> SEQUENCE: 685
acacagagca aagagggca tcgtgtccct aagaaatgga aacttcctat ctcagagtac    60
a                                                                    61

<210> SEQ ID NO 686
<211> LENGTH: 61
<212> TYPE: DNA
<213> ORGANISM: Homo sapiens

<400> SEQUENCE: 686
acacagagca aagagggca tcgtgtccct cagaaatgga aacttcctat ctcagagtac    60
a                                                                    61

<210> SEQ ID NO 687
<211> LENGTH: 61
<212> TYPE: DNA
<213> ORGANISM: Homo sapiens

<400> SEQUENCE: 687
acttgggtca aagaccatgt aaatcgcgag attgtggttt gaattacagc ccatgcagtg    60
t                                                                    61

<210> SEQ ID NO 688
<211> LENGTH: 61
<212> TYPE: DNA
<213> ORGANISM: Homo sapiens

<400> SEQUENCE: 688
acttgggtca aagaccatgt aaatcgcgag gttgtggttt gaattacagc ccatgcagtg    60
t                                                                    61

<210> SEQ ID NO 689
<211> LENGTH: 61
<212> TYPE: DNA
<213> ORGANISM: Homo sapiens

<400> SEQUENCE: 689
gttttcattg ttttggcat atctgcccca atcaggatcc tactcaggtg ctggggctgt    60
c                                                                    61

<210> SEQ ID NO 690
<211> LENGTH: 61
<212> TYPE: DNA
<213> ORGANISM: Homo sapiens

<400> SEQUENCE: 690
gttttcattg ttttggcat atctgcccca gtcaggatcc tactcaggtg ctggggctgt    60
c                                                                    61

<210> SEQ ID NO 691
<211> LENGTH: 61

```
<212> TYPE: DNA
<213> ORGANISM: Homo sapiens

<400> SEQUENCE: 691
acctccttca agaagccttc ctggacacta agcctcagcg actccctctc cactgaactt    60
c                                                                    61

<210> SEQ ID NO 692
<211> LENGTH: 61
<212> TYPE: DNA
<213> ORGANISM: Homo sapiens

<400> SEQUENCE: 692
acctccttca agaagccttc ctggacacta tgcctcagcg actccctctc cactgaactt    60
c                                                                    61

<210> SEQ ID NO 693
<211> LENGTH: 61
<212> TYPE: DNA
<213> ORGANISM: Homo sapiens

<400> SEQUENCE: 693
acttatccat tttattttt gatgcatttc aaagtaagtt gcagacatca tatacatcac     60
a                                                                    61

<210> SEQ ID NO 694
<211> LENGTH: 61
<212> TYPE: DNA
<213> ORGANISM: Homo sapiens

<400> SEQUENCE: 694
acttatccat tttattttt gatgcatttc gaagtaagtt gcagacatca tatacatcac     60
a                                                                    61

<210> SEQ ID NO 695
<211> LENGTH: 61
<212> TYPE: DNA
<213> ORGANISM: Homo sapiens

<400> SEQUENCE: 695
tgtggctcag cccagcagtg ttaggaagga aagcaccagg tgaaagttct tggtgccctc    60
c                                                                    61

<210> SEQ ID NO 696
<211> LENGTH: 61
<212> TYPE: DNA
<213> ORGANISM: Homo sapiens

<400> SEQUENCE: 696
tgtggctcag cccagcagtg ttaggaagga gagcaccagg tgaaagttct tggtgccctc    60
c                                                                    61

<210> SEQ ID NO 697
<211> LENGTH: 61
<212> TYPE: DNA
<213> ORGANISM: Homo sapiens

<400> SEQUENCE: 697
ctgcctccag ctgagtagcg tttgtttgaa actggtgcag actaaggcag caagccagcc    60
a                                                                    61
```

<210> SEQ ID NO 698
<211> LENGTH: 61
<212> TYPE: DNA
<213> ORGANISM: Homo sapiens

<400> SEQUENCE: 698
ctgcctccag ctgagtagcg tttgtttgaa gctggtgcag actaaggcag caagccagcc    60
a                                                                    61

<210> SEQ ID NO 699
<211> LENGTH: 61
<212> TYPE: DNA
<213> ORGANISM: Homo sapiens

<400> SEQUENCE: 699
catgtcaggt cctgcgtgct atcaggggag actttcactc atctctaact ggctcccaat    60
c                                                                    61

<210> SEQ ID NO 700
<211> LENGTH: 61
<212> TYPE: DNA
<213> ORGANISM: Homo sapiens

<400> SEQUENCE: 700
catgtcaggt cctgcgtgct atcaggggag cctttcactc atctctaact ggctcccaat    60
c                                                                    61

<210> SEQ ID NO 701
<211> LENGTH: 61
<212> TYPE: DNA
<213> ORGANISM: Homo sapiens

<400> SEQUENCE: 701
tgatgaggaa aataatttgc ttaccacaac atagttagta cagttagtaa gagaagaggt    60
c                                                                    61

<210> SEQ ID NO 702
<211> LENGTH: 61
<212> TYPE: DNA
<213> ORGANISM: Homo sapiens

<400> SEQUENCE: 702
tgatgaggaa aataatttgc ttaccacaac gtagttagta cagttagtaa gagaagaggt    60
c                                                                    61

<210> SEQ ID NO 703
<211> LENGTH: 61
<212> TYPE: DNA
<213> ORGANISM: Homo sapiens

<400> SEQUENCE: 703
gttgaaactt gtgaatccat gtctctagaa ccgcagtgaa gactaacgca gtcgtcatga    60
a                                                                    61

<210> SEQ ID NO 704
<211> LENGTH: 61
<212> TYPE: DNA
<213> ORGANISM: Homo sapiens

<400> SEQUENCE: 704

```
gttgaaactt gtgaatccat gtctctagaa gcgcagtgaa gactaacgca gtcgtcatga    60
a                                                                  61

<210> SEQ ID NO 705
<211> LENGTH: 61
<212> TYPE: DNA
<213> ORGANISM: Homo sapiens

<400> SEQUENCE: 705
catttcagat tcaaggctcc tccttctgtt ctcagtttac taagagtttc ttttaatttt    60
t                                                                  61

<210> SEQ ID NO 706
<211> LENGTH: 61
<212> TYPE: DNA
<213> ORGANISM: Homo sapiens

<400> SEQUENCE: 706
catttcagat tcaaggctcc tccttctgtt gtcagtttac taagagtttc ttttaatttt    60
t                                                                  61

<210> SEQ ID NO 707
<211> LENGTH: 61
<212> TYPE: DNA
<213> ORGANISM: Homo sapiens

<400> SEQUENCE: 707
taaatcttcc ctgcctgcct cgtgacctac aatcatttcc caagctcacc tatgcccatg    60
a                                                                  61

<210> SEQ ID NO 708
<211> LENGTH: 61
<212> TYPE: DNA
<213> ORGANISM: Homo sapiens

<400> SEQUENCE: 708
taaatcttcc ctgcctgcct cgtgacctac catcatttcc caagctcacc tatgcccatg    60
a                                                                  61

<210> SEQ ID NO 709
<211> LENGTH: 61
<212> TYPE: DNA
<213> ORGANISM: Homo sapiens

<400> SEQUENCE: 709
gcttcttttg ctgacacaca ggactttccc ataaggcggt gccctgagca gtactgggga    60
a                                                                  61

<210> SEQ ID NO 710
<211> LENGTH: 61
<212> TYPE: DNA
<213> ORGANISM: Homo sapiens

<400> SEQUENCE: 710
gcttcttttg ctgacacaca ggactttccc gtaaggcggt gccctgagca gtactgggga    60
a                                                                  61

<210> SEQ ID NO 711
<211> LENGTH: 61
```

```
<212> TYPE: DNA
<213> ORGANISM: Homo sapiens

<400> SEQUENCE: 711
accagtgact ggagactcag ctacttccag acgttaaaag ctgatagagg aagcccagta    60
g                                                                    61

<210> SEQ ID NO 712
<211> LENGTH: 61
<212> TYPE: DNA
<213> ORGANISM: Homo sapiens

<400> SEQUENCE: 712
accagtgact ggagactcag ctacttccag gcgttaaaag ctgatagagg aagcccagta    60
g                                                                    61

<210> SEQ ID NO 713
<211> LENGTH: 61
<212> TYPE: DNA
<213> ORGANISM: Homo sapiens

<400> SEQUENCE: 713
atttttgtga cagatataca gctaagagat atgcaacgac gtgaatgaat aactatagta    60
t                                                                    61

<210> SEQ ID NO 714
<211> LENGTH: 61
<212> TYPE: DNA
<213> ORGANISM: Homo sapiens

<400> SEQUENCE: 714
atttttgtga cagatataca gctaagagat gtgcaacgac gtgaatgaat aactatagta    60
t                                                                    61

<210> SEQ ID NO 715
<211> LENGTH: 61
<212> TYPE: DNA
<213> ORGANISM: Homo sapiens

<400> SEQUENCE: 715
tgtgtatgta caatgttatt agatattctg aaactgttat tcaaagtgtt tgtatctact    60
a                                                                    61

<210> SEQ ID NO 716
<211> LENGTH: 61
<212> TYPE: DNA
<213> ORGANISM: Homo sapiens

<400> SEQUENCE: 716
tgtgtatgta caatgttatt agatattctg caactgttat tcaaagtgtt tgtatctact    60
a                                                                    61

<210> SEQ ID NO 717
<211> LENGTH: 61
<212> TYPE: DNA
<213> ORGANISM: Homo sapiens

<400> SEQUENCE: 717
attttaatcc caatacatag tatgaatcct attgcttttc ctctcaagtc tcagagatgt    60
g                                                                    61
```

<210> SEQ ID NO 718
<211> LENGTH: 61
<212> TYPE: DNA
<213> ORGANISM: Homo sapiens

<400> SEQUENCE: 718
attttaatcc caatacatag tatgaatcct gttgcttttc ctctcaagtc tcagagatgt    60
g                                                                   61

<210> SEQ ID NO 719
<211> LENGTH: 61
<212> TYPE: DNA
<213> ORGANISM: Homo sapiens

<400> SEQUENCE: 719
tagtcatgaa agaaaaggtg atcaccctac attgaaacca agtacaattt atagcatctc    60
t                                                                   61

<210> SEQ ID NO 720
<211> LENGTH: 61
<212> TYPE: DNA
<213> ORGANISM: Homo sapiens

<400> SEQUENCE: 720
tagtcatgaa agaaaaggtg atcaccctac gttgaaacca agtacaattt atagcatctc    60
t                                                                   61

<210> SEQ ID NO 721
<211> LENGTH: 61
<212> TYPE: DNA
<213> ORGANISM: Homo sapiens

<400> SEQUENCE: 721
aactcctttt gaagagtctc tgagctaaca agtcaacatc agcataaagt aatgcagcct    60
g                                                                   61

<210> SEQ ID NO 722
<211> LENGTH: 61
<212> TYPE: DNA
<213> ORGANISM: Homo sapiens

<400> SEQUENCE: 722
aactcctttt gaagagtctc tgagctaaca cgtcaacatc agcataaagt aatgcagcct    60
g                                                                   61

<210> SEQ ID NO 723
<211> LENGTH: 61
<212> TYPE: DNA
<213> ORGANISM: Homo sapiens

<400> SEQUENCE: 723
aataacttca tttctcaggt cctgtcagcc actggatccc acaaaactct gcagagattt    60
t                                                                   61

<210> SEQ ID NO 724
<211> LENGTH: 61
<212> TYPE: DNA
<213> ORGANISM: Homo sapiens

<400> SEQUENCE: 724

```
ataacttca tttctcaggt cctgtcagcc gctggatccc acaaaactct gcagagattt    60
t                                                                  61

<210> SEQ ID NO 725
<211> LENGTH: 61
<212> TYPE: DNA
<213> ORGANISM: Homo sapiens

<400> SEQUENCE: 725
agttgataag aatcaagtga aattaagatt atcaggctgt cattgtcatc cctatcaggg   60
g                                                                  61

<210> SEQ ID NO 726
<211> LENGTH: 61
<212> TYPE: DNA
<213> ORGANISM: Homo sapiens

<400> SEQUENCE: 726
agttgataag aatcaagtga aattaagatt gtcaggctgt cattgtcatc cctatcaggg   60
g                                                                  61

<210> SEQ ID NO 727
<211> LENGTH: 61
<212> TYPE: DNA
<213> ORGANISM: Homo sapiens

<400> SEQUENCE: 727
gtacaatcta catggtcttt aggagaatta aatgagtaat gctcaataaa ggtcagtatt   60
c                                                                  61

<210> SEQ ID NO 728
<211> LENGTH: 61
<212> TYPE: DNA
<213> ORGANISM: Homo sapiens

<400> SEQUENCE: 728
gtacaatcta catggtcttt aggagaatta gatgagtaat gctcaataaa ggtcagtatt   60
c                                                                  61

<210> SEQ ID NO 729
<211> LENGTH: 61
<212> TYPE: DNA
<213> ORGANISM: Homo sapiens

<400> SEQUENCE: 729
aggtccagag acacagcttt gcaactgaca acaggtttca ttttctctac caaggaaaac   60
t                                                                  61

<210> SEQ ID NO 730
<211> LENGTH: 61
<212> TYPE: DNA
<213> ORGANISM: Homo sapiens

<400> SEQUENCE: 730
aggtccagag acacagcttt gcaactgaca tcaggtttca ttttctctac caaggaaaac   60
t                                                                  61

<210> SEQ ID NO 731
<211> LENGTH: 61
```

```
<212> TYPE: DNA
<213> ORGANISM: Homo sapiens

<400> SEQUENCE: 731
tattcctcta tgccatctag tttggcactt agaatttaag gtagttttct tggtatttat      60
a                                                                     61

<210> SEQ ID NO 732
<211> LENGTH: 61
<212> TYPE: DNA
<213> ORGANISM: Homo sapiens

<400> SEQUENCE: 732
tattcctcta tgccatctag tttggcactt ggaatttaag gtagttttct tggtatttat      60
a                                                                     61

<210> SEQ ID NO 733
<211> LENGTH: 61
<212> TYPE: DNA
<213> ORGANISM: Homo sapiens

<400> SEQUENCE: 733
tatatataca cagattttc aattctaata cctaggatga catatgcaca atgttttat        60
a                                                                     61

<210> SEQ ID NO 734
<211> LENGTH: 61
<212> TYPE: DNA
<213> ORGANISM: Homo sapiens

<400> SEQUENCE: 734
tatatataca cagattttc aattctaata gctaggatga catatgcaca atgttttat        60
a                                                                     61

<210> SEQ ID NO 735
<211> LENGTH: 61
<212> TYPE: DNA
<213> ORGANISM: Homo sapiens

<400> SEQUENCE: 735
ttcctttatt gaccaaataa acgtatttcc aagtctattt cttattctta tttcagatta      60
a                                                                     61

<210> SEQ ID NO 736
<211> LENGTH: 61
<212> TYPE: DNA
<213> ORGANISM: Homo sapiens

<400> SEQUENCE: 736
ttcctttatt gaccaaataa acgtatttcc gagtctattt cttattctta tttcagatta      60
a                                                                     61

<210> SEQ ID NO 737
<211> LENGTH: 61
<212> TYPE: DNA
<213> ORGANISM: Homo sapiens

<400> SEQUENCE: 737
gaaactagac atcttgttac atgaagagtt aagagctaat ttatttgtta caaatctcac      60
a                                                                     61
```

<210> SEQ ID NO 738
<211> LENGTH: 61
<212> TYPE: DNA
<213> ORGANISM: Homo sapiens

<400> SEQUENCE: 738
gaaactagac atcttgttac atgaagagtt cagagctaat ttatttgtta caaatctcac    60
a                                                                    61

<210> SEQ ID NO 739
<211> LENGTH: 61
<212> TYPE: DNA
<213> ORGANISM: Homo sapiens

<400> SEQUENCE: 739
caacacagtg ttcaatgtgg gagccaatcg aatttcatct ctgcaaatag catacatgca    60
t                                                                    61

<210> SEQ ID NO 740
<211> LENGTH: 61
<212> TYPE: DNA
<213> ORGANISM: Homo sapiens

<400> SEQUENCE: 740
caacacagtg ttcaatgtgg gagccaatcg catttcatct ctgcaaatag catacatgca    60
t                                                                    61

<210> SEQ ID NO 741
<211> LENGTH: 61
<212> TYPE: DNA
<213> ORGANISM: Homo sapiens

<400> SEQUENCE: 741
ctgtgagctg ctgttgggac tgagacatga atggactgta ctccctgcag cttttacac    60
t                                                                    61

<210> SEQ ID NO 742
<211> LENGTH: 61
<212> TYPE: DNA
<213> ORGANISM: Homo sapiens

<400> SEQUENCE: 742
ctgtgagctg ctgttgggac tgagacatga gtggactgta ctccctgcag cttttacac    60
t                                                                    61

<210> SEQ ID NO 743
<211> LENGTH: 61
<212> TYPE: DNA
<213> ORGANISM: Homo sapiens

<400> SEQUENCE: 743
tgagatgtga ggatactgca ctttccacag attttttgctc atgctgctta cctgggaagg    60
g                                                                    61

<210> SEQ ID NO 744
<211> LENGTH: 61
<212> TYPE: DNA
<213> ORGANISM: Homo sapiens

<400> SEQUENCE: 744

```
tgagatgtga ggatactgca ctttccacag cttttttgctc atgctgctta cctgggaagg    60
g                                                                     61

<210> SEQ ID NO 745
<211> LENGTH: 61
<212> TYPE: DNA
<213> ORGANISM: Homo sapiens

<400> SEQUENCE: 745
gacttgccct caccccataa ttaaattatc atccgagatc acagagttgt acatcttata    60
g                                                                    61

<210> SEQ ID NO 746
<211> LENGTH: 61
<212> TYPE: DNA
<213> ORGANISM: Homo sapiens

<400> SEQUENCE: 746
gacttgccct caccccataa ttaaattatc gtccgagatc acagagttgt acatcttata    60
g                                                                    61

<210> SEQ ID NO 747
<211> LENGTH: 61
<212> TYPE: DNA
<213> ORGANISM: Homo sapiens

<400> SEQUENCE: 747 gggaggggc agtcatgtct gtttcctgac atattcattg gcctgaggga caatttctct     60
c                                                                    61

<210> SEQ ID NO 748
<211> LENGTH: 61
<212> TYPE: DNA
<213> ORGANISM: Homo sapiens

<400> SEQUENCE: 748 gggaggggc agtcatgtct gtttcctgac gtattcattg gcctgaggga caatttctct     60
c                                                                    61

<210> SEQ ID NO 749
<211> LENGTH: 61
<212> TYPE: DNA
<213> ORGANISM: Homo sapiens

<400> SEQUENCE: 749
actaaagaaa catttgttgt taagcctaat atgctgacct atgtgcctgc atttttttt     60
t                                                                    61

<210> SEQ ID NO 750
<211> LENGTH: 61
<212> TYPE: DNA
<213> ORGANISM: Homo sapiens

<400> SEQUENCE: 750
actaaagaaa catttgttgt taagcctaat gtgctgacct atgtgcctgc atttttttt     60
t                                                                    61

<210> SEQ ID NO 751
<211> LENGTH: 61
```

<212> TYPE: DNA
<213> ORGANISM: Homo sapiens

<400> SEQUENCE: 751 cttggccag atggtattga caaatgaaac ataatcagtg atgaattaga aaaaggtgt    60
t                                                                 61

<210> SEQ ID NO 752
<211> LENGTH: 61
<212> TYPE: DNA
<213> ORGANISM: Homo sapiens

<400> SEQUENCE: 752 cttggccag atggtattga caaatgaaac gtaatcagtg atgaattaga aaaaggtgt    60
t                                                                 61

<210> SEQ ID NO 753
<211> LENGTH: 50
<212> TYPE: DNA
<213> ORGANISM: Homo sapiens

<400> SEQUENCE: 753
tcactaaaga aatgaagatg ttagttggga ctcaggctag gtcatcctcg             50

<210> SEQ ID NO 754
<211> LENGTH: 50
<212> TYPE: DNA
<213> ORGANISM: Homo sapiens

<400> SEQUENCE: 754
acccattccc acctaaaggg ttttattctg aaacgcttct ctgctcaaaa             50

<210> SEQ ID NO 755
<211> LENGTH: 50
<212> TYPE: DNA
<213> ORGANISM: Homo sapiens

<400> SEQUENCE: 755
cattctcttt tttcttgtta gtgtcaccaa cctgaggctt ctctgttgta             50

<210> SEQ ID NO 756
<211> LENGTH: 50
<212> TYPE: DNA
<213> ORGANISM: Homo sapiens

<400> SEQUENCE: 756
taaaaggtac ttcatatttt tgacaatgaa atgaaaatgc tgcatacata             50

<210> SEQ ID NO 757
<211> LENGTH: 50
<212> TYPE: DNA
<213> ORGANISM: Homo sapiens

<400> SEQUENCE: 757
atgcctgagt gaggacccac tcctaccgat tttagtgaga gatgcacttc             50

<210> SEQ ID NO 758
<211> LENGTH: 50
<212> TYPE: DNA
<213> ORGANISM: Homo sapiens

<400> SEQUENCE: 758
gattccaagc tgagggaaca ggaggtgcaa cggtgagggt gtgttggtat             50

```
<210> SEQ ID NO 759
<211> LENGTH: 50
<212> TYPE: DNA
<213> ORGANISM: Homo sapiens

<400> SEQUENCE: 759
acaattcctg tttctgtgtg agctttaagg attttttttcc ttttctccta        50

<210> SEQ ID NO 760
<211> LENGTH: 50
<212> TYPE: DNA
<213> ORGANISM: Homo sapiens

<400> SEQUENCE: 760
ttttattcag accctatttta tcagattaaa gatgagttct tctgacctct         50

<210> SEQ ID NO 761
<211> LENGTH: 50
<212> TYPE: DNA
<213> ORGANISM: Homo sapiens

<400> SEQUENCE: 761
actccaacag aggagcttat aagcctagct gggggagtag aacacattag          50

<210> SEQ ID NO 762
<211> LENGTH: 50
<212> TYPE: DNA
<213> ORGANISM: Homo sapiens

<400> SEQUENCE: 762
tctcattcct tttatgtgca gttttaggtg acttcctcaa attccccaaa          50

<210> SEQ ID NO 763
<211> LENGTH: 50
<212> TYPE: DNA
<213> ORGANISM: Homo sapiens

<400> SEQUENCE: 763
ctgcccagat tcagcaattc ttagaaaata actgagaagt aaagtgtaga          50

<210> SEQ ID NO 764
<211> LENGTH: 50
<212> TYPE: DNA
<213> ORGANISM: Homo sapiens

<400> SEQUENCE: 764
gagagagaac gtttccttaa gctggatgaa atagcattgg atcagaggac          50

<210> SEQ ID NO 765
<211> LENGTH: 50
<212> TYPE: DNA
<213> ORGANISM: Homo sapiens

<400> SEQUENCE: 765
taaaagaaag cccttatcca cctactagtc acatatggga aattaacagg          50

<210> SEQ ID NO 766
<211> LENGTH: 50
<212> TYPE: DNA
<213> ORGANISM: Homo sapiens

<400> SEQUENCE: 766
accgagtttg gcatagactt gaaattaagg actaagatca gtctccagag          50
```

```
<210> SEQ ID NO 767
<211> LENGTH: 50
<212> TYPE: DNA
<213> ORGANISM: Homo sapiens

<400> SEQUENCE: 767
agtataaatg tgatcaaatt gcctcttcta ttctcatgta aattttagcc          50

<210> SEQ ID NO 768
<211> LENGTH: 50
<212> TYPE: DNA
<213> ORGANISM: Homo sapiens

<400> SEQUENCE: 768
acaaagcagc ccctaggtgc caggctgcat gtgagccaaa gagagaaaaa          50

<210> SEQ ID NO 769
<211> LENGTH: 50
<212> TYPE: DNA
<213> ORGANISM: Homo sapiens

<400> SEQUENCE: 769
caatgaaagg catcgtgcct aagatctata agctttgaag gacctatgaa          50

<210> SEQ ID NO 770
<211> LENGTH: 50
<212> TYPE: DNA
<213> ORGANISM: Homo sapiens

<400> SEQUENCE: 770
cttctggaaa taattttacc tttgtcgtca tccatcctgt cgatcaaata          50

<210> SEQ ID NO 771
<211> LENGTH: 50
<212> TYPE: DNA
<213> ORGANISM: Homo sapiens

<400> SEQUENCE: 771
ggcgttgtct aagctcattg actgtgtgca aaggacaaat gatttctcac          50

<210> SEQ ID NO 772
<211> LENGTH: 50
<212> TYPE: DNA
<213> ORGANISM: Homo sapiens

<400> SEQUENCE: 772
acccattccc acctaaaggg ttttattctg aaacgcttct ctgctcaaat          50

<210> SEQ ID NO 773
<211> LENGTH: 50
<212> TYPE: DNA
<213> ORGANISM: Homo sapiens

<400> SEQUENCE: 773
ttttattcag accctattta tcagattaaa gatgagttct tctgacctca          50

<210> SEQ ID NO 774
<211> LENGTH: 50
<212> TYPE: DNA
<213> ORGANISM: Homo sapiens

<400> SEQUENCE: 774
actccaacag aggagcttat aagcctagct gggggagtag aacacattac          50
```

<210> SEQ ID NO 775
<211> LENGTH: 50
<212> TYPE: DNA
<213> ORGANISM: Homo sapiens

<400> SEQUENCE: 775
tctcattcct tttatgtgca gttttaggtg acttcctcaa attccccaat          50

<210> SEQ ID NO 776
<211> LENGTH: 50
<212> TYPE: DNA
<213> ORGANISM: Homo sapiens

<400> SEQUENCE: 776
accgagtttg gcatagactt gaaattaagg actaagatca gtctccagac          50

<210> SEQ ID NO 777
<211> LENGTH: 50
<212> TYPE: DNA
<213> ORGANISM: Homo sapiens

<400> SEQUENCE: 777
tagctcccat aattcctatg tgtgctggaa aggacccggt gagaggtaat          50

<210> SEQ ID NO 778
<211> LENGTH: 50
<212> TYPE: DNA
<213> ORGANISM: Homo sapiens

<400> SEQUENCE: 778
aaatgaggat ataggcactg agctgagtgc tactgtgcat tcctgaacca          50

<210> SEQ ID NO 779
<211> LENGTH: 50
<212> TYPE: DNA
<213> ORGANISM: Homo sapiens

<400> SEQUENCE: 779
aatagaagag tagaaacagt catgggtcca ccctgaggat ctccagtgac          50

<210> SEQ ID NO 780
<211> LENGTH: 50
<212> TYPE: DNA
<213> ORGANISM: Homo sapiens

<400> SEQUENCE: 780
caactctggc aacttccttt agaggacagc gtctagttct gtcattatac          50

<210> SEQ ID NO 781
<211> LENGTH: 50
<212> TYPE: DNA
<213> ORGANISM: Homo sapiens

<400> SEQUENCE: 781
tctgccctaa acaaataagt attttattac agaagaagag gaaaattgaa          50

<210> SEQ ID NO 782
<211> LENGTH: 50
<212> TYPE: DNA
<213> ORGANISM: Homo sapiens

<400> SEQUENCE: 782
agtcatcctc atggtcttgc tttctgtctc attcactcct atgcattgtc          50

<210> SEQ ID NO 783
<211> LENGTH: 50
<212> TYPE: DNA
<213> ORGANISM: Homo sapiens

<400> SEQUENCE: 783
ctacatccag aatgagtttt tgtaggctag ctggctcttc agttctccag          50

<210> SEQ ID NO 784
<211> LENGTH: 50
<212> TYPE: DNA
<213> ORGANISM: Homo sapiens

<400> SEQUENCE: 784
cagattactc tgtagaaagt accttcatgg catgccatga gcatatcact          50

<210> SEQ ID NO 785
<211> LENGTH: 50
<212> TYPE: DNA
<213> ORGANISM: Homo sapiens

<400> SEQUENCE: 785
ggatggatct tcagatccat ccctagaggg tatcaagggt tgagcaagaa          50

<210> SEQ ID NO 786
<211> LENGTH: 50
<212> TYPE: DNA
<213> ORGANISM: Homo sapiens

<400> SEQUENCE: 786
ttttaagtat gtgtttatta ccgtattatt taatctaccc cctaattacc          50

<210> SEQ ID NO 787
<211> LENGTH: 50
<212> TYPE: DNA
<213> ORGANISM: Homo sapiens

<400> SEQUENCE: 787
attgaaacca gtgagcatgc acatatatgt catttcatag cctgtgctaa          50

<210> SEQ ID NO 788
<211> LENGTH: 50
<212> TYPE: DNA
<213> ORGANISM: Homo sapiens

<400> SEQUENCE: 788
aactgtctaa cctacatgac aaaacacacc tcctcaggga gatagctgaa          50

<210> SEQ ID NO 789
<211> LENGTH: 50
<212> TYPE: DNA
<213> ORGANISM: Homo sapiens

<400> SEQUENCE: 789
attaaaagga gatcatatga gtggtccttc gtccaataca attggtatcc          50

<210> SEQ ID NO 790
<211> LENGTH: 50
<212> TYPE: DNA
<213> ORGANISM: Homo sapiens

<400> SEQUENCE: 790
aactctatgc atgttgtcta tggggactgc agagtattca tatttacaaa          50

```
<210> SEQ ID NO 791
<211> LENGTH: 50
<212> TYPE: DNA
<213> ORGANISM: Homo sapiens

<400> SEQUENCE: 791
ttctgtgcag actccagtca gccacattgg ttccaactga tttcagctag          50

<210> SEQ ID NO 792
<211> LENGTH: 50
<212> TYPE: DNA
<213> ORGANISM: Homo sapiens

<400> SEQUENCE: 792
aagaaataga caatgaagga aagctgtcaa acttcttgga ttttctggat          50

<210> SEQ ID NO 793
<211> LENGTH: 50
<212> TYPE: DNA
<213> ORGANISM: Homo sapiens

<400> SEQUENCE: 793
agtctggatg aatgctcccc aaagacaggg ttcaaggaat taccacaatg          50

<210> SEQ ID NO 794
<211> LENGTH: 50
<212> TYPE: DNA
<213> ORGANISM: Homo sapiens

<400> SEQUENCE: 794
ggagcgtgac agcattgctt cacctccctt ctttggtcct aaaattaggt          50

<210> SEQ ID NO 795
<211> LENGTH: 50
<212> TYPE: DNA
<213> ORGANISM: Homo sapiens

<400> SEQUENCE: 795
atgtgtcaag agagtaaaga agtccaaatc caggctgatc tggttttcaa          50

<210> SEQ ID NO 796
<211> LENGTH: 50
<212> TYPE: DNA
<213> ORGANISM: Homo sapiens

<400> SEQUENCE: 796
tctaaacgaa gcagatcttc aggcagccgt gttaggtatg atgtccccga          50

<210> SEQ ID NO 797
<211> LENGTH: 50
<212> TYPE: DNA
<213> ORGANISM: Homo sapiens

<400> SEQUENCE: 797
attctgatct tccttaacaa gcgtttctag aaggggatgc agagagtgtc          50

<210> SEQ ID NO 798
<211> LENGTH: 50
<212> TYPE: DNA
<213> ORGANISM: Homo sapiens

<400> SEQUENCE: 798
caaatcatca aaatatataa tccaggaaaa ttttcattat tctcaccttt          50
```

<210> SEQ ID NO 799
<211> LENGTH: 50
<212> TYPE: DNA
<213> ORGANISM: Homo sapiens

<400> SEQUENCE: 799
gtccctgtct tatttatctc tgggctacca gcattgtggg atatggtaca            50

<210> SEQ ID NO 800
<211> LENGTH: 50
<212> TYPE: DNA
<213> ORGANISM: Homo sapiens

<400> SEQUENCE: 800
tgagcaaaag ggccagccag gctcagagcc tgctactctg aagtctggca            50

<210> SEQ ID NO 801
<211> LENGTH: 50
<212> TYPE: DNA
<213> ORGANISM: Homo sapiens

<400> SEQUENCE: 801
aagactctgt tgttaattga ctgtaccctg gtgtgatgcg ccatcaggtc            50

<210> SEQ ID NO 802
<211> LENGTH: 50
<212> TYPE: DNA
<213> ORGANISM: Homo sapiens

<400> SEQUENCE: 802
cagaccaagg agaaggtgct gttccttgaa actaacaccc acattgttac            50

<210> SEQ ID NO 803
<211> LENGTH: 50
<212> TYPE: DNA
<213> ORGANISM: Homo sapiens

<400> SEQUENCE: 803
tccatgaata ggcattttat gtcaattctt taacgttgat atgttaagtt            50

<210> SEQ ID NO 804
<211> LENGTH: 50
<212> TYPE: DNA
<213> ORGANISM: Homo sapiens

<400> SEQUENCE: 804
tgctcatttt ggcaactgtg tccttccctc ttttactagc tgatattctg            50

<210> SEQ ID NO 805
<211> LENGTH: 50
<212> TYPE: DNA
<213> ORGANISM: Homo sapiens

<400> SEQUENCE: 805
agggcctggc actgctgacc ccaccttgtt ttccctccta ctctcccttc            50

<210> SEQ ID NO 806
<211> LENGTH: 50
<212> TYPE: DNA
<213> ORGANISM: Homo sapiens

<400> SEQUENCE: 806
tttatagcaa ggaggccttt gggctttaaa atcctcactt tatttacatc            50

<210> SEQ ID NO 807
<211> LENGTH: 50
<212> TYPE: DNA
<213> ORGANISM: Homo sapiens

<400> SEQUENCE: 807
ctgctctgat gccataaaac tgtaaaatca gctcagtaag cttctgagta        50

<210> SEQ ID NO 808
<211> LENGTH: 50
<212> TYPE: DNA
<213> ORGANISM: Homo sapiens

<400> SEQUENCE: 808
tggccgtccc tttgctaact accctatacc actaaaccac cctatactct        50

<210> SEQ ID NO 809
<211> LENGTH: 50
<212> TYPE: DNA
<213> ORGANISM: Homo sapiens

<400> SEQUENCE: 809
aaggtgaggt ctgggagtct tgggtcctgg cagacaagga gatgggatga        50

<210> SEQ ID NO 810
<211> LENGTH: 50
<212> TYPE: DNA
<213> ORGANISM: Homo sapiens

<400> SEQUENCE: 810
tttgtcatgt atctcagtgt ttcatttacc ttccatttgc tgtatgcccc        50

<210> SEQ ID NO 811
<211> LENGTH: 50
<212> TYPE: DNA
<213> ORGANISM: Homo sapiens

<400> SEQUENCE: 811
tcggaagaag tgaacaacat agagtaaagc accagcataa ccaaaatgac        50

<210> SEQ ID NO 812
<211> LENGTH: 50
<212> TYPE: DNA
<213> ORGANISM: Homo sapiens

<400> SEQUENCE: 812
tgtttcagtt gaagatgtta tatttattca cccttctgt ttctgcccat         50

<210> SEQ ID NO 813
<211> LENGTH: 50
<212> TYPE: DNA
<213> ORGANISM: Homo sapiens

<400> SEQUENCE: 813
tttttattgc aggaatatta gcctgaaaag gtttatccag aatcagtcgg        50

<210> SEQ ID NO 814
<211> LENGTH: 50
<212> TYPE: DNA
<213> ORGANISM: Homo sapiens

<400> SEQUENCE: 814
caaaacactt cacccactgc tcagctctttt gaaactactc agtgcagata       50

<210> SEQ ID NO 815
<211> LENGTH: 50
<212> TYPE: DNA
<213> ORGANISM: Homo sapiens

<400> SEQUENCE: 815
cttgggaggt cagcctcaag gtagaggccc ttactgctct ggaaatagtc    50

<210> SEQ ID NO 816
<211> LENGTH: 50
<212> TYPE: DNA
<213> ORGANISM: Homo sapiens

<400> SEQUENCE: 816
ccatgtcctg tgcaactaca gggagtcaaa gggttttcca ctggagcctg    50

<210> SEQ ID NO 817
<211> LENGTH: 50
<212> TYPE: DNA
<213> ORGANISM: Homo sapiens

<400> SEQUENCE: 817
agaaaaggaa aaagaacttt gaccctctgt tttgggtaga tgtcgatgaa    50

<210> SEQ ID NO 818
<211> LENGTH: 50
<212> TYPE: DNA
<213> ORGANISM: Homo sapiens

<400> SEQUENCE: 818
gtacacctaa aaaatgccca cccaaaatag aaatgttgag ttattaccaa    50

<210> SEQ ID NO 819
<211> LENGTH: 50
<212> TYPE: DNA
<213> ORGANISM: Homo sapiens

<400> SEQUENCE: 819
ttggaagagg gctcaggtgt ttgggaattt gatcaaatat ctttcctttg    50

<210> SEQ ID NO 820
<211> LENGTH: 50
<212> TYPE: DNA
<213> ORGANISM: Homo sapiens

<400> SEQUENCE: 820
tcctctagct agtgcccata cagaaaattc tatcaccata caaaatttaa    50

<210> SEQ ID NO 821
<211> LENGTH: 50
<212> TYPE: DNA
<213> ORGANISM: Homo sapiens

<400> SEQUENCE: 821
gttccagctt tggcttccga agtctatttg tcacaaaagt gcctcctgtt    50

<210> SEQ ID NO 822
<211> LENGTH: 50
<212> TYPE: DNA
<213> ORGANISM: Homo sapiens

<400> SEQUENCE: 822
tatagatgaa cccaagctga agaaacagag ccacttcagt gaccatctac    50

```
<210> SEQ ID NO 823
<211> LENGTH: 50
<212> TYPE: DNA
<213> ORGANISM: Homo sapiens

<400> SEQUENCE: 823
ctctttgcaa aagttagtgt gcttatatta aggtcaggaa ggtagaagtg            50

<210> SEQ ID NO 824
<211> LENGTH: 50
<212> TYPE: DNA
<213> ORGANISM: Homo sapiens

<400> SEQUENCE: 824
aatgggataa tgaccacaaa ggcatttcag agatcttcaa gacatagcta            50

<210> SEQ ID NO 825
<211> LENGTH: 50
<212> TYPE: DNA
<213> ORGANISM: Homo sapiens

<400> SEQUENCE: 825
gctaaaggcc ctcatggaga gaagacagtc cattaacagc tactctaaat            50

<210> SEQ ID NO 826
<211> LENGTH: 50
<212> TYPE: DNA
<213> ORGANISM: Homo sapiens

<400> SEQUENCE: 826
aacaagttat tccatgcttc agtctctctt tctcctctag atcacaaagg            50

<210> SEQ ID NO 827
<211> LENGTH: 50
<212> TYPE: DNA
<213> ORGANISM: Homo sapiens

<400> SEQUENCE: 827
ttgtggttcc cttacacccc catctctgta aatagcctca tatttgagta            50

<210> SEQ ID NO 828
<211> LENGTH: 50
<212> TYPE: DNA
<213> ORGANISM: Homo sapiens

<400> SEQUENCE: 828
ttccaattgt tttgatgttg cgattactta attattccat ctggaattta            50

<210> SEQ ID NO 829
<211> LENGTH: 50
<212> TYPE: DNA
<213> ORGANISM: Homo sapiens

<400> SEQUENCE: 829
tcaaacattg cttctgcgct attctctttc ttcttctgga acttcaacta            50

<210> SEQ ID NO 830
<211> LENGTH: 50
<212> TYPE: DNA
<213> ORGANISM: Homo sapiens

<400> SEQUENCE: 830
gagctatagt taaggaggca acaaaaaact gttaaaaagt tcagagcaag            50
```

<210> SEQ ID NO 831
<211> LENGTH: 50
<212> TYPE: DNA
<213> ORGANISM: Homo sapiens

<400> SEQUENCE: 831
catcatacca agagttattt tctaactctg agacagtttg ttgggtgtga            50

<210> SEQ ID NO 832
<211> LENGTH: 50
<212> TYPE: DNA
<213> ORGANISM: Homo sapiens

<400> SEQUENCE: 832
agtcctgaga ccagataaga tcacctcagg aatgaatata gatagggaag            50

<210> SEQ ID NO 833
<211> LENGTH: 50
<212> TYPE: DNA
<213> ORGANISM: Homo sapiens

<400> SEQUENCE: 833
cgatgtcaca tgcctaaaac atggcatagc tggcatctga atatttgttc            50

<210> SEQ ID NO 834
<211> LENGTH: 50
<212> TYPE: DNA
<213> ORGANISM: Homo sapiens

<400> SEQUENCE: 834
ccttagctgc atgtggctct acacatttat ttatccactg accatgtcaa            50

<210> SEQ ID NO 835
<211> LENGTH: 50
<212> TYPE: DNA
<213> ORGANISM: Homo sapiens

<400> SEQUENCE: 835
ctgaacgaaa agttcatttt acttatacat tacatataat tagactccca            50

<210> SEQ ID NO 836
<211> LENGTH: 50
<212> TYPE: DNA
<213> ORGANISM: Homo sapiens

<400> SEQUENCE: 836
ctggttctgg agacagaagc tatgagttca gtgctacata actctctctc            50

<210> SEQ ID NO 837
<211> LENGTH: 50
<212> TYPE: DNA
<213> ORGANISM: Homo sapiens

<400> SEQUENCE: 837
gtaatttctt aaaataagac aacaatgaag tttgcttatc aattgacttt            50

<210> SEQ ID NO 838
<211> LENGTH: 50
<212> TYPE: DNA
<213> ORGANISM: Homo sapiens

<400> SEQUENCE: 838
atagactaaa atcttttctt ttggtctatt ttggtgaaaa gcagatatta            50

<210> SEQ ID NO 839
<211> LENGTH: 50
<212> TYPE: DNA
<213> ORGANISM: Homo sapiens

<400> SEQUENCE: 839
ttgagctgaa ggaggcttgg atctgagaga ctgaatgtag aagagtcccc           50

<210> SEQ ID NO 840
<211> LENGTH: 50
<212> TYPE: DNA
<213> ORGANISM: Homo sapiens

<400> SEQUENCE: 840
tttggctctg atctgtctta atagtcttat ctgaatcttc tctgacccca           50

<210> SEQ ID NO 841
<211> LENGTH: 50
<212> TYPE: DNA
<213> ORGANISM: Homo sapiens

<400> SEQUENCE: 841
tggtatgtgt aagtttttaa cacatgtgta gaccctggtc tatgcaagca           50

<210> SEQ ID NO 842
<211> LENGTH: 50
<212> TYPE: DNA
<213> ORGANISM: Homo sapiens

<400> SEQUENCE: 842
tatagatatt tttgaacagc agcccagtac ctggatgttg ctagatgtga           50

<210> SEQ ID NO 843
<211> LENGTH: 50
<212> TYPE: DNA
<213> ORGANISM: Homo sapiens

<400> SEQUENCE: 843
cgtttccata atgacagatg cttcttaaac attcagcttc tgtttcccaa           50

<210> SEQ ID NO 844
<211> LENGTH: 50
<212> TYPE: DNA
<213> ORGANISM: Homo sapiens

<400> SEQUENCE: 844
tgcccctcac ttttgcttaa gaaagcctga cgggttctat tctttgcaac           50

<210> SEQ ID NO 845
<211> LENGTH: 50
<212> TYPE: DNA
<213> ORGANISM: Homo sapiens

<400> SEQUENCE: 845
gaaagtggaa ggtgattttc tgagtttcct tggaaacctg agtccttata           50

<210> SEQ ID NO 846
<211> LENGTH: 50
<212> TYPE: DNA
<213> ORGANISM: Homo sapiens

<400> SEQUENCE: 846
gctgagctgc tgtaattaag ctttgattag ccggctataa attcccttc            50

```
<210> SEQ ID NO 847
<211> LENGTH: 50
<212> TYPE: DNA
<213> ORGANISM: Homo sapiens

<400> SEQUENCE: 847
tgaaacagag aggctcaatc tggtggagtc aaaatgcaaa gacgtgttgg            50

<210> SEQ ID NO 848
<211> LENGTH: 50
<212> TYPE: DNA
<213> ORGANISM: Homo sapiens

<400> SEQUENCE: 848
gagatcaaaa ctccagcttc ggtgcacagg agaacacaga acctcctccc            50

<210> SEQ ID NO 849
<211> LENGTH: 50
<212> TYPE: DNA
<213> ORGANISM: Homo sapiens

<400> SEQUENCE: 849
acctagaggt gggcattgag gcatgtgggt tgatgtatga ggttccttgg            50

<210> SEQ ID NO 850
<211> LENGTH: 50
<212> TYPE: DNA
<213> ORGANISM: Homo sapiens

<400> SEQUENCE: 850
atcagtcaat ctttccaact cccttctctg taataacact acgctaggtc            50

<210> SEQ ID NO 851
<211> LENGTH: 50
<212> TYPE: DNA
<213> ORGANISM: Homo sapiens

<400> SEQUENCE: 851
tgggacttcc aggggctcag cctaaggatg gtgcccccag tgtttattcc            50

<210> SEQ ID NO 852
<211> LENGTH: 50
<212> TYPE: DNA
<213> ORGANISM: Homo sapiens

<400> SEQUENCE: 852
ccccacatac catgttggcc tctcttacca tgaacagcaa cactcgtgac            50

<210> SEQ ID NO 853
<211> LENGTH: 50
<212> TYPE: DNA
<213> ORGANISM: Homo sapiens

<400> SEQUENCE: 853
attctagttt cctataactg ggaagtctcg ctgtgagttg acttctgtat            50

<210> SEQ ID NO 854
<211> LENGTH: 50
<212> TYPE: DNA
<213> ORGANISM: Homo sapiens

<400> SEQUENCE: 854
ttttacaaac aaagcacaaa accagagact gaagaacact tttggaagca            50
```

<210> SEQ ID NO 855
<211> LENGTH: 50
<212> TYPE: DNA
<213> ORGANISM: Homo sapiens

<400> SEQUENCE: 855
ctccctccag aaagttccaa tgctttggct gtgcatcaca tctaatatgg          50

<210> SEQ ID NO 856
<211> LENGTH: 50
<212> TYPE: DNA
<213> ORGANISM: Homo sapiens

<400> SEQUENCE: 856
atcacatcta atatggagag gcacccttcc ccatgagtcc tgccaggcaa          50

<210> SEQ ID NO 857
<211> LENGTH: 50
<212> TYPE: DNA
<213> ORGANISM: Homo sapiens

<400> SEQUENCE: 857
tgtataccct gcctaatttc atcaattctc agaccaccag tgctgtaaaa          50

<210> SEQ ID NO 858
<211> LENGTH: 50
<212> TYPE: DNA
<213> ORGANISM: Homo sapiens

<400> SEQUENCE: 858
gctatgaaaa ggaggcgagt gtgtagccca ttcagctgat gggaagccca          50

<210> SEQ ID NO 859
<211> LENGTH: 50
<212> TYPE: DNA
<213> ORGANISM: Homo sapiens

<400> SEQUENCE: 859
tcacatcagc acggcaagca tgggaagatg ggagaaaatg gagactcaga          50

<210> SEQ ID NO 860
<211> LENGTH: 50
<212> TYPE: DNA
<213> ORGANISM: Homo sapiens

<400> SEQUENCE: 860
acacacatta aatatcctta ctcaatccag ctttaccaag gagagctcat          50

<210> SEQ ID NO 861
<211> LENGTH: 50
<212> TYPE: DNA
<213> ORGANISM: Homo sapiens

<400> SEQUENCE: 861
gcaattccag tcaacccatg ataaaaccgg tttggttcaa ttttagtaac          50

<210> SEQ ID NO 862
<211> LENGTH: 50
<212> TYPE: DNA
<213> ORGANISM: Homo sapiens

<400> SEQUENCE: 862
acatgggcac aggctcagcg ggactcctgg aatgttctct ctttctccac          50

<210> SEQ ID NO 863
<211> LENGTH: 50
<212> TYPE: DNA
<213> ORGANISM: Homo sapiens

<400> SEQUENCE: 863
aataggtgta ttctgagaac tgcaaatgca gagcagtaaa aagcggagac           50

<210> SEQ ID NO 864
<211> LENGTH: 50
<212> TYPE: DNA
<213> ORGANISM: Homo sapiens

<400> SEQUENCE: 864
ggtttccaac tgcctccatt tgctaaggtt ggtcatgggg tatttgagag           50

<210> SEQ ID NO 865
<211> LENGTH: 50
<212> TYPE: DNA
<213> ORGANISM: Homo sapiens

<400> SEQUENCE: 865
ggccagttca ctttaacagg aaaaggaaat tgctttgctc ttaggtaagc           50

<210> SEQ ID NO 866
<211> LENGTH: 50
<212> TYPE: DNA
<213> ORGANISM: Homo sapiens

<400> SEQUENCE: 866
acagggcaga cattagtcac acagtggaga cttcgtgctc agagaagaga           50

<210> SEQ ID NO 867
<211> LENGTH: 50
<212> TYPE: DNA
<213> ORGANISM: Homo sapiens

<400> SEQUENCE: 867
catgcatgtt aatacagaat aatgaatttt aggaactggg tctccagcct           50

<210> SEQ ID NO 868
<211> LENGTH: 50
<212> TYPE: DNA
<213> ORGANISM: Homo sapiens

<400> SEQUENCE: 868
ttatgtaaaa ctaagaattt taactgtatt ctaacctgtt tctctagcca           50

<210> SEQ ID NO 869
<211> LENGTH: 50
<212> TYPE: DNA
<213> ORGANISM: Homo sapiens

<400> SEQUENCE: 869
tctgagctct gccatttact ctctgtatta cctcagacaa gttacataat           50

<210> SEQ ID NO 870
<211> LENGTH: 50
<212> TYPE: DNA
<213> ORGANISM: Homo sapiens

<400> SEQUENCE: 870
tctgtaacat caaaaaagtt aatagtcacc accctaggga catctgagaa           50

```
<210> SEQ ID NO 871
<211> LENGTH: 50
<212> TYPE: DNA
<213> ORGANISM: Homo sapiens

<400> SEQUENCE: 871
ttcacggctt gtgtcaaaca tctaaaatct agaatattct tgtttgacgg          50

<210> SEQ ID NO 872
<211> LENGTH: 50
<212> TYPE: DNA
<213> ORGANISM: Homo sapiens

<400> SEQUENCE: 872
agatgttcat gctctaatcc ttagaacctg taactattac tttacatgac          50

<210> SEQ ID NO 873
<211> LENGTH: 50
<212> TYPE: DNA
<213> ORGANISM: Homo sapiens

<400> SEQUENCE: 873
cctaggcctt tgccctggca ctgatggtgc aactttgggc aagtcagcaa          50

<210> SEQ ID NO 874
<211> LENGTH: 50
<212> TYPE: DNA
<213> ORGANISM: Homo sapiens

<400> SEQUENCE: 874
aggctcaaga tggcagtggt catcctattt ccagtttaac ggactcttac          50

<210> SEQ ID NO 875
<211> LENGTH: 50
<212> TYPE: DNA
<213> ORGANISM: Homo sapiens

<400> SEQUENCE: 875
aaagttcaga aagtgatgcc tgcattcagt taaaagaccc aaactctgac          50

<210> SEQ ID NO 876
<211> LENGTH: 50
<212> TYPE: DNA
<213> ORGANISM: Homo sapiens

<400> SEQUENCE: 876
gaaaggaagg aaatctcaat gaactgacat ggattgattt ccaggatata          50

<210> SEQ ID NO 877
<211> LENGTH: 50
<212> TYPE: DNA
<213> ORGANISM: Homo sapiens

<400> SEQUENCE: 877
ggagaaatat tttcagactg ctgcttggtg gtgtcctctc tccaaacttc          50

<210> SEQ ID NO 878
<211> LENGTH: 50
<212> TYPE: DNA
<213> ORGANISM: Homo sapiens

<400> SEQUENCE: 878
cgttgtgtat tcatgatggt ggcatgttgc ctttcctccc ctccatatca          50
```

```
<210> SEQ ID NO 879
<211> LENGTH: 50
<212> TYPE: DNA
<213> ORGANISM: Homo sapiens

<400> SEQUENCE: 879
aattaaccct tccatatttt agatgggtcc taaagcacat tgcattcaac            50

<210> SEQ ID NO 880
<211> LENGTH: 50
<212> TYPE: DNA
<213> ORGANISM: Homo sapiens

<400> SEQUENCE: 880
ctttaataaa attccaaggc attactcgaa taggccagat gattgaaaag            50

<210> SEQ ID NO 881
<211> LENGTH: 50
<212> TYPE: DNA
<213> ORGANISM: Homo sapiens

<400> SEQUENCE: 881
tctggattcc agagccccac aggacccttt gtgtccacag tgctgacaca            50

<210> SEQ ID NO 882
<211> LENGTH: 50
<212> TYPE: DNA
<213> ORGANISM: Homo sapiens

<400> SEQUENCE: 882
tgaaatattt tcatgcattg cctcagagga agggtgaccg aaggagagct            50

<210> SEQ ID NO 883
<211> LENGTH: 50
<212> TYPE: DNA
<213> ORGANISM: Homo sapiens

<400> SEQUENCE: 883
aaagaccagc tagacaaaaa taaattagta aataaataca gaacttgaac            50

<210> SEQ ID NO 884
<211> LENGTH: 50
<212> TYPE: DNA
<213> ORGANISM: Homo sapiens

<400> SEQUENCE: 884
ctaccttccc ctccagtgta atcaagggaa ataagatgac ataccttcat            50

<210> SEQ ID NO 885
<211> LENGTH: 50
<212> TYPE: DNA
<213> ORGANISM: Homo sapiens

<400> SEQUENCE: 885
ctttgtcatc atagcttgaa acttctggaa ctctggccga ttaatgcctg            50

<210> SEQ ID NO 886
<211> LENGTH: 50
<212> TYPE: DNA
<213> ORGANISM: Homo sapiens

<400> SEQUENCE: 886
atcattaaaa ggagctaata ttactacctt cttgataatg ttggtgggtt            50
```

<210> SEQ ID NO 887
<211> LENGTH: 50
<212> TYPE: DNA
<213> ORGANISM: Homo sapiens

<400> SEQUENCE: 887
attctctcaa atctaaggat gaactgcatt ccagtaaaac tttaagtaaa           50

<210> SEQ ID NO 888
<211> LENGTH: 50
<212> TYPE: DNA
<213> ORGANISM: Homo sapiens

<400> SEQUENCE: 888
tttcactgac acaggcaaat ttttctgttg agagggatga gtctgaaggc           50

<210> SEQ ID NO 889
<211> LENGTH: 50
<212> TYPE: DNA
<213> ORGANISM: Homo sapiens

<400> SEQUENCE: 889
cacacaaaag cctcaagcta gccctctgc ggtagcaccg gcccatgtgt            50

<210> SEQ ID NO 890
<211> LENGTH: 50
<212> TYPE: DNA
<213> ORGANISM: Homo sapiens

<400> SEQUENCE: 890
tccatctcag tgcactctca atcttatcga tgacctattg tctaaagtaa           50

<210> SEQ ID NO 891
<211> LENGTH: 50
<212> TYPE: DNA
<213> ORGANISM: Homo sapiens

<400> SEQUENCE: 891 ctcccttct ccctgggggc aattggttgt aataggaaga ttacaggtta            50

<210> SEQ ID NO 892
<211> LENGTH: 50
<212> TYPE: DNA
<213> ORGANISM: Homo sapiens

<400> SEQUENCE: 892
ttgtttcttg tgtggataaa agatttttgt aaagtgtata taggtaccac           50

<210> SEQ ID NO 893
<211> LENGTH: 50
<212> TYPE: DNA
<213> ORGANISM: Homo sapiens

<400> SEQUENCE: 893
acaacaaaag cctagtctct ctagctaaag gactaagaac ggggcagcct           50

<210> SEQ ID NO 894
<211> LENGTH: 50
<212> TYPE: DNA
<213> ORGANISM: Homo sapiens

<400> SEQUENCE: 894
acctctccat ttcctcacta gggtggagtc agaaaacttc atggagagac           50

<210> SEQ ID NO 895
<211> LENGTH: 50
<212> TYPE: DNA
<213> ORGANISM: Homo sapiens

<400> SEQUENCE: 895
gccaaaatcc tactcaaaaa ccaaagtggg taggatttgt tttcagtggg        50

<210> SEQ ID NO 896
<211> LENGTH: 50
<212> TYPE: DNA
<213> ORGANISM: Homo sapiens

<400> SEQUENCE: 896
aatttctatt aatctgtttg agttcactga ttcttagttg tgttgagtcc        50

<210> SEQ ID NO 897
<211> LENGTH: 50
<212> TYPE: DNA
<213> ORGANISM: Homo sapiens

<400> SEQUENCE: 897
ttctgattcc tcagcaatat aatcccatga tccacattta gtttgtactt        50

<210> SEQ ID NO 898
<211> LENGTH: 50
<212> TYPE: DNA
<213> ORGANISM: Homo sapiens

<400> SEQUENCE: 898
gatacggcta ttctgaaggt tcagagatgt acttatttcc tggaagatca        50

<210> SEQ ID NO 899
<211> LENGTH: 50
<212> TYPE: DNA
<213> ORGANISM: Homo sapiens

<400> SEQUENCE: 899
cctgtttctt aatgtggggc tttatagcta gtgtagctgc ttcttaaaac        50

<210> SEQ ID NO 900
<211> LENGTH: 50
<212> TYPE: DNA
<213> ORGANISM: Homo sapiens

<400> SEQUENCE: 900
cctagtgata cggttggtat tcatattaaa agtaaacatt tggattgcca        50

<210> SEQ ID NO 901
<211> LENGTH: 50
<212> TYPE: DNA
<213> ORGANISM: Homo sapiens

<400> SEQUENCE: 901
ccaggagctt atcaccctcc ccctacacac aggtaagggg tagcatgtgc        50

<210> SEQ ID NO 902
<211> LENGTH: 50
<212> TYPE: DNA
<213> ORGANISM: Homo sapiens

<400> SEQUENCE: 902
gagacagaag tgaacagaat cgttctgatc aagggctgta agtactagaa        50

<210> SEQ ID NO 903
<211> LENGTH: 50
<212> TYPE: DNA
<213> ORGANISM: Homo sapiens

<400> SEQUENCE: 903
agccaatttt cacattcatg aaaattttag tctcattttt ataaatgcca          50

<210> SEQ ID NO 904
<211> LENGTH: 50
<212> TYPE: DNA
<213> ORGANISM: Homo sapiens

<400> SEQUENCE: 904
ttaggaatta gatttatgga gcaaaaatat cctacattac agaataagag          50

<210> SEQ ID NO 905
<211> LENGTH: 50
<212> TYPE: DNA
<213> ORGANISM: Homo sapiens

<400> SEQUENCE: 905
caaacaaatc atatccaaac cacagcacca tatgagccca caattctact          50

<210> SEQ ID NO 906
<211> LENGTH: 50
<212> TYPE: DNA
<213> ORGANISM: Homo sapiens

<400> SEQUENCE: 906
atcctttatc ttttgactaa accagtcggt tttctacact gctttatttc          50

<210> SEQ ID NO 907
<211> LENGTH: 50
<212> TYPE: DNA
<213> ORGANISM: Homo sapiens

<400> SEQUENCE: 907
catagagtct aaaagtagag ctttgatgtc taccaactaa ttgagctacc          50

<210> SEQ ID NO 908
<211> LENGTH: 50
<212> TYPE: DNA
<213> ORGANISM: Homo sapiens

<400> SEQUENCE: 908
tctggttatg gtacacacct gttctttgtg tcactgactt tggtcaatac          50

<210> SEQ ID NO 909
<211> LENGTH: 50
<212> TYPE: DNA
<213> ORGANISM: Homo sapiens

<400> SEQUENCE: 909
aataggtact gacaggttga gtcatccgtc caggtcccat aggcgtaagt          50

<210> SEQ ID NO 910
<211> LENGTH: 50
<212> TYPE: DNA
<213> ORGANISM: Homo sapiens

<400> SEQUENCE: 910
tctgaacaat ttgggatctc ttttaacttg agggtctctt tcgactacta          50

<210> SEQ ID NO 911
<211> LENGTH: 50
<212> TYPE: DNA
<213> ORGANISM: Homo sapiens

<400> SEQUENCE: 911
acaactattt ctgtatttac ttcattgtct ccaaagtgct agagtgcata        50

<210> SEQ ID NO 912
<211> LENGTH: 50
<212> TYPE: DNA
<213> ORGANISM: Homo sapiens

<400> SEQUENCE: 912
gactcacaca aggaaagcag ctgttcagca taaaccacat ggttgtacag        50

<210> SEQ ID NO 913
<211> LENGTH: 50
<212> TYPE: DNA
<213> ORGANISM: Homo sapiens

<400> SEQUENCE: 913
acttcgctcc agtacttctc cccttggctt attttgcttt gcatctttga        50

<210> SEQ ID NO 914
<211> LENGTH: 50
<212> TYPE: DNA
<213> ORGANISM: Homo sapiens

<400> SEQUENCE: 914
tataagccga ttctgagagt gggtgctgac atatggaagt gttttttgaca       50

<210> SEQ ID NO 915
<211> LENGTH: 50
<212> TYPE: DNA
<213> ORGANISM: Homo sapiens

<400> SEQUENCE: 915
tccccatcca aaaggtaaca tagcaagcct gactgttatc ctttgaaaga        50

<210> SEQ ID NO 916
<211> LENGTH: 50
<212> TYPE: DNA
<213> ORGANISM: Homo sapiens

<400> SEQUENCE: 916
catgtcccaa caatcatttc tgattactca ggattctaca gttcaactgc        50

<210> SEQ ID NO 917
<211> LENGTH: 50
<212> TYPE: DNA
<213> ORGANISM: Homo sapiens

<400> SEQUENCE: 917
tttatttaaa gctaccgaaa actagtaaat ctgagtcttc atgaataggg        50

<210> SEQ ID NO 918
<211> LENGTH: 50
<212> TYPE: DNA
<213> ORGANISM: Homo sapiens

<400> SEQUENCE: 918
agcctgaatc ctataatcat gtccccacat atctaagttt taggagttca        50

```
<210> SEQ ID NO 919
<211> LENGTH: 50
<212> TYPE: DNA
<213> ORGANISM: Homo sapiens

<400> SEQUENCE: 919
aacccacctt tcctctttcc ttccttattc ctcttctaca cagtcttcat            50

<210> SEQ ID NO 920
<211> LENGTH: 50
<212> TYPE: DNA
<213> ORGANISM: Homo sapiens

<400> SEQUENCE: 920
acactagtat aggagaaggt gacagatttg ggggtttgaa aagaatggag            50

<210> SEQ ID NO 921
<211> LENGTH: 50
<212> TYPE: DNA
<213> ORGANISM: Homo sapiens

<400> SEQUENCE: 921
agaaaacttt gttctgataa agctctagaa ttaattttc tctaatgcag             50

<210> SEQ ID NO 922
<211> LENGTH: 50
<212> TYPE: DNA
<213> ORGANISM: Homo sapiens

<400> SEQUENCE: 922
aaagaacaga agaccttcag ggaactagag tttctgagag caaggtgaga            50

<210> SEQ ID NO 923
<211> LENGTH: 50
<212> TYPE: DNA
<213> ORGANISM: Homo sapiens

<400> SEQUENCE: 923
agaaatcact acttctgcat ctttgaagtt attaatagtg gcggtatatt            50

<210> SEQ ID NO 924
<211> LENGTH: 50
<212> TYPE: DNA
<213> ORGANISM: Homo sapiens

<400> SEQUENCE: 924
ggttacccca aaacttagtg acttaaaaca atagccattt atgtagctca            50

<210> SEQ ID NO 925
<211> LENGTH: 50
<212> TYPE: DNA
<213> ORGANISM: Homo sapiens

<400> SEQUENCE: 925
atgagaggga gtggtaggta cttgctcctt gttagcagaa cagaatagct            50

<210> SEQ ID NO 926
<211> LENGTH: 50
<212> TYPE: DNA
<213> ORGANISM: Homo sapiens

<400> SEQUENCE: 926
ttggtcctgg tggtctggaa acttcctttg cctttaccag aaagctttac            50
```

<210> SEQ ID NO 927
<211> LENGTH: 50
<212> TYPE: DNA
<213> ORGANISM: Homo sapiens

<400> SEQUENCE: 927
taggccctgc ctccaagtgt cctgaggatt gaatgagtca gtatgctgcc    50

<210> SEQ ID NO 928
<211> LENGTH: 50
<212> TYPE: DNA
<213> ORGANISM: Homo sapiens

<400> SEQUENCE: 928
tggaaagaca taggttatcc agtccattaa aggtgttgtg tatctaatct    50

<210> SEQ ID NO 929
<211> LENGTH: 50
<212> TYPE: DNA
<213> ORGANISM: Homo sapiens

<400> SEQUENCE: 929
tctccaaatg cttgctttgg tttattttgt aggtgggaat ctgacagcta    50

<210> SEQ ID NO 930
<211> LENGTH: 50
<212> TYPE: DNA
<213> ORGANISM: Homo sapiens

<400> SEQUENCE: 930
ttttgagtgc aacgttcctt ttcatttatg attggaagtt gtttctcaga    50

<210> SEQ ID NO 931
<211> LENGTH: 50
<212> TYPE: DNA
<213> ORGANISM: Homo sapiens

<400> SEQUENCE: 931
aatttaggta aaccataacc aaggtgattc taggtactta attctcacac    50

<210> SEQ ID NO 932
<211> LENGTH: 50
<212> TYPE: DNA
<213> ORGANISM: Homo sapiens

<400> SEQUENCE: 932
caaacaagca aacgattcat aaacctaggg ccaacctgag tataatacaa    50

<210> SEQ ID NO 933
<211> LENGTH: 50
<212> TYPE: DNA
<213> ORGANISM: Homo sapiens

<400> SEQUENCE: 933
ggaaacattt agagcatttt gaaattgtca ttacattaat atgcttaatc    50

<210> SEQ ID NO 934
<211> LENGTH: 50
<212> TYPE: DNA
<213> ORGANISM: Homo sapiens

<400> SEQUENCE: 934
taatctgtct acaagcctct ttgctaatat acttactaaa atcagcacta    50

<210> SEQ ID NO 935
<211> LENGTH: 50
<212> TYPE: DNA
<213> ORGANISM: Homo sapiens

<400> SEQUENCE: 935
tcagctgctt tagctatcac agctaagtca ccagatctgt aaatgaagaa        50

<210> SEQ ID NO 936
<211> LENGTH: 50
<212> TYPE: DNA
<213> ORGANISM: Homo sapiens

<400> SEQUENCE: 936
gaagaaaagc atgcccacaa tcactacttt gtaacattgt gatgggggga        50

<210> SEQ ID NO 937
<211> LENGTH: 50
<212> TYPE: DNA
<213> ORGANISM: Homo sapiens

<400> SEQUENCE: 937
ggggctaaga ctcagcttaa ccatcttggg ctgcatgctc tatttctgga        50

<210> SEQ ID NO 938
<211> LENGTH: 50
<212> TYPE: DNA
<213> ORGANISM: Homo sapiens

<400> SEQUENCE: 938
agtagctgtt tattaacctt aagccagtga atgcttttaa ttgatgacct        50

<210> SEQ ID NO 939
<211> LENGTH: 50
<212> TYPE: DNA
<213> ORGANISM: Homo sapiens

<400> SEQUENCE: 939
cttggtagca tatgttattt tttgacatta ataatagtca ttatgaccga        50

<210> SEQ ID NO 940
<211> LENGTH: 50
<212> TYPE: DNA
<213> ORGANISM: Homo sapiens

<400> SEQUENCE: 940
cagctggagg ccattattct aagtgaacag aaaaccaaat actgcttgtc        50

<210> SEQ ID NO 941
<211> LENGTH: 50
<212> TYPE: DNA
<213> ORGANISM: Homo sapiens

<400> SEQUENCE: 941
tgcatgtgtt cctggagcaa catacacaca gtttgcagga gccaaagtac        50

<210> SEQ ID NO 942
<211> LENGTH: 50
<212> TYPE: DNA
<213> ORGANISM: Homo sapiens

<400> SEQUENCE: 942
gacaactaag cacaatgatt ctaagcagga gtctttcagg actgaaaaaa        50

<210> SEQ ID NO 943
<211> LENGTH: 50
<212> TYPE: DNA
<213> ORGANISM: Homo sapiens

<400> SEQUENCE: 943
ccactgagag tgaatgtcta atgggagatg ggaaaaggcc taagatataa     50

<210> SEQ ID NO 944
<211> LENGTH: 50
<212> TYPE: DNA
<213> ORGANISM: Homo sapiens

<400> SEQUENCE: 944
aattcagagt catccttgac tctcctcttt ccccacctcc aatgttcagt     50

<210> SEQ ID NO 945
<211> LENGTH: 50
<212> TYPE: DNA
<213> ORGANISM: Homo sapiens

<400> SEQUENCE: 945
cttgcctttg ttctctctta atggtgcctt ttaatggaca aagcttttaa     50

<210> SEQ ID NO 946
<211> LENGTH: 50
<212> TYPE: DNA
<213> ORGANISM: Homo sapiens

<400> SEQUENCE: 946
atgtgaaatt ttggcaaatt atgaaaaaat ttattttta c attgtgtttt     50

<210> SEQ ID NO 947
<211> LENGTH: 50
<212> TYPE: DNA
<213> ORGANISM: Homo sapiens

<400> SEQUENCE: 947
gtgtagtata ttagtcaacg taggttcagt tgcactgcag taagaatccc     50

<210> SEQ ID NO 948
<211> LENGTH: 50
<212> TYPE: DNA
<213> ORGANISM: Homo sapiens

<400> SEQUENCE: 948
tcatgcttat gtcctatgat gtgcacataa acatttggcc aaagcctttc     50

<210> SEQ ID NO 949
<211> LENGTH: 50
<212> TYPE: DNA
<213> ORGANISM: Homo sapiens

<400> SEQUENCE: 949
tcatctatgg acttttccca ggggtaactc tgataccact aactgcatct     50

<210> SEQ ID NO 950
<211> LENGTH: 50
<212> TYPE: DNA
<213> ORGANISM: Homo sapiens

<400> SEQUENCE: 950
acaggccgtc attctaacac tgtcattcaa aatgggattt tcttccttga     50

```
<210> SEQ ID NO 951
<211> LENGTH: 50
<212> TYPE: DNA
<213> ORGANISM: Homo sapiens

<400> SEQUENCE: 951
tagttgagga aatcaaggca gaaaaagatt aatgacagtc aatttcacag        50

<210> SEQ ID NO 952
<211> LENGTH: 50
<212> TYPE: DNA
<213> ORGANISM: Homo sapiens

<400> SEQUENCE: 952
ttccactaat ggactcctag gtattccatc actcagctta attttctcgg        50

<210> SEQ ID NO 953
<211> LENGTH: 50
<212> TYPE: DNA
<213> ORGANISM: Homo sapiens

<400> SEQUENCE: 953
ttgtcaagga aatggatgtg caatgcttct ttttgagctc tgtcttttc         50

<210> SEQ ID NO 954
<211> LENGTH: 50
<212> TYPE: DNA
<213> ORGANISM: Homo sapiens

<400> SEQUENCE: 954
tctcaggcct aggcttttat aagatttctg ttgatgcaga agctactgac        50

<210> SEQ ID NO 955
<211> LENGTH: 50
<212> TYPE: DNA
<213> ORGANISM: Homo sapiens

<400> SEQUENCE: 955
accaggctat ttgaacccat tcagttatct ctggctcatg cacctcatcc        50

<210> SEQ ID NO 956
<211> LENGTH: 50
<212> TYPE: DNA
<213> ORGANISM: Homo sapiens

<400> SEQUENCE: 956
acagaaggca cattctcatg cacagatgca tattcatcca gcaagtattc        50

<210> SEQ ID NO 957
<211> LENGTH: 50
<212> TYPE: DNA
<213> ORGANISM: Homo sapiens

<400> SEQUENCE: 957
ctgacaagag tgcatttgat tgctgaaacc agttcagctg gctaagggtc        50

<210> SEQ ID NO 958
<211> LENGTH: 50
<212> TYPE: DNA
<213> ORGANISM: Homo sapiens

<400> SEQUENCE: 958
tatataactc taaggtcatg gtaattaata tgttttctat tgctgtgtat        50
```

<210> SEQ ID NO 959
<211> LENGTH: 50
<212> TYPE: DNA
<213> ORGANISM: Homo sapiens

<400> SEQUENCE: 959
tctaggaact ccaataaact tacaggatga ttggagggta agaaggtcag       50

<210> SEQ ID NO 960
<211> LENGTH: 50
<212> TYPE: DNA
<213> ORGANISM: Homo sapiens

<400> SEQUENCE: 960
gcagtctcat cgctttgtcc agcatgcact tcttcctgct tgtctgcact       50

<210> SEQ ID NO 961
<211> LENGTH: 50
<212> TYPE: DNA
<213> ORGANISM: Homo sapiens

<400> SEQUENCE: 961
atgatgttgt cctagtgata tgctgggaac tgtacttact gttcctccag       50

<210> SEQ ID NO 962
<211> LENGTH: 50
<212> TYPE: DNA
<213> ORGANISM: Homo sapiens

<400> SEQUENCE: 962
cttgcatggg gattatattt ctgtgtccca ttgatacctg gctttgtcac       50

<210> SEQ ID NO 963
<211> LENGTH: 50
<212> TYPE: DNA
<213> ORGANISM: Homo sapiens

<400> SEQUENCE: 963
gagtttctta catattttgg atattaatcc cttgtcaaac aacttgcaaa       50

<210> SEQ ID NO 964
<211> LENGTH: 50
<212> TYPE: DNA
<213> ORGANISM: Homo sapiens

<400> SEQUENCE: 964
ctcctgtgtt ttttttttg gtgtgtgtgt gtttatatcc tccactggca       50

<210> SEQ ID NO 965
<211> LENGTH: 50
<212> TYPE: DNA
<213> ORGANISM: Homo sapiens

<400> SEQUENCE: 965
aagttttttg cctttggcaa atgtttatcc ctggaaaatc agaatgcctg       50

<210> SEQ ID NO 966
<211> LENGTH: 50
<212> TYPE: DNA
<213> ORGANISM: Homo sapiens

<400> SEQUENCE: 966
tctaattaaa gcttgcccct acagcagctg ggaaacagcc atgtttatcc       50

<210> SEQ ID NO 967
<211> LENGTH: 50
<212> TYPE: DNA
<213> ORGANISM: Homo sapiens

<400> SEQUENCE: 967
gactggtttt atgaaatcat gatgaaatct cttcctccaa agttgcttct            50

<210> SEQ ID NO 968
<211> LENGTH: 50
<212> TYPE: DNA
<213> ORGANISM: Homo sapiens

<400> SEQUENCE: 968
actgccacat gagaaggaga cgaggaagtg tcccgatctt gagatatcat            50

<210> SEQ ID NO 969
<211> LENGTH: 50
<212> TYPE: DNA
<213> ORGANISM: Homo sapiens

<400> SEQUENCE: 969
ccattactaa catcttgcat tagtggcata tttatcacta ctaagcgacc            50

<210> SEQ ID NO 970
<211> LENGTH: 50
<212> TYPE: DNA
<213> ORGANISM: Homo sapiens

<400> SEQUENCE: 970
gcgtgaagac taagtagacg tgctattacc ctcctcggtt ggctccagca            50

<210> SEQ ID NO 971
<211> LENGTH: 50
<212> TYPE: DNA
<213> ORGANISM: Homo sapiens

<400> SEQUENCE: 971
gatttggctt tggggataac tgactgtctc ttcccctagc accagagatc            50

<210> SEQ ID NO 972
<211> LENGTH: 50
<212> TYPE: DNA
<213> ORGANISM: Homo sapiens

<400> SEQUENCE: 972
gtctggaaca acattcacta taagagtgaa aatcagcatt gtggaaaaac            50

<210> SEQ ID NO 973
<211> LENGTH: 50
<212> TYPE: DNA
<213> ORGANISM: Homo sapiens

<400> SEQUENCE: 973
ctcagtggcc tgcaaataat gatatctgat cagtaaatac aaagaaaaac            50

<210> SEQ ID NO 974
<211> LENGTH: 50
<212> TYPE: DNA
<213> ORGANISM: Homo sapiens

<400> SEQUENCE: 974
agtgtcaagt aagtggtcgg gggaagtgct ctaagagttc aaagtaggag            50

<210> SEQ ID NO 975
<211> LENGTH: 50
<212> TYPE: DNA
<213> ORGANISM: Homo sapiens

<400> SEQUENCE: 975
gagggtccca gctggggctc ttggtcaatt agactccttg cattcaaaga    50

<210> SEQ ID NO 976
<211> LENGTH: 50
<212> TYPE: DNA
<213> ORGANISM: Homo sapiens

<400> SEQUENCE: 976
tctttcatgg ggcacgagaa taagcacatg gtttttactg agcgcctatc    50

<210> SEQ ID NO 977
<211> LENGTH: 50
<212> TYPE: DNA
<213> ORGANISM: Homo sapiens

<400> SEQUENCE: 977
ggggaattaa atgtgctatt tccctttttc ggtaccctaa gacctgagta    50

<210> SEQ ID NO 978
<211> LENGTH: 50
<212> TYPE: DNA
<213> ORGANISM: Homo sapiens

<400> SEQUENCE: 978
atttcctccc ttctatcttc ccagtccatc tcataccata catttattgg    50

<210> SEQ ID NO 979
<211> LENGTH: 50
<212> TYPE: DNA
<213> ORGANISM: Homo sapiens

<400> SEQUENCE: 979
cactaaacct cagctcattt tgtatttaaa aatggggcta attatgccca    50

<210> SEQ ID NO 980
<211> LENGTH: 50
<212> TYPE: DNA
<213> ORGANISM: Homo sapiens

<400> SEQUENCE: 980
aaccccacat ttcttcagac agtggaatcc aatcactcag ccttcaataa    50

<210> SEQ ID NO 981
<211> LENGTH: 50
<212> TYPE: DNA
<213> ORGANISM: Homo sapiens

<400> SEQUENCE: 981
aatttttcta agtcacccag agtagatttc tgttgcttcc aaacaaagaa    50

<210> SEQ ID NO 982
<211> LENGTH: 50
<212> TYPE: DNA
<213> ORGANISM: Homo sapiens

<400> SEQUENCE: 982
ctgtgatgaa ttaatgtgct tggggttcac tgggtttctt cagtctgtga    50

<210> SEQ ID NO 983
<211> LENGTH: 50
<212> TYPE: DNA
<213> ORGANISM: Homo sapiens

<400> SEQUENCE: 983
ttacccaaac tcccttgcag ctggggttta tagacatggt ctatgttcta    50

<210> SEQ ID NO 984
<211> LENGTH: 50
<212> TYPE: DNA
<213> ORGANISM: Homo sapiens

<400> SEQUENCE: 984
atgaatctga ctctgtgtac acaagtatcc cttacactca agcagatgtc    50

<210> SEQ ID NO 985
<211> LENGTH: 50
<212> TYPE: DNA
<213> ORGANISM: Homo sapiens

<400> SEQUENCE: 985
tgagaaaatt gttctttctg atggagaagc agtgtagtgt agtatcaaca    50

<210> SEQ ID NO 986
<211> LENGTH: 50
<212> TYPE: DNA
<213> ORGANISM: Homo sapiens

<400> SEQUENCE: 986
cagttataat gtgggaatta aaacatataa tctgtttacc tcagatctta    50

<210> SEQ ID NO 987
<211> LENGTH: 50
<212> TYPE: DNA
<213> ORGANISM: Homo sapiens

<400> SEQUENCE: 987
ccctccaatt tccactaaac tgacttttttt cctcacattt ccaaaatagg    50

<210> SEQ ID NO 988
<211> LENGTH: 50
<212> TYPE: DNA
<213> ORGANISM: Homo sapiens

<400> SEQUENCE: 988
tttcactact gagagtgact atatctgaat tctacccact tggataatca    50

<210> SEQ ID NO 989
<211> LENGTH: 50
<212> TYPE: DNA
<213> ORGANISM: Homo sapiens

<400> SEQUENCE: 989
tggggttatt gagtgattca agaggaacaa tgaagatcct tggaaagtaa    50

<210> SEQ ID NO 990
<211> LENGTH: 50
<212> TYPE: DNA
<213> ORGANISM: Homo sapiens

<400> SEQUENCE: 990
ttgggcctat gttttcttca aaatgcatta acattctgat tttctgtatt    50

```
<210> SEQ ID NO 991
<211> LENGTH: 50
<212> TYPE: DNA
<213> ORGANISM: Homo sapiens

<400> SEQUENCE: 991
gtttctcagg tgtgtgtcct aagcaccctc aagcttgaga tactaggaga            50

<210> SEQ ID NO 992
<211> LENGTH: 50
<212> TYPE: DNA
<213> ORGANISM: Homo sapiens

<400> SEQUENCE: 992
aagactcttt acccctttt tcttgtccag aactttttg atgttaacct              50

<210> SEQ ID NO 993
<211> LENGTH: 50
<212> TYPE: DNA
<213> ORGANISM: Homo sapiens

<400> SEQUENCE: 993
cttaacgaat tattccaaca tataccaata agttcaattc catgctaaga            50

<210> SEQ ID NO 994
<211> LENGTH: 50
<212> TYPE: DNA
<213> ORGANISM: Homo sapiens

<400> SEQUENCE: 994
cttgtcatct tatttcatct tgacccatct ttgggagagg cttcctgtta            50

<210> SEQ ID NO 995
<211> LENGTH: 50
<212> TYPE: DNA
<213> ORGANISM: Homo sapiens

<400> SEQUENCE: 995
ggaaggggaa atgggaggta taggagtaag tgactttta ggggaaatga             50

<210> SEQ ID NO 996
<211> LENGTH: 50
<212> TYPE: DNA
<213> ORGANISM: Homo sapiens

<400> SEQUENCE: 996
atttccttta ggaacctttc ctaaacgctg ttttgtgccc tgtaacgata            50

<210> SEQ ID NO 997
<211> LENGTH: 50
<212> TYPE: DNA
<213> ORGANISM: Homo sapiens

<400> SEQUENCE: 997
aggaatgagt ttcatgaggc caatacatgg tccattgtgg gagacagccc            50

<210> SEQ ID NO 998
<211> LENGTH: 50
<212> TYPE: DNA
<213> ORGANISM: Homo sapiens

<400> SEQUENCE: 998
aattgcataa gctactttct ggtagacttc aatgagttca agagtccttt            50
```

<210> SEQ ID NO 999
<211> LENGTH: 50
<212> TYPE: DNA
<213> ORGANISM: Homo sapiens

<400> SEQUENCE: 999
cttggtttga actatgcggt tgtactctga gataggaagt ttccatttct            50

<210> SEQ ID NO 1000
<211> LENGTH: 50
<212> TYPE: DNA
<213> ORGANISM: Homo sapiens

<400> SEQUENCE: 1000
cagtccgaga cggaacgttg acttgggtca aagaccatgt aaatcgcgag            50

<210> SEQ ID NO 1001
<211> LENGTH: 50
<212> TYPE: DNA
<213> ORGANISM: Homo sapiens

<400> SEQUENCE: 1001
gcaataagtg tggataatgg gttttcattg ttttttggcat atctgcccca           50

<210> SEQ ID NO 1002
<211> LENGTH: 50
<212> TYPE: DNA
<213> ORGANISM: Homo sapiens

<400> SEQUENCE: 1002
ccaggcaata aatactggag aagttcagtg gagagggagt cgctgaggct            50

<210> SEQ ID NO 1003
<211> LENGTH: 50
<212> TYPE: DNA
<213> ORGANISM: Homo sapiens

<400> SEQUENCE: 1003
aaatcactca gatgtgtttg tgtgatgtat atgatgtctg caacttactt            50

<210> SEQ ID NO 1004
<211> LENGTH: 50
<212> TYPE: DNA
<213> ORGANISM: Homo sapiens

<400> SEQUENCE: 1004
aatgaattag cagtgagctg ggagggcacc aagaactttc acctggtgct            50

<210> SEQ ID NO 1005
<211> LENGTH: 50
<212> TYPE: DNA
<213> ORGANISM: Homo sapiens

<400> SEQUENCE: 1005
aagtcctgta aatgttcctc ctgcctccag ctgagtagcg tttgtttgaa            50

<210> SEQ ID NO 1006
<211> LENGTH: 50
<212> TYPE: DNA
<213> ORGANISM: Homo sapiens

<400> SEQUENCE: 1006
agtgaatgtt gtgagaacat gattgggagc cagttagaga tgagtgaaag            50

<210> SEQ ID NO 1007
<211> LENGTH: 50
<212> TYPE: DNA
<213> ORGANISM: Homo sapiens

<400> SEQUENCE: 1007
cacagatgaa gaaagtggct tgatgaggaa aataatttgc ttaccacaac    50

<210> SEQ ID NO 1008
<211> LENGTH: 50
<212> TYPE: DNA
<213> ORGANISM: Homo sapiens

<400> SEQUENCE: 1008
attcggaatt gaagctgctg ttgaaacttg tgaatccatg tctctagaac    50

<210> SEQ ID NO 1009
<211> LENGTH: 50
<212> TYPE: DNA
<213> ORGANISM: Homo sapiens

<400> SEQUENCE: 1009
ggagactttt gtacaagctc atttcagatt caaggctcct ccttctgttc    50

<210> SEQ ID NO 1010
<211> LENGTH: 50
<212> TYPE: DNA
<213> ORGANISM: Homo sapiens

<400> SEQUENCE: 1010
agaagtttta aattaagtat tcatgggcat aggtgagctt gggaaatgat    50

<210> SEQ ID NO 1011
<211> LENGTH: 50
<212> TYPE: DNA
<213> ORGANISM: Homo sapiens

<400> SEQUENCE: 1011
caatttgttt ctcctcaagt gcttcttttg ctgacacaca ggactttccc    50

<210> SEQ ID NO 1012
<211> LENGTH: 50
<212> TYPE: DNA
<213> ORGANISM: Homo sapiens

<400> SEQUENCE: 1012
cattgccttt cttcccctga ctactgggct tcctctatca gcttttaacg    50

<210> SEQ ID NO 1013
<211> LENGTH: 50
<212> TYPE: DNA
<213> ORGANISM: Homo sapiens

<400> SEQUENCE: 1013
agacctaaga aatggaataa atactatagt tattcattca cgtcgttgca    50

<210> SEQ ID NO 1014
<211> LENGTH: 50
<212> TYPE: DNA
<213> ORGANISM: Homo sapiens

<400> SEQUENCE: 1014
gacttctgga tcatacagta tgtgtatgta caatgttatt agatattctg    50

<210> SEQ ID NO 1015
<211> LENGTH: 50
<212> TYPE: DNA
<213> ORGANISM: Homo sapiens

<400> SEQUENCE: 1015
caaaagagga acctaacaca cacatctctg agacttgaga ggaaaagcaa      50

<210> SEQ ID NO 1016
<211> LENGTH: 50
<212> TYPE: DNA
<213> ORGANISM: Homo sapiens

<400> SEQUENCE: 1016
tttaacctcc ctgacatgtt tagtcatgaa agaaaaggtg atcaccctac      50

<210> SEQ ID NO 1017
<211> LENGTH: 50
<212> TYPE: DNA
<213> ORGANISM: Homo sapiens

<400> SEQUENCE: 1017
cttcatctcc agcggctttt aactcctttt gaagagtctc tgagctaaca      50

<210> SEQ ID NO 1018
<211> LENGTH: 50
<212> TYPE: DNA
<213> ORGANISM: Homo sapiens

<400> SEQUENCE: 1018
tttcttccct cattttcctt ataacttca tttctcaggt cctgtcagcc      50

<210> SEQ ID NO 1019
<211> LENGTH: 50
<212> TYPE: DNA
<213> ORGANISM: Homo sapiens

<400> SEQUENCE: 1019
gccctgctgc ctcctgggaa agttgataag aatcaagtga aattaagatt      50

<210> SEQ ID NO 1020
<211> LENGTH: 50
<212> TYPE: DNA
<213> ORGANISM: Homo sapiens

<400> SEQUENCE: 1020
tcaaaattgg cattataatg gtacaatcta catggtcttt aggagaatta      50

<210> SEQ ID NO 1021
<211> LENGTH: 50
<212> TYPE: DNA
<213> ORGANISM: Homo sapiens

<400> SEQUENCE: 1021
aatgcaccca gctaaattca ggtccagaga cacagctttg caactgacaa      50

<210> SEQ ID NO 1022
<211> LENGTH: 50
<212> TYPE: DNA
<213> ORGANISM: Homo sapiens

<400> SEQUENCE: 1022
agaagtgttg gtccatctat tattcctcta tgccatctag tttggcactt      50

<210> SEQ ID NO 1023
<211> LENGTH: 50
<212> TYPE: DNA
<213> ORGANISM: Homo sapiens

<400> SEQUENCE: 1023
cacttaacac aaacatgtgt atatatacac agatttttca attctaatac                50

<210> SEQ ID NO 1024
<211> LENGTH: 50
<212> TYPE: DNA
<213> ORGANISM: Homo sapiens

<400> SEQUENCE: 1024
gcactcttct ctatcagagc ttcctttatt gaccaaataa acgtatttcc                50

<210> SEQ ID NO 1025
<211> LENGTH: 50
<212> TYPE: DNA
<213> ORGANISM: Homo sapiens

<400> SEQUENCE: 1025
caattgattg aggcattgac tgtgagattt gtaacaaata aattagctct                50

<210> SEQ ID NO 1026
<211> LENGTH: 50
<212> TYPE: DNA
<213> ORGANISM: Homo sapiens

<400> SEQUENCE: 1026
gtggctgaaa tactaacttc caacacagtg ttcaatgtgg gagccaatcg                50

<210> SEQ ID NO 1027
<211> LENGTH: 50
<212> TYPE: DNA
<213> ORGANISM: Homo sapiens

<400> SEQUENCE: 1027
gggtggggtc ccaggcaagc agtgtaaaaa gctgcaggga gtacagtcca                50

<210> SEQ ID NO 1028
<211> LENGTH: 50
<212> TYPE: DNA
<213> ORGANISM: Homo sapiens

<400> SEQUENCE: 1028
tccaaccatg gagagcaggg cccttcccag gtaagcagca tgagcaaaaa                50

<210> SEQ ID NO 1029
<211> LENGTH: 50
<212> TYPE: DNA
<213> ORGANISM: Homo sapiens

<400> SEQUENCE: 1029
ttgcagccat atccaatgtt gacttgccct caccccataa ttaaattatc                50

<210> SEQ ID NO 1030
<211> LENGTH: 50
<212> TYPE: DNA
<213> ORGANISM: Homo sapiens

<400> SEQUENCE: 1030
tagagcggtc ccatgactgg gagagaaatt gtccctcagg ccaatgaata                50

<210> SEQ ID NO 1031
<211> LENGTH: 50
<212> TYPE: DNA
<213> ORGANISM: Homo sapiens

<400> SEQUENCE: 1031
acttttcagt tatcagatca actaaagaaa catttgttgt taagcctaat    50

<210> SEQ ID NO 1032
<211> LENGTH: 50
<212> TYPE: DNA
<213> ORGANISM: Homo sapiens

<400> SEQUENCE: 1032
gcaagtgtgt tcttagtggt ctttggccag atggtattga caaatgaaac    50

<210> SEQ ID NO 1033
<211> LENGTH: 50
<212> TYPE: DNA
<213> ORGANISM: Homo sapiens

<400> SEQUENCE: 1033
caactctggc aacttccttt agaggacagc gtctagttct gtcattatag    50

<210> SEQ ID NO 1034
<211> LENGTH: 50
<212> TYPE: DNA
<213> ORGANISM: Homo sapiens

<400> SEQUENCE: 1034
agtcatcctc atggtcttgc tttctgtctc attcactcct atgcattgtg    50

<210> SEQ ID NO 1035
<211> LENGTH: 50
<212> TYPE: DNA
<213> ORGANISM: Homo sapiens

<400> SEQUENCE: 1035
ctacatccag aatgagtttt tgtaggctag ctggctcttc agttctccac    50

<210> SEQ ID NO 1036
<211> LENGTH: 50
<212> TYPE: DNA
<213> ORGANISM: Homo sapiens

<400> SEQUENCE: 1036
agtctggatg aatgctcccc aaagacaggg ttcaaggaat taccacaatc    50

<210> SEQ ID NO 1037
<211> LENGTH: 50
<212> TYPE: DNA
<213> ORGANISM: Homo sapiens

<400> SEQUENCE: 1037
agggcctggc actgctgacc ccaccttgtt ttccctccta ctctcccttg    50

<210> SEQ ID NO 1038
<211> LENGTH: 50
<212> TYPE: DNA
<213> ORGANISM: Homo sapiens

<400> SEQUENCE: 1038
tttttattgc aggaatatta gcctgaaaag gtttatccag aatcagtcgc    50

<210> SEQ ID NO 1039
<211> LENGTH: 50
<212> TYPE: DNA
<213> ORGANISM: Homo sapiens

<400> SEQUENCE: 1039
tcctctagct agtgcccata cagaaaattc tatcaccata caaaatttat                  50

<210> SEQ ID NO 1040
<211> LENGTH: 50
<212> TYPE: DNA
<213> ORGANISM: Homo sapiens

<400> SEQUENCE: 1040
ctggttctgg agacagaagc tatgagttca gtgctacata actctctctg                  50

<210> SEQ ID NO 1041
<211> LENGTH: 50
<212> TYPE: DNA
<213> ORGANISM: Homo sapiens

<400> SEQUENCE: 1041
gcaattccag tcaacccatg ataaaaccgg tttggttcaa ttttagtaag                  50

<210> SEQ ID NO 1042
<211> LENGTH: 50
<212> TYPE: DNA
<213> ORGANISM: Homo sapiens

<400> SEQUENCE: 1042
atcattaaaa ggagctaata ttactacctt cttgataatg ttggtgggta                  50

<210> SEQ ID NO 1043
<211> LENGTH: 50
<212> TYPE: DNA
<213> ORGANISM: Homo sapiens

<400> SEQUENCE: 1043
ttgtttcttg tgtggataaa agatttttgt aaagtgtata taggtaccag                  50

<210> SEQ ID NO 1044
<211> LENGTH: 50
<212> TYPE: DNA
<213> ORGANISM: Homo sapiens

<400> SEQUENCE: 1044
gccaaaatcc tactcaaaaa ccaaagtggg taggatttgt tttcagtggc                  50

<210> SEQ ID NO 1045
<211> LENGTH: 50
<212> TYPE: DNA
<213> ORGANISM: Homo sapiens

<400> SEQUENCE: 1045
cctgtttctt aatgtggggc tttatagcta gtgtagctgc ttcttaaaag                  50

<210> SEQ ID NO 1046
<211> LENGTH: 50
<212> TYPE: DNA
<213> ORGANISM: Homo sapiens

<400> SEQUENCE: 1046
catagagtct aaaagtagag ctttgatgtc taccaactaa ttgagctacg                  50

<210> SEQ ID NO 1047
<211> LENGTH: 50
<212> TYPE: DNA
<213> ORGANISM: Homo sapiens

<400> SEQUENCE: 1047
acaactattt ctgtatttac ttcattgtct ccaaagtgct agagtgcatt    50

<210> SEQ ID NO 1048
<211> LENGTH: 50
<212> TYPE: DNA
<213> ORGANISM: Homo sapiens

<400> SEQUENCE: 1048
agaaaacttt gttctgataa agctctagaa ttaattttc tctaatgcac    50

<210> SEQ ID NO 1049
<211> LENGTH: 50
<212> TYPE: DNA
<213> ORGANISM: Homo sapiens

<400> SEQUENCE: 1049
tcagctgctt tagctatcac agctaagtca ccagatctgt aaatgaagat    50

<210> SEQ ID NO 1050
<211> LENGTH: 50
<212> TYPE: DNA
<213> ORGANISM: Homo sapiens

<400> SEQUENCE: 1050
tgcatgtgtt cctggagcaa catacacaca gtttgcagga gccaaagtag    50

<210> SEQ ID NO 1051
<211> LENGTH: 50
<212> TYPE: DNA
<213> ORGANISM: Homo sapiens

<400> SEQUENCE: 1051
ttgtcaagga aatggatgtg caatgcttct ttttgagctc tgtcttttg    50

<210> SEQ ID NO 1052
<211> LENGTH: 50
<212> TYPE: DNA
<213> ORGANISM: Homo sapiens

<400> SEQUENCE: 1052
tctaggaact ccaataaact tacaggatga ttggagggta agaaggtcac    50

<210> SEQ ID NO 1053
<211> LENGTH: 50
<212> TYPE: DNA
<213> ORGANISM: Homo sapiens

<400> SEQUENCE: 1053
gcagtctcat cgctttgtcc agcatgcact tcttcctgct tgtctgcaca    50

<210> SEQ ID NO 1054
<211> LENGTH: 50
<212> TYPE: DNA
<213> ORGANISM: Homo sapiens

<400> SEQUENCE: 1054
aagttttttg cctttggcaa atgtttatcc ctggaaaatc agaatgcctc    50

```
<210> SEQ ID NO 1055
<211> LENGTH: 50
<212> TYPE: DNA
<213> ORGANISM: Homo sapiens

<400> SEQUENCE: 1055
cagttataat gtgggaatta aaacatataa tctgtttacc tcagatcttt          50

<210> SEQ ID NO 1056
<211> LENGTH: 50
<212> TYPE: DNA
<213> ORGANISM: Homo sapiens

<400> SEQUENCE: 1056
ccctccaatt tccactaaac tgactttttt cctcacattt ccaaaatagc          50

<210> SEQ ID NO 1057
<211> LENGTH: 50
<212> TYPE: DNA
<213> ORGANISM: Homo sapiens

<400> SEQUENCE: 1057
ccaggcaata aatactggag aagttcagtg gagagggagt cgctgaggca          50

<210> SEQ ID NO 1058
<211> LENGTH: 50
<212> TYPE: DNA
<213> ORGANISM: Homo sapiens

<400> SEQUENCE: 1058
attcggaatt gaagctgctg ttgaaacttg tgaatccatg tctctagaag          50

<210> SEQ ID NO 1059
<211> LENGTH: 50
<212> TYPE: DNA
<213> ORGANISM: Homo sapiens

<400> SEQUENCE: 1059
ggagactttt gtacaagctc atttcagatt caaggctcct ccttctgttg          50

<210> SEQ ID NO 1060
<211> LENGTH: 50
<212> TYPE: DNA
<213> ORGANISM: Homo sapiens

<400> SEQUENCE: 1060
aatgcaccca gctaaattca ggtccagaga cacagctttg caactgacat          50

<210> SEQ ID NO 1061
<211> LENGTH: 50
<212> TYPE: DNA
<213> ORGANISM: Homo sapiens

<400> SEQUENCE: 1061
cacttaacac aaacatgtgt atatatacac agatttttca attctaatag          50
```

METHOD FOR DETERMINATION OF PROGRESSION RISK OF GLAUCOMA

CROSS-REFERENCE TO RELATED APPLICATIONS

This application is a National Stage of PCT/JP2008/057533, filed on Apr. 17, 2008, which claims priority to Japanese patent application JP 2007-108688, filed on Apr. 17, 2007.

TECHNICAL FIELD

The present invention relates to a method of detecting the presence of a single nucleotide polymorphism associated with the progression of glaucoma, or a single nucleotide polymorphism with a high progressive risk of glaucoma, and a kit used in the detection method.

BACKGROUND ART

Glaucoma is a disease which causes a characteristic optic nerve cupping and an impairment in a visual field by retinal ganglion cell death. An elevation in an intraocular pressure is considered to be a major cause for the nerve cupping and the impairment in the visual field in glaucoma. On the other hand, there is also glaucoma in which an intraocular pressure is held within a normal range in statistical calculation, and even in this case, it is considered that glaucoma develops because the intraocular pressure is at a sufficiently high level for causing the impairment in a visual field for an individual.

The basic treatment for glaucoma is to maintain an intraocular pressure at a low level, and it is necessary to consider the causes for a high intraocular pressure in order to maintain a low intraocular pressure. Therefore, in the diagnosis of glaucoma, it is important to classify the types of glaucoma in accordance with the levels of intraocular pressures and causes therefor. As the causes for an elevation in an intraocular pressure, the presence or absence of closure of angle which is a major drainage pathway for an aqueous humor filling an eye is important. From these viewpoints, the primary glaucoma is roughly classified into the two groups of closed-angle glaucoma accompanying angle closure and open-angle glaucoma without accompanying angle closure. Among them, the open-angle glaucoma is classified into open-angle glaucoma, in a narrow sense, accompanying an elevation in an intraocular pressure, i.e. primary open-angle glaucoma, and normal tension glaucoma in which an intraocular pressure is held within a normal range.

It is known from old times that glaucoma is associated with inheritance. It is reported that 5 to 50% of individuals with open-angle glaucoma have a family history, and it is generally understood that 20 to 25% of individuals have hereditary causes. Based on these reports, studies on a search for a gene responsible for glaucoma are performed. As a result, it is reported that a mutation in myocilin (MYOC) gene is associated with open-angle glaucoma (See Patent Publication: 1), and that a mutation in optineurin gene (OPTN) is associated with normal tension glaucoma (See Non-Patent Publication: 1). However, all the genetic causes of glaucoma cannot be explained only by these genes, and the presence of unknown glaucoma-related genes is expected.

On the other hand, a single nucleotide polymorphism means that a substitution mutation in which a single base is changed into another base is found in base sequences of the genome of an individual, and the mutation exists in a certain frequency, generally a frequency of about 1% or more, in the population of an organism species. A single nucleotide polymorphism exists at intron or exon on genes, or any of the regions of the genome other than these.

Patent Publication 1: Japanese Patent-Laid Open No. 2002-306165

Non Patent Publication 1: Rezaie T and eleven others, *Science*, 2002, 295(5557), 1077-1079.

DISCLOSURE OF INVENTION

Problems to be Solved by the Invention

Generally, an intraocular pressure or an ocular fundus photograph is used as a simple examination for glaucoma; however, these examinations do not necessarily lead to a definite diagnosis for glaucoma. Usually, in addition to these, visual field examinations are performed; however, there are some disadvantages that the examination is carried out for a long period of time, causing burdens on patients, and that one must be accustomed to the examination, so that initial examination results have low reliability.

On the other hand, as mentioned above, the involvement of hereditary causes is strongly suspected in the onset of glaucoma, but critical responsible genes are not identified. On the other hand, even if the involvement of a single gene to the disease cannot be explained by a mutation or polymorphism, it is considered that there are numerous mutations or polymorphisms of a gene of which involvement to glaucoma is relatively moderate, and the involvement of hereditary causes to the onset of glaucoma can be explained by a combined action of each of these mutations or polymorphisms.

The inventors have remarked on a polymorphism on the genome, especially a single nucleotide polymorphism, in order to find a gene associated with glaucoma.

In addition, glaucoma is a disease that progresses gradually over a long period of time; however, some of the patients with fast progression are known empirically. The reasons of the existence of the patients with fast progression of glaucoma are unknown, and the involvement of hereditary factors is suspected. By finding polymorphisms involved in the progression of glaucoma, a person having a polymorphism which is found in a high frequency in patients with the fast progression of glaucoma is predicted to have a high progressive risk of glaucoma, whereby the prediction can be used in designing of the treatment plan, in a manner that a more carefully handled treatment and a follow-up in a high frequency are carried out, the progression of glaucoma is controlled, and the like. Further, a clinical trial for studying whether or not a candidate substance for a glaucoma therapeutic drug is actually usable for the glaucoma therapeutic drug requires a long period of time for trials; however, the period of a clinical trial of a candidate substance for a glaucoma therapeutic drug can be shortened by performing a clinical trial on gathered patients having polymorphisms involved in the progression of glaucoma in the present invention. In addition, a glaucoma therapeutic drug selected according to a clinical trial as described above has a possibility of being especially effective in the treatment of glaucoma of which progression is fast.

An object of the present invention is to provide a method of detecting a single nucleotide polymorphism involved in the progression of glaucoma, thereby predicting a progressive risk of glaucoma, and a kit used in the detection method.

Means to Solve the Problems

The present inventors have found a single nucleotide polymorphism associated with the progression of glaucoma by a comprehensive analysis of known polymorphic sites existing on the genome of patients with fast progression and patients with slow progression in the glaucoma patients, and further found an allele identified in a high frequency in patients with fast progression of glaucoma and an opposite allele thereof, and a genotype identified in a high frequency in patients with fast progression of glaucoma, which is a combination of each of the alleles, in the single nucleotide polymorphism. Furthermore, the present inventors have found that a determination on whether or not a sample donor is a person who is more likely to suffer from the progression of glaucoma can be made at an even higher precision by performing the determination in a combination of these plural single nucleotide polymorphisms associated with the progression of glaucoma. Thus, the present invention has been perfected thereby.

Concretely, the present invention relates to:

[1] a method of determining the presence or the absence of a glaucoma risk, including the steps of:
   detecting in vitro an allele and/or a genotype of a single nucleotide polymorphism which is located on a 31st base of a base sequence, in a sample from a subject, wherein the base sequence is at least one base sequence selected from the group consisting of base sequences shown in SEQ ID NOs: 203 to 752 or a complementary sequence thereto (step A), and
   comparing the allele and/or the genotype detected in the step A with at least one of an allele and/or a genotype, containing a high-risk allele, in the base sequences shown in SEQ ID NOs: 203 to 752 (step B),
wherein the presence of a glaucoma risk is determined in a case where the allele detected in the step A is the high-risk allele, or
wherein the presence of a glaucoma risk is determined in a case where the genotype detected in the step A is a homozygote of the genotype containing the high-risk allele or a heterozygote when the high-risk allele complies with a dominant genetic model, or
wherein the presence of a glaucoma risk is determined in a case where the genotype detected in the step A is a homozygote of the genotype containing the high-risk allele when the high-risk allele complies with a recessive genetic model;

[2] a method of determining the presence or the absence of a glaucoma risk, including the steps of:
   detecting in vitro, in a sample from a subject, an allele and/or a genotype of a single nucleotide polymorphism which is located on a 31st base of a base sequence in a nucleic acid molecule, wherein the nucleic acid molecule comprises at least one base sequence selected from the group consisting of base sequences shown in SEQ ID NOs: 203 to 752 or a complementary sequence thereto (step C1), or
   detecting in vitro, in a sample from a subject, an allele and/or a genotype of a single nucleotide polymorphism, using a nucleic acid molecule comprising a base sequence containing at least one base sequence selected from the group consisting of base sequences shown in SEQ ID NOs: 753 to 1061 or a complementary sequence thereto (step C2), and
   comparing the allele and/or the genotype detected in the step C1 or C2 with at least one nucleic acid molecule comprising an allele and/or a genotype, containing a high-risk allele, in the base sequences shown in the SEQ ID NOs: 203 to 752 (step D),
wherein the presence of a glaucoma risk is determined in a case where the allele detected in the step C1 or C2 is the high-risk allele, or
wherein the presence of a glaucoma risk is determined in a case where the genotype detected in the step C1 or C2 is a homozygote of the genotype containing the high-risk allele or a heterozygote when the high-risk allele complies with a dominant genetic model, or
wherein the presence of a glaucoma risk is determined in a case where the genotype detected in the step C1 or C2 is a homozygote of the genotype containing the high-risk allele when the high-risk allele complies with a recessive genetic model;

[3] a kit of determining the presence or the absence of a glaucoma risk, containing
   a nucleic acid molecule comprising at least one base sequence selected from the group consisting of base sequences shown in SEQ ID NOs: 203 to 752 or a complementary sequence thereto, or a partial sequence thereof, wherein the nucleic acid molecule comprises a single nucleotide polymorphism which is located on a 31st base of a base sequence, and/or
   a nucleic acid molecule comprising a base sequence containing at least one base sequence selected from the group consisting of base sequences shown in SEQ ID NOs: 753 to 1061 or a complementary sequence thereto,
wherein the kit is for use in detecting in vitro an allele and/or a genotype of a single nucleotide polymorphism in a sample from a subject;

[4] a method of determining the presence or the absence of a glaucoma risk, including the following steps of:
step (i): extracting a nucleic acid molecule from a sample from a subject,
step (ii): detecting an allele of a single nucleotide polymorphism which is located on a 31st base of a base sequence, wherein the base sequence is at least one base sequence selected from base sequences shown in SEQ ID NOs: 203 to 752 or a complementary sequence thereto, for the nucleic acid molecule extracted in the step (i), and
step (iii): determining the presence or the absence of a glaucoma risk, based on the allele detected in the step (ii);

[5] use of a nucleic acid molecule for determining a glaucoma risk, wherein the nucleic acid molecule comprises at least one base sequence, the base sequence being a base sequence selected from the group consisting of base sequences shown in SEQ ID NOs: 203 to 752 or a complementary sequence thereto, or a partial sequence thereof, wherein the nucleic acid molecule comprises an allele and/or a genotype of a single nucleotide polymorphism which is located on a 31st base of a base sequence;

[6] a method of diagnosing glaucoma, including the steps of:
   detecting in vitro an allele and/or a genotype of a single nucleotide polymorphism which is located on a 31st base of a base sequence, in a sample from a subject, wherein the base sequence is at least one base sequence selected from the group consisting of base sequences shown in SEQ ID NOs: 203 to 752 or a complementary sequence thereto (step E), and
   comparing the allele and/or the genotype detected in the step E with at least one of an allele and/or a genotype, containing a high-risk allele, in the base sequences shown in SEQ ID NOs: 203 to 752 (step F),
wherein the subject is diagnosed as glaucoma in a case where the allele detected in the step E is the high-risk allele, or
wherein the subject is diagnosed as glaucoma in a case where the genotype detected in the step E is a homozygote of the genotype containing the high-risk allele or a heterozygote when the high-risk allele complies with a dominant genetic model, or wherein the subject is diagnosed as glaucoma in a case where the genotype detected in the step E is a homozygote of the genotype containing the high-risk allele when the high-risk allele complies with a recessive genetic model; and

[7] a method of determining a progressive risk of glaucoma, including the following steps of:

step (I): determining the presence or the absence of the progressive risk of glaucoma, with the method as defined in claim 3, step (II): determining that a further risk determination is needed, in a case where the presence of the progressive risk is determined in the step (I) for any one of single nucleotide polymorphisms, and step (III): further determining the presence or the absence of the progressive risk of glaucoma, with the method as defined in claim 5, in a case of being determined that a further risk determination is needed in the step (II).

EFFECTS OF THE INVENTION

According to the method of the present invention, the presence or the absence of the progressive risk of glaucoma in a sample donor can be determined, and further the level of the risk can be predicted, by analyzing an allele or a genotype of a single nucleotide polymorphism in the present invention contained in a nucleic acid molecule derived from the genome existing in a sample. A sample donor can be provided with a preventive measure for glaucoma, or can receive appropriate treatments, on the basis of this risk. In addition, the method is useful because the period of a clinical trial for a glaucoma therapeutic drug can be shortened by selecting patients with a high progressive risk of glaucoma using a single nucleotide polymorphism associated with the progression of glaucoma in the present invention, and performing a clinical trial for a glaucoma therapeutic drug.

BEST MODE FOR CARRYING OUT THE INVENTION

The present invention is a method of determining the presence or the absence of a glaucoma risk, including the step of detecting in vitro an allele and/or a genotype having at least one single nucleotide polymorphism using at least one single nucleotide polymorphism (hereinafter may be referred to as SNP) contained in a base sequence selected from the group consisting of specified base sequences or a complementary sequence thereto, wherein the method of determining the presence or the absence of a glaucoma risk further includes the step of:

comparing the allele and/or the genotype detected in the step with at least one of an allele and/or a genotype, containing a high-risk allele, in the specified base sequences, in a sample from a subject, wherein the presence of a glaucoma risk is determined in a case where the detected allele is the high-risk allele, or wherein the presence of a glaucoma risk is determined in a case where the detected genotype is a homozygote of the genotype containing the high-risk allele or a heterozygote when the high-risk allele complies with a dominant genetic model, or wherein the presence of a glaucoma risk is determined in a case where the detected genotype is a homozygote of the genotype containing the high-risk allele when the high-risk allele complies with a recessive genetic model. A great feature of the present invention resides in that a single nucleotide polymorphism associated with the progression of glaucoma is found, further that in the single nucleotide polymorphism, an allele identified in a high frequency in progressive glaucoma cases and an opposite allele thereof, and a genotype, which is a combination of each of the alleles identified in a high frequency in progressive glaucoma cases are found, and used. The polymorphism as used herein refers to a matter that a diversity is found in sequences of a specified location on the genome in a certain organism species, and a site at which the polymorphism exists (hereinafter also referred to as polymorphic site) refers to a site on the genome that a single nucleotide polymorphism is found.

In addition, the allele as used herein refers to each of types having a different base from each other that can be taken in a certain polymorphic site. The genotype as used herein refers to a combination of opposite alleles in a certain polymorphic site. Further, in a certain polymorphic site, there are three types for a genotype which is a combination of opposite alleles, wherein a combination of the same alleles is referred to as a homozygote, and a combination of different alleles is referred to as a heterozygote.

The opposite allele as used herein refers to another allele corresponding to a specified allele among the alleles constituting a certain single nucleotide polymorphism.

In the present invention, the single nucleotide polymorphism associated with glaucoma refers to a single nucleotide polymorphism associated with the onset of glaucoma or a single nucleotide polymorphism associated with the progression of glaucoma. In other words, the single nucleotide polymorphism associated with the onset of glaucoma refers to a single nucleotide polymorphism in which each allele or each genotype frequency in the single nucleotide polymorphism significantly differs in a statistical analysis at a given p-value between glaucoma patients and non-patients; and the single nucleotide polymorphism associated with the progression of glaucoma refers to a single nucleotide polymorphism in which each allele or each genotype frequency in the single nucleotide polymorphism significantly differs in a statistical analysis at a given p-value between the progressive glaucoma cases and the nonprogressive glaucoma cases.

In the present invention, the high-risk allele refers to an allele having a higher frequency in a progressive glaucoma group than that of a nonprogressive glaucoma group among each of the alleles of the single nucleotide polymorphism associated with glaucoma. On the other hand, in the present invention, the low-risk allele refers to an allele opposite to the high-risk allele in a certain polymorphic site.

In addition, the homozygote and the heterozygote of a genotype are defined in the same manner as in the high-risk allele and the low-risk allele. In other words, in certain polymorphic sites, a combination of high-risk alleles or low-risk alleles themselves is referred to a homozygote, and a combination of a high-risk allele and a low-risk allele is referred to as a heterozygote.

An embodiment where allele frequencies of the progressive glaucoma group and the nonprogressive glaucoma group are statistically compared is referred to as an allele model, and an embodiment where genotype frequencies thereof are compared is referred to as a genotype model. There are a dominant genetic model and a recessive genetic model in the genotype models, wherein the former means an embodiment where both a homozygote of high-risk alleles and a heterozygote are involved with the progressive risk, and the latter means an embodiment where a homozygote of a high-risk allele is involved with the progressive risk.

In the present invention, the glaucoma risk refers to a risk concerning glaucoma. The progressive risk of glaucoma refers to a possibility of fast progression of glaucoma determined by susceptibility to a disease in a case where a patient suffers from glaucoma (or will suffer from the glaucoma in future). In the present invention, the prediction of a risk refers to a determination of the presence or the absence of a future risk at the present stage, or determining the level of a future risk at the present stage.

Also, the glaucoma as used herein means preferably open-angle glaucoma (OAG) or normal tension glaucoma (NTG), and the open-angle glaucoma, when used without specifying otherwise, means primary open-angle glaucoma (POAG) in a narrow sense, without embracing normal tension glaucoma.

A method of identifying a single nucleotide polymorphism associated with glaucoma will be explained hereinbelow.

In the present invention, in selecting the single nucleotide polymorphism associated with glaucoma, in particular, a candidate single nucleotide polymorphism is selected by the steps including extracting a total DNA from blood of each of patients with fast progression of glaucoma, i.e. progressive glaucoma cases, and patients with slow progression of glaucoma, i.e. nonprogressive glaucoma cases, and comparing allele or genotype frequencies of individual single nucleotide polymorphisms in the progressive glaucoma cases and the nonprogressive glaucoma cases using known single nucleotide polymorphisms of about 500,000 on the human genome as an index. Further, the allele or genotype frequencies of individual single nucleotide polymorphisms for the single nucleotide polymorphisms that are selected as candidates are obtained for progressive glaucoma cases and nonprogressive glaucoma cases that are different from the sample groups mentioned above. By combining these results, a single nucleotide polymorphism of which difference in frequencies is recognized with high statistical significance is found. Here, although the details will be explained in the section of Examples, the progressive glaucoma cases refer to patients who are found to show progression in visual field within a certain period of time, even though a treatment by an intraocular pressure-lowering drug or surgical operation is given, and the nonprogressive glaucoma cases refer to patients of which progression in the visual field is inhibited by these treatments. Here, a group composed of the progressive glaucoma cases is referred to as a progressive glaucoma group, and a group composed of the nonprogressive glaucoma cases is referred to as a nonprogressive glaucoma group. By using the alleles or genotypes having a single nucleotide polymorphism associated with the progression of glaucoma found according to these analyses, the determination of the presence or the absence of the progressive risk of glaucoma, and the prediction of the level of a progressive risk can be enabled. Although the details will be explained in the section of Examples, a single nucleotide polymorphism associated with glaucoma disclosed in the present invention can be identified according to a method given below.

(Identification of Single Nucleotide Polymorphism Associated with Glaucoma)

First, a total DNA is extracted from blood of each of progressive glaucoma cases and nonprogressive glaucoma cases. The total DNA in blood can be extracted by any known methods; for example, a DNA can be extracted by binding a DNA eluted by lysing cells to surfaces of magnetic beads coated with silica, and separating and collecting the DNA utilizing a magnetic force.

The kind of a base in a single nucleotide polymorphism in the extracted DNA sample, i.e. an allele having a single nucleotide polymorphism can be identified by any methods, including, for example, a method using an immobilized probe described later, or the like. Upon the identification, a probe used in the detection can be designed on the basis of the sequence information of a single nucleotide polymorphism of interest and surrounding sequences thereof. When the probe is designed, the sequence information obtained from the database for known single nucleotide polymorphisms such as dbSNP can be used as a reference. As to a probe used in the detection of a single nucleotide polymorphism, the detection can be made with either a probe complementary to a sense strand of the genome, or a probe complementary to an anti-sense strand. Although the details will be described later, a kit in which probes capable of detecting single nucleotide polymorphisms existing on the human genome are immobilized in large amounts, thereby making it possible to determine alleles of numerous single nucleotide polymorphisms in a single operation is commercially available, and whereby an allele in a sample can be efficiently determined using the kit. Many of the kits also have the constitution that the alleles that are opposite to each other contained in one sample are detected in a single operation, so that a genotype can be determined.

The single nucleotide polymorphism associated with glaucoma can be determined by previously identifying an allele existing on DNA from progressive glaucoma cases and nonprogressive glaucoma cases according to the method as mentioned above, statistically comparing each of the allele frequencies and the genotype frequencies in a progressive glaucoma group against a nonprogressive glaucoma group, and determining whether or not a difference that a p-value is below the significance level as defined by a given standard is caused in at least one of the allele frequencies and the genotype frequencies. In a case where the difference is caused, the allele frequencies or genotype frequencies for these factors in the progressive glaucoma group and the nonprogressive glaucoma group are compared to determine whether any of the alleles or genotypes are identified in a high frequency in the progressive glaucoma group.

In the statistical analysis, for example, a chi-square test can be used. Type I error caused by multiple comparisons can be corrected by a known correction method, for example, Bonferroni method. In a case where a correction is based on Bonferroni correction, for example, a significance level can be obtained by dividing a p-value of $5 \times 10^{-2}$ by the number of multiple comparisons, i.e. the number of polymorphisms to be compared in the chi-square test. A single nucleotide polymorphism below the significance level determined in the manner described above can be selected as a more preferred single nucleotide polymorphism, and a method used in other known multiple corrections, for example, an FDR method or a permutation method may also be used in the selection of a preferred single nucleotide polymorphism. However, a known multiple correction method such as Bonferroni correction is a method presupposing that the phenomenon of carrying out multiple analyses is completely independent; on the other hand, there are some cases where the phenomenon is not completely independent because linkage disequilibrium is found in a single nucleotide polymorphism as described later. In other words, in the case as mentioned above, it is considered that overcorrection takes place when correction is carried out according to Bonferroni method. Especially, in the analysis of a single nucleotide polymorphism over the whole genome as in the present invention, factors to be statistically compared are highly enormous in number; therefore, a p-value is drastically lowered when multiple corrections are performed, so that a possibility of an oversight of a single nucleotide polymorphism associated with a disease becomes high (Schymick J C et al., *Lancet Neurology.* 2007: 6: 322-8; Van Steen K et al., *Nature Genetics.* 2005: 37: 683-691). An academically preferred multiple correction method is not yet established, and as other correction methods, correction by another known correction method can be carried out, or a significance level can be set at any appropriate levels within the range that would not be below the significance level according to the Bonferroni correction. When any appropriate level is set, for example, the significance level in a case where about 500,000 single nucleotide polymorphisms are analyzed repeatedly of $5\times10^{-2}$ is used, more preferably $1\times10^{-2}$, even more preferably $1\times10^{-3}$, even more preferably $1\times10^{-4}$, even more preferably $3\times10^{-5}$, and even more preferably $1\times10^{-5}$. As described later, the adjustment of the significance level as described above is useful from the fact that it is confirmed that a single nucleotide polymorphism identified to be associated with glaucoma in the present invention exists continuously in a certain region on the genome.

In addition, in general, it is known that type I error and the statistical power are inversely proportional. A method of maintaining the statistical power while lowering type I error includes a method of performing a single nucleotide polymorphism analysis in two divided steps (Skol A. D. et al., *Nature Genetics*. 2006: 38: 209-213). For example, in a case where a single nucleotide polymorphism analysis is carried out for a fixed number of samples, firstly, analysis of enormous single nucleotide polymorphisms over the whole genome for a part of samples thereof is carried out as primary analysis, and secondly, analysis of single nucleotide polymorphisms narrowed down in the first analysis to some degree is carried out for the remainder samples as secondary analysis. In this case, in both of the analyses, a single nucleotide polymorphism may be selected so as to have a relatively low p-value, for example, 0.05; preferably, a single nucleotide polymorphism serving as a candidate in the first analysis may be selected at a given significance level, and the selected single nucleotide polymorphism may be further analyzed using another sample. On the other hand, it is more preferable that the results of the first analysis and the secondary analysis are not individually statistically analyzed but these results are combined and analyzed. In the case as mentioned above, the two analytical results can be combined by a known method of meta-analysis, for example, Mantel-Haenszel method (Mantel N et al., *Journal of the National Cancer Institute* 1959: 22: 719-748). When the analytical results are combined according to a meta-analysis method such as Mantel-Haenszel method, the significance level for the selection of a single nucleotide polymorphism in individual analysis is not needed to be at the level of Bonferroni correction, and the significance level may be set by taking narrowing-down efficiency or the like into consideration. On the other hand, upon determination of whether or not a single nucleotide polymorphism is significant by a p-value combined by a meta-analysis method such as Mantel-Haenszel method, it is preferable to use a significance level with considering multiple comparisons. Here, the Mantel-Haenszel method refers to a method of combining analytical results by weighting the results obtained by multiple analyses when a chi-square test or the like is carried out. A statistical parameter combined by Mantel-Haenszel method includes, in addition to the p-value, an odds ratio described later or the like.

A single nucleotide polymorphism for the detection of the allele or genotype associated with glaucoma is preferably a single nucleotide polymorphism having a p-value of $1\times10^{-3}$ or less, more preferably a single nucleotide polymorphism having a p-value of $3\times10^{-4}$ or less, even more preferably a single nucleotide polymorphism having a p-value of $1\times10^{-4}$ or less, and even more preferably a single nucleotide polymorphism having a p-value of $3\times10^{-5}$ or less, when the single nucleotide polymorphism for the detection is based on the results obtained in a single analysis using, for example, a microarray in which about 500,000 single nucleotide polymorphisms are detected in a single operation. When the results are obtained by combining multiple analytical results according to a meta-analysis method such as Mantel-Haenszel method, the single nucleotide polymorphism for the detection is preferably a single nucleotide polymorphism having a p-value of $1\times10^{-2}$ or less, more preferably a single nucleotide polymorphism having a p-value of $3\times10^{-3}$ or less, even more preferably a single nucleotide polymorphism having a p-value of $1\times10^{-4}$ or less, and even more preferably a single nucleotide polymorphism having a p-value of $3\times10^{-4}$ or less.

It is preferable that a sufficient number of single nucleotide polymorphisms are analyzed, in order to obtain highly reliable results upon analysis. For example, a polymorphic site having a low determination rate of each single nucleotide polymorphism to the whole sample, i.e. a low call rate, is likely to have a high rate of typing errors, so that the reliability is not high. Therefore, it is preferable that the analysis is performed using a single nucleotide polymorphism having a sufficiently high call rate. As to the call rate that serves as a standard of accepting or rejecting a single nucleotide polymorphism, for example, it is preferable that a single nucleotide polymorphism showing a call rate of preferably 70%, more preferably 75%, even more preferably 80%, even more preferably 85%, and even more preferably 90% or more is employed.

Besides them, factors that can be considered upon analysis are Hardy-Weinberg's equilibrium and minor allele frequency.

The Hardy-Weinberg's equilibrium means that a distribution frequency of the opposite alleles in a certain gene locus is constant even after generations, in a genetically homogeneous population having a sufficient number of individuals formed by panmixia without a mutation or selection pressure. Whether or not the Hardy-Weinberg's equilibrium is established can be confirmed by some known methods, for example, a chi-square test and a direct probability calculation method of Fischer. In a population of a sufficient number, it is considered that the Hardy-Weinberg's equilibrium is established by a single panmixia, i.e. the Hardy-Weinberg's equilibrium is established as long as inbreeding does not exist. Therefore, generally, under the assumption that the Hardy-Weinberg's equilibrium is established in the general population, analysis of the Hardy-Weinberg's equilibrium is used for the purpose of detecting errors of genotype determination of a sample. However, even if the Hardy-Weinberg's equilibrium is established as a whole, when a certain genotype is unevenly distributed in a disease group or a control group in a certain gene locus, for example, there are some cases where a certain genotype has a predominant influence on a disease, or the like; therefore, said analysis can be omitted, in a case where a search for disease-associated genes is carried out.

The minor allele frequency refers to an allele frequency with a lower frequency of the frequencies of two alleles in a case where single nucleotide polymorphisms are contained in two alleles. It is possible that a threshold thereof is arbitrarily set. As mentioned above, it is preferable that a single nucleotide polymorphism having a minor allele frequency of below 1% is rejected, because the concept of a single nucleotide polymorphism is in that the single nucleotide polymorphism has a minor allele frequency exceeding about 1%. On the other hand, there is a possibility that an allele having a very high or very low allele frequency in a disease group has a predominant influence on a disease. It is considered that polymorphisms of which relative involvement to a disease is relatively low are multiply involved in search of polymorphisms causative of multi-factorial diseases; therefore, for the purpose of searching the polymorphisms as mentioned above, an analysis excluding a frequency of a certain level or lower, for example, a minor allele of less than 5% can be a preferred means. On the other hand, in order to search polymorphisms that have predominant influences on a disease, it is effective not to reject the polymorphisms of the minor allele frequency.

From the allele or genotype associated with glaucoma thus obtained, the information such as a location on the genome at which a single nucleotide polymorphism exists, the sequence information, a gene in which a single nucleotide polymorphism exists or a gene existing in the neighborhood, discrimination of intron or exon or a function thereof in a case where the single nucleotide polymorphism exists on the gene, and a homologous gene in other organism species can be obtained, by referring to the database of known sequences such as GenBank, or the database of known single nucleotide polymorphisms such as dbSNP, whereby a nucleic acid molecule used in the present invention is obtained, on the basis of the information, and a probe or the like used in the present invention can be designed.

As the criteria for determining the presence or the absence of a risk in a single nucleotide polymorphism associated with glaucoma determined as mentioned above, a high-risk allele is defined. As mentioned above, in the present invention, the high-risk allele refers to an allele having a higher frequency in a progressive glaucoma group than that of a nonprogressive glaucoma group among each of the alleles of single nucleotide polymorphisms associated with glaucoma, and in the present invention, the low-risk allele refers to an allele opposite to a high-risk allele in a certain polymorphic site.

The determination of the presence or the absence of a progressive risk can be carried out according to an allele or a genotype.

In a case where the determination is carried out according to an allele, the presence of the progressive risk is determined for the single nucleotide polymorphism because of having a high-risk allele.

In a case where the determination is carried out according to a genotype, the progressive risk is determined by taking into consideration whether the high-risk allele complies with a dominant genetic model, or with a recessive genetic model. In a certain polymorphic site, when the frequency of a homozygote of the high-risk allele and a heterozygote is significantly high in a progressive glaucoma group as compared to that of a nonprogressive glaucoma group, it is said that these genotypes comply with a dominant genetic model. The presence of a progressive risk is determined for the single nucleotide polymorphism in a case where the genotype is a homozygote of the high-risk allele or a heterozygote, when the high-risk allele complies with a dominant genetic model. On the other hand, when the frequency of a homozygote of the high-risk allele is significantly high in a progressive glaucoma group as compared to that of a nonprogressive glaucoma group, it is said that these genotypes comply with a recessive genetic model. The presence of a progressive risk is determined for the single nucleotide polymorphism in a case where the genotype is a homozygote of the high-risk allele, when the high-risk allele complies with a recessive genetic model.

The determination of the presence or the absence of a progressive risk can be also carried out according to a low-risk allele. As mentioned above, the low-risk allele is an allele opposite to a high-risk allele, i.e. an allele identified in a high frequency in a nonprogressive glaucoma group. In a case where the determination is carried out according to an allele, the presence of a progressive risk is determined for the single nucleotide polymorphism because of not having a low-risk allele.

The same applies to a case of a genotype as well. When the determination is carried out according to a genotype, the presence of a progressive risk is determined by taking into consideration whether the low-risk allele complies with a dominant genetic model, or with a recessive genetic model. In a certain polymorphic site, when the frequency of a homozygote of the low-risk allele and a heterozygote is significantly high in a nonprogressive glaucoma group as compared to that of a progressive glaucoma group, it is said that these genotypes comply with a dominant genetic model. The presence of the progressive risk is determined for the single nucleotide polymorphism in a case where the genotype is not a homozygote of the low-risk allele or a heterozygote, when the low-risk allele complies with a dominant genetic model. On the other hand, when the frequency of a homozygote of the low-risk allele is significantly high in a nonprogressive glaucoma group as compared to that of a progressive glaucoma group, it is said that these genotypes comply with a recessive genetic model. The presence of the progressive risk is determined for the single nucleotide polymorphism in a case where the genotype is not a homozygote of the low-risk allele, when the low-risk allele complies with a recessive genetic model.

As to whether the determination is carried out using a method for any of an allele, a dominant genetic model, and a recessive genetic model, the same method as in a method where a p-value judged to be significant is obtained can be used. In a case where the methods where a p-value judged to be significant is obtained exist in a plurality for one single nucleotide polymorphism, any of these methods may be used, and preferably, the same method as in a method where the lowest p-value is calculated is used.

Generally, in a single nucleotide polymorphism associated with a disease, a relative risk or an odds ratio is used as an index of an extent of the strength of the association that exists between one allele or genotype and the presence or the absence of a disease.

Generally, the relative risk refers to a ratio of an incidence rate in a group with a risk factor to an incidence rate in a group without a risk factor. On the other hand, the odds ratio generally refers to a ratio obtained by dividing odds, which is a ratio of a proportion of individuals with a risk factor to a proportion of individuals without a risk factor in a patient group, by odds obtained in a non-patient group in the same manner, which is in many cases used in a case-control study as in the present invention. The odds ratio in the present invention is determined on the basis of the allele frequency or the genotype frequency. In other words, the odds ratio of a single nucleotide polymorphism associated with the progression refers to a value obtained by calculating a quotient obtained in a ratio of an allele or genotype frequency to another allele or genotype frequency in a progressive glaucoma group, over a ratio of frequencies obtained in the same manner in a nonprogressive glaucoma group. In the present invention, an extent to which a progressive risk of glaucoma increases can be predicted by comparing a case of having a certain allele or genotype to a case of having an allele or genotype other than the above, using these indices. For example, when an odds ratio of a certain allele in a certain single nucleotide polymorphism is greater than 1, the allele is an allele found in a high frequency in a progressive glaucoma group, in which the larger the odds ratio, the higher the progressive risk of glaucoma for a sample donor having the allele. On the other hand, when an odds ratio of an allele is less than 1, the allele is an opposite allele of the allele that is identified in a high frequency in a disease, in which the smaller the odds ratio, the lower the progressive risk of glaucoma for a sample donor having the allele. The risk of a disease can also be predicted in the same manner for a genotype.

In the present invention, the value of the odds ratio would be always greater than 1 by obtaining an odds ratio based on the high-risk allele. The risk prediction in a combination of plural single nucleotide polymorphisms is facilitated by defining so that the odds ratio is greater than 1 when having the high-risk allele as mentioned above.

Although the details are shown by the numerical formulas in the section of Examples, in a case where an odds ratio is obtained for an allele, the odds ratio may be a value obtained by calculating a quotient obtained in a ratio of the high-risk allele frequency to the low-risk allele frequency in a progressive glaucoma group, over a ratio of the high-risk allele frequency to the low-risk allele frequency in a nonprogressive glaucoma group. In order to obtain an odds ratio in a genotype, the odds ratio is obtained by taking into consideration whether the high-risk allele complies with a dominant genetic model, or with a recessive genetic model. In other words, a homozygote of the high-risk allele and a heterozygote becomes a risk factor when the high-risk allele complies with a dominant genetic model, and a homozygote of the high-risk allele becomes a risk factor when the high-risk allele complies with a recessive genetic model. Therefore, when the high-risk allele complies with a dominant genetic model, the odds ratio may be obtained by obtaining the sum of the homozygote frequency of the high-risk allele and the heterozygote frequency in a progressive glaucoma group, and calculating a quotient obtained in a ratio of the above sum to the homozygote frequency of the low-risk allele, over a ratio of frequencies obtained in the same manner in a nonprogressive glaucoma group. When the high-risk allele complies with a recessive genetic model, the odds ratio may be obtained by obtaining the sum of the homozygote frequency of the low-risk allele and the heterozygote frequency in a progressive glaucoma group, and calculating a quotient obtained in a ratio of the homozygote frequency of the high-risk allele to the above sum, over a ratio of frequencies obtained in the same manner in a nonprogressive glaucoma group.

Further, the reliability of a single nucleotide polymorphism used in the prediction of a risk can be confirmed with an odds ratio. As mentioned above, the meaning for the prediction of a risk reverses in a case where the odds ratio is 1 or more and a case where the odds ratio is 1 or less. Therefore, in a case where a calculated 95% confidence interval of the odds ratio includes 1, it cannot be said that the reliability for the prediction of a risk for the odds ratio as mentioned above would be high.

In addition, in a case where a progressive risk of glaucoma is predicted by a combination of single nucleotide polymorphisms of the present invention, the level of the risk can be predicted by using the level of the odds ratio.

In the odds ratio according to an allele, the odds ratio of combined two or more single nucleotide polymorphisms can be calculated according to the following formula:

$$(RA1_{comb}RA2_{comb})/(RA3_{comb}RA4_{comb})$$

wherein
$RA1_{comb}$: an allele frequency in a case where at least one allele is a high-risk allele in a progressive glaucoma group;
$RA2_{comb}$: an allele frequency in a case where all the alleles are low-risk alleles in the progressive glaucoma group;
$RA3_{comb}$: an allele frequency corresponding to $RA1_{comb}$ in a nonprogressive glaucoma group; and
$RA4_{comb}$: an allele frequency in a case where all the alleles are low-risk alleles in the nonprogressive glaucoma group.

For example, in a case where two single nucleotide polymorphisms associated with the progressive risk of glaucoma are combined, an odds is determined by dividing the frequencies in a progressive glaucoma group all having high-risk alleles of a single nucleotide polymorphism, or having any one of high-risk alleles, by the frequency in the progressive glaucoma group not having any one of high-risk alleles. The odds ratio in a case of a combination of the single nucleotide polymorphisms can be determined by calculating a ratio of said odds to the odds of that in a nonprogressive glaucoma group obtained in the same manner.

In order to obtain an odds ratio according to a combination in cases of genotypes, the odds ratio is obtained by taking into consideration whether the high-risk allele complies with a dominant genetic model, or with a recessive genetic model, in the same manner as that alone.

In the odds ratio according to a dominant genetic model, the odds ratio of combined two or more single nucleotide polymorphisms can be calculated according to the following formula:

$$(RGd1_{comb}RGd2_{comb})/(RGd3_{comb}RGd4_{comb})$$

wherein
$RGd1_{comb}$: a frequency at which at least one genotype is a homozygote of a high-risk allele or a heterozygote, in a progressive glaucoma group;
$RGd2_{comb}$: a frequency at which all the genotypes are homozygotes of a low-risk allele in the progressive glaucoma group;
$RGd3_{comb}$: a frequency of the genotype corresponding to $RGd1_{comb}$ in a nonprogressive glaucoma group; and
$RGd4_{comb}$: a frequency at which all the genotypes are homozygotes of a low-risk allele in the nonprogressive glaucoma group.

For example, in a case where both the high-risk alleles of the two single nucleotide polymorphisms comply with a dominant genetic model, the odds ratio may be obtained by calculating a quotient obtained in a ratio of the frequency at which any of the two single nucleotide polymorphisms are a homozygote of a high-risk allele or a heterozygote in a progressive glaucoma group to the frequency at which both the two single nucleotide polymorphisms are a homozygote of a low-risk allele in the progressive glaucoma group, over a ratio of frequencies of those obtained in the same manner in a nonprogressive glaucoma group.

In the odds ratio according to a recessive genetic model, the odds ratio of combined two or more single nucleotide polymorphisms can be calculated according to the following formula:

$$(RGr1_{comb}RGr2_{comb})/(RGr3_{comb}RGr4_{comb})$$

wherein
$RGr1_{comb}$: a frequency at which at least one genotype is a homozygote of a high-risk allele, in a progressive glaucoma group;
$RGr2_{comb}$: a frequency at which all the genotypes are homozygotes of a low-risk allele in the progressive glaucoma group;
$RGr3_{comb}$: a frequency of the genotype corresponding to $RGr1_{comb}$ in a nonprogressive glaucoma group; and
$RGr4_{comb}$: a frequency at which all the genotypes are homozygotes of a low-risk allele in the nonprogressive glaucoma group.

In a case where both the high-risk alleles of the two single nucleotide polymorphisms comply with a recessive genetic model, the odds ratio may be obtained by calculating a quotient obtained in a ratio of the frequency at which any of the two single nucleotide polymorphisms are a homozygote of a high-risk allele in a progressive glaucoma group to the frequency at which both the two single nucleotide polymorphisms are a homozygote of a low-risk allele in the progressive glaucoma group, over a ratio of frequencies of those obtained in the same manner in a nonprogressive glaucoma group. Here, the odds ratio for a combination of single nucleotide polymorphisms can also be calculated by combining single nucleotide polymorphisms having different genetic forms.

Generally, the odds ratio increases by combining two or more single nucleotide polymorphisms, as compared to a case where these single nucleotide polymorphisms are used alone. Therefore, by a combination of two or more single nucleotide polymorphisms, a sample donor with a higher progressive risk of glaucoma would be identified, whereby the improvement in the precision of the prediction can be made possible, as compared to the case where a single nucleotide polymorphism is used alone.

In order to confirm the improvement of the precision of the prediction of a progressive risk of glaucoma according to a combination of single nucleotide polymorphisms in the present invention, a multivariate analysis can be employed. As the multivariate analysis method, a method well known to one of ordinary skill in the art such as logistic regression analysis method, discriminant analysis method, multiple linear regression analysis method, or proportional hazard analysis method can be employed, among which the logistic regression analysis method is effective in a case where a dichotomous variable such as the presence or the absence of a progressive risk of glaucoma is handled.

The logistic regression analysis method refers to a method of analyzing a degree to which multiple independent variables ($\Pi$) contribute in order to describe a single dependent variable ($\Phi$) (*Wakariyasui Igaku Tokeigaku* (*Easy Medical Statistics*), pp. 148-179, Toshio MORIZANE, Medical Tribune). By performing the logistic regression analysis, a regression coefficient ($\lambda$) for each independent variable can be obtained, and this regression coefficient can be utilized as an index showing a degree to which each independent variable describes a dependent variable. In addition, a dependent variable on each obtained independent variable can be calculated by substituting this regression coefficient into the following formula:

$$\Phi=1/\{1+\exp[-(\lambda 0+\lambda 1\Pi 1+\lambda 2\Pi 2+\lambda 3\Pi 3+\ldots)]\}$$

Here, when the logistic regression analysis is performed, the independent variables $\Pi$ used in analysis can be previously narrowed down using a stepwise method or the like. The stepwise method refers to a method for selecting independent variables $\Pi$ so as to maximize the regression coefficients by adding an optional independent variable $\Pi$. In other words, it means that after the regression coefficient is maximized by adding an arbitrary independent variable $\Pi$, the same outcome is obtained even if another independent variable $\Pi$ is further added.

In the present invention, by combining any two or more single nucleotide polymorphisms determined to be involved in the progression of glaucoma, the extent to which the precision of the prediction of a progressive risk is improved can be known, as compared to that where each of the single nucleotide polymorphisms is used alone. Concretely, the above formula is obtained according to logistic regression analysis by using each of any two or more single nucleotide polymorphisms as an independent variable $\Pi$ (homozygote of one allele=0, heterozygote=1, homozygote of an opposite allele=2). In each sample, a dependent variable $\Phi$ is calculated by substituting a variable for each single nucleotide polymorphism into this formula. When a dependent variable $\Phi$ is greater than a given threshold (for example, 0.5), this sample donor is determined to be a progressive glaucoma case. The determination results are collated with the matter of whether the sample donor having a single nucleotide polymorphism was actually a progressive glaucoma case. According to the combination of the two or more single nucleotide polymorphisms in the present invention, an improvement in a concordance proportion is confirmed, whereby the precision improvement by the combination can be confirmed.

In addition, the single nucleotide polymorphisms which exist in genetically sufficiently close locations to each other are inherited in linkage, not inherited independently, in some cases. In a certain population, a state in which a linkage as described above is held regardless of occurrence of a recombination by mating is referred to as a linkage disequilibrium, and a unit holding the linkage is referred to a haplotype block or an LD block.

In the experiment results by the present inventors, it is found that a single nucleotide polymorphism associated with glaucoma actually may exist in clusters in a relatively closely on the genome in some cases. It is considered that these regions belong to an LD block associated with glaucoma. In order to determine an LD block associated with glaucoma, the LD block can be determined by analyzing single nucleotide polymorphisms which exist in the region as many as possible by the method mentioned above, and applying an algorithm to determine an LD block, for example, an EM algorithm. In addition, when the single nucleotide polymorphism associated with glaucoma in the present invention belongs to a known LD block, the LD block can be considered as an LD block associated with glaucoma. Genome Browser provided on the internet web sites by California University at Santa Cruz, or the like can be consulted for a known LD block.

Because a single nucleotide polymorphism that belongs to an LD block associated with glaucoma is linked to a single nucleotide polymorphism associated with glaucoma identified according to the experiments of the present inventors, it can be considered that the single nucleotide polymorphism that belongs to an LD block associated with glaucoma also associates with glaucoma in the same manner; therefore, the single nucleotide polymorphism is used in the prediction of an onset risk or progressive risk of glaucoma. In addition, by re-determining a sequence within the LD block associated with glaucoma, or a sequence surrounding the single nucleotide polymorphism associated with glaucoma that is identified according to the experiments by the present inventors, there is a possibility that an unknown single nucleotide polymorphism which is linked with the single nucleotide polymorphism, in other words, which is associated with the onset of glaucoma or the progression thereof, is found. Whether or not the found single nucleotide polymorphism is actually associated with the onset of glaucoma or the progress thereof can be determined by comparing an allele or genotype frequency of a disease group with that of a control group in the same manner as explained above.

In the present invention, an intronic single nucleotide polymorphism (iSNP) refers to one in which a single nucleotide polymorphism is identified in intron. A coding single nucleotide polymorphism (cSNP) refers to one that is accompanied by a change in an amino acid sequence, such as a codon in which the single nucleotide polymorphism is mutated to a codon encoding other amino acids or a termination codon, among those in which single nucleotide polymorphisms exist in regions translated in a protein. A silent single nucleotide polymorphism (sSNP) refers to one without accompanying a change in an amino acid sequence, among those in which a single nucleotide polymorphism is identified in a coding region. A genomic single nucleotide polymorphism (gSNP) refers to one in which a single nucleotide polymorphism exists in a region not encoding the gene on the genome. A regulatory polymorphism (rSNP) refers to a single nucleotide polymorphism existing in a site that is thought to be involved in the transcriptional regulation.

As described above, a single nucleotide polymorphism may exist in any location on the genome, any cases of which can be associated with a disease. In a case where a single nucleotide polymorphism exists in the intron or a non-coding region, there may be some cases where the single nucleotide polymorphism may influence a gene expression control, or splicing that takes place after the gene transcription or stability of mRNA. In a case where a single nucleotide polymorphism exists in the coding region, by substitution of its base, a codon corresponding to a certain amino acid may be changed to a codon corresponding to a different amino acid, or may undergo a change, for example, a change to a termination codon, or the like, which may lead to a change in the structure of a protein encoded thereby. Changes in expression levels or functions of genes by these changes consequently lead to changes in expression levels or functions of proteins encoded by the genes, which can be causes for various diseases. In a case where the genomic single nucleotide polymorphism is associated with a disease, there is a possibility that a region including the polymorphic site is actually translated, and influences in some way to other gene expressions. In a case where a silent single nucleotide polymorphism is associated with a disease, it is considered that a different polymorphism associating with the disease exists in the surrounding of the single nucleotide polymorphism, and the polymorphism and the silent single nucleotide polymorphism are linked, so that the association with the disease is found. Similarly, in a single nucleotide polymorphism other than the silent single nucleotide polymorphism, even when the single nucleotide polymorphism itself is not a direct cause for glaucoma but links to a polymorphism which is the true cause for glaucoma existing in the surrounding, the association of these single nucleotide polymorphisms and glaucoma may be found in some cases. In the case as described above, as described later, a polymorphism which is causative of glaucoma can be found by re-sequencing the surrounding of the single nucleotide polymorphism in the present invention. However, in any case, these single nucleotide polymorphisms can be also used for the purpose of predicting a progressive risk of glaucoma, regardless of whether or not these would be the true causes for the disease.

(Nucleic Acid Molecule Comprising Allele Associated with Glaucoma)

In an embodiment of the present invention, there are provided a nucleic acid molecule having a single nucleotide polymorphism associated with glaucoma, and a nucleic acid molecule comprising a sequence complementary to the nucleic acid molecule comprising a single nucleotide polymorphism associated with glaucoma.

The nucleic acid molecule comprising a single nucleotide polymorphism associated with glaucoma or the nucleic acid molecule having a sequence complementary to the nucleic acid molecule can be used as a marker for determining the level of the progressive risk of glaucoma. Further, these nucleic acid molecules can be used as a probe for detecting an allele or an opposite allele thereof identified in a high frequency in progressive glaucoma cases, or determining a genotype, in the single nucleotide polymorphism. In addition, in a case where the single nucleotide polymorphism exists on exon or in the neighborhood thereof, these nucleic acid molecules can be used in the detection of transcripts of genes.

The nucleic acid molecule constituting the genome of an eukaryote is constituted by double strands of a sense strand and an antisense strand complementary to the sense strand. In other words, the single nucleotide polymorphism also exists on the sense strand and the antisense strand, and the nucleic acid molecule of the present invention embraces both of these strands because the detection of a single nucleotide polymorphism of both the strands is equally significant.

Nucleic acid molecules comprising any one of single nucleotide polymorphisms listed in Tables 1 and 2, Tables 5 to 25, Tables 26 to 28 and Tables 29 to 70 shown later, nucleic acid molecules comprising any single nucleotide polymorphisms existing in a region or on a gene determined by the linkage disequilibrium data or the like listed in Tables 3 and 4 shown later, and nucleic acid molecules complementary to these nucleic acid molecules are all embraced in the nucleic acid molecule of the present invention.

In an embodiment of the present invention, the nucleic acid molecule of the present invention is preferably nucleic acid molecules comprising a single nucleotide polymorphism listed in Tables 1 and 2, Tables 26 to 28 or Tables 52 to 70 shown later, or nucleic acid molecules complementary thereto, wherein in a case where the single nucleotide polymorphism is gSNP, the nucleic acid molecule is a nucleic acid molecule comprising a sequence from a next base of a known single nucleotide polymorphism on an upstream side of the sense strand to a base before a known single nucleotide polymorphism on a downstream side, or a nucleic acid molecule comprising a sequence complementary thereto, in a case where the single nucleotide polymorphism is iSNP, sSNP or cSNP, the nucleic acid molecule is a nucleic acid molecule comprising a full length of the gene on the genome including the single nucleotide polymorphism, a nucleic acid molecule comprising a sequence complementary thereto, and a nucleic acid molecule containing a complementary DNA (cDNA) molecule comprising the single nucleotide polymorphism or a sequence complementary thereto, in a case where the single nucleotide polymorphism is rSNP, the nucleic acid molecule is a nucleic acid molecule comprising a sequence from a next base of a known single nucleotide polymorphism on an upstream side of the sense strand to a full length of the gene existing downstream of a promoter region in which the single nucleotide polymorphism exists, or a nucleic acid molecule comprising a sequence complementary thereto.

The nucleic acid molecule in the present invention is not limited whether it is a deoxyribonucleic acid, a ribonucleic acid, or a peptide nucleic acid, and a nucleic acid molecule comprising a mixed sequence thereof is also embraced in the present invention. In a case where a ribonucleic acid is used in the nucleic acid molecule in the present invention, in the sequence of the nucleic acid molecule in the present invention (including a sequence complementary thereto), thymine may be read as uracil. In addition, these nucleic acid molecules may be subjected to chemical modifications as occasion demands, within the range that would not impair a function to be used in the present invention. In this case, the function refers to a function of accomplishing the purpose of using the nucleic acid molecule.

The nucleic acid molecule in the present invention can be synthesized by a known method, for example, a phosphoramidite method, on the basis of the sequence information disclosed herein, or the sequence information obtained by searching the information disclosed herein with the database. The nucleic acid molecule can be synthesized using a commercially available DNA synthesizer. In addition, the nucleic acid molecule in the present invention can be obtained from a sample comprising DNA from human according to a known method such as a PCR method, or in some nucleic acid molecules, can be obtained from a sample containing RNA from human according to a known method such as an RT-PCR method. As to primers that are necessary for the obtainment, one of ordinary skill in the art can design the primers on the basis of the sequence information disclosed herein, or the sequence information that can be searched from ID of the database disclosed herein. For example, in a case where a PCR method is used, primers having about 10 to about 30 bases that have sequences homologous to a part of the sequences of the nucleic acid molecule of interest can be used, and in a case where an RT-PCR method is used, the nucleic acid molecule can be obtained by carrying out reverse transcription reaction using an oligo dT primer, or a random hexamer, or the like to prepare cDNA, and amplifying a sequence of interest in the cDNA by the PCR method mentioned above.

The nucleic acid molecule has a length of preferably from 16 to 55 bases, and more preferably from 23 to 27 bases or 47 to 53 bases. It is preferable that the nucleic acid molecule is a nucleic acid molecule containing the polymorphic site mentioned above and a surrounding sequence thereof, or a sequence complementary thereto.

When a nucleic acid molecule comprising a single nucleotide polymorphism associated with the progression of glaucoma is selected, in a case where the nucleic acid molecule is selected based on the results obtained in a single analysis using a microarray in which, for example, 500,000 nucleic acid molecules are detected in a single operation, the nucleic acid molecule in the present invention is preferably a nucleic acid molecule having a p-value of $1 \times 10^{-3}$ or less, more preferably a nucleic acid molecule having a p-value of $3 \times 10^{-4}$ or less, even more preferably a nucleic acid molecule having a p-value of $1 \times 10^{-4}$ or less, and even more preferably a nucleic acid molecule having a p-value of $3 \times 10^{-5}$ or less. In a case where plural analytic results are combined and obtained according to a method of meta-analysis, such as Mantel-Haenszel method, the nucleic acid molecule is preferably a nucleic acid molecule having a p-value of $1 \times 10^{-2}$ or less, more preferably a nucleic acid molecule having a p-value of $3 \times 10^{-3}$ or less, even more preferably a nucleic acid molecule having a p-value of $1 \times 10^{-3}$ or less, even more preferably a nucleic acid molecule having a p-value of $3 \times 10^{-4}$ or less, and even more preferably a nucleic acid molecule having a p-value of $1 \times 10^{-4}$ or less.

As a different means of selecting a preferred nucleic acid molecule, a significance level is set according to a known multiple correction method, whereby a preferred nucleic acid molecule can be selected. In a case where a correction is based on Bonferroni correction, for example, a significance level can be obtained by dividing a p-value of $5 \times 10^{-2}$ by the number of multiple comparisons, i.e. the number of polymorphisms to be compared in the chi-square test. A nucleic acid molecule having a single nucleotide polymorphism below the significance level thus obtained may be selected as a more preferred nucleic acid molecule. Upon the selection, Bonferroni correction may be performed using a p-value that is combined according to a method of meta-analysis, such as Mantel-Haenszel method, and the number of single nucleotide polymorphisms to be subject for the meta-analysis. Other known methods used in multiple corrections, for example, an FDR method or a permutation method may be used in the selection of a preferred nucleic acid molecule.

(Method of Detecting Single Nucleotide Polymorphism Associated with Glaucoma and Method of Predicting Progressive Risk of Glaucoma)

Another embodiment of the present invention provides a method of detecting the presence or absence of an allele or genotype having a high frequency in progressive glaucoma cases in a sample containing a nucleic acid molecule from the genome. The samples may be any ones so long as the nucleic acid molecules from the genome can be extracted, and for example, blood, white blood cells, hair root, hair, saliva, oral mucosa cells, skin, tissues such as muscles or organs obtained by biopsy, or the like can be used.

As mentioned above, the nucleic acid molecule constituting the genome of an eukaryote is constituted by a sense strand and an antisense strand that are complementary to each other, and the determination of the allele of the single nucleotide polymorphism in the present invention can also be performed by detecting any one of the bases of the sense strand and the antisense strand of the polymorphic site.

As mentioned above, in the method of determining the presence or the absence of the allele or genotype in a sample containing a nucleic acid molecule, any means can be used. For example, hybridization is carried out using a probe specific to each of the alleles, preferably a probe in the present invention described later, which is designed based on the sequence information disclosed in the present invention, and each of the alleles can be detected by detecting signals therefor. In addition, each of the alleles opposite to each other, in other words, an allele having a high association to a disease for a certain single nucleotide polymorphism and an allele having a low association thereto are each provided with different labels, and a probe capable of hybridizing these alleles to a polymorphic site, or an immobilized probe such as a microarray in which each of alleles opposite to each other is immobilized is used, whereby each of the alleles opposite to each other contained in the same sample can be detected. In the constitution as described above, not only the alleles of the sample, but also the genotypes can be determined. In addition, in a case where an immobilized probe such as a microarray in which each of the alleles opposite to each other is immobilized on the same carrier is used, a constitution that the hybridization is carried out in a single operation, and that the detection is carried out in a single operation can be also taken.

As another method of detecting a single nucleotide polymorphism in the present invention, the following method can be utilized. Examples of a method of hybridization using a probe are Taqman method, Invader (registered trademark) method, LightCycler method, cyclin probe method, MPSS method, beads-array method, and the like, and any of these methods can be employed. As to the probe for detecting the same allele, a more preferred probe may differ in some cases depending upon a method used in the detection. The determination of the allele or genotype of the single nucleotide polymorphism in the present invention does not depend upon the detection method, and it is preferable to use a suitable probe depending upon the detection method.

The Taqman method is a method of detecting a genetic polymorphism using an oligoprobe having a given length in which a fluorescent substance is bound to a 5'-side, and a quencher is bound to a 3'-side. The presence or absence of the polymorphism is determined by hybridizing a probe to a nucleic acid molecule having a polymorphism of interest, cutting off a part of the probe on the 5'-side by a PCR reaction, and measuring a fluorescent amount emitted by a fluorescent substance.

The Invader method is a method of detecting a genetic polymorphism using a probe (reporter) which has a sequence common to a 3'-side of a nucleic acid molecule having a polymorphism, but the sequence on a 5'-side being completely different therefrom, and a probe (invader) having only a sequence common to a 5'-side. The nucleic acid molecules of interest and these two probes are hybridized, a product is then treated with a nuclease, a part of the cut-out reporter probe is hybridized with a probe for detection having a fluorescent substance and a quencher, a hybridization product is treated with a nuclease, and the fluorescent substance is released, whereby the presence or absence of the polymorphism is determined by a fluorescent amount thereof.

The LightCycler method is a method of detecting a polymorphism including the step of hybridizing a polymorphic detection probe having a fluorescent substance and an anchor probe having a quencher, to a nucleic acid molecule comprising a polymorphism previously amplified by PCR. If the hybridized DNA is gradually heated, the polymorphic detection probe is released when a given temperature is reached, and the presence or absence of the polymorphism is determined by measuring this fluorescent amount.

The cyclin probe method is a polymorphic analysis method utilizing a probe having a fluorescent substance or a quencher on each end of a DNA (DRD probe), wherein DNA sequences are bound in a manner that both ends of an RNA sequence having a sequence complementary to a polymorphic site of a nucleic acid molecule of interest are sandwiched. A DRD probe is hybridized to a nucleic acid molecule of interest previously amplified by PCR or the like, RNase is allowed to act on this complex, and a fluorescent dye is released, whereby the presence or absence of the polymorphism is determined by measuring this fluorescent amount.

The MPSS method is a method of performing polymorphic analysis using an encoded adaptor probe and a decoder probe. The encoded adaptor probe is an oligo DNA having a 4-bases long protruding end on a 5'-side, subsequently a recognition sequence for a restriction enzyme BbvI, and a single-stranded sequence bound to a decoder probe on a 3'-side. On the other hand, the decoder probe is a single-stranded oligo DNA having a fluorescent substance on a 3'-side, and the decoder probe containing 4 different sequences, each sequence specifically hybridizing to a single encoded adaptor probe. The nucleic acid molecule having a polymorphism is previously immobilized on beads, and an initiation adaptor containing a recognition sequence for BbvI is bound thereto, to digest with BbvI to form a 4-bases long protruding end. The ligation with the encoded adaptor probe is carried out sequentially from a 3'-side of the protruding 4 bases, and the sequence of the bound encoded adaptor is detected with a specified decoder probe.

The beads array method is a method of performing the determination of a genotype including the step of combining beads to which a probe for allele detection and an oligonucleotide (address sequence) specifying the location information on the array of signals detected by the probe for allele detection are bound. For example, there are Golden Gate Assay using beads immobilized with only an address sequence (23 bases) of Illumina, and Infinium (registered trademark) Assay using beads in which probes (50 bases) for allele detection are bound to an address sequence (30 bases). In both the methods, which location on an array the probes for allele detection are bound can be known for each of the beads arranged arbitrarily on the array, on the basis of the address sequence.

The method of the Golden Gate Assay will be shown hereinbelow. In the detection of a single nucleotide polymorphism, two kinds of probes (allele-specific probes) specifically hybridizing to each allele, and a probe capable of specifically hybridizing to a sequence located 1 to 20 bases downstream on the 3'-side of the single nucleotide polymorphism (downstream sequence recognition probe) are used. In the downstream sequence recognition probe, an address sequence for specifying the location on the array is provided. In addition, these three probes contain a sequence to which universal primers described later are bound. The three probes are annealed with a genomic DNA, and a DNA polymerase and a ligase are added thereto. By carrying out an extension reaction and a ligation reaction, an allele-specific product ligating a gap between the allele-specific probe and the downstream sequence recognition probe is formed. A reaction for PCR is carried out with this allele-specific product as a template using two kinds of fluorescent-labeled universal primers, each being specific to each allele, and a universal primer bound to the downstream sequence recognition probe. A labeled PCR product is hybridized to an oligonucleotide immobilized on beads via an address sequence. The fluorescence on the beads is detected with a confocal laser scanner, thereby determining an allele and a genotype.

The method of the Infinium Assay will be shown hereinbelow. An array by Illumina [Illumina, iSelect™ Genotyping BeadChip] described later is in accordance with this method. There are two methods in the detection of an allele by this array. In one method, two kinds of probes (probes for allele detection of 50 bases long, Infinium I type) only differing by a base at a 3'-end, wherein the 3'-end is a site for detecting a single nucleotide polymorphism, are used. Whole genome amplification for a genomic DNA is previously carried out, and fragmentation with an enzyme is carried out. The probe and the fragmented genomic DNA are hybridized, and thereafter an allele-specific extension reaction takes place, whereby a base on the downstream (3'-side) by a single base of a polymorphic site labeled with a single kind of a fluorescent dye is incorporated corresponding to the probe. In another method, one kind of probe without having an allele-specific sequence of a single nucleotide polymorphism in the probe is used (probe for allele detection of 50 bases, Infinium II type). A 3'-end of this probe has a sequence up to a single base upstream (5'-side) from a polymorphic site. The probe and the fragmented genomic DNA are hybridized, and according to a single base extension reaction, a base labeled with either one of two kinds of fluorescent dyes is incorporated corresponding to a single nucleotide polymorphic site of interest. In both the methods, the fluorescence is detected by a confocal laser scanner, thereby determining an allele and a genotype.

Here, the details of properties for length, modification and the like of probes used in the hybridization method mentioned above will be described later.

In addition, a method without carrying out hybridization with a probe includes PCR-RFLP method, SSCP method, mass spectrometry and direct sequencing method.

The PCR-RFLP method is a method including the steps of forming different DNA fragments according to enzymatic digestion of a nucleic acid molecule having a polymorphism due to the existence of a polymorphism in a cleavage site of the restriction enzyme in the nucleic acid molecule, and determining the presence or absence of a polymorphism from a difference in electrophoretic patterns thereof. A nucleic acid molecule of interest is amplified by PCR, this amplified fragment is cleaved with a restriction enzyme, and a fragment formed electrophoretically is analyzed. The length of the nucleic acid molecule comprising an amplified polymorphism is usually from 50 to 10,000 base pairs, and more preferably from 100 to 1,000 base pairs.

The SSCP method is a method including the steps of amplifying a nucleic acid molecule having a polymorphism by PCR, forming a single-stranded DNA, electrophoresing the product, and determining the presence or absence of a polymorphism from a difference in the electrophoretic patterns thereof. The nucleic acid molecule of interest is amplified by PCR, and a single-stranded DNA is formed by subjecting this amplified fragment to heat or an alkali treatment. This single-stranded DNA forms a base sequence-specific higher-order structure; therefore, if these amplified fragments are electrophoresed, a difference in the electrophoretic mobility is found due to the difference in its structure. The primer used in PCR is labeled with a radioisotope or fluorescent substance. In addition, the length of the nucleic acid molecule comprising an amplified polymorphism is usually from 50 to 10,000 base pairs, and more preferably from 100 to 1,000 base pairs.

The mass spectrometry is a method including the steps of ionizing a polymer with a matrix and a laser or the like, accelerating the ionized polymer in a high electric field to allow a flight to a detector, and identifying mass from a difference in the flight time, or the like. This mass spectrometry is combined with the above primer extension method or the like to detect a polymorphism. Concretely, a single base extension reaction is carried out with a primer complementary to a sequence up to a single base upstream of a polymorphic site of a nucleic acid molecule having a polymorphism, any one of 4 kinds of dideoxyribonucleotides, and deoxyribonucleic acids other than those corresponding the above, and a difference in mass of nucleic acid products having different sequences incorporated in a 3'-end is determined, whereby a polymorphism can be identified.

The direct sequencing method is a method of directly reading off a base sequence of a nucleic acid molecule having a polymorphism. Representative methods are called Sanger method (dideoxy method). A primer that is unlabeled or labeled with a radioisotope or a fluorescent substance is bound to a nucleic acid molecule of interest, an extension reaction with Klenow enzyme or the like is stopped with four kinds of dideoxyribonucleotides that are unlabeled or labeled with a radioisotope or a fluorescent substance, the product is digested with a restriction enzyme, and a DNA fragment generated is separated by electrophoresis. The base sequence of a 3'-end is read off in the order of fragments having a lower molecular weight on the basis of an electrophoretic image, thereby a base sequence containing a few bases before and after a polymorphism is determined. As a modified method thereof, there is a method called a primer extension method. This is a method including the steps of carrying out a single base extension reaction using a primer complementary to a sequence up to a single base upstream of a polymorphic site of a nucleic acid molecule having a polymorphism, and reading off any one of the sequences of the 4 kinds of dideoxyribonucleotides incorporated in the 3-end. There are various methods in the identification of this dideoxyribonucleotides; for example, 4 kinds of nucleotides are labeled with different fluorescent substances, and separated and identified electrophoretically. In addition, a method of converting pyrophosphoric acid formed during an extension reaction to ATP, and identifying its ATP from luminescence of luciferase is also employed. The length of the primer used in the extension reaction is usually from 10 to 300 base pairs, and preferably from 15 to 25 base pairs.

In the present invention, the hybridization means that a nucleic acid molecule having a certain sequence is associated with a nucleic acid molecule complementary to at least a part of the nucleic acid molecule via a hydrogen bond on the basis of base sequences that are complementary to each other. The kind of the complementary nucleic acid molecule associated with the original nucleic acid molecule may be identical or different, and a nucleic acid constituting these nucleic acid molecules can be a deoxyribonucleic acid, a ribonucleic acid, or a peptide nucleic acid. In these nucleic acid molecules, when referred to the ribonucleic acid, in the sequence of the nucleic acid molecule (including a complementary sequence), thymine may be read as uracil.

The stringent conditions in the present invention mean conditions in which a nucleic acid molecule having a sequence complementary to a partial sequence of a nucleic acid molecule having a certain sequence is specifically hybridized to the nucleic acid molecule (Fred M. Ausuble et al., *Current Protocols in Molecular Biology*, 2.10.1-2.10.16, John Wiley and Sons, Inc). Concrete examples of the conditions as described above include conditions such as a temperature lower than a melting temperature (Tm) of a complex formed between a nucleic acid molecule having a certain sequence and a complementary nucleic acid molecule hybridized to the nucleic acid molecule by preferably from about 5° to about 30° C., and by more preferably about 10° to about 25° C., a reaction solution for hybridization, such as SSC (mixed solution of sodium chloride and sodium citrate) in a concentration of 0.01 to 6-folds, SSPE (mixed solution of sodium chloride, sodium dihydrogenphosphate, and EDTA) or MES (a mixed solution of 2-(N-morpholino)ethanesulfonic acid and tetramethylammonium chloride) buffer, and hydrogen ion concentrations of a pH of from 6 to 8. For example, the stringent conditions in a case where an immobilized probe is prepared by immobilizing a 25 by DNA probe include conditions of hybridization at 49° C. in the MES buffer (hydrogen ion concentrations being from 6.5 to 6.7) in a 1-fold concentration, and sequentially washing with SSC (hydrogen ion concentrations being 8.0) in a 6-fold concentration at 25° C., and thereafter SSC (hydrogen ion concentrations being 8.0) in a 0.6-fold concentration at 45° C.

In the present invention, the term allele-specific (or specific to allele) means that the allele is contained in a sequence from the genome including the polymorphic site or in a prepared nucleic acid molecule including the polymorphic site, or a certain nucleic acid molecule is capable of specifically hybridizing under stringent conditions to a nucleic acid molecule having a sequence containing the allele in the polymorphic site, in other words, in the manner of being capable of discriminating the allele and the opposite allele.

Base sequences of 61 bases in length including a single nucleotide polymorphism associated with the progression of glaucoma, disclosed in the present invention, are composed of two pairs of base sequences which differ only by a base in the center (i.e. 31st base) (i.e. those pairs are consisting of a sequence having odd number of SEQ ID No. and a sequence having even number of SEQ ID No.), and the 31st base is a polymorphic site. The high-risk alleles in the polymorphic sites are listed in Tables 26 to 28 or Tables 52 to 70 given later. In any of these single nucleotide polymorphisms, in a case where the existence of an allele that exists in a high frequency in progressive glaucoma cases is determined, a high-risk allele in a sample is detected, whereby the existence of the allele that exists in a high frequency in progressive glaucoma cases can be determined.

In addition, as to any single nucleotide polymorphisms associated with the progression of glaucoma identified above, the genotype can be determined by detecting the presence or the absence of each of the alleles opposite to each other contained in one sample. In detail, in a case where only a certain allele is detected, the genotype is a homozygote of the allele, and in a case where two alleles are detected, the genotype is a heterozygote having the two alleles. In at least one of these single nucleotide polymorphisms, by detecting a genotype, it is determined whether or not the genotype that is identified in a higher frequency in a progressive glaucoma group than that of a nonprogressive glaucoma group exists in a sample. In other words, in the single nucleotide polymorphism mentioned above, when the high-risk allele complies with a dominant genetic model, a homozygote of the high-risk allele or a heterozygote is a genotype that is identified in a higher frequency in a progressive glaucoma group than that of a nonprogressive glaucoma group, and when the high-risk allele complies with a recessive genetic model, a homozygote of the high-risk allele is a genotype that is identified in a higher frequency in a progressive glaucoma group than that of a nonprogressive glaucoma group. It is preferable that each of the opposite alleles is measured in a single operation, from the viewpoint of reducing judgmental error.

The sample is analyzed in the manner described above, and in a case where the allele or genotype that is identified in a higher frequency in a progressive glaucoma group than that of a nonprogressive glaucoma group exists in the sample, there are some high probabilities that a glaucoma patient donating the sample is predicted to have a high progressive risk of glaucoma, and that an individual donating the sample who is suspected of having glaucoma should be diagnosed as a progressive glaucoma case, and an individual donating the sample not having glaucoma at the present point is predicted to have a fast progression of glaucoma in a case of an onset of glaucoma in future.

In the method of detecting a single nucleotide polymorphism associated with glaucoma and the method of predicting a progressive risk of glaucoma in the present invention, the single nucleotide polymorphism used in the detection is a single nucleotide polymorphism which is located on a 31st base of a base sequence, wherein the base sequence is at least one base sequence selected from the group consisting of base sequences shown in SEQ ID NOs: 203 to 752 or a complementary sequence thereto, more preferably a single nucleotide polymorphism which is located on a 31st base of a base sequence, wherein the base sequence is at least one base sequence selected from the group consisting of base sequences shown in SEQ ID NOs: 203 to 240 or a complementary sequence thereto, even more preferably a single nucleotide polymorphism which is located on a 31st base of a base sequence, wherein the base sequence is at least one base sequence selected from the group consisting of pairs of base sequences containing a single nucleotide polymorphism listed below or a complementary sequence thereto, wherein, as mentioned above, in the pairs of SEQ ID NOs: shown in a to s, each of the pairs of sequences corresponds to one single nucleotide polymorphism, and each of the base sequences is a base sequence containing an allele opposite to each other of the single nucleotide polymorphism in a 31st base:

a: SEQ ID NO: 203 and/or SEQ ID NO: 204,
b: SEQ ID NO: 205 and/or SEQ ID NO: 206,
c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216,
h: SEQ ID NO: 217 and/or SEQ ID NO: 218,
i: SEQ ID NO: 219 and/or SEQ ID NO: 220,
j: SEQ ID NO: 221 and/or SEQ ID NO: 222,
k: SEQ ID NO: 223 and/or SEQ ID NO: 224,
l: SEQ ID NO: 225 and/or SEQ ID NO: 226,
m: SEQ ID NO: 227 and/or SEQ ID NO: 228,
n: SEQ ID NO: 229 and/or SEQ ID NO: 230,
o: SEQ ID NO: 231 and/or SEQ ID NO: 232,
p: SEQ ID NO: 233 and/or SEQ ID NO: 234,
q: SEQ ID NO: 235 and/or SEQ ID NO: 236,
r: SEQ ID NO: 237 and/or SEQ ID NO: 238, and
s: SEQ ID NO: 239 and/or SEQ ID NO: 240.

In a case where any one of the single nucleotide polymorphisms is used, especially, it is preferable that an allele of a single nucleotide polymorphism located on a 31st base of a base sequence is used, wherein the base sequence is at least one base sequence selected from the group consisting of the following base sequences containing a single nucleotide polymorphism:

SEQ ID NO: 203, SEQ ID NO: 205, SEQ ID NO: 207, SEQ ID NO: 210, SEQ ID NO: 212, SEQ ID NO: 214, SEQ ID NO: 215, SEQ ID NO: 218, SEQ ID NO: 220, SEQ ID NO: 222, SEQ ID NO: 223, SEQ ID NO: 226, SEQ ID NO: 228, SEQ ID NO: 230, SEQ ID NO: 232, SEQ ID NO: 233, SEQ ID NO: 236, SEQ ID NO: 238, and SEQ ID NO: 240, or a complementary sequence thereto.

Here, these sequences are sequences containing a high-risk allele in each of polymorphic sites.

Further, the precision of the determination of a future progressive risk of glaucoma can be improved by detecting a combination of two or more of alleles or genotypes associated with glaucoma in the present invention, using one sample.

For the single nucleotide polymorphisms to be combined, any ones can be used so long as they are a single nucleotide polymorphism in the present invention, preferably a single nucleotide polymorphism having a low p-value, and more preferably a single nucleotide polymorphism of which p-value obtained by combining the results obtained in two analyses by a meta-analysis method, such as Mantel-Haenszel method, is determined to be significant even below the level of Bonferroni correction. In addition, from a different viewpoint, it is preferable to use a single nucleotide polymorphism that is confirmed to contribute to the improvement in the precision of the risk prediction by a combination according to the logistic regression analysis described later. On the other hand, since the single nucleotide polymorphisms in a state of linkage disequilibrium mentioned above show the same behavior, in a case where plural single nucleotide polymorphisms in a state of linkage disequilibrium are combined, risks of glaucoma based on the same region may be evaluated unnecessarily seriously in some cases. In a case where a risk of a disease is predicted by combining the single nucleotide polymorphisms in the present invention, when it is intended to evaluate all the risks in even weighting, it is preferable that the prediction is carried out employing only one of the single nucleotide polymorphisms in the state of linkage disequilibrium, in a case that the plural single nucleotide polymorphisms that are in the state of linkage disequilibrium mentioned above are contained.

In a case where a risk is predicted according to a combination of any two or more single nucleotide polymorphisms in the present invention, a progressive risk of glaucoma can be predicted using the regression formula obtained by the logistic regression analysis. Concretely, the regression formula according to the logistic regression analysis is obtained by respectively using each of the any two or more single nucleotide polymorphisms as an independent variable Π (homozygote of one allele=0, heterozygote=1, homozygote of an opposite allele=2). In each sample, a dependent variable Φ is calculated by substituting a value corresponding to each single nucleotide polymorphism into this formula. When a dependent variable Φ is greater than a given threshold (for example, 0.5), the determination can be made that this sample donor has a progressive risk.

In the method of detecting a single nucleotide polymorphism associated with glaucoma and the method of predicting a progressive risk of glaucoma in the present invention, in a case where any two or more single nucleotide polymorphisms are combined, the single nucleotide polymorphisms used in the detection are preferably single nucleotide polymorphisms which are located on 31st bases of base sequences, wherein the base sequences are base sequences containing two or more different single nucleotide polymorphisms, selected from the group consisting of base sequences shown in SEQ ID NOs: 203 to 752 or a complementary sequence thereto, more preferably single nucleotide polymorphisms which are located on 31st bases of base sequences, wherein the base sequences are base sequences containing two or more different single nucleotide polymorphisms, selected from the group consisting of base sequences shown in SEQ ID NOs: 203 to 240 or a complementary sequence thereto, even more preferably single nucleotide polymorphisms which are located on 31st bases of base sequences, wherein the base sequences are base sequences containing two or more different single nucleotide polymorphisms, selected from the group consisting of pairs of base sequences containing a single nucleotide polymorphism listed below or a complementary sequence thereto, wherein, as mentioned above, in the pairs of SEQ ID NOs: shown in a to s, each of the pairs of sequences corresponds to one single nucleotide polymorphism, and each of the base sequences is a base sequence containing an allele opposite to each other of the single nucleotide polymorphism in a 31st base:

a: SEQ ID NO: 203 and/or SEQ ID NO: 204,
b: SEQ ID NO: 205 and/or SEQ ID NO: 206,
c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216,
h: SEQ ID NO: 217 and/or SEQ ID NO: 218,
i: SEQ ID NO: 219 and/or SEQ ID NO: 220,
j: SEQ ID NO: 221 and/or SEQ ID NO: 222,
k: SEQ ID NO: 223 and/or SEQ ID NO: 224,
l: SEQ ID NO: 225 and/or SEQ ID NO: 226,
m: SEQ ID NO: 227 and/or SEQ ID NO: 228,
n: SEQ ID NO: 229 and/or SEQ ID NO: 230,
o: SEQ ID NO: 231 and/or SEQ ID NO: 232,
p: SEQ ID NO: 233 and/or SEQ ID NO: 234,
q: SEQ ID NO: 235 and/or SEQ ID NO: 236,
r: SEQ ID NO: 237 and/or SEQ ID NO: 238, and
s: SEQ ID NO: 239 and/or SEQ ID NO: 240, and even more preferably single nucleotide polymorphisms which are located on 31st bases of base sequences, wherein the base sequences are base sequences containing 10 or more different single nucleotide polymorphisms, selected from the group consisting of pairs of base sequences containing a single nucleotide polymorphism listed above or a complementary sequence thereto, and even more preferably single nucleotide polymorphisms which are located on 31st bases of base sequences, wherein the base sequences are base sequences containing all the different single nucleotide polymorphisms, selected from the group consisting of pairs of base sequences containing a single nucleotide polymorphism listed above or a complementary sequence thereto.

In addition, it is preferable that the single nucleotide polymorphisms to be used in combination are those that are not in the state of linkage disequilibrium, and from this viewpoint, in all the embodiments of the combinations mentioned above, supposing that a group composed of a single nucleotide polymorphism which is located on a 31st base of a base sequence, wherein the base sequence is a base sequence belonging to the group consisting of:

c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216, and
h: SEQ ID NO: 217 and/or SEQ ID NO: 218, or a complementary sequence thereto, is named as a single nucleotide polymorphism of Group 1, a group composed of a single nucleotide polymorphism which is located on a 31st base of a base sequence, wherein the base sequence is a base sequence belonging to the group consisting of:

i: SEQ ID NO: 219 and/or SEQ ID NO: 220, and
j: SEQ ID NO: 221 and/or SEQ ID NO: 222, or a complementary sequence thereto, is named as a single nucleotide polymorphism of Group 2, it is preferable to use any one of the single nucleotide polymorphisms in Group 1 in a case that the single nucleotide polymorphisms belonging to Group 1 are used, and/or any one of the single nucleotide polymorphisms in Group 2 in a case that the single nucleotide polymorphisms belonging to Group 2 are used.

Further, in all the embodiments of the combinations mentioned above, it is preferable that an allele of a single nucleotide polymorphism located on a 31st base of a base sequence is used, wherein the base sequence is a base sequence containing two or more different single nucleotide polymorphisms, selected from the group consisting of the following base sequences containing a single nucleotide polymorphism:

SEQ ID NO: 203, SEQ ID NO: 205, SEQ ID NO: 207, SEQ ID NO: 210, SEQ ID NO: 212, SEQ ID NO: 214, SEQ ID NO: 215, SEQ ID NO: 218, SEQ ID NO: 220, SEQ ID NO: 222, SEQ ID NO: 223, SEQ ID NO: 226, SEQ ID NO: 228, SEQ ID NO: 230, SEQ ID NO: 232, SEQ ID NO: 233, SEQ ID NO: 236, SEQ ID NO: 238, and SEQ ID NO: 240, or a complementary sequence thereto.

Here, these base sequences are sequences containing a high-risk allele in each of polymorphic sites.

(Probe Capable of Detecting Allele Associated with Glaucoma)

In another embodiment of the present invention, an allele-specific nucleic acid molecule or probe (hereinafter referred to as probe) capable of detecting an allele associated with glaucoma, and a method of detecting an allele or a genotype associated with glaucoma using the probe are provided.

Any probes may be used so long as the probe is capable of hybridizing under the stringent conditions to an allele-specific sequence, in a polymorphic site of the single nucleotide polymorphism associated with glaucoma in the present invention. The determination of the allele in a polymorphic site can be made by detecting any one of polymorphic sites of the sense strand and the antisense strand on the genome; therefore, the probe in the present invention embraces any one of sequences complementary to a sequence specific to an allele of the sense strand and sequences complementary to a sequence specific to an allele of the antisense strand, in other words, sequences specific to an allele of the sense strand. The probe in the present invention can also be used in the detection of cDNA or mRNA, containing a single nucleotide polymorphism in the present invention. In a case where the probe is used in the detection of cDNA or mRNA, a probe in which the single nucleotide polymorphism exists in exon or neighborhood thereof is used.

The probes capable of detecting each of alleles of the single nucleotide polymorphisms listed in Tables 1 and 2, Tables 5 to 25, Tables 26 to 28, Tables 29 to 51, or Tables 52 to 70 given later or a complementary strand thereto, and the probes capable of specifically detecting each of alleles of any single nucleotide polymorphisms that exist in a region associated with glaucoma listed in Tables 3 and 4 or Tables 71 to 81 given later or a complementary strand thereto are all embraced in the probe in the present invention. In a case where, for example, the obtained results are based on a single analysis using a microarray in which a probe capable of specifically detecting each of alleles of 500,000 single nucleotide polymorphisms, or a complementary strand thereto, is detected in a single operation, the probe of the present invention is preferably a probe capable of specifically detecting each of alleles of a single nucleotide polymorphism or a complementary strand thereto, of which p-value is $1 \times 10^{-3}$ or less, more preferably a probe capable of specifically detecting each of alleles of a single nucleotide polymorphism or a complementary strand thereto, of which p-value is $3 \times 10^{-4}$ or less, even more preferably a probe capable of specifically detecting each of alleles of a single nucleotide polymorphism or a complementary strand thereto, of which p-value is $1 \times 10^{-4}$ or less, and even more preferably a probe capable of specifically detecting each of alleles of a single nucleotide polymorphism or a complementary strand thereto, of which p-value is $3 \times 10^{-5}$ or less. In a case where plural analytical results are combined and obtained according to a method of meta-analysis, such as Mantel-Haenszel method, the probe is preferably a probe capable of specifically detecting each of alleles of a single nucleotide polymorphism or a complementary strand thereto, of which p-value is $1 \times 10^{-2}$ or less, more preferably a probe capable of specifically detecting each of alleles of a single nucleotide polymorphism or a complementary strand thereto, of which p-value is $3 \times 10^{-3}$ or less, even more preferably a probe capable of specifically detecting each of alleles of a single nucleotide polymorphism or a complementary strand thereto, of which p-value is $1 \times 10^{-3}$ or less, even more preferably a probe capable of specifically detecting each of alleles of a single nucleotide polymorphism or a complementary strand thereto, of which p-value is $3 \times 10^{-4}$ or less, and even more preferably a probe capable of specifically detecting each of alleles of a single nucleotide polymorphism or a complementary strand thereto, of which p-value is $1 \times 10^{-4}$ or less.

The probe in the present invention preferably contains an allele-specific sequence or a complementary strand thereto, and even more preferably in the probe in the present invention, a sequence contributing to an allele-specific hybridization consists only of an allele-specific sequence or a complementary strand thereto. To the probe in the present invention, a spacer or any sequences of several bases that are not from an allele-specific sequence for the purpose of providing stabilization or the like can be added in an end, within the range that the probe is capable of hybridizing to the sequence under the stringent conditions. The added sequence is preferably a sequence that does not take a three-dimensional structure, such as a hairpin structure.

The probe can be provided with any labels for use in the detection. Any labels to be provided to the probe that are ordinarily used can be used, and in general, a fluorescent label such as FITC or Cy3, biotin, an enzyme label such as an alkaline phosphatase and horseradish peroxidase, or the like is usable. In a case where a biotin label is used, streptavidin capable of specifically binding to biotin is previously provided with a further detectable label, and the labeled streptavidin is used as a secondary label. A labeled anti-biotin antibody can also be used in place of the labeled streptavidin. As a method of providing a label to a probe, any known methods may be used, and the methods are well known to one of ordinary skill in the art. An arbitrary sequence which serves as a spacer as mentioned above may be added to the probe, and the spacer may be provided with a label. A reagent for labeling a probe, a labeled streptavidin, a labeled anti-biotin antibody or the like is commercially available as a reagent, and can also be purchased.

The probe in the present invention is not limited whether it is a deoxyribonucleic acid, a ribonucleic acid, or a peptide nucleic acid, and a probe containing a mixed sequence thereof is also embraced in the present invention, so long as the probe is capable of specifically hybridizing to a nucleic acid molecule comprising an allele of interest. In a case where a probe containing a ribonucleic acid is used as the probe in the present invention, in the sequence of the probe in the present invention (including a sequence complementary thereto), thymine may read as uracil. In addition, the probe in the present invention may be subjected to chemical modifications as needed, so long as the probe is capable of specifically hybridizing under stringent conditions to a nucleic acid molecule having an allele of interest. As the method of providing a chemical label, any known methods may be used.

The probe for the detection can be reacted with the sample in the state of solution and then detected by a known method, or previously immobilized to a carrier. The probe can take the form of an immobilized probe obtained by previously immobilizing a probe corresponding to each of the alleles of several to several hundred-thousand different single nucleotide polymorphisms to a location defined on a solid carrier in the number of from one to dozen probes per one single nucleotide polymorphism, reacting a sample to the immobilized probes, scanning a signal generated from a hybridized probe, and analyzing the scanned data with a computer, which is a so-called microarray. In a case where the probe takes the form of an immobilized probe, the largest number of the immobilized probes are limited by immobilization density and area of immobilized sites for the probes.

In a case where the probe takes the form of an immobilized probe as described above, signals on the solid phase from the nucleic acid molecule having a labeled target allele can be detected by previously labeling a nucleic acid molecule in a sample by a known method, and binding the labeled nucleic acid molecule with an immobilized unlabeled probe in the present invention, or by binding a nucleic acid molecule having an allele to be detected to an immobilized unlabeled probe in the present invention, and thereafter labeling the product according to a known method.

The immobilization can be carried out by any of known method, and for example, a method such as synthetic oligo-print or spotting photolithograph can be used. Also, the material for the carrier is not limited, and a generally used material, for example, a polymer such as a polycarbonate or a polystyrene, glass, silicon crystal or the like can be used. In addition, in order to enhance adhesive strength of the nucleic acids, a carrier may be provided with a coating such as cationization before the immobilization. In addition, in order to prevent nonspecific nucleic acids from being adsorbed to a carrier, blocking can be carried out with a known blocking agent after the immobilization. The blocking agent as mentioned above may be any ones so long as the blocking agent is capable of controlling the nonspecific nucleic acids from being adsorbed to the carrier, and for example, salmon sperm DNA, Denhardt's solution, Cot-I DNA extracted from human placenta, an anionic surfactant such as sodium dodecyl sulfate, a nonionic surfactant such as polyoxyethylene sorbitan monolaurate, or the like can be used.

In addition, in a case where the probe is immobilized, it is possible to construct that each of the opposite alleles contained in one sample is detected under the same operation by immobilizing a probe specific to each of the alleles opposite to each other on the same carrier. In the construction as described above, not only the alleles but also the genotypes in the samples can be determined.

It is preferable that the probe used in the detection of the allele is a probe having a length of preferably from 16 to 55 bases, more preferably from 23 to 27 bases or 47 to 53 bases, and even more preferably 25 bases in total of a length of the polymorphic site and some bases before and after the polymorphic site, the probe containing the polymorphic site mentioned above and a surrounding sequence thereof, or a sequence complementary thereto, that the probe is a probe containing the polymorphic site mentioned above and a 5'-upstream side thereof, preferably a sequence of 49 bases (i.e. a sequence of 50 bases), the probe containing the polymorphic site mentioned above and a surrounding sequence thereof, or a sequence complementary thereto, or that the probe is a probe containing a sequence of 50 bases on a 5'-upstream side of the polymorphic site mentioned above, the probe having a sequence adjoining the polymorphic site mentioned above, or a sequence complementary thereto.

An even more preferred probe used in the detection of the allele is:
1) a probe capable of specifically detecting an allele of the single nucleotide polymorphism, containing the polymorphic site mentioned above and a sequence of 12 bases each before and after the polymorphic site, i.e. a sequence of 25 bases in length, and the probe containing the polymorphic site mentioned above and a surrounding sequence thereof, or a sequence complementary thereto, or
2a) a probe capable of specifically detecting an allele of the single nucleotide polymorphism, containing the polymorphic site mentioned above and a sequence of 49 bases on the 5'-upstream side thereof (i.e. sequence of 50 bases), and the probe containing a sequence containing the polymorphic site mentioned above or a sequence complementary thereto, or
2b) a probe capable of specifically detecting an allele of the single nucleotide polymorphism, having a sequence of 50 bases on a 5'-upstream side of the polymorphic site mentioned above, and the probe having a sequence adjoining the polymorphic site mentioned above, or a sequence complementary thereto.

In the method of detecting a single nucleotide polymorphism associated with glaucoma and the method of predicting a progressive risk of glaucoma in the present invention, the probe usable in the detection is a probe containing a single nucleotide polymorphism which is located on a 31st base of a base sequence, wherein the base sequence is at least one base sequence selected from the group consisting of base sequences shown in SEQ ID NOs: 203 to 752 or a complementary sequence thereto, or a partial sequence thereof, and/or a probe having a base sequence containing at least one base sequence selected from the group consisting of base sequences shown in SEQ ID NOs: 753 to 1061 or a complementary sequence thereto, more preferably a probe containing a single nucleotide polymorphism which is located on a 31st base of a base sequence, wherein the base sequence is at least one base sequence selected from the group consisting of base sequences shown in SEQ ID NOs: 203 to 240 or a complementary sequence thereto, or a partial sequence thereof, and/or a probe having a base sequence containing at least one base sequence selected from the group consisting of base sequences shown in SEQ ID NOs: 753 to 776 or a complementary sequence thereto, and even more preferably a probe containing a single nucleotide polymorphism which is located on a 31st base of a base sequence, wherein the base sequence is at least one base sequence selected from following Group A consisting of pairs of base sequences a to s containing a single nucleotide polymorphism or a complementary sequence thereto, or a partial sequence thereof, and/or a probe containing a base sequence, wherein the base sequence is at least one base sequence or a pair of base sequences, selected from Group B consisting of base sequences aa to ss or pairs of the base sequences, or a complementary sequence thereto, wherein in pairs of SEQ ID NOs: shown in a to s, each of the pairs of sequences corresponds to one single nucleotide polymorphism, and each of the base sequences is a base sequence containing an allele opposite to each other of the single nucleotide polymorphism on a 31st base, and in SEQ ID NOs: shown in aa to ss or pairs of the SEQ ID NOs:, each of the base sequences or the pairs of the base sequences is a sequence for the probe or a pair of sequences for the probes, used in the detection of one single nucleotide polymorphism, wherein a and aa, b and bb, c and cc, d and dd, e and ee, f and ff, g and gg, h and hh, i and ii, j and jj, k and kk, l and ll, m and mm, n and nn, o and oo, p and pp, q and qq, r and rr, and s and ss respectively correspond to the same single nucleotide polymorphism, Group A
a: SEQ ID NO: 203 and/or SEQ ID NO: 204,
b: SEQ ID NO: 205 and/or SEQ ID NO: 206,
c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216,
h: SEQ ID NO: 217 and/or SEQ ID NO: 218,
i: SEQ ID NO: 219 and/or SEQ ID NO: 220,
j: SEQ ID NO: 221 and/or SEQ ID NO: 222,
k: SEQ ID NO: 223 and/or SEQ ID NO: 224,
l: SEQ ID NO: 225 and/or SEQ ID NO: 226,
m: SEQ ID NO: 227 and/or SEQ ID NO: 228,
n: SEQ ID NO: 229 and/or SEQ ID NO: 230,
o: SEQ ID NO: 231 and/or SEQ ID NO: 232,
p: SEQ ID NO: 233 and/or SEQ ID NO: 234,
q: SEQ ID NO: 235 and/or SEQ ID NO: 236,
r: SEQ ID NO: 237 and/or SEQ ID NO: 238, and
s: SEQ ID NO: 239 and/or SEQ ID NO: 240, and
Group B
aa: SEQ ID NO: 753,
bb: SEQ ID NO: 754 and/or SEQ ID NO: 772,
cc: SEQ ID NO: 755,
dd: SEQ ID NO: 756,
ee: SEQ ID NO: 757,
ff: SEQ ID NO: 758,
gg: SEQ ID NO: 759,
hh: SEQ ID NO: 760 and/or SEQ ID NO: 773,
ii: SEQ ID NO: 761 and/or SEQ ID NO: 774,
jj: SEQ ID NO: 762 and/or SEQ ID NO: 775, kk: SEQ ID NO: 763,
ll: SEQ ID NO: 764,
mm: SEQ ID NO: 765,
nn: SEQ ID NO: 766 and/or SEQ ID NO: 776,
oo: SEQ ID NO: 767,
pp: SEQ ID NO: 768,
qq: SEQ ID NO: 769,
rr: SEQ ID NO: 770, and
ss: SEQ ID NO: 771.

In a case where any one of the single nucleotide polymorphisms is used, especially, it is preferable that in Group A, a probe containing an allele of a single nucleotide polymorphism located on a 31st base of a base sequence is used, wherein the base sequence is at least one base sequence selected from the group consisting of the following base sequences containing a single nucleotide polymorphism:
SEQ ID NO: 203, SEQ ID NO: 205, SEQ ID NO: 207, SEQ ID NO: 210, SEQ ID NO: 212, SEQ ID NO: 214, SEQ ID NO: 215, SEQ ID NO: 218, SEQ ID NO: 220, SEQ ID NO: 222, SEQ ID NO: 223, SEQ ID NO: 226, SEQ ID NO: 228, SEQ ID NO: 230, SEQ ID NO: 232, SEQ ID NO: 233, SEQ ID NO: 236, SEQ ID NO: 238, and SEQ ID NO: 240,
or a complementary sequence thereto, or a partial sequence thereof, and
in Group B, a probe containing a base sequence containing at least one base sequence selected from the group consisting of the following base sequences:
SEQ ID NO: 753, SEQ ID NO: 754, SEQ ID NO: 755, SEQ ID NO: 756, SEQ ID NO: 757, SEQ ID NO: 758, SEQ ID NO: 759, SEQ ID NO: 760, SEQ ID NO: 761, SEQ ID NO: 775, SEQ ID NO: 763, SEQ ID NO: 764, SEQ ID NO: 765, SEQ ID NO: 766, SEQ ID NO: 767, SEQ ID NO: 768, SEQ ID NO: 769, SEQ ID NO: 770, and SEQ ID NO: 771,
or a complementary sequence thereto is used.
Here, these base sequences are sequences corresponding to a probe used in the detection of a high-risk allele.

In the method of detecting a single nucleotide polymorphism associated with glaucoma and the method of predicting a progressive risk of glaucoma in the present invention, in a case where any two or more single nucleotide polymorphisms are combined, the probes usable in the detection are preferably probes containing a single nucleotide polymorphism which is located on a 31st base of a base sequence, wherein the base sequence is a base sequence containing a single nucleotide polymorphism, selected from the group consisting of base sequences shown in SEQ ID NOs: 203 to 752 or a complementary sequence thereto, or a partial sequence thereof, and/or probes having a base sequence containing a base sequence selected from the group consisting of base sequences shown in SEQ ID NOs: 753 to 1061 or a complementary sequence thereto, wherein the probes are probes corresponding to two or more different single nucleotide polymorphisms thereof,
more preferably probes containing a single nucleotide polymorphism which is located on a 31st base of a base sequence, wherein the base sequence is a base sequence containing a single nucleotide polymorphism, selected from the group consisting of base sequences shown in SEQ ID NOs: 203 to 240 or a complementary sequence thereto, or a partial sequence thereof, and/or probes having a base sequence containing a base sequence selected from the group consisting of base sequences shown in SEQ ID NOs: 753 to 776 or a complementary sequence thereto, wherein the probes are probes corresponding to two or more different single nucleotide polymorphisms thereof, and
even more preferably probes containing a single nucleotide polymorphism which is located on a 31st base of a base sequence, wherein the base sequence is a base sequence containing a single nucleotide polymorphism selected from following Group A consisting of pairs of base sequences a to s containing a single nucleotide polymorphism or a complementary sequence thereto, or a partial sequence thereof, and/or two or more different probes having a base sequence, wherein the base sequence contains base sequences or a pair of base sequences, selected from Group B consisting of base sequences aa to ss or pairs of the base sequences, or a complementary sequence thereto,
wherein in pairs of SEQ ID NOs: shown in a to s, each of the pairs of sequences corresponds to one single nucleotide polymorphism, and each of the base sequences is a base sequence containing an allele opposite to each other of the single nucleotide polymorphism on a 31st base, and
in SEQ ID NOs: shown in aa to ss or pairs of the SEQ ID NOs:, each of the base sequences or the pairs of the base sequences is a sequence for the probe or a pair of sequences for the probes, used in the detection of one single nucleotide polymorphism,
wherein a and aa, b and bb, c and cc, d and dd, e and ee, f and ff, g and gg, h and hh, i and ii, j and jj, k and kk, l and ll, m and mm, n and nn, o and oo, p and pp, q and qq, r and rr, and s and ss respectively correspond to the same single nucleotide polymorphism,
Group A
a: SEQ ID NO: 203 and/or SEQ ID NO: 204,
b: SEQ ID NO: 205 and/or SEQ ID NO: 206,
c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216,
h: SEQ ID NO: 217 and/or SEQ ID NO: 218,
i: SEQ ID NO: 219 and/or SEQ ID NO: 220,
j: SEQ ID NO: 221 and/or SEQ ID NO: 222,
k: SEQ ID NO: 223 and/or SEQ ID NO: 224,
l: SEQ ID NO: 225 and/or SEQ ID NO: 226,
m: SEQ ID NO: 227 and/or SEQ ID NO: 228,
n: SEQ ID NO: 229 and/or SEQ ID NO: 230,
o: SEQ ID NO: 231 and/or SEQ ID NO: 232,
p: SEQ ID NO: 233 and/or SEQ ID NO: 234,
q: SEQ ID NO: 235 and/or SEQ ID NO: 236,
r: SEQ ID NO: 237 and/or SEQ ID NO: 238, and
s: SEQ ID NO: 239 and/or SEQ ID NO: 240, and
Group B
aa: SEQ ID NO: 753,
bb: SEQ ID NO: 754 and/or SEQ ID NO: 772,
cc: SEQ ID NO: 755,
dd: SEQ ID NO: 756,
ee: SEQ ID NO: 757,
ff: SEQ ID NO: 758,
gg: SEQ ID NO: 759,
hh: SEQ ID NO: 760 and/or SEQ ID NO: 773,
ii: SEQ ID NO: 761 and/or SEQ ID NO: 774,
jj: SEQ ID NO: 762 and/or SEQ ID NO: 775,
kk: SEQ ID NO: 763,
ll: SEQ ID NO: 764,
mm: SEQ ID NO: 765,
nn: SEQ ID NO: 766 and/or SEQ ID NO: 776,
oo: SEQ ID NO: 767,
pp: SEQ ID NO: 768,
qq: SEQ ID NO: 769,
rr: SEQ ID NO: 770, and
ss: SEQ ID NO: 771,
even more preferably probes containing a single nucleotide polymorphism which is located on a 31st base of a base sequence, wherein the base sequence is a base sequence containing a single nucleotide polymorphism selected from Group A listed above consisting of pairs of the base sequences containing the single nucleotide polymorphism or a complementary sequence thereto, or a partial sequence thereof, and/or probes having a base sequence, wherein the base sequence contains a base sequence selected from Group B listed above consisting of pairs of the base sequences or a complementary sequence thereto, wherein the probes are probes corresponding to 10 or more different single nucleotide polymorphisms thereof, and even more preferably probes containing a single nucleotide polymorphism which is located on a 31st base of a base sequence, wherein the base sequence is a base sequence containing a single nucleotide polymorphism selected from Group A listed above consisting of pairs of the base sequences containing the single nucleotide polymorphism or a complementary sequence thereto, or a partial sequence thereof, and/or probes having a base sequence, wherein the base sequence contains a base sequence selected from Group B listed above consisting of pairs of the base sequences or a complementary sequence thereto, wherein the probes are probes corresponding to all the different single nucleotide polymorphisms thereof.

In addition, it is preferable that the single nucleotide polymorphisms to be used in combination are those that are not in the state of linkage disequilibrium, and from this viewpoint, in all the embodiments of the combinations mentioned above, supposing that, in Group A, a group composed of a base sequence containing a single nucleotide polymorphism which is located on a 31st base of a base sequence, wherein the base sequence is a base sequence belonging to the group consisting of:
c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216, and
h: SEQ ID NO: 217 and/or SEQ ID NO: 218,
or a complementary sequence thereto, or a partial sequence thereof, is named as a base sequence of Group 1,
a group composed of a base sequence containing a single nucleotide polymorphism which is located on a 31st base of a base sequence, wherein the base sequence is a base sequence belonging to the group consisting of:
i: SEQ ID NO: 219 and/or SEQ ID NO: 220, and
j: SEQ ID NO: 221 and/or SEQ ID NO: 222,
or a complementary sequence thereto, or a partial sequence thereof, is named as a base sequence of Group 2, and
that in Group B,
a group composed of a base sequence containing a base sequence belonging to the group consisting of:
cc: SEQ ID NO: 755,
dd: SEQ ID NO: 756,
ee: SEQ ID NO: 757,
ff: SEQ ID NO: 758,
gg: SEQ ID NO: 759, and
hh: SEQ ID NO: 760 and/or SEQ ID NO: 773,
or a complementary sequence thereto, is named as a base sequence of Group 1, and
a group composed of a base sequence containing a base sequence belonging to the group consisting of:
ii: SEQ ID NO: 761 and/or SEQ ID NO: 774, and
jj: SEQ ID NO: 762 and/or SEQ ID NO: 775,
or a complementary sequence thereto, is named as a base sequence of Group 2, it is preferable to use
a probe containing any one of the base sequences in Group 1 in a case that the base sequences belonging to Group 1 are used, and/or
a probe containing any one of the base sequences in Group 2 in a case that the base sequences belonging to Group 2 are used.

Further, in all the embodiment of the combinations mentioned above, in Group A, a probe containing an allele of a single nucleotide polymorphism located on a 31st base of a base sequence, wherein the base sequence is a base sequence containing a single nucleotide polymorphism selected from the group consisting of the following base sequences containing a single nucleotide polymorphism:
SEQ ID NO: 203, SEQ ID NO: 205, SEQ ID NO: 207, SEQ ID NO: 210, SEQ ID NO: 212, SEQ ID NO: 214, SEQ ID NO: 215, SEQ ID NO: 218, SEQ ID NO: 220, SEQ ID NO: 222, SEQ ID NO: 223, SEQ ID NO: 226, SEQ ID NO: 228, SEQ ID NO: 230, SEQ ID NO: 232, SEQ ID NO: 233, SEQ ID NO: 236, SEQ ID NO: 238, and SEQ ID NO: 240,
or a complementary sequence thereto, or a partial sequence thereof, is preferred, and
in Group B, a probe containing a base sequence containing a base sequence selected from the group consisting of the following base sequences:
SEQ ID NO: 753, SEQ ID NO: 754, SEQ ID NO: 755, SEQ ID NO: 756, SEQ ID NO: 757, SEQ ID NO: 758, SEQ ID NO: 759, SEQ ID NO: 760, SEQ ID NO: 761, SEQ ID NO: 775, SEQ ID NO: 763, SEQ ID NO: 764, SEQ ID NO: 765, SEQ ID NO: 766, SEQ ID NO: 767, SEQ ID NO: 768, SEQ ID NO: 769, SEQ ID NO: 770, and SEQ ID NO: 771,
or a complementary sequence thereto is preferred.

Here, these base sequences are sequences corresponding to a probe used in the detection of a high-risk allele.

The probe in a case where a Taqman method is used in the detection of an allele usually has a length of preferably from 10 to 300 bases, and contains the polymorphic site mentioned above and a surrounding sequence thereof, or a sequence complementary thereto, and the probe also contains a fluorescent substance and a quencher. More preferably, the probe has a length of 20 to 60 bases, and contains the polymorphic site mentioned above and a surrounding sequence thereof, or a sequence complementary thereto, and the probe contains a fluorescent substance and a quencher.

The probes in a case where an Invader method is used in the detection of an allele comprise a probe (reporter) which have a common sequence to a 3'-side of the polymorphic site mentioned above and a sequence on a 5'-side being completely different therefrom, and a probe (invader) only composed of the common sequence to a 5'-side. These probes usually have a length of preferably from 10 to 300 bases, and more preferably a length of from 20 to 60 bases.

The probe in a case where a LightCycler method is used in the detection of an allele, usually has a length of preferably from 10 to 300 bases, and contains the polymorphic site mentioned above and a surrounding sequence thereof, or a sequence complementary thereto, and the probe contains a fluorescent substance and a quencher. More preferably, the probe has a length of 20 to 60 bases, and contains the polymorphic site mentioned above and a surrounding sequence thereof, or a sequence complementary thereto, and the probe contains a fluorescent substance and a quencher.

The probe in a case where a cyclin probe method is used in the detection of an allele is a probe in which DNA sequences are bound in a manner that both ends of an RNA sequence having the polymorphic site and a surrounding sequence thereof, or a sequence complementary thereto, are sandwiched, and each of DNA ends has a fluorescent substance or a quencher. These probes usually have a length of preferably from 10 to 300 bases, and contain the polymorphic site mentioned above and a surrounding sequence thereof, or a sequence complementary thereto. More preferably, the probe has a length of 20 to 60 bases, and contains the polymorphic site mentioned above and a surrounding sequence thereof, or a sequence complementary thereto.

The probes in a case where an MPSS method is used in the detection of an allele comprise an oligo DNA (encoded adaptor probe) having a protruding end of 4 bases on a 5'-side, subsequently a recognition sequence for a restriction enzyme BbvI, and a single-stranded sequence to which a decoder probe is bound on a 3'-side, and a single strand oligo DNA (decoder probe) which has fluorescent substance on a 3'-side, and containing 4 different sequences, each sequence specifically hybridizing to one of the encoded adaptor probes. Here, a DNA sequence is bound in a manner that both ends of an RNA sequence having the polymorphic site mentioned above and a surrounding sequence thereof, or a sequence complementary thereto, are sandwiched, and each of DNA ends has a fluorescent substance or a quencher. The encoded adaptor probe usually has a length of preferably from 10 to 300 base pairs, and more preferably from 15 to 40 base pairs. On the other hand, the decoder probe usually has a length of preferably from 10 to 300 base pairs, and more preferably from 5 to 30 base pairs.

(Kit of Detecting Allele Associated with Glaucoma)

In another embodiment of the present invention, a kit of detecting a single nucleotide polymorphism associated with glaucoma is provided.

The kit of the present invention (or a composition for predicting a risk) embraces all those kits so long as the allele or genotype of any one of single nucleotide polymorphisms associated with glaucoma disclosed in the present invention can be detected in a nucleic acid molecule in a sample. As mentioned above, the kit of the present invention may be those that detect a base of either the sense strand or the antisense strand of the single nucleotide polymorphism, or those that detect bases of both the strands. In a case where the kit of the present invention is based on the results obtained in a single analysis using a microarray for a kit of detecting an allele or genotype associated with glaucoma for detecting, for example, 500,000 single nucleotide polymorphisms in a single operation, the kit is preferably a kit of detecting an allele or genotype associated with glaucoma for single nucleotide polymorphisms having a p-value of $1 \times 10^{-4}$ or less listed in Tables 26 to 28 set forth below, more preferably a kit of detecting an allele or genotype associated with glaucoma for single nucleotide polymorphisms having a p-value of $3 \times 10^{-4}$ or less, even more preferably a kit of detecting an allele or genotype associated with glaucoma for single nucleotide polymorphisms having a p-value of $1 \times 10^{-4}$ or less, and even more preferably a kit of detecting an allele or genotype associated with glaucoma for single nucleotide polymorphisms having a p-value of $3 \times 10^{-5}$ or less. In a case where the plural analytic results are combined and obtained according to a method of meta-analysis, such as Mantel-Haenszel method, the kit is preferably a kit of detecting an allele or genotype associated with glaucoma for single nucleotide polymorphisms having a p-value listed in Tables 52 to 70 set forth below of $1 \times 10^{-2}$ or less, more preferably a kit of detecting an allele or genotype associated with glaucoma for single nucleotide polymorphisms having a p-value of $3 \times 10^{-3}$ or less, even more preferably a kit of detecting an allele or genotype associated with glaucoma for single nucleotide polymorphisms having a p-value of $1 \times 10^{-3}$ or less, even more preferably a kit of detecting an allele or genotype associated with glaucoma for single nucleotide polymorphisms having a p-value of $3 \times 10^{-4}$ or less, and even more preferably a kit of detecting an allele or genotype associated with glaucoma for single nucleotide polymorphisms having a p-value of $1 \times 10^{-4}$ or less.

A kit of detecting both an allele identified in a high frequency in the progressive glaucoma group mentioned above and an allele opposite to the allele is also one embodiment of the present invention. In a case where a kit as described above is used, as already explained, a genotype of each of the alleles can also be determined.

By detecting the presence of an allele or a genotype that is identified in a high frequency in the progressive glaucoma group in the sample using the kit of the present invention, a progressive risk of a glaucoma patient can be predicted, and a progressive risk upon future onset of glaucoma of an individual not having glaucoma at the present stage can be predicted, or the diagnosis of an individual who is suspected of glaucoma can be made for glaucoma.

In addition, as mentioned above, a kit for determining alleles that are opposite to each other in a single operation can be prepared by using a probe specific to each of the alleles that are opposite to each other, and providing different labels to the probes, or providing in the form of a microarray or beads array as mentioned above.

The precision for the prediction of the progressive risk of glaucoma or the determination of whether or not precise visual field examinations are required can also be improved by providing a kit having the constitution of detecting these plural alleles or genotypes using one sample. Even in the constitution as described above, a constitution can be taken that the detection is carried out in a single operation by having the form of probes provided with different labels, or the form of the microarray or beads array mentioned above.

In the method of detecting a single nucleotide polymorphism associated with glaucoma and the method of predicting a progressive risk of glaucoma in the present invention, the kit usable in detecting or predicting a risk is a kit of detecting a single nucleotide polymorphism associated with the progression of glaucoma or a kit of predicting a progressive risk of glaucoma, using a nucleic acid molecule containing a single nucleotide polymorphism which is located on a 31st base of a base sequence, wherein the base sequence is at least one base sequence selected from the group consisting of base sequences shown in SEQ ID NOs: 203 to 752 or a complementary sequence thereto, or a partial sequence thereof, and/or a kit of detecting a single nucleotide polymorphism associated with the progression of glaucoma or a kit of predicting a progressive risk of glaucoma, using a nucleic acid molecule comprising a base sequence containing at least one base sequence selected from the group consisting of base sequences shown in SEQ ID NOs: 753 to 1061 or a complementary sequence thereto, more preferably a kit of detecting a single nucleotide polymorphism associated with the progression of glaucoma or a kit of predicting a progressive risk of glaucoma, using a nucleic acid molecule containing a single nucleotide polymorphism which is located on a 31st base of a base sequence, wherein the base sequence is at least one base sequence selected from the group consisting of base sequences shown in SEQ ID NOs: 203 to 240 or a complementary sequence thereto, or a partial sequence thereof, and/or a kit of detecting a single nucleotide polymorphism associated with the progression of glaucoma or a kit of predicting a progressive risk of glaucoma, using a nucleic acid molecule comprising a base sequence containing at least one base sequence selected from the group consisting of base sequences shown in SEQ ID NOs: 753 to 776 or a complementary sequence thereto, even more preferably a kit of detecting a single nucleotide polymorphism associated with the progression of glaucoma or a kit of predicting a progressive risk of glaucoma, using a nucleic acid molecule containing a single nucleotide polymorphism which is located on a 31st base of a base sequence, wherein the base sequence is at least one base sequence selected from following Group A consisting of pairs of base sequences a to s containing a single nucleotide polymorphism or a complementary sequence thereto, or a partial sequence thereof, and/or a kit of detecting a single nucleotide polymorphism associated with the progression of glaucoma or a kit of predicting a progressive risk of glaucoma, using a nucleic acid molecule comprising a base sequence containing at least one base sequence or a pair of base sequences, selected from Group B consisting of base sequences aa to ss or pairs of the base sequences, or a complementary sequence thereto, wherein in pairs of SEQ ID NOs: shown in a to s, each of the pairs of sequences corresponds to one single nucleotide polymorphism, and each of the base sequences is a base sequence containing an allele opposite to each other of the single nucleotide polymorphism on a 31st base, and in SEQ ID NOs: shown in aa to ss or pairs of the SEQ ID NOs:, each of the base sequences or the pairs of the base sequences is a sequence for the nucleic acid molecule or a pair of sequences for the nucleic acid molecule, used in the detection of one single nucleotide polymorphism, wherein a and aa, b and bb, c and cc, d and dd, e and ee, f and ff, g and gg, h and hh, i and ii, j and jj, k and kk, l and ll, m and mm, n and nn, o and oo, p and pp, q and qq, r and rr, and s and ss, respectively correspond to the same single nucleotide polymorphism, Group A
a: SEQ ID NO: 203 and/or SEQ ID NO: 204,
b: SEQ ID NO: 205 and/or SEQ ID NO: 206,
c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216,
h: SEQ ID NO: 217 and/or SEQ ID NO: 218,
i: SEQ ID NO: 219 and/or SEQ ID NO: 220,
j: SEQ ID NO: 221 and/or SEQ ID NO: 222,
k: SEQ ID NO: 223 and/or SEQ ID NO: 224,
l: SEQ ID NO: 225 and/or SEQ ID NO: 226,
m: SEQ ID NO: 227 and/or SEQ ID NO: 228,
n: SEQ ID NO: 229 and/or SEQ ID NO: 230,
o: SEQ ID NO: 231 and/or SEQ ID NO: 232,
p: SEQ ID NO: 233 and/or SEQ ID NO: 234,
q: SEQ ID NO: 235 and/or SEQ ID NO: 236,
r: SEQ ID NO: 237 and/or SEQ ID NO: 238, and
s: SEQ ID NO: 239 and/or SEQ ID NO: 240, and Group B
aa: SEQ ID NO: 753,
bb: SEQ ID NO: 754 and/or SEQ ID NO: 772,
cc: SEQ ID NO: 755,
dd: SEQ ID NO: 756,
ee: SEQ ID NO: 757,
ff: SEQ ID NO: 758,
gg: SEQ ID NO: 759,
hh: SEQ ID NO: 760 and/or SEQ ID NO: 773,
ii: SEQ ID NO: 761 and/or SEQ ID NO: 774,
jj: SEQ ID NO: 762 and/or SEQ ID NO: 775,
kk: SEQ ID NO: 763,
ll: SEQ ID NO: 764,
mm: SEQ ID NO: 765,
nn: SEQ ID NO: 766 and/or SEQ ID NO: 776,
oo: SEQ ID NO: 767,
pp: SEQ ID NO: 768,
qq: SEQ ID NO: 769,
rr: SEQ ID NO: 770, and
ss: SEQ ID NO: 771.

In a case where any one of the single nucleotide polymorphisms is used, especially, in Group A, preferred is a kit of detecting a single nucleotide polymorphism associated with the progression of glaucoma or predicting a progressive risk of glaucoma, using a nucleic acid molecule containing an allele of a single nucleotide polymorphism located on a 31st base of a base sequence, wherein the base sequence is at least one base sequence selected from the group consisting of the following base sequences containing a single nucleotide polymorphism:

SEQ ID NO: 203, SEQ ID NO: 205, SEQ ID NO: 207, SEQ ID NO: 210, SEQ ID NO: 212, SEQ ID NO: 214, SEQ ID NO: 215, SEQ ID NO: 218, SEQ ID NO: 220, SEQ ID NO: 222, SEQ ID NO: 223, SEQ ID NO: 226, SEQ ID NO: 228, SEQ ID NO: 230, SEQ ID NO: 232, SEQ ID NO: 233, SEQ ID NO: 236, SEQ ID NO: 238, and SEQ ID NO: 240, or a complementary sequence thereto, or a partial sequence thereof, and in Group B, preferred is a kit of detecting a single nucleotide polymorphism associated with the progression of glaucoma or predicting a progressive risk of glaucoma, using a nucleic acid molecule comprising a base sequence containing a base sequence selected from the group consisting of the following base sequences:

SEQ ID NO: 753, SEQ ID NO: 754, SEQ ID NO: 755, SEQ ID NO: 756, SEQ ID NO: 757, SEQ ID NO: 758, SEQ ID NO: 759, SEQ ID NO: 760, SEQ ID NO: 761, SEQ ID NO: 775, SEQ ID NO: 763, SEQ ID NO: 764, SEQ ID NO: 765, SEQ ID NO: 766, SEQ ID NO: 767, SEQ ID NO: 768, SEQ ID NO: 769, SEQ ID NO: 770, and SEQ ID NO: 771, or a complementary sequence thereto.

Here, these base sequences are sequences corresponding to a nucleic acid molecule used in the detection of a high-risk allele.

In the method of detecting a single nucleotide polymorphism associated with glaucoma and the method of predicting a progressive risk of glaucoma in the present invention, in a case where any two or more single nucleotide polymorphisms are combined, the kit usable in detecting or predicting a risk is preferably a kit of detecting a single nucleotide polymorphism associated with the progression of glaucoma or a kit of predicting a progressive risk of glaucoma, using a nucleic acid molecule comprising a single nucleotide polymorphism which is located on a 31st base of a base sequence, wherein the base sequence is a base sequence containing a single nucleotide polymorphism, selected from the group consisting of base sequences shown in SEQ ID NOs: 203 to 752 or a complementary sequence thereto, or a partial sequence thereof, and/or a kit of detecting a single nucleotide polymorphism associated with the progression of glaucoma or a kit of predicting a progressive risk of glaucoma, using a nucleic acid molecule comprising a base sequence containing a base sequence selected from the group consisting of base sequences shown in SEQ ID NOs: 753 to 1061 or a complementary sequence thereto, wherein the kit is a kit corresponding to two or more different single nucleotide polymorphisms thereof, more preferably a kit of detecting a single nucleotide polymorphism associated with the progression of glaucoma or a kit of predicting a progressive risk of glaucoma, using a nucleic acid molecule containing a single nucleotide polymorphism which is located on a 31st base of a base sequence, wherein the base sequence is a base sequence containing a single nucleotide polymorphism, selected from the group consisting of base sequences shown in SEQ ID NOs: 203 to 240 or a complementary sequence thereto, or a partial sequence thereof, and/or a kit of detecting a single nucleotide polymorphism associated with the progression of glaucoma or a kit of predicting a progressive risk of glaucoma, using a nucleic acid molecule comprising a base sequence containing a base sequence selected from the group consisting of base sequences shown in SEQ ID NOs: 753 to 776 or a complementary sequence thereto, wherein the kit is a kit corresponding to two or more different single nucleotide polymorphisms thereof, even more preferably a kit of detecting a single nucleotide polymorphism associated with the progression of glaucoma or a kit of predicting a progressive risk of glaucoma, using a nucleic acid molecule comprising a single nucleotide polymorphism which is located on a 31st base of a base sequence, wherein the base sequence is a base sequence containing a single nucleotide polymorphism, selected from the following Group A consisting of the following pairs of base sequences a to s containing a single nucleotide polymorphism or a complementary sequence thereto, or a partial sequence thereof, and/or a kit of detecting a single nucleotide polymorphism associated with the progression of glaucoma or a kit of predicting a progressive risk of glaucoma, using a nucleic acid molecule comprising a base sequence, wherein the base sequence contains a base sequence or a pair of base sequences, selected from Group B consisting of base sequences aa to ss or pairs of the base sequences, or a complementary sequence thereto, wherein the kit is a kit corresponding to two or more different single nucleotide polymorphisms thereof, wherein in pairs of SEQ ID NOs: shown in a to s, each of the pairs of sequences corresponds to one single nucleotide polymorphism, and each of the base sequences is a base sequence containing an allele opposite to each other of the single nucleotide polymorphism on a 31st base, and in SEQ ID NOs: shown in aa to ss or pairs of the SEQ ID NOs:, each of the base sequences or the pair of base sequences is a sequence for the nucleic acid molecule or a pair of sequences for the nucleic acid molecule, used in the detection of one single nucleotide polymorphism, wherein a and aa, b and bb, c and cc, d and dd, e and ee, f and ff, g and gg, h and hh, i and ii, j and jj, k and kk, l and ll, m and mm, n and nn, o and oo, p and pp, q and qq, r and rr, and s and ss respectively correspond to the same single nucleotide polymorphism, Group A
a: SEQ ID NO: 203 and/or SEQ ID NO: 204,
b: SEQ ID NO: 205 and/or SEQ ID NO: 206,
c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216,
h: SEQ ID NO: 217 and/or SEQ ID NO: 218,
i: SEQ ID NO: 219 and/or SEQ ID NO: 220,
j: SEQ ID NO: 221 and/or SEQ ID NO: 222,
k: SEQ ID NO: 223 and/or SEQ ID NO: 224,
l: SEQ ID NO: 225 and/or SEQ ID NO: 226,
m: SEQ ID NO: 227 and/or SEQ ID NO: 228,
n: SEQ ID NO: 229 and/or SEQ ID NO: 230,
o: SEQ ID NO: 231 and/or SEQ ID NO: 232,
p: SEQ ID NO: 233 and/or SEQ ID NO: 234,
q: SEQ ID NO: 235 and/or SEQ ID NO: 236,
r: SEQ ID NO: 237 and/or SEQ ID NO: 238, and
s: SEQ ID NO: 239 and/or SEQ ID NO: 240, and
Group B
aa: SEQ ID NO: 753,
bb: SEQ ID NO: 754 and/or SEQ ID NO: 772,
cc: SEQ ID NO: 755,
dd: SEQ ID NO: 756,
ee: SEQ ID NO: 757,
ff: SEQ ID NO: 758,
gg: SEQ ID NO: 759,
hh: SEQ ID NO: 760 and/or SEQ ID NO: 773,
ii: SEQ ID NO: 761 and/or SEQ ID NO: 774,
jj: SEQ ID NO: 762 and/or SEQ ID NO: 775,
kk: SEQ ID NO: 763,
ll: SEQ ID NO: 764,
mm: SEQ ID NO: 765,
nn: SEQ ID NO: 766 and/or SEQ ID NO: 776,
oo: SEQ ID NO: 767,
pp: SEQ ID NO: 768,
qq: SEQ ID NO: 769,
rr: SEQ ID NO: 770, and
ss: SEQ ID NO: 771, even more preferably a kit of detecting a single nucleotide polymorphism associated with the progression of glaucoma or a kit of predicting a progressive risk of glaucoma, using a nucleic acid molecule containing a single nucleotide polymorphism which is located on a 31st base of a base sequence, wherein the base sequence is a base sequence containing a single nucleotide polymorphism, selected from Group A consisting of pairs of the base sequences containing a single nucleotide polymorphism listed above or a complementary sequence thereto, or a partial sequence thereof, and/or a kit of detecting a single nucleotide polymorphism associated with the progression of glaucoma or a kit of predicting a progressive risk of glaucoma, using a nucleic acid molecule comprising a base sequence containing a base sequence selected from Group B consisting of pairs of the base sequences listed above or a complementary sequence thereto, wherein the kit is a kit corresponding to ten or more different single nucleotide polymorphisms thereof, and even more preferably a kit of detecting a single nucleotide polymorphism associated with the progression of glaucoma or a kit of predicting a progressive risk of glaucoma, using a nucleic acid molecule comprising a single nucleotide polymorphism which is located on a 31st base of a base sequence, wherein the base sequence is a base sequence containing a single nucleotide polymorphism, selected from Group A consisting of pairs of the base sequences containing a single nucleotide polymorphism listed above or a complementary sequence thereto, or a partial sequence thereof, and/or a kit of detecting a single nucleotide polymorphism associated with the progression of glaucoma or a kit of predicting a progressive risk of glaucoma, using a nucleic acid molecule comprising a base sequence containing a base sequence selected from Group B consisting of pairs of the base sequences listed above or a complementary sequence thereto, wherein the kit is a kit corresponding to all the different single nucleotide polymorphisms thereof.

In addition, it is preferable that the single nucleotide polymorphisms to be used in combination are those that are not in the state of linkage disequilibrium, and from this viewpoint, in all the embodiments of the combinations mentioned above, supposing that, in Group A, a group composed of a base sequence containing a single nucleotide polymorphism which is located on a 31st base of a base sequence, wherein the base sequence is a base sequence belonging to the group consisting of:
c: SEQ ID NO: 207 and/or SEQ ID NO: 208,
d: SEQ ID NO: 209 and/or SEQ ID NO: 210,
e: SEQ ID NO: 211 and/or SEQ ID NO: 212,
f: SEQ ID NO: 213 and/or SEQ ID NO: 214,
g: SEQ ID NO: 215 and/or SEQ ID NO: 216, and
h: SEQ ID NO: 217 and/or SEQ ID NO: 218,
or a complementary sequence thereto, or a partial sequence thereof, is named as a base sequence of Group 1,
a group composed of a base sequence containing a single nucleotide polymorphism which is located on a 31st base of a base sequence, wherein the base sequence is a base sequence belonging to the group consisting of:
i: SEQ ID NO: 219 and/or SEQ ID NO: 220, and
j: SEQ ID NO: 221 and/or SEQ ID NO: 222,
or a complementary sequence thereto, or a partial sequence thereof, is named as a base sequence of Group 2, and
that in Group B,
a group composed of a base sequence containing a base sequence belonging to the group consisting of:
SEQ ID NO: 755,
SEQ ID NO: 756,
SEQ ID NO: 757,
SEQ ID NO: 758,
SEQ ID NO: 759, and
SEQ ID NO: 760 and/or SEQ ID NO: 773,
or a complementary sequence thereto, is named as a base sequence of Group 1,
a group composed of a base sequence containing a base sequence belonging to the group consisting of:
SEQ ID NO: 761 and/or SEQ ID NO: 774, and
SEQ ID NO: 762 and/or SEQ ID NO: 775,
or a complementary sequence thereto, is named as a base sequence of Group 2,
it is preferable to use
a kit of detecting a single nucleotide polymorphism associated with the progression of glaucoma or a kit of predicting a progressive risk of glaucoma, using a nucleic acid molecule comprising any one of the base sequences in Group 1 when the base sequences belonging to Group 1 are used, and/or
a kit of detecting a single nucleotide polymorphism associated with the progression of glaucoma or a kit of predicting a progressive risk of glaucoma, using a nucleic acid molecule comprising any one of the base sequences in Group 2 when the base sequences belonging to Group 2 are used.

In all the embodiments of the combinations mentioned above, in Group A, preferred is a kit of detecting a single nucleotide polymorphism associated with the progression of glaucoma or a kit of predicting a progressive risk of glaucoma, using a nucleic acid molecule comprising an allele of a single nucleotide polymorphism located on a 31st base of a base sequence, wherein the base sequence is a base sequence containing a single nucleotide polymorphism, selected from the group consisting of the following base sequences containing a single nucleotide polymorphism:
SEQ ID NO: 203, SEQ ID NO: 205, SEQ ID NO: 207, SEQ ID NO: 210, SEQ ID NO: 212, SEQ ID NO: 214, SEQ ID NO: 215, SEQ ID NO: 218, SEQ ID NO: 220, SEQ ID NO: 222, SEQ ID NO: 223, SEQ ID NO: 226, SEQ ID NO: 228, SEQ ID NO: 230, SEQ ID NO: 232, SEQ ID NO: 233, SEQ ID NO: 236, SEQ ID NO: 238, and SEQ ID NO: 240,
or a complementary sequence thereto, or a partial sequence thereof, and in Group B, preferred is a kit of detecting a single nucleotide polymorphism associated with the progression of glaucoma or a kit of predicting a progressive risk of glaucoma, using a nucleic acid molecule comprising a base sequence containing a base sequence selected from the group consisting of the following base sequences:
SEQ ID NO: 753, SEQ ID NO: 754, SEQ ID NO: 755, SEQ ID NO: 756, SEQ ID NO: 757, SEQ ID NO: 758, SEQ ID NO: 759, SEQ ID NO: 760, SEQ ID NO: 761, SEQ ID NO: 775, SEQ ID NO: 763, SEQ ID NO: 764, SEQ ID NO: 765, SEQ ID NO: 766, SEQ ID NO: 767, SEQ ID NO: 768, SEQ ID NO: 769, SEQ ID NO: 770, and SEQ ID NO: 771,
or a complementary sequence thereto.

Here, these base sequences are sequences corresponding to a nucleic acid molecule used in the detection of a high-risk allele.

(Method of Predicting Progressive Risk of Glaucoma, Including Performing the Predicting Risk in Two-Steps or Multi-Steps)

When a prediction of a progressive risk of glaucoma using a single nucleotide polymorphism in the present invention is carried out, it can be performed in two or more steps as follows; candidates who are considered that precise prediction of a progressive risk of glaucoma is necessary are selected, and the candidates are subjected to detailed prediction of a risk.

In a case where prediction of a risk is performed in two or more multi-steps, first, prediction of a progressive risk of glaucoma mentioned above is preformed on at least one single nucleotide polymorphism in the present invention, preferably any one or several single nucleotide polymorphisms, and subsequently, prediction of detailed risks may be performed using a combination of the single nucleotide polymorphisms of the present invention mentioned above. The number of combinations may be further increased as occasion demands, whereby precision of the prediction of a risk can also be improved. As described above, by performing prediction of a risk in two or more multi-steps, the reduction in costs for performing the prediction of a risk and the prediction of a risk in a high precision can be both accomplished.

The prediction of a risk in an initial step may be a convenient method of predicting a risk. For example, a method of predicting a risk so that an immobilized probe capable of detecting at least one of the single nucleotide polymorphisms, preferably any one or several single nucleotide polymorphisms, is immobilized in a manner that at least one of the single nucleotide polymorphisms in the present invention is detectable is a convenient method, and can be realized at a low cost. Here, as to a method for nucleic acid extraction in this case, a kit that can be realized according to a known technique, or a commercially available simple kit for nucleic acid extraction can be used. It is convenient to use a method including the steps of using, for example, an enzyme-labeled probe as the immobilized probe used in the prediction of a risk as described above, and detecting the probe according to a colorimetric method. As to the samples used in the detection, those that are obtained in a relatively low penetration, such as saliva, oral mucosa cells, urine, hair root, blood or white blood cells are preferred.

The prediction of a risk in a next step may be a method of predicting a risk with an emphasis on precision. For example, the detection of a single nucleotide polymorphism associated with the progression of glaucoma is carried out by combining two or more single nucleotide polymorphisms in the present invention mentioned above, whereby prediction of a risk may be performed in a high precision.

By performing prediction of a risk in two or more multi-steps, the precision for prediction of a risk can be improved, while reducing the costs or lowering a burden on a subject at an initial step to a minimum level.

In addition, an individual who has an allele or genotype on the genome that is identified in a high frequency in progressive glaucoma cases disclosed in the present invention has a high risk of the fast progression of glaucoma, and an individual who does not have an allele or genotype that is identified in a high frequency in the progressive glaucoma cases has a low risk of the fast progression of glaucoma. The period of the clinical trial for a candidate substance for a glaucoma therapeutic drug can be shortened by selecting patients having a high risk of the fast progression of glaucoma according to the present invention, and performing a clinical trial of a candidate substance of the glaucoma therapeutic drug.

EXAMPLES

The present invention will be specifically described hereinbelow by Examples, and Examples are given for illustration purposes for a better comprehension of the present invention, without intending to limit the scope of the present invention thereto. Here, in the following Examples, as to generally used molecular biological methods that are not specifically described in detail, methods and conditions described in a textbook such as *Molecular Cloning* (Joseph Sambrook et al., *Molexular Cloning—A Laboratory Manual*, 3rd Edition, Cold Spring Harbor Laboratory Press, 2001) or the like are used.

In the present invention, a total DNA was extracted from blood of each of patients diagnosed as glaucoma, and non-patients diagnosed as being not with glaucoma and determined not to have any family history in glaucoma according to a medical interview, and gene loci associated with the disease were analyzed based on about 500,000 known single nucleotide polymorphisms on the human genome as an index to determine an association of a single nucleotide polymorphism and the disease. In addition, patients with fast progression of glaucoma, i.e. progressive glaucoma cases, and patients with slow progression of glaucoma, i.e. nonprogressive glaucoma cases were subjected to the identification of a single nucleotide polymorphism and the association of the single nucleotide polymorphism with the progression in the same manner as above.

Example 1

DNA Extraction from Specimens

In DNA extraction from specimens, a commercially available automated nucleic acid extraction apparatus (QUIAGEN, BIOROBOT (registered trademark) EZ1), and a kit for extraction of a nucleic acid (EZ1 DNA Blood 350 µl Kit) compatible to the extraction apparatus and in which nucleic acids absorbed to magnetic beads were collected by a magnetic force were used. A total DNA was extracted in accordance with the instruction manuals of the apparatus and kit. According to the present method, a total DNA of about 5 µg was obtained from 350 µL of a blood specimen.

Example 2

Analysis of Single Nucleotide Polymorphism

In the analysis of single nucleotide polymorphisms, a commercially available microarray type single nucleotide polymorphism analysis kit (Affimetrix (GeneChip(registered trademark) Human Mapping 500K) (hereinafter also referred to as microarray) capable of analyzing about 500,000 known single nucleotide polymorphisms on the human genome was used. In the detection of single nucleotide polymorphisms, a scanner (Affimetrix (GeneChip(registered trademark) Scanner 3000)) compatible to the kit was used. In the analysis of single nucleotide polymorphisms, a specialized analysis software (Affimetrix (GTYPE(registered trademark))) was used.

The total DNA extracted in Example 1 was treated in accordance with the instruction manuals of the kit and apparatus, and applied to a microarray, and a single nucleotide polymorphism existing on the DNA extracted from the specimen was analyzed. Briefly explaining, a sample obtained by treating 250 ng of a total DNA with a restriction enzyme NspI and a sample obtained by treating 250 ng of a total DNA with a restriction enzyme StyI were prepared, and amplified by a PCR method with adaptors bound to the protruding ends of each of the samples. A PCR product was collected, and fragmented with DNaseI, and the ends of the fragmented PCR products were biotin-labeled using the labeling reagent contained in the kit. A buffer for hybridization was added to the PCR products that were already fragmented at both ends and labeled, the mixture was heat-treated at 99° C. for 10 minutes, and incubated at 49° C. for 1 minute, and the resulting mixture was injected to a microarray for NspI-treated sample or a microarray for StyI-treated sample depending on a firstly treated restriction enzyme, and hybridized at 49° C. for 16 to 18 hours. After the termination of hybridization, the microarray was stained with streptavidin-phycoerythrin. A fluorescence from phycoerythrin bound via biotin and streptavidin to DNA ends of samples hybridized with an immobilized allele-specific probe was read using the scanner mentioned above, and analyzed with the software mentioned above. Probes corresponding to about 250,000 single nucleotide polymorphisms each are previously immobilized to the microarray for NspI-treated sample and the microarray for StyI-treated sample, respectively, and analytical results for about 500,000 single nucleotide polymorphisms per one sample were obtained by combination of both the results. According to the present method, opposite alleles of each of the single nucleotide polymorphisms were read with a single operation, and consequently, a genotype was determined. In this case, it was determined that the genotype was a heterozygote in a case where both signals from each of the alleles constituting a single nucleotide polymorphism were detected, and that the genotype was a homozygote of the detected allele in a case where only either one of the signals was detected.

Here, in accordance with the instruction manual of the kit, as the probe immobilized to the kit, a probe for a sense strand or a probe for an antisense strand of the genome is used. In addition, according to the datasheet of the kit, the determination results for the present kit using 270 samples and those in HapMap are compared for single nucleotide polymorphisms overlapping between single nucleotide polymorphisms reported in the HapMap project and single nucleotide polymorphisms in the kit. As a result, a concordance rate of the single nucleotide polymorphisms shows 99% or more.

Example 3

Comparison of Single Nucleotide Polymorphisms Between Glaucoma Patients and Non-Patients The comparison on single nucleotide polymorphisms associated with a disease was made in accordance with the method used in the studies on genes responsible for age-related macular degeneration by Klein et al (*Science*, 308, 385, 2005).

Primary open-angle glaucoma patients and normal tension glaucoma patients that were diagnosed on the basis of Guidelines offered by Japan Glaucoma Society were assigned to a glaucoma patient group, and healthy individuals that were confirmed to have no family history of glaucoma according to a medical interview were assigned to a non-patient group. Blood donated under the consent on free will of the participants after having sufficiently explained the contents of studies from 418 cases of the glaucoma patient group and 300 controls of the non-patient group was used as specimens, a total DNA was extracted from the specimens according to the method described in Example 1, and the analysis of single nucleotide polymorphisms was performed according to the method described in Example 2. The analytical results of a single nucleotide polymorphism obtained in each of the patients were stored in the Laboratory Information Management System (World Fusion, LaboServer) adopting a relational database. A specialized analysis program for a single nucleotide polymorphism was created and loaded within the system, and the analysis was performed as follows: A single nucleotide polymorphism considered to have a high experimental reliability was extracted by rejecting a single nucleotide polymorphism having a call rate of less than 90% in both the glaucoma patient group and the non-patient group, a single nucleotide polymorphism having a difference in call rates between the glaucoma patient group and the non-patient group by 5% or more, a single nucleotide polymorphism having a minor allele frequency of less than 5%, and a single nucleotide polymorphism that is determined to deviate from the Hardy-Weinberg's equilibrium under conditions of a p-value of $1\times10^{-4}$ or less according to a chi-square test, and allele frequencies and genotype frequencies of the single nucleotide polymorphisms were compared between the groups. The allele frequencies and the genotype frequencies were statistically compared according to the chi-square test. As to single nucleotide polymorphisms showing a p-value of $1\times10^{-3}$ or less, cluster images serving as a basis for the determination of a genotype were confirmed. In a case where the determination of a genotype was made regardless of unclearness of the separation among clusters, the single nucleotide polymorphism was considered to be a non-subject of the analysis. In other words, the errors in the determination of a genotype were excluded by this step. The evaluation of the cluster was performed without informing the names of single nucleotide polymorphisms and the critical rates. Single nucleotide polymorphisms of which allele or genotype shows association with glaucoma at a p-value of $1\times10^{-4}$ or less, i.e. $-\log P$ of 4 or more are listed in Tables 1 to 2. Here, the odds ratio for association of an allele with a disease, and the odds ratio for association of a genotype with a disease in each of the tables, respectively, were calculated on the basis of the following formulas (1) to (5).

Allele Frequency=Number of Detection of an Allele in Group/Total Number of Detection of Alleles in Group    formula (1)

Genotype Frequency=Number of Detection of a Genotype in Group/Total Number of Detection of Genotypes in Group    formula (2)

Odds Ratio for Allele=[(Number of Detection of an Allele Identified in High Frequency in Glaucoma Patient Group, in Glaucoma Patient Group)/(Number of Detection of an Allele Opposite to the Allele Identified in High Frequency in Glaucoma Patient Group, in Glaucoma Patient Group)]/[(Number of Detection of the Allele Identified in High Frequency in Glaucoma Patient Group, in Non-Patient Group)/(Number of Detection of the Allele Opposite to the Allele Identified in High Frequency in Glaucoma Patient Group, in Non-Patient Group)]    formula (3)

Odds Ratio for Genotype of Homozygote=[(Number of Detection of a Genotype Having Homozygote of an Allele Identified in High Frequency in Glaucoma Patient Group, in Glaucoma Patient Group)/(Number of Detection of a Genotype Having Homozygote of an Allele Identified in High Frequency in Non-Patient Group, in Glaucoma Patient Group)]/[(Number of Detection of the Genotype Having Homozygote of the Allele Identified in High Frequency in Glaucoma Patient Group, in Non-Patient Group)/(Number of Detection of the Genotype Having Homozygote of the Allele Identified in High Frequency in Non-Patient Group, in Non-Patient Group)]    formula (4)

Odds Ratio for Genotype of Heterozygote=[(Number of Detection of a Genotype of Heterozygote in Glaucoma Patient Group)/(Number of Detection of a Genotype Having Homozygote of an Allele Identified in High Frequency in Non-Patient Group, in Glaucoma Patient Group)]/[(Number of Detection of the Genotype Having Homozygote in Non-Patient Group)/(Number of Detection of the Genotype Having Homozygote of the Allele Identified in High Frequency in Non-Patient Group, in Non-Patient Group)]    formula (5)

TABLE 1

| dbSNP ID | Allele1/ Allele2 | Exon, Intron | Chromosome | Physical Location | Critical rate, Allele ($-\log P$) | High-Risk Allele Frequency in Glaucoma Patient Group | High-Risk Allele Frequency in Non-Patient Group |
|---|---|---|---|---|---|---|---|
| rs12632110 | A/G | SEMA3F Intron18 (NM_004186.2) | 3 | 50199229 | 4.27 | 0.54 | 0.44 |
| rs2233476 | A/C | CYB561D2 Exon1 (NM_007022.3) | 3 | 50363387 | 5.57 | 0.55 | 0.42 |
| rs9852677 | C/T | GNAI2 Intron4 (NM_002070.1) | 3 | 50266621 | 5.27 | 0.56 | 0.44 |
| rs2236944 | G/T | GNAI2 Intron4 (NM_002070.1) | 3 | 50267197 | 5.00 | 0.55 | 0.43 |
| rs6786523 | A/G | CACNA2D2 Intron2 (NM_006030.1) | 3 | 50499225 | 4.05 | 0.60 | 0.49 |
| rs1467913 | G/T | CACNA2D2 Intron2 (NM_006030.1) | 3 | 50500021 | 4.22 | 0.60 | 0.50 |
| rs2004243 | A/G | LOC51337 +641 bp (NM_016647.1) | 8 | 143815988 | 4.46 | 0.45 | 0.34 |
| rs3761980 | C/T | SLC26A8 −1529 bp (NM_052961.2), SLC26A8 −1636 bp (NM_138718.1) | 6 | 36101884 | 4.12 | 0.93 | 0.87 |
| rs16884919 | A/G | MAPK14 Intron10 (NM_001315.1), MAPK14 Intron10 (NM_139012.1), MAPK14 Intron9 (NM_139014.1), MAPK14 +982 bp (NM_139013.1) | 6 | 36179495 | 4.12 | 0.93 | 0.87 |
| rs16883860 | C/T | MAPK14 Intron1 (NM_139013.1), MAPK14 Intron1 (NM_001315.1), | 6 | 36110440 | 4.42 | 0.94 | 0.87 |

TABLE 1-continued

| dbSNP ID | | | | | | | |
|---|---|---|---|---|---|---|---|
| | | MAPK14 Intron1 (NM_139012.1), MAPK14 Intron1 (NM_139014.1) | | | | | |
| rs10513095 | G/T | CLSTN2 Intron1 (NM_022131.1) | 3 | 141219021 | 4.52 | 0.84 | 0.75 |
| rs7081455 | A/C | PLXDC2 +69770 bp (NM_032812.7) | 10 | 20678891 | 4.33 | 0.83 | 0.74 |
| rs7850541 | C/T | GBGT1 −11253 bp (NM_021996.3) | 9 | 133080108 | 4.15 | 0.76 | 0.66 |
| rs10116267 | C/T | PSAT1 Intron5 (NM_021154.3), PSAT1 Intron5 (NM_058179.2) | 9 | 78151286 | 4.24 | 0.78 | 0.69 |
| rs10116231 | A/G | PSAT1 Intron5 (NM_021154.3), PSAT1 Intron5 (NM_058179.2) | 9 | 78151153 | 4.11 | 0.78 | 0.69 |
| rs6813301 | G/T | MGC45800 +203455 bp (NM_178838.2) | 4 | 183234501 | 4.16 | 0.12 | 0.06 |
| rs11945595 | C/T | MGC45800 +201900 bp (NM_178838.2) | 4 | 183236056 | 4.07 | 0.12 | 0.06 |
| rs2049723 | A/G | SPON1 −17894 bp (NM_006108.1) | 11 | 13922920 | 4.78 | 0.76 | 0.65 |
| rs1159623 | C/G | CNTN5 Intron2 (NM_014361.2), CNTN5 Intron2 (NM_175566.1) | 11 | 98877941 | 4.18 | 0.45 | 0.34 |
| rs7109406 | A/C | CNTN5 Intron2 (NM_014361.2), CNTN5 Intron2 (NM_175566.1) | 11 | 98867701 | 4.17 | 0.45 | 0.35 |

| dbSNP ID | High-Risk Allele | Odds Ratio (Formula 3) | Critical rate, Genotype (−logP) | Odds Ratio (Homozygote1) (Formula 4) | Odds Ratio (Heterozygote) (Formula 5) | Sequence Containing Allele 1 | Sequence Containing Allele 2 |
|---|---|---|---|---|---|---|---|
| rs12632110 | Allele 1 | 1.54 | 3.60 | 2.34 | 1.71 | SEQ ID No: 1 | SEQ ID No: 2 |
| rs2233476 | Allele 1 | 1.66 | 4.91 | 2.75 | 1.84 | SEQ ID No: 3 | SEQ ID No: 4 |
| rs9852677 | Allele 2 | 1.63 | 4.62 | 2.70 | 1.80 | SEQ ID No: 5 | SEQ ID No: 6 |
| rs2236944 | Allele 2 | 1.61 | 4.41 | 2.60 | 1.84 | SEQ ID No: 7 | SEQ ID No: 8 |
| rs6786523 | Allele 1 | 1.53 | 3.60 | 2.46 | 1.80 | SEQ ID No: 9 | SEQ ID No: 10 |
| rs1467913 | Allele 2 | 1.54 | 3.73 | 2.49 | 1.79 | SEQ ID No: 11 | SEQ ID No: 12 |
| rs2004243 | Allele 1 | 1.58 | 3.85 | 2.25 | 1.78 | SEQ ID No: 13 | SEQ ID No: 14 |
| rs3761980 | Allele 2 | 2.05 | 3.48 | 6.40 | 3.13 | SEQ ID No: 15 | SEQ ID No: 16 |
| rs16884919 | Allele 2 | 2.05 | 3.48 | 6.40 | 3.13 | SEQ ID No: 17 | SEQ ID No: 18 |
| rs16883860 | Allele 2 | 2.14 | 3.74 | 6.41 | 3.00 | SEQ ID No: 19 | SEQ ID No: 20 |
| rs10513095 | Allele 2 | 1.73 | 3.73 | 3.02 | 1.74 | SEQ ID No: 21 | SEQ ID No: 22 |
| rs7081455 | Allele 1 | 1.70 | 3.91 | 1.91 | 0.98 | SEQ ID No: 23 | SEQ ID No: 24 |
| rs7850541 | Allele 1 | 1.60 | 3.89 | 3.35 | 2.33 | SEQ ID No: 25 | SEQ ID No: 26 |
| rs10116267 | Allele 1 | 1.63 | 3.50 | 2.18 | 1.24 | SEQ ID No: 27 | SEQ ID No: 28 |
| rs10116231 | Allele 2 | 1.61 | 3.37 | 2.18 | 1.26 | SEQ ID No: 29 | SEQ ID No: 30 |
| rs6813301 | Allele 2 | 2.24 | 3.67 | 2.07 | 2.45 | SEQ ID No: 31 | SEQ ID No: 32 |
| rs11945595 | Allele 2 | 2.24 | 3.37 | 2.04 | 2.45 | SEQ ID No: 33 | SEQ ID No: 34 |
| rs2049723 | Allele 1 | 1.66 | 3.96 | 2.87 | 1.83 | SEQ ID No: 35 | SEQ ID No: 36 |
| rs1159623 | Allele 2 | 1.55 | 3.88 | 2.21 | 1.84 | SEQ ID No: 37 | SEQ ID No: 38 |
| rs7109406 | Allele 2 | 1.55 | 4.01 | 2.17 | 1.89 | SEQ ID No: 39 | SEQ ID No: 40 |

TABLE 2

| dbSNP ID | Allele1/ Allele2 | Exon, Intron | Chromosome | Physical Location | Critical rate, Allele (−logP) | High-Risk Allele Frequency in Glaucoma Patient Group | High-Risk Allele Frequency in Non-Patient Group |
|---|---|---|---|---|---|---|---|
| rs4763559 | C/G | KLRA1 +10130 bp (NM_006611.1) | 12 | 10622909 | 4.48 | 0.75 | 0.65 |
| rs4763531 (rs9739469) | A/G | KLRA1 +3474 bp (NM_006611.1) | 12 | 10629565 | 4.11 | 0.74 | 0.65 |
| rs2125094 | C/T | KLRA1 +11027 bp (NM_006611.1) | 12 | 10622012 | 4.38 | 0.74 | 0.64 |
| rs2233476 | A/C | CYB561D2 Exon1 (NM_007022.3) | 3 | 50363387 | 5.57 | 0.55 | 0.42 |
| rs9852677 | C/T | GNAI2 Intron4 (NM_002070.1) | 3 | 50266621 | 5.27 | 0.56 | 0.44 |
| rs2236944 | G/T | GNAI2 Intron4 (NM_002070.1) | 3 | 50267197 | 5.00 | 0.55 | 0.43 |
| rs4430902 | A/G | GULP1 Intron1 (NM_016315.1) | 2 | 189010443 | 3.57 | 0.85 | 0.77 |
| rs10804020 | C/T | GULP1 Intron1 (NM_016315.1) | 2 | 189028382 | 2.93 | 0.84 | 0.77 |
| rs13137759 | C/T | DKFZp686L1814 Intron2 (NM_194282.1) | 4 | 84262335 | 3.39 | 0.82 | 0.74 |
| rs11737784 | A/C | DKFZp686L1814 −11708 bp (NM_194282.1) | 4 | 84300869 | 3.15 | 0.81 | 0.74 |
| rs9498701 | C/T | GRIK2 Intron6 (NM_021956.2), GRIK2 Intron6 (NM_175768.1) | 6 | 102336911 | 0.93 | 0.59 | 0.55 |
| rs9322609 | A/G | GRIK2 Intron8 (NM_021956.2), GRIK2 Intron8 (NM_175768.1) | 6 | 102357540 | 0.67 | 0.58 | 0.55 |
| rs10130333 | A/C | CHES1 Intron2 (NM_005197.1) | 14 | 88929499 | 3.97 | 0.69 | 0.59 |
| rs11133030 | C/T | FBXO8 +139977 bp (NM_012180.1) | 4 | 175346521 | 2.16 | 0.70 | 0.63 |
| rs2220757 | A/C | BARX2 +108243 bp (NM_003658.3) | 11 | 128935268 | 1.34 | 0.71 | 0.66 |
| rs7109406 | A/C | CNTN5 Intron2 (NM_014361.2), CNTN5 Intron2 (NM_175566.1) | 11 | 98867701 | 4.17 | 0.45 | 0.35 |
| rs2347897 | C/T | LOC402300 Intron2 (XM_377974), CALD1 Intron1 (NM_004342.5), CALD1 Intron1 (NM_033138.2), CALD1 Intron1 (NM_033157.2), CALD1 −95572 bp (NM_033139.2), CALD1 −95572 bp (NM_033140.2) | 7 | 133937842 | 2.98 | 0.39 | 0.31 |

TABLE 2-continued

| dbSNP ID | | | | | | |
|---|---|---|---|---|---|---|
| rs7794696 | A/G | LOC402300 Intron1 (XM_377974), CALD1 Intron1 (NM_004342.5), CALD1 Intron1 (NM_033138.2), CALD1 Intron1 (NM_033157.2), CALD1 −72140 bp (NM_033139.2), CALD1 −72140 bp (NM_033140.2) | 7 | 133961274 | 3.29 | 0.39 | 0.30 |
| rs803594 | C/G | VGLL2 −7136 bp (NM_153453.1), VGLL2 −7152 bp (NM_182645.2) | 6 | 117686278 | 0.94 | 0.21 | 0.18 |
| rs762164 | A/C | RUNX1 Intron5 (NM_001754.2) | 21 | 35140644 | 0.52 | 0.44 | 0.42 |

| dbSNP ID | High-Risk Allele | Odds Ratio (Formula 3) | Critical rate, Genotype (−logP) | Odds Ratio (Homozygote1) (Formula 4) | Odds Ratio (Heterozygote) (Formula 5) | Sequence Containing Allele 1 | Sequence Containing Allele 2 |
|---|---|---|---|---|---|---|---|
| rs4763559 | Allele 2 | 1.62 | 3.70 | 2.32 | 1.34 | SEQ ID No: 41 | SEQ ID No: 42 |
| rs4763531 (rs9739469) | Allele 1 | 1.58 | 3.31 | 2.29 | 1.39 | SEQ ID No: 43 | SEQ ID No: 44 |
| rs2125094 | Allele 1 | 1.61 | 3.59 | 2.34 | 1.37 | SEQ ID No: 45 | SEQ ID No: 46 |
| rs2233476 | Allele 1 | 1.66 | 4.91 | 2.75 | 1.84 | SEQ ID No: 47 | SEQ ID No: 48 |
| rs9852677 | Allele 2 | 1.63 | 4.62 | 2.70 | 1.80 | SEQ ID No: 49 | SEQ ID No: 50 |
| rs2236944 | Allele 2 | 1.61 | 4.41 | 2.60 | 1.84 | SEQ ID No: 51 | SEQ ID No: 52 |
| rs4430902 | Allele 1 | 1.64 | 4.48 | 1.14 | 0.54 | SEQ ID No: 53 | SEQ ID No: 54 |
| rs10804020 | Allele 1 | 1.54 | 4.10 | 1.02 | 0.50 | SEQ ID No: 55 | SEQ ID No: 56 |
| rs13137759 | Allele 2 | 1.58 | 4.23 | 1.32 | 0.64 | SEQ ID No: 57 | SEQ ID No: 58 |
| rs11737784 | Allele 2 | 1.54 | 4.14 | 1.25 | 0.61 | SEQ ID No: 59 | SEQ ID No: 60 |
| rs9498701 | Allele 2 | 1.19 | 4.10 | 1.17 | 0.57 | SEQ ID No: 61 | SEQ ID No: 62 |
| rs9322609 | Allele 2 | 1.14 | 4.04 | 1.11 | 0.55 | SEQ ID No: 63 | SEQ ID No: 64 |
| rs10130333 | Allele 1 | 1.54 | 4.36 | 2.73 | 2.46 | SEQ ID No: 65 | SEQ ID No: 66 |
| rs11133030 | Allele 1 | 1.36 | 4.01 | 2.46 | 2.79 | SEQ ID No: 67 | SEQ ID No: 68 |
| rs2220757 | Allele 2 | 1.26 | 4.03 | 0.95 | 0.50 | SEQ ID No: 69 | SEQ ID No: 70 |
| rs7109406 | Allele 2 | 1.55 | 4.01 | 2.17 | 1.89 | SEQ ID No: 71 | SEQ ID No: 72 |
| rs2347897 | Allele 1 | 1.45 | 4.05 | 1.58 | 2.02 | SEQ ID No: 73 | SEQ ID No: 74 |
| rs7794696 | Allele 2 | 1.49 | 4.01 | 1.67 | 1.99 | SEQ ID No: 75 | SEQ ID No: 76 |
| rs803594 | Allele 2 | 1.24 | 4.31 | 0.49 | 1.90 | SEQ ID No: 77 | SEQ ID No: 78 |
| rs762164 | Allele 2 | 1.12 | 4.02 | 1.05 | 1.98 | SEQ ID No: 79 | SEQ ID No: 80 |

Tables 1 and 2 list dbSNP ID number or Affimetrix Array ID number specifying known single nucleotide polymorphisms obtained, each of bases constituting Allele 1 and Allele 2, the exon, intron information (in a case where a single nucleotide polymorphism exists on a gene, the gene name and the exon or intron in which SNP exists are shown, and in a case where a single nucleotide polymorphism does not exist on a gene, neighboring genes and a distance between the gene and the single nucleotide polymorphism are shown), the chromosome number at which a single nucleotide polymorphism exists, the physical location of a single nucleotide polymorphism, the p-value for an allele according to a chi-square test (−log P), the high-risk allele frequencies in the glaucoma patient group and the non-patient group, the type of the high-risk allele (indicating whether the high-risk allele is Allele 1 or Allele 2), the odds ratio for an allele, the p-value for a genotype according to a chi-square test (−log P), the odds ratio for a genotype of a homozygote and the odds ratio for a genotype of a heterozygote, and SEQ ID NO of the sequence containing Allele 1 and Allele 2 in each of the polymorphic sites. Here, one of ordinary skill in the art can obtain the information for sequences or alleles of the single nucleotide polymorphisms from dbSNP ID number or Affimetrix array ID number mentioned above.

When the allele or genotype frequencies listed in Tables 1 to 2 were compared between the non-patients without family history and the glaucoma patients, a statistical difference was found. By determining an allele of any one of these single nucleotide polymorphisms, whether or not an allele that is identified in a higher frequency in the glaucoma patient group than that of the non-patient group exists in the sample can be determined.

Specifically, when a first single nucleotide polymorphism listed in Tables 1 and 2 is explained as an example, one polymorphic site exists in a nucleic acid molecule shown in SEQ ID NO: 1 or 2 occupying a gene locus homologous to each other. In detail, a single nucleotide polymorphism is associated with the onset of glaucoma, of which 31st base is either A (Allele 1) or G (Allele 2), wherein Allele 1 indicated as a high-risk allele, that is, an allele of being A in the single nucleotide polymorphism is identified in a high frequency in the glaucoma patient group. Further, using the odds ratio for an allele, or the odds ratio for a genotype of a homozygote and the odds ratio for a genotype of a heterozygote, the degree of which the risk of a disease increases can be predicted in a case of having the allele or genotype. Similarly, all the sequences disclosed in Tables 1 and 2 have a polymorphic site associated with glaucoma in the sequence, and one allele or at least one genotype in the polymorphic site is identified in a high frequency in the glaucoma patient group.

According to the above studies, 40 single nucleotide polymorphisms of which alleles or genotypes were associated with glaucoma at a p-value of $1 \times 10^{-4}$ or less existing in clusters in relatively adjacent regions on the genome were found in 21 regions.

The allele or genotype identified in a high frequency in the glaucoma patient group of a single nucleotide polymorphism listed in Tables 1 and 2 can be used as a marker showing that an onset risk of glaucoma is high. On the other hand, an allele that is opposite to the allele or a genotype other than the genotype can be used as a marker showing that an onset risk of glaucoma is low.

Next, the surrounding regions and/or genes of the single nucleotide polymorphisms listed in Tables 1 and 2 were determined on the basis of the database provided by the HapMap project. In detail, regions in which single nucleotide polymorphisms that were considered to be in a linkage disequilibrium with the single nucleotide polymorphisms listed in Tables 1 and 2 exist were determined, on the basis of the linkage disequilibrium data in combination of the Japanese and the Chinese in the HapMap project.

Also, in a case where the single nucleotide polymorphism listed in Tables 1 and 2 exists in the linkage disequilibrium region containing the gene, the physical location and the gene name of the region were determined. On the other hand, in a case where the single nucleotide polymorphism listed in Tables 1 and 2 exists in the linkage disequilibrium region without containing the gene, only the physical location of the region was determined. In addition, in a case where the single nucleotide polymorphism listed in Tables 1 and 2 exists on one gene beyond the linkage disequilibrium region, only the gene name was determined.

A single nucleotide polymorphism of which p-value is lowest in each region is considered to be a single nucleotide polymorphism representing the region. Tables 3 and 4 list a single nucleotide polymorphism representing the region, the chromosome number at which the region exists, the physical location of the region (start point and end point) and the gene name contained in the region.

TABLE 3

| Representative SNP (SNP with Lowest p-value of the Region) | Chromo-some | Start Point of Physical Location | End Point of Physical Location | Genes Contained in the Region |
|---|---|---|---|---|
| rs16883860 | 6 | 36,014,367 | 36,248,614 | SLC26A8 DPRXP2 MAPK14 MAPK13 |
| rs2233476 | 3 | 49,952,596 | 50,516,561 | RBM6 RBM5 SEMA3F GNAT1 SLC38A3 GNAI2 SEMA3B FLJ38608 C3orf45 IFRD2 |

TABLE 3-continued

| Representative SNP (SNP with Lowest p-value of the Region) | Chromo-some | Start Point of Physical Location | End Point of Physical Location | Genes Contained in the Region |
|---|---|---|---|---|
|  |  |  |  | HYAL3 NAT6 HYAL1 HYAL2 TUSC2 RASSF1 ZMYND10 TUSC4 CYB561D2 TMEM115 CACNA2D2 |
| rs2004243 | 8 | 143,691,186 | 143,902,698 | ARC AK092432 JRK PSCA LY6K LOC51337 C8orf55 SLURP1 LYPDC2 LYNX1 AK126845 LY6D LYPD2 |
| rs10513095 | 3 | — | — | CLSTN2 |
| rs7081455 | 10 | 20,663,479 | 20,716,201 | no gene |
| rs7850541 | 9 | 134,756,557 | 135,192,865 | TSC1 GFI1B LOC158078 GTF3C5 CEL CELP RALGDS GBGT1 OBP2B LOC286310 ABO LOC653163 SURF6 |

TABLE 4

| Representative SNP (SNP with Lowest p-value of the Region) | Chromo-some | Start Point of Physical Location | End Point of Physical Location | Genes Contained in the Region |
|---|---|---|---|---|
| rs7109406 | 11 | — | — | CNTN5 |
| rs4763559 | 12 | 10,535,930 | 10,724,935 | LOC255308 KLRA1 FLJ10292 STYK1 |
| rs10116267 | 9 | — | — | PSAT1 |
| rs6813301 | 4 | 183,058,962 | 183,243,277 | LOC643296 |
| rs2049723 | 11 | 13,851,048 | 14,245,926 | SPON1 |
| rs9498701 | 6 | — | — | GRIK2 |
| rs2233476 | 3 | 49,952,596 | 50,516,561 | RBM6 RBM5 SEMA3F GNAT1 SLC38A3 GNAI2 SEMA3B FLJ38608 C3orf45 IFRD2 HYAL3 NAT6 HYAL1 HYAL2 TUSC2 |

TABLE 4-continued

| Representative SNP (SNP with Lowest p-value of the Region) | Chromosome | Start Point of Physical Location | End Point of Physical Location | Genes Contained in the Region |
|---|---|---|---|---|
| rs10130333 | 14 | 88,697,458 | 89,155,209 | RASSF1<br>ZMYND10<br>TUSC4<br>CYB561D2<br>TMEM115<br>CACNA2D2<br>CHES1<br>LOC646224<br>CAP2P1<br>LOC400236 |
| rs4430902 | 2 | 188,904,662 | 189,286,159 | GULP1 |
| rs13137759 | 4 | 83,800,064 | 84,215,995 | SCD4<br>SEC31L1<br>THAP9<br>DKFZp686L1814<br>COPS4 |
| rs11133030 | 4 | 175,234,727 | 175,450,910 | FBXO8<br>KIAA1712 |
| rs762164 | 21 | 35,049,200 | 35,343,511 | RUNX1 |
| rs7109406 | 11 | — | — | CNTN5 |
| rs2220757 | 11 | 128,920,427 | 128,953,084 | no gene |
| rs803594 | 6 | 117,682,814 | 117,853,711 | VGLL2<br>ROS1 |
| rs2347897 | 7 | — | — | CALD1 |

The region listed in Tables 3 and 4 is a region or gene considered to be linked with a single nucleotide polymorphism listed in Tables 3 and 4 which is associated with glaucoma in the present invention, and a single nucleotide polymorphism which exists in these regions or genes is considered to be linked with a single nucleotide polymorphism in the present invention. In other words, any single nucleotide polymorphisms which exist in these regions are linked with the single nucleotide polymorphism which exists in the region as listed in Tables 3 and 4, and any of these single nucleotide polymorphisms can be used in the prediction of a risk of glaucoma in the same manner.

Also, a single nucleotide polymorphism of which allele or genotype shows association with glaucoma at a p-value of $1 \times 10^{-3}$ or less, i.e. $-\log P$ of 3 or more, is also listed in Tables 5 to 25.

TABLE 5

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs2139539 | COL16A1 +69 bp (NM_001856.2) | 1 | 31,786,872 | 3.99 | 0.87 | 0.80 | 1.75 | 3.81 | 7.12 | 4.52 |
| rs693421 | ZP4 −45155 bp (NM_021186.2) | 1 | 234,425,131 | 3.53 | 0.55 | 0.45 | 1.48 | 3.77 | 2.14 | 2.02 |
| rs2038845 | CACNA1S Intron2 (NM_000069.1) | 1 | 197,799,070 | 0.57 | 0.41 | 0.39 | 1.13 | 3.76 | 1.00 | 1.89 |
| rs4040617 | LOC284591 Intron2 (XM_211529) | 1 | 819,185 | 0.24 | 0.17 | 0.15 | 1.09 | 3.68 | ND | 0.75 |
| rs540782 | ZP4 −43104 bp (NM_021186.2) | 1 | 234,423,080 | 3.43 | 0.56 | 0.46 | 1.47 | 3.52 | 2.09 | 1.96 |
| rs2040073 | LOC339442 −148785 bp (XM_378855) | 1 | 38,498,317 | 3.58 | 0.38 | 0.29 | 1.52 | 3.38 | 1.93 | 1.80 |
| rs547984 | ZP4 −42951 bp (NM_021186.2) | 1 | 234,422,927 | 3.48 | 0.55 | 0.46 | 1.47 | 3.35 | 2.10 | 1.88 |
| rs10798882 | PEF Intron1 (NM_012392.1) | 1 | 31,777,640 | 3.52 | 0.86 | 0.79 | 1.67 | 3.35 | 6.05 | 3.84 |
| rs2499601 | ZP4 −50960 bp (NM_021186.2) | 1 | 234,430,936 | 3.24 | 0.55 | 0.46 | 1.45 | 3.23 | 2.05 | 1.89 |
| rs909002 | COL16A1 Intron44 (NM_001856.2) | 1 | 31,808,728 | 3.47 | 0.84 | 0.77 | 1.63 | 3.19 | 4.38 | 2.94 |
| rs2147798 | CACNA1S Intron3 (NM_000069.1) | 1 | 197,793,475 | 1.22 | 0.56 | 0.51 | 1.22 | 3.14 | 1.58 | 2.09 |
| rs10752589 | CSF3R −53414 bp (NM_000760.2), CSF3R −53414 bp (NM_156038.2), | 1 | 36,671,016 | 3.61 | 0.18 | 0.11 | 1.77 | 3.13 | 2.06 | 1.92 |

TABLE 5-continued

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs2236913 | CSF3R −53414 bp (NM_156039.2), CSF3R −53414 bp (NM_172313.1) PSEN2 Intron5 (NM_000447.1), PSEN2 Intron5 (NM_012486.1) | 1 | 223,380,860 | 0.61 | 0.35 | 0.33 | 1.14 | 3.13 | 0.88 | 1.74 |
| rs10518601 | ELTD1 −94220 bp (XM_371262) | 1 | 79,312,758 | 0.27 | 0.79 | 0.78 | 1.08 | 3.08 | 3.51 | 4.57 |
| rs17102821 | ELTD1 −89304 bp (XM_371262) | 1 | 79,307,842 | 0.28 | 0.80 | 0.78 | 1.09 | 3.08 | 3.52 | 4.57 |
| rs7525498 | ELTD1 −102412 bp (XM_371262) | 1 | 79,320,950 | 0.30 | 0.80 | 0.78 | 1.09 | 3.04 | 3.53 | 4.54 |
| rs2359112 | MGC15882 +194951 bp (NM_032884.2) | 1 | 34,548,776 | 0.58 | 0.30 | 0.27 | 1.15 | 3.03 | 5.23 | 0.86 |
| rs1892116 | ELYS Intron2 (NM_175865.1), ELYS Intron2 (NM_015446.1) | 1 | 243,406,363 | 3.15 | 0.75 | 0.67 | 1.49 | 2.91 | 2.89 | 2.07 |
| rs7524405 | PEF Intron1 (NM_012392.1) | 1 | 31,777,672 | 3.27 | 0.84 | 0.77 | 1.59 | 2.89 | 3.77 | 2.54 |
| rs704709 | MGC39558 Intron8 (NM_152490.1) | 1 | 231,947,005 | 3.45 | 0.61 | 0.52 | 1.48 | 2.83 | 2.20 | 1.39 |
| rs1951626 | SERPINC1 −5704 bp (NM_000488.1) | 1 | 170,623,758 | 3.34 | 0.38 | 0.30 | 1.49 | 2.66 | 2.33 | 1.43 |
| rs11163089 | MGC34032 Intron4 (NM_152697.2) | 1 | 75,490,567 | 3.31 | 0.85 | 0.77 | 1.61 | 2.55 | 2.70 | 1.75 |
| rs10430126 | LOC388630 +22072 bp (XM_371250) | 1 | 47,934,070 | 3.10 | 0.64 | 0.55 | 1.45 | 2.54 | 2.08 | 1.33 |

TABLE 6

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs16865980 | RNF144 +120346 bp (NM_014746.2) | 2 | 7,255,254 | 1.98 | 0.24 | 0.18 | 1.41 | 3.96 | 0.84 | 1.99 |
| rs4953262 | PRKCE Intron1 (NM_005400.2) | 2 | 45,952,444 | 0.15 | 0.53 | 0.52 | 1.04 | 3.75 | 1.01 | 0.53 |
| rs10170220 | GULP1 Intron2 (NM_016315.1) | 2 | 189,123,624 | 2.80 | 0.84 | 0.78 | 1.53 | 3.68 | 1.03 | 0.53 |
| rs6717705 | VIT Intron1 (NM_053276.2) | 2 | 36,838,198 | 2.80 | 0.88 | 0.82 | 1.60 | 3.62 | 18.77 | 14.09 |
| rs759428 | VIT Intron1 (NM_053276.2) | 2 | 36,844,694 | 2.76 | 0.88 | 0.82 | 1.59 | 3.58 | 18.68 | 14.12 |
| rs4670589 | VIT Intron1 (NM_053276.2) | 2 | 36,840,872 | 2.72 | 0.88 | 0.82 | 1.59 | 3.57 | 18.77 | 14.29 |
| rs10931358 | GULP1 Intron2 (NM_016315.1) | 2 | 189,096,087 | 2.69 | 0.84 | 0.77 | 1.52 | 3.55 | 1.02 | 0.53 |
| rs11124532 | VIT Intron1 (NM_053276.2) | 2 | 36,840,580 | 2.65 | 0.88 | 0.82 | 1.58 | 3.50 | 18.48 | 14.14 |
| rs828868 | MGC22014 Intron8 (XM_371501) | 2 | 74,236,159 | 3.37 | 0.66 | 0.57 | 1.47 | 3.48 | 2.06 | 1.10 |
| rs11677028 | LOC339789 Intron9 (NM_207358.1) | 2 | 8,309,297 | 1.34 | 0.71 | 0.66 | 1.26 | 3.45 | 2.50 | 2.92 |
| rs6431929 | LOC339789 +41877 bp (NM_207358.1) | 2 | 8,255,994 | 1.22 | 0.69 | 0.65 | 1.24 | 3.43 | 2.32 | 2.78 |

TABLE 6-continued

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs2421844 | SLC4A5 Intron5 (NM_033323.2), SLC4A5 Intron5 (NM_133478.1), SLC4A5 Intron5 (NM_133479.1), SLC4A5 Intron1 (NM_021196.2) | 2 | 74,451,749 | 3.42 | 0.48 | 0.38 | 1.48 | 3.43 | 2.39 | 1.13 |
| rs7559118 | FLJ34870 Intron4 (NM_207481.1) | 2 | 133,706,762 | 2.37 | 0.64 | 0.56 | 1.37 | 3.34 | 2.15 | 2.25 |
| rs17754672 | PELI1 −61125 bp (NM_020651.2) | 2 | 64,312,259 | 2.49 | 0.24 | 0.17 | 1.49 | 3.27 | 6.36 | 1.11 |
| rs7584987 | QPCT +129689 bp (NM_012413.2) | 2 | 37,641,805 | 2.56 | 0.44 | 0.37 | 1.39 | 3.26 | 2.40 | 1.03 |
| rs7571760 | CDC42EP3 +127985 bp (NM_006449.3) | 2 | 37,654,409 | 3.06 | 0.40 | 0.31 | 1.46 | 3.13 | 2.69 | 1.17 |
| rs6724538 | QPCT +127553 bp (NM_012413.2) | 2 | 37,639,669 | 3.33 | 0.42 | 0.32 | 1.48 | 3.12 | 2.49 | 1.16 |
| rs13387588 | SLC4A5 Intron2 (NM_033323.2), SLC4A5 Intron2 (NM_133478.1), SLC4A5 Intron2 (NM_133479.1), SLC4A5 −19990 bp (NM_021196.2) | 2 | 74,473,795 | 3.27 | 0.48 | 0.39 | 1.46 | 3.10 | 2.29 | 1.15 |
| rs7601299 | SP110 Intron3 (NM_004509.2), SP110 Intron3 (NM_080424.1), SP110 Intron3 (NM_004510.2) | 2 | 230,903,499 | 1.26 | 0.91 | 0.88 | 1.39 | 3.08 | ND | ND |

TABLE 7

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs1198825 | RAMP1 −3950 bp (NM_005855.1) | 2 | 238,546,337 | 3.82 | 0.44 | 0.34 | 1.52 | 3.07 | 2.23 | 1.57 |
| rs10930321 | STK39 −102538 bp (NM_013233.1) | 2 | 169,032,150 | 3.70 | 0.44 | 0.34 | 1.51 | 3.04 | 2.42 | 1.40 |
| SNP_A-2170785 | LTBP1 Intron2 (NM_206943.1), LTBP1 −181297 bp (NM_000627.2) | 2 | 33,090,031 | 1.24 | 0.78 | 0.73 | 1.27 | 3.01 | 3.21 | 3.52 |
| rs12611812 | CNTNAP5 Intron3 (NM_130773.2), CNTNAP5 Intron3 (NM_138996.1) | 2 | 124,776,344 | 1.80 | 0.59 | 0.52 | 1.30 | 3.00 | 1.52 | 0.79 |
| rs11123034 | CNTNAP5 Intron3 (NM_130773.2), CNTNAP5 Intron3 (NM_138996.1) | 2 | 124,776,617 | 1.80 | 0.59 | 0.52 | 1.30 | 3.00 | 1.52 | 0.79 |
| rs7581836 | SLC4A5 −7735 bp (NM_033323.2), SLC4A5 −7735 bp (NM_133478.1), SLC4A5 −7735 bp (NM_133479.1), SLC4A5 −35247 bp (NM_021196.2) | 2 | 74,489,052 | 3.18 | 0.49 | 0.40 | 1.45 | 2.95 | 2.24 | 1.17 |

TABLE 7-continued

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs4430896 | KBTBD9 −239670 bp (XM_496546) | 2 | 23,246,431 | 3.58 | 0.75 | 0.66 | 1.54 | 2.94 | 1.91 | 1.12 |
| rs7574012 | QPCT +126765 bp (NM_012413.2) | 2 | 37,638,881 | 3.04 | 0.41 | 0.32 | 1.45 | 2.81 | 2.49 | 1.22 |
| rs9309484 | DCTN1 +1471 bp (NM_023019.1), DCTN1 +1471 bp (NM_004082.2) | 2 | 74,498,466 | 3.06 | 0.49 | 0.40 | 1.44 | 2.77 | 2.16 | 1.16 |
| rs4666488 | ODD −128777 bp (NM_145260.1) | 2 | 19,608,777 | 3.13 | 0.36 | 0.28 | 1.48 | 2.67 | 1.90 | 1.65 |
| rs3771738 | SLC4A5 Intron5 (NM_033323.2), SLC4A5 Intron5 (NM_133478.1), SLC4A5 Intron5 (NM_133479.1), SLC4A5 Intron1 (NM_021196.2) | 2 | 74,452,572 | 3.04 | 0.48 | 0.40 | 1.43 | 2.65 | 2.14 | 1.19 |
| rs4848607 | FLJ14816 −60027 bp (NM_032845.1) | 2 | 120,999,954 | 3.28 | 0.75 | 0.66 | 1.50 | 2.58 | 2.33 | 1.61 |
| rs4668312 | LOC389059 −20365 bp (XM_374017) | 2 | 171,432,334 | 3.04 | 0.74 | 0.65 | 1.47 | 2.58 | 1.80 | 1.08 |
| rs4411759 | HTLF Intron2 (NM_002158.2) | 2 | 48,468,133 | 3.16 | 0.55 | 0.46 | 1.44 | 2.57 | 2.07 | 1.57 |
| rs2268794 | SRD5A2 Intron1 (NM_000348.2) | 2 | 31,691,055 | 3.01 | 0.20 | 0.13 | 1.63 | 2.55 | 5.02 | 1.46 |
| rs11676168 | HTLF Intron1 (NM_002158.2) | 2 | 48,465,842 | 3.15 | 0.55 | 0.46 | 1.44 | 2.52 | 2.07 | 1.54 |

TABLE 8

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs4667649 | SP5 +8390 bp (XM_371581) | 2 | 171,408,395 | 3.21 | 0.73 | 0.65 | 1.49 | 2.43 | 1.93 | 1.23 |
| rs6745010 | LRP1B +648365 bp (NM_018557.1) | 2 | 140,174,363 | 3.09 | 0.91 | 0.86 | 1.75 | 2.42 | 3.69 | 2.17 |
| rs2356232 | SP5 +12276 bp (XM_371581) | 2 | 171,412,281 | 3.19 | 0.73 | 0.65 | 1.49 | 2.41 | 1.92 | 1.23 |
| rs7608898 | SP5 +23719 bp (XM_371581) | 2 | 171,423,724 | 3.19 | 0.73 | 0.65 | 1.48 | 2.41 | 1.92 | 1.23 |
| rs10184230 | LOC389059 −25058 bp (XM_374017) | 2 | 171,427,641 | 3.19 | 0.73 | 0.65 | 1.48 | 2.41 | 1.92 | 1.23 |
| rs6433243 | LOC389059 −21697 bp (XM_374017) | 2 | 171,431,002 | 3.19 | 0.73 | 0.65 | 1.48 | 2.41 | 1.92 | 1.23 |
| rs10930437 | SP5 +6843 bp (XM_371581) | 2 | 171,406,848 | 3.15 | 0.73 | 0.64 | 1.48 | 2.40 | 1.92 | 1.22 |
| rs1566993 | DPP10 +503127 bp (NM_020868.1) | 2 | 116,821,290 | 3.13 | 0.96 | 0.91 | 2.10 | 2.40 | 4.55 | 2.22 |
| rs1990702 | LRP2 +8346 bp (NM_004525.1) | 2 | 169,802,022 | 3.04 | 0.71 | 0.63 | 1.46 | 2.36 | 2.00 | 1.32 |
| rs10183959 | NEDL2 Intron1 (XM_038999) | 2 | 197,139,030 | 3.15 | 0.93 | 0.88 | 1.89 | 2.35 | 3.17 | 1.72 |
| rs6746374 | LOC389059 −7686 bp (XM_374017) | 2 | 171,445,013 | 3.03 | 0.74 | 0.66 | 1.47 | 2.34 | 1.95 | 1.25 |
| rs6599252 | SCN10A Intron12 (NM_006514.1) | 3 | 38,764,695 | 0.14 | 0.48 | 0.47 | 1.04 | 3.94 | 1.17 | 0.56 |

TABLE 8-continued

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs7612549 | LOC285307 +209732 bp (XM_211837) | 3 | 34,789,105 | 2.18 | 0.44 | 0.36 | 1.35 | 3.93 | 2.38 | 0.88 |
| rs1012728 | FLJ22419 Intron4 (NM_024697.1) | 3 | 21,519,300 | 2.60 | 0.49 | 0.41 | 1.39 | 3.84 | 1.76 | 2.08 |
| rs13097360 | GBE1 −805292 bp (NM_000158.1) | 3 | 82,698,727 | 1.55 | 0.82 | 0.77 | 1.34 | 3.22 | 0.56 | 0.32 |
| rs33954719 | SGEF Intron6 (NM_015595.2) | 3 | 155,359,077 | 1.70 | 0.65 | 0.58 | 1.30 | 3.07 | 2.09 | 2.33 |
| rs1462840 | LOC285194 +426618 bp (XM_379207) | 3 | 118,345,185 | 2.84 | 0.63 | 0.54 | 1.42 | 3.07 | 2.23 | 2.03 |
| rs17013665 | LOC440947 −8774 bp (XM_496633) | 3 | 23,718,507 | 3.79 | 0.71 | 0.62 | 1.53 | 3.05 | 2.42 | 1.69 |
| rs2044757 | SGEF Intron5 (NM_015595.2) | 3 | 155,352,950 | 1.58 | 0.65 | 0.59 | 1.28 | 3.05 | 2.03 | 2.32 |
| rs1503075 | ALCAM −279337 bp (NM_001627.1) | 3 | 106,289,543 | 3.46 | 0.13 | 0.07 | 1.93 | 3.01 | ND | 1.84 |
| rs6550308 | LOC285307 +332200 bp (XM_211837) | 3 | 34,911,573 | 3.08 | 0.48 | 0.39 | 1.44 | 2.98 | 1.90 | 1.78 |
| rs12494849 | CACNA2D2 Intron2 (NM_006030.1) | 3 | 50,499,562 | 3.61 | 0.59 | 0.49 | 1.48 | 2.89 | 2.20 | 1.52 |
| rs3755827 | ZNF312 −1350 bp (NM_018008.2) | 3 | 62,335,411 | 3.69 | 0.81 | 0.73 | 1.61 | 2.88 | 2.43 | 1.51 |
| rs9881866 | ALCAM −264171 bp (NM_001627.1) | 3 | 106,304,709 | 3.32 | 0.15 | 0.09 | 1.81 | 2.87 | 1.97 | 1.97 |
| rs34329202 | LOC389099 −54783 bp (XM_371621) | 3 | 22,240,837 | 3.37 | 0.92 | 0.86 | 1.83 | 2.82 | 1.99 | 1.01 |
| rs10935365 | CLSTN2 Intron1 (NM_022131.1) | 3 | 141,227,766 | 3.47 | 0.84 | 0.76 | 1.61 | 2.77 | 2.61 | 1.62 |

TABLE 9

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs2138789 | GRK7 Intron2 (NM_139209.1) | 3 | 142,991,449 | 3.33 | 0.14 | 0.08 | 1.86 | 2.67 | 3.28 | 1.88 |
| rs6550783 | LOC440947 −8191 bp (XM_496633) | 3 | 23,719,090 | 3.18 | 0.69 | 0.61 | 1.47 | 2.48 | 2.18 | 1.51 |
| rs779701 | GRM7 Intron7 (NM_181875.1), GRM7 Intron7 (NM_000844.2), GRM7 Intron7 (NM_181874.1) | 3 | 7,493,772 | 3.03 | 0.33 | 0.25 | 1.48 | 2.48 | 1.80 | 1.64 |
| rs2216524 | IL1RAP Intron7 (NM_134470.2), IL1RAP Intron7 (NM_002182.2) | 3 | 191,824,803 | 3.03 | 0.86 | 0.79 | 1.59 | 2.47 | 1.99 | 1.18 |
| rs3922704 | FLJ31579 Intron3 (NM_153268.1) | 3 | 112,983,875 | 3.06 | 0.88 | 0.82 | 1.66 | 2.44 | 2.09 | 1.20 |
| rs7641653 | LOC389105 −266407 bp (XM_374037) | 3 | 35,093,422 | 3.06 | 0.40 | 0.32 | 1.45 | 2.43 | 2.08 | 1.50 |
| rs2193877 | IL1RAP Intron7 (NM_134470.2), | 3 | 191,825,144 | 3.05 | 0.85 | 0.79 | 1.59 | 2.41 | 2.15 | 1.30 |

TABLE 9-continued

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs4624606 | IL1RAP Intron7 (NM_002182.2) IL1RAP Intron9 (NM_002182.2), IL1RAP +6172 bp (NM_134470.2) | 3 | 191,836,948 | 3.07 | 0.84 | 0.78 | 1.58 | 2.40 | 2.50 | 1.59 |
| rs4858594 | THRB Intron2 (NM_000461.2) | 3 | 24,248,858 | 3.02 | 0.69 | 0.61 | 1.45 | 2.21 | 1.95 | 1.33 |
| rs10454254 | LOC285441 Intron1 (XM_379295) | 4 | 187,735,925 | 1.17 | 0.81 | 0.77 | 1.27 | 3.70 | 0.60 | 0.33 |
| rs13110551 | CCRN4L −116225 bp (NM_012118.2) | 4 | 140,178,323 | 2.59 | 0.58 | 0.50 | 1.38 | 3.56 | 2.22 | 2.18 |
| rs1503539 | MAD2L1 +168679 bp (NM_002358.2) | 4 | 121,169,516 | 3.91 | 0.38 | 0.28 | 1.56 | 3.53 | 3.05 | 1.40 |
| rs3804100 | TLR2 Exon2 (NM_003264.2) | 4 | 154,983,014 | 3.96 | 0.74 | 0.64 | 1.57 | 3.37 | 2.72 | 1.84 |
| rs4516662 | CCRN4L −116103 bp (NM_012118.2) | 4 | 140,178,445 | 2.22 | 0.57 | 0.50 | 1.34 | 3.27 | 2.08 | 2.12 |
| rs10009731 | STX18 −141961 bp (NM_016930.2) | 4 | 4,803,808 | 2.34 | 0.83 | 0.77 | 1.46 | 3.23 | 6.58 | 5.41 |
| rs7676755 | CYP4V2 Intron2 (NM_207352.1) | 4 | 187,490,196 | 0.68 | 0.80 | 0.78 | 1.18 | 3.22 | 3.26 | 4.09 |
| rs10517556 | LOC391656 −135832 bp (XM_373027) | 4 | 62,947,647 | 2.42 | 0.51 | 0.43 | 1.37 | 3.21 | 1.75 | 1.96 |
| rs16996478 | UNC5C −11150 bp (NM_003728.2) | 4 | 96,838,490 | 3.98 | 0.20 | 0.12 | 1.80 | 3.17 | 3.11 | 1.79 |
| rs10517578 | LOC285533 Intron4 (NM_173662.1) | 4 | 155,005,757 | 3.89 | 0.74 | 0.65 | 1.56 | 3.15 | 2.47 | 1.61 |
| rs34415360 | LOC132391 −118159 bp (XM_497978) | 4 | 117,081,308 | 3.45 | 0.29 | 0.21 | 1.57 | 3.01 | 3.26 | 1.28 |
| rs930438 | CENPC1 +97050 bp (NM_001812.1) | 4 | 68,069,912 | 3.27 | 0.82 | 0.75 | 1.57 | 2.84 | 3.33 | 2.31 |

TABLE 10

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs17279573 | KIAA0922 +22425 bp (NM_015196.2) | 4 | 154,937,893 | 3.34 | 0.68 | 0.60 | 1.48 | 2.74 | 2.31 | 1.66 |
| rs11727442 | TLR2 −23144 bp (NM_003264.2) | 4 | 154,943,527 | 3.42 | 0.69 | 0.60 | 1.49 | 2.73 | 2.22 | 1.49 |
| rs1027690 | MAD2L1 +191047 bp (NM_002358.2) | 4 | 121,147,148 | 3.22 | 0.43 | 0.34 | 1.46 | 2.63 | 2.24 | 1.45 |
| rs16891164 | LOC441009 +88767 bp (XM_498965) | 4 | 14,590,288 | 3.15 | 0.96 | 0.92 | 2.12 | 2.63 | ND | ND |
| rs13107767 | LOC152519 +6607 bp (NM_207330.1) | 4 | 47,886,619 | 3.44 | 0.60 | 0.50 | 1.47 | 2.62 | 2.07 | 1.39 |
| rs1980391 | LOC389239 −207565 bp (XM_371714) | 4 | 165,986,419 | 3.18 | 0.62 | 0.53 | 1.45 | 2.60 | 1.99 | 1.23 |
| rs7376639 | LOC132391 −82192 bp (XM_497978) | 4 | 117,117,275 | 3.04 | 0.29 | 0.21 | 1.52 | 2.56 | 2.90 | 1.27 |

TABLE 10-continued

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs4256218 | SCD4 Intron1 (NM_024906.1) | 4 | 84,047,858 | 3.28 | 0.89 | 0.82 | 1.69 | 2.55 | 2.70 | 1.59 |
| rs972469 | FSTL5 +959616 bp (NM_020116.2) | 4 | 161,703,038 | 3.06 | 0.40 | 0.32 | 1.45 | 2.47 | 2.27 | 1.36 |
| rs6829490 | TXK +894 bp (NM_003328.1) | 4 | 47,908,795 | 3.23 | 0.57 | 0.48 | 1.45 | 2.46 | 2.04 | 1.46 |
| rs3804099 | TLR2 Exon2 (NM_003264.2) | 4 | 154,982,261 | 3.07 | 0.71 | 0.63 | 1.46 | 2.45 | 2.24 | 1.57 |
| rs4392496 | KIAA0922 Intron3 (NM_015196.2) | 4 | 154,800,110 | 3.10 | 0.46 | 0.37 | 1.44 | 2.41 | 2.04 | 1.47 |
| rs4568220 | LOC344988 Intron2 (XM_293671) | 4 | 121,413,055 | 3.23 | 0.11 | 0.06 | 2.04 | 2.40 | 3.19 | 2.00 |
| rs33964061 | TXK +1806 bp (NM_003328.1) | 4 | 47,907,883 | 3.11 | 0.57 | 0.48 | 1.43 | 2.34 | 2.00 | 1.46 |
| rs6447614 | TXK +804 bp (NM_003328.1) | 4 | 47,908,885 | 3.11 | 0.57 | 0.48 | 1.43 | 2.34 | 2.00 | 1.46 |
| rs12655405 | PDZK3 −33552 bp (NM_015022.2), PDZK3 −33552 bp (NM_178140.1) | 5 | 31,801,198 | 0.80 | 0.93 | 0.91 | 1.33 | 3.88 | 0.13 | 0.06 |
| rs4515309 | NNT +296580 bp (NM_012343.2), NNT +296836 bp (NM_182977.1) | 5 | 44,037,927 | 1.77 | 0.12 | 0.08 | 1.56 | 3.74 | 0.00 | 2.02 |
| rs1377489 | MTRR +135148 bp (NM_024010.1), MTRR +135148 bp (NM_002454.1) | 5 | 8,089,385 | 1.15 | 0.82 | 0.78 | 1.28 | 3.56 | 20.15 | 19.82 |
| rs309593 | CSPG2 Intron10 (NM_004385.2) | 5 | 82,884,337 | 3.95 | 0.43 | 0.33 | 1.54 | 3.45 | 2.43 | 1.64 |
| rs6579788 | TCOF1 −25018 bp (NM_000356.1) | 5 | 149,692,410 | 1.15 | 0.37 | 0.32 | 1.23 | 3.43 | 2.27 | 0.80 |
| rs6451268 | FLJ25422 Intron11 (NM_145000.2) | 5 | 36,291,121 | 1.39 | 0.61 | 0.56 | 1.25 | 3.38 | 1.85 | 2.30 |
| rs529279 | C5orf13 −5941 bp (NM_004772.1) | 5 | 111,126,776 | 3.20 | 0.30 | 0.22 | 1.53 | 2.90 | 3.30 | 1.31 |
| rs298091 | PDE4D −114328 bp (NM_006203.3) | 5 | 59,032,360 | 3.58 | 0.82 | 0.74 | 1.61 | 2.86 | 2.37 | 1.43 |
| rs3097776 | FAT2 Intron2 (NM_001447.1) | 5 | 150,916,554 | 3.34 | 0.72 | 0.63 | 1.49 | 2.77 | 2.01 | 1.23 |
| rs11750584 | FLJ40243 −22454 bp (NM_173489.2) | 5 | 41,129,616 | 3.13 | 0.20 | 0.13 | 1.64 | 2.68 | 1.86 | 1.80 |

TABLE 11

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs11748095 | FBXL17 −103066 bp (NM_022824.1) | 5 | 107,848,076 | 3.18 | 0.50 | 0.41 | 1.45 | 2.66 | 1.95 | 1.66 |
| rs1428470 | LY64 −8157 bp (NM_005582.1) | 5 | 66,536,525 | 3.15 | 0.80 | 0.72 | 1.53 | 2.64 | 1.93 | 1.16 |
| rs11167493 | CSF1R +19417 bp (NM_005211.2) | 5 | 149,393,634 | 3.02 | 0.12 | 0.07 | 1.92 | 2.52 | ND | 1.77 |
| rs6891720 | LY64 −7944 bp (NM_005582.1) | 5 | 66,536,312 | 3.04 | 0.80 | 0.72 | 1.51 | 2.52 | 1.91 | 1.16 |
| rs4246764 | LY64 −384319 bp (NM_005582.1) | 5 | 66,912,687 | 3.00 | 0.29 | 0.21 | 1.51 | 2.46 | 2.43 | 1.54 |
| rs429419 | ADAMTS12 Intron17 (NM_030955.1) | 5 | 33,624,092 | 3.12 | 0.91 | 0.85 | 1.76 | 2.44 | 3.75 | 2.20 |
| rs298063 | PDE4D −88343 bp (NM_006203.3) | 5 | 59,006,375 | 3.15 | 0.82 | 0.75 | 1.55 | 2.44 | 2.11 | 1.32 |
| rs818725 | ADAMTS12 Intron17 (NM_030955.1) | 5 | 33,624,060 | 3.05 | 0.91 | 0.86 | 1.74 | 2.37 | 3.66 | 2.17 |
| rs4285312 | NEDD9 −191677 bp (NM_006403.2), NEDD9 −191687 bp (NM_182966.1) | 6 | 11,532,564 | 3.28 | 0.16 | 0.10 | 1.76 | 3.87 | 1.07 | 2.27 |
| rs4840196 | GRIK2 Intron8 (NM_021956.2), GRIK2 Intron8 (NM_175768.1) | 6 | 102,359,520 | 0.96 | 0.60 | 0.55 | 1.19 | 3.72 | 1.19 | 0.60 |

TABLE 11-continued

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs4075603 | NEDD9 −191609 bp (NM_006403.2), NEDD9 −191619 bp (NM_182966.1) | 6 | 11,532,496 | 3.09 | 0.16 | 0.10 | 1.73 | 3.67 | 1.04 | 2.22 |
| rs2764236 | GRIK2 Intron9 (NM_021956.2), GRIK2 Intron9 (NM_175768.1) | 6 | 102,389,150 | 0.83 | 0.59 | 0.56 | 1.17 | 3.61 | 1.15 | 0.59 |
| rs4840195 | GRIK2 Intron8 (NM_021956.2), GRIK2 Intron8 (NM_175768.1) | 6 | 102,359,490 | 0.84 | 0.59 | 0.55 | 1.17 | 3.55 | 1.18 | 0.60 |
| rs372534 | AOF1 Intron8 (XM_173173) | 6 | 18,295,895 | 3.02 | 0.68 | 0.59 | 1.45 | 3.50 | 2.40 | 2.31 |
| rs6907963 | LOC442154 Intron1 (XM_498036) | 6 | 4,903,481 | 2.45 | 0.88 | 0.83 | 1.56 | 3.18 | 16.95 | 13.09 |
| rs6916915 | EGFL11 −135926 bp (NM_198283.1) | 6 | 66,398,533 | 3.44 | 0.54 | 0.45 | 1.47 | 3.08 | 2.18 | 1.20 |
| rs3857597 | LOC442216 −86680 bp (XM_498099) | 6 | 51,020,014 | 3.84 | 0.22 | 0.14 | 1.73 | 3.07 | 2.60 | 1.76 |
| rs902287 | EGFL11 −127786 bp (NM_198283.1) | 6 | 66,390,393 | 3.31 | 0.51 | 0.42 | 1.46 | 3.05 | 2.19 | 1.16 |
| rs7761118 | MAPK14 Intron9 (NM_139013.1), MAPK14 Intron9 (NM_001315.1), MAPK14 Intron9 (NM_139012.1), MAPK14 Intron9 (NM_139014.1) | 6 | 36,176,281 | 3.63 | 0.93 | 0.87 | 1.95 | 3.05 | 4.77 | 2.39 |

TABLE 12

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs9473926 | LOC442216 −10440 bp (XM_498099) | 6 | 50,943,774 | 3.30 | 0.54 | 0.45 | 1.46 | 2.90 | 2.17 | 1.69 |
| rs1206153 | KIAA1900 Intron6 (NM_052904.1) | 6 | 97,652,757 | 3.02 | 0.56 | 0.47 | 1.43 | 2.80 | 1.95 | 1.08 |
| rs16871306 | NEDD9 −153598 bp (NM_006403.2), NEDD9 −153608 bp (NM_182966.1) | 6 | 11,494,485 | 3.04 | 0.09 | 0.04 | 2.17 | 2.52 | ND | 2.22 |
| rs9398995 | ENPP1 Intron1 (NM_006208.1) | 6 | 132,181,896 | 3.12 | 0.58 | 0.48 | 1.44 | 2.51 | 2.06 | 1.59 |
| rs9358578 | LOC389370 Intron1 (XM_374162) | 6 | 22,810,626 | 3.27 | 0.44 | 0.35 | 1.47 | 2.46 | 2.12 | 1.39 |
| rs10488281 | PRES Intron2 (NM_206883.1), PRES Intron2 (NM_206884.1), PRES Intron2 (NM_206885.1), PRES Intron2 (NM_198999.1) | 7 | 102,663,783 | 1.13 | 0.48 | 0.44 | 1.21 | 3.64 | 1.66 | 0.72 |
| rs2215164 | COBL Intron1 (NM_015198.2) | 7 | 51,093,537 | 1.75 | 0.88 | 0.83 | 1.44 | 3.60 | 0.32 | 0.17 |
| rs2299257 | PON1 Intron4 (NM_000446.3) | 7 | 94,587,416 | 3.65 | 0.37 | 0.28 | 1.54 | 3.43 | 2.01 | 1.80 |
| rs1075737 | PRES Intron2 (NM_206883.1), PRES Intron2 (NM_206884.1), PRES Intron2 (NM_206885.1), PRES Intron2 (NM_198999.1) | 7 | 102,665,144 | 0.99 | 0.48 | 0.44 | 1.19 | 3.41 | 1.60 | 0.72 |
| rs10232532 | CPA5 −3205 bp (NM_080385.2) | 7 | 129,575,431 | 0.30 | 0.52 | 0.50 | 1.07 | 3.24 | 1.18 | 1.94 |
| rs3917538 | PON1 Intron5 (NM_000446.3) | 7 | 94,582,544 | 3.50 | 0.51 | 0.42 | 1.47 | 3.16 | 2.20 | 1.16 |
| rs1222418 | FLJ32786 Intron12 (NM_144648.1) | 7 | 133,334,253 | 3.72 | 0.17 | 0.10 | 1.89 | 3.14 | 10.10 | 1.72 |
| rs2966701 | TAS2R41 +27695 bp (NM_176883.1) | 7 | 142,720,419 | 3.59 | 0.13 | 0.07 | 2.01 | 3.13 | 2.48 | 2.15 |
| rs10271531 | HGF +217504 bp (NM_000601.3) | 7 | 80,758,592 | 3.78 | 0.42 | 0.33 | 1.52 | 3.11 | 2.46 | 1.41 |
| rs12700287 | DNAH11 Intron8 (NM_003777.1) | 7 | 21,385,860 | 3.76 | 0.96 | 0.92 | 2.39 | 3.10 | ND | ND |
| rs10228385 | LOC401324 +47600 bp (XM_379484) | 7 | 35,236,926 | 3.79 | 0.84 | 0.76 | 1.65 | 3.07 | 2.21 | 1.26 |
| rs4726533 | PRSS1 −172004 bp (NM_002769.2) | 7 | 141,771,615 | 0.57 | 0.39 | 0.36 | 1.13 | 3.07 | 1.71 | 0.72 |

TABLE 13

| dbSNP ID | Exon, Intron | Chromosome | Physical Location | Critical rate, Allele (-logP) | High-Risk Allele Frequency in Glaucoma Patient Group | High-Risk Allele Frequency in Non-Patient Group | Odds Ratio (Formula 3) | Critical rate, Genotype (-logP) | Odds Ratio (Homozygote) (Formula 4) | Odds Ratio (Heterozygote) (Formula 5) |
|---|---|---|---|---|---|---|---|---|---|---|
| rs2285652 | OSBPL3 Intron22 (NM_015550.2), OSBPL3 Intron21 (NM_145320.1), OSBPL3 Intron21 (NM_145321.1), OSBPL3 Intron20 (NM_145322.1), OSBPL3 Intron22 (NM_145323.1), OSBPL3 Intron21 (NM 145324.1) | 7 | 24,617,110 | 3.56 | 0.84 | 0.77 | 1.64 | 3.02 | 3.55 | 2.33 |
| rs10250170 | TPK1 Intron8 (NM_022445.2) | 7 | 143,650,537 | 0.69 | 0.12 | 0.10 | 1.24 | 3.02 | 0.11 | 1.67 |
| rs2966712 | TAS2R41 −7843 bp (NM_176883.1) | 7 | 142,683,960 | 3.22 | 0.11 | 0.06 | 1.97 | 3.02 | 0.82 | 2.20 |
| rs1001148 | COBL Intron1 (NM_015198.2) | 7 | 51,094,084 | 1.40 | 0.88 | 0.84 | 1.37 | 3.01 | 0.32 | 0.18 |
| rs17167646 | FLJ32786 Intron16 (NM_144648.1) | 7 | 133,365,708 | 3.50 | 0.15 | 0.09 | 1.84 | 2.93 | 9.85 | 1.66 |
| rs930688 | FLJ32786 Intron16 (NM_144648.1) | 7 | 133,366,047 | 3.50 | 0.15 | 0.09 | 1.84 | 2.93 | 9.85 | 1.66 |
| rs991162 | FLJ32110 −9270 bp (NM_181646.2) | 7 | 88,024,134 | 3.55 | 0.15 | 0.09 | 1.89 | 2.91 | 2.49 | 1.98 |
| rs2592845 | LOC401324 +94391 bp (XM_379484) | 7 | 35,283,717 | 3.07 | 0.77 | 0.69 | 1.51 | 2.90 | 3.17 | 2.30 |
| rs10228514 | LOC401324 +47709 bp (XM_379484) | 7 | 35,237,035 | 3.55 | 0.83 | 0.75 | 1.62 | 2.86 | 2.20 | 1.30 |
| rs10488110 | LOC340268 Intron1 (XM_294634) | 7 | 9,827,710 | 3.41 | 0.11 | 0.06 | 2.07 | 2.81 | ND | 1.89 |
| rs975910 | HIC +252683 bp (NM_199072.2) | 7 | 114,505,890 | 3.53 | 0.94 | 0.88 | 1.98 | 2.72 | 5.49 | 3.05 |
| rs2893506 | LOC401324 +25585 bp (XM_379484) | 7 | 35,214,911 | 3.52 | 0.83 | 0.75 | 1.60 | 2.69 | 2.47 | 1.58 |
| rs10236415 | LOC401324 +28462 bp (XM_379484) | 7 | 35,217,788 | 3.52 | 0.83 | 0.75 | 1.60 | 2.69 | 2.47 | 1.58 |
| rs9640055 | GLCCI1 Intron1 (XM_166529) | 7 | 7,802,756 | 3.27 | 0.82 | 0.75 | 1.57 | 2.65 | 2.55 | 1.62 |
| rs2592860 | LOC401324 +14726 bp (XM_379484) | 7 | 35,204,052 | 3.25 | 0.71 | 0.63 | 1.48 | 2.52 | 2.15 | 1.45 |
| rs6961391 | NUP205 −1742 bp (XM_371954) | 7 | 134,698,206 | 3.12 | 0.73 | 0.65 | 1.47 | 2.52 | 2.11 | 1.36 |
| rs115357 | FLJ13842 +130801 bp (NM_024645.1) | 8 | 40,376,469 | 1.62 | 0.31 | 0.25 | 1.32 | 3.49 | 1.01 | 1.90 |
| rs2977752 | LOC441352 +55834 bp (XM_499115) | 8 | 72,715,809 | 1.84 | 0.58 | 0.52 | 1.30 | 3.39 | 1.87 | 2.19 |
| rs10504440 | LOC389667 +50257 bp (XM_372046) | 8 | 70,255,391 | 2.06 | 0.70 | 0.64 | 1.35 | 3.32 | 2.77 | 2.73 |
| rs2470722 | GEM −2381 bp (NM_005261.2), GEM −2381 bp (NM_181702.1) | 8 | 95,346,114 | 1.12 | 0.77 | 0.73 | 1.25 | 3.28 | 0.79 | 0.45 |

TABLE 14

| dbSNP ID | Exon, Intron | Chromosome | Physical Location | Critical rate, Allele (-logP) | High-Risk Allele Frequency in Glaucoma Patient Group | High-Risk Allele Frequency in Non-Patient Group | Odds Ratio (Formula 3) | Critical rate, Genotype (-logP) | Odds Ratio (Homozygote) (Formula 4) | Odds Ratio (Heterozygote) (Formula 5) |
|---|---|---|---|---|---|---|---|---|---|---|
| rs12898 | CTSB +629 bp (NM_001908.2), CTSB +629 bp (NM_147780.1), CTSB +629 bp (NM_147781.1), CTSB +629 bp (NM_147782.1), CTSB +629 bp (NM 147783.1) | 8 | 11,738,607 | 2.92 | 0.49 | 0.40 | 1.42 | 3.27 | 1.81 | 1.90 |
| rs6991723 | ZNF596 +33933 bp (NM_173539.1) | 8 | 221,272 | 2.75 | 0.58 | 0.49 | 1.40 | 3.25 | 2.08 | 2.04 |
| rs16904092 | MGC27434 Intron1 (NM_145050.2) | 8 | 130,571,112 | 1.05 | 0.90 | 0.87 | 1.33 | 3.19 | 0.16 | 0.09 |
| rs6468360 | LOC286135 −35034 bp (XM_379573) | 8 | 29,863,536 | 2.01 | 0.55 | 0.48 | 1.32 | 3.16 | 1.78 | 0.86 |
| rs4736872 | FLJ13842 Intron5 (NM_024645.1) | 8 | 40,570,858 | 0.36 | 0.63 | 0.61 | 1.09 | 3.12 | 1.54 | 2.26 |
| rs10958627 | FLJ13842 Intron5 (NM_024645.1) | 8 | 40,594,675 | 0.03 | 0.47 | 0.47 | 1.01 | 3.08 | 0.96 | 1.75 |
| rs16935718 | LOC389667 +60391 bp (XM_372046) | 8 | 70,265,525 | 1.87 | 0.74 | 0.68 | 1.34 | 3.07 | 3.16 | 3.04 |
| rs1605950 | PXMP3 −574113 bp (NM_000318.1) | 8 | 78,649,107 | 0.82 | 0.28 | 0.25 | 1.19 | 3.07 | 0.78 | 1.73 |
| rs2513858 | STARS −43515 bp (NM_139166.2) | 8 | 107,895,164 | 0.07 | 0.65 | 0.65 | 1.02 | 3.05 | 1.49 | 2.29 |
| rs16935744 | LOC389667 +75414 bp (XM_372046) | 8 | 70,280,548 | 1.80 | 0.74 | 0.68 | 1.33 | 3.04 | 3.05 | 2.98 |
| rs2272767 | CTSB Intron1 (NM_001908.2), CTSB Intron3 (NM_147780.1), CTSB Intron2 (NM_147781.1), CTSB Intron2 (NM_147782.1), CTSB Intron2 (NM 147783.1) | 8 | 11,748,468 | 2.69 | 0.48 | 0.40 | 1.40 | 3.01 | 1.75 | 1.85 |
| rs705998 | LOC389667 +90010 bp (XM_372046) | 8 | 70,295,144 | 1.55 | 0.71 | 0.65 | 1.29 | 3.01 | 2.51 | 2.69 |
| rs12545915 | SNTG1 Intron2 (NM_018967.1) | 8 | 51,329,479 | 3.39 | 0.85 | 0.77 | 1.62 | 2.91 | 1.82 | 1.01 |
| rs6999627 | SNTG1 Intron2 (NM_018967.1) | 8 | 51,340,728 | 3.27 | 0.85 | 0.78 | 1.61 | 2.77 | 1.81 | 1.02 |
| rs3757916 | RBPMS Intron9 (NM_006867.1) | 8 | 30,545,447 | 0.43 | 0.34 | 1.45 | 2.62 | 1.96 | 1.62 |  |
| rs2729482 | LOC169355 Intron9 (NM_194294.1) | 8 | 39,975,804 | 3.10 | 0.11 | 0.06 | 2.07 | 2.61 | 3.62 | 2.00 |
| rs7823902 | LOC286129 Intron2 (XM_209910) | 8 | 26,963,854 | 3.20 | 0.34 | 0.26 | 1.50 | 2.58 | 2.12 | 1.56 |
| rs11783765 | GTF2E2 Intron7 (NM_002095.3) | 8 | 30,556,550 | 3.12 | 0.40 | 0.32 | 1.46 | 2.55 | 2.17 | 1.51 |

TABLE 15

| dbSNP ID | Exon, Intron | Chromosome | Physical Location | Critical rate, Allele (-logP) | High-Risk Allele Frequency in Glaucoma Patient Group | High-Risk Allele Frequency in Non-Patient Group | Odds Ratio (Formula 3) | Critical rate, Genotype (-logP) | Odds Ratio (Homozygote) (Formula 4) | Odds Ratio (Heterozygote) (Formula 5) |
|---|---|---|---|---|---|---|---|---|---|---|
| rs17758599 | SNTG1 Intron1 (NM_018967.1) | 8 | 51,109,255 | 3.14 | 0.85 | 0.78 | 1.59 | 2.49 | 2.77 | 1.78 |
| rs2468705 | KCNK9 +75721 bp (NM_016601.2) | 8 | 140,618,265 | 3.08 | 0.28 | 0.20 | 1.53 | 2.45 | 2.48 | 1.52 |
| rs6474298 | FLJ13842 −168006 bp (NM_024645.1) | 8 | 41,042,506 | 3.23 | 0.81 | 0.73 | 1.55 | 2.45 | 2.27 | 1.48 |
| rs17473451 | TUSC3 −73601 bp (NM_006765.2), TUSC3 −73601 bp (NM_178234.1) | 8 | 15,368,500 | 3.05 | 0.79 | 0.71 | 1.51 | 2.43 | 1.98 | 1.24 |
| rs6559770 | SLC28A3 +116711 bp (NM_022127.1) | 9 | 84,005,935 | 2.83 | 0.47 | 0.38 | 1.41 | 3.55 | 1.82 | 1.96 |
| rs10984339 | LOC442434 +182746 bp (XM_498343) | 9 | 118,798,668 | 1.63 | 0.42 | 0.36 | 1.28 | 3.18 | 1.34 | 1.89 |
| rs920753 | LOC389771 −178380 bp (XM_374296) | 9 | 89,862,442 | 0.11 | 0.27 | 0.26 | 1.04 | 3.13 | 0.55 | 1.55 |
| rs411102 | LOC347265 +48076 bp (XM_294590) | 9 | 99,196,524 | 3.28 | 0.16 | 0.10 | 1.79 | 3.06 | 1.50 | 2.03 |
| rs1342022 | ANXA1 −61274 bp (NM_000700.1) | 9 | 72,935,061 | 1.37 | 0.60 | 0.54 | 1.24 | 3.05 | 1.34 | 0.70 |
| rs10972299 | VCP +4230 bp (NM_007126.2) | 9 | 35,042,331 | 3.54 | 0.95 | 0.89 | 2.09 | 3.01 | 2.57 | 15.88 |
| rs303612 | LOC340511 −47888 bp (XM_295261) | 9 | 103,142,920 | 0.20 | 0.61 | 0.59 | 1.05 | 3.01 | 1.39 | 2.12 |
| rs1316814 | BARX1 −25445 bp (NM_021570.2) | 9 | 93,822,273 | 3.20 | 0.57 | 0.48 | 1.45 | 2.80 | 2.27 | 1.60 |
| rs1538844 | JMJD2C Intron8 (NM_015061.1) | 9 | 6,953,799 | 3.07 | 0.41 | 0.33 | 1.46 | 2.78 | 1.91 | 1.70 |
| rs2148591 | PCSK5 −63459 bp (NM_006200.2) | 9 | 75,671,716 | 3.11 | 0.45 | 0.36 | 1.45 | 2.72 | 2.28 | 1.21 |
| rs932881 | JMJD2C +1849 bp (NM_015061.1) | 9 | 7,167,496 | 3.25 | 0.78 | 0.70 | 1.52 | 2.53 | 2.37 | 1.61 |
| rs10764881 | MGMT −70674 bp (NM_002412.1) | 10 | 131,153,821 | 0.91 | 0.72 | 0.68 | 1.20 | 3.94 | 5.56 | 6.03 |
| rs1649035 | TFAM +176804 bp (NM_003201.1), TFAM +187289 bp (NM_012251.1) | 10 | 60,002,707 | 3.82 | 0.61 | 0.51 | 1.51 | 3.94 | 2.56 | 2.09 |
| rs782394 | LOC387721 −251645 bp (XM_370585) | 10 | 130,349,442 | 2.06 | 0.54 | 0.47 | 1.33 | 3.70 | 1.75 | 0.80 |
| rs1649048 | TFAM +168385 bp (NM_003201.1), TFAM +178870 bp (NM_012251.1) | 10 | 59,994,288 | 3.54 | 0.60 | 0.51 | 1.48 | 3.54 | 2.36 | 1.99 |
| rs7477330 | TFAM +162217 bp (NM_003201.1), TFAM +172702 bp (NM_012251.1) | 10 | 59,988,130 | 3.63 | 0.60 | 0.51 | 1.49 | 3.52 | 2.38 | 1.95 |
| rs17157033 | LOC439960 −30545 bp (XM_498478) | 10 | 44,613,470 | 2.88 | 0.96 | 0.92 | 2.14 | 3.45 | ND | ND |
| rs10458653 | PCBD −54076 bp (NM_000281.1) | 10 | 72,369,768 | 0.63 | 0.25 | 0.22 | 1.16 | 3.45 | 5.56 | 0.82 |

TABLE 16

| dbSNP ID | Exon, Intron | Chromosome | Physical Location | Critical rate, Allele (-logP) | High-Risk Allele Frequency in Glaucoma Patient Group | High-Risk Allele Frequency in Non-Patient Group | Odds Ratio (Formula 3) | Critical rate, Genotype (-logP) | Odds Ratio (Homozygote) (Formula 4) | Odds Ratio (Heterozygote) (Formula 5) |
|---|---|---|---|---|---|---|---|---|---|---|
| rs3849969 | SEC24C Intron12 (NM_004922.2), SEC24C Intron11 (NM_198597.1) | 10 | 75,196,005 | 3.36 | 0.27 | 0.19 | 1.57 | 3.44 | 1.58 | 1.92 |
| rs1658438 | TFAM +170686 bp (NM_003201.1), TFAM +181171 bp (NM_012251.1) | 10 | 59,996,589 | 3.56 | 0.60 | 0.51 | 1.48 | 3.43 | 2.35 | 1.92 |
| rs1649039 | TFAM +174144 bp (NM_003201.1), TFAM +184629 bp (NM_012251.1) | 10 | 60,000,047 | 3.59 | 0.60 | 0.50 | 1.48 | 3.43 | 2.34 | 1.91 |
| rs1658456 | TFAM +148429 bp (NM_003201.1), TFAM +158914 bp (NM_012251.1) | 10 | 59,974,332 | 3.54 | 0.60 | 0.51 | 1.48 | 3.40 | 2.33 | 1.91 |
| rs1649060 | TFAM +154583 bp (NM_003201.1), TFAM +165068 bp (NM_012251.1) | 10 | 59,980,486 | 3.54 | 0.60 | 0.51 | 1.48 | 3.40 | 2.33 | 1.91 |
| rs17130394 | HABP2 −103263 bp (NM_004132.2) | 10 | 115,199,512 | 3.18 | 0.84 | 0.77 | 1.59 | 3.40 | 1.38 | 0.71 |
| rs10763558 | TFAM +186037 bp (NM_003201.1), TFAM +196522 bp (NM_012251.1) | 10 | 60,011,940 | 3.62 | 0.60 | 0.50 | 1.49 | 3.36 | 2.33 | 1.87 |
| rs10763556 | TFAM +185501 bp (NM_003201.1), TFAM +195986 bp (NM_012251.1) | 10 | 60,011,404 | 3.53 | 0.60 | 0.50 | 1.48 | 3.34 | 2.33 | 1.89 |
| rs7902091 | CTNNA3 Intron7 (NM_013266.1) | 10 | 68,268,298 | 2.66 | 0.51 | 0.43 | 1.39 | 3.33 | 1.98 | 0.94 |
| rs1210065 | TMEM23 Intron5 (NM_147156.3) | 10 | 51,882,795 | 2.61 | 0.41 | 0.34 | 1.40 | 3.31 | 1.59 | 1.89 |
| rs10994838 | ACF Intron1 (NM_014576.2), ACF Intron1 (NM_138932.1), ACF Intron1 (NM_138933.1) | 10 | 52,312,506 | 1.16 | 0.36 | 0.32 | 1.23 | 3.31 | 2.21 | 0.80 |
| rs11189912 | SH2D4B +793340 bp (NM_207372.1) | 10 | 83,189,636 | 3.27 | 0.92 | 0.86 | 1.83 | 3.15 | 1.07 | 0.52 |
| rs1028534 | TMEM23 Intron3 (NM_147156.3) | 10 | 51,898,627 | 2.47 | 0.66 | 0.59 | 1.38 | 3.10 | 2.22 | 2.21 |
| rs1203392 | TMEM23 Intron5 (NM_147156.3) | 10 | 51,874,999 | 2.46 | 0.41 | 0.34 | 1.38 | 3.08 | 1.57 | 1.85 |
| rs7910849 | LOC220929 +29028 bp (NM_182755.1) | 10 | 31,144,546 | 3.06 | 0.74 | 0.66 | 1.48 | 3.08 | 1.69 | 0.93 |
| rs7904101 | TMEM23 −7099 bp (NM_147156.3) | 10 | 52,060,842 | 1.38 | 0.37 | 0.32 | 1.26 | 3.05 | 1.12 | 1.81 |
| rs4474374 | LOC439991 −14752 bp (XM_495838) | 10 | 85,647,711 | 0.14 | 0.33 | 0.32 | 1.04 | 3.05 | 1.98 | 0.69 |
| rs11016249 | MKI67 −323870 bp (NM_002417.2) | 10 | 130,138,328 | 3.24 | 0.69 | 0.60 | 1.47 | 2.90 | 2.42 | 1.91 |

TABLE 17

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs2092832 | SH2D4B +843746 bp (NM_207372.1) | 10 | 83,240,049 | 3.58 | 0.94 | 0.88 | 1.99 | 2.88 | 3.15 | 1.55 |
| rs4934425 | ANKRD22 Intron1 (NM_144590.1) | 10 | 90,599,698 | 3.05 | 0.64 | 0.55 | 1.44 | 2.83 | 2.29 | 1.86 |
| rs2688612 | PLAU −17730 bp (NM_002658.1) | 10 | 75,323,211 | 3.57 | 0.42 | 0.33 | 1.50 | 2.81 | 2.28 | 1.45 |
| rs10883820 | CNNM2 Intron1 (NM_017649.3), CNNM2 Intron1 (NM_199076.1), CNNM2 +77286 bp (NM_199077.1) | 10 | 104,754,651 | 3.37 | 0.90 | 0.84 | 1.76 | 2.78 | 2.47 | 1.34 |
| rs7074084 | TFAM +146618 bp (NM_003201.1), TFAM +157103 bp (NM_012251.1) | 10 | 59,972,521 | 3.20 | 0.59 | 0.49 | 1.44 | 2.77 | 2.16 | 1.69 |
| rs1649023 | TFAM +129923 bp (NM_003201.1), TFAM +140408 bp (NM_012251.1) | 10 | 59,955,826 | 3.11 | 0.59 | 0.50 | 1.44 | 2.69 | 2.13 | 1.69 |
| rs1649080 | TFAM +137397 bp (NM_003201.1), TFAM +147882 bp (NM_012251.1) | 10 | 59,963,300 | 3.11 | 0.59 | 0.50 | 1.44 | 2.69 | 2.13 | 1.69 |
| rs1303970 | TFAM +142580 bp (NM_003201.1), TFAM +153065 bp (NM_012251.1) | 10 | 59,968,483 | 3.11 | 0.59 | 0.50 | 1.44 | 2.69 | 2.13 | 1.69 |
| rs3829154 | ECHDC3 −1630 bp (NM_024693.2) | 10 | 11,822,759 | 3.17 | 0.49 | 0.40 | 1.44 | 2.61 | 2.16 | 1.29 |
| rs1926029 | NT5C2 Intron11 (NM_012229.2) | 10 | 104,845,660 | 3.20 | 0.91 | 0.85 | 1.75 | 2.57 | 3.18 | 1.80 |
| rs2802493 | LOC283034 +233953 bp (XM_210860) | 10 | 43,873,585 | 3.15 | 0.39 | 0.31 | 1.47 | 2.50 | 2.27 | 1.38 |
| rs718641 | ECHDC3 −4475 bp (NM_024693.2) | 10 | 11,819,914 | 3.08 | 0.49 | 0.40 | 1.44 | 2.49 | 2.12 | 1.30 |
| rs7913781 | ZWINT −792415 bp (NM_007057.2), ZWINT −792415 bp (NM_032997.1) | 10 | 58,583,444 | 3.22 | 0.18 | 0.11 | 1.72 | 2.46 | 4.17 | 1.49 |
| rs7894588 | CNNM2 Intron1 (NM_017649.3), CNNM2 Intron1 (NM_199076.1), CNNM2 +68655 bp (NM_199077.1) | 10 | 104,746,020 | 3.08 | 0.91 | 0.85 | 1.72 | 2.46 | 2.41 | 1.35 |
| rs1569868 | SH2D4B +852561 bp (NM_207372.1) | 10 | 83,248,857 | 3.13 | 0.93 | 0.88 | 1.88 | 2.45 | 3.12 | 1.65 |
| rs10883843 | NT5C2 −6408 bp (NM_012229.2) | 10 | 104,937,483 | 3.03 | 0.91 | 0.85 | 1.71 | 2.41 | 2.39 | 1.35 |
| rs7074395 | NT5C2 +2984 bp (NM_012229.2) | 10 | 104,834,918 | 3.00 | 0.91 | 0.85 | 1.71 | 2.39 | 2.39 | 1.35 |

TABLE 18

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs10829630 | MGMT +6919 bp (NM_002412.1) | 10 | 131,462,275 | 3.02 | 0.58 | 0.49 | 1.43 | 2.21 | 1.96 | 1.40 |
| rs923811 | BARX2 +93402 bp (NM_003658.3) | 11 | 128,920,427 | 0.82 | 0.67 | 0.63 | 1.17 | 3.76 | 0.91 | 0.49 |
| rs4937431 | BARX2 +124127 bp (NM_003658.3) | 11 | 128,951,152 | 1.56 | 0.44 | 0.38 | 1.27 | 3.24 | 2.05 | 0.85 |
| rs11021202 | MGC33371 +224211 bp (NM_144664.3) | 11 | 94,917,555 | 3.28 | 0.14 | 0.08 | 1.85 | 3.18 | 1.33 | 2.17 |
| rs497776 | MAML2 Intron1 (NM_032427.1) | 11 | 95,597,312 | 2.23 | 0.80 | 0.74 | 1.42 | 3.06 | 3.58 | 3.31 |
| rs11602121 | LOC399921 Intron4 (XM_374904) | 11 | 70,237,526 | 1.45 | 0.29 | 0.24 | 1.30 | 3.00 | 5.91 | 1.01 |
| rs11220171 | CNTN5 Intron2 (NM_014361.2), CNTN5 Intron2 (NM_175566.1) | 11 | 98,866,935 | 3.46 | 0.36 | 0.28 | 1.51 | 2.95 | 2.04 | 1.67 |
| rs4307718 | LOC440033 +175532 bp (XM_498512) | 11 | 23,320,437 | 3.48 | 0.96 | 0.92 | 2.27 | 2.90 | ND | ND |
| rs1384483 | LOC440033 +63001 bp (XM_498512) | 11 | 23,207,906 | 3.23 | 0.13 | 0.07 | 1.90 | 2.78 | ND | 1.79 |
| rs500629 | ZBTB16 Intron3 (NM_006006.3) | 11 | 113,550,770 | 3.13 | 0.29 | 0.22 | 1.52 | 2.72 | 1.88 | 1.69 |
| rs1507527 | LOC387754 −33940 bp (XM_373490) | 11 | 13,882,655 | 3.25 | 0.77 | 0.69 | 1.51 | 2.72 | 2.23 | 1.39 |
| rs2007052 | SPON1 −37564 bp (NM_006108.1) | 11 | 13,903,250 | 3.21 | 0.77 | 0.68 | 1.51 | 2.69 | 2.24 | 1.40 |
| rs7935243 | PHACS Intron3 (NM_032592.1) | 11 | 44,050,992 | 3.13 | 0.80 | 0.72 | 1.53 | 2.67 | 2.95 | 2.11 |
| rs562160 | CHORDC1 −291532 bp (NM_012124.1) | 11 | 89,887,386 | 3.12 | 0.82 | 0.75 | 1.55 | 2.57 | 2.91 | 2.02 |
| rs474530 | DLG2 Intron1 (NM_001364.1) | 11 | 83,930,298 | 3.02 | 0.95 | 0.91 | 2.00 | 2.56 | ND | ND |
| rs493622 | CHORDC1 −286443 bp (NM_012124.1) | 11 | 89,882,297 | 3.04 | 0.82 | 0.75 | 1.54 | 2.45 | 2.76 | 1.89 |
| rs610160 | GRIA4 Intron3 (NM_000829.1) | 11 | 105,220,105 | 3.06 | 0.20 | 0.14 | 1.64 | 2.25 | 3.19 | 1.42 |
| rs10844107 | BICD1 −37784 bp (NM_001714.1) | 12 | 32,113,668 | 0.28 | 0.24 | 0.23 | 1.08 | 3.48 | 5.00 | 0.75 |
| rs10862853 | LOC387871 +436103 bp (XM_373539) | 12 | 83,274,707 | 1.19 | 0.82 | 0.78 | 1.28 | 3.34 | 3.97 | 4.53 |
| rs979879 | SLC6A15 +353475 bp (NM_182767.2), SLC6A15 +375211 bp (NM_018057.3) | 12 | 83,403,423 | 1.63 | 0.83 | 0.78 | 1.36 | 3.33 | 4.41 | 4.61 |
| rs11116400 | SLC6A15 +425437 bp (NM_182767.2), SLC6A15 +447173 bp (NM_018057.3) | 12 | 83,331,461 | 1.53 | 0.83 | 0.78 | 1.34 | 3.33 | 4.38 | 4.65 |
| rs2611284 | SLC6A15 +335334 bp (NM_182767.2), SLC6A15 +357070 bp (NM_018057.3) | 12 | 83,421,564 | 1.66 | 0.83 | 0.78 | 1.36 | 3.31 | 4.41 | 4.57 |

TABLE 19

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs10746324 | SLC6A15 +349318 bp (NM_182767.2), SLC6A15 +371054 bp (NM_018057.3) | 12 | 83,407,580 | 1.61 | 0.83 | 0.78 | 1.36 | 3.29 | 4.38 | 4.57 |
| rs11056970 | LMO3 +34143 bp (NM_018640.3), LMO3 +34143 bp (NM_001001395.1) | 12 | 16,558,431 | 3.21 | 0.86 | 0.79 | 1.63 | 3.27 | 3.21 | 3.17 |
| rs4766663 | OAS1 +7223 bp (NM_002534.1), OAS1 +5266 bp (NM_016816.1) | 12 | 111,825,694 | 3.28 | 0.20 | 0.13 | 1.68 | 3.12 | 12.40 | 1.52 |
| rs7134411 | FLJ25056 +34943 bp (NM_182530.1) | 12 | 68,673,713 | 0.33 | 0.51 | 0.49 | 1.08 | 3.12 | 1.17 | 0.61 |
| rs1382851 | FLJ36004 −92384 bp (NM_152590.1) | 12 | 25,689,829 | 2.11 | 0.58 | 0.51 | 1.33 | 3.10 | 1.86 | 2.07 |
| rs7295295 | LOC387871 +418915 bp (XM_373539) | 12 | 83,257,519 | 1.84 | 0.82 | 0.76 | 1.38 | 3.09 | 4.09 | 4.00 |
| rs1380405 | SLC6A15 +351862 bp (NM_182767.2), SLC6A15 +373598 bp (NM_018057.3) | 12 | 83,405,036 | 1.56 | 0.83 | 0.79 | 1.35 | 3.08 | 4.25 | 4.38 |
| rs11116414 | SLC6A15 +389377 bp (NM_182767.2), SLC6A15 +411113 bp (NM_018057.3) | 12 | 83,367,521 | 1.46 | 0.83 | 0.79 | 1.33 | 3.07 | 4.21 | 4.42 |
| rs2468302 | SLC6A15 +354456 bp (NM_182767.2), SLC6A15 +376192 bp (NM_018057.3) | 12 | 83,402,442 | 1.46 | 0.83 | 0.79 | 1.33 | 3.07 | 4.21 | 4.42 |
| rs2555255 | LOC144742 +11128 bp (XM_378388) | 12 | 118,173,222 | 0.08 | 0.25 | 0.24 | 1.03 | 3.04 | 3.04 | 0.72 |
| rs2072133 | OAS3 Exon16 (NM_006187.2) | 12 | 111,871,980 | 3.71 | 0.68 | 0.59 | 1.51 | 3.03 | 2.27 | 1.46 |
| rs1647106 | THRAP2 +168009 bp (NM_015335.2) | 12 | 114,691,094 | 3.67 | 0.33 | 0.24 | 1.56 | 3.02 | 2.29 | 1.63 |
| rs10779090 | LOC387871 +423693 bp (XM_373539) | 12 | 83,262,297 | 1.14 | 0.82 | 0.78 | 1.27 | 3.01 | 3.58 | 4.04 |
| rs2125093 | KLRA1 +10392 bp (NM_006611.1) | 12 | 10,622,647 | 3.52 | 0.77 | 0.68 | 1.54 | 2.92 | 2.11 | 1.27 |
| rs900610 | MGC50559 Intron2 (NM_173802.2) | 12 | 31,707,890 | 3.14 | 0.16 | 0.10 | 1.75 | 2.91 | 1.47 | 1.98 |
| rs10772350 | STYK1 −7029 bp (NM_018423.1) | 12 | 10,724,935 | 3.08 | 0.71 | 0.62 | 1.47 | 2.83 | 1.91 | 1.11 |
| rs4767030 | OAS1 +3826 bp (NM_002534.1), OAS1 +1869 bp (NM_016816.1) | 12 | 111,822,297 | 3.40 | 0.21 | 0.14 | 1.68 | 2.81 | 3.49 | 1.66 |
| rs1647110 | THRAP2 +163373 bp (NM_015335.2) | 12 | 114,695,730 | 3.37 | 0.29 | 0.21 | 1.56 | 2.76 | 2.29 | 1.62 |

TABLE 20

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs1859336 | OAS3 −8940 bp (NM_006187.2) | 12 | 111,830,029 | 3.06 | 0.21 | 0.14 | 1.63 | 2.58 | 4.24 | 1.57 |
| rs1700369 | LOC441646 Intron8 (XM_497358) | 12 | 126,367,113 | 3.00 | 0.95 | 0.90 | 1.97 | 2.55 | 1.54 | 0.71 |
| rs7134391 | OAS1 +10940 bp (NM_002534.1), OAS1 +8983 bp (NM_016816.1) | 12 | 111,829,411 | 3.09 | 0.20 | 0.14 | 1.63 | 2.50 | 3.57 | 1.57 |
| rs2270152 | VWF Intron49 (NM_000552.2) | 12 | 5,931,330 | 3.16 | 0.86 | 0.80 | 1.62 | 2.48 | 2.47 | 1.50 |
| rs4767040 | OAS3 −2232 bp (NM_006187.2) | 12 | 111,836,737 | 3.07 | 0.20 | 0.14 | 1.63 | 2.48 | 3.56 | 1.56 |
| rs10774679 | OAS3 −1501 bp (NM_006187.2) | 12 | 111,837,468 | 3.06 | 0.20 | 0.14 | 1.63 | 2.47 | 3.58 | 1.56 |
| rs11104300 | HGNT-IV-H −287319 bp (NM_013244.2) | 12 | 86,022,432 | 3.05 | 0.21 | 0.15 | 1.61 | 2.44 | 3.37 | 1.52 |
| rs10735079 | OAS3 Intron2 (NM_006187.2) | 12 | 111,842,728 | 3.03 | 0.20 | 0.14 | 1.62 | 2.44 | 3.56 | 1.55 |
| rs7961953 | DKFZp762A217 Intron1 (NM_152588.1) | 12 | 81,594,304 | 3.02 | 0.34 | 0.26 | 1.48 | 2.43 | 2.28 | 1.48 |
| rs261912 | ETNK1 Intron6 (NM_018638.3) | 12 | 22,728,208 | 3.01 | 0.85 | 0.78 | 1.58 | 2.43 | 3.04 | 2.02 |
| rs4145280 | G30 +266246 bp (XM_498445) | 13 | 104,643,155 | 0.25 | 0.51 | 0.50 | 1.06 | 3.95 | 1.12 | 0.55 |
| rs4772238 | CLYBL −20285 bp (NM_206808.1), CLYBL −20285 bp (NM_138280.3) | 13 | 99,202,794 | 0.14 | 0.12 | 0.11 | 1.06 | 3.78 | 0.00 | 1.53 |
| rs9519091 | SLC10A2 −518655 bp (NM_000452.1) | 13 | 103,035,852 | 1.56 | 0.49 | 0.43 | 1.27 | 3.58 | 1.48 | 2.06 |
| rs3916959 | G30 +269026 bp (XM_498445) | 13 | 104,640,379 | 0.25 | 0.51 | 0.50 | 1.06 | 3.58 | 1.12 | 0.57 |
| rs9558509 | G30 +271368 bp (XM_498445) | 13 | 104,638,037 | 0.27 | 0.51 | 0.50 | 1.07 | 3.47 | 1.13 | 0.58 |
| rs9300981 | G30 +469126 bp (XM_498445) | 13 | 104,440,279 | 3.79 | 0.63 | 0.53 | 1.52 | 3.14 | 2.32 | 1.75 |
| rs1606405 | SLITRK1 +664827 bp (NM_052910.1) | 13 | 82,684,518 | 1.37 | 0.55 | 0.50 | 1.24 | 3.10 | 1.47 | 0.74 |
| rs10492680 | LOC400123 −23647 bp (XM_378411) | 13 | 39,702,836 | 3.01 | 0.93 | 0.88 | 1.83 | 2.46 | 6.22 | 3.50 |
| rs7150435 | ALKBH +19861 bp (NM_006020.1) | 14 | 77,189,287 | 0.00 | 0.53 | 0.53 | 1.00 | 3.42 | 1.09 | 1.92 |
| rs759363 | CHES1 Intron3 (NM_005197.1) | 14 | 88,828,894 | 3.89 | 0.32 | 0.23 | 1.59 | 3.29 | 2.36 | 1.69 |
| rs11159897 | CHES1 Intron3 (NM_005197.1) | 14 | 88,829,194 | 3.89 | 0.32 | 0.23 | 1.59 | 3.29 | 2.36 | 1.69 |
| rs4902116 | LOC401778 +110022 bp (XM_377343) | 14 | 61,774,890 | 2.61 | 0.57 | 0.49 | 1.38 | 3.12 | 1.93 | 1.98 |
| rs2241127 | CHES1 Intron2 (NM_005197.1) | 14 | 88,892,969 | 1.47 | 0.31 | 0.26 | 1.29 | 3.11 | 0.99 | 1.80 |

TABLE 21

| dbSNP ID | Exon, Intron | Chromo-some | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homo-zygote) (Formula 4) | Odds Ratio (Hetero-zygote) (Formula 5) |
|---|---|---|---|---|---|---|---|---|---|---|
| rs10148022 | LOC283584 −265499 bp (XM_211108) | 14 | 85,864,556 | 0.85 | 0.32 | 0.29 | 1.19 | 3.07 | 0.84 | 1.72 |
| rs1571379 | SEL1L −289804 bp (NM_005065.3) | 14 | 81,359,690 | 3.60 | 0.73 | 0.63 | 1.53 | 3.03 | 2.22 | 1.36 |
| rs11622536 | KCNK10 −72402 bp (NM_138318.1), KCNK10 −20310 bp (NM_138317.1), KCNK10 −16406 bp (NM_021161.3) | 14 | 87,879,410 | 0.64 | 0.77 | 0.75 | 1.16 | 3.00 | 0.64 | 0.38 |
| rs2816632 | BRF1 Intron2 (NM_001519.2), BRF1 −27133 bp (NM_145685.1), BRF1 −26587 bp (NM_145696.1) | 14 | 104,812,400 | 3.27 | 0.21 | 0.14 | 1.64 | 2.78 | 4.49 | 1.36 |
| rs1106845 | STELLAR +19768 bp (XM_375075) | 14 | 35,931,107 | 3.26 | 0.11 | 0.06 | 2.06 | 2.71 | ND | 1.98 |
| rs17115925 | SEL1L −271331 bp (NM_005065.3) | 14 | 81,341,217 | 3.00 | 0.72 | 0.64 | 1.46 | 2.39 | 2.22 | 1.56 |
| rs7176242 | ATP10A +44699 bp (NM_024490.2) | 15 | 23,428,814 | 0.19 | 0.85 | 0.85 | 1.07 | 3.26 | 0.09 | 0.06 |
| rs16969520 | CIB2 Intron1 (NM_006383.2) | 15 | 76,204,239 | 2.36 | 0.35 | 0.28 | 1.39 | 3.19 | 1.38 | 1.86 |
| rs10902569 | ADAMTS17 Intron3 (NM_139057.1) | 15 | 98,663,829 | 0.08 | 0.67 | 0.67 | 1.03 | 3.10 | 0.64 | 0.41 |
| rs11071129 | UNC13C +173927 bp (XM_496070) | 15 | 52,882,022 | 0.20 | 0.59 | 0.58 | 1.05 | 3.08 | 1.37 | 2.11 |
| rs1441354 | FLJ13710 −290691 bp (NM_024817.1) | 15 | 69,517,251 | 0.22 | 0.25 | 0.24 | 1.07 | 3.07 | 5.71 | 0.78 |
| rs11631211 | ATP10A +61309 bp (NM_024490.2) | 15 | 23,412,204 | 0.22 | 0.86 | 0.85 | 1.08 | 3.06 | 0.10 | 0.07 |
| rs12592527 | UNC13C +174082 bp (XM_496070) | 15 | 52,882,177 | 0.27 | 0.60 | 0.58 | 1.07 | 3.05 | 1.42 | 2.13 |
| rs4144951 | FLJ38736 Intron17 (NM_182758.1) | 15 | 51,643,802 | 3.40 | 0.16 | 0.09 | 1.82 | 2.73 | 2.80 | 1.87 |
| rs2654216 | EFTUD1 +28186 bp (NM_024580.3) | 15 | 80,181,440 | 3.18 | 0.60 | 0.51 | 1.44 | 2.57 | 2.14 | 1.54 |
| rs8026133 | SLCO3A1 −26936 bp (NM_013272.2) | 15 | 90,171,014 | 3.10 | 0.16 | 0.10 | 1.74 | 2.48 | 4.60 | 1.66 |
| rs4780091 | LOC440268 +506 bp (XM_496063) | 15 | 31,271,629 | 3.26 | 0.63 | 0.54 | 1.46 | 2.46 | 2.02 | 1.37 |
| rs17191316 | ANXA2 +144537 bp (NM_004039.1) | 15 | 58,282,291 | 3.23 | 0.07 | 0.03 | 2.61 | 2.37 | ND | 2.22 |
| rs12597526 | USP10 +4263 bp (NM_005153.1) | 16 | 83,374,937 | 1.28 | 0.38 | 0.33 | 1.24 | 3.91 | 2.51 | 0.81 |
| rs2133803 | LOC149329 −13263 bp (XM_086494) | 16 | 59,665,671 | 1.32 | 0.81 | 0.76 | 1.30 | 3.52 | 4.13 | 4.60 |
| rs288601 | CDH8 −492870 bp (NM_001796.2) | 16 | 61,120,407 | 1.81 | 0.53 | 0.47 | 1.30 | 3.35 | 1.61 | 0.77 |
| rs1819829 | FLJ31547 Intron9 (NM_145024.1) | 16 | 54,444,785 | 2.53 | 0.79 | 0.73 | 1.46 | 3.32 | 4.58 | 3.80 |

TABLE 22

| dbSNP ID | Exon, Intron | Chromo-some | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homo-zygote) (Formula 4) | Odds Ratio (Hetero-zygote) (Formula 5) |
|---|---|---|---|---|---|---|---|---|---|---|
| rs2541639 | HBZ +531 bp (NM_005332.2) | 16 | 145,034 | 2.77 | 0.22 | 0.16 | 1.55 | 3.13 | 1.23 | 1.90 |
| rs372657 | LOC283867 −312819 bp (XM_378606) | 16 | 64,480,523 | 3.63 | 0.24 | 0.16 | 1.65 | 2.84 | 3.03 | 1.56 |
| rs173840 | LOC283867 −313113 bp (XM_378606) | 16 | 64,480,817 | 3.63 | 0.24 | 0.16 | 1.65 | 2.84 | 3.03 | 1.56 |
| rs4843428 | FOXL1 +137429 bp (NM_005250.1) | 16 | 85,308,297 | 3.20 | 0.88 | 0.81 | 1.66 | 2.75 | 1.89 | 1.05 |
| rs254353 | LOC283867 −301507 bp (XM_378606) | 16 | 64,469,211 | 3.33 | 0.19 | 0.12 | 1.71 | 2.71 | 4.73 | 1.57 |
| rs4077853 | PLCG2 Intron27 (NM_002661.1) | 16 | 80,528,471 | 3.16 | 0.35 | 0.27 | 1.49 | 2.62 | 2.17 | 1.57 |
| rs3859079 | CDH13 −112144 bp (NM_001257.2) | 16 | 81,105,935 | 3.17 | 0.66 | 0.58 | 1.46 | 2.51 | 2.17 | 1.60 |
| rs8062968 | LOC283867 −298359 bp (XM_378606) | 16 | 64,466,063 | 3.05 | 0.24 | 0.17 | 1.57 | 2.49 | 1.99 | 1.68 |
| rs11074523 | HS3ST2 Intron1 (NM_006043.1) | 16 | 22,734,434 | 3.11 | 0.80 | 0.73 | 1.53 | 2.48 | 2.40 | 1.56 |
| rs8045067 | WWOX −1063753 bp (NM_130844.1), WWOX −1063753 bp (NM_130791.1), WWOX −1063753 bp (NM_016373.1), WWOX −1063753 bp (NM_018560.4), WWOX −48197 bp (NM_130792.1) | 16 | 77,754,805 | 3.35 | 0.75 | 0.67 | 1.52 | 2.43 | 2.17 | 1.49 |
| rs12443833 | WWOX −1063238 bp (NM_130844.1), WWOX −1063238 bp (NM_130791.1), WWOX −1063238 bp (NM_016373.1), WWOX −1063238 bp (NM_018560.4), WWOX −48712 bp (NM_130792.1) | 16 | 77,754,290 | 3.17 | 0.72 | 0.63 | 1.48 | 2.38 | 2.11 | 1.45 |
| rs1877821 | RGS9 −9409 bp (NM_003835.1) | 17 | 60,605,878 | 1.17 | 0.75 | 0.71 | 1.25 | 3.80 | 3.21 | 3.78 |
| rs9896245 | RGS9 −11066 bp (NM_003835.1) | 17 | 60,604,218 | 1.45 | 0.75 | 0.70 | 1.29 | 3.65 | 3.30 | 3.62 |
| rs1029754 | LOC401887 +487202 bp (XM_497555) | 17 | 66,236,699 | 2.11 | 0.89 | 0.84 | 1.51 | 3.62 | 0.23 | 0.12 |
| rs17808998 | NTN1 Intron2 (NM_004822.1) | 17 | 8,919,207 | 2.23 | 0.63 | 0.56 | 1.35 | 3.30 | 1.57 | 0.81 |
| rs9895463 | SPACA3 −6355 bp (NM_173847.2) | 17 | 28,336,640 | 0.01 | 0.58 | 0.58 | 1.00 | 3.23 | 1.23 | 2.04 |
| rs11868422 | RPH3AL Intron1 (NM_006987.2) | 17 | 198,072 | 3.62 | 0.21 | 0.14 | 1.71 | 3.05 | 2.06 | 1.85 |
| rs1877823 | RGS9 +3136 bp (NM_003835.1) | 17 | 60,657,405 | 1.20 | 0.77 | 0.73 | 1.26 | 3.03 | 3.22 | 3.52 |

TABLE 23

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs8065080 | TRPV1 Exon11 (NM_080706.1), TRPV1 Exon12 (NM_080705.1), TRPV1 Exon12 (NM_018727.3), TRPV1 Exon13 (NM_080704.1) | 17 | 3,427,196 | 3.67 | 0.69 | 0.60 | 1.51 | 2.88 | 2.25 | 1.51 |
| rs8082149 | LOC342600 Intron2 (XM_292624) | 17 | 51,927,894 | 3.52 | 0.92 | 0.86 | 1.85 | 2.66 | 3.49 | 1.99 |
| rs2269459 | POLR2A Intron22 (NM_000937.2) | 17 | 7,353,762 | 3.11 | 0.79 | 0.72 | 1.52 | 2.51 | 2.46 | 1.63 |
| rs2072255 | KIAA0672 Intron10 (XM_375408) | 17 | 12,793,117 | 3.09 | 0.21 | 0.14 | 1.63 | 2.43 | 3.35 | 1.53 |
| rs9788983 | RPH3AL Intron6 (NM_006987.2) | 17 | 129,457 | 3.05 | 0.89 | 0.82 | 1.65 | 2.40 | 3.21 | 2.00 |
| rs1879610 | LOC441825 +255198 bp (XM_497596) | 18 | 73,469,750 | 1.98 | 0.95 | 0.91 | 1.72 | 3.48 | 0.26 | 0.11 |
| rs11876045 | LOC441816 −222690 bp (XM_497584) | 18 | 20,564,102 | 3.73 | 0.28 | 0.20 | 1.61 | 3.41 | 1.79 | 1.88 |
| rs17070861 | BCL2 Intron1 (NM_000633.1), BCL2 +78655 bp (NM_000657.1) | 18 | 59,057,460 | 0.72 | 0.94 | 0.93 | 1.33 | 3.34 | ND | ND |
| rs1790870 | CYB5 +163 bp (NM_001914.1), CYB5 +163 bp (NM_148923.1) | 18 | 70,071,349 | 3.86 | 0.86 | 0.78 | 1.70 | 3.30 | 1.99 | 1.06 |
| rs1790858 | CYB5 Intron3 (NM_001914.1), CYB5 Intron3 (NM_148923.1) | 18 | 70,075,799 | 3.74 | 0.86 | 0.78 | 1.68 | 3.18 | 1.99 | 1.08 |
| rs17187933 | LOC441816 −214621 bp (XM_497584) | 18 | 20,556,033 | 3.55 | 0.26 | 0.18 | 1.62 | 3.11 | 1.86 | 1.81 |
| rs17088997 | CYB5 +3361 bp (NM_001914.1), CYB5 +3361 bp (NM_148923.1) | 18 | 70,068,151 | 3.62 | 0.86 | 0.78 | 1.67 | 3.07 | 1.95 | 1.06 |
| rs1372481 | LOC390856 Intron1 (XM_497590) | 18 | 49,466,756 | 3.51 | 0.96 | 0.92 | 2.35 | 3.07 | 1.52 | 0.58 |
| rs10468763 | CLUL1 Intron5 (NM_014410.4), CLUL1 Intron5 (NM_199167.1) | 18 | 622,239 | 0.40 | 0.22 | 0.21 | 1.12 | 3.06 | 0.50 | 1.61 |
| rs3862680 | DCC Intron1 (NM_005215.1) | 18 | 48,184,338 | 3.65 | 0.60 | 0.50 | 1.49 | 2.97 | 2.24 | 1.56 |
| rs3910695 | LOC390856 Intron1 (XM_497590) | 18 | 49,464,638 | 3.35 | 0.96 | 0.92 | 2.28 | 2.90 | 1.53 | 0.60 |
| rs3862681 | DCC Intron1 (NM_005215.1) | 18 | 48,184,688 | 3.53 | 0.60 | 0.50 | 1.48 | 2.84 | 2.19 | 1.54 |
| rs7238490 | METTL4 +571947 bp (NM_022840.2) | 18 | 1,955,583 | 3.40 | 0.71 | 0.62 | 1.49 | 2.72 | 2.04 | 1.27 |
| rs9951036 | LOC390856 Intron1 (XM_497590) | 18 | 49,515,735 | 3.18 | 0.96 | 0.92 | 2.23 | 2.72 | 1.52 | 0.62 |

TABLE 24

| dbSNP ID | Exon, Intron | Chromosome | Physical Location | Critical rate, Allele (−logP) | High-Risk Allele Frequency in Glaucoma Patient Group | High-Risk Allele Frequency in Non-Patient Group | Odds Ratio (Formula 3) | Critical rate, Genotype (−logP) | Odds Ratio (Homozygote) (Formula 4) | Odds Ratio (Heterozygote) (Formula 5) |
|---|---|---|---|---|---|---|---|---|---|---|
| rs339858 | LOC441816 −124776 bp (XM_497584) | 18 | 20,466,188 | 3.14 | 0.16 | 0.10 | 1.75 | 2.70 | 1.95 | 1.90 |
| rs11151937 | CYB5 +4859 bp (NM_001914.1), CYB5 +4859 bp (NM_148923.1) | 18 | 70,066,653 | 3.06 | 0.53 | 0.44 | 1.43 | 2.68 | 2.01 | 1.68 |
| rs8094863 | LOC390855 Intron3 (XM_497589) | 18 | 47,458,218 | 3.17 | 0.50 | 0.41 | 1.44 | 2.55 | 2.12 | 1.32 |
| rs17260163 | LOC441816 −250775 bp (XM_497584) | 18 | 20,592,187 | 3.13 | 0.29 | 0.21 | 1.53 | 2.54 | 2.21 | 1.59 |
| rs8086430 | LOC147468 +250079 bp (XM_091809) | 18 | 20,600,317 | 3.10 | 0.29 | 0.21 | 1.52 | 2.51 | 2.20 | 1.58 |
| rs16940484 | C18orf17 Intron6 (NM_153211.1) | 18 | 19,936,298 | 3.09 | 0.34 | 0.26 | 1.49 | 2.51 | 2.02 | 1.58 |
| rs7229080 | LOC390856 Intron1 (XM_497590) | 18 | 49,503,583 | 3.19 | 0.97 | 0.93 | 2.28 | 2.49 | 3.03 | 1.30 |
| rs10502927 | LOC390855 Intron3 (XM_497589) | 18 | 47,502,071 | 3.01 | 0.49 | 0.41 | 1.43 | 2.45 | 2.09 | 1.27 |
| rs17660384 | ZNF175 −10715 bp (NM_007147.2) | 19 | 56,755,628 | 3.53 | 0.21 | 0.14 | 1.69 | 3.02 | 5.12 | 1.57 |
| rs2864107 | ZNF175 −5504 bp (NM_007147.2) | 19 | 56,760,839 | 3.40 | 0.21 | 0.14 | 1.68 | 2.90 | 4.82 | 1.58 |
| rs1433083 | FLJ12644 Exon5 (NM_023074.2) | 19 | 57,085,796 | 3.14 | 0.95 | 0.91 | 2.07 | 2.66 | ND | ND |
| rs6097745 | BCAS1 Intron3 (NM_003657.1) | 20 | 52,101,533 | 1.67 | 0.29 | 0.24 | 1.33 | 3.56 | 1.00 | 1.92 |
| rs2870304 | BCAS1 Intron3 (NM_003657.1) | 20 | 52,106,624 | 1.74 | 0.30 | 0.25 | 1.33 | 3.49 | 1.06 | 1.91 |
| rs8123014 | C20orf23 +571310 bp (XM_024704.3) | 20 | 15,629,440 | 2.16 | 0.75 | 0.68 | 1.38 | 3.20 | 1.23 | 0.66 |
| rs6115865 | C20orf194 −37687 bp (XM_045421) | 20 | 3,307,303 | 3.63 | 0.38 | 0.29 | 1.52 | 2.87 | 2.29 | 1.52 |
| rs7268851 | C20orf17 Intron2 (NM_173485.2) | 20 | 51,501,200 | 3.45 | 0.73 | 0.65 | 1.51 | 2.86 | 2.08 | 1.27 |
| rs6134494 | LOC440753 +240718 bp (XM_498845) | 20 | 12,196,345 | 3.12 | 0.22 | 0.15 | 1.61 | 2.86 | 1.59 | 1.86 |
| rs3817879 | PLCB1 Intron3 (NM_015192.2), PLCB1 Intron3 (NM_182734.1) | 20 | 8,470,921 | 3.17 | 0.80 | 0.72 | 1.54 | 2.52 | 2.65 | 1.89 |
| rs2743246 | MATN4 Intron5 (NM_003833.2), MATN4 Intron4 (NM_030590.1), MATN4 Intron3 (NM_030592.1) | 20 | 43,362,112 | 3.10 | 0.88 | 0.81 | 1.64 | 2.43 | 2.97 | 1.85 |
| rs6014430 | KIAA1755 Intron2 (XM_028810) | 20 | 36,305,948 | 3.05 | 0.11 | 0.06 | 1.94 | 2.03 | 3.66 | 1.69 |
| rs2154450 | RUNX1 Intron5 (NM_001754.2) | 21 | 35,141,436 | 0.85 | 0.44 | 0.40 | 1.18 | 3.94 | 1.14 | 2.01 |
| rs4817695 | RUNX1 Intron5 (NM_001754.2) | 21 | 35,141,187 | 0.66 | 0.44 | 0.41 | 1.14 | 3.69 | 1.10 | 1.94 |
| rs2825423 | LOC388817 +373452 bp (XM_371409) | 21 | 19,526,124 | 3.31 | 0.26 | 0.19 | 1.58 | 2.64 | 3.09 | 1.38 |

TABLE 25

| dbSNP ID | Exon, Intron | Chromosome | Physical Location | Critical rate, Allele (-logP) | High-Risk Allele Frequency in Glaucoma Patient Group | High-Risk Allele Frequency in Non-Patient Group | Odds Ratio (Formula 3) | Critical rate, Genotype (-logP) | Odds Ratio (Homozygote) (Formula 4) | Odds Ratio (Heterozygote) (Formula 5) |
|---|---|---|---|---|---|---|---|---|---|---|
| rs4823324 | E46L Intron10 (NM_013236.1) | 22 | 44,558,660 | 3.69 | 0.51 | 0.41 | 1.49 | 3.04 | 2.26 | 1.32 |
| rs2857648 | NF2 Intron10 (NM_181825.1), NF2 Intron8 (NM_181831.1), NF2 Intron10 (NM_000268.2), NF2 Intron10 (NM_016418.4), NF2 Intron11 (NM_181826.1), NF2 Intron10 (NM_181827.1), NF2 Intron9 (NM_181828.1), NF2 Intron9 (NM_181829.1), NF2 Intron8 (NM_181830.1), NF2 Intron10 (NM_181832.1), NF2 Intron4 (NM_181833.1), NF2 Intron5 (NM_181834.1), NF2 Intron8 (NM 181835.1) | 22 | 28,391,122 | 3.02 | 0.73 | 0.65 | 1.46 | 2.79 | 1.67 | 0.95 |
| rs6006787 | FBLN1 +65094 bp (NM_006487.2), FBLN1 +60443 bp (NM_001996.2), FBLN1 +58104 bp (NM_006485.2), FBLN1 +22671 bp (NM_006486.2) | 22 | 44,340,222 | 3.31 | 0.50 | 0.40 | 1.46 | 2.72 | 2.22 | 1.38 |
| rs572159 | LOC284898 -273642 bp (XM_379044) | 22 | 26,054,663 | 3.11 | 0.94 | 0.89 | 1.92 | 2.48 | 4.67 | 2.44 |
| rs467812 | C22orf19 Intron2 (NM_003678.3) | 22 | 28,265,503 | 3.22 | 0.27 | 0.19 | 1.56 | 2.48 | 2.23 | 1.57 |
| rs5765558 | E46L -24767 bp (NM_013236.1) | 22 | 44,363,516 | 3.05 | 0.58 | 0.49 | 1.43 | 2.34 | 2.01 | 1.37 |
| rs6006179 | C22orf19 Intron19 (NM_003678.3) | 22 | 28,231,255 | 3.03 | 0.27 | 0.20 | 1.53 | 2.33 | 2.19 | 1.55 |

Tables 5 to 25 list dbSNP ID number or Affimetrix Array ID number for specifying known single nucleotide polymorphisms obtained, the exon, intron information (in a case where a single nucleotide polymorphism exists on a gene, the gene name and the exon or intron in which SNP exists are shown, and in a case where a single nucleotide polymorphism does not exist on a gene, neighboring genes and a distance between the gene and the single nucleotide polymorphism are shown), the chromosome number at which the single nucleotide polymorphism exists, the physical location of the single nucleotide polymorphism, the p-value for an allele according to a chi-square test (-log P), the high-risk allele frequencies in the glaucoma patient group and the non-patient group, the odds ratio for an allele, the p-value for a genotype according to a chi-square test (-log P), the odds ratio for a genotype of a homozygote, and the odds ratio for a genotype of a heterozygote. Here, in the tables, a portion of which odds ratio is indicated as ND shows a case where any one of the number of detection in the denominator is 0, so that the odds ratio could not be calculated.

According to the above studies, 413 single nucleotide polymorphisms of which alleles or genotypes were associated with glaucoma at a p-value of $1 \times 10^{-3}$ or less were found.

When the allele or genotype frequencies listed in Tables 5 to 25 were compared between the non-patients without having family history and the glaucoma patients, a statistical difference was found. By determining an allele of any one of these single nucleotide polymorphisms, whether or not an allele that is identified in a higher frequency in the glaucoma patient group than that of the non-patient group exists in the sample can be determined.

Example 4

Comparison of Single Nucleotide Polymorphisms Between Progressive Glaucoma Cases and Nonprogressive Glaucoma Cases The comparison on single nucleotide polymorphisms was made for progressive glaucoma cases and nonprogressive glaucoma cases in the same manner as in Example 3.

Concretely, blood donated under the consent on free will of the participants after having sufficiently explained the contents of studies from 210 cases of patients with progressive visual loss within a given time period, despite the treatments for lowering an intraocular pressure such as a drug for lowering an intraocular pressure or a surgical operation (progressive glaucoma cases), and 175 cases of patients without the progression (nonprogressive glaucoma cases), among the primary open-angle glaucoma patients and the normal tension glaucoma patients diagnosed on the basis of Guidelines offered by Japan Glaucoma Society, was used as a specimen, and alleles frequencies and genotypes frequencies between the groups were also compared by performing the analysis in the same manner as in Example 3. Alleles frequencies and genotype frequencies were statistically compared according to the chi-square test in the same manner. Single nucleotide polymorphisms of which alleles or genotypes show association with the progression of glaucoma at a p-value of $1 \times 10^{-4}$ or less, i.e. -log P of 4 or more are listed in Tables 26 to 28. Here, the odds ratio for association of an allele with the progression of glaucoma, and the odds ratio for association of a genotype with the progression of glaucoma in each of the tables, respectively were calculated on the basis of the following formulas (6) to (8).

Odds Ratio for Allele=[(Number of Detection of an Allele Identified in High Frequency in Progressive Glaucoma Group, in Progressive Glaucoma Group)/(Number of Detection of an Allele Opposite to the Allele Identified in High Frequency in Progressive Glaucoma Group, in Progressive Glaucoma Group)]/[(Number of Detection of the Allele Identified in High Frequency in Progressive Glaucoma Group, in Nonprogressive Glaucoma Group)/(Number of Detection of the Allele Opposite to the Allele Identified in High Frequency in Progressive Glaucoma Group, in Nonprogressive Glaucoma Group)]   formula (6)

Odds Ratio for Genotype of Homozygote=[(Number of Detection of a Genotype Having Homozygote of an Allele Identified in High Frequency in Progressive Glaucoma Group, in Progressive Glaucoma Group)/(Number of Detection of a Genotype Having Homozygote of an Allele Identified in High Frequency in Nonprogressive Glaucoma Group, in Progressive Glaucoma Group)]/[(Number of Detection of the Genotype Having Homozygote of the Allele Identified in High Frequency in Progressive Glaucoma Group, in Nonprogressive Glaucoma Group)/(Number of Detection of the Genotype Having Homozygote of the Allele Identified in High Frequency in Nonprogressive Glaucoma Group, in Nonprogressive Glaucoma Group)]     formula (7)

Odds Ratio for Genotype of Heterozygote=[(Number of Detection of a Genotype of Heterozygote in Progressive Glaucoma Group)/(Number of Detection of a Genotype Having Homozygote of an Allele Identified in High Frequency in Nonprogressive Glaucoma Group, in Progressive Glaucoma Group)]/[(Number of Detection of the Genotype of Heterozygote in Nonprogressive Glaucoma Group)/(Number of Detection of the Genotype Having Homozygote of the Allele Identified in High Frequency in Nonprogressive Glaucoma Group, in Nonprogressive Glaucoma Group)]     formula (8)

TABLE 26

| dbSNP ID | Allele1/Allele2 | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|---|
| rs11211059 | A/G | EIF2B3 Intron4 (NM_020365.1) | 1 | 45,099,311 | 0.28 | 0.77 | 0.75 |
| rs4927088 | C/T | SSBP3 Intron4 (NM_145716.1), SSBP3 Intron4 (NM_018070.2) | 1 | 54,487,224 | 1.10 | 0.60 | 0.54 |
| rs10172264 | G/T | LOC402072 +152420 bp (XM_377741) | 2 | 53,313,788 | 4.32 | 0.20 | 0.09 |
| rs10460373 | G/T | UBE2E3 −372131 bp (NM_182678.1), UBE2E3 −372361 bp (NM_006357.2) | 2 | 181,298,487. | 3.24 | 0.82 | 0.72 |
| rs1520855 | C/T | FLJ12519 −24239 bp (NM_032168.1) | 2 | 190,107,426 | 1.13 | 0.65 | 0.59 |
| rs1827101 | C/T | ITPR1 +2326 bp (NM_002222.1) | 3 | 4,866,407 | 1.36 | 0.75 | 0.69 |
| rs4635691 | C/G | ITPR1 +2783 bp (NM_002222.1) | 3 | 4,866,864 | 1.24 | 0.75 | 0.69 |
| rs9819062 | A/C | ITPR1 +14847 bp (NM_002222.1) | 3 | 4,878,928 | 1.41 | 0.75 | 0.68 |
| rs12638937 | G/T | ITPR1 +15316 bp (NM_002222.1) | 3 | 4,879,397 | 1.32 | 0.75 | 0.69 |
| rs3805345 | A/G | PAPSS1 Intron5 (NM_005443.4) | 4 | 108,943,706 | 3.56 | 0.65 | 0.52 |
| rs3805347 | C/T | PAPSS1 Intron5 (NM_005443.4) | 4 | 108,959,666 | 3.70 | 0.67 | 0.53 |
| rs17066530 | A/G | LOC285501 +636489 bp (XM_209640) | 4 | 179,923,545 | 4.60 | 0.92 | 0.81 |
| rs405806 | A/C | LOC441062 +175809 bp (XM_498994) | 5 | 18,167,512 | 4.03 | 0.55 | 0.41 |
| rs401889 | A/G | LOC441062 +175873 bp (XM_498994) | 5 | 18,167,576 | 4.60 | 0.53 | 0.38 |
| rs4308461 | A/C | SV2C −75087 bp (XM_043493) | 5 | 75,339,908 | 4.03 | 0.79 | 0.66 |
| rs2547455 | C/T | SV2C −33137 bp (XM_043493) | 5 | 75,381,858 | 4.40 | 0.80 | 0.67 |
| rs2042974 | C/G | LHFPL2 −11058 bp (NM_005779.1) | 5 | 77,852,925 | 1.24 | 0.86 | 0.81 |
| rs7719483 | A/C | LHFPL2 −19056 bp (NM_005779.1) | 5 | 77,860,923 | 0.88 | 0.86 | 0.82 |
| rs17215893 | C/T | LHFPL2 −20235 bp (NM_005779.1) | 5 | 77,862,102 | 0.85 | 0.86 | 0.82 |
| rs10045987 | C/T | LHFPL2 −31149 bp (NM_005779.1) | 5 | 77,873,016 | 0.88 | 0.86 | 0.82 |
| rs11949567 | A/G | LHFPL2 −35281 bp (NM_005779.1) | 5 | 77,877,148 | 0.88 | 0.86 | 0.82 |
| rs11950379 | A/G | LHFPL2 −35775 bp (NM_005779.1) | 5 | 77,877,642 | 0.79 | 0.85 | 0.82 |
| rs6860516 | A/G | LHFPL2 −35961 bp (NM_005779.1) | 5 | 77,877,828 | 0.88 | 0.86 | 0.82 |
| rs6881598 | A/G | LHFPL2 −37710 bp (NM_005779.1) | 5 | 77,879,577 | 0.88 | 0.86 | 0.82 |

| dbSNP ID | High Risk Allele | Odds Ratio (Formula 6) | Critical rate, Genotype (−logP) | Odds Ratio (Homozygote1) (Formula 7) | Odds Ratio (Heterozygote) (Formula 8) | Sequence Containing Allele 1 | Sequence Containing Allele 2 |
|---|---|---|---|---|---|---|---|
| rs11211059 | Allele 2 | 1.12 | 4.51 | 9.28 | 15.68 | SEQ ID No: 81 | SEQ ID No: 82 |
| rs4927088 | Allele 1 | 1.29 | 4.56 | 2.12 | 3.61 | SEQ ID No: 83 | SEQ ID No: 84 |
| rs10172264 | Allele 1 | 2.43 | 3.91 | 2.54 | 2.85 | SEQ ID No: 85 | SEQ ID No: 86 |
| rs10460373 | Allele 1 | 1.81 | 4.16 | 1.42 | 0.54 | SEQ ID No: 87 | SEQ ID No: 88 |
| rs1520855 | Allele 1 | 1.31 | 4.67 | 2.51 | 4.22 | SEQ ID No: 89 | SEQ ID No: 90 |
| rs1827101 | Allele 2 | 1.39 | 4.66 | 0.73 | 0.29 | SEQ ID No: 91 | SEQ ID No: 92 |
| rs4635691 | Allele 1 | 1.36 | 4.25 | 0.76 | 0.31 | SEQ ID No: 93 | SEQ ID No: 94 |
| rs9819062 | Allele 1 | 1.39 | 4.23 | 0.81 | 0.33 | SEQ ID No: 95 | SEQ ID No: 96 |
| rs12638937 | Allele 1 | 1.38 | 4.03 | 0.80 | 0.33 | SEQ ID No: 97 | SEQ ID No: 98 |
| rs3805345 | Allele 2 | 1.73 | 4.10 | 2.57 | 0.94 | SEQ ID No: 99 | SEQ ID No: 100 |
| rs3805347 | Allele 2 | 1.77 | 4.07 | 2.92 | 1.09 | SEQ ID No: 101 | SEQ ID No: 102 |
| rs17066530 | Allele 1 | 2.62 | 4.15 | 4.56 | 1.55 | SEQ ID No: 103 | SEQ ID No: 104 |
| rs405806 | Allele 2 | 1.77 | 3.38 | 2.95 | 2.11 | SEQ ID No: 105 | SEQ ID No: 106 |
| rs401889 | Allele 2 | 1.86 | 4.14 | 3.23 | 2.37 | SEQ ID No: 107 | SEQ ID No: 108 |
| rs4308461 | Allele 1 | 1.89 | 3.12 | 3.36 | 1.81 | SEQ ID No: 109 | SEQ ID No: 110 |
| rs2547455 | Allele 1 | 1.97 | 3.63 | 3.03 | 1.39 | SEQ ID No: 111 | SEQ ID No: 112 |
| rs2042974 | Allele 2 | 1.47 | 4.37 | ND | ND | SEQ ID No: 113 | SEQ ID No: 114 |
| rs7719483 | Allele 2 | 1.34 | 5.18 | ND | ND | SEQ ID No: 115 | SEQ ID No: 116 |
| rs17215893 | Allele 1 | 1.34 | 5.14 | ND | ND | SEQ ID No: 117 | SEQ ID No: 118 |
| rs10045987 | Allele 2 | 1.34 | 5.18 | ND | ND | SEQ ID No: 119 | SEQ ID No: 120 |
| rs11949567 | Allele 2 | 1.34 | 5.18 | ND | ND | SEQ ID No: 121 | SEQ ID No: 122 |
| rs11950379 | Allele 2 | 1.31 | 4.97 | ND | ND | SEQ ID No: 123 | SEQ ID No: 124 |
| rs6860516 | Allele 1 | 1.34 | 5.18 | ND | ND | SEQ ID No: 125 | SEQ ID No: 126 |
| rs6881598 | Allele 2 | 1.34 | 5.18 | ND | ND | SEQ ID No: 127 | SEQ ID No: 128 |

TABLE 27

| dbSNP ID | Allele1/Allele2 | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|---|
| rs6886783 | C/T | LHFPL2 −37765 bp (NM_005779.1) | 5 | 77,879,632 | 0.88 | 0.86 | 0.82 |
| rs6877525 | C/T | LHFPL2 −38871 bp (NM_005779.1) | 5 | 77,880,738 | 0.88 | 0.86 | 0.82 |
| rs12697888 | C/T | LHFPL2 −53535 bp (NM_005779.1) | 5 | 77,895,402 | 0.88 | 0.86 | 0.82 |
| rs1978629 | C/T | LHFPL2 −56045 bp (NM_005779.1) | 5 | 77,897,912 | 0.88 | 0.86 | 0.82 |
| rs10076149 | C/G | LHFPL2 −68743 bp (NM_005779.1) | 5 | 77,910,610 | 0.88 | 0.86 | 0.82 |
| rs730781 | C/T | LHFPL2 −84106 bp (NM_005779.1) | 5 | 77,925,973 | 0.85 | 0.86 | 0.82 |
| rs9461154 | C/T | LRRC16 −112934 bp (NM_017640.2) | 6 | 25,506,014 | 1.41 | 0.32 | 0.25 |
| rs13193932 | C/G | ARHGAP18 Intron1 (NM_033515.2) | 6 | 130,008,475 | 1.70 | 0.83 | 0.76 |
| rs17070863 | A/G | LOC441173 +172209 bp (XM_496827) | 6 | 141,772,290 | 4.46 | 0.55 | 0.40 |
| rs1877885 | C/G | LOC340268 Intron1 (XM_294634) | 7 | 9,625,295 | 4.29 | 0.60 | 0.45 |
| rs1913603 | A/C | LOC340268 Intron1 (XM_294634) | 7 | 9,664,816 | 4.03 | 0.64 | 0.49 |
| rs10230371 | A/G | HDAC9 Intron21 (NM_058176.1), HDAC9 Intron21 (NM_178423.1), HDAC9 Intron19 (NM_178425.1), HDAC9 +186432 bp (NM_014707.1), HDAC9 +19625 bp (NM_058177.1) | 7 | 18,668,137 | 1.05 | 0.41 | 0.35 |
| rs17152739 | A/G | LOC401384 +201741 bp (XM_379506) | 7 | 78,935,541 | 4.66 | 0.78 | 0.64 |
| rs4316157 | C/T | LOC340357 Intron3 (XM_499106) | 8 | 12,677,322 | 4.65 | 0.48 | 0.33 |
| rs10503907 | A/G | NRG1 −233743 bp (NM_013958.1), NRG1 −233775 bp (NM_013957.1), NRG1 −233799 bp (NM_004495.1), NRG1 −233842 bp (NM_013961.1), NRG1 −234103 bp (NM_013964.1), NRG1 −234127 bp (NM_013960.1), NRG1 −234143 bp (NM_013956.1), NRG1 −281336 bp (NM_013962.1), NRG1 −332731 bp (NM_013959.1) | 8 | 32,291,552 | 4.11 | 0.92 | 0.83 |

| dbSNP ID | High Risk Allele | Odds Ratio (Formula 6) | Critical rate, Genotype (−logP) | Odds Ratio (Homozygote1) (Formula 7) | Odds Ratio (Heterozygote) (Formula 8) | Sequence Containing Allele 1 | Sequence Containing Allele 2 |
|---|---|---|---|---|---|---|---|
| rs6886783 | Allele 1 | 1.34 | 5.18 | ND | ND | SEQ ID No: 129 | SEQ ID No: 130 |
| rs6877525 | Allele 2 | 1.34 | 5.18 | ND | ND | SEQ ID No: 131 | SEQ ID No: 132 |
| rs12697888 | Allele 1 | 1.34 | 5.18 | ND | ND | SEQ ID No: 133 | SEQ ID No: 134 |
| rs1978629 | Allele 2 | 1.34 | 5.18 | ND | ND | SEQ ID No: 135 | SEQ ID No: 136 |
| rs10076149 | Allele 2 | 1.34 | 5.18 | ND | ND | SEQ ID No: 137 | SEQ ID No: 138 |
| rs730781 | Allele 1 | 1.34 | 5.09 | ND | ND | SEQ ID No: 139 | SEQ ID No: 140 |
| rs9461154 | Allele 2 | 1.39 | 4.01 | 11.34 | 0.85 | SEQ ID No: 141 | SEQ ID No: 142 |
| rs13193932 | Allele 2 | 1.52 | 4.30 | 22.83 | 26.08 | SEQ ID No: 143 | SEQ ID No: 144 |
| rs17070863 | Allele 2 | 1.86 | 3.61 | 3.42 | 1.72 | SEQ ID No: 145 | SEQ ID No: 146 |
| rs1877885 | Allele 2 | 1.80 | 3.67 | 3.45 | 2.04 | SEQ ID No: 147 | SEQ ID No: 148 |
| rs1913603 | Allele 2 | 1.79 | 3.75 | 3.85 | 2.37 | SEQ ID No: 149 | SEQ ID No: 150 |
| rs10230371 | Allele 1 | 1.29 | 4.38 | 1.11 | 2.63 | SEQ ID No: 151 | SEQ ID No: 152 |
| rs17152739 | Allele 2 | 1.98 | 3.78 | 3.43 | 1.65 | SEQ ID No: 153 | SEQ ID No: 154 |
| rs4316157 | Allele 2 | 1.89 | 3.65 | 3.29 | 1.88 | SEQ ID No: 155 | SEQ ID No: 156 |
| rs10503907 | Allele 1 | 2.46 | 3.27 | 8.80 | 3.83 | SEQ ID No: 157 | SEQ ID No: 158 |

TABLE 28

| dbSNP ID | Allele1/Allele2 | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|---|
| rs9650336 | C/T | LOC286140 −47376 bp (XM_209913) | 8 | 38,625,315 | 4.11 | 0.67 | 0.53 |
| rs1541082 | A/C | PIP5K1B Intron15 (NM_003558.1) | 9 | 68,851,654 | 4.05 | 0.37 | 0.24 |
| rs4979255 | C/T | LOC442430 −50518 bp (XM_498339) | 9 | 107,542,392 | 1.50 | 0.69 | 0.61 |
| rs2395453 | C/G | KCNMA1 Intron18 (NM_002247.2) | 10 | 78,411,565 | 1.77 | 0.60 | 0.51 |
| rs2131216 | A/T | KCNMA1 Intron18 (NM_002247.2) | 10 | 78,426,609 | 1.67 | 0.59 | 0.51 |
| rs7112492 | A/C | LDHA −10601 bp (NM_005566.1) | 11 | 18,362,086 | 3.70 | 0.38 | 0.26 |
| rs4755605 | C/T | LOC387761 −170163 bp (XM_373495) | 11 | 42,404,449 | 3.08 | 0.57 | 0.45 |

TABLE 28-continued

| dbSNP ID | | | Chromosome | Physical location | p-value allele (-logP) | High Risk Allele Frequency (Progressive) | High Risk Allele Frequency (Nonprogressive) |
|---|---|---|---|---|---|---|---|
| rs10892454 | A/C | LOC440070 +32494 bp (XM_498530) | 11 | 119,148,037 | 0.09 | 0.47 | 0.47 |
| rs4269933 | C/T | LOC440070 +38035 bp (XM_498530) | 11 | 119,153,578 | 0.08 | 0.47 | 0.47 |
| rs2322728 | A/G | FLJ40224 +258937 bp (NM_173579.1) | 11 | 126,640,100 | 0.04 | 0.28 | 0.28 |
| rs4350423 | A/G | FLJ40126 Intron18 (NM_173599.1), SLC2A13 Intron6 (NM_052885.1) | 12 | 38,515,235 | 4.28 | 0.24 | 0.13 |
| rs10784314 | C/T | PPM1H Intron4 (XM_350880) | 12 | 61,442,746 | 1.93 | 0.85 | 0.78 |
| rs4408378 | A/G | LOC401725 +252078 bp (XM_377278) | 12 | 82,300,515 | 4.01 | 0.82 | 0.70 |
| rs11059862 | A/G | DKFZp761O2018 +33295 bp (XM_044062) | 12 | 127,750,629 | 4.11 | 0.94 | 0.85 |
| rs17184839 | A/G | LOC440142 +13577 bp (XM_495960) | 13 | 59,763,528 | 4.07 | 0.14 | 0.05 |
| rs7212115 | G/T | LOC400573 −182083 bp (XM_378649) | 17 | 10,832,202 | 4.05 | 0.88 | 0.78 |
| rs295869 | C/T | LOC388375 +71591 bp (XM_373726) | 17 | 32,221,458 | 2.76 | 0.44 | 0.33 |
| rs6045676 | C/G | PDYN +18232 bp (NM_024411.2) | 20 | 1,889,171 | 4.11 | 0.35 | 0.22 |
| rs909882 | A/G | CHD6 Intron24 (NM_032221.3) | 20 | 39,509,923 | 4.37 | 0.81 | 0.68 |
| rs6017164 | C/T | C20orf65 −26539 bp (NM_176791.2) | 20 | 41,815,520 | 4.15 | 0.55 | 0.40 |
| rs7275647 | A/G | NCAM2 Intron5 (NM_004540.2) | 21 | 21,586,912 | 4.62 | 0.69 | 0.55 |
| rs2837255 | A/C | PCP4 −17259 bp (NM_006198.1) | 21 | 40,143,991 | 4.33 | 0.70 | 0.56 |

| dbSNP ID | High Risk Allele | Odds Ratio (Formula 6) | Critical rate, Genotype (−logP) | Odds Ratio (Homozygote1) (Formula 7) | Odds Ratio (Heterozygote) (Formula 8) | Sequence Containing Allele 1 | Sequence Containing Allele 2 |
|---|---|---|---|---|---|---|---|
| rs9650336 | Allele 1 | 1.80 | 4.06 | 2.58 | 1.02 | SEQ ID No: 159 | SEQ ID No: 160 |
| rs1541082 | Allele 1 | 1.87 | 3.54 | 4.89 | 1.65 | SEQ ID No: 161 | SEQ ID No: 162 |
| rs4979255 | Allele 1 | 1.39 | 4.03 | 1.16 | 0.46 | SEQ ID No: 163 | SEQ ID No: 164 |
| rs2395453 | Allele 1 | 1.42 | 4.73 | 1.68 | 0.55 | SEQ ID No: 165 | SEQ ID No: 166 |
| rs2131216 | Allele 2 | 1.40 | 4.14 | 1.72 | 0.59 | SEQ ID No: 167 | SEQ ID No: 168 |
| rs7112492 | Allele 2 | 1.80 | 4.03 | 2.25 | 2.50 | SEQ ID No: 169 | SEQ ID No: 170 |
| rs4755605 | Allele 1 | 1.63 | 4.13 | 3.34 | 3.05 | SEQ ID No: 171 | SEQ ID No: 172 |
| rs10892454 | Allele 1 | 1.03 | 4.12 | 1.29 | 0.45 | SEQ ID No: 173 | SEQ ID No: 174 |
| rs4269933 | Allele 2 | 1.03 | 4.20 | 1.29 | 0.44 | SEQ ID No: 175 | SEQ ID No: 176 |
| rs2322728 | Allele 2 | 1.02 | 4.00 | 3.53 | 0.55 | SEQ ID No: 177 | SEQ ID No: 178 |
| rs4350423 | Allele 2 | 2.20 | 3.41 | 8.59 | 1.82 | SEQ ID No: 179 | SEQ ID No: 180 |
| rs10784314 | Allele 1 | 1.62 | 5.56 | ND | ND | SEQ ID No: 181 | SEQ ID No: 182 |
| rs4408378 | Allele 1 | 1.97 | 3.22 | 3.63 | 1.81 | SEQ ID No: 183 | SEQ ID No: 184 |
| rs11059862 | Allele 1 | 2.61 | 3.33 | 5.98 | 2.27 | SEQ ID No: 185 | SEQ ID No: 186 |
| rs17184839 | Allele 1 | 2.98 | 3.54 | ND | 3.09 | SEQ ID No: 187 | SEQ ID No: 188 |
| rs7212115 | Allele 2 | 2.17 | 2.12 | 2.65 | 1.55 | SEQ ID No: 189 | SEQ ID No: 190 |
| rs295869 | Allele 1 | 1.60 | 4.93 | 1.80 | 3.00 | SEQ ID No: 191 | SEQ ID No: 192 |
| rs6045676 | Allele 2 | 1.91 | 3.66 | 2.90 | 2.23 | SEQ ID No: 193 | SEQ ID No: 194 |
| rs909882 | Allele 1 | 2.01 | 3.58 | 4.37 | 2.25 | SEQ ID No: 195 | SEQ ID No: 196 |
| rs6017164 | Allele 2 | 1.80 | 3.44 | 3.33 | 1.62 | SEQ ID No: 197 | SEQ ID No: 198 |
| rs7275647 | Allele 1 | 1.89 | 3.98 | 3.18 | 1.43 | SEQ ID No: 199 | SEQ ID No: 200 |
| rs2837255 | Allele 1 | 1.86 | 3.37 | 3.28 | 1.82 | SEQ ID No: 201 | SEQ ID No: 202 |

Tables 26 to 28 list dbSNP ID number or Affimetrix Array ID number specifying known single nucleotide polymorphisms obtained, each of bases constituting Allele 1 and Allele 2, the exon, intron information (in a case where a single nucleotide polymorphism exists on a gene, the gene name and the exon or intron in which SNP exists are shown, and in a case where a single nucleotide polymorphism does not exist on a gene, neighboring genes and a distance between the gene and the single nucleotide polymorphism are shown), the chromosome number at which the single nucleotide polymorphism exists, the physical location of the single nucleotide polymorphism, the p-value for an allele according to a chi-square test (−log P), the high-risk allele frequencies in the progressive glaucoma group and the nonprogressive glaucoma group, the type of the high-risk allele (indicating whether the high-risk allele is Allele 1 or Allele 2), the odds ratio for an allele, the p-value for genotype according to a chi-square test (−log P), the odds ratio for a genotype of a homozygote, the odds ratio for a genotype of a heterozygote, and SEQ ID NO of the sequence containing Allele 1 and SEQ ID NO of the sequence containing Allele 2 in each of the polymorphic sites. Here, in the tables, a portion of which odds ratio is indicated as ND shows a case where any one of the number of detection in the denominator is 0, so that the odds ratio could not be calculated.

According to the above studies, 61 single nucleotide polymorphisms of which alleles or genotypes were associated with the progression of glaucoma at a p-value of $1\times10^{-4}$ or less were found.

When the allele or genotype frequencies listed in Tables 26 to 28 were compared between the progressive glaucoma cases and the nonprogressive glaucoma cases, a statistical difference was found. By determining an allele of any one of these single nucleotide polymorphisms, whether or not an allele that is identified in a higher frequency in the progressive glaucoma group than that of the nonprogressive glaucoma group exists in the sample can be determined.

The allele or genotype identified in a high frequency in the progressive glaucoma group for a single nucleotide polymorphism listed in Tables 26 to 28 can be used as a marker showing that a progressive risk of glaucoma is high. On the other hand, an allele that is opposite to the allele or a genotype other than the genotype can be used as a marker showing that a progressive risk of glaucoma is low.

Also, a single nucleotide polymorphism of which allele or genotype shows association with the progression of glaucoma at a p-value of $1\times10^{-3}$ or less, i.e. −log P of 3 or more, is listed in Tables 29 to 51.

TABLE 29

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs1920146 | FMO3 −14117 bp (NM_006894.3) | 1 | 167,777,607 | 3.00 | 0.16 |
| rs594105 | C8A Intron4 (NM_000562.1) | 1 | 57,055,277 | 0.82 | 0.65 |
| rs490647 | GRIK3 +23871 bp (NM_000831.2) | 1 | 36,911,836 | 3.13 | 0.39 |
| rs10489624 | C8A Intron6 (NM_000562.1) | 1 | 57,061,635 | 0.83 | 0.65 |
| rs11117962 | LOC128153 +9779 bp (NM_138796.2) | 1 | 214,438,658 | 1.33 | 0.60 |
| rs868162 | NPHP4 Intron22 (NM_015102.2) | 1 | 5,868,502 | 0.74 | 0.76 |
| rs525798 | GRIK3 +25728 bp (NM_000831.2) | 1 | 36,909,979 | 3.12 | 0.40 |
| rs11120300 | SMYD2 Intron11 (NM_020197.1) | 1 | 210,897,894 | 1.38 | 0.08 |
| rs10494300 | KCNN3 Intron3 (NM_170782.1), KCNN3 Intron3 (NM_002249.3) | 1 | 151,539,619 | 3.13 | 0.61 |
| rs17401966 | KIF1B Intron24 (NM_015074.2), KIF1B +18633 bp (NM_183416.2) | 1 | 10,319,737 | 2.53 | 0.28 |
| rs687328 | GADD45A −40088 bp (NM_001924.2) | 1 | 67,822,816 | 3.19 | 0.75 |
| rs7517439 | EIF2B3 +3647 bp (NM_020365.1) | 1 | 44,981,960 | 0.01 | 0.75 |
| rs479714 | GRIK3 +26576 bp (NM_000831.2) | 1 | 36,909,131 | 2.84 | 0.39 |
| rs7528341 | GRIK3 +125440 bp (NM_000831.2) | 1 | 36,810,267 | 3.27 | 0.75 |
| rs1339411 | KCNK2 +61589 bp (NM_014217.1) | 1 | 211,859,142 | 3.20 | 0.33 |
| rs947130 | LOC391075 −11088 bp (XM_497702) | 1 | 119,728,774 | 3.47 | 0.82 |
| rs7534078 | SYT2 Intron1 (NM_177402.3) | 1 | 199,346,710 | 3.84 | 0.37 |
| rs479779 | GRIK3 +10551 bp (NM_000831.2) | 1 | 36,925,156 | 3.03 | 0.39 |
| rs2993076 | GRIK3 +5529 bp (NM_000831.2) | 1 | 36,930,178 | 3.00 | 0.36 |
| rs11590929 | LMO4 +403174 bp (NM_006769.2) | 1 | 87,926,458 | 3.65 | 0.96 |
| rs1416658 | KCNK2 +6613 bp (NM_014217.1) | 1 | 211,804,166 | 3.28 | 0.32 |
| rs4652921 | GRIK3 +91841 bp (NM_000831.2) | 1 | 36,843,866 | 3.22 | 0.66 |
| rs10157596 | SLC35F3 −17535 bp (NM_173508.1) | 1 | 230,329,879 | 3.29 | 0.71 |
| rs1416659 | KCNK2 +6647 bp (NM_014217.1) | 1 | 211,804,200 | 3.17 | 0.31 |

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs1920146 | 0.08 | 2.14 | 3.79 | 0.78 | 3.05 |
| rs594105 | 0.60 | 1.24 | 3.74 | 0.95 | 0.41 |
| rs490647 | 0.28 | 1.69 | 3.43 | 1.92 | 2.39 |
| rs10489624 | 0.60 | 1.24 | 3.39 | 1.00 | 0.44 |
| rs11117962 | 0.53 | 1.34 | 3.32 | 1.49 | 0.60 |
| rs868162 | 0.72 | 1.25 | 3.32 | 0.41 | 0.21 |
| rs525798 | 0.28 | 1.68 | 3.28 | 1.97 | 2.33 |
| rs11120300 | 0.04 | 1.90 | 3.14 | 0.23 | 4.08 |
| rs10494300 | 0.49 | 1.64 | 3.14 | 2.56 | 1.09 |
| rs17401966 | 0.19 | 1.68 | 3.09 | 17.83 | 1.28 |
| rs687328 | 0.63 | 1.71 | 3.07 | 3.66 | 3.07 |
| rs7517439 | 0.75 | 1.01 | 3.05 | 4.99 | 7.80 |
| rs479714 | 0.28 | 1.64 | 3.01 | 1.86 | 2.26 |
| rs7528341 | 0.63 | 1.73 | 2.97 | 2.40 | 1.14 |
| rs1339411 | 0.22 | 1.76 | 2.91 | 2.53 | 2.08 |
| rs947130 | 0.71 | 1.86 | 2.89 | 4.69 | 2.75 |
| rs7534078 | 0.25 | 1.84 | 2.89 | 2.83 | 1.87 |
| rs479779 | 0.28 | 1.67 | 2.86 | 2.00 | 2.16 |
| rs2993076 | 0.25 | 1.69 | 2.84 | 2.00 | 2.15 |
| rs11590929 | 0.89 | 2.98 | 2.83 | 4.15 | 1.35 |
| rs1416658 | 0.21 | 1.79 | 2.82 | 2.63 | 2.02 |
| rs4652921 | 0.54 | 1.67 | 2.81 | 2.56 | 1.25 |
| rs10157596 | 0.59 | 1.71 | 2.80 | 3.48 | 2.28 |
| rs1416659 | 0.21 | 1.77 | 2.79 | 2.48 | 2.04 |

TABLE 30

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs11120527 | KCNK2 Intron6 (NM_014217.1) | 1 | 211,796,452 | 3.16 | 0.32 |
| rs10494994 | KCNK2 Intron5 (NM_014217.1) | 1 | 211,750,602 | 3.50 | 0.26 |
| rs6665581 | VAMP4 −9932 bp (NM_201994.1), VAMP4 −9932 bp (NM_003762.1) | 1 | 168,452,803 | 3.09 | 0.39 |
| rs12120152 | VAMP4 −12595 bp (NM_201994.1), VAMP4 −12595 bp (NM_003762.2) | 1 | 168,455,466 | 3.09 | 0.39 |
| rs2293325 | CD3Z Intron1 (NM_000734.2), CD3Z Intron1 (NM_198053.1) | 1 | 164,157,804 | 3.18 | 0.78 |

TABLE 30-continued

| DBSNP_ID | Exon, Intron | Chromosome | Physical Location | Critical rate, Allele (-logP) | High-Risk Allele Frequency in Progressive Glaucoma Group |
|---|---|---|---|---|---|
| rs6577539 | CA6 −16705 bp (NM_001215.1) | 1 | 8,923,501 | 3.16 | 0.94 |
| rs34305923 | GRIK3 +122474 bp (NM_000831.2) | 1 | 36,813,233 | 3.10 | 0.74 |
| rs1315219 | FLJ23129 Intron7 (NM_024763.3), FLJ23129 Intron7 (NM_207014.1) | 1 | 67,031,546 | 3.32 | 0.58 |
| rs10798603 | VAMP4 Intron4 (NM_201994.1), VAMP4 Intron4 (NM_003762.2) | 1 | 168,412,039 | 3.37 | 0.36 |
| rs1317252 | TDE2L Intron2 (NM_178865.2) | 1 | 31,566,351 | 3.25 | 0.91 |
| rs12024194 | VAMP4 −12277 bp (NM_201994.1), VAMP4 −12277 bp (NM_003762.2) | 1 | 168,455,148 | 3.21 | 0.22 |
| rs10489250 | VAMP4 −4860 bp (NM_201994.1), VAMP4 −4860 bp (NM_003762.2) | 1 | 168,447,731 | 3.03 | 0.22 |
| rs271351 | LOC391025 −173869 bp (XM_372775) | 1 | 29,821,213 | 3.21 | 0.16 |
| rs6689380 | LOC339535 −409013 bp (XM_378941) | 1 | 235,384,371 | 3.08 | 0.97 |
| rs9943293 | VAMP4 +14337 bp (NM_201994.1), VAMP4 +18093 bp (NM_003762.2) | 1 | 168,386,625 | 3.03 | 0.34 |
| rs4342884 | VAMP4 Intron4 (NM_201994.1), VAMP4 Intron4 (NM_003762.2) | 1 | 168,416,489 | 3.03 | 0.36 |
| rs11691504 | UBE2E3 −377923 bp (NM_182678.1), UBE2E3 −378153 bp (NM_006357.2) | 2 | 181,292,695 | 3.11 | 0.82 |

| DBSNP_ID | High-Risk Allele Frequency in Nonprogressive Glaucoma Group | Odds Ratio (Formula 6) | Critical rate, Genotype (-logP) | Odds Ratio (Homozygote) (Formula 7) | Odds Ratio (Heterozygote) (Formula 8) |
|---|---|---|---|---|---|
| rs11120527 | 0.21 | 1.77 | 2.79 | 2.49 | 2.05 |
| rs10494994 | 0.16 | 1.93 | 2.76 | 3.29 | 1.97 |
| rs6665581 | 0.27 | 1.69 | 2.72 | 3.73 | 1.38 |
| rs12120152 | 0.27 | 1.69 | 2.72 | 3.73 | 1.38 |
| rs2293325 | 0.67 | 1.74 | 2.69 | 2.74 | 1.41 |
| rs6577539 | 0.87 | 2.40 | 2.69 | ND | ND |
| rs34305923 | 0.62 | 1.69 | 2.66 | 2.43 | 1.23 |
| rs1315219 | 0.45 | 1.67 | 2.63 | 2.78 | 1.54 |
| rs10798603 | 0.24 | 1.77 | 2.60 | 3.30 | 1.65 |
| rs1317252 | 0.82 | 2.10 | 2.51 | 4.36 | 2.10 |
| rs12024194 | 0.13 | 1.95 | 2.44 | 4.16 | 1.86 |
| rs10489250 | 0.13 | 1.91 | 2.28 | 3.12 | 1.91 |
| rs271351 | 0.08 | 2.22 | 2.23 | 4.90 | 1.96 |
| rs6689380 | 0.92 | 3.08 | 2.17 | ND | ND |
| rs9943293 | 0.23 | 1.71 | 2.16 | 2.67 | 1.65 |
| rs4342884 | 0.25 | 1.72 | 2.11 | 2.81 | 1.52 |
| rs11691504 | 0.72 | 1.79 | 3.96 | 1.41 | 0.55 |

TABLE 31

| DBSNP_ID | Exon, Intron | Chromosome | Physical Location | Critical rate, Allele (-logP) | High-Risk Allele Frequency in Progressive Glaucoma Group |
|---|---|---|---|---|---|
| rs9679229 | UBE2E3 −350430 bp (NM_182678.1), UBE2E3 −350660 bp (NM_006357.2) | 2 | 181,320,188 | 3.05 | 0.82 |
| rs11691031 | C2orf29 −90020 bp (NM_017546.3) | 2 | 101,237,876 | 1.36 | 0.49 |
| rs714545 | UBE2E3 −463121 bp (NM_182678.1), UBE2E3 −463351 bp (NM_006357.2) | 2 | 181,207,497 | 3.54 | 0.81 |
| rs10931418 | FLJ12519 −41124 bp (NM_032168.1) | 2 | 190,090,541 | 0.90 | 0.65 |
| rs4667078 | UBE2E3 −367916 bp (NM_182678.1), UBE2E3 −368146 bp (NM_006357.2) | 2 | 181,302,702 | 2.87 | 0.81 |
| rs1355216 | SCN7A −183021 bp (NM_002976.1) | 2 | 167,352,006 | 3.14 | 0.86 |
| rs11695159 | FLJ12519 −22944 bp (NM_032168.1) | 2 | 190,108,721 | 0.79 | 0.64 |
| rs13032853 | FLJ12519 Intron1 (NM_032168.1) | 2 | 190,134,918 | 1.05 | 0.65 |
| rs733830 | C2orf29 −91059 bp (NM_017546.3) | 2 | 101,236,837 | 1.54 | 0.49 |
| rs16833004 | GLS −41329 bp (NM_014905.2) | 2 | 191,529,780 | 2.52 | 0.97 |
| rs11563200 | TRPM8 Intron25 (NM_024080.3) | 2 | 234,706,809 | 0.01 | 0.58 |
| rs10930240 | SCN7A −162624 bp (NM_002976.1) | 2 | 167,331,609 | 2.96 | 0.87 |
| rs9287871 | SCN7A −162839 bp (NM_002976.1) | 2 | 167,331,824 | 2.96 | 0.87 |
| rs16860887 | LOC91526 Intron15 (NM_153697.1) | 2 | 197,723,413 | 3.53 | 0.90 |
| rs1840111 | UBE2E3 −484947 bp (NM_182678.1), UBE2E3 −485177 bp (NM_006357.2) | 2 | 181,185,671 | 3.05 | 0.77 |
| rs934706 | NXPH2 −373561 bp (XM_371573) | 2 | 139,745,104 | 1.84 | 0.21 |
| rs7420360 | EPHA4 +369107 bp (NM_004438.3) | 2 | 221,739,407 | 0.50 | 0.41 |
| rs6739369 | FLJ20701 Intron3 (NM_017933.3) | 2 | 229,738,357 | 3.71 | 0.18 |
| rs4850410 | LOC91526 Intron15 (NM_153697.1) | 2 | 197,745,675 | 3.81 | 0.93 |
| rs1453054 | UBE2E3 −485205 bp (NM_182678.1), UBE2E3 −485435 bp (NM_006357.2) | 2 | 181,185,413 | 3.18 | 0.78 |

TABLE 31-continued

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs9679229 | 0.72 | 1.77 | 3.90 | 1.41 | 0.55 |
| rs11691031 | 0.42 | 1.34 | 3.85 | 1.62 | 2.75 |
| rs714545 | 0.70 | 1.85 | 3.76 | 1.88 | 0.76 |
| rs10931418 | 0.59 | 1.26 | 3.61 | 2.14 | 3.40 |
| rs4667078 | 0.72 | 1.74 | 3.57 | 1.42 | 0.58 |
| rs1355216 | 0.77 | 1.91 | 3.55 | 1.25 | 0.50 |
| rs11695159 | 0.59 | 1.23 | 3.47 | 2.07 | 3.32 |
| rs13032853 | 0.59 | 1.29 | 3.45 | 2.20 | 3.33 |
| rs733830 | 0.41 | 1.38 | 3.31 | 1.73 | 2.57 |
| rs16833004 | 0.92 | 2.77 | 3.29 | 1.02 | 0.15 |
| rs11563200 | 0.57 | 1.01 | 3.27 | 0.70 | 0.35 |
| rs10930240 | 0.78 | 1.86 | 3.25 | 1.26 | 0.53 |
| rs9287871 | 0.78 | 1.86 | 3.25 | 1.26 | 0.53 |
| rs16860887 | 0.81 | 2.15 | 3.23 | 2.07 | 0.82 |
| rs1840111 | 0.66 | 1.71 | 3.22 | 1.84 | 0.79 |
| rs934706 | 0.15 | 1.60 | 3.22 | ND | 0.99 |
| rs7420360 | 0.38 | 1.16 | 3.21 | 0.93 | 2.18 |
| rs6739369 | 0.08 | 2.39 | 3.20 | 4.06 | 2.60 |
| rs4850410 | 0.84 | 2.40 | 3.20 | 2.97 | 1.13 |
| rs1453054 | 0.67 | 1.75 | 3.13 | 2.03 | 0.90 |

TABLE 32

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs10186570 | UBE2E3 −482951 bp (NM_182678.1), UBE2E3 −483181 bp (NM_006357.2) | 2 | 181,187,667 | 2.67 | 0.78 |
| rs4076919 | FLJ10116 +86710 bp (NM_018000.1) | 2 | 216,546,324 | 3.09 | 0.83 |
| rs968871 | FLJ32955 +20953 bp (NM_153041.1) | 2 | 150,428,575 | 3.81 | 0.45 |
| rs968873 | FLJ32955 +20796 bp (NM_153041.1) | 2 | 150,428,732 | 3.81 | 0.45 |
| rs13426748 | LOC91526 Intron15 (NM_153697.1) | 2 | 197,723,066 | 3.39 | 0.90 |
| rs2564118 | FLJ32312 Intron4 (NM_144709.1) | 2 | 61,144,940 | 1.22 | 0.52 |
| rs1468981 | KLF7 +36314 bp (NM_003709.1) | 2 | 207,734,721 | 0.36 | 0.59 |
| rs1641385 | FLJ32955 +20086 bp (NM_153041.1) | 2 | 150,429,442 | 3.71 | 0.45 |
| rs16825626 | FLJ20701 Intron3 (NM_017933.3) | 2 | 229,744,146 | 3.38 | 0.17 |
| rs4261668 | MYL1 Intron3 (NM_079422.1), MYL1 Intron3 (NM_079420.1) | 2 | 210,987,818 | 3.62 | 0.35 |
| rs848241 | FLJ32955 Intron3 (NM_153041.1) | 2 | 150,460,159 | 3.55 | 0.43 |
| rs1196155 | PPP1R1C Intron2 (XM_087137) | 2 | 182,746,778 | 3.43 | 0.68 |
| rs1104870 | ALK Intron15 (NM_004304.3) | 2 | 29,366,069 | 3.60 | 0.17 |
| rs12692654 | KCNH7 Intron2 (NM_033272.2), KCNH7 Intron2 (NM_173162.1) | 2 | 163,309,182 | 3.36 | 0.77 |
| rs4667333 | FLJ32955 Intron3 (NM_153041.1) | 2 | 150,461,734 | 3.44 | 0.44 |
| rs787433 | LOC401014 +29562 bp (XM_379141) | 2 | 145,697,590 | 3.44 | 0.42 |
| rs1196185 | PPP1R1C Intron2 (XM_087137) | 2 | 182,710,465 | 3.33 | 0.67 |
| rs10496018 | LOC402072 +151618 bp (XM_377741) | 2 | 53,312,986 | 3.28 | 0.16 |
| rs7582411 | LOC91526 Intron15 (NM_153697.1) | 2 | 197,738,392 | 3.10 | 0.91 |
| rs1529404 | MYCN +99328 bp (NM_005378.3) | 2 | 16,137,052 | 3.29 | 0.88 |
| rs1608976 | FLJ32955 Intron3 (NM_153041.1) | 2 | 150,460,868 | 3.20 | 0.44 |
| rs2701664 | PPP1R1C Intron2 (XM_087137) | 2 | 182,734,170 | 3.22 | 0.67 |
| rs1196160 | PPP1R1C Intron3 (XM_087137) | 2 | 182,753,518 | 3.22 | 0.67 |

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs10186570 | 0.68 | 1.65 | 3.08 | 1.62 | 0.71 |
| rs4076919 | 0.73 | 1.80 | 3.07 | 1.92 | 0.86 |
| rs968871 | 0.31 | 1.77 | 3.06 | 3.17 | 1.75 |
| rs968873 | 0.31 | 1.77 | 3.06 | 3.17 | 1.75 |
| rs13426748 | 0.81 | 2.11 | 3.06 | 2.01 | 0.82 |
| rs2564118 | 0.45 | 1.32 | 3.06 | 1.97 | 0.70 |
| rs1468981 | 0.56 | 1.12 | 3.04 | 0.99 | 0.46 |
| rs1641385 | 0.32 | 1.75 | 2.97 | 3.13 | 1.73 |
| rs16825626 | 0.08 | 2.27 | 2.94 | 3.11 | 2.51 |
| rs4261668 | 0.23 | 1.81 | 2.91 | 3.39 | 1.81 |
| rs848241 | 0.31 | 1.73 | 2.87 | 3.02 | 1.78 |
| rs1196155 | 0.55 | 1.71 | 2.87 | 3.23 | 2.15 |

TABLE 32-continued

| DBSNP_ID | | | | | |
|---|---|---|---|---|---|
| rs1104870 | 0.08 | 2.36 | 2.85 | 6.13 | 2.33 |
| rs12692654 | 0.65 | 1.76 | 2.83 | 2.82 | 1.44 |
| rs4667333 | 0.31 | 1.72 | 2.78 | 3.00 | 1.77 |
| rs787433 | 0.30 | 1.72 | 2.78 | 3.29 | 1.54 |
| rs1196185 | 0.55 | 1.68 | 2.78 | 3.08 | 2.11 |
| rs10496018 | 0.07 | 2.29 | 2.72 | 2.53 | 2.53 |
| rs7582411 | 0.83 | 2.13 | 2.71 | 2.16 | 0.89 |
| rs1529404 | 0.79 | 1.98 | 2.67 | 6.63 | 3.70 |
| rs1608976 | 0.31 | 1.70 | 2.67 | 3.00 | 1.81 |
| rs2701664 | 0.55 | 1.66 | 2.61 | 2.94 | 2.00 |
| rs1196160 | 0.55 | 1.66 | 2.61 | 2.94 | 2.00 |

TABLE 33

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs1358105 | FLJ32955 +17818 bp (NM_153041.1) | 2 | 150,431,710 | 3.30 | 0.39 |
| rs1724855 | FLJ32955 Intron3 (NM_153041.1) | 2 | 150,455,469 | 3.22 | 0.43 |
| rs17589066 | DNAH7 Intron48 (NM_018897.1) | 2 | 196,522,530 | 3.05 | 0.83 |
| rs31276 | FLJ20701 Intron3 (NM_017933.3) | 2 | 229,746,025 | 3.08 | 0.19 |
| rs7569506 | FLJ39822 +44702 bp (NM_173512.1) | 2 | 165,535,617 | 3.15 | 0.85 |
| rs16838454 | KIAA1679 Intron9 (XM_046570) | 2 | 137,843,162 | 3.08 | 0.16 |
| rs17041614 | ITPR1 +16975 bp (NM_002222.1) | 3 | 4,881,056 | 1.28 | 0.75 |
| rs784288 | MDS1 Intron2 (NM_004991.1) | 3 | 170,453,933 | 3.72 | 0.79 |
| rs6773050 | CDGAP Intron10 (XM_291085) | 3 | 120,606,504 | 2.34 | 0.64 |
| rs6792308 | ITPR1 +11521 bp (NM_002222.1) | 3 | 4,875,602 | 1.14 | 0.73 |
| rs1828652 | PLSCR4 Intron6 (NM_020353.1) | 3 | 147,397,711 | 3.96 | 0.47 |
| rs1877268 | LOC93556 +73662 bp (XM_376284) | 3 | 170,104,751 | 2.31 | 0.37 |
| rs16852789 | LOC93556 +75467 bp (XM_376284) | 3 | 170,106,556 | 2.31 | 0.37 |
| rs11920980 | LOC440985 −77863 bp (XM_498948) | 3 | 154,176,162 | 1.13 | 0.57 |
| rs7429749 | FTHFD Intron1 (NM_012190.2), FTHFD Intron1 (NM_144776.1) | 3 | 127,371,520 | 2.65 | 0.21 |
| rs7624272 | SEMA5B Intron1 (NM_018987.1) | 3 | 124,178,241 | 3.01 | 0.10 |
| rs6763643 | MYRIP Intron3 (NM_015460.1) | 3 | 40,072,995 | 0.70 | 0.38 |
| rs4685335 | RAFTLIN Intron4 (NM_015150.1) | 3 | 16,423,640 | 0.62 | 0.47 |
| rs12490570 | LOC152118 −107632 bp (XM_098163) | 3 | 154,577,350 | 3.96 | 0.92 |
| rs7371987 | CCR3 +10346 bp (NM_001837.2), CCR3 +10346 bp (NM_178329.1) | 3 | 46,293,512 | 3.21 | 0.31 |
| rs3957816 | PCCB −13296 bp (NM_000532.2) | 3 | 137,438,550 | 3.71 | 0.25 |
| rs9839623 | CCR3 +15697 bp (NM_001837.2), CCR3 +15697 bp (NM_178329.1) | 3 | 46,298,863 | 3.07 | 0.31 |
| rs17016781 | RARB Intron3 (NM_000965.2), RARB Intron3 (NM_016152.2) | 3 | 25,580,890 | 3.62 | 0.65 |

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs1358105 | 0.27 | 1.72 | 2.59 | 3.20 | 1.60 |
| rs1724855 | 0.31 | 1.68 | 2.56 | 2.86 | 1.72 |
| rs17589066 | 0.72 | 1.82 | 2.53 | 4.89 | 2.95 |
| rs31276 | 0.11 | 2.02 | 2.53 | 6.18 | 2.03 |
| rs7569506 | 0.76 | 1.87 | 2.53 | 3.48 | 1.81 |
| rs16838454 | 0.08 | 2.23 | 1.70 | 2.79 | 1.93 |
| rs17041614 | 0.69 | 1.37 | 3.98 | 0.79 | 0.33 |
| rs784288 | 0.67 | 1.85 | 3.79 | 7.54 | 4.94 |
| rs6773050 | 0.53 | 1.53 | 3.56 | 2.99 | 3.29 |
| rs6792308 | 0.67 | 1.33 | 3.52 | 0.83 | 0.37 |
| rs1828652 | 0.34 | 1.78 | 3.49 | 2.66 | 2.23 |
| rs1877268 | 0.27 | 1.55 | 3.41 | 1.49 | 2.45 |
| rs16852789 | 0.27 | 1.55 | 3.41 | 1.49 | 2.45 |
| rs11920980 | 0.50 | 1.30 | 3.36 | 1.54 | 0.59 |
| rs7429749 | 0.13 | 1.85 | 3.23 | ND | 2.16 |
| rs7624272 | 0.04 | 2.83 | 3.22 | ND | 3.06 |
| rs6763643 | 0.34 | 1.22 | 3.17 | 2.51 | 0.67 |
| rs4685335 | 0.43 | 1.19 | 3.15 | 1.22 | 2.39 |
| rs12490570 | 0.82 | 2.35 | 3.05 | 5.13 | 2.26 |
| rs7371987 | 0.20 | 1.78 | 3.02 | 6.91 | 1.56 |
| rs3957816 | 0.14 | 2.01 | 2.97 | 5.03 | 1.91 |
| rs9839623 | 0.21 | 1.76 | 2.91 | 6.79 | 1.53 |
| rs17016781 | 0.51 | 1.72 | 2.88 | 2.77 | 1.46 |

TABLE 34

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs453570 | CISH +6457 bp (NM_013324.4), CISH +6457 bp (NM_145071.1) | 3 | 50,612,473 | 3.25 | 0.67 |
| rs13096142 | CCR3 −1944 bp (NM_001837.2), CCR3 −1944 bp (NM_178329.1) | 3 | 46,256,748 | 3.04 | 0.35 |
| rs696518 | STAG1 Intron21 (NM_005862.1) | 3 | 137,602,998 | 3.63 | 0.28 |
| rs6446245 | DOCK3 Intron5 (NM_004947.2) | 3 | 51,012,298 | 3.15 | 0.66 |
| rs16833788 | SEMA5B −6558 bp (NM_018987.1) | 3 | 124,236,700 | 3.37 | 0.10 |
| rs6440881 | LOC152118 −56902 bp (XM_098163) | 3 | 154,628,080 | 3.51 | 0.90 |
| rs10510568 | RARB Intron3 (NM_000965.2), RARB Intron3 (NM_016152.2) | 3 | 25,577,736 | 3.24 | 0.64 |
| rs16833786 | SEMA5B −5978 bp (NM_018987.1) | 3 | 124,236,120 | 3.26 | 0.10 |
| rs1545105 | LOC389100 +81379 bp (XM_374035) | 3 | 29,199,691 | 3.01 | 0.37 |
| rs9883170 | LOC389100 +82213 bp (XM_374035) | 3 | 29,198,857 | 3.04 | 0.37 |
| rs17016778 | RARB Intron3 (NM_000965.2), RARB Intron3 (NM_016152.2) | 3 | 25,580,286 | 3.28 | 0.64 |
| rs2174746 | LOC152118 −103841 bp (XM_098163) | 3 | 154,581,141 | 3.52 | 0.92 |
| rs11712746 | KCNMB2 −262329 bp (NM_181361.1), KCNMB2 −284723 bp (NM_005832.3) | 3 | 179,474,597 | 3.12 | 0.25 |
| rs684773 | PCCB −12843 bp (NM_000532.2) | 3 | 137,439,003 | 3.26 | 0.22 |
| rs695983 | STAG1 Intron29 (NM_005862.1) | 3 | 137,547,245 | 3.33 | 0.24 |
| rs1154988 | LOC391581 −434 bp (XM_497940) | 3 | 137,407,889 | 3.23 | 0.23 |
| rs2232248 | HEMK1 Exon3 (NM_016173.1) | 3 | 50,584,628 | 3.11 | 0.66 |
| rs696081 | PCCB Intron13 (NM_000532.2) | 3 | 137,529,887 | 3.21 | 0.26 |
| rs2140450 | PPP2R3A Intron5 (NM_002718.3), PPP2R3A Intron4 (NM_181897.1) | 3 | 137,252,444 | 3.01 | 0.33 |

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs453570 | 0.55 | 1.68 | 2.88 | 3.30 | 1.85 |
| rs13096142 | 0.24 | 1.71 | 2.87 | 4.85 | 1.39 |
| rs696518 | 0.16 | 1.94 | 2.87 | 4.86 | 1.74 |
| rs6446245 | 0.54 | 1.65 | 2.80 | 3.11 | 2.26 |
| rs16833788 | 0.03 | 3.22 | 2.78 | ND | 3.29 |
| rs6440881 | 0.80 | 2.10 | 2.74 | 6.57 | 3.53 |
| rs10510568 | 0.52 | 1.67 | 2.70 | 2.90 | 1.58 |
| rs16833786 | 0.03 | 3.16 | 2.68 | ND | 3.23 |
| rs1545105 | 0.26 | 1.68 | 2.67 | 2.20 | 2.04 |
| rs9883170 | 0.26 | 1.69 | 2.64 | 2.26 | 2.00 |
| rs17016778 | 0.52 | 1.67 | 2.61 | 2.73 | 1.53 |
| rs2174746 | 0.83 | 2.26 | 2.61 | 5.02 | 2.39 |
| rs11712746 | 0.15 | 1.87 | 2.60 | 6.36 | 1.74 |
| rs684773 | 0.13 | 1.98 | 2.58 | 5.71 | 1.84 |
| rs695983 | 0.14 | 1.94 | 2.58 | 5.20 | 1.72 |
| rs1154988 | 0.13 | 1.98 | 2.55 | 5.68 | 1.85 |
| rs2232248 | 0.55 | 1.65 | 2.55 | 2.94 | 1.85 |
| rs696081 | 0.16 | 1.86 | 2.49 | 4.24 | 1.72 |
| rs2140450 | 0.23 | 1.72 | 2.47 | 3.87 | 1.50 |

TABLE 35

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs6440874 | LOC152118 −101011 bp (XM_098163) | 3 | 154,583,971 | 3.33 | 0.92 |
| rs9852831 | LOC152118 −133737 bp (XM_098163) | 3 | 154,551,245 | 3.19 | 0.90 |
| rs9822326 | LOC339894 Intron2 (XM_379230) | 3 | 158,286,267 | 3.17 | 0.54 |
| rs548288 | PCCB Intron1 (NM_000532.2) | 3 | 137,452,453 | 3.09 | 0.23 |
| rs7428299 | EDEM1 +469242 bp (XM_376201) | 3 | 5,705,884 | 3.02 | 0.68 |
| rs12648912 | PAPSS1 +17033 bp (NM_005443.4) | 4 | 108,875,394 | 3.91 | 0.64 |
| rs1865328 | LYAR +1510 bp (NM_017816.1) | 4 | 4,386,001 | 0.23 | 0.50 |
| rs531823 | QDPR +272295 bp (NM_000320.1) | 4 | 16,891,997 | 3.28 | 0.64 |
| rs2642849 | UGT2B4 +7559 bp (NM_021139.1) | 4 | 70,519,085 | 3.18 | 0.55 |
| rs2736463 | UGT2B4 +17920 bp (NM_021139.1) | 4 | 70,508,724 | 3.08 | 0.55 |
| rs11734419 | MAML3 Intron2 (NM_018717.2) | 4 | 141,040,368 | 3.22 | 0.46 |
| rs12502059 | PAPSS1 Intron4 (NM_005443.4) | 4 | 108,962,816 | 3.03 | 0.61 |
| rs4697446 | DHX15 +259479 bp (NM_001358.1) | 4 | 23,945,891 | 3.30 | 0.38 |
| rs7692155 | KIAA1109 −44906 bp (XM_371706) | 4 | 123,386,649 | 3.06 | 0.72 |

TABLE 35-continued

| | | | | | |
|---|---|---|---|---|---|
| rs17605639 | LOC389204 −297625 bp (XM_374079) | 4 | 27,290,099 | 3.09 | 0.80 |
| rs584374 | PPARGC1A −165848 bp (NM_013261.2) | 4 | 23,733,817 | 3.55 | 0.11 |
| rs17134333 | EPB41L4A Intron2 (NM_022140.2) | 5 | 111,670,626 | 2.67 | 0.71 |
| rs7718321 | EPB41L4A Intron1 (NM_022140.2) | 5 | 111,697,251 | 0.93 | 0.69 |
| rs7712363 | LOC389319 −181104 bp (XM_374134) | 5 | 125,542,548 | 1.03 | 0.76 |
| rs10076364 | LOC389319 −212764 bp (XM_374134) | 5 | 125,510,888 | 0.93 | 0.75 |
| rs7703461 | SV2C Intron3 (XM_043493) | 5 | 75,529,168 | 3.78 | 0.40 |
| rs194229 | MGC10067 −22589 bp (NM_145049.1) | 5 | 158,600,287 | 1.24 | 0.50 |
| rs10478702 | LOC389319 −173069 bp (XM_374134) | 5 | 125,550,583 | 1.04 | 0.76 |
| rs17134365 | EPB41L4A Intron1 (NM_022140.2) | 5 | 111,694,455 | 1.04 | 0.72 |
| rs11743891 | FSTL4 Intron3 (XM_048786) | 5 | 132,838,807 | 0.29 | 0.42 |
| rs166296 | SEMA6A Intron3 (NM_020796.2) | 5 | 115,861,466 | 3.48 | 0.38 |
| rs17731499 | KIBRA Intron1 (NM_015238.1) | 5 | 167,697,178 | 3.53 | 0.25 |

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs6440874 | 0.83 | 2.21 | 2.45 | 4.99 | 2.44 |
| rs9852831 | 0.82 | 2.08 | 2.43 | 5.05 | 2.57 |
| rs9822326 | 0.42 | 1.64 | 2.41 | 2.56 | 1.39 |
| rs548288 | 0.13 | 1.91 | 2.34 | 4.47 | 1.76 |
| rs7428299 | 0.56 | 1.64 | 2.27 | 2.67 | 1.81 |
| rs12648912 | 0.51 | 1.76 | 3.67 | 2.92 | 1.24 |
| rs1865328 | 0.48 | 1.08 | 3.41 | 1.21 | 0.48 |
| rs531823 | 0.51 | 1.67 | 2.94 | 1.78 | 0.67 |
| rs2642849 | 0.43 | 1.64 | 2.90 | 2.77 | 2.13 |
| rs2736463 | 0.43 | 1.63 | 2.86 | 2.72 | 2.15 |
| rs11734419 | 0.34 | 1.67 | 2.79 | 2.64 | 1.96 |
| rs12502059 | 0.49 | 1.64 | 2.75 | 2.62 | 1.22 |
| rs4697446 | 0.26 | 1.73 | 2.67 | 3.40 | 1.64 |
| rs7692155 | 0.61 | 1.67 | 2.60 | 3.39 | 2.28 |
| rs17605639 | 0.70 | 1.76 | 2.50 | 3.93 | 2.53 |
| rs584374 | 0.04 | 3.20 | 1.90 | 5.93 | 1.94 |
| rs17134333 | 0.60 | 1.63 | 3.71 | 1.80 | 0.69 |
| rs7718321 | 0.64 | 1.27 | 3.38 | 0.94 | 0.42 |
| rs7712363 | 0.71 | 1.32 | 3.38 | 0.59 | 0.28 |
| rs10076364 | 0.70 | 1.29 | 3.27 | 0.67 | 0.32 |
| rs7703461 | 0.27 | 1.80 | 3.27 | 3.99 | 1.35 |
| rs194229 | 0.43 | 1.32 | 3.20 | 1.57 | 2.53 |
| rs10478702 | 0.70 | 1.32 | 3.19 | 0.71 | 0.33 |
| rs17134365 | 0.66 | 1.30 | 3.12 | 0.92 | 0.42 |
| rs11743891 | 0.40 | 1.10 | 3.11 | 1.75 | 0.58 |
| rs166296 | 0.26 | 1.76 | 3.07 | 4.18 | 1.40 |
| rs17731499 | 0.14 | 1.97 | 3.04 | 9.22 | 1.51 |

TABLE 36

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs2055375 | LOC441075 +72079 bp (XM_499000) | 5 | 60,566,977 | 3.56 | 0.26 |
| rs1560026 | LOC389319 −225968 bp (XM_374134) | 5 | 125,497,684 | 0.82 | 0.74 |
| rs16869864 | PTGER4 −300343 bp (NM_000958.2) | 5 | 40,415,446 | 3.36 | 0.21 |
| rs7736074 | SLC6A19 −12310 bp (XM_291120) | 5 | 1,242,456 | 3.35 | 0.65 |
| rs581318 | LOC441075 +56653 bp (XM_499000) | 5 | 60,551,551 | 3.24 | 0.25 |
| rs30182 | SV2C −30159 bp (XM_043493) | 5 | 75,384,836 | 3.46 | 0.84 |
| rs7723981 | PTGER4 −275120 bp (NM_000958.2) | 5 | 40,440,669 | 3.16 | 0.20 |
| rs10473185 | PTGER4 −304865 bp (NM_000958.2) | 5 | 40,410,924 | 3.06 | 0.20 |
| rs10041973 | ZSWIM6 −51723 bp (XM_035299) | 5 | 60,612,035 | 3.19 | 0.11 |
| rs4958734 | GALNT10 Intron9 (NM_198321.2), GALNT10 Intron2 (NM_017540.3) | 5 | 153,769,698 | 3.05 | 0.94 |
| rs10079115 | ZSWIM6 −71664 bp (XM_035299) | 5 | 60,592,094 | 3.04 | 0.11 |
| rs4379148 | ZSWIM6 −72613 bp (XM_035299) | 5 | 60,591,145 | 3.03 | 0.11 |
| rs1501905 | SV2C Intron1 (XM_043493) | 5 | 75,433,640 | 3.04 | 0.79 |
| rs30196 | SV2C −1688 bp (XM_043493) | 5 | 75,413,307 | 3.06 | 0.78 |
| rs158563 | LOC91942 Intron1 (NM_174889.2) | 5 | 60,290,761 | 3.44 | 0.20 |
| rs10939888 | ZSWIM6 −72737 bp (XM_035299) | 5 | 60,591,021 | 3.00 | 0.14 |
| rs12696980 | ZSWIM6 −71733 bp (XM_035299) | 5 | 60,592,025 | 3.00 | 0.14 |
| rs2328883 | LRRC16 −108438 bp (NM_017640.2) | 6 | 25,510,510 | 1.85 | 0.33 |
| rs531970 | EPHA7 −35391 bp (NM_004440.2) | 6 | 94,221,384 | 1.06 | 0.46 |
| rs880226 | LRRC16 −108666 bp (NM_017640.2) | 6 | 25,510,282 | 2.02 | 0.33 |
| rs9469615 | MLN −45140 bp (NM_002418.1) | 6 | 33,924,911 | 1.24 | 0.86 |
| rs600709 | NCOA7 Intron2 (NM_181782.2) | 6 | 126,175,082 | 2.48 | 0.88 |

TABLE 36-continued

| DBSNP_ID | | Chromosome | Physical Location | Critical rate, Allele (-logP) | High-Risk Allele Frequency in Progressive Glaucoma Group |
|---|---|---|---|---|---|
| rs7767107 | LOC441173 Intron1 (XM_496827) | 6 | 142,237,572 | 3.49 | 0.30 |
| rs1336272 | LOC441173 −23126 bp (XM_496827) | 6 | 142,286,367 | 3.54 | 0.31 |
| rs595805 | NRN1 −34495 bp (NM_016588.2) | 6 | 5,987,127 | 1.27 | 0.65 |
| rs763075 | LOC442255 +235684 bp (XM_498140) | 6 | 122,253,219 | 0.20 | 0.71 |

| DBSNP_ID | High-Risk Allele Frequency in Nonprogressive Glaucoma Group | Odds Ratio (Formula 6) | Critical rate, Genotype (-logP) | Odds Ratio (Homozygote) (Formula 7) | Odds Ratio (Heterozygote) (Formula 8) |
|---|---|---|---|---|---|
| rs2055375 | 0.15 | 1.97 | 3.03 | 7.10 | 1.84 |
| rs1560026 | 0.69 | 1.26 | 3.00 | 0.67 | 0.33 |
| rs16869864 | 0.12 | 2.04 | 2.96 | 5.54 | 2.19 |
| rs7736074 | 0.52 | 1.69 | 2.76 | 3.00 | 2.07 |
| rs581318 | 0.15 | 1.89 | 2.75 | 6.89 | 1.73 |
| rs30182 | 0.73 | 1.89 | 2.74 | 4.40 | 2.54 |
| rs7723981 | 0.11 | 2.04 | 2.67 | 5.19 | 2.13 |
| rs10473185 | 0.11 | 2.00 | 2.58 | 5.23 | 2.09 |
| rs10041973 | 0.04 | 2.75 | 2.48 | ND | 2.55 |
| rs4958734 | 0.87 | 2.33 | 2.36 | 4.20 | 1.77 |
| rs10079115 | 0.04 | 2.68 | 2.34 | ND | 2.48 |
| rs4379148 | 0.04 | 2.75 | 2.32 | ND | 2.53 |
| rs1501905 | 0.68 | 1.73 | 2.29 | 3.12 | 1.94 |
| rs30196 | 0.67 | 1.72 | 2.25 | 2.77 | 1.65 |
| rs158563 | 0.10 | 2.19 | 2.19 | 4.28 | 1.69 |
| rs10939888 | 0.07 | 2.26 | 2.16 | 6.78 | 2.02 |
| rs12696980 | 0.07 | 2.26 | 2.16 | 6.78 | 2.02 |
| rs2328883 | 0.25 | 1.49 | 3.89 | 11.95 | 0.95 |
| rs531970 | 0.40 | 1.28 | 3.84 | 2.25 | 0.65 |
| rs880226 | 0.24 | 1.53 | 3.80 | 11.95 | 0.99 |
| rs9469615 | 0.81 | 1.45 | 3.52 | 0.18 | 0.08 |
| rs600709 | 0.80 | 1.80 | 3.48 | 0.39 | 0.16 |
| rs7767107 | 0.19 | 1.86 | 3.35 | 2.24 | 2.29 |
| rs1336272 | 0.19 | 1.86 | 3.31 | 2.37 | 2.25 |
| rs595805 | 0.58 | 1.33 | 3.31 | 1.29 | 0.54 |
| rs763075 | 0.69 | 1.08 | 3.23 | 0.41 | 0.22 |

TABLE 37

| DBSNP_ID | Exon, Intron | Chromosome | Physical Location | Critical rate, Allele (-logP) | High-Risk Allele Frequency in Progressive Glaucoma Group |
|---|---|---|---|---|---|
| rs13213414 | LOC441173 Intron1 (XM_496827) | 6 | 142,262,919 | 3.60 | 0.31 |
| rs16886390 | TMEM30A Intron1 (NM_018247.1) | 6 | 76,038,298 | 1.18 | 0.87 |
| rs1322867 | TBX18 −222373 bp (XM_496819) | 6 | 85,752,991 | 1.35 | 0.35 |
| rs2152589 | LOC441173 Intron1 (XM_496827) | 6 | 142,250,761 | 3.51 | 0.31 |
| rs3798425 | MYO6 Intron29 (XM_376516) | 6 | 76,664,270 | 2.57 | 0.83 |
| rs9496008 | LOC441173 +181779 bp (XM_496827) | 6 | 141,762,720 | 3.74 | 0.54 |
| rs9349248 | PHACTR1 −204207 bp (XM_166420) | 6 | 12,621,612 | 0.77 | 0.57 |
| rs12200432 | PHACTR1 −201248 bp (XM_166420) | 6 | 12,624,571 | 0.44 | 0.58 |
| rs6570564 | LOC285740 +20195 bp (XM_379438) | 6 | 143,896,965 | 3.35 | 0.52 |
| rs9399445 | LOC285740 +16163 bp (XM_379438) | 6 | 143,900,997 | 3.41 | 0.55 |
| rs4713376 | C6orf214 +7329 bp (NM_207496.1) | 6 | 30,881,293 | 3.37 | 0.17 |
| rs9484507 | LOC441173 +179848 bp (XM_496827) | 6 | 141,764,651 | 3.93 | 0.53 |
| rs9379712 | C6orf32 −187336 bp (NM_015864.2) | 6 | 25,172,898 | 3.15 | 0.59 |
| rs7754052 | LOC441173 Intron1 (XM_496827) | 6 | 142,254,496 | 3.20 | 0.32 |
| rs9496179 | LOC441173 Intron1 (XM_496827) | 6 | 142,254,945 | 3.20 | 0.32 |
| rs2039560 | LOC441173 +145925 bp (XM_496827) | 6 | 141,798,574 | 3.40 | 0.67 |
| rs10485223 | PRDM13 +130551 bp (NM_021620.2) | 6 | 100,300,726 | 3.31 | 0.79 |
| rs4240580 | PRDM13 +138012 bp (NM_021620.2) | 6 | 100,308,187 | 3.51 | 0.79 |
| rs9393611 | C6orf32 −188810 bp (NM_015864.2) | 6 | 25,174,372 | 3.03 | 0.59 |
| rs9356960 | C6orf32 −188588 bp (NM_015864.2) | 6 | 25,174,150 | 3.07 | 0.59 |
| rs9367520 | ELOVL5 Intron1 (NM_021814.2) | 6 | 53,271,883 | 3.41 | 0.35 |
| rs12195469 | C6orf214 Intron1 (NM_207496.1) | 6 | 30,897,587 | 3.21 | 0.16 |
| rs17826560 | PRDM13 +132124 bp (NM_021620.2) | 6 | 100,302,299 | 3.29 | 0.79 |
| rs1915463 | VMP −52946 bp (NM_080723.2) | 6 | 24,181,383 | 3.24 | 0.53 |
| rs17070891 | LOC441173 +153727 bp (XM_496827) | 6 | 141,790,772 | 3.27 | 0.55 |
| rs1402406 | VMP −35757 bp (NM_080723.2) | 6 | 24,198,572 | 3.06 | 0.57 |
| rs10947096 | C6orf214 +14748 bp (NM_207496.1) | 6 | 30,873,874 | 3.08 | 0.13 |

TABLE 37-continued

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs13213414 | 0.19 | 1.87 | 3.15 | 2.59 | 2.17 |
| rs16886390 | 0.82 | 1.47 | 3.14 | 0.78 | 0.27 |
| rs1322867 | 0.28 | 1.38 | 3.14 | 1.00 | 2.24 |
| rs2152589 | 0.20 | 1.85 | 3.14 | 2.52 | 2.17 |
| rs3798425 | 0.74 | 1.70 | 3.13 | 1.29 | 0.56 |
| rs9496008 | 0.40 | 1.73 | 3.04 | 3.06 | 1.62 |
| rs9349248 | 0.52 | 1.22 | 3.03 | 1.32 | 0.55 |
| rs12200432 | 0.55 | 1.14 | 3.01 | 1.09 | 0.49 |
| rs6570564 | 0.40 | 1.67 | 3.00 | 2.89 | 2.05 |
| rs9399445 | 0.42 | 1.68 | 2.97 | 2.98 | 2.01 |
| rs4713376 | 0.08 | 2.27 | 2.94 | 3.11 | 2.51 |
| rs9484507 | 0.39 | 1.80 | 2.93 | 2.98 | 1.58 |
| rs9379712 | 0.47 | 1.64 | 2.92 | 2.80 | 1.28 |
| rs7754052 | 0.21 | 1.77 | 2.88 | 2.37 | 2.09 |
| rs9496179 | 0.21 | 1.77 | 2.88 | 2.37 | 2.09 |
| rs2039560 | 0.54 | 1.70 | 2.84 | 3.04 | 1.71 |
| rs10485223 | 0.68 | 1.80 | 2.83 | 4.45 | 2.68 |
| rs4240580 | 0.68 | 1.82 | 2.81 | 3.79 | 2.25 |
| rs9393611 | 0.47 | 1.62 | 2.79 | 2.70 | 1.26 |
| rs9356960 | 0.47 | 1.63 | 2.78 | 2.81 | 1.33 |
| rs9367520 | 0.23 | 1.82 | 2.76 | 4.12 | 1.62 |
| rs12195469 | 0.08 | 2.22 | 2.75 | 3.06 | 2.43 |
| rs17826560 | 0.68 | 1.79 | 2.73 | 4.08 | 2.50 |
| rs1915463 | 0.41 | 1.66 | 2.61 | 2.72 | 1.84 |
| rs17070891 | 0.42 | 1.66 | 2.60 | 2.79 | 1.61 |
| rs1402406 | 0.45 | 1.62 | 2.59 | 2.63 | 2.00 |
| rs10947096 | 0.06 | 2.44 | 2.57 | ND | 2.47 |

TABLE 38

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs9403498 | FUCA2 −18431 bp (NM_032020.3) | 6 | 143,892,987 | 3.04 | 0.63 |
| rs1402405 | VMP −35853 bp (NM_080723.2) | 6 | 24,198,476 | 3.13 | 0.58 |
| rs7740547 | SLC22A16 Intron1 (NM_033125.2) | 6 | 110,897,601 | 3.13 | 0.49 |
| rs221712 | SLC22A16 Intron4 (NM_033125.2) | 6 | 110,869,519 | 3.18 | 0.49 |
| rs17577123 | C6orf10 +2945 bp (NM_006781.2) | 6 | 32,365,525 | 3.07 | 0.11 |
| rs7802749 | PPP1R9A Intron4 (XM_371933) | 7 | 94,432,292 | 1.20 | 0.53 |
| rs6965857 | DLD −36997 bp (NM_000108.2) | 7 | 107,068,565 | 0.76 | 0.65 |
| rs11972734 | CREB3L2 −6085 bp (NM_194071.1) | 7 | 137,150,143 | 3.19 | 0.26 |
| rs1621819 | C1GALT1 +30350 bp (NM_020156.1) | 7 | 7,087,571 | 3.80 | 0.61 |
| rs1514880 | LOC340268 Intron1 (XM_294634) | 7 | 9,664,527 | 3.39 | 0.60 |
| rs12669138 | LOC340268 Intron1 (XM_294634) | 7 | 9,564,997 | 2.83 | 0.65 |
| rs698408 | SND1 Intron8 (NM_014390.1) | 7 | 126,939,887 | 2.61 | 0.30 |
| rs7458284 | LOC340268 Intron1 (XM_294634) | 7 | 9,670,774 | 3.37 | 0.39 |
| rs3757760 | SND1 Intron16 (NM_014390.1) | 7 | 127,252,147 | 3.23 | 0.30 |
| rs2241291 | SND1 Intron16 (NM_014390.1), NAG8 Exon1 (NM_014411.1) | 7 | 127,232,825 | 3.27 | 0.30 |
| rs17156635 | CREB5 Intron1 (NM_182899.2), CREB5 −56415 bp (NM_182898.1), CREB5 −79505 bp (NM_004904.1) | 7 | 28,168,969 | 3.16 | 0.23 |
| rs1638213 | C1GALT1 +33234 bp (NM_020156.1) | 7 | 7,090,455 | 3.36 | 0.60 |
| rs320785 | LOC340268 −6464 bp (XM_294634) | 7 | 9,532,629 | 3.41 | 0.59 |
| rs1796121 | C1GALT1 +33624 bp (NM_020156.1) | 7 | 7,090,845 | 3.24 | 0.59 |
| rs3757759 | SND1 Intron16 (NM_014390.1) | 7 | 127,288,765 | 3.12 | 0.33 |
| rs12530870 | KIAA1706 −11363 bp (NM_030636.1) | 7 | 35,954,741 | 3.00 | 0.81 |
| rs17152703 | LOC401384 +195612 bp (XM_379506) | 7 | 78,929,412 | 3.33 | 0.85 |
| rs10441198 | LOC442363 −76453 bp (XM_498255) | 7 | 144,098,654 | 3.17 | 0.60 |

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs9403498 | 0.51 | 1.63 | 2.56 | 2.89 | 2.01 |
| rs1402405 | 0.45 | 1.63 | 2.53 | 2.63 | 1.91 |
| rs7740547 | 0.37 | 1.64 | 2.43 | 2.66 | 1.33 |
| rs221712 | 0.37 | 1.65 | 2.39 | 2.64 | 1.39 |
| rs17577123 | 0.04 | 2.71 | 1.95 | 3.88 | 2.47 |

TABLE 38-continued

|  |  |  |  |  |  |
|---|---|---|---|---|---|
| rs7802749 | 0.46 | 1.32 | 3.58 | 1.78 | 0.61 |
| rs6965857 | 0.60 | 1.23 | 3.13 | 1.00 | 0.45 |
| rs11972734 | 0.16 | 1.86 | 3.12 | 15.95 | 1.54 |
| rs1621819 | 0.47 | 1.76 | 3.11 | 3.14 | 2.03 |
| rs1514880 | 0.46 | 1.70 | 3.09 | 3.25 | 2.24 |
| rs12669138 | 0.54 | 1.60 | 3.08 | 3.15 | 2.74 |
| rs698408 | 0.21 | 1.66 | 3.03 | 1.55 | 2.28 |
| rs7458284 | 0.27 | 1.74 | 2.87 | 3.81 | 1.44 |
| rs3757760 | 0.19 | 1.81 | 2.85 | 2.51 | 2.08 |
| rs2241291 | 0.19 | 1.81 | 2.81 | 2.63 | 2.04 |
| rs17156635 | 0.13 | 1.99 | 2.80 | 14.75 | 1.50 |
| rs1638213 | 0.47 | 1.67 | 2.72 | 2.82 | 1.90 |
| rs320785 | 0.46 | 1.68 | 2.71 | 2.84 | 1.73 |
| rs1796121 | 0.47 | 1.65 | 2.58 | 2.74 | 1.84 |
| rs3757759 | 0.22 | 1.74 | 2.57 | 3.27 | 1.80 |
| rs12530870 | 0.71 | 1.76 | 2.42 | 3.98 | 2.76 |
| rs17152703 | 0.75 | 1.89 | 2.37 | 3.41 | 2.01 |
| rs10441198 | 0.48 | 1.64 | 2.36 | 2.41 | 1.33 |

TABLE 39

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs13225076 | LOC285984 −162101 bp (XM_208373) | 7 | 84,095,361 | 3.16 | 0.86 |
| rs17171658 | C7orf11 +13816 bp (NM_138701.1) | 7 | 39,931,767 | 3.02 | 0.78 |
| rs826824 | CNTNAP2 Intron9 (NM_014141.3) | 7 | 146,496,639 | 3.04 | 0.74 |
| rs6993934 | FBXO16 +12541 bp (NM_172366.2) | 8 | 28,329,307 | 0.01 | 0.27 |
| rs1425735 | EBF2 +148803 bp (NM_022659.1) | 8 | 25,608,687 | 1.50 | 0.66 |
| rs6991277 | PTDSS1 +53377 bp (NM_014754.1) | 8 | 97,469,327 | 3.10 | 0.93 |
| rs6981589 | LOC286186 Intron1 (XM_379586) | 8 | 66,612,011 | 2.30 | 0.66 |
| rs4394361 | LOC157657 −172125 bp (NM_177965.2) | 8 | 96,522,738 | 3.55 | 0.24 |
| rs3133744 | LOC157657 −252889 bp (NM_177965.2) | 8 | 96,603,502 | 3.53 | 0.31 |
| rs10113800 | LOC157657 −163565 bp (NM_177965.2) | 8 | 96,514,178 | 3.12 | 0.23 |
| rs6601569 | C8orf7 −14730 bp (XM_088376) | 8 | 11,110,988 | 3.45 | 0.93 |
| rs10105301 | LOC286186 +84181 bp (XM_379586) | 8 | 66,517,616 | 3.04 | 0.27 |
| rs6995270 | SIAT4A Intron2 (NM_003033.2), SIAT4A Intron2 (NM_173344.1) | 8 | 134,582,401 | 3.02 | 0.51 |
| rs10811638 | CDKN2A +44473 bp (NM_000077.3), CDKN2A +44473 bp (NM_058197.2), CDKN2A +44473 bp (NM_058195.2) | 9 | 21,913,279 | 0.15 | 0.42 |
| rs10869589 | PCSK5 −314572 bp (NM_006200.2) | 9 | 75,420,603 | 2.09 | 0.72 |
| rs10967964 | MOBKL2B Intron1 (NM_024761.3) | 9 | 27,485,920 | 3.13 | 0.23 |
| rs2518713 | CDKN2A +38086 bp (NM_000077.3), CDKN2A +38086 bp (NM_058197.2), CDKN2A +38086 bp (NM_058195.2) | 9 | 21,919,666 | 0.38 | 0.44 |
| rs10781440 | LOC392347 Intron1 (XM_373298) | 9 | 68,992,320 | 3.89 | 0.37 |
| rs1412066 | DBC1 −33786 bp (NM_014618.1) | 9 | 119,245,041 | 3.06 | 0.93 |
| rs7022939 | LOC347273 +139903 bp (XM_294592) | 9 | 100,568,349 | 1.91 | 0.36 |
| rs4744780 | PCSK5 Intron9 (NM_006200.2) | 9 | 75,952,602 | 3.30 | 0.50 |

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs13225076 | 0.76 | 1.93 | 2.31 | 3.53 | 1.92 |
| rs17171658 | 0.67 | 1.75 | 2.31 | 2.98 | 1.70 |
| rs826824 | 0.63 | 1.69 | 2.26 | 2.60 | 1.52 |
| rs6993934 | 0.27 | 1.00 | 3.56 | 0.37 | 1.81 |
| rs1425735 | 0.58 | 1.38 | 3.28 | 1.37 | 0.57 |
| rs6991277 | 0.85 | 2.28 | 3.26 | 0.74 | 0.26 |
| rs6981589 | 0.56 | 1.52 | 3.13 | 2.85 | 3.04 |
| rs4394361 | 0.13 | 2.04 | 3.09 | 10.03 | 1.97 |
| rs3133744 | 0.19 | 1.90 | 2.97 | 4.79 | 1.84 |
| rs10113800 | 0.14 | 1.92 | 2.70 | 10.58 | 1.76 |
| rs6601569 | 0.85 | 2.32 | 2.66 | 7.14 | 3.26 |
| rs10105301 | 0.17 | 1.81 | 2.63 | 2.22 | 2.10 |
| rs6995270 | 0.39 | 1.62 | 2.37 | 2.71 | 1.49 |
| rs10811638 | 0.41 | 1.06 | 3.80 | 0.84 | 2.27 |
| rs10869589 | 0.63 | 1.52 | 3.59 | 5.09 | 5.18 |
| rs10967964 | 0.13 | 1.95 | 3.55 | 1.34 | 2.62 |
| rs2518713 | 0.41 | 1.13 | 3.39 | 1.01 | 2.32 |
| rs10781440 | 0.24 | 1.85 | 3.34 | 3.48 | 1.97 |
| rs1412066 | 0.85 | 2.19 | 3.25 | 0.97 | 0.35 |

TABLE 39-continued

| | | | | | |
|---|---|---|---|---|---|
| rs7022939 | 0.28 | 1.48 | 3.21 | 1.32 | 2.30 |
| rs4744780 | 0.37 | 1.68 | 3.18 | 2.85 | 2.21 |

TABLE 40

| DBSNP_ID | Exon, Intron | Chromosome | Physical Location | Critical rate, Allele (−logP) | High-Risk Allele Frequency in Progressive Glaucoma Group |
|---|---|---|---|---|---|
| rs4743420 | LOC347273 +139198 bp (XM_294592) | 9 | 100,567,644 | 1.93 | 0.36 |
| rs10815959 | PTPRD −82533 bp (NM_002839.1), PTPRD −82533 bp (NM_130391.1), PTPRD −82533 bp (NM_130392.1), PTPRD −82533 bp (NM_130393.1) | 9 | 8,806,479 | 3.11 | 0.58 |
| rs953924 | FLJ31810 Intron3 (NM_152570.1) | 9 | 28,313,673 | 2.54 | 0.85 |
| rs4836767 | DBC1 −34887 bp (NM_014618.1) | 9 | 119,246,142 | 3.24 | 0.93 |
| rs4977749 | CDKN2A +40425 bp (NM_000077.3), CDKN2A +40425 bp (NM_058197.2), CDKN2A +40425 bp (NM_058195.2) | 9 | 21,917,327 | 0.38 | 0.44 |
| rs10512277 | LOC347273 +138909 bp (XM_294592) | 9 | 100,567,355 | 2.02 | 0.36 |
| rs9299341 | LOC347273 +141993 bp (XM_294592) | 9 | 100,570,439 | 2.02 | 0.36 |
| rs10491692 | DOCK8 Intron13 (NM_203447.1) | 9 | 336,887 | 0.35 | 0.16 |
| rs2780197 | C9orf39 Intron13 (NM_017738.1) | 9 | 17,416,186 | 3.83 | 0.81 |
| rs7038186 | C9orf39 Intron10 (NM_017738.1) | 9 | 17,388,616 | 3.69 | 0.81 |
| rs2773395 | C9orf28 −119663 bp (XM_088525) | 9 | 126,049,019 | 3.39 | 0.36 |
| rs1412067 | DBC1 −35540 bp (NM_014618.1) | 9 | 119,246,795 | 3.08 | 0.93 |
| rs11144406 | OSTF1 +226491 bp (NM_012383.3) | 9 | 75,217,808 | 3.39 | 0.20 |
| rs10869690 | PIP5K1B Intron15 (NM_003558.1) | 9 | 68,851,241 | 3.37 | 0.38 |
| rs10969339 | LOC401497 +655774 bp (XM_376822) | 9 | 29,723,159 | 3.13 | 0.88 |
| rs16929359 | DMRT2 +392458 bp (NM_006557.3), DMRT2 +392458 bp (NM_181872.1) | 9 | 1,440,010 | 3.62 | 0.11 |
| rs943509 | OSTF1 +226788 bp (NM_012383.3) | 9 | 75,218,105 | 3.18 | 0.37 |
| rs10869686 | PIP5K1B Intron15 (NM_003558.1) | 9 | 68,850,168 | 3.22 | 0.37 |
| rs10869553 | OSTF1 +235138 bp (NM_012383.3) | 9 | 75,226,455 | 3.09 | 0.20 |
| rs12554461 | RCL1 +4195 bp (NM_005772.2) | 9 | 4,855,256 | 3.19 | 0.41 |
| rs4142436 | DMRT2 +396648 bp (NM_006557.3), DMRT2 +396648 bp (NM_181872.1) | 9 | 1,444,200 | 3.23 | 0.13 |

| DBSNP_ID | High-Risk Allele Frequency in Nonprogressive Glaucoma Group | Odds Ratio (Formula 6) | Critical rate, Genotype (−logP) | Odds Ratio (Homozygote) (Formula 7) | Odds Ratio (Heterozygote) (Formula 8) |
|---|---|---|---|---|---|
| rs4743420 | 0.27 | 1.49 | 3.17 | 1.33 | 2.29 |
| rs10815959 | 0.46 | 1.63 | 3.15 | 2.73 | 2.41 |
| rs953924 | 0.77 | 1.74 | 3.10 | 18.06 | 14.20 |
| rs4836767 | 0.85 | 2.24 | 3.09 | 1.46 | 0.53 |
| rs4977749 | 0.41 | 1.13 | 3.09 | 1.02 | 2.22 |
| rs10512277 | 0.27 | 1.50 | 3.08 | 1.41 | 2.27 |
| rs9299341 | 0.27 | 1.50 | 3.08 | 1.41 | 2.27 |
| rs10491692 | 0.14 | 1.17 | 3.08 | 0.00 | 1.80 |
| rs2780197 | 0.70 | 1.90 | 3.05 | 3.93 | 2.16 |
| rs7038186 | 0.69 | 1.87 | 2.96 | 3.91 | 2.20 |
| rs2773395 | 0.24 | 1.77 | 2.94 | 2.98 | 1.97 |
| rs1412067 | 0.85 | 2.20 | 2.92 | 1.45 | 0.54 |
| rs11144406 | 0.11 | 2.10 | 2.91 | 5.39 | 2.22 |
| rs10869690 | 0.26 | 1.74 | 2.85 | 3.90 | 1.51 |
| rs10969339 | 0.79 | 1.95 | 2.77 | 11.71 | 6.74 |
| rs16929359 | 0.04 | 3.02 | 2.70 | ND | 2.53 |
| rs943509 | 0.25 | 1.72 | 2.70 | 3.80 | 1.45 |
| rs10869686 | 0.26 | 1.73 | 2.68 | 3.74 | 1.52 |
| rs10869553 | 0.11 | 2.01 | 2.62 | 5.19 | 2.10 |
| rs12554461 | 0.29 | 1.69 | 2.60 | 2.49 | 1.90 |
| rs4142436 | 0.06 | 2.49 | 2.54 | 3.92 | 2.56 |

TABLE 41

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs7048937 | LOC392347 Intron2 (XM_373298) | 9 | 68,975,807 | 3.16 | 0.38 | 0.27 |
| rs7034303 | LOC392347 Intron2 (XM_373298) | 9 | 68,976,425 | 3.16 | 0.38 | 0.27 |
| rs6560584 | LOC392347 Intron2 (XM_373298) | 9 | 68,976,726 | 3.16 | 0.38 | 0.27 |
| rs7850573 | LOC392347 Intron2 (XM_373298) | 9 | 68,976,814 | 3.16 | 0.38 | 0.27 |
| rs2584554 | C9orf39 Intron13 (NM_017738.1) | 9 | 17,416,808 | 3.13 | 0.80 | 0.70 |
| rs1547335 | LOC401497 +621065 bp (XM_376822) | 9 | 29,757,868 | 3.11 | 0.77 | 0.66 |
| rs3781158 | KCNMA1 Intron18 (NM_002247.2) | 10 | 78,426,444 | 1.61 | 0.60 | 0.51 |
| rs10823349 | HK1 Intron5 (NM_033497.1), HK1 Intron5 (NM_033498.1), HK1 Intron6 (NM_033500.1), HK1 Intron2 (NM_033496.1), HK1 Intron2 (NM_000188.1) | 10 | 70,779,704 | 3.56 | 0.90 | 0.80 |
| rs17388160 | KCNMA1 Intron18 (NM_002247.2) | 10 | 78,415,943 | 1.81 | 0.66 | 0.57 |
| rs1801041 | DNA2L Exon21 (XM_166103) | 10 | 69,844,713 | 1.49 | 0.80 | 0.73 |
| rs11001963 | KCNMA1 Intron18 (NM_002247.2) | 10 | 78,430,965 | 2.23 | 0.70 | 0.60 |
| rs4454609 | PHYH +15499 bp (NM_006214.2) | 10 | 13,344,307 | 2.46 | 0.66 | 0.55 |
| rs4589168 | HK1 Intron10 (NM_033497.1), HK1 Intron10 (NM_033498.1), HK1 Intron11 (NM_033500.1), HK1 Intron7 (NM_033496.1), HK1 Intron7 (NM_000188.1) | 10 | 70,800,223 | 3.18 | 0.89 | 0.81 |
| rs7093891 | XPNPEP1 +21493 bp (NM_020383.2) | 10 | 111,593,021 | 3.00 | 0.69 | 0.57 |
| rs10762840 | LOC283050 Intron4 (XM_378238) | 10 | 80,483,339 | 3.86 | 0.39 | 0.26 |
| rs9416465 | ZWINT +273128 bp (NM_007057.2), ZWINT +273128 bp (NM_032997.1) | 10 | 57,514,084 | 3.32 | 0.82 | 0.71 |
| rs7903897 | LOC285444 +40505 bp (XM_497256) | 10 | 135,321,566 | 3.05 | 0.61 | 0.49 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs7048937 | 1.70 | 2.52 | 2.57 | 1.85 |
| rs7034303 | 1.70 | 2.52 | 2.57 | 1.85 |
| rs6560584 | 1.70 | 2.52 | 2.57 | 1.85 |
| rs7850573 | 1.70 | 2.52 | 2.57 | 1.85 |
| rs2584554 | 1.78 | 2.50 | 3.38 | 1.91 |
| rs1547335 | 1.73 | 2.25 | 2.90 | 1.82 |
| rs3781158 | 1.39 | 3.96 | 1.65 | 0.59 |
| rs10823349 | 2.13 | 3.90 | 1.05 | 0.39 |
| rs17388160 | 1.44 | 3.79 | 1.47 | 0.57 |
| rs1801041 | 1.45 | 3.58 | 0.78 | 0.33 |
| rs11001963 | 1.52 | 3.57 | 1.55 | 0.63 |
| rs4454609 | 1.55 | 3.56 | 3.42 | 3.45 |
| rs4589168 | 2.01 | 3.45 | 1.15 | 0.45 |
| rs7093891 | 1.64 | 3.31 | 2.15 | 0.92 |
| rs10762840 | 1.81 | 3.12 | 3.29 | 1.83 |
| rs9416465 | 1.85 | 2.78 | 3.55 | 1.81 |
| rs7903897 | 1.63 | 2.72 | 2.68 | 2.21 |

TABLE 42

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs2496057 | C10orf112 Intron20 (XM_295865) | 10 | 19,623,674 | 3.05 | 0.56 | 0.44 |
| rs1500763 | ZWINT +308458 bp (NM_007057.2), ZWINT +308458 bp (NM_032997.1) | 10 | 57,478,754 | 3.03 | 0.86 | 0.77 |
| rs2151078 | PCDH15 Intron3 (NM_033056.2) | 10 | 55,864,965 | 3.11 | 0.95 | 0.88 |
| rs1881716 | LDHA Intron5 (NM_005566.1) | 11 | 18,381,594 | 3.40 | 0.38 | 0.26 |
| rs7107489 | LOC119710 +809442 bp (NM_138787.2) | 11 | 37,446,835 | 1.46 | 0.65 | 0.58 |
| rs6590698 | SPAS1 +396277 bp (NM_174927.1) | 11 | 132,819,450 | 1.09 | 0.72 | 0.66 |
| rs4274186 | LDHA Intron2 (NM_005566.1) | 11 | 18,375,295 | 3.41 | 0.38 | 0.26 |
| rs7927545 | MGC71806 Intron3 (NM_198516.1) | 11 | 11,403,040 | 3.75 | 0.60 | 0.46 |
| rs10792820 | PICALM Intron12 (NM_007166.1) | 11 | 85,381,622 | 0.44 | 0.49 | 0.46 |
| rs9326253 | LOC440070 +34118 bp (XM_498530) | 11 | 119,149,661 | 0.13 | 0.60 | 0.59 |
| rs12576681 | MGC71806 Intron3 (NM_198516.1) | 11 | 11,402,663 | 3.67 | 0.31 | 0.19 |
| rs10837846 | LOC387761 −159308 bp (XM_373495) | 11 | 42,393,594 | 2.69 | 0.59 | 0.47 |
| rs1462674 | LOC387761 −160223 bp (XM_373495) | 11 | 42,394,509 | 2.71 | 0.59 | 0.47 |
| rs1386239 | LOC338645 Intron5 (XM_370616) | 11 | 24,774,285 | 2.73 | 0.11 | 0.05 |
| rs10837854 | LOC387761 −227349 bp (XM_373495) | 11 | 42,461,635 | 2.09 | 0.56 | 0.47 |

TABLE 42-continued

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs504105 | FLJ37874 +3946 bp (NM_182603.1) | 11 | 82,641,607 | 3.17 | 0.57 | 0.45 |
| rs524441 | FLJ37874 +1045 bp (NM_182603.1) | 11 | 82,638,706 | 3.11 | 0.56 | 0.44 |
| rs681367 | FLJ37874 +1111 bp (NM_182603.1) | 11 | 82,638,772 | 3.10 | 0.56 | 0.44 |
| rs628223 | MDS025 +4340 bp (NM_021825.3) | 11 | 82,645,812 | 3.10 | 0.56 | 0.44 |
| rs6484897 | MGC71806 Intron3 (NM_198516.1) | 11 | 11,401,879 | 3.15 | 0.31 | 0.20 |
| rs4937173 | KIRREL3 Intron1 (NM_032531.1) | 11 | 126,034,466 | 3.37 | 0.43 | 0.31 |
| rs11220587 | KIRREL3 Intron1 (NM_032531.1) | 11 | 126,082,725 | 3.35 | 0.50 | 0.37 |
| rs2252070 | MMP13 −77 bp (NM_002427.2) | 11 | 102,331,749 | 3.46 | 0.60 | 0.47 |
| rs693253 | KIRREL3 Intron1 (NM_032531.1) | 11 | 126,032,975 | 3.40 | 0.44 | 0.31 |
| rs4937174 | KIRREL3 Intron1 (NM_032531.1) | 11 | 126,034,593 | 3.21 | 0.43 | 0.31 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs2496057 | 1.62 | 2.57 | 2.75 | 1.90 |
| rs1500763 | 1.88 | 2.54 | 5.27 | 2.80 |
| rs2151078 | 2.49 | 2.21 | 3.40 | 1.37 |
| rs1881716 | 1.74 | 3.86 | 2.09 | 2.48 |
| rs7107489 | 1.37 | 3.69 | 2.69 | 3.66 |
| rs6590698 | 1.32 | 3.60 | 5.44 | 6.70 |
| rs4274186 | 1.76 | 3.58 | 2.15 | 2.41 |
| rs7927545 | 1.73 | 3.58 | 3.11 | 1.30 |
| rs10792820 | 1.15 | 3.46 | 1.48 | 0.53 |
| rs9326253 | 1.05 | 3.27 | 0.73 | 0.36 |
| rs12576681 | 1.88 | 3.23 | 6.26 | 1.53 |
| rs10837846 | 1.57 | 3.09 | 3.22 | 2.55 |
| rs1462674 | 1.57 | 3.07 | 3.22 | 2.53 |
| rs1386239 | 2.48 | 3.06 | 0.00 | 3.10 |
| rs10837854 | 1.47 | 3.05 | 2.58 | 2.69 |
| rs504105 | 1.64 | 3.05 | 2.97 | 1.30 |
| rs524441 | 1.63 | 2.93 | 2.90 | 1.29 |
| rs681367 | 1.63 | 2.91 | 2.90 | 1.31 |
| rs628223 | 1.63 | 2.91 | 2.90 | 1.31 |
| rs6484897 | 1.78 | 2.90 | 5.97 | 1.41 |
| rs4937173 | 1.71 | 2.90 | 2.75 | 1.96 |
| rs11220587 | 1.68 | 2.88 | 2.99 | 1.31 |
| rs2252070 | 1.69 | 2.82 | 2.88 | 1.55 |
| rs693253 | 1.71 | 2.77 | 2.85 | 1.82 |
| rs4937174 | 1.68 | 2.74 | 2.66 | 1.92 |

TABLE 43

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs12800710 | LPXN Intron7 (NM_004811.1) | 11 | 58,071,116 | 3.73 | 0.87 | 0.77 |
| rs10898459 | EED Intron6 (NM_003797.2), EED Intron6 (NM_152991.1) | 11 | 85,650,587 | 3.14 | 0.60 | 0.48 |
| rs3862632 | KIRREL3 Intron1 (NM_032531.1) | 11 | 126,054,713 | 3.21 | 0.43 | 0.31 |
| rs11229555 | CNTF +15485 bp (NM_000614.2), ZFP91-CNTF +15485 bp (NM_170768.1) | 11 | 58,165,263 | 3.57 | 0.87 | 0.77 |
| rs1451316 | OR1S2 +1990 bp (XM_166916) | 11 | 57,725,262 | 3.06 | 0.53 | 0.41 |
| rs7108068 | KIRREL3 Intron1 (NM_032531.1) | 11 | 126,035,753 | 3.18 | 0.43 | 0.31 |
| rs10896715 | OR1S1 +5325 bp (XM_166917) | 11 | 57,745,095 | 3.38 | 0.84 | 0.74 |
| rs2298608 | CNTF +11265 bp (NM_000614.2), ZFP91-CNTF +11265 bp (NM_170768.1) | 11 | 58,161,043 | 3.47 | 0.87 | 0.77 |
| rs655316 | MMP13 −5902 bp (NM_002427.2) | 11 | 102,337,574 | 3.07 | 0.58 | 0.46 |
| rs161130 | LOC387810 −172677 bp (XM_373513) | 11 | 112,160,184 | 3.15 | 0.83 | 0.73 |
| rs7102784 | LOC399898 +878 bp (XM_374885) | 11 | 57,813,314 | 3.08 | 0.88 | 0.79 |
| rs11175627 | LOC400046 +33814 bp (XM_378362) | 12 | 63,691,379 | 3.08 | 0.27 | 0.17 |
| rs7302136 | DKFZp761O2018 +35186 bp (XM_044062) | 12 | 127,752,520 | 3.91 | 0.94 | 0.85 |
| rs11175622 | LOC400046 +28983 bp (XM_378362) | 12 | 63,686,548 | 2.98 | 0.27 | 0.17 |
| rs7136577 | LOC400046 +35244 bp (XM_378362) | 12 | 63,692,809 | 2.98 | 0.27 | 0.17 |
| rs2169856 | LOC441639 +48092 bp (XM_497345) | 12 | 53,858,919 | 1.26 | 0.72 | 0.66 |
| rs7962260 | FLJ40126 Intron18 (NM_173599.1), SLC2A13 Intron6 (NM_052885.1) | 12 | 38,510,570 | 3.77 | 0.24 | 0.13 |
| rs7296095 | LOC440112 −115952 bp (XM_498548) | 12 | 114,337,597 | 2.55 | 0.28 | 0.19 |
| rs7959848 | LOC401725 +200037 bp (XM_377278) | 12 | 82,248,474 | 3.88 | 0.45 | 0.32 |
| rs12227382 | DKFZp761O2018 +36420 bp (XM_044062) | 12 | 127,753,754 | 3.72 | 0.94 | 0.85 |
| rs11059865 | DKFZp761O2018 +34801 bp (XM_044062) | 12 | 127,752,135 | 3.58 | 0.94 | 0.86 |
| rs4882448 | LOC401725 +200630 bp (XM_377278) | 12 | 82,249,067 | 3.62 | 0.44 | 0.31 |
| rs4473002 | FLJ40126 Intron18 (NM_173599.1), SLC2A13 Intron6 (NM_052885.1) | 12 | 38,541,898 | 3.40 | 0.24 | 0.14 |

TABLE 43-continued

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs12800710 | 2.04 | 2.73 | 3.91 | 2.08 |
| rs10898459 | 1.64 | 2.72 | 2.89 | 2.06 |
| rs3862632 | 1.68 | 2.66 | 2.70 | 1.86 |
| rs11229555 | 2.01 | 2.59 | 3.88 | 2.12 |
| rs1451316 | 1.63 | 2.58 | 2.53 | 1.97 |
| rs7108068 | 1.67 | 2.58 | 2.74 | 1.79 |
| rs10896715 | 1.88 | 2.51 | 3.08 | 1.65 |
| rs2298608 | 1.99 | 2.51 | 3.83 | 2.12 |
| rs655316 | 1.62 | 2.49 | 2.74 | 1.57 |
| rs161130 | 1.83 | 2.35 | 3.18 | 1.78 |
| rs7102784 | 1.94 | 2.25 | 3.65 | 1.98 |
| rs11175627 | 1.83 | 3.15 | 16.90 | 1.47 |
| rs7302136 | 2.54 | 3.13 | 5.80 | 2.27 |
| rs11175622 | 1.79 | 3.10 | 16.58 | 1.46 |
| rs7136577 | 1.79 | 3.10 | 16.58 | 1.46 |
| rs2169856 | 1.35 | 3.06 | 0.97 | 0.45 |
| rs7962260 | 2.07 | 3.05 | 8.32 | 1.68 |
| rs7296095 | 1.68 | 3.05 | 10.32 | 1.19 |
| rs7959848 | 1.79 | 3.02 | 3.10 | 1.75 |
| rs12227382 | 2.48 | 2.94 | 5.75 | 2.33 |
| rs11059865 | 2.48 | 2.92 | 4.34 | 1.67 |
| rs4882448 | 1.76 | 2.85 | 3.01 | 1.76 |
| rs4473002 | 1.97 | 2.82 | 8.19 | 1.58 |

TABLE 44

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs7968509 | FLJ40126 Intron18 (NM_173599.1), SLC2A13 Intron6 (NM_052885.1) | 12 | 38,541,115 | 3.46 | 0.24 | 0.13 |
| rs7956512 | LOC401725 +199585 bp (XM_377278) | 12 | 82,248,022 | 3.71 | 0.46 | 0.32 |
| rs4768188 | FLJ40126 Intron18 (NM_173599.1), SLC2A13 Intron7 (NM_052885.1) | 12 | 38,507,445 | 3.46 | 0.25 | 0.15 |
| rs10877835 | SLC2A13 Intron3 (NM_052885.1) | 12 | 38,637,759 | 3.13 | 0.15 | 0.07 |
| rs11116586 | SLC6A15 +106086 bp (NM_182767.2), SLC6A15 +127822 bp (NM_018057.3) | 12 | 83,650,812 | 3.08 | 0.73 | 0.62 |
| rs908440 | TRHDE +374236 bp (NM_013381.1) | 12 | 71,719,925 | 3.11 | 0.73 | 0.62 |
| rs7485210 | LOC116437 −10703 bp (XM_378394) | 12 | 130,163,733 | 3.19 | 0.57 | 0.45 |
| rs10862927 | SLC6A15 +113194 bp (NM_182767.2), SLC6A15 +134930 bp (NM_018057.3) | 12 | 83,643,704 | 3.01 | 0.73 | 0.62 |
| rs4765680 | CACNA1C Intron3 (NM_000719.3) | 12 | 2,427,360 | 3.03 | 0.96 | 0.90 |
| rs4643164 | LOC122335 −355849 bp (XM_063084) | 13 | 106,724,352 | 0.88 | 0.38 | 0.33 |
| rs2802402 | HTR2A −215185 bp (NM_000621.1) | 13 | 46,583,361 | 2.21 | 0.30 | 0.21 |
| rs17640758 | DNAJD1 +11297 bp (NM_013238.1) | 13 | 42,590,879 | 2.16 | 0.14 | 0.08 |
| rs2282267 | CLMN Intron12 (NM_024734.2) | 14 | 94,729,648 | 3.75 | 0.69 | 0.55 |
| rs2208986 | SLC35F4 −84786 bp (XM_292260) | 14 | 57,218,154 | 0.82 | 0.76 | 0.71 |
| rs4304940 | SLC35F4 −89221 bp (XM_292260) | 14 | 57,222,589 | 0.84 | 0.75 | 0.71 |
| rs1028591 | LOC283547 −65737 bp (XM_378454) | 14 | 38,495,490 | 0.43 | 0.64 | 0.61 |
| rs7148801 | AKAP6 Intron7 (NM_004274.3) | 14 | 32,206,647 | 3.68 | 0.95 | 0.88 |
| rs3180753 | CLMN Intron12 (NM_024734.2) | 14 | 94,729,500 | 3.64 | 0.68 | 0.55 |
| rs2150324 | OR4L1 −2371 bp (XM_063310) | 14 | 19,595,673 | 0.29 | 0.54 | 0.52 |
| rs10483416 | AKAP6 Intron7 (NM_004274.3) | 14 | 32,145,585 | 3.27 | 0.81 | 0.70 |
| rs6571593 | NPAS3 Intron2 (NM_022123.1), NPAS3 Intron3 (NM_173159.1) | 14 | 32,865,564 | 3.22 | 0.48 | 0.36 |
| rs2282273 | CLMN Intron11 (NM_024734.2) | 14 | 94,730,437 | 3.41 | 0.66 | 0.54 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs7968509 | 1.99 | 2.82 | 7.74 | 1.66 |
| rs7956512 | 1.75 | 2.79 | 2.82 | 1.72 |
| rs4768188 | 2.01 | 2.69 | 6.02 | 1.63 |
| rs10877835 | 2.28 | 2.50 | 4.03 | 2.36 |
| rs11116586 | 1.68 | 2.48 | 2.41 | 1.27 |
| rs908440 | 1.69 | 2.48 | 3.10 | 1.95 |
| rs7485210 | 1.64 | 2.46 | 2.66 | 1.59 |
| rs10862927 | 1.67 | 2.40 | 2.40 | 1.29 |
| rs4765680 | 2.66 | 2.38 | ND | ND |

TABLE 44-continued

| | | | | | |
|---|---|---|---|---|---|
| | rs4643164 | 1.26 | 3.63 | 3.26 | 0.70 |
| | rs2802402 | 1.59 | 3.39 | 1.16 | 2.38 |
| | rs17640758 | 1.91 | 3.07 | 0.00 | 2.48 |
| | rs2282267 | 1.76 | 3.33 | 3.22 | 1.59 |
| | rs2208986 | 1.26 | 3.29 | 0.70 | 0.33 |
| | rs4304940 | 1.27 | 3.22 | 0.72 | 0.34 |
| | rs1028591 | 1.14 | 3.20 | 0.82 | 0.39 |
| | rs7148801 | 2.80 | 3.18 | 2.11 | 0.64 |
| | rs3180753 | 1.74 | 3.11 | 3.01 | 1.53 |
| | rs2150324 | 1.10 | 3.07 | 1.11 | 0.49 |
| | rs10483416 | 1.79 | 2.95 | 2.07 | 0.95 |
| | rs6571593 | 1.67 | 2.93 | 2.02 | 2.29 |
| | rs2282273 | 1.70 | 2.91 | 3.07 | 1.66 |

TABLE 45

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs1622029 | LOC283583 −1366892 bp (XM_211092) | 14 | 83,697,804 | 3.52 | 0.71 | 0.58 |
| rs8003168 | RGS6 −36445 bp (NM_004296.3) | 14 | 71,433,141 | 3.09 | 0.47 | 0.35 |
| rs10498642 | DICER1 Intron9 (NM_030621.2), DICER1 Intron8 (NM_177438.1) | 14 | 94,658,292 | 3.42 | 0.62 | 0.49 |
| rs9646147 | LRFN5 −190930 bp (NM_152447.2) | 14 | 40,956,160 | 3.19 | 0.92 | 0.84 |
| rs1187627 | CLMN Intron9 (NM_024734.2) | 14 | 94,734,482 | 3.50 | 0.59 | 0.46 |
| SNP_A-18219 | MAMDC1 −1035952 bp (NM_182830.2) | 14 | 47,918,097 | 3.37 | 0.59 | 0.47 |
| rs14042 | FLJ45244 Exon2 (NM_207443.1) | 14 | 94,715,773 | 3.38 | 0.56 | 0.43 |
| rs1187626 | CLMN Intron9 (NM_024734.2) | 14 | 94,735,610 | 3.38 | 0.60 | 0.47 |
| rs1211448 | CLMN Intron9 (NM_024734.2) | 14 | 94,734,970 | 3.28 | 0.59 | 0.46 |
| rs848117 | SLC25A21 Intron3 (NM_030631.1) | 14 | 36,326,610 | 3.15 | 0.12 | 0.05 |
| rs12900219 | NDN −100017 bp (NM_002487.2) | 15 | 21,583,560 | 3.84 | 0.93 | 0.85 |
| rs2247154 | TLE3 +105451 bp (NM_005078.1) | 15 | 68,024,022 | 2.86 | 0.82 | 0.72 |
| rs12324063 | ATP10A Intron3 (NM_024490.2) | 15 | 23,540,049 | 3.60 | 0.43 | 0.30 |
| rs16941388 | MYO1E −6977 bp (NM_004998.1) | 15 | 57,459,340 | 3.32 | 0.94 | 0.86 |
| rs3863401 | LRRC28 Intron6 (NM_144598.2) | 15 | 97,698,743 | 3.59 | 0.61 | 0.48 |
| rs12591327 | TLN2 +69488 bp (NM_015059.1) | 15 | 60,990,221 | 3.18 | 0.64 | 0.51 |
| rs7173844 | LRRC28 Intron6 (NM_144598.2) | 15 | 97,694,416 | 3.49 | 0.61 | 0.48 |
| rs1717831 | NDN −95082 bp (NM_002487.2) | 15 | 21,578,625 | 3.06 | 0.90 | 0.82 |
| rs4410020 | MGC26690 −7119 bp (NM_152450.1) | 15 | 57,510,545 | 3.02 | 0.63 | 0.51 |
| rs7198530 | CHD9 −179353 bp (NM_025134.2) | 16 | 51,641,067 | 1.00 | 0.17 | 0.13 |
| rs9937509 | CHD9 −162783 bp (NM_025134.2) | 16 | 51,657,637 | 1.00 | 0.18 | 0.14 |
| rs436962 | CDH11 +25906 bp (NM_001797.2), CDH11 +25906 bp (NM_033664.1) | 16 | 63,512,280 | 1.68 | 0.84 | 0.77 |
| rs4309380 | LOC440339 +245434 bp (XM_498634) | 16 | 13,523,196 | 3.83 | 0.32 | 0.20 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs1622029 | 1.74 | 2.83 | 3.23 | 2.07 |
| rs8003168 | 1.64 | 2.81 | 2.21 | 2.13 |
| rs10498642 | 1.68 | 2.80 | 2.91 | 1.97 |
| rs9646147 | 2.19 | 2.76 | ND | ND |
| rs1187627 | 1.69 | 2.75 | 2.82 | 1.79 |
| SNP_A-18219 | 1.67 | 2.72 | 2.68 | 1.38 |
| rs14042 | 1.67 | 2.72 | 2.86 | 1.70 |
| rs1187626 | 1.68 | 2.71 | 2.88 | 1.80 |
| rs1211448 | 1.66 | 2.60 | 2.74 | 1.82 |
| rs848117 | 2.62 | 2.43 | ND | 2.34 |
| rs12900219 | 2.46 | 3.79 | 1.48 | 0.48 |
| rs2247154 | 1.74 | 3.05 | 1.62 | 0.71 |
| rs12324063 | 1.74 | 2.82 | 2.80 | 1.82 |
| rs16941388 | 2.42 | 2.79 | 2.83 | 1.07 |
| rs3863401 | 1.71 | 2.79 | 2.85 | 1.66 |
| rs12591327 | 1.65 | 2.75 | 2.88 | 1.51 |
| rs7173844 | 1.69 | 2.70 | 2.79 | 1.73 |
| rs1717831 | 2.03 | 2.51 | 2.45 | 1.10 |
| rs4410020 | 1.64 | 2.46 | 2.76 | 2.01 |
| rs7198530 | 1.40 | 3.77 | 0.00 | 2.13 |
| rs9937509 | 1.39 | 3.74 | 0.00 | 2.11 |
| rs436962 | 1.54 | 3.73 | 0.71 | 0.28 |
| rs4309380 | 1.89 | 3.47 | 2.73 | 2.23 |

TABLE 46

| DBSNP_ID | Exon, Intron | Chromosome | Physical Location | Critical rate, Allele (-logP) | High-Risk Allele Frequency in Progressive Glaucoma Group | High-Risk Allele Frequency in Nonprogressive Glaucoma Group |
|---|---|---|---|---|---|---|
| rs35146 | CDH11 Intron12 (NM_001797.2), CDH11 Intron12 (NM_033664.1) | 16 | 63,541,382 | 2.24 | 0.86 | 0.79 |
| rs35572 | LOC390735 −442487 bp (XM_497515) | 16 | 62,385,041 | 1.02 | 0.85 | 0.81 |
| rs35165 | CDH11 +5537 bp (NM_001797.2), CDH11 +5537 bp (NM_033664.1) | 16 | 63,532,649 | 1.89 | 0.85 | 0.78 |
| rs9302502 | LOC440339 +251309 bp (XM_498634) | 16 | 13,517,321 | 3.58 | 0.33 | 0.21 |
| rs35192 | CDH11 Intron4 (NM_001797.2), CDH11 Intron4 (NM_033664.1) | 16 | 63,587,141 | 2.72 | 0.87 | 0.78 |
| rs16968101 | CDH11 +28144 bp (NM_001797.2), CDH11 +28144 bp (NM_033664.1) | 16 | 63,510,042 | 1.89 | 0.86 | 0.79 |
| rs412474 | CDH11 +15454 bp (NM_001797.2), CDH11 +15454 bp (NM_033664.1) | 16 | 63,522,732 | 2.15 | 0.86 | 0.79 |
| rs429065 | CDH11 +22043 bp (NM_001797.2), CDH11 +22043 bp (NM_033664.1) | 16 | 63,516,143 | 2.11 | 0.86 | 0.79 |
| rs1554401 | CDH11 Intron4 (NM_001797.2), CDH11 Intron4 (NM_033664.1) | 16 | 63,588,839 | 1.62 | 0.49 | 0.41 |
| rs35162 | CDH11 +5129 bp (NM_001797.2), CDH11 +5129 bp (NM_033664.1) | 16 | 63,533,057 | 2.08 | 0.86 | 0.79 |
| rs35216 | CDH11 Intron8 (NM_001797.2), CDH11 Intron8 (NM_033664.1) | 16 | 63,572,992 | 2.08 | 0.86 | 0.79 |
| rs40116 | CDH11 Intron8 (NM_001797.2), CDH11 Intron8 (NM_033664.1) | 16 | 63,572,366 | 2.07 | 0.86 | 0.79 |
| rs28216 | CDH11 Exon7 (NM_001797.2), CDH11 Exon7 (NM_033664.1) | 16 | 63,579,615 | 2.07 | 0.86 | 0.79 |

| DBSNP_ID | Odds Ratio (Formula 6) | Critical rate, Genotype (-logP) | Odds Ratio (Homozygote) (Formula 7) | Odds Ratio (Heterozygote) (Formula 8) |
|---|---|---|---|---|
| rs35146 | 1.70 | 3.43 | 0.76 | 0.31 |
| rs35572 | 1.38 | 3.42 | ND | ND |
| rs35165 | 1.61 | 3.37 | 0.67 | 0.28 |
| rs9302502 | 1.84 | 3.36 | 2.44 | 2.24 |
| rs35192 | 1.85 | 3.31 | ND | ND |
| rs16968101 | 1.61 | 3.30 | 0.67 | 0.28 |
| rs412474 | 1.68 | 3.28 | 0.76 | 0.32 |
| rs429065 | 1.67 | 3.23 | 0.76 | 0.32 |
| rs1554401 | 1.39 | 3.21 | 2.24 | 0.76 |
| rs35162 | 1.66 | 3.19 | 0.75 | 0.32 |
| rs35216 | 1.66 | 3.15 | 0.77 | 0.33 |
| rs40116 | 1.65 | 3.14 | 0.76 | 0.33 |
| rs28216 | 1.65 | 3.14 | 0.76 | 0.33 |

TABLE 47

| DBSNP_ID | Exon, Intron | Chromosome | Physical Location | Critical rate, Allele (-logP) | High-Risk Allele Frequency in Progressive Glaucoma Group | High-Risk Allele Frequency in Nonprogressive Glaucoma Group |
|---|---|---|---|---|---|---|
| rs35140 | CDH11 Intron11 (NM_001797.2), CDH11 Intron11 (NM_033664.1) | 16 | 63,548,272 | 2.03 | 0.86 | 0.79 |
| rs9925034 | A2BP1 Intron2 (NM_018723.2), A2BP1 −804582 bp (NM_145891.1), A2BP1 −804582 bp (NM_145892.1), A2BP1 −804582 bp (NM_145893.1) | 16 | 6,518,170 | 1.07 | 0.48 | 0.41 |
| rs460538 | CDH11 +22417 bp (NM_001797.2), CDH11 +22417 bp (NM_033664.1) | 16 | 63,515,769 | 2.03 | 0.86 | 0.79 |
| rs1079008 | CDH11 Intron2 (NM_001797.2), CDH11 Intron2 (NM_033664.1) | 16 | 63,628,424 | 1.48 | 0.85 | 0.79 |
| rs35164 | CDH11 +5484 bp (NM_001797.2), CDH11 +5484 bp (NM_033664.1) | 16 | 63,532,702 | 1.99 | 0.86 | 0.79 |
| rs35214 | CDH11 Intron8 (NM_001797.2), CDH11 Intron8 (NM_033664.1) | 16 | 63,573,409 | 2.02 | 0.86 | 0.79 |
| rs35200 | CDH11 Intron7 (NM_001797.2), CDH11 Intron7 (NM_033664.1) | 16 | 63,579,045 | 2.02 | 0.86 | 0.79 |
| rs13333495 | LOC440339 +265091 bp (XM_498634) | 16 | 13,503,539 | 3.31 | 0.32 | 0.21 |
| rs16962155 | LOC440339 +272794 bp (XM_498634) | 16 | 13,495,836 | 3.13 | 0.32 | 0.21 |
| rs6500718 | A2BP1 −257472 bp (NM_018723.2), A2BP1 −1571091 bp (NM_145891.1), | 16 | 5,751,661 | 3.43 | 0.95 | 0.88 |

TABLE 47-continued

| | | | | | |
|---|---|---|---|---|---|
| rs12595990 | A2BP1 −1571091 bp (NM_145892.1), A2BP1 −1571091 bp (NM_145893.1) LOC92017 Intron9 (XM_042234) | 16 | 12,378,613 | 3.07 | 0.51 | 0.39 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs35140 | 1.64 | 3.12 | 0.75 | 0.32 |
| rs9925034 | 1.29 | 3.10 | 1.40 | 2.42 |
| rs460538 | 1.65 | 3.09 | 0.76 | 0.32 |
| rs1079008 | 1.49 | 3.09 | 0.50 | 0.23 |
| rs35164 | 1.64 | 3.08 | 0.74 | 0.32 |
| rs35214 | 1.64 | 3.08 | 0.76 | 0.33 |
| rs35200 | 1.64 | 3.08 | 0.76 | 0.33 |
| rs13333495 | 1.79 | 3.03 | 2.39 | 2.14 |
| rs16962155 | 1.75 | 2.81 | 2.34 | 2.07 |
| rs6500718 | 2.65 | 2.74 | ND | ND |
| rs12595990 | 1.63 | 2.52 | 2.69 | 1.30 |

TABLE 48

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs8062798 | A2BP1 −253070 bp (NM_018723.2), A2BP1 −1566689 bp (NM_145891.1), A2BP1 −1566689 bp (NM_145892.1), A2BP1 −1566689 bp (NM_145893.1) | 16 | 5,756,063 | 3.02 | 0.95 | 0.89 |
| rs1816581 | CBLN1 +57699 bp (NM_004352.1) | 16 | 47,812,497 | 3.26 | 0.41 | 0.29 |
| rs1898359 | CBLN1 +57192 bp (NM_004352.1) | 16 | 47,813,004 | 3.26 | 0.41 | 0.29 |
| rs9898312 | SOCS3 +39255 bp (NM_003955.3) | 17 | 73,825,204 | 0.49 | 0.54 | 0.50 |
| rs231005 | PMP22 +34074 bp (NM_153322.1), PMP22 +34074 bp (NM_153321.1), PMP22 +34074 bp (NM_000304.2) | 17 | 15,039,748 | 2.71 | 0.69 | 0.58 |
| rs10438771 | BRIP1 +31746 bp (NM_032043.1) | 17 | 57,083,021 | 0.02 | 0.26 | 0.25 |
| rs2074159 | LGP2 Intron11 (NM_024119.1) | 17 | 37,510,024 | 1.71 | 0.86 | 0.80 |
| rs4890199 | RPH3AL +18823 bp (NM_006987.2) | 17 | 43,474 | 2.70 | 0.10 | 0.04 |
| rs230923 | PMP22 +16078 bp (NM_153322.1), PMP22 +16078 bp (NM_153321.1), PMP22 +16078 bp (NM_000304.2) | 17 | 15,057,744 | 2.05 | 0.68 | 0.59 |
| rs1553072 | FLJ35773 +12632 bp (NM_152599.2) | 17 | 8,628,576 | 3.20 | 0.24 | 0.14 |
| rs917593 | MGC45562 Intron2 (NM_152349.1) | 17 | 36,070,052 | 3.08 | 0.30 | 0.19 |
| rs17057804 | LOC284274 −273821 bp (XM_378756) | 18 | 71,542,467 | 0.03 | 0.29 | 0.29 |
| rs11872151 | GTSCR1 −653277 bp (XM_496277) | 18 | 67,282,963 | 2.77 | 0.97 | 0.91 |
| rs11150900 | LOC284274 −284312 bp (XM_378756) | 18 | 71,552,958 | 0.37 | 0.67 | 0.64 |
| rs1551434 | GTSCR1 −637101 bp (XM_496277) | 18 | 67,266,787 | 3.59 | 0.95 | 0.87 |
| rs8098925 | LOC400655 −175143 bp (XM_378753) | 18 | 69,257,838 | 3.34 | 0.64 | 0.51 |
| rs1828132 | LOC284276 Intron2 (XM_378757) | 18 | 72,388,920 | 3.23 | 0.52 | 0.40 |
| rs8088082 | PPP4R1 −42712 bp (NM_005134.1) | 18 | 9,647,279 | 3.49 | 0.21 | 0.11 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs8062798 | 2.50 | 2.38 | ND | ND |
| rs1816581 | 1.70 | 2.35 | 2.66 | 1.60 |
| rs1898359 | 1.70 | 2.35 | 2.66 | 1.60 |
| rs9898312 | 1.15 | 3.67 | 1.43 | 2.74 |
| rs231005 | 1.60 | 3.43 | 3.86 | 3.49 |
| rs10438771 | 1.01 | 3.27 | 0.44 | 1.86 |
| rs2074159 | 1.57 | 3.25 | ND | ND |
| rs4890199 | 2.60 | 3.17 | 0.48 | 3.74 |
| rs230923 | 1.50 | 3.06 | 3.63 | 3.58 |
| rs1553072 | 1.93 | 2.60 | 6.76 | 1.70 |
| rs917593 | 1.78 | 2.35 | 3.73 | 1.60 |
| rs17057804 | 1.01 | 3.88 | 2.55 | 0.53 |
| rs11872151 | 2.74 | 3.77 | 0.46 | 0.10 |
| rs11150900 | 1.13 | 3.50 | 0.73 | 0.35 |
| rs1551434 | 2.71 | 3.13 | 2.07 | 0.65 |
| rs8098925 | 1.69 | 2.88 | 2.84 | 1.41 |
| rs1828132 | 1.67 | 2.81 | 2.89 | 1.28 |
| rs8088082 | 2.08 | 2.68 | 6.23 | 1.85 |

TABLE 49

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs2587428 | CDH7 +60322 bp (NM_033646.1), CDH7 +60323 bp (NM_004361.2) | 18 | 61,759,477 | 3.15 | 0.50 | 0.38 |
| rs6565975 | LOC441825 +102358 bp (XM_497596) | 18 | 73,316,910 | 3.19 | 0.75 | 0.63 |
| rs10451358 | ANKRD12 Intron7 (NM_015208.2) | 18 | 9,207,471 | 3.05 | 0.43 | 0.31 |
| rs1942583 | LOC441825 +112581 bp (XM_497596) | 18 | 73,327,133 | 3.02 | 0.72 | 0.61 |
| rs12051936 | LOC441825 +96235 bp (XM_497596) | 18 | 73,310,787 | 3.11 | 0.60 | 0.47 |
| rs4482359 | LOC440479 +52521 bp (XM_498693) | 18 | 10,180,764 | 3.16 | 0.64 | 0.51 |
| rs12462868 | FLJ36445 +22374 bp (NM_153233.1) | 19 | 41,163,676 | 2.44 | 0.30 | 0.21 |
| rs7260296 | NTE +9039 bp (NM_006702.2) | 19 | 7,541,689 | 0.57 | 0.62 | 0.58 |
| rs1102152 | KCTD15 +36141 bp (NM_024076.1) | 19 | 39,033,129 | 3.59 | 0.66 | 0.53 |
| rs4802905 | PPP2R1A Intron11 (NM_014225.3) | 19 | 57,415,907 | 2.59 | 0.66 | 0.55 |
| rs734380 | RPS5 Intron1 (NM_001009.2) | 19 | 63,590,775 | 2.85 | 0.52 | 0.41 |
| rs1072678 | ZNF600 +14950 bp (NM_198457.1) | 19 | 57,944,329 | 3.53 | 0.14 | 0.06 |
| rs734379 | RPS5 Intron1 (NM_001009.2) | 19 | 63,590,994 | 3.11 | 0.61 | 0.49 |
| rs6132862 | LOC400840 +29346 bp (XM_375912) | 20 | 25,669,248 | 3.95 | 0.37 | 0.24 |
| rs4572656 | PTPRT +22230 bp (NM_007050.3), PTPRT +22230 bp (NM_133170.1) | 20 | 40,112,577 | 3.60 | 0.89 | 0.79 |
| rs119416 | KCNB1 Intron1 (NM_004975.2) | 20 | 47,469,004 | 3.98 | 0.70 | 0.56 |
| rs6019825 | KCNB1 Intron1 (NM_004975.2) | 20 | 47,472,824 | 3.55 | 0.56 | 0.43 |
| rs6045666 | PDYN +18899 bp (NM_024411.2) | 20 | 1,888,504 | 3.67 | 0.34 | 0.22 |
| rs6138601 | KIAA0980 −32244 bp (NM_025176.3) | 20 | 25,487,486 | 3.69 | 0.39 | 0.26 |
| rs6035140 | PTPNS1 +15755 bp (NM_080792.1) | 20 | 1,884,292 | 3.67 | 0.35 | 0.23 |
| rs12480036 | CHD6 Intron1 (NM_032221.3) | 20 | 39,629,243 | 3.84 | 0.80 | 0.69 |
| rs6138598 | KIAA0980 −6294 bp (NM_025176.3) | 20 | 25,461,536 | 3.44 | 0.38 | 0.26 |
| rs517578 | SIRPB2 −50868 bp (NM_018556.2), SIRPB2 −50868 bp (NM_080816.1) | 20 | 1,637,270 | 3.30 | 0.42 | 0.30 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs2587428 | 1.64 | 2.60 | 2.56 | 1.91 |
| rs6565975 | 1.71 | 2.57 | 3.30 | 2.24 |
| rs10451358 | 1.65 | 2.54 | 3.05 | 1.32 |
| rs1942583 | 1.66 | 2.42 | 3.03 | 2.17 |
| rs12051936 | 1.63 | 2.33 | 2.56 | 1.70 |
| rs4482359 | 1.66 | 2.30 | 2.51 | 1.46 |
| rs12462868 | 1.64 | 3.69 | 11.93 | 1.05 |
| rs7260296 | 1.18 | 3.37 | 1.89 | 3.13 |
| rs1102152 | 1.73 | 3.18 | 2.64 | 2.56 |
| rs4802905 | 1.58 | 3.13 | 2.04 | 0.85 |
| rs734380 | 1.59 | 3.11 | 2.72 | 2.35 |
| rs1072678 | 2.59 | 2.92 | ND | 2.53 |
| rs734379 | 1.63 | 2.86 | 3.24 | 1.95 |
| rs6132862 | 1.86 | 3.67 | 2.58 | 2.31 |
| rs4572656 | 2.08 | 3.41 | 1.95 | 0.77 |
| rs119416 | 1.79 | 3.40 | 3.04 | 1.48 |
| rs6019825 | 1.70 | 3.29 | 3.06 | 1.30 |
| rs6045666 | 1.85 | 3.28 | 2.73 | 2.16 |
| rs6138601 | 1.80 | 3.23 | 2.64 | 2.11 |
| rs6035140 | 1.83 | 3.14 | 2.65 | 2.09 |
| rs12480036 | 1.89 | 3.13 | 4.18 | 2.36 |
| rs6138598 | 1.76 | 3.11 | 2.45 | 2.13 |
| rs517578 | 1.70 | 3.11 | 2.38 | 2.16 |

TABLE 50

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs2050223 | C20orf23 +550936 bp (NM_024704.3) | 20 | 15,649,814 | 1.97 | 0.65 | 0.56 |
| rs926663 | MAFB +68744 bp (NM_005461.3) | 20 | 38,679,189 | 2.89 | 0.47 | 0.35 |
| rs6072407 | CHD6 Intron2 (NM_032221.3) | 20 | 39,596,216 | 3.83 | 0.82 | 0.71 |
| rs6138532 | ENTPD6 −5585 bp (NM_001247.1) | 20 | 25,118,787 | 3.00 | 0.45 | 0.33 |
| rs6083320 | CST5 −31324 bp (NM_001900.2) | 20 | 23,839,641 | 3.26 | 0.41 | 0.29 |
| rs2076147 | ZHX3 Exon4 (NM_015035.2) | 20 | 39,246,420 | 3.68 | 0.50 | 0.37 |
| rs1857051 | CST5 −33523 bp (NM_001900.2) | 20 | 23,841,840 | 3.35 | 0.50 | 0.38 |
| rs4810317 | CHD6 +8124 bp (NM_032221.3) | 20 | 39,456,460 | 3.54 | 0.81 | 0.70 |
| rs6089908 | KCNQ2 Intron10 (NM_004518.2), | 20 | 61,519,098 | 3.33 | 0.90 | 0.81 |

TABLE 50-continued

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| | KCNQ2 Intron11 (NM_172106.1), KCNQ2 Intron12 (NM_172107.1), KCNQ2 Intron11 (NM_172108.1), KCNQ2 +16378 bp (NM_172109.1) | | | | | |
| rs6095508 | KCNB1 Intron1 (NM_004975.2) | 20 | 47,461,578 | 3.30 | 0.58 | 0.45 |
| rs4812180 | LOC284757 +371993 bp (XM_496478) | 20 | 58,704,985 | 3.73 | 0.09 | 0.03 |
| rs6115458 | FLJ38374 −66026 bp (NM_182583.1) | 20 | 25,917,265 | 3.19 | 0.38 | 0.26 |
| rs1321001 | CDH22 Intron7 (NM_021248.1) | 20 | 44,250,143 | 3.08 | 0.64 | 0.51 |
| rs3761258 | C20orf45 −727 bp (NM_016045.1) | 20 | 57,051,991 | 3.08 | 0.97 | 0.92 |
| rs94967 | LOC150084 +21299 bp (XM_086761) | 21 | 40,117,177 | 3.96 | 0.78 | 0.65 |
| rs4816657 | LOC150084 Intron4 (XM_086761) | 21 | 40,068,705 | 3.77 | 0.77 | 0.65 |
| rs2837211 | LOC150084 Intron4 (XM_086761) | 21 | 40,070,264 | 3.64 | 0.77 | 0.65 |
| rs1018350 | LOC150084 Intron4 (XM_086761) | 21 | 40,070,715 | 3.64 | 0.77 | 0.65 |
| rs463903 | LOC150084 Intron8 (XM_086761) | 21 | 40,087,547 | 3.51 | 0.77 | 0.65 |
| rs2837248 | PCP4 −19612 bp (NM_006198.1) | 21 | 40,141,638 | 3.50 | 0.67 | 0.55 |
| rs2178882 | LOC150084 Intron5 (XM_086761) | 21 | 40,075,682 | 3.44 | 0.77 | 0.65 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs2050223 | 1.46 | 3.08 | 1.66 | 0.70 |
| rs926663 | 1.61 | 3.08 | 2.29 | 2.27 |
| rs6072407 | 1.92 | 3.07 | 4.47 | 2.58 |
| rs6138532 | 1.66 | 3.04 | 2.44 | 2.24 |
| rs6083320 | 1.70 | 3.02 | 4.16 | 1.53 |
| rs2076147 | 1.72 | 3.01 | 2.99 | 1.82 |
| rs1857051 | 1.68 | 2.90 | 3.22 | 1.65 |
| rs4810317 | 1.85 | 2.89 | 3.27 | 1.68 |
| rs6089908 | 2.16 | 2.76 | 2.60 | 1.09 |
| rs6095508 | 1.67 | 2.74 | 2.94 | 1.83 |
| rs4812180 | 3.77 | 2.72 | ND | 3.14 |
| rs6115458 | 1.71 | 2.51 | 2.56 | 1.84 |
| rs1321001 | 1.65 | 2.47 | 2.84 | 1.74 |
| rs3761258 | 3.07 | 2.44 | ND | ND |
| rs94967 | 1.88 | 3.72 | 5.80 | 3.59 |
| rs4816657 | 1.83 | 3.07 | 3.69 | 2.12 |
| rs2837211 | 1.80 | 2.96 | 3.66 | 2.14 |
| rs1018350 | 1.80 | 2.96 | 3.66 | 2.14 |
| rs463903 | 1.78 | 2.86 | 3.63 | 2.17 |
| rs2837248 | 1.71 | 2.83 | 3.10 | 1.94 |
| rs2178882 | 1.80 | 2.73 | 3.61 | 2.20 |

TABLE 51

| DBSNP_ID | Exon, Intron | Chromosome | Physical Location | Critical rate, Allele (−logP) | High-Risk Allele Frequency in Progressive Glaucoma Group | High-Risk Allele Frequency in Nonprogressive Glaucoma Group |
|---|---|---|---|---|---|---|
| rs4816658 | LOC150084 Intron5 (XM_086761) | 21 | 40,075,924 | 3.53 | 0.77 | 0.65 |
| rs458406 | LOC150084 Intron8 (XM_086761) | 21 | 40,089,698 | 3.32 | 0.77 | 0.65 |
| rs2837220 | LOC150084 Intron6 (XM_086761) | 21 | 40,082,808 | 3.39 | 0.73 | 0.61 |
| rs12627261 | LOC150084 Intron6 (XM_086761) | 21 | 40,085,416 | 3.39 | 0.73 | 0.61 |
| rs1571713 | LOC150084 Intron5 (XM_086761) | 21 | 40,075,065 | 3.32 | 0.77 | 0.65 |
| rs2826774 | NCAM2 Intron5 (NM_004540.2) | 21 | 21,588,847 | 3.34 | 0.60 | 0.47 |
| rs465258 | LOC150084 Intron8 (XM_086761) | 21 | 40,093,614 | 3.22 | 0.76 | 0.65 |
| rs369977 | LOC388814 +131764 bp (XM_373926) | 21 | 15,532,948 | 3.02 | 0.68 | 0.57 |
| rs5750009 | LOC402059 Intron8 (XM_497817) | 22 | 33,679,879 | 2.13 | 0.81 | 0.73 |
| rs1013513 | LOC402059 Intron8 (XM_497817) | 22 | 33,678,294 | 2.12 | 0.81 | 0.73 |
| rs5999654 | LOC402059 Intron8 (XM_497817) | 22 | 33,682,537 | 2.12 | 0.81 | 0.73 |
| rs1139056 | CECR1 Exon7 (NM_177405.1), CECR1 Exon9 (NM_017424.2) | 22 | 16,035,732 | 3.28 | 0.26 | 0.15 |
| rs5759839 | LOC388882 Intron4 (XM_371455) | 22 | 22,141,794 | 3.04 | 0.59 | 0.47 |

| DBSNP_ID | Odds Ratio (Formula 6) | Critical rate, Genotype (−logP) | Odds Ratio (Homozygote) (Formula 7) | Odds Ratio (Heterozygote) (Formula 8) |
|---|---|---|---|---|
| rs4816658 | 1.82 | 2.72 | 3.32 | 1.92 |
| rs458406 | 1.75 | 2.69 | 3.46 | 2.07 |
| rs2837220 | 1.73 | 2.65 | 2.91 | 1.67 |
| rs12627261 | 1.73 | 2.65 | 2.91 | 1.67 |
| rs1571713 | 1.76 | 2.65 | 3.38 | 1.99 |
| rs2826774 | 1.68 | 2.62 | 2.81 | 1.71 |
| rs465258 | 1.73 | 2.62 | 3.45 | 2.10 |

TABLE 51-continued

| | | | | |
|---|---|---|---|---|
| rs369977 | 1.64 | 2.37 | 2.50 | 1.39 |
| rs5750009 | 1.58 | 3.68 | 12.15 | 11.55 |
| rs1013513 | 1.58 | 3.43 | 11.57 | 10.59 |
| rs5999654 | 1.58 | 3.43 | 11.57 | 10.59 |
| rs1139056 | 1.90 | 2.50 | 3.23 | 1.91 |
| rs5759839 | 1.62 | 2.36 | 2.61 | 1.55 |

Tables 29 to 51 list dbSNP ID number or Affimetrix Array ID number specifying known single nucleotide polymorphisms obtained, the exon, intron information (in a case where a single nucleotide polymorphism exists on a gene, the gene name and the exon or intron in which SNP exists are shown, and in a case where a single nucleotide polymorphism does not exist on a gene, neighboring genes and a distance between the gene and the single nucleotide polymorphism are shown), the chromosome number at which the single nucleotide polymorphism exists, the physical location of the single nucleotide polymorphism, the p-value for an allele according to a chi-square test ($-\log P$), the high-risk allele frequencies in the progressive glaucoma group and the nonprogressive glaucoma group, the odds ratio for an allele, the p-value for a genotype according to a chi-square test ($-\log P$), the odds ratio for a genotype of a homozygote, and the odds ratio for a genotype of a heterozygote. Here, in the tables, a portion of which odds ratio is indicated as ND shows a case where any one of the number of detection in the denominator is 0, so that the odds ratio could not be calculated.

According to the above studies, 480 single nucleotide polymorphisms of which alleles or genotypes were associated with the progression of glaucoma at a p-value of $1\times10^{-3}$ or less were found.

When the allele or genotype frequencies listed in Tables 29 to 51 were compared between the progressive glaucoma cases and the nonprogressive glaucoma cases, a statistical difference was found. By determining an allele of any one of these single nucleotide polymorphisms, whether or not an allele that is identified in a higher frequency in the progressive glaucoma group than that of the nonprogressive glaucoma group exists in the sample can be determined.

Example 5

Confirmation of Novel Single Nucleotide Polymorphisms by Sequencing Method of Surrounding of Specified Single Nucleotide Polymorphisms Surrounding sequences of single nucleotide polymorphisms described in Tables 1 to 2 or Tables 26 to 28 are subjected to re-sequencing, so that the detection of a single nucleotide polymorphism can be confirmed, and that an unknown single nucleotide polymorphism that possibly exists can be identified. The re-sequencing can be performed according to any known methods, and for example, the re-sequencing can be performed by a direct sequencing method.

Example 6

In order to determine the single nucleotide polymorphisms associated with glaucoma identified in Example 3 or 4, or the alleles and genotypes of known single nucleotide polymorphisms existing in the surrounding sequences of the single nucleotide polymorphisms listed in Tables 1 to 51, an immobilized probe can be prepared. A known single nucleotide polymorphism can be referred to, for example, the database of dbSNP or J SNP. In the immobilized probe, for example, an oligonucleotide probe designed so as to maximize its sensitivity, specificity or reproducibility for several probes to several hundred-thousand probes can be loaded. The immobilized probe can be produced according to a method such as a method of synthesizing an oligonucleotide on a solid carrier or a method including the steps of previously synthesizing an oligonucleotide and immobilizing the oligonucleotide in a high density on a solid carrier.

Example 7

The presence or the absence of the progression of glaucoma can be determined at a more accurate level using the immobilized probe produced in Example 6. A probe for detecting a single nucleotide polymorphism associated with a disease is plurally combined, so that the level of which the progressive risk of glaucoma increases is evaluated. In a case where a value exceeds a threshold, it is determined that the progression of glaucoma takes place.

In addition, using the immobilized probe produced in Example 6, the single nucleotide polymorphism existing on the genome of the glaucoma patients and that of the non-glaucoma patients can be compared. There is a possibility that single nucleotide polymorphisms existing in locations with an adjacent distance to each other are linked and inherited by linkage disequilibrium. There is a possibility that single nucleotide polymorphisms linked with the single nucleotide polymorphisms listed in Tables 1 and 2 or Tables 26 to 28 can be identified by the immobilized probe, so that it can be expected that a single nucleotide polymorphism having an even stronger association with glaucoma is found.

Example 8

Design of Custom Array

In order to maintain a statistical power while lowering type I error, candidate single nucleotide polymorphisms associated with the progression of glaucoma identified in the primary analysis of Example 4 were subjected to a secondary analysis of a single nucleotide polymorphism in separately collected samples using an array for analyzing a single nucleotide polymorphism designed in an original style (hereinafter, referred to as a custom array).

For the custom array, a kit for analyzing a single nucleotide polymorphism commercially available from Illumina [Illumina, iSelect™ Genotyping BeadChip] was used. For 531 single nucleotide polymorphisms associated with the progression of glaucoma showing a p-value of $1\times10^{-3}$ or less in Example 4, the designing of a probe for specifically detecting these single nucleotide polymorphisms was tried. Since these probes are randomly immobilized to the substrate via beads, the step of specifying a location of the beads (decoding) is needed. A probe for detecting a single nucleotide polymorphism of which location was unable to be specified in a process of decoding was excluded from the subject for analysis. As a result, the preparation of a custom array capable of typing 477 single nucleotide polymorphisms out of 531 single nucleotide polymorphisms is made possible, and the custom array was used in the analysis of a single nucleotide polymorphism described later. Here, as described in the section of Infinium (registered trademark) assay in a beads-array method, in these assay methods, there are two methods, i.e. a method using one kind of a probe and a method using two kinds of probes. Basically, in the detection of one single nucleotide polymorphism, one kind of the probe was used, and two probes were used for some single nucleotide polymorphisms.

Example 9

Analysis of Single Nucleotide Polymorphism Using Custom Array

The experiment was performed in accordance with the instruction manuals of the custom array kit and the analyzing instrument of Illumina, using specialized reagents contained in the kit. Briefly, the experimental procedures will be explained as follows. A reagent specialized in the treatment of the genome and a sodium hydroxide solution were added to 150 to 300 ng of the total DNA extracted in Example 1. Next, an enzyme for amplifying a whole genome was added thereto, and the mixture was incubated at 37° C. for 20 to 24 hours, and a whole genome was amplified. Further, an enzyme for fragmentation was added thereto, and the mixture was incubated at 37° C. for one hour. After the DNA was precipitated with isopropanol, a reagent for solubilization was added to the precipitates, and the mixture was suspended at 48° C. for one hour. A mixture was heat-denatured at 95° C. for 20 minutes, and this solution was injected into the custom array, and hybridization was carried out at 48° C. for 16 to 24 hours.

After the hybridization, an allele-specific extension reaction or a single base extension reaction was performed for each probe, and the fluorescent signals were amplified. The signals were read with a scanner (Illumina, BeadArray Reader) compatible to the kit. In addition, a specialized software (Illumina, BeadStudio 3.1) was used in the analysis of the single nucleotide polymorphisms. According to the present analytical method, the opposite alleles of a single nucleotide polymorphism can be determined simultaneously, and the genotypes were determined on the basis of the analytical results. The genotype was determined to be a heterozygote when both the signals of each of the alleles constituting a single nucleotide polymorphism were detected, and the genotype was determined to be a homozygote of the detected allele when only one of the signals of the alleles was detected.

The precision of the determination of a genotype was confirmed for all the single nucleotide polymorphisms to be analyzed on the basis of a cluster image showing a distribution of fluorescent signals, in accordance with Infinium (registered trademark) Genotyping Data Analysis, an analyzing manual of Illumina. The genotypes of the single nucleotide polymorphisms that are determined accurately are indicated on the image as three clusters of fluorescent signals that are completely separated from each other (two kinds of homozygotes and a heterozygote).

On the other hand, boundary lines of the three clusters become unclear for the single nucleotide polymorphisms that are not determined accurately. In a case where a degree of separation of the clusters is determined not to be high according to analysis software, the cluster image of the single nucleotide polymorphism was reconfirmed. In a case where a genotype was determined regardless of unclearness of the clusters, the sample was excluded from the subsequent analytical operations. Here, the confirmation of the cluster image was carried out under masking, in other words, in a state that the names of single nucleotide polymorphisms and p-values could not be compared with the single nucleotide polymorphisms. Here, the single nucleotide polymorphisms overlapping between the custom array used in the secondary analysis and GeneChip Human Mapping 500K of Affimetrix used in the primary analysis showed a concordance rate of 99% or more, when the concordance rates of the determination of genotypes were compared using 104 samples.

Example 10

Determination of Genotypes in Progressive Glaucoma Cases and Nonprogressive Cases Of primary open-angle glaucoma patients and normal tension glaucoma patients diagnosed on the basis of Guidelines offered by Japan Glaucoma Society, patients whose visual loss is progressed despite the treatment of lowering an intraocular pressure, such as an agent for lowering an intraocular pressure or surgical treatment within a certain period of time were assigned to a progressive glaucoma group, and patients without the progression were assigned to a nonprogressive glaucoma group. The determination of the progression of the visual loss was made, with reference to the standards used in The Advanced Glaucoma Intervention Study (the AIGS investigators, *Ophthalmology* 1994 101: 1445-1455).

For the present analysis, the same samples used in Example 4 for performing the primary analysis were not used, and new samples were collected. Blood donated under the consent on free will of the participants after having sufficiently explained the contents of studies from 110 cases of the progressive glaucoma group and 113 cases of the nonprogressive glaucoma group, each group being different from those of Example 4 was used as a specimen, a total DNA was extracted according to the method described in Example 1, and the analysis of single nucleotide polymorphisms was performed according to the method described in Example 9. The analytical results of a single nucleotide polymorphism obtained in each of the samples were stored in the Laboratory Information Management System (World Fusion, LaboServer) adopting a relational database. A specialized analysis program for a single nucleotide polymorphism was created and loaded within the system, and the analysis described as follows was performed. In detail, a single nucleotide polymorphism considered to have a high experimental reliability was extracted by rejecting a single nucleotide polymorphism having a call rate of less than 90% in both the progressive glaucoma group and the nonprogressive glaucoma group, and a single nucleotide polymorphism having a minor allele frequency of less than 5%.

Example 11

Meta-Analysis

In a meta-analysis, the Mantel-Haenszel method was used (*Wakariyasui Igaku Tokeigaku* (*Easy Medical Statistics*), pp. 48-80, Toshio MORIZANE, Medical Tribune). In detail, 464 single nucleotide polymorphisms considered to have a high experimental reliability in both of the methods described in Example 4 and Example 10 were subjected to statistical comparisons of the allele frequency and two genotype frequencies (a dominant genetic model and a recessive genetic model) using Mantel-Haenszel chi-square test. Single nucleotide polymorphisms of which any one of an allele model, a dominant genetic model, and a recessive genetic model shows association with glaucoma at a p-value of $1.1 \times 10^{-4}$ or less (the level of Bonferroni correction corresponding to p<0.05 when 464 times of multiple comparisons were performed), that is, −log P of 3.96 or more, are listed in Table 52.

The calculations of the Mantel-Haenszel chi-square test, and the odds ratio in the Mantel-Haenszel method for these single nucleotide polymorphisms, and a 95% confidence interval were performed according to the following procedures.

A Mantel-Haenszel chi-square value was determined for the allele model, the dominant genetic model, and the recessive genetic model, and a p-value was calculated by comparing the value with the chi-square distribution of a degree of freedom of 1.

The Mantel-Haenszel chi-square value ($\chi A_{MH}^2$) of the allele model was calculated according to the following formulas.

$$EA_i = xA_i mA_i / NA_i$$

$$VA_i = \frac{mA_i nA_i xA_i yA_i}{NA_i^2 (NA_i - 1)}$$

$$\chi A_{MH}^2 = \frac{\left[\left|\sum_{i=1}^{k}(hA_i - EA_i)\right| - 0.5\right]^2}{\sum_{i=1}^{k} VA_i}$$

$xA_i$: a total number of detection of a high-risk allele,
$yA_i$: a total number of detection of a low-risk allele,
$mA_i$: a total number of detection of alleles in the progressive glaucoma group,
$nA_i$: a total number of detection of alleles in the nonprogressive glaucoma group,
$NA_i$: a total number of detection of alleles, and
$hA_i$: the number of detection of a high-risk allele in the progressive glaucoma group.

The Mantel-Haenszel chi-square value ($\chi D_{MH}^2$) of the dominant genetic model was calculated according to the following formulas.

$$ED_i = xD_i mD_i / ND_i$$

$$VD_i = \frac{mD_i nD_i xD_i yD_i}{ND_i^2 (ND_i - 1)}$$

$$\chi D_{MH}^2 = \frac{\left[\left|\sum_{i=1}^{k}(hD_i - ED_i)\right| - 0.5\right]^2}{\sum_{i=1}^{k} VD_i}$$

$xD_i$: the sum of a total number of detection of a homozygote of a high-risk allele and a total number of detection of a heterozygote,
$yD_i$: a total number of detection of a homozygote of a low-risk allele,
$mD_i$: a total number of detection of genotypes in the progressive glaucoma group,
$nD_i$: a total number of detection of genotypes in the nonprogressive glaucoma group,
$ND_i$: a total number of detection of genotypes, and
$hD_i$: the sum of the number of detection of a homozygote of a high-risk allele and the number of detection of a heterozygote in the progressive glaucoma group.

The Mantel-Haenszel chi-square value ($\chi R_{MH}^2$) of the recessive genetic model was calculated according to the following formulas.

$$ER_i = xR_i mR_i / NR_i$$

$$VR_i = \frac{mR_i nR_i xR_i yR_i}{NR_i^2 (NR_i - 1)}$$

$$\chi R_{MH}^2 = \frac{\left[\left|\sum_{i=1}^{k}(hR_i - ER_i)\right| - 0.5\right]^2}{\sum_{i=1}^{k} VR_i}$$

$xR_i$: a total number of detection of a homozygote of a high-risk allele,
$yR_i$: the sum of a total number of detection of a homozygote of a low-risk allele and a total number of detection of a heterozygote,
$mR_i$: a total number of detection of genotypes in the progressive glaucoma group,
$nR_i$: a total number of detection of genotypes in the nonprogressive glaucoma group,
$NR_i$: a total number of detection of genotypes, and
$hR_i$: the number of detection of a homozygote of a high-risk allele in the progressive glaucoma group.

The odds ratio in the Mantel-Haenszel test was calculated for the allele model, the dominant genetic model, and the recessive genetic model.

The odds ratio in the Mantel-Haenszel test ($ORa_{MH}$) for the allele model was calculated according to the following formula.

$$ORa_{MH} = \frac{\sum_{i=1}^{k} Aa_i Da_i / Za_i}{\sum_{i=1}^{k} Ba_i Ca_i / Za_i}$$

$Aa_i$: the number of detection of a high-risk allele in the progressive glaucoma group,
$Ba_i$: the number of detection of a low-risk allele in the progressive glaucoma group,
$Ca_i$: the number of detection of a high-risk allele in the nonprogressive glaucoma group,
$Da_i$: the number of detection of a low-risk allele in the nonprogressive glaucoma group, and
$Za_i$: a total number of detection of alleles.

The odds ratio in the Mantel-Haenszel test ($ORd_{MH}$) for the dominant genetic model was calculated according to the following formula.

$$ORd_{MH} = \frac{\sum_{i=1}^{k} Ad_i Dd_i / Zd_i}{\sum_{i=1}^{k} Bd_i Cd_i / Zd_i}$$

$Ad_i$: the sum of the number of detection of a homozygote of a high-risk allele in the progressive glaucoma group and the number of detection of a heterozygote in the progressive glaucoma group, Bd$_i$: the number of detection of a homozygote of a low-risk allele in the progressive glaucoma group, Cd$_i$: the sum of the number of detection of a homozygote of a high-risk allele in the nonprogressive glaucoma group and the number of detection of a heterozygote in the nonprogressive glaucoma group, Dd$_i$: the number of detection of a homozygote of a low-risk allele in the nonprogressive glaucoma group, and Zd$_i$: a total number of detection of genotypes.

The odds ratio in the Mantel-Haenszel test (ORr$_{MH}$) for the recessive genetic model was calculated according to the following formula.

$$ORr_{MH} = \frac{\sum_{i=1}^{k} Ar_i Dr_i / Zr_i}{\sum_{i=1}^{k} Br_i Cr_i / Zr_i}$$

Ar$_i$: the number of detection of a homozygote of a high-risk allele in the progressive glaucoma group, Br$_i$: the sum of the number of detection of a heterozygote in the progressive glaucoma group and the number of detection of a homozygote of a low-risk allele in the progressive glaucoma group, Cr$_i$: the number of detection of a homozygote of a high-risk allele in the nonprogressive glaucoma group, Dr$_i$: the sum of the number of detection of a heterozygote in the nonprogressive glaucoma group and the number of detection of a homozygote of a low-risk allele in the nonprogressive glaucoma group, and Zr$_i$: a total number of detection of genotypes.

A 95% confidence interval of the odds ratio in the Mantel-Haenszel test was calculated for the allele model, the dominant genetic model, and the recessive genetic model.

The 95% confidence interval (95% CI$_A$) for the allele model was calculated according to the following formulas.

$$PA_i = \frac{aA_i + dA_i}{zA_i}, QAi = \frac{bA_i + cA_i}{zA_i}, RA_i = \frac{aA_i dA_i}{zA_i}, SA_i = \frac{bA_i cA_i}{zA_i}$$

$$VarA = \frac{\sum_{i=1}^{k} PA_i RA_i}{2\left(\sum_{i=1}^{k} RA_i\right)^2} + \frac{\sum_{i=1}^{k}(PA_i SA_i + QA_i RA_i)}{2\sum_{i=1}^{k} RA_i \sum_{i=1}^{k} SA_i} + \frac{\sum_{i=1}^{k} QA_i SA_i}{2\left(\sum_{i=1}^{k} SA_i\right)^2}$$

$$95\% \ CI_A = \exp(\log ORa_{MH} \pm 1.96\sqrt{VarA})$$

aA$_i$: the number of detection of a high-risk allele in the progressive glaucoma group, bA$_i$: the number of detection of a low-risk allele in the progressive glaucoma group, cA$_i$: the number of detection of a high-risk allele in the nonprogressive glaucoma group, dA$_i$: the number of detection of a low-risk allele in the nonprogressive glaucoma group, zA$_i$: a total number of detection of alleles, and ORa$_{MH}$: an odds ratio in Mantel-Haenszel test for an allele model.

A 95% confidence interval (95% CI$_d$) for the dominant genetic model was calculated according to the following formulas.

$$PD_i = \frac{aD_i + dD_i}{zD_i}, QDi = \frac{bD_i + cD_i}{zD_i}, RD_i = \frac{aD_i dD_i}{zD_i}, SD_i = \frac{bD_i cD_i}{zD_i}$$

$$VarD = \frac{\sum_{i=1}^{k} PD_i RD_i}{2\left(\sum_{i=1}^{k} RD_i\right)^2} + \frac{\sum_{i=1}^{k}(PD_i SD_i + QD_i RD_i)}{2\sum_{i=1}^{k} RD_i \sum_{i=1}^{k} SD_i} + \frac{\sum_{i=1}^{k} QD_i SD_i}{2\left(\sum_{i=1}^{k} SD_i\right)^2}$$

$$95\% \ CI_d = \exp(\log ORd_{MH} \pm 1.96\sqrt{VarD})$$

aD$_i$: the sum of the number of detection of a homozygote of a high-risk allele in the progressive glaucoma group and the number of detection of a heterozygote in the progressive glaucoma group, bD$_i$: the number of detection of a homozygote of a low-risk allele in the progressive glaucoma group, cD$_i$: the sum of the number of detection of a homozygote of a high-risk allele in the nonprogressive glaucoma group and the number of detection of a heterozygote in the nonprogressive glaucoma group, dD$_i$: the number of detection of a homozygote of a low-risk allele in the nonprogressive glaucoma group, zD$_i$: a total number of detection of genotypes, and ORd$_{MH}$: an odds ratio in Mantel-Haenszel test for a dominant genetic model.

A 95% confidence interval (95% CI$_r$) for the recessive genetic model was calculated according to the following formulas.

$$PR_i = \frac{aR_i + dR_i}{zR_i}, QRi = \frac{bR_i + cR_i}{zR_i}, RR_i = \frac{aR_i dR_i}{zR_i}, SR_i = \frac{bR_i cR_i}{zR_i}$$

$$VarR = \frac{\sum_{i=1}^{k} PR_i RR_i}{2\left(\sum_{i=1}^{k} RR_i\right)^2} + \frac{\sum_{i=1}^{k}(PR_i SR_i + QR_i RR_i)}{2\sum_{i=1}^{k} RR_i \sum_{i=1}^{k} SR_i} + \frac{\sum_{i=1}^{k} QR_i SR_i}{2\left(\sum_{i=1}^{k} SR_i\right)^2}$$

$$95\% \ CI_r = \exp(\log ORr_{MH} \pm 1.96\sqrt{VarR})$$

aR$_i$: the number of detection of a homozygote of a high-risk allele in the progressive glaucoma group, bR$_i$: the sum of the number of detection of a heterozygote in the progressive glaucoma group and the number of detection of a homozygote of a low-risk allele in the progressive glaucoma group, cR$_i$: the number of detection of a homozygote of a high-risk allele in the nonprogressive glaucoma group, dR$_i$: the sum of the number of detection of a heterozygote in the nonprogressive glaucoma group and the number of detection of a homozygote of a low-risk allele in the nonprogressive glaucoma group, zR$_i$: a total number of detection of genotypes, and ORr$_{MH}$: an odds ratio in Mantel-Haenszel test for a recessive genetic model.

TABLE 52

| dBSNP ID | Chromosome | Physical Location | Exon, Intron | Linkage Disequilibrium | Allele 1 | Allele 2 |
|---|---|---|---|---|---|---|
| rs10483416 | 14 | 32,145,585 | AKAP6 Intron7 (NM_004274.3) | | A | G |
| rs4076919 | 2 | 216,546,324 | FLJ10116 +86710 bp (NM_018000.1) | | A | T |
| rs1358105 | 2 | 150,431,710 | FLJ32955 +17818 bp (NM_153041.1) | LD1 | A | C |
| rs1641385 | 2 | 150,429,442 | FLJ32955 +20086 bp (NM_153041.1) | LD1 | A | G |
| rs968871 | 2 | 150,428,575 | FLJ32955 +20953 bp (NM_153041.1) | LD1 | A | G |
| rs848241 | 2 | 150,460,159 | FLJ32955 Intron3 (NM_153041.1) | LD1 | A | G |
| rs4667333 | 2 | 150,461,734 | FLJ32955 Intron3 (NM_153041.1) | LD1 | A | G |
| rs1724855 | 2 | 150,455,469 | FLJ32955 Intron3 (NM_153041.1) | LD1 | A | T |
| rs2395453 | 10 | 78,411,565 | KCNMA1 Intron18 (NM_002247.2) | LD2 | C | G |
| rs2131216 | 10 | 78,426,609 | KCNMA1 Intron18 (NM_002247.2) | LD2 | A | T |
| rs4316157 | 8 | 12,677,322 | LOC340357 Intron3 (XM_499106) | | A | G |
| rs10781440 | 9 | 68,992,320 | LOC392347 Intron1 (XM_373298) | | A | G |
| rs6132862 | 20 | 25,669,248 | LOC400840 +29346 bp (XM_375912) | | A | G |
| rs787433 | 2 | 145,697,590 | LOC401014 +29562 bp (XM_379141) | | C | G |
| rs10172264 | 2 | 53,313,788 | LOC402072 +152420 bp (XM_377741) | | A | C |
| rs4802905 | 19 | 57,415,907 | PPP2R1A Intron11 (NM_014225.3) | | A | G |
| rs12554461 | 9 | 4,855,256 | RCL1 +4195 bp (NM_005772.2) | | A | G |
| rs166296 | 5 | 115,861,466 | SEMA6A Intron3 (NM_020796.2) | | A | G |
| rs4927088 | 1 | 54,487,224 | SSBP3 Intron4 (NM_145716.1), SSBP3 Intron4 (NM_018070.2) | | A | G |

| dBSNP ID | High-Risk Allele | High-Risk Allele Frequency in Progressive Glaucoma Group | High-Risk Allele Frequency in Nonprogressive Glaucoma Group | Mantel-Haenszel Test p-value | Mantel-Haenszel Test Model | Odds Ratio |
|---|---|---|---|---|---|---|
| rs10483416 | A | 0.80 | 0.70 | 0.000037 | Recessive | 2.01 |
| rs4076919 | A | 0.84 | 0.75 | 0.000017 | Recessive | 2.12 |
| rs1358105 | A | 0.41 | 0.28 | 0.000005 | Allele | 1.76 |
| rs1641385 | G | 0.46 | 0.34 | 0.000044 | Allele | 1.64 |
| rs968871 | G | 0.46 | 0.34 | 0.000036 | Allele | 1.64 |
| rs848241 | G | 0.45 | 0.33 | 0.000061 | Allele | 1.62 |
| rs4667333 | A | 0.45 | 0.34 | 0.000075 | Allele | 1.62 |
| rs1724855 | T | 0.44 | 0.33 | 0.000093 | Allele | 1.61 |
| rs2395453 | G | 0.60 | 0.52 | 0.000021 | Recessive | 2.19 |
| rs2131216 | T | 0.59 | 0.52 | 0.000107 | Recessive | 2.04 |
| rs4316157 | A | 0.48 | 0.33 | 0.000000 | Allele | 1.84 |
| rs10781440 | G | 0.37 | 0.27 | 0.000051 | Dominant | 1.98 |
| rs6132862 | G | 0.36 | 0.25 | 0.000028 | Dominant | 2.02 |
| rs787433 | G | 0.42 | 0.31 | 0.000072 | Allele | 1.62 |
| rs10172264 | C | 0.19 | 0.11 | 0.000075 | Dominant | 2.13 |
| rs4802905 | A | 0.67 | 0.59 | 0.000073 | Recessive | 2.01 |
| rs12554461 | G | 0.41 | 0.31 | 0.000096 | Dominant | 1.94 |
| rs166296 | G | 0.38 | 0.26 | 0.000020 | Allele | 1.72 |
| rs4927088 | G | 0.58 | 0.54 | 0.000096 | Dominant | 2.29 |

| dBSNP ID | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|
| rs10483416 | 1.4-2.8 | SEQ ID No: 203 | SEQ ID No: 204 | SEQ ID No: 753 | |
| rs4076919 | 1.5-3 | SEQ ID No: 205 | SEQ ID No: 206 | SEQ ID No: 754 | SEQ ID No: 772 |
| rs1358105 | 1.4-2.3 | SEQ ID No: 207 | SEQ ID No: 208 | SEQ ID No: 755 | |
| rs1641385 | 1.3-2.1 | SEQ ID No: 209 | SEQ ID No: 210 | SEQ ID No: 756 | |
| rs968871 | 1.3-2.1 | SEQ ID No: 211 | SEQ ID No: 212 | SEQ ID No: 757 | |
| rs848241 | 1.3-2.1 | SEQ ID No: 213 | SEQ ID No: 214 | SEQ ID No: 758 | |
| rs4667333 | 1.3-2 | SEQ ID No: 215 | SEQ ID No: 216 | SEQ ID No: 759 | |
| rs1724855 | 1.3-2 | SEQ ID No: 217 | SEQ ID No: 218 | SEQ ID No: 760 | SEQ ID No: 773 |
| rs2395453 | 1.5-3.1 | SEQ ID No: 219 | SEQ ID No: 220 | SEQ ID No: 761 | SEQ ID No: 774 |
| rs2131216 | 1.4-2.9 | SEQ ID No: 221 | SEQ ID No: 222 | SEQ ID No: 762 | SEQ ID No: 775 |
| rs4316157 | 1.5-2.3 | SEQ ID No: 223 | SEQ ID No: 224 | SEQ ID No: 763 | |
| rs10781440 | 1.4-2.8 | SEQ ID No: 225 | SEQ ID No: 226 | SEQ ID No: 764 | |
| rs6132862 | 1.5-2.8 | SEQ ID No: 227 | SEQ ID No: 228 | SEQ ID No: 765 | |
| rs787433 | 1.3-2.1 | SEQ ID No: 229 | SEQ ID No: 230 | SEQ ID No: 766 | SEQ ID No: 776 |
| rs10172264 | 1.5-3.1 | SEQ ID No: 231 | SEQ ID No: 232 | SEQ ID No: 767 | |
| rs4802905 | 1.4-2.8 | SEQ ID No: 233 | SEQ ID No: 234 | SEQ ID No: 768 | |
| rs12554461 | 1.4-2.7 | SEQ ID No: 235 | SEQ ID No: 236 | SEQ ID No: 769 | |
| rs166296 | 1.3-2.2 | SEQ ID No: 237 | SEQ ID No: 238 | SEQ ID No: 770 | |
| rs4927088 | 1.5-3.5 | SEQ ID No: 239 | SEQ ID No: 240 | SEQ ID No: 771 | |

Table 52 lists dbSNP ID number specifying known single nucleotide polymorphisms obtained, the chromosome number at which a single nucleotide polymorphism exists, the physical location of a single nucleotide polymorphism, the exon, intron information (in a case where a single nucleotide polymorphism exists on a gene, the gene name and the exon or intron in which SNP exists are shown, and in a case where a single nucleotide polymorphism does not exist on a gene, neighboring genes and a distance between the gene and the single nucleotide polymorphism are shown), the information on the linkage disequilibrium state (the numbers of LD1 and LD2 were assigned to single nucleotide polymorphisms which exist in the same linkage disequilibrium region), each of bases constituting Allele 1 and Allele 2, the base of a high-risk allele, high-risk allele frequencies of the progressive glaucoma group and the nonprogressive glaucoma group, the p-value in a test method having the lowest p-value among three Mantel-Haenszel tests (allele frequency, dominant genetic model, and recessive genetic model), the kinds of the tests thereof, the odds ratio thereof, the 95% confidence interval thereof, SEQ ID NO: of the sequence containing Allele 1 and SEQ ID NO: of the sequence containing Allele 2 in each of the polymorphic sites, and SEQ ID NO: or SEQ ID NOs: showing a base sequence of a probe used in a secondary analysis (basically, both the alleles are detected by the same probe, and in a case where the alleles are discriminated using two kinds of probes, both the sequences are listed together). Here, one of ordinary skill in the art can obtain the information for sequences or alleles of the single nucleotide polymorphisms from dbSNP ID number listed above.

When the allele or genotype frequencies of the single nucleotide polymorphisms listed in Table 52 were compared between the nonprogressive glaucoma group and the progressive glaucoma group, a statistical difference was found according to Mantel-Haenszel chi-square test. By determining an allele of any one of these single nucleotide polymorphisms in the same manner as that in Example 4, whether or not an allele that is identified in a higher frequency in the progressive glaucoma group than that of the nonprogressive glaucoma group exists in the sample can be determined.

According to the above studies, 19 single nucleotide polymorphisms of which alleles or genotypes were associated with glaucoma at a p-value of $1.1\times10^{-4}$ or less existing in clusters in relatively adjacent regions on the genome were found in 13 regions.

An allele identified in a high frequency in the progressive glaucoma group for single nucleotide polymorphisms listed in Table 52 (in other words, a high-risk allele) or a genotype (in other words, a homozygote of a high-risk allele or a heterozygote when the high-risk allele complies with a dominant genetic model, or a homozygote of a high-risk allele when the high-risk allele complies with a recessive genetic model) can be used as a marker showing that a progressive risk of glaucoma is high. On the other hand, an allele that is opposite to the allele or a genotype other than the genotype can be used as a marker showing that a progressive risk of glaucoma is low.

Similarly, a single nucleotide polymorphism of which allele or genotype shows association with the progression of glaucoma at a p-value of $1\times10^{-2}$ or less, i.e. −log P of 2 or more is listed in Tables 53 to 70.

TABLE 53

| dBSNP ID | Chromosome | Physical Location | Exon, Intron | Allele 1 | Allele 2 | High-Risk Allele |
|---|---|---|---|---|---|---|
| rs6500718 | 16 | 5,751,661 | A2BP1 −257472 bp (NM_018723.2), A2BP1 −1571091 bp (NM_145891.1), A2BP1 −1571091 bp (NM_145892.1), A2BP1 −1571091 bp (NM_145893.1) | A | C | A |
| rs7148801 | 14 | 32,206,647 | AKAP6 Intron7 (NM_004274.3) | A | G | A |
| rs1104870 | 2 | 29,366,069 | ALK Intron15 (NM_004304.3) | A | G | A |
| rs13193932 | 6 | 130,008,475 | ARHGAP18 Intron1 (NM_033515.2) | C | G | C |
| rs1621819 | 7 | 7,087,571 | C1GALT1 +30350 bp (NM_020156.1) | A | G | G |
| rs1638213 | 7 | 7,090,455 | C1GALT1 +33234 bp (NM_020156.1) | C | G | G |
| rs1796121 | 7 | 7,090,845 | C1GALT1 +33624 bp (NM_020156.1) | C | G | G |
| rs2050223 | 20 | 15,649,814 | C20orf23 +550936 bp (NM_024704.3) | A | G | A |
| rs6017164 | 20 | 41,815,520 | C20orf65 −26539 bp (NM_176791.2) | A | G | A |
| rs11691031 | 2 | 101,237,876 | C2orf29 −90020 bp (NM_017546.3) | A | G | G |
| rs733830 | 2 | 101,236,837 | C2orf29 −91059 bp (NM_017546.3) | A | G | A |
| rs17171658 | 7 | 39,931,767 | C7orf11 +13816 bp (NM_138701.1) | A | C | C |
| rs6601569 | 8 | 11,110,988 | C8orf7 −14730 bp (XM_088376) | A | G | G |
| rs2773395 | 9 | 126,049,019 | C9orf28 −119663 bp (XM_088525) | A | C | A |
| rs7038186 | 9 | 17,388,616 | C9orf39 Intron10 (NM_017738.1) | A | C | A |

| dBSNP ID | High-Risk Allele Frequency in Progressive Glaucoma Group | High-Risk Allele Frequency in Nonprogressive Glaucoma Group | Mantel-Haenszel Test p-value | Mantel-Haenszel Test Model | Odds Ratio | 95% Confidence Interval |
|---|---|---|---|---|---|---|
| rs6500718 | 0.94 | 0.90 | 0.005469 | Allele | 1.85 | 1.2-2.9 |
| rs7148801 | 0.94 | 0.89 | 0.000405 | Recessive | 2.30 | 1.4-3.6 |
| rs1104870 | 0.16 | 0.11 | 0.006447 | Allele | 1.63 | 1.1-2.3 |
| rs13193932 | 0.81 | 0.78 | 0.001225 | Dominant | 3.82 | 1.7-8.6 |
| rs1621819 | 0.58 | 0.48 | 0.000735 | Allele | 1.50 | 1.2-1.9 |
| rs1638213 | 0.57 | 0.47 | 0.001155 | Allele | 1.46 | 1.2-1.8 |
| rs1796121 | 0.57 | 0.47 | 0.001418 | Allele | 1.45 | 1.2-1.8 |
| rs2050223 | 0.64 | 0.59 | 0.002597 | Recessive | 1.69 | 1.2-2.4 |
| rs6017164 | 0.51 | 0.42 | 0.003116 | Allele | 1.42 | 1.1-1.8 |
| rs11691031 | 0.49 | 0.44 | 0.000418 | Dominant | 1.93 | 1.3-2.8 |
| rs733830 | 0.49 | 0.44 | 0.000865 | Dominant | 1.85 | 1.3-2.7 |
| rs17171658 | 0.77 | 0.68 | 0.002217 | Allele | 1.51 | 1.2-2 |
| rs6601569 | 0.92 | 0.85 | 0.000375 | Allele | 1.96 | 1.4-2.8 |
| rs2773395 | 0.33 | 0.26 | 0.002485 | Dominant | 1.66 | 1.2-2.3 |
| rs7038186 | 0.70 | 0.62 | 0.006790 | Allele | 1.41 | 1.1-1.8 |

TABLE 53-continued

| dBSNP ID | Sequence Containing Allele 1 | Sequence Containing Allele 2 | Sequence 1 for Secondary Analysis Probe | Sequence 2 for Secondary Analysis Probe |
|---|---|---|---|---|
| rs6500718 | SEQ ID No: 241 | SEQ ID No: 242 | SEQ ID No: 777 | |
| rs7148801 | SEQ ID No: 243 | SEQ ID No: 244 | SEQ ID No: 778 | |
| rs1104870 | SEQ ID No: 245 | SEQ ID No: 246 | SEQ ID No: 779 | |
| rs13193932 | SEQ ID No: 247 | SEQ ID No: 248 | SEQ ID No: 780 | SEQ ID No: 1033 |
| rs1621819 | SEQ ID No: 249 | SEQ ID No: 250 | SEQ ID No: 781 | |
| rs1638213 | SEQ ID No: 251 | SEQ ID No: 252 | SEQ ID No: 782 | SEQ ID No: 1034 |
| rs1796121 | SEQ ID No: 253 | SEQ ID No: 254 | SEQ ID No: 783 | SEQ ID No: 1035 |
| rs2050223 | SEQ ID No: 255 | SEQ ID No: 256 | SEQ ID No: 784 | |
| rs6017164 | SEQ ID No: 257 | SEQ ID No: 258 | SEQ ID No: 785 | |
| rs11691031 | SEQ ID No: 259 | SEQ ID No: 260 | SEQ ID No: 786 | |
| rs733830 | SEQ ID No: 261 | SEQ ID No: 262 | SEQ ID No: 787 | |
| rs17171658 | SEQ ID No: 263 | SEQ ID No: 264 | SEQ ID No: 788 | |
| rs6601569 | SEQ ID No: 265 | SEQ ID No: 266 | SEQ ID No: 789 | |
| rs2773395 | SEQ ID No: 267 | SEQ ID No: 268 | SEQ ID No: 790 | |
| rs7038186 | SEQ ID No: 269 | SEQ ID No: 270 | SEQ ID No: 791 | |

TABLE 54

| dBSNP ID | Chromosome | Physical Location | Exon, Intron | Allele 1 | Allele 2 | High-Risk Allele |
|---|---|---|---|---|---|---|
| rs2780197 | 9 | 17,416,186 | C9orf39 Intron13 (NM_017738.1) | A | G | G |
| rs2584554 | 9 | 17,416,808 | C9orf39 Intron13 (NM_017738.1) | C | G | C |
| rs6577539 | 1 | 8,923,501 | CA6 −16705bp(NM_001215.1) | A | G | A |
| rs1816581 | 16 | 47,812,497 | CBLN1 +57699 bp (NM_004352.1) | A | G | A |
| rs2293325 | 1 | 164,157,804 | CD3Z Intron1 (NM_000734.2), CD3Z Intron1 (NM_198053.1) | A | G | G |
| rs6773050 | 3 | 120,606,504 | CDGAP Intron10 (XM_291085) | A | G | A |
| rs1554401 | 16 | 63,588,839 | CDH11 Intron 4(NM_001797.2), CDH11 Intron4 (NM_033664.1) | A | G | A |
| rs1321001 | 20 | 44,250,143 | CDH22 Intron7 (NM_021248.1) | A | C | A |
| rs4810317 | 20 | 39,456,460 | CHD6 +8124 bp (NM_032221.3) | A | G | G |
| rs12480036 | 20 | 39,629,243 | CHD6 Intron1 (NM_032221.3) | A | G | A |
| rs6072407 | 20 | 39,596,216 | CHD6 Intron2 (NM_032221.3) | A | G | G |
| rs909882 | 20 | 39,509,923 | CHD6 Intron24 (NM_032221.3) | A | G | A |
| rs7198530 | 16 | 51,641,067 | CHD9 −179353 bp (NM_025134.2) | A | C | A |
| rs453570 | 3 | 50,612,473 | CISH +6457 bp (NM_013324.4), CISH +6457 bp (NM_145071.1) | C | G | C |
| rs2282273 | 14 | 94,730,437 | CLMN Intron11 (NM_024734.2) | A | G | A |

| dBSNP ID | High-Risk Allele Frequency in Progressive Glaucoma Group | High-Risk Allele Frequency in Nonprogressive Glaucoma Group | Mantel-Haenszel Test p-value | Mantel-Haenszel Test Model | Odds Ratio | 95% Confidence Interval |
|---|---|---|---|---|---|---|
| rs2780197 | 0.80 | 0.72 | 0.001857 | Allele | 1.53 | 1.2-2 |
| rs2584554 | 0.79 | 0.72 | 0.006818 | Allele | 1.45 | 1.1-1.9 |
| rs6577539 | 0.94 | 0.90 | 0.009973 | Recessive | 1.81 | 1.2-2.9 |
| rs1816581 | 0.40 | 0.31 | 0.002274 | Allele | 1.46 | 1.1-1.9 |
| rs2293325 | 0.77 | 0.70 | 0.003712 | Allele | 1.47 | 1.1-1.9 |
| rs6773050 | 0.61 | 0.54 | 0.002115 | Dominant | 1.98 | 1.3-3.1 |
| rs1554401 | 0.46 | 0.41 | 0.002996 | Recessive | 1.91 | 1.2-2.9 |
| rs1321001 | 0.62 | 0.54 | 0.006422 | Allele | 1.39 | 1.1-1.8 |
| rs4810317 | 0.80 | 0.74 | 0.005706 | Allele | 1.47 | 1.1-1.9 |
| rs12480036 | 0.80 | 0.73 | 0.006334 | Allele | 1.46 | 1.1-1.9 |
| rs6072407 | 0.82 | 0.75 | 0.003421 | Allele | 1.52 | 1.1-2 |
| rs909882 | 0.80 | 0.72 | 0.002054 | Allele | 1.54 | 1.2-2 |
| rs7198530 | 0.17 | 0.13 | 0.009306 | Dominant | 1.64 | 1.1-2.4 |
| rs453570 | 0.65 | 0.56 | 0.001906 | Allele | 1.46 | 1.1-1.8 |
| rs2282273 | 0.65 | 0.57 | 0.005007 | Allele | 1.40 | 1.1-1.8 |

| dBSNP ID | Sequence Containing Allele 1 | Sequence Containing Allele 2 | Sequence 1 for Secondary Analysis Probe | Sequence 2 for Secondary Analysis Probe |
|---|---|---|---|---|
| rs2780197 | SEQ ID No: 271 | SEQ ID No: 272 | SEQ ID No: 792 | |
| rs2584554 | SEQ ID No: 273 | SEQ ID No: 274 | SEQ ID No: 793 | SEQ ID No: 1036 |
| rs6577539 | SEQ ID No: 275 | SEQ ID No: 276 | SEQ ID No: 794 | |
| rs1816581 | SEQ ID No: 277 | SEQ ID No: 278 | SEQ ID No: 795 | |
| rs2293325 | SEQ ID No: 279 | SEQ ID No: 280 | SEQ ID No: 796 | |
| rs6773050 | SEQ ID No: 281 | SEQ ID No: 282 | SEQ ID No: 797 | |
| rs1554401 | SEQ ID No: 283 | SEQ ID No: 284 | SEQ ID No: 798 | |
| rs1321001 | SEQ ID No: 285 | SEQ ID No: 286 | SEQ ID No: 799 | |

TABLE 54-continued

| | | | | |
|---|---|---|---|---|
| rs4810317 | SEQ ID No: 287 | SEQ ID No: 288 | SEQ ID No: 800 | |
| rs12480036 | SEQ ID No: 289 | SEQ ID No: 290 | SEQ ID No: 801 | |
| rs6072407 | SEQ ID No: 291 | SEQ ID No: 292 | SEQ ID No: 802 | |
| rs909882 | SEQ ID No: 293 | SEQ ID No: 294 | SEQ ID No: 803 | |
| rs7198530 | SEQ ID No: 295 | SEQ ID No: 296 | SEQ ID No: 804 | |
| rs453570 | SEQ ID No: 297 | SEQ ID No: 298 | SEQ ID No: 805 | SEQ ID No: 1037 |
| rs2282273 | SEQ ID No: 299 | SEQ ID No: 300 | SEQ ID No: 806 | |

TABLE 55

| dBSNP ID | Chromosome | Physical Location | Exon, Intron | Allele 1 | Allele 2 | High-Risk Allele |
|---|---|---|---|---|---|---|
| rs3180753 | 14 | 94,729,500 | CLMN Intron12 (NM_024734.2) | A | G | G |
| rs2282267 | 14 | 94,729,648 | CLMN Intron12 (NM_024734.2) | A | G | A |
| rs1187627 | 14 | 94,734,482 | CLMN Intron9 (NM_024734.2) | A | G | G |
| rs1187626 | 14 | 94,735,610 | CLMN Intron9 (NM_024734.2) | A | G | G |
| rs17156635 | 7 | 28,168,969 | CREB5 Intron1 (NM_182899.2), CREB5 −56415 bp (NM_182898.1), CREB5 −79505 bp (NM_004904.1) | A | G | A |
| rs6083320 | 20 | 23,839,641 | CST5 −31324 bp (NM_001900.2) | A | G | A |
| rs10498642 | 14 | 94,658,292 | DICER1 Intron9 (NM_030621.2), DICER1 Intron8(NM_177438.1) | C | G | C |
| rs11059862 | 12 | 127,750,629 | DKFZp761O2018 +33295 bp (XM_044062) | A | G | A |
| rs11059865 | 12 | 127,752,135 | DKFZp761O2018 +34801 bp (XM_044062) | A | G | G |
| rs7302136 | 12 | 127,752,520 | DKFZp761O2018 +35186 bp (XM_044062) | A | G | G |
| rs12227382 | 12 | 127,753,754 | DKFZp761O2018 +36420 bp (XM_044062) | A | G | A |
| rs16929359 | 9 | 1,440,010 | DMRT2 +392458 bp (NM_006557.3), DMRT2 +392458 bp (NM_181872.1) | A | G | A |
| rs4142436 | 9 | 1,444,200 | DMRT2 +396648 bp (NM_006557.3), DMRT2 +396648 bp (NM_181872.1) | A | G | A |
| rs1801041 | 10 | 69,844,713 | DNA2L Exon21 (XM_166103) | A | T | A |
| rs17640758 | 13 | 42,590,879 | DNAJD1 +11297 bp (NM_013238.1) | A | C | A |

| dBSNP ID | High-Risk Allele Frequency in Progressive Glaucoma Group | High-Risk Allele Frequency in Nonprogressive Glaucoma Group | Mantel-Haenszel Test p-value | Mantel-Haenszel Test Model | Odds Ratio | 95% Confidence Interval |
|---|---|---|---|---|---|---|
| rs3180753 | 0.67 | 0.59 | 0.002886 | Allele | 1.43 | 1.1-1.8 |
| rs2282267 | 0.67 | 0.59 | 0.003047 | Allele | 1.43 | 1.1-1.8 |
| rs1187627 | 0.59 | 0.49 | 0.000667 | Allele | 1.49 | 1.2-1.9 |
| rs1187626 | 0.59 | 0.50 | 0.001214 | Recessive | 1.83 | 1.3-2.6 |
| rs17156635 | 0.21 | 0.16 | 0.002094 | Recessive | 6.31 | 2-20.4 |
| rs6083320 | 0.40 | 0.33 | 0.006655 | Recessive | 2.13 | 1.2-3.7 |
| rs10498642 | 0.61 | 0.52 | 0.002984 | Allele | 1.42 | 1.1-1.8 |
| rs11059862 | 0.91 | 0.85 | 0.004946 | Allele | 1.68 | 1.2-2.4 |
| rs11059865 | 0.91 | 0.86 | 0.009337 | Recessive | 1.72 | 1.1-2.6 |
| rs7302136 | 0.91 | 0.86 | 0.006401 | Allele | 1.65 | 1.2-2.4 |
| rs12227382 | 0.91 | 0.86 | 0.008366 | Allele | 1.63 | 1.1-23 |
| rs16929359 | 0.10 | 0.06 | 0.008247 | Allele | 1.84 | 1.2-2.9 |
| rs4142436 | 0.12 | 0.07 | 0.002699 | Dominant | 1.99 | 1.3-3.1 |
| rs1801041 | 0.79 | 0.74 | 0.004254 | Recessive | 1.64 | 1.2-2.3 |
| rs17640758 | 0.14 | 0.09 | 0.005083 | Dominant | 1.80 | 1.2-2.7 |

| dBSNP ID | Sequence Containing Allele 1 | Sequence Containing Allele 2 | Sequence 1 for Secondary Analysis Probe | Sequence 2 for Secondary Analysis Probe |
|---|---|---|---|---|
| rs3180753 | SEQ ID No: 301 | SEQ ID No: 302 | SEQ ID No: 807 | |
| rs2282267 | SEQ ID No: 303 | SEQ ID No: 304 | SEQ ID No: 808 | |
| rs1187627 | SEQ ID No: 305 | SEQ ID No: 306 | SEQ ID No: 809 | |
| rs1187626 | SEQ ID No: 307 | SEQ ID No: 308 | SEQ ID No: 810 | |
| rs17156635 | SEQ ID No: 309 | SEQ ID No: 310 | SEQ ID No: 811 | |
| rs6083320 | SEQ ID No: 311 | SEQ ID No: 312 | SEQ ID No: 812 | |
| rs10498642 | SEQ ID No: 313 | SEQ ID No: 314 | SEQ ID No: 813 | SEQ ID No: 1038 |
| rs11059862 | SEQ ID No: 315 | SEQ ID No: 316 | SEQ ID No: 814 | |
| rs11059865 | SEQ ID No: 317 | SEQ ID No: 318 | SEQ ID No: 815 | |
| rs7302136 | SEQ ID No: 319 | SEQ ID No: 320 | SEQ ID No: 816 | |
| rs12227382 | SEQ ID No: 321 | SEQ ID No: 322 | SEQ ID No: 817 | |
| rs16929359 | SEQ ID No: 323 | SEQ ID No: 324 | SEQ ID No: 818 | |
| rs4142436 | SEQ ID No: 325 | SEQ ID No: 326 | SEQ ID No: 819 | |
| rs1801041 | SEQ ID No: 327 | SEQ ID No: 328 | SEQ ID No: 820 | SEQ ID No: 1039 |
| rs17640758 | SEQ ID No: 329 | SEQ ID No: 330 | SEQ ID No: 821 | |

TABLE 56

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs6446245 | 3 | 51,012,298 | DOCK3 Intron5 (NM_004947.2) | A | C | C | 0.63 | 0.55 |
| rs7428299 | 3 | 5,705,884 | EDEM1 +469242 bp (XM_376201) | A | G | A | 0.68 | 0.59 |
| rs10898459 | 11 | 85,650,587 | EED Intron6 (NM_003797.2), EED Intron6 (NM_152991.1) | A | G | A | 0.61 | 0.52 |
| rs6138532 | 20 | 25,118,787 | ENTPD6 −5585 bp (NM_001247.1) | A | G | A | 0.41 | 0.35 |
| rs7420360 | 2 | 221,739,147 | EPHA4 +369107 bp (NM_004438.3) | A | G | G | 0.42 | 0.38 |
| rs531970 | 6 | 94,221,384 | EPHA7 −35391 bp (NM_004440.2) | A | G | A | 0.46 | 0.41 |
| rs1520855 | 2 | 190,107,426 | FLJ12519 −24239 bp (NM_032168.1) | A | G | G | 0.64 | 0.63 |
| rs10931418 | 2 | 190,090,541 | FLJ12519 −41124 bp (NM_032168.1) | A | G | A | 0.64 | 0.63 |
| rs13032853 | 2 | 190,134,918 | FLJ12519 Intron1 (NM_032168.1) | A | G | G | 0.64 | 0.63 |
| rs6739369 | 2 | 229,738,357 | FLJ20701 Intron3 (NM_017933.3) | A | C | C | 0.16 | 0.11 |
| rs1608976 | 2 | 150,460,868 | FLJ32955 Intron3 (NM_153041.1) | A | G | G | 0.45 | 0.34 |
| rs12462868 | 19 | 41,163,676 | FLJ36445 +22374 bp (NM_153233.1) | A | G | A | 0.28 | 0.22 |
| rs524441 | 11 | 82,638,706 | FLJ37874 +1045 bp (NM_182603.1) | A | G | A | 0.57 | 0.47 |
| rs681367 | 11 | 82,638,772 | FLJ37874 +1111 bp (NM_182603.1) | A | G | A | 0.57 | 0.47 |
| rs504105 | 11 | 82,641,607 | FLJ37874 +3946 bp (NM_182603.1) | C | G | G | 0.58 | 0.48 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs6446245 | 0.003599 | Dominant | 1.93 | 1.2-3 | SEQ ID No: 331 | SEQ ID No: 332 | SEQ ID No: 822 | |
| rs7428299 | 0.000777 | Allele | 1.51 | 1.2-1.9 | SEQ ID No: 333 | SEQ ID No: 334 | SEQ ID No: 823 | |
| rs10898459 | 0.000836 | Dominant | 2.12 | 1.4-3.3 | SEQ ID No: 335 | SEQ ID No: 336 | SEQ ID No: 824 | |
| rs6138532 | 0.008530 | Dominant | 1.59 | 1.1-2.2 | SEQ ID No: 337 | SEQ ID No: 338 | SEQ ID No: 825 | |
| rs7420360 | 0.001408 | Dominant | 1.76 | 1.2-2.5 | SEQ ID No: 339 | SEQ ID No: 340 | SEQ ID No: 826 | |
| rs531970 | 0.002310 | Recessive | 1.98 | 1.3-3.1 | SEQ ID No: 341 | SEQ ID No: 342 | SEQ ID No: 827 | |
| rs1520855 | 0.001652 | Dominant | 2.10 | 1.3-3.3 | SEQ ID No: 343 | SEQ ID No: 344 | SEQ ID No: 828 | |
| rs10931418 | 0.006060 | Dominant | 1.90 | 1.2-3 | SEQ ID No: 345 | SEQ ID No: 346 | SEQ ID No: 829 | |
| rs13032853 | 0.005897 | Dominant | 1.90 | 1.2-3 | SEQ ID No: 347 | SEQ ID No: 348 | SEQ ID No: 830 | |
| rs6739369 | 0.009245 | Dominant | 1.68 | 1.1-2.5 | SEQ ID No: 349 | SEQ ID No: 350 | SEQ ID No: 831 | |
| rs1608976 | 0.000125 | Allele | 1.60 | 1.3-2 | SEQ ID No: 351 | SEQ ID No: 352 | SEQ ID No: 832 | |
| rs12462868 | 0.004086 | Recessive | 3.00 | 1.4-6.3 | SEQ ID No: 353 | SEQ ID No: 354 | SEQ ID No: 833 | |
| rs524441 | 0.000377 | Allele | 1.52 | 1.2-1.9 | SEQ ID No: 355 | SEQ ID No: 356 | SEQ ID No: 834 | |
| rs681367 | 0.000382 | Allele | 1.52 | 1.2-1.9 | SEQ ID No: 357 | SEQ ID No: 358 | SEQ ID No: 835 | |
| rs504105 | 0.000338 | Allele | 1.52 | 1.2-1.9 | SEQ ID No: 359 | SEQ ID No: 360 | SEQ ID No: 836 | SEQ ID No: 1040 |

TABLE 57

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs7569506 | 2 | 165,535,617 | FLJ39822 +44702 bp (NM_173512.1) | A | G | A | 0.85 | 0.79 |
| rs4350423 | 12 | 38,515,235 | FLJ40126 Intron18 (NM_173599.1), SLC2A13 Intron6 (NM_052885.1) | A | G | G | 0.20 | 0.13 |
| rs7962260 | 12 | 38,510,570 | FLJ40126 Intron18 (NM_173599.1), SLC2A13 Intron6 (NM_052885.1) | A | G | A | 0.20 | 0.14 |
| rs7968509 | 12 | 38,541,115 | FLJ40126 Intron18 (NM_173599.1), SLC2A13 Intron6 (NM_052885.1) | A | G | A | 0.20 | 0.14 |
| rs2322728 | 11 | 126,640,100 | FLJ40224 +258937 bp (NM_173579.1) | A | G | G | 0.29 | 0.27 |
| rs687328 | 1 | 67,822,816 | GADD45A −40088 bp (NM_001924.2) | A | G | G | 0.73 | 0.66 |
| rs479779 | 1 | 36,925,156 | GRIK3 +10551 bp (NM_000831.2) | A | G | A | 0.38 | 0.28 |
| rs34305923 | 1 | 36,813,233 | GRIK3 +122474 bp (NM_000831.2) | A | G | G | 0.72 | 0.64 |
| rs7528341 | 1 | 36,810,267 | GRIK3 +125440 bp (NM_000831.2) | A | G | G | 0.74 | 0.64 |
| rs490647 | 1 | 36,911,836 | GRIK3 +23871 bp (NM_000831.2) | A | G | G | 0.38 | 0.28 |
| rs525798 | 1 | 36,909,979 | GRIK3 +25728 bp (NM_000831.2) | A | C | C | 0.39 | 0.29 |
| rs479714 | 1 | 36,909,131 | GRIK3 +26576 bp (NM_000831.2) | A | G | A | 0.38 | 0.28 |
| rs4652921 | 1 | 36,843,866 | GRIK3 +91841 bp (NM_000831.2) | A | G | G | 0.65 | 0.55 |
| rs10230371 | 7 | 18,668,137 | HDAC9 Intron21 (NM_058176.1), HDAC9 Intron21 (NM_178423.1), HDAC9 Intron19 (NM_178425.1), HDAC9 +186432 bp (NM_014707.1), HDAC9 +19625 bp (NM_058177.1) | A | G | A | 0.41 | 0.37 |
| rs2232248 | 3 | 50,584,628 | HEMK1 Exon3 (NM_016173.1) | A | C | C | 0.65 | 0.56 |

TABLE 57-continued

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs7569506 | 0.006402 | Allele | 1.51 | 1.1-2 | SEQ ID No: 361 | SEQ ID No: 362 | SEQ ID No: 837 | |
| rs4350423 | 0.003164 | Allele | 1.61 | 1.2-2.2 | SEQ ID No: 363 | SEQ ID No: 364 | SEQ ID No: 838 | |
| rs7962260 | 0.006443 | Allele | 1.55 | 1.1-2.1 | SEQ ID No: 365 | SEQ ID No: 366 | SEQ ID No: 839 | |
| rs7968509 | 0.008215 | Allele | 1.53 | 1.1-2.1 | SEQ ID No: 367 | SEQ ID No: 368 | SEQ ID No: 840 | |
| rs2322728 | 0.008947 | Recessive | 2.44 | 1.2-4.8 | SEQ ID No: 369 | SEQ ID No: 370 | SEQ ID No: 841 | |
| rs687328 | 0.000202 | Dominant | 2.91 | 1.7-5.1 | SEQ ID No: 371 | SEQ ID No: 372 | SEQ ID No: 842 | |
| rs479779 | 0.000387 | Allele | 1.56 | 1.2-2 | SEQ ID No: 373 | SEQ ID No: 374 | SEQ ID No: 843 | |
| rs34305923 | 0.001496 | Recessive | 1.71 | 1.2-2.4 | SEQ ID No: 375 | SEQ ID No: 376 | SEQ ID No: 844 | |
| rs7528341 | 0.000317 | Recessive | 1.83 | 1.3-2.6 | SEQ ID No: 377 | SEQ ID No: 378 | SEQ ID No: 845 | |
| rs490647 | 0.000256 | Dominant | 1.85 | 1.3-2.6 | SEQ ID No: 379 | SEQ ID No: 380 | SEQ ID No: 846 | |
| rs525798 | 0.000319 | Dominant | 1.83 | 1.3-2.5 | SEQ ID No: 381 | SEQ ID No: 382 | SEQ ID No: 847 | |
| rs479714 | 0.000543 | Dominant | 1.79 | 1.3-2.5 | SEQ ID No: 383 | SEQ ID No: 384 | SEQ ID No: 848 | |
| rs4652921 | 0.000539 | Allele | 1.51 | 1.2-1.9 | SEQ ID No: 385 | SEQ ID No: 386 | SEQ ID No: 849 | |
| rs10230371 | 0.000412 | Dominant | 1.84 | 1.3-2.6 | SEQ ID No: 387 | SEQ ID No: 388 | SEQ ID No: 850 | |
| rs2232248 | 0.001927 | Allele | 1.45 | 1.1-1.8 | SEQ ID No: 389 | SEQ ID No: 390 | SEQ ID No: 851 | |

TABLE 58

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs4589168 | 10 | 70,800,223 | HK1 Intron10 (NM_033497.1), HK1 Intron10 (NM_033498.1), HK1 Intron11 (NM_033500.1), HK1 Intron7 (NM_033496.1), HK1 Intron7 (NM_000188.1) | A | C | A | 0.88 | 0.83 |
| rs10823349 | 10 | 70,779,704 | HK1 Intron5 (NM_033497.1), HK1 Intron5 (NM_033498.1), HK1 Intron6 (NM_033500.1), HK1 Intron2 (NM_033496.1), HK1 Intron2 (NM_000188.1) | A | C | C | 0.88 | 0.83 |
| rs1339411 | 1 | 211,859,142 | KCNK2 +61589 bp (NM_014217.1) | A | G | A | 0.31 | 0.24 |
| rs1416658 | 1 | 211,804,166 | KCNK2 +6613 bp (NM_014217.1) | A | C | C | 0.30 | 0.22 |
| rs1416659 | 1 | 211,804,200 | KCNK2 +6647 b9 (NM_014217.1) | A | G | G | 0.30 | 0.22 |
| rs11120527 | 1 | 211,796,452 | KCNK2 Intron6 (NM_014217.1) | A | C | A | 0.30 | 0.22 |
| rs17388160 | 10 | 78,415,943 | KCNMA1 Intron18 (NM_002247.2) | A | G | G | 0.65 | 0.59 |
| rs3781158 | 10 | 78,426,444 | KCNMA1 Intron18 (NM_002247.2) | A | G | A | 0.59 | 0.53 |
| rs11712746 | 3 | 179,474,597 | KCNMB2 −262329 bp (NM_181361.1), KCNMB2 −284723 bp (NM_005832.3) | A | G | A | 0.24 | 0.16 |
| rs10494300 | 1 | 151,539,619 | KCNN3 Intron3 (NM_170782.1), KCNN3 Intron3 (NM_002249.3) | C | G | G | 0.60 | 0.51 |
| rs6089908 | 20 | 61,519,098 | KCNQ2 Intron10 (NM_004518.2), KCNQ2 Intron11 (NM_172106.1), KCNQ2 Intron12 (NM_172107.1), KCNQ2 Intron11 (NM_172108.1), KCNQ2 +16378 bp (NM_172109.1) | A | G | G | 0.91 | 0.85 |
| rs6138601 | 20 | 25,487,486 | KIAA0980 −32244 bp (NM_025176.3) | A | G | A | 0.37 | 0.27 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs4589168 | 0.004245 | Recessive | 1.72 | 1.2-2.5 | SEQ ID No: 391 | SEQ ID No: 392 | SEQ ID No: 852 | |
| rs10823349 | 0.002179 | Recessive | 1.78 | 1.2-2.6 | SEQ ID No: 393 | SEQ ID No: 394 | SEQ ID No: 853 | |
| rs1339411 | 0.003451 | Dominant | 1.63 | 1.2-2.3 | SEQ ID No: 395 | SEQ ID No: 396 | SEQ ID No: 854 | |
| rs1416658 | 0.002224 | Allele | 1.51 | 1.2-2 | SEQ ID No: 397 | SEQ ID No: 398 | SEQ ID No: 855 | |
| rs1416659 | 0.002680 | Allele | 1.50 | 1.2-2 | SEQ ID No: 399 | SEQ ID No: 400 | SEQ ID No: 856 | |
| rs11120527 | 0.002240 | Allele | 1.51 | 1.2-2 | SEQ ID No: 401 | SEQ ID No: 402 | SEQ ID No: 857 | |
| rs17388160 | 0.000142 | Recessive | 1.93 | 1.4-2.7 | SEQ ID No: 403 | SEQ ID No: 404 | SEQ ID No: 858 | |
| rs3781158 | 0.000145 | Recessive | 2.00 | 1.4-2.9 | SEQ ID No: 405 | SEQ ID No: 406 | SEQ ID No: 859 | |
| rs11712746 | 0.001381 | Allele | 1.62 | 1.2-2.2 | SEQ ID No: 407 | SEQ ID No: 408 | SEQ ID No: 860 | |
| rs10494300 | 0.001030 | Allele | 1.47 | 1.2-1.9 | SEQ ID No: 409 | SEQ ID No: 410 | SEQ ID No: 861 | SEQ ID No: 1041 |
| rs6089908 | 0.001286 | Recessive | 1.93 | 1.3-2.9 | SEQ ID No: 411 | SEQ ID No: 412 | SEQ ID No: 862 | |
| rs6138601 | 0.000204 | Dominant | 1.87 | 1.3-2.6 | SEQ ID No: 413 | SEQ ID No: 414 | SEQ ID No: 863 | |

TABLE 59

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs6138598 | 20 | 25,461,536 | KIAA0980 −6294 bp (NM_025176.3) | A | G | A | 0.36 | 0.27 |
| rs7692155 | 4 | 123,386,649 | KIAA1109 −44906 bp (XM_371706) | A | G | A | 0.70 | 0.62 |
| rs7112492 | 11 | 18,362,086 | LDHA −10601 bp (NM_005566.1) | A | C | C | 0.37 | 0.29 |
| rs4274186 | 11 | 18,375,295 | LDHA Intron2 (NM_005566.1) | A | G | G | 0.37 | 0.29 |
| rs1881716 | 11 | 18,381,594 | LDHA Intron5 (NM_005566.1) | A | G | A | 0.37 | 0.29 |
| rs11590929 | 1 | 87,926,458 | LMO4 +403174 bp (NM_006769.2) | A | G | G | 0.96 | 0.91 |
| rs4643164 | 13 | 106,724,352 | LOC122335 −355849 bp (XM_063084) | A | C | A | 0.36 | 0.32 |
| rs11117962 | 1 | 214,438,658 | LOC128153 +9779 bp (NM_138796.2) | A | G | G | 0.60 | 0.52 |
| rs94967 | 21 | 40,117,177 | LOC150084 +21299 bp (XM_086761) | A | G | A | 0.75 | 0.66 |
| rs4816657 | 21 | 40,068,705 | LOC150084 Intron4 (XM_086761) | A | C | C | 0.75 | 0.66 |
| rs1018350 | 21 | 40,070,715 | LOC150084 Intron4 (XM_086761) | A | C | A | 0.75 | 0.66 |
| rs2837211 | 21 | 40,070,264 | LOC150084 Intron4 (XM_086761) | A | C | C | 0.75 | 0.66 |
| rs1571713 | 21 | 40,075,065 | LOC150084 Intron5 (XM_086761) | A | G | A | 0.75 | 0.66 |
| rs2837220 | 21 | 40,082,808 | LOC150084 Intron6 (XM_086761) | A | G | G | 0.70 | 0.61 |
| rs463903 | 21 | 40,087,547 | LOC150084 Intron8 (XM_086761) | A | G | A | 0.75 | 0.66 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs6138598 | 0.000168 | Dominant | 1.88 | 1.4-2.6 | SEQ ID No: 415 | SEQ ID No: 416 | SEQ ID No: 864 | |
| rs7692155 | 0.004467 | Allele | 1.42 | 1.1-1.8 | SEQ ID No: 417 | SEQ ID No: 418 | SEQ ID No: 865 | |
| rs7112492 | 0.000534 | Dominant | 1.78 | 1.3-2.5 | SEQ ID No: 419 | SEQ ID No: 420 | SEQ ID No: 866 | |
| rs4274186 | 0.001542 | Dominant | 1.71 | 1.2-2.4 | SEQ ID No: 421 | SEQ ID No: 422 | SEQ ID No: 867 | |
| rs1881716 | 0.000737 | Dominant | 1.76 | 1.3-2.4 | SEQ ID No: 423 | SEQ ID No: 424 | SEQ ID No: 868 | |
| rs11590929 | 0.000640 | Allele | 2.30 | 1.4-3.7 | SEQ ID No: 425 | SEQ ID No: 426 | SEQ ID No: 869 | |
| rs4643164 | 0.006498 | Recessive | 2.17 | 1.2-3.8 | SEQ ID No: 427 | SEQ ID No: 428 | SEQ ID No: 870 | |
| rs11117962 | 0.000571 | Recessive | 1.88 | 1.3-2.7 | SEQ ID No: 429 | SEQ ID No: 430 | SEQ ID No: 871 | |
| rs94967 | 0.000624 | Allele | 1.56 | 1.2-2 | SEQ ID No: 431 | SEQ ID No: 432 | SEQ ID No: 872 | |
| rs4816657 | 0.001021 | Allele | 1.52 | 1.2-2 | SEQ ID No: 433 | SEQ ID No: 434 | SEQ ID No: 873 | |
| rs1018350 | 0.001261 | Allele | 1.51 | 1.2-1.9 | SEQ ID No: 435 | SEQ ID No: 436 | SEQ ID No: 874 | |
| rs2837211 | 0.001261 | Allele | 1.51 | 1.2-1.9 | SEQ ID No: 437 | SEQ ID No: 438 | SEQ ID No: 875 | |
| rs1571713 | 0.002192 | Allele | 1.49 | 1.2-1.9 | SEQ ID No: 439 | SEQ ID No: 440 | SEQ ID No: 876 | |
| rs2837220 | 0.001120 | Allele | 1.50 | 1.2-1.9 | SEQ ID No: 441 | SEQ ID No: 442 | SEQ ID No: 877 | |
| rs463903 | 0.001553 | Allele | 1.50 | 1.2-1.9 | SEQ ID No: 443 | SEQ ID No: 444 | SEQ ID No: 878 | |

TABLE 60

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs465258 | 21 | 40,093,614 | LOC150084 Intron8 (XM_086761) | A | G | A | 0.74 | 0.66 |
| rs6440874 | 3 | 154,583,971 | LOC152118 −101011 bp (XM_098163) | A | G | G | 0.90 | 0.85 |
| rs2174746 | 3 | 154,581,141 | LOC152118 −103841 bp (XM_098163) | A | G | A | 0.90 | 0.85 |
| rs12490570 | 3 | 154,577,350 | LOC152118 −107632 bp (XM_098163) | A | C | A | 0.90 | 0.84 |
| rs6440881 | 3 | 154,628,080 | LOC152118 −56902 bp (XM_098163) | A | C | A | 0.88 | 0.82 |
| rs10113800 | 8 | 96,514,178 | LOC157657 −163565 bp (NM_177965.2) | A | G | A | 0.22 | 0.15 |
| rs4394361 | 8 | 96,522,738 | LOC157657 −172125 bp (NM_177965.2) | A | C | A | 0.23 | 0.15 |
| rs1622029 | 14 | 83,697,804 | LOC283583 −1366892 bp (XM_211092) | A | T | A | 0.70 | 0.60 |
| rs1828132 | 18 | 72,388,920 | LOC284276 Intron2 (XM_378757) | A | G | A | 0.50 | 0.41 |
| rs4812180 | 20 | 58,704,985 | LOC284757 +371993 bp (XM_496478) | A | G | G | 0.08 | 0.04 |
| rs9399445 | 6 | 143,900,997 | LOC285740 +16163 bp (XM_379438) | A | G | A | 0.53 | 0.45 |
| rs6570564 | 6 | 143,896,965 | LOC285740 +20726 bp (XM_379438) | A | G | G | 0.51 | 0.42 |
| rs9650336 | 8 | 38,625,315 | LOC286140 −47376 bp (XM_209913) | A | G | G | 0.66 | 0.56 |
| rs12669138 | 7 | 9,564,997 | LOC340268 Intron1 (XM_294634) | C | G | C | 0.63 | 0.56 |
| rs1913603 | 7 | 9,664,816 | LOC340268 Intron1 (XM_294634) | A | C | C | 0.61 | 0.52 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs465258 | 0.002055 | Allele | 1.49 | 1.2-1.9 | SEQ ID No: 445 | SEQ ID No: 446 | SEQ ID No: 879 | |
| rs6440874 | 0.008965 | Allele | 1.61 | 1.1-2.3 | SEQ ID No: 447 | SEQ ID No: 448 | SEQ ID No: 880 | |
| rs2174746 | 0.006770 | Allele | 1.63 | 1.1-2.3 | SEQ ID No: 449 | SEQ ID No: 450 | SEQ ID No: 881 | |
| rs12490570 | 0.004737 | Allele | 1.65 | 1.2-2.3 | SEQ ID No: 451 | SEQ ID No: 452 | SEQ ID No: 882 | |
| rs6440881 | 0.005426 | Allele | 1.58 | 1.1-2.2 | SEQ ID No: 453 | SEQ ID No: 454 | SEQ ID No: 883 | |

TABLE 60-continued

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs10113800 | 0.001831 | Allele | 1.62 | 1.2-2.2 | SEQ ID No: 455 | SEQ ID No: 456 | SEQ ID No: 884 | |
| rs4394361 | 0.000936 | Allele | 1.67 | 1.2-2.3 | SEQ ID No: 457 | SEQ ID No: 458 | SEQ ID No: 885 | |
| rs1622029 | 0.000203 | Allele | 1.58 | 1.2-2 | SEQ ID No: 459 | SEQ ID No: 460 | SEQ ID No: 886 | SEQ ID No: 1042 |
| rs1828132 | 0.001879 | Recessive | 1.93 | 1.3-2.9 | SEQ ID No: 461 | SEQ ID No: 462 | SEQ ID No: 887 | |
| rs4812180 | 0.004895 | Allele | 2.07 | 1.2-3.4 | SEQ ID No: 463 | SEQ ID No: 464 | SEQ ID No: 888 | |
| rs9399445 | 0.004216 | Allele | 1.40 | 1.1-1.8 | SEQ ID No: 465 | SEQ ID No: 466 | SEQ ID No: 889 | |
| rs6570564 | 0.003855 | Allele | 1.41 | 1.1-1.8 | SEQ ID No: 467 | SEQ ID No: 468 | SEQ ID No: 890 | |
| rs9650336 | 0.000158 | Recessive | 1.91 | 1.4-2.7 | SEQ ID No: 469 | SEQ ID No: 470 | SEQ ID No: 891 | |
| rs12669138 | 0.000574 | Dominant | 2.22 | 1.4-3.5 | SEQ ID No: 471 | SEQ ID No: 472 | SEQ ID No: 892 | SEQ ID No: 1043 |
| rs1913603 | 0.001215 | Dominant | 2.09 | 1.3-3.3 | SEQ ID No: 473 | SEQ ID No: 474 | SEQ ID No: 893 | |

TABLE 61

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs1514880 | 7 | 9,664,527 | LOC340268 Intron1 (XM_294634) | A | G | G | 0.58 | 0.51 |
| rs1877885 | 7 | 9,625,295 | LOC340268 Intron1 (XM_294634) | C | G | C | 0.58 | 0.49 |
| rs7458284 | 7 | 9,670,774 | LOC340268 Intron1 (XM_294634) | A | G | G | 0.37 | 0.29 |
| rs10512277 | 9 | 100,567,355 | LOC347273 +138909 bp (XM_294592) | A | G | G | 0.35 | 0.28 |
| rs4743420 | 9 | 100,567,644 | LOC347273 +139198 bp (XM_294592) | A | C | A | 0.34 | 0.28 |
| rs7022939 | 9 | 100,568,349 | LOC347273 +139903 bp (XM_294592) | C | G | G | 0.35 | 0.28 |
| rs9299341 | 9 | 100,570,439 | LOC347273 +141993 bp (XM_294592) | A | G | G | 0.35 | 0.28 |
| rs161130 | 11 | 112,160,184 | LOC387810 −172677 bp (XM_373513) | A | G | G | 0.81 | 0.73 |
| rs295869 | 17 | 32,221,458 | LOC388375 +71591 bp (XM_373726) | A | G | G | 0.42 | 0.36 |
| rs369977 | 21 | 15,532,948 | LOC388814 +131764 bp (XM_373926) | A | G | G | 0.69 | 0.61 |
| rs17605639 | 4 | 27,290,099 | LOC389204 −297625 bp (XM_374079) | A | G | G | 0.79 | 0.69 |
| rs10478702 | 5 | 125,550,583 | LOC389319 −173069 bp (XM_374134) | A | G | G | 0.75 | 0.71 |
| rs7712363 | 5 | 125,542,548 | LOC389319 −181104 bp (XM_374134) | A | C | C | 0.75 | 0.71 |
| rs10076364 | 5 | 125,510,888 | LOC389319 −212764 bp (XM_374134) | C | G | C | 0.74 | 0.70 |
| rs1560026 | 5 | 125,497,684 | LOC389319 −225968 bp (XM_374134) | A | C | A | 0.73 | 0.69 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs1514880 | 0.001614 | Dominant | 2.00 | 1.3-3.1 | SEQ ID No: 475 | SEQ ID No: 476 | SEQ ID No: 894 | |
| rs1877885 | 0.001965 | Dominant | 1.90 | 1.3-2.9 | SEQ ID No: 477 | SEQ ID No: 478 | SEQ ID No: 895 | SEQ ID No: 1044 |
| rs7458284 | 0.002537 | Recessive | 2.38 | 1.4-4.2 | SEQ ID No: 479 | SEQ ID No: 480 | SEQ ID No: 896 | |
| rs10512277 | 0.001943 | Dominant | 1.68 | 1.2-2.3 | SEQ ID No: 481 | SEQ ID No: 482 | SEQ ID No: 897 | |
| rs4743420 | 0.002543 | Dominant | 1.66 | 1.2-2.3 | SEQ ID No: 483 | SEQ ID No: 484 | SEQ ID No: 898 | |
| rs7022939 | 0.001943 | Dominant | 1.68 | 1.2-2.3 | SEQ ID No: 485 | SEQ ID No: 486 | SEQ ID No: 899 | SEQ ID No: 1045 |
| rs9299341 | 0.001943 | Dominant | 1.68 | 1.2-2.3 | SEQ ID No: 487 | SEQ ID No: 488 | SEQ ID No: 900 | |
| rs161130 | 0.000992 | Allele | 1.59 | 1.2-2.1 | SEQ ID No: 489 | SEQ ID No: 490 | SEQ ID No: 901 | |
| rs295869 | 0.001370 | Dominant | 1.73 | 1.2-2.4 | SEQ ID No: 491 | SEQ ID No: 492 | SEQ ID No: 902 | |
| rs369977 | 0.003698 | Allele | 1.43 | 1.1-1.8 | SEQ ID No: 493 | SEQ ID No: 494 | SEQ ID No: 903 | |
| rs17605639 | 0.000220 | Allele | 1.65 | 1.3-2.1 | SEQ ID No: 495 | SEQ ID No: 496 | SEQ ID No: 904 | |
| rs10478702 | 0.005653 | Recessive | 1.59 | 1.1-2.2 | SEQ ID No: 497 | SEQ ID No: 498 | SEQ ID No: 905 | |
| rs7712363 | 0.005438 | Recessive | 1.60 | 1.1-2.2 | SEQ ID No: 499 | SEQ ID No: 500 | SEQ ID No: 906 | |
| rs10076364 | 0.002399 | Recessive | 1.67 | 1.2-2.3 | SEQ ID No: 501 | SEQ ID No: 502 | SEQ ID No: 907 | SEQ ID No: 1046 |
| rs1560026 | 0.002114 | Recessive | 1.68 | 1.2-2.3 | SEQ ID No: 503 | SEQ ID No: 504 | SEQ ID No: 908 | |

TABLE 62

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs271351 | 1 | 29,821,213 | LOC391025 −173869 bp (XM_372775) | A | G | A | 0.15 | 0.09 |
| rs947130 | 1 | 119,728,774 | LOC391075 −11088 bp (XM_497702) | A | G | G | 0.82 | 0.76 |
| rs1154988 | 3 | 137,407,889 | LOC391581 −434 bp (XM_497940) | A | T | A | 0.20 | 0.13 |
| rs6560584 | 9 | 68,976,726 | LOC392347 Intron2 (XM_373298) | A | G | A | 0.39 | 0.28 |
| rs7034303 | 9 | 68,976,425 | LOC392347 Intron2 (XM_373298) | A | G | G | 0.39 | 0.28 |
| rs7048937 | 9 | 68,975,807 | LOC392347 Intron2 (XM_373298) | A | G | G | 0.39 | 0.28 |

TABLE 62-continued

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs7850573 | 9 | 68,976,814 | LOC392347 Intron2 (XM_373298) | A | G | G | 0.39 | 0.28 |
| rs11175622 | 12 | 63,686,548 | LOC400046 +28983 bp (XM_378362) | A | G | A | 0.28 | 0.20 |
| rs11175627 | 12 | 63,691,379 | LOC400046 +33814 bp (XM_378362) | A | G | G | 0.28 | 0.19 |
| rs7136577 | 12 | 63,692,809 | LOC400046 +35244 bp (XM_378362) | A | C | C | 0.28 | 0.20 |
| rs7212115 | 17 | 10,832,202 | LOC400573 −182083 bp (XM_378649) | A | C | A | 0.87 | 0.81 |
| rs8098925 | 18 | 69,257,838 | LOC400655 −175143 bp (XM_378753) | A | G | G | 0.63 | 0.56 |
| rs17152703 | 7 | 78,929,412 | LOC401384 +195612 bp (XM_379506) | C | G | C | 0.83 | 0.77 |
| rs17152739 | 7 | 78,935,541 | LOC401384 +201741 bp (XM_379506) | A | G | G | 0.75 | 0.67 |
| rs7959848 | 12 | 82,248,474 | LOC401725 +200037 bp (XM_377278) | A | G | G | 0.43 | 0.36 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs271351 | 0.004629 | Allele | 1.71 | 1.2-2.5 | SEQ ID No: 505 | SEQ ID No: 506 | SEQ ID No: 909 | |
| rs947130 | 0.008087 | Allele | 1.46 | 1.1-1.9 | SEQ ID No: 507 | SEQ ID No: 508 | SEQ ID No: 910 | |
| rs1154988 | 0.002265 | Allele | 1.66 | 1.2-2.3 | SEQ ID No: 509 | SEQ ID No: 510 | SEQ ID No: 911 | SEQ ID No: 1047 |
| rs6560584 | 0.000148 | Allele | 1.61 | 1.3-2.1 | SEQ ID No: 511 | SEQ ID No: 512 | SEQ ID No: 912 | |
| rs7034303 | 0.000161 | Allele | 1.60 | 1.3-2 | SEQ ID No: 513 | SEQ ID No: 514 | SEQ ID No: 913 | |
| rs7048937 | 0.000161 | Allele | 1.60 | 1.3-2 | SEQ ID No: 515 | SEQ ID No: 516 | SEQ ID No: 914 | |
| rs7850573 | 0.000161 | Allele | 1.60 | 1.3-2 | SEQ ID No: 517 | SEQ ID No: 518 | SEQ ID No: 915 | |
| rs11175622 | 0.001063 | Allele | 1.58 | 1.2-2.1 | SEQ ID No: 519 | SEQ ID No: 520 | SEQ ID No: 916 | |
| rs11175627 | 0.000923 | Allele | 1.60 | 1.2-2.1 | SEQ ID No: 521 | SEQ ID No: 522 | SEQ ID No: 917 | |
| rs7136577 | 0.001063 | Allele | 1.58 | 1.2-2.1 | SEQ ID No: 523 | SEQ ID No: 524 | SEQ ID No: 918 | |
| rs7212115 | 0.004979 | Allele | 1.59 | 1.1-2.2 | SEQ ID No: 525 | SEQ ID No: 526 | SEQ ID No: 919 | |
| rs8098925 | 0.009580 | Allele | 1.37 | 1.1-1.7 | SEQ ID No: 527 | SEQ ID No: 528 | SEQ ID No: 920 | |
| rs17152703 | 0.005507 | Allele | 1.51 | 1.1-2 | SEQ ID No: 529 | SEQ ID No: 530 | SEQ ID No: 921 | SEQ ID No: 1048 |
| rs17152739 | 0.002274 | Allele | 1.48 | 1.2-1.9 | SEQ ID No: 531 | SEQ ID No: 532 | SEQ ID No: 922 | |
| rs7959848 | 0.008743 | Allele | 1.37 | 1.1-1.7 | SEQ ID No: 533 | SEQ ID No: 534 | SEQ ID No: 923 | |

TABLE 63

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs5750009 | 22 | 33,679,879 | LOC402059 Intron8 (XM_497817) | A | G | G | 0.79 | 0.75 |
| rs10892454 | 11 | 119,148,037 | LOC440070 +32494 bp (XM_498530) | A | C | A | 0.48 | 0.46 |
| rs4269933 | 11 | 119,153,578 | LOC440070 +38035 bp (XM_498530) | A | G | A | 0.48 | 0.46 |
| rs7296095 | 12 | 114,337,597 | LOC440112 −115952 bp (XM_498548) | A | G | G | 0.28 | 0.20 |
| rs9302502 | 16 | 13,517,321 | LOC440339 +251309 bp (XM_498634) | A | G | G | 0.32 | 0.22 |
| rs13333495 | 16 | 13,503,539 | LOC440339 +265091 bp (XM_498634) | A | G | G | 0.31 | 0.22 |
| rs16962155 | 16 | 13,495,836 | LOC440339 +272794 bp (XM_498634) | A | G | G | 0.31 | 0.22 |
| rs17070891 | 6 | 141,790,772 | LOC441173 +153727 bp (XM_496827) | A | G | A | 0.53 | 0.46 |
| rs17070863 | 6 | 141,772,290 | LOC441173 +172209 bp (XM_496827) | A | G | G | 0.53 | 0.45 |
| rs9484507 | 6 | 141,764,651 | LOC441173 +179848 bp (XM_496827) | A | G | A | 0.52 | 0.44 |
| rs9496008 | 6 | 141,762,720 | LOC441173 +181779 bp (XM_496827) | A | G | G | 0.52 | 0.45 |
| rs1336272 | 6 | 142,286,367 | LOC441173 −23126 bp (XM_496827) | A | T | T | 0.30 | 0.22 |
| rs7767107 | 6 | 142,237,572 | LOC441173 Intron1 (XM_496827) | A | C | A | 0.29 | 0.22 |
| rs2152589 | 6 | 142,250,761 | LOC441173 Intron1 (XM_496827) | A | G | A | 0.30 | 0.23 |
| rs13213414 | 6 | 142,262,919 | LOC441173 Intron1 (XM_496827) | A | G | G | 0.30 | 0.23 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs5750009 | 0.007709 | Dominant | 2.86 | 1.3-6.2 | SEQ ID No: 535 | SEQ ID No: 536 | SEQ ID No: 924 | |
| rs10892454 | 0.005874 | Recessive | 1.83 | 1.2-2.8 | SEQ ID No: 537 | SEQ ID No: 538 | SEQ ID No: 925 | |
| rs4269933 | 0.005488 | Recessive | 1.83 | 1.2-2.8 | SEQ ID No: 539 | SEQ ID No: 540 | SEQ ID No: 926 | |
| rs7296095 | 0.003482 | Allele | 1.50 | 1.1-2 | SEQ ID No: 541 | SEQ ID No: 542 | SEQ ID No: 927 | |
| rs9302502 | 0.000258 | Allele | 1.63 | 1.3-2.1 | SEQ ID No: 543 | SEQ ID No: 544 | SEQ ID No: 928 | |
| rs13333495 | 0.000327 | Allele | 1.62 | 1.2-2.1 | SEQ ID No: 545 | SEQ ID No: 546 | SEQ ID No: 929 | |
| rs16962155 | 0.000367 | Allele | 1.61 | 1.2-2.1 | SEQ ID No: 547 | SEQ ID No: 548 | SEQ ID No: 930 | |
| rs17070891 | 0.001173 | Recessive | 1.91 | 1.3-2.8 | SEQ ID No: 549 | SEQ ID No: 550 | SEQ ID No: 931 | |
| rs17070863 | 0.000396 | Recessive | 2.05 | 1.4-3.1 | SEQ ID No: 551 | SEQ ID No: 552 | SEQ ID No: 932 | |
| rs9484507 | 0.000890 | Recessive | 1.98 | 1.3-3 | SEQ ID No: 553 | SEQ ID No: 554 | SEQ ID No: 933 | |
| rs9496008 | 0.000882 | Recessive | 1.97 | 1.3-2.9 | SEQ ID No: 555 | SEQ ID No: 556 | SEQ ID No: 934 | |
| rs1336272 | 0.001778 | Dominant | 1.69 | 1.2-2.4 | SEQ ID No: 557 | SEQ ID No: 558 | SEQ ID No: 935 | SEQ ID No: 1049 |
| rs7767107 | 0.001274 | Dominant | 1.72 | 1.2-2.4 | SEQ ID No: 559 | SEQ ID No: 560 | SEQ ID No: 936 | |
| rs2152589 | 0.003172 | Dominant | 1.64 | 1.2-2.3 | SEQ ID No: 561 | SEQ ID No: 562 | SEQ ID No: 937 | |
| rs13213414 | 0.003185 | Dominant | 1.64 | 1.2-2.3 | SEQ ID No: 563 | SEQ ID No: 564 | SEQ ID No: 938 | |

TABLE 64

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs7754052 | 6 | 142,254,496 | LOC441173 Intron1 (XM_496827) | A | G | A | 0.31 | 0.24 |
| rs9496179 | 6 | 142,254,945 | LOC441173 Intron1 (XM_496827) | A | G | G | 0.31 | 0.24 |
| rs2169856 | 12 | 53,858,919 | LOC441639 +48092 bp (XM_497345) | C | G | G | 0.73 | 0.68 |
| rs4979255 | 9 | 107,542,392 | LOC442430 −50518 bp (XM_498339) | A | G | G | 0.66 | 0.62 |
| rs16860887 | 2 | 197,723,413 | LOC91526 Intron15 (NM_153697.1) | A | C | A | 0.90 | 0.83 |
| rs13426748 | 2 | 197,723,066 | LOC91526 Intron15 (NM_153697.1) | A | G | A | 0.90 | 0.84 |
| rs4850410 | 2 | 197,745,675 | LOC91526 Intron15 (NM_153697.1) | A | G | A | 0.92 | 0.86 |
| rs7582411 | 2 | 197,738,392 | LOC91526 Intron15 (NM_153697.1) | A | G | G | 0.91 | 0.85 |
| rs12595990 | 16 | 12,378,613 | LOC92017 Intron9 (XM_042234) | A | G | G | 0.49 | 0.39 |
| rs16852789 | 3 | 170,106,556 | LOC93556 +75467 bp (XM_376284) | A | G | A | 0.35 | 0.30 |
| rs12800710 | 11 | 58,071,116 | LFXN Intron7 (NM_004811.1) | A | G | G | 0.83 | 0.77 |
| rs2328883 | 6 | 25,510,510 | LRRC16 −108438 bp (NM_017640.2) | A | G | A | 0.32 | 0.28 |
| rs880226 | 6 | 25,510,282 | LRRC16 −108666 bp (NM_017640.2) | A | G | G | 0.32 | 0.27 |
| rs9461154 | 6 | 25,506,014 | LRRC16 −112934 bp (NM_017640.2) | A | G | A | 0.32 | 0.28 |
| rs3863401 | 15 | 97,698,743 | LRRC28 Intron6 (NM_144598.2) | C | G | G | 0.59 | 0.50 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs7754052 | 0.003495 | Dominant | 1.63 | 1.2-2.3 | SEQ ID No: 565 | SEQ ID No: 566 | SEQ ID No: 939 | |
| rs9496179 | 0.003920 | Dominant | 1.62 | 1.2-2.3 | SEQ ID No: 567 | SEQ ID No: 568 | SEQ ID No: 940 | |
| rs2169856 | 0.005853 | Recessive | 1.59 | 1.1-2.2 | SEQ ID No: 569 | SEQ ID No: 570 | SEQ ID No: 941 | SEQ ID No: 1050 |
| rs4979255 | 0.008140 | Recessive | 1.57 | 1.1-2.2 | SEQ ID No: 571 | SEQ ID No: 572 | SEQ ID No: 942 | |
| rs16860887 | 0.000450 | Recessive | 1.98 | 1.4-2.9 | SEQ ID No: 573 | SEQ ID No: 574 | SEQ ID No: 943 | |
| rs13426748 | 0.000601 | Recessive | 1.95 | 1.3-2.9 | SEQ ID No: 575 | SEQ ID No: 576 | SEQ ID No: 944 | |
| rs4850410 | 0.000623 | Recessive | 2.04 | 1.4-3.1 | SEQ ID No: 577 | SEQ ID No: 578 | SEQ ID No: 945 | |
| rs7582411 | 0.001709 | Recessive | 1.90 | 1.3-2.8 | SEQ ID No: 579 | SEQ ID No: 580 | SEQ ID No: 946 | |
| rs12595990 | 0.000870 | Recessive | 2.07 | 1.3-3.2 | SEQ ID No: 581 | SEQ ID No: 582 | SEQ ID No: 947 | |
| rs16852789 | 0.008064 | Dominant | 1.57 | 1.1-2.2 | SEQ ID No: 583 | SEQ ID No: 584 | SEQ ID No: 948 | |
| rs12800710 | 0.009214 | Allele | 1.47 | 1.1-2 | SEQ ID No: 585 | SEQ ID No: 586 | SEQ ID No: 949 | |
| rs2328883 | 0.000622 | Recessive | 3.40 | 1.7-6.8 | SEQ ID No: 587 | SEQ ID No: 588 | SEQ ID No: 950 | |
| rs880226 | 0.000709 | Recessive | 3.37 | 1.7-6.8 | SEQ ID No: 589 | SEQ ID No: 590 | SEQ ID No: 951 | |
| rs9461154 | 0.000622 | Recessive | 3.40 | 1.7-6.8 | SEQ ID No: 591 | SEQ ID No: 592 | SEQ ID No: 952 | |
| rs3863401 | 0.001713 | Allele | 1.45 | 1.1-1.8 | SEQ ID No: 593 | SEQ ID No: 594 | SEQ ID No: 953 | SEQ ID No: 1051 |

TABLE 65

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs7173844 | 15 | 97,694,416 | LRRC28 Intron6 (NM_144598.2) | A | G | G | 0.59 | 0.50 |
| rs926663 | 20 | 38,679,189 | MAFB +68744 bp (NM_005461.3) | A | G | G | 0.45 | 0.37 |
| rs11734419 | 4 | 141,040,368 | MAML3 Intron2 (NM_018717.2) | A | G | G | 0.44 | 0.37 |
| rs628223 | 11 | 82,645,812 | MDS025 +4340 bp (NM_021825.3) | A | G | A | 0.57 | 0.47 |
| rs784288 | 3 | 170,453,933 | MDS1 Intron2 (NM_004991.1) | A | G | G | 0.78 | 0.69 |
| rs194229 | 5 | 158,600,287 | MGC10067 −22589 bp (NM_145049.1) | C | G | G | 0.51 | 0.45 |
| rs7927545 | 11 | 11,403,040 | MGC71806 Intron3 (NM_198516.1) | A | T | A | 0.57 | 0.48 |
| rs10967964 | 9 | 27,485,920 | MOBKL2B Intron1 (NM_024761.3) | A | C | A | 0.24 | 0.16 |
| rs1529404 | 2 | 16,137,052 | MYCN +99328 bp (NM_005378.3) | A | G | A | 0.87 | 0.81 |
| rs4261668 | 2 | 210,987,818 | MYL1 Intron3 (NM_079422.1), MYL1 Intron3 (NM_079420.1) | A | G | G | 0.36 | 0.26 |
| rs16941388 | 15 | 57,459,340 | MYO1E −6977 bp (NM_004998.1) | A | G | G | 0.92 | 0.88 |
| rs3798425 | 6 | 76,664,270 | MYO6 Intron29 (XM_376516) | C | G | G | 0.82 | 0.74 |
| rs6763643 | 3 | 40,072,995 | MYRIP Intron3 (NM_015460.1) | A | G | G | 0.38 | 0.34 |
| rs7275647 | 21 | 21,586,912 | NCAM2 Intron5 (NM_004540.2) | A | G | A | 0.65 | 0.57 |
| rs12900219 | 15 | 21,583,560 | NDN −100017 bp (NM_002487.2) | A | G | G | 0.92 | 0.85 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs7173844 | 0.001964 | Allele | 1.44 | 1.1-1.8 | SEQ ID No: 595 | SEQ ID No: 596 | SEQ ID No: 954 | |
| rs926663 | 0.000663 | Dominant | 1.82 | 1.3-2.6 | SEQ ID No: 597 | SEQ ID No: 598 | SEQ ID No: 955 | |
| rs11734419 | 0.007706 | Dominant | 1.60 | 1.1-2.3 | SEQ ID No: 599 | SEQ ID No: 600 | SEQ ID No: 956 | |
| rs628223 | 0.000386 | Allele | 1.52 | 1.2-1.9 | SEQ ID No: 601 | SEQ ID No: 602 | SEQ ID No: 957 | |

TABLE 65-continued

| dBSNP ID | p-value | Model | Odds Ratio | 95% CI | Seq 1 | Seq 2 | Seq 3 | Seq 4 |
|---|---|---|---|---|---|---|---|---|
| rs784288 | 0.000432 | Allele | 1.60 | 1.2-2.1 | SEQ ID No: 603 | SEQ ID No: 604 | SEQ ID No: 958 | |
| rs194229 | 0.000255 | Dominant | 1.98 | 1.4-2.9 | SEQ ID No: 605 | SEQ ID No: 606 | SEQ ID No: 959 | SEQ ID No: 1052 |
| rs7927545 | 0.003494 | Allele | 1.41 | 1.1-1.8 | SEQ ID No: 607 | SEQ ID No: 608 | SEQ ID No: 960 | SEQ ID No: 1053 |
| rs10967964 | 0.000249 | Dominant | 1.93 | 1.4-2.7 | SEQ ID No: 609 | SEQ ID No: 610 | SEQ ID No: 961 | |
| rs1529404 | 0.004076 | Allele | 1.59 | 1.2-2.2 | SEQ ID No: 611 | SEQ ID No: 612 | SEQ ID No: 962 | |
| rs4261668 | 0.000108 | Allele | 1.64 | 1.3-2.1 | SEQ ID No: 613 | SEQ ID No: 614 | SEQ ID No: 963 | |
| rs16941388 | 0.008343 | Recessive | 1.77 | 1.2-2.7 | SEQ ID No: 615 | SEQ ID No: 616 | SEQ ID No: 964 | |
| rs3798425 | 0.000829 | Recessive | 1.77 | 1.3-2.5 | SEQ ID No: 617 | SEQ ID No: 618 | SEQ ID No: 965 | SEQ ID No: 1054 |
| rs6763643 | 0.005066 | Recessive | 2.07 | 1.2-3.4 | SEQ ID No: 619 | SEQ ID No: 620 | SEQ ID No: 966 | |
| rs7275647 | 0.004628 | Allele | 1.40 | 1.1-1.8 | SEQ ID No: 621 | SEQ ID No: 622 | SEQ ID No: 967 | |
| rs12900219 | 0.000310 | Recessive | 2.09 | 1.4-3.1 | SEQ ID No: 623 | SEQ ID No: 624 | SEQ ID No: 968 | |

TABLE 66

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs1717831 | 15 | 21,578,625 | NDN −95082 bp (NM_002487.2) | A | C | C | 0.89 | 0.83 |
| rs10503907 | 8 | 32,291,552 | NRG1 −233743 bp (NM_013958.1), NRG1 −233775 bp (NM_013957.1), NRG1 −233799 bp (NM_004495.1), NRG1 −233842 bp (NM_013961.1), NRG1 −234103 bp (NM_013964.1), NRG1 −234127 bp (NM_013960.1), NRG1 −234143 bp (NM_013956.1), NRG1 −281336 bp (NM_013962.1), NRG1 −332731 bp (NM_013959.1) | A | G | A | 0.93 | 0.86 |
| rs595805 | 6 | 5,987,127 | NRN1 −34495 bp (NM_016588.2) | A | G | G | 0.64 | 0.59 |
| rs943509 | 9 | 75,218,105 | OSTF1 +226788 bp (NM_012383.3) | A | G | G | 0.35 | 0.27 |
| rs3805347 | 4 | 108,959,666 | PAPSS1 Intron5 (NM_005443.4) | A | G | A | 0.62 | 0.56 |
| rs684773 | 3 | 137,439,003 | PCCB −12843 bp (NM_000532.2) | A | C | A | 0.20 | 0.13 |
| rs3957816 | 3 | 137,438,550 | PCCB −13296 bp (NM_000532.2) | A | G | G | 0.22 | 0.15 |
| rs548288 | 3 | 137,452,453 | PCCB Intron1 (NM_000532.2) | A | G | A | 0.21 | 0.14 |
| rs696081 | 3 | 137,529,887 | PCCB Intron13 (NM_000532.2) | A | G | A | 0.23 | 0.16 |
| rs2151078 | 10 | 55,864,965 | PCDH15 Intron3 (NM_033056.2) | A | G | A | 0.95 | 0.89 |
| rs2837255 | 21 | 40,143,991 | PCP4 −17259 bp (NM_006198.1) | A | C | A | 0.68 | 0.58 |
| rs2837248 | 21 | 40,141,638 | PCP4 −19612 bp (NM_006198.1) | A | G | G | 0.66 | 0.58 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs1717831 | 0.003212 | Recessive | 1.75 | 1.2-2.5 | SEQ ID No: 625 | SEQ ID No: 626 | SEQ ID No: 969 | |
| rs10503907 | 0.000276 | Allele | 2.02 | 1.4-3 | SEQ ID No: 627 | SEQ ID No: 628 | SEQ ID No: 970 | |
| rs595805 | 0.002840 | Recessive | 1.68 | 1.2-2.4 | SEQ ID No: 629 | SEQ ID No: 630 | SEQ ID No: 971 | |
| rs943509 | 0.003765 | Allele | 1.45 | 1.1-1.9 | SEQ ID No: 631 | SEQ ID No: 632 | SEQ ID No: 972 | |
| rs3805347 | 0.009262 | Recessive | 1.59 | 1.1-2.3 | SEQ ID No: 633 | SEQ ID No: 634 | SEQ ID No: 973 | |
| rs684773 | 0.001687 | Allele | 1.67 | 1.2-2.3 | SEQ ID No: 635 | SEQ ID No: 636 | SEQ ID No: 974 | |
| rs3957816 | 0.001412 | Allele | 1.64 | 1.2-2.2 | SEQ ID No: 637 | SEQ ID No: 638 | SEQ ID No: 975 | |
| rs548288 | 0.003173 | Allele | 1.60 | 1.2-2.2 | SEQ ID No: 639 | SEQ ID No: 640 | SEQ ID No: 976 | |
| rs696081 | 0.004050 | Allele | 1.54 | 1.1-2.1 | SEQ ID No: 641 | SEQ ID No: 642 | SEQ ID No: 977 | |
| rs2151078 | 0.000379 | Allele | 2.25 | 1.4-3.5 | SEQ ID No: 643 | SEQ ID No: 644 | SEQ ID No: 978 | |
| rs2837255 | 0.000724 | Allele | 1.51 | 1.2-1.9 | SEQ ID No: 645 | SEQ ID No: 646 | SEQ ID No: 979 | |
| rs2837248 | 0.002496 | Allele | 1.44 | 1.1-1.8 | SEQ ID No: 647 | SEQ ID No: 648 | SEQ ID No: 980 | |

TABLE 67

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs10869589 | 9 | 75,420,603 | PCSK5 −314572 bp (NM_006200.2) | A | C | C | 0.71 | 0.65 |
| rs6045666 | 20 | 1,888,504 | PDYN +18899 bp (NM_024411.2) | A | G | A | 0.32 | 0.24 |
| rs12200432 | 6 | 12,624,571 | PHACTR1 −201248 bp (XM_166420) | A | G | G | 0.56 | 0.54 |
| rs9349248 | 6 | 12,621,612 | PHACTR1 −204207 bp (XM_166420) | A | G | G | 0.55 | 0.51 |
| rs1828652 | 3 | 147,397,711 | PLSCR4 Intron6 (NM_020353.1) | A | G | A | 0.44 | 0.39 |
| rs1196185 | 2 | 182,710,465 | PPP1R1C Intron2 (XM_087137) | A | T | T | 0.65 | 0.56 |
| rs1196155 | 2 | 182,746,778 | PPP1R1C Intron2 (XM_087137) | C | G | G | 0.66 | 0.57 |

TABLE 67-continued

| dBSNP ID | | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs2701664 | 2 | 182,734,170 | PPP1R1C Intron2 (XM_087137) | A | G | A | 0.65 | 0.56 |
| rs1196160 | 2 | 182,733,518 | PPP1R1C Intron3 (XM_087137) | A | G | A | 0.65 | 0.56 |
| rs7802749 | 7 | 94,432,292 | PPP1R9A Intron4 (XM_371933) | A | G | A | 0.54 | 0.44 |
| rs10485223 | 6 | 100,300,726 | PRDM13 +130551 bp (NM_021620.2) | A | G | G | 0.77 | 0.70 |
| rs17826560 | 6 | 100,302,299 | PRDM13 +132124 bp (NM_021620.2) | A | G | A | 0.77 | 0.70 |
| rs4240580 | 6 | 100,308,187 | PRDM13 +138012 bp (NM_021620.2) | A | G | A | 0.77 | 0.70 |
| rs6991277 | 8 | 97,469,327 | PTDSS1 +53377 bp (NM_014754.1) | A | G | A | 0.92 | 0.87 |
| rs6035140 | 20 | 1,884,292 | PTPNS1 +15755 bp (NM_080792.1) | A | G | G | 0.33 | 0.24 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs10869589 | 0.000721 | Dominant | 2.89 | 1.6-5.3 | SEQ ID No: 649 | SEQ ID No: 650 | SEQ ID No: 981 | |
| rs6045666 | 0.001071 | Allele | 1.54 | 1.2-2 | SEQ ID No: 651 | SEQ ID No: 652 | SEQ ID No: 982 | |
| rs12200432 | 0.009685 | Recessive | 1.62 | 1.1-2.3 | SEQ ID No: 653 | SEQ ID No: 654 | SEQ ID No: 983 | |
| rs9349248 | 0.002906 | Recessive | 1.77 | 1.2-2.6 | SEQ ID No: 655 | SEQ ID No: 656 | SEQ ID No: 984 | |
| rs1828652 | 0.003839 | Dominant | 1.65 | 1.2-2.3 | SEQ ID No: 657 | SEQ ID No: 658 | SEQ ID No: 985 | |
| rs1196185 | 0.002825 | Allele | 1.43 | 1.1-1.8 | SEQ ID No: 659 | SEQ ID No: 660 | SEQ ID No: 986 | SEQ ID No: 1055 |
| rs1196155 | 0.003038 | Allele | 1.43 | 1.1-1.8 | SEQ ID No: 661 | SEQ ID No: 662 | SEQ ID No: 987 | SEQ ID No: 1056 |
| rs2701664 | 0.003373 | Allele | 1.42 | 1.1-1.8 | SEQ ID No: 663 | SEQ ID No: 664 | SEQ ID No: 988 | |
| rs1196160 | 0.004951 | Allele | 1.40 | 1.1-1.8 | SEQ ID No: 665 | SEQ ID No: 666 | SEQ ID No: 989 | |
| rs7802749 | 0.000155 | Recessive | 2.16 | 1.4-3.2 | SEQ ID No: 667 | SEQ ID No: 668 | SEQ ID No: 990 | |
| rs10485223 | 0.003464 | Dominant | 2.95 | 1.4-6.1 | SEQ ID No: 669 | SEQ ID No: 670 | SEQ ID No: 991 | |
| rs17826560 | 0.003472 | Dominant | 2.85 | 1.4-5.8 | SEQ ID No: 671 | SEQ ID No: 672 | SEQ ID No: 992 | |
| rs4240580 | 0.004890 | Dominant | 2.60 | 1.3-5.1 | SEQ ID No: 673 | SEQ ID No: 674 | SEQ ID No: 993 | |
| rs6991277 | 0.002092 | Recessive | 1.93 | 1.3-2.9 | SEQ ID No: 675 | SEQ ID No: 676 | SEQ ID No: 994 | |
| rs6035140 | 0.000560 | Allele | 1.57 | 1.2-2 | SEQ ID No: 677 | SEQ ID No: 678 | SEQ ID No: 995 | |

TABLE 68

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs10815959 | 9 | 8,806,479 | PTPRD −82533 bp (NM_002839.1), PTPRD −82533 bp (NM_130391.1), PTPRD −82533 bp (NM_130392.1), PTPRD −82533 bp (NM_130393.1) | A | G | G | 0.58 | 0.49 |
| rs4572656 | 20 | 40,112,577 | PTPRT +22230 bp (NM_007050.3), PTPRT +22230 bp (NM_133170.1) | A | G | G | 0.87 | 0.81 |
| rs8003168 | 14 | 71,433,141 | RGS6 −36445 bp (NM_004296.3) | A | G | G | 0.46 | 0.38 |
| rs734380 | 19 | 63,590,775 | RPS5 Intron1 (NM_001009.2) | A | C | C | 0.50 | 0.42 |
| rs734379 | 19 | 63,590,994 | RPS5 Intron1 (NM_001009.2) | A | G | A | 0.58 | 0.50 |
| rs16833786 | 3 | 124,236,120 | SEMA5B −5978 bp (NM_018987.1) | A | G | G | 0.09 | 0.05 |
| rs16833788 | 3 | 124,236,700 | SEMA5B −6558 bp (NM_018987.1) | A | T | A | 0.09 | 0.05 |
| rs7624272 | 3 | 124,178,241 | SEMA5B Intron1 (NM_018987.1) | A | G | G | 0.10 | 0.06 |
| rs6995270 | 8 | 134,582,401 | SIAT4A Intron2 (NM_003033.2), SIAT4A Intron2 (NM_173344.1) | A | G | G | 0.51 | 0.42 |
| rs517578 | 20 | 1,637,270 | SIRPB2 −50868 bp (NM_018556.2), SIRPB2 −50868 bp (NM_080816.1) | A | G | A | 0.40 | 0.32 |
| rs10877835 | 12 | 38,637,759 | SLC2A13 Intron3 (NM_052885.1) | A | C | A | 0.14 | 0.08 |
| rs11116586 | 12 | 83,650,812 | SLC6A15 +106086 bp (NM_182767.2), SLC6A15 +127822 bp (NM_018057.3) | A | G | A | 0.71 | 0.63 |
| rs10862927 | 12 | 83,643,704 | SLC6A15 +113194 bp (NM_182767.2), SLC6A15 +134930 bp (NM_018057.3) | C | G | G | 0.71 | 0.63 |
| rs7736074 | 5 | 1,242,456 | SLC6A19 −12310 bp (XM_291120) | C | G | G | 0.63 | 0.54 |
| rs3757759 | 7 | 127,288,765 | SND1 Intron16 (NM_014390.1) | A | C | C | 0.33 | 0.25 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs10815959 | 0.001073 | Allele | 1.47 | 1.2-1.9 | SEQ ID No: 679 | SEQ ID No: 680 | SEQ ID No: 996 | |
| rs4572656 | 0.001522 | Recessive | 1.80 | 1.3-2.6 | SEQ ID No: 681 | SEQ ID No: 682 | SEQ ID No: 997 | |
| rs8003168 | 0.002336 | Dominant | 1.70 | 1.2-2.4 | SEQ ID No: 683 | SEQ ID No: 684 | SEQ ID No: 998 | |
| rs734380 | 0.000556 | Dominant | 1.91 | 1.3-2.8 | SEQ ID No: 685 | SEQ ID No: 686 | SEQ ID No: 999 | |
| rs734379 | 0.004407 | Allele | 1.40 | 1.1-1.8 | SEQ ID No: 687 | SEQ ID No: 688 | SEQ ID No: 1000 | |
| rs16833786 | 0.006753 | Dominant | 1.99 | 1.2-3.3 | SEQ ID No: 689 | SEQ ID No: 690 | SEQ ID No: 1001 | |
| rs16833788 | 0.005712 | Dominant | 2.01 | 1.2-3.3 | SEQ ID No: 691 | SEQ ID No: 692 | SEQ ID No: 1002 | SEQ ID No: 1057 |
| rs7624272 | 0.005254 | Dominant | 1.99 | 1.2-3.2 | SEQ ID No: 693 | SEQ ID No: 694 | SEQ ID No: 1003 | |
| rs6995270 | 0.001415 | Allele | 1.46 | 1.2-1.8 | SEQ ID No: 695 | SEQ ID No: 696 | SEQ ID No: 1004 | |
| rs517578 | 0.000543 | Dominant | 1.80 | 1.3-2.5 | SEQ ID No: 697 | SEQ ID No: 698 | SEQ ID No: 1005 | |

TABLE 68-continued

| dBSNP ID | | | | | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs10877835 | 0.001628 | Allele | 1.86 | 1.3-2.7 | SEQ ID No: 699 | SEQ ID No: 700 | SEQ ID No: 1006 | |
| rs11116586 | 0.002119 | Allele | 1.47 | 1.1-1.9 | SEQ ID No: 701 | SEQ ID No: 702 | SEQ ID No: 1007 | |
| rs10862927 | 0.002381 | Allele | 1.46 | 1.1-1.9 | SEQ ID No: 703 | SEQ ID No: 704 | SEQ ID No: 1008 | SEQ ID No: 1058 |
| rs7736074 | 0.002001 | Allele | 1.45 | 1.1-1.8 | SEQ ID No: 705 | SEQ ID No: 706 | SEQ ID No: 1009 | SEQ ID No: 1059 |
| rs3757759 | 0.001359 | Allele | 1.52 | 1.2-2 | SEQ ID No: 707 | SEQ ID No: 708 | SEQ ID No: 1010 | |

TABLE 69

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs3757760 | 7 | 127,252,147 | SND1 Intron16 (NM_014390.1) | A | G | G | 0.30 | 0.23 |
| rs2241291 | 7 | 127,232,825 | SND1 Intron16 (NM_014390.1), NAG8 Exon1 (NM_014411.2) | A | G | A | 0.30 | 0.23 |
| rs698408 | 7 | 126,939,887 | SND1 Intron8 (NM_014390.1) | A | G | G | 0.30 | 0.24 |
| rs696518 | 3 | 137,602,998 | STAG1 Intron21 (NM_005862.1) | A | C | A | 0.24 | 0.17 |
| rs695983 | 3 | 137,547,245 | STAG1 Intron29 (NM_005862.1) | A | G | G | 0.21 | 0.14 |
| rs2547455 | 5 | 75,381,858 | SV2C −33137 bp (XM_043493) | A | G | G | 0.78 | 0.71 |
| rs4308461 | 5 | 75,339,908 | SV2C −75087 bp (XM_043493) | A | C | A | 0.78 | 0.70 |
| rs7703461 | 5 | 75,529,168 | SV2C Intron3 (XM_043493) | A | G | A | 0.38 | 0.28 |
| rs7534078 | 1 | 199,346,710 | SYT2 Intron1 (NM_177402.3) | A | G | A | 0.36 | 0.27 |
| rs2247154 | 15 | 68,024,022 | TLE3 +105451 bp (NM_005078.1) | A | G | A | 0.80 | 0.75 |
| rs12591327 | 15 | 60,990,221 | TLN2 +69488 bp (NM_015059.1) | A | T | T | 0.62 | 0.53 |
| rs16886390 | 6 | 76,038,298 | TMEM30A Intron1 (NM_018247.1) | A | G | A | 0.88 | 0.82 |
| rs9679229 | 2 | 181,320,188 | UBE2E3 −350430 bp (NM_182678.1), UBE2E3 −350660 bp (NM_006357.2) | C | G | G | 0.79 | 0.73 |
| rs4667078 | 2 | 181,302,702 | UBE2E3 −367916 bp (NM_182678.1), UBE2E3 −368146 bp (NM_006357.2) | A | G | G | 0.79 | 0.73 |
| rs10460373 | 2 | 181,298,487 | UBE2E3 −372131 bp (NM_182678.1), UBE2E3 −372361 bp (NM_006357.2) | A | C | C | 0.80 | 0.73 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs3757760 | 0.002990 | Dominant | 1.65 | 1.2-2.3 | SEQ ID No: 709 | SEQ ID No: 710 | SEQ ID No: 1011 | |
| rs2241291 | 0.003295 | Dominant | 1.64 | 1.2-2.3 | SEQ ID No: 711 | SEQ ID No: 712 | SEQ ID No: 1012 | |
| rs698408 | 0.007498 | Dominant | 1.57 | 1.1-2.2 | SEQ ID No: 713 | SEQ ID No: 714 | SEQ ID No: 1013 | |
| rs696518 | 0.003186 | Allele | 1.55 | 1.2-2.1 | SEQ ID No: 715 | SEQ ID No: 716 | SEQ ID No: 1014 | |
| rs695983 | 0.002581 | Allele | 1.61 | 1.2-2.2 | SEQ ID No: 717 | SEQ ID No: 718 | SEQ ID No: 1015 | |
| rs2547455 | 0.004139 | Allele | 1.47 | 1.1-1.9 | SEQ ID No: 719 | SEQ ID No: 720 | SEQ ID No: 1016 | |
| rs4308461 | 0.002704 | Allele | 1.49 | 1.1-1.9 | SEQ ID No: 721 | SEQ ID No: 722 | SEQ ID No: 1017 | |
| rs7703461 | 0.000109 | Recessive | 3.09 | 1.7-5.5 | SEQ ID No: 723 | SEQ ID No: 724 | SEQ ID No: 1018 | |
| rs7534078 | 0.000752 | Allele | 1.54 | 1.2-2 | SEQ ID No: 725 | SEQ ID No: 726 | SEQ ID No: 1019 | |
| rs2247154 | 0.002275 | Recessive | 1.68 | 1.2-2.4 | SEQ ID No: 727 | SEQ ID No: 728 | SEQ ID No: 1020 | |
| rs12591327 | 0.001432 | Recessive | 1.78 | 1.2-2.5 | SEQ ID No: 729 | SEQ ID No: 730 | SEQ ID No: 1021 | SEQ ID No: 1060 |
| rs16886390 | 0.000151 | Recessive | 2.15 | 1.4-3.2 | SEQ ID No: 731 | SEQ ID No: 732 | SEQ ID No: 1022 | |
| rs9679229 | 0.001212 | Recessive | 1.73 | 1.2-2.4 | SEQ ID No: 733 | SEQ ID NO: 734 | SEQ ID No: 1023 | SEQ ID No: 1061 |
| rs4667078 | 0.001875 | Recessive | 1.69 | 1.2-2.4 | SEQ ID No: 735 | SEQ ID No: 736 | SEQ ID No: 1024 | |
| rs10460373 | 0.001107 | Recessive | 1.73 | 1.2-2.4 | SEQ ID No: 737 | SEQ ID No: 738 | SEQ ID No: 1025 | |

TABLE 70

| dBSNP ID | Chromosome | Physical Location | Exon, Intron | Allele 1 | Allele 2 | High-Risk Allele | High-Risk Allele Frequency in Progressive Glaucoma Group | High-Risk Allele Frequency in Nonprogressive Glaucoma Group |
|---|---|---|---|---|---|---|---|---|
| rs11691504 | 2 | 181,292,695 | UBE2E3 −377923 bp (NM_182678.1), UBE2E3 −378153 bp (NM_006357.2) | A | C | A | 0.79 | 0.73 |
| rs1840111 | 2 | 181,185,671 | UBE2E3 −484947 bp (NM_182678.1), UBE2E3 −485177 bp (NM_006357.2) | A | G | G | 0.74 | 0.68 |
| rs1453054 | 2 | 181,185,413 | UBE2E3 −485205 bp (NM_182678.1), UBE2E3 −485435 bp (NM_006357.2) | A | C | C | 0.75 | 0.69 |
| rs2736463 | 4 | 70,508,724 | UGT2B4 +17920 bp (NM_021139.1) | A | G | G | 0.55 | 0.44 |
| rs7093891 | 10 | 111,593,021 | XPNPEP1 +21493 bp (NM_020383.2) | A | G | G | 0.68 | 0.61 |

TABLE 70-continued

| dBSNP ID | | | | | | | | | |
|---|---|---|---|---|---|---|---|---|---|
| rs2076147 | 20 | 39,246,420 | ZHX3 Exon4 (NM_015035.2) | | A | G | A | 0.48 | 0.41 |
| rs9416465 | 10 | 57,514,084 | ZWINT +273128 bp (NM_007057.2), ZWINT +273128 bp (NM_032997.1) | | A | G | G | 0.81 | 0.74 |

| dBSNP ID | Mantel-Haenszel Test p-value | Mantel-Haenszel Test Model | Odds Ratio | 95% Confidence Interval | Sequence Containing Allele 1 | Sequence Containing Allele 2 | Sequence 1 for Secondary Analysis Probe | Sequence 2 for Secondary Analysis Probe |
|---|---|---|---|---|---|---|---|---|
| rs11691504 | 0.001937 | Recessive | 1.69 | 1.2-2.3 | SEQ ID No: 739 | SEQ ID No: 740 | SEQ ID No: 1026 | |
| rs1840111 | 0.006435 | Recessive | 1.58 | 1.1-2.2 | SEQ ID No: 741 | SEQ ID No: 742 | SEQ ID No: 1027 | |
| rs1453054 | 0.006785 | Recessive | 1.57 | 1.1-20 | SEQ ID No: 743 | SEQ ID No: 744 | SEQ ID No: 1028 | |
| rs2736463 | 0.000142 | Allele | 1.56 | 1.2-2 | SEQ ID No: 745 | SEQ ID No: 746 | SEQ ID No: 1029 | |
| rs7093891 | 0.001935 | Recessive | 1.70 | 1.2-2.4 | SEQ ID No: 747 | SEQ ID No: 748 | SEQ ID No: 1030 | |
| rs2076147 | 0.008262 | Dominant | 1.62 | 1.1-2.3 | SEQ ID No: 749 | SEQ ID No: 750 | SEQ ID No: 1031 | |
| rs9416465 | 0.009354 | Allele | 1.45 | 1.1-1.9 | SEQ ID No: 751 | SEQ ID No: 752 | SEQ ID No: 1032 | |

The single nucleotide polymorphisms listed in Tables 53 to 70 can be also used as a marker for predicting a progressive risk of glaucoma in the same manner.

Next, regions and/or genes of the surrounding of single nucleotide polymorphism listed in Table 52 were determined by making reference to the database provided by the HapMap project. In detail, regions in which the single nucleotide polymorphism considered to be in a linkage disequilibrium with the single nucleotide polymorphisms listed in Table 52 exists were determined, on the basis of the linkage disequilibrium data in combination of the Japanese and the Chinese in the HapMap project.

Also, in a case where the single nucleotide polymorphism listed in Table 52 exists in the linkage disequilibrium region containing genes, the physical location of the region and the gene name were determined. On the other hand, in a case where the single nucleotide polymorphism listed in Table 52 exists in the linkage disequilibrium region without containing the genes, only the physical location of the region was determined. In addition, in a case where the single nucleotide polymorphism listed in Table 52 exists on one gene beyond the linkage disequilibrium region, the gene name and the physical location of the gene were determined.

A single nucleotide polymorphism of which p-value is the lowest for each region is considered to be a single nucleotide polymorphism representing the region, and Tables 71 to 81 list a single nucleotide polymorphism representing the region, the chromosome number at which the region exists, the physical location of the region (start point and end point) and the gene name contained in the region.

TABLE 71

| Representative Single Nucleotide Polymorphism in the Region (Single Nucleotide Polymorphism with Lowest p-value) | Chromosome | Start Location | End Location | Genes in the Region |
|---|---|---|---|---|
| rs6577539 | 1 | 8,919,302 | 8,937,444 | — |
| rs271351 | 1 | 29,730,945 | 29,826,068 | — |
| rs490647 | 1 | 36,746,869 | 37,168,937 | GRIK3 |
| rs4927088 | 1 | 54,404,217 | 54,584,113 | SSBP3 |
| rs687328 | 1 | 67,652,235 | 67,824,796 | — |
| rs11590929 | 1 | 87,841,409 | 87,950,062 | — |
| rs947130 | 1 | 119,723,364 | 119,807,964 | HSD3B1 |
| rs10494300 | 1 | 151,492,990 | 151,655,827 | KCNN3 |
| rs2293325 | 1 | 164,125,293 | 164,219,505 | CD3Z |
| rs7534078 | 1 | 199,296,545 | 199,563,030 | SYT2 JARID1B AK125746 |
| rs1416658 | 1 | 211,567,280 | 211,867,016 | KCNK2 |
| rs11117962 | 1 | 214,193,090 | 214,568,804 | SPATA17 |
| rs1529404 | 2 | 16,119,969 | 16,137,052 | — |
| rs1104870 | 2 | 29,196,209 | 30,056,083 | FLJ34931 ALK RSNL2 |
| rs10172264 | 2 | 53,257,353 | 53,405,293 | — |
| rs11691031 | 2 | 100,895,131 | 101,274,767 | NPAS2 RPL31 TBC1D8 |
| rs787433 | 2 | 145,590,348 | 145,799,392 | — |
| rs1358105 | 2 | 150,299,586 | 150,541,213 | FLJ32955 |
| rs7569506 | 2 | 165,366,767 | 165,555,753 | COBLL1 |

TABLE 72

| Representative Single Nucleotide Polymorphism in the Region (Single Nucleotide Polymorphism with Lowest p-value) | Chromosome | Start Location | End Location | Genes in the Region |
|---|---|---|---|---|
| rs10460373 | 2 | 181,134,445 | 181,453,645 | — |
| rs1196185 | 2 | 182,676,057 | 182,807,925 | PPP1R1C |
| rs1520855 | 2 | 189,708,226 | 190,181,703 | WDR75 COL5A2 |
| rs16860887 | 2 | 197,523,235 | 197,888,268 | PGAP1 ANKRD44 |
| rs4261668 | 2 | 210,923,619 | 211,070,689 | MYL1 |
| rs4076919 | 2 | 216,497,213 | 216,578,828 | — |
| rs7420360 | 2 | 221,677,221 | 221,753,564 | — |
| rs6739369 | 2 | 229,714,194 | 229,961,562 | PID1 |
| rs7428299 | 3 | 5,570,819 | 5,773,991 | — |
| rs6763643 | 3 | 39,826,307 | 40,276,808 | MYRIP |

TABLE 73

| Representative Single Nucleotide Polymorphism in the Region (Single Nucleotide Polymorphism with Lowest p-value) | Chromosome | Start Location | End Location | Genes in the Region |
|---|---|---|---|---|
| rs453570 | 3 | 49,686,439 | 51,799,207 | APEH MST1 RNF123 AMIGO3 GMPPB IHPK1 LOC389118 C3orf54 UBA7 TRAIP CAMKV MST1R MON1A RBM6 RBM5 SEMA3F GNAT1 SLC38A3 GNAI2 SEMA3B IFRD2 NAT6 C3orf45 HYAL3 HYAL1 HYAL2 TUSC2 RASSF1 ZMYND10 TUSC4 CYB561D2 TMEM115 CACNA2D2 C3orf18 HEMK1 CISH MAPKAPK3 DOCK3 ARMET RBM15B VPRBP RAD54L2 TEX264 GRM2 |

TABLE 74

| Representative Single Nucleotide Polymorphism in the Region (Single Nucleotide Polymorphism with Lowest p-value) | Chromosome | Start Location | End Location | Genes in the Region |
|---|---|---|---|---|
| rs6773050 | 3 | 120,495,910 | 120,761,171 | CDGAP CD80 BC003192 TMEM39A AK126736 MDS010 C3orf1 |
| rs7624272 | 3 | 124,110,731 | 124,251,512 | SEMA5B |
| rs3957816 | 3 | 137,167,265 | 137,992,964 | PPP2R3A RNF184 PCCB STAG1 |
| rs1828652 | 3 | 147,390,338 | 147,696,420 | PLSCR2 PLSCR4 |
| rs12490570 | 3 | 154,551,245 | 154,737,123 | LOC152118 |
| rs784288 | 3 | 170,068,388 | 170,864,176 | MDS1 EV11 |
| rs11712746 | 3 | 179,224,760 | 179,591,920 | — |
| rs17605639 | 4 | 27,256,221 | 27,298,338 | — |
| rs2736463 | 4 | 70,403,494 | 70,521,560 | — |
| rs3805347 | 4 | 108,823,267 | 108,999,023 | PAPSS1 |
| rs7692155 | 4 | 123,377,225 | 123,922,063 | KIAA1109 CR936613 IL2 Tenr IL21 |
| rs11734419 | 4 | 140,995,151 | 141,432,838 | MAML3 |
| rs7736074 | 5 | 1,212,749 | 1,276,385 | AK096054 SLC6A19 |

TABLE 75

| Representative Single Nucleotide Polymorphism in the Region (Single Nucleotide Polymorphism with Lowest p-value) | Chromosome | Start Location | End Location | Genes in the Region |
|---|---|---|---|---|
| rs7703461 | 5 | 75,337,998 | 75,657,172 | SV2C |
| rs166296 | 5 | 115,752,543 | 115,938,450 | SEMA6A |
| rs1560026 | 5 | 125,151,015 | 125,717,338 | — |
| rs194229 | 5 | 158,058,265 | 158,756,752 | EBF FLJ31951 MGC10067 IL12B |
| rs595805 | 6 | 5,940,860 | 6,265,923 | F13A1 NRN1 |
| rs9349248 | 6 | 12,554,461 | 12,626,674 | — |
| rs9461154 | 6 | 25,387,627 | 25,728,737 | LRRC16A |
| rs16886390 | 6 | 75,850,763 | 76,260,216 | COL12A1 FILIP1 COX7A2 TMEM30A |
| rs3798425 | 6 | 76,074,522 | 76,686,994 | FILIP1 SENP6 MYO6 |
| rs531970 | 6 | 94,007,862 | 94,384,201 | EPHA7 |
| rs10485223 | 6 | 100,160,966 | 100,372,844 | PRDM13 |
| rs13193932 | 6 | 129,939,934 | 130,073,063 | ARHGAP18 |
| rs17070863 | 6 | 141,512,817 | 141,829,487 | — |

TABLE 76

| Representative Single Nucleotide Polymorphism in the Region (Single Nucleotide Polymorphism with Lowest p-value) | Chromosome | Start Location | End Location | Genes in the Region |
|---|---|---|---|---|
| rs7767107 | 6 | 141,944,499 | 142,393,247 | AK097143 |
| rs6570564 | 6 | 143,882,061 | 144,194,015 | PHACTR2 |
| rs1621819 | 7 | 6,940,080 | 7,128,749 | C1GALT1 AJ132443 |
| rs12669138 | 7 | 9,422,364 | 9,677,953 | — |
| rs10230371 | 7 | 18,308,609 | 18,810,233 | HDAC9 |
| rs17156635 | 7 | 28,112,180 | 28,638,749 | CREB5 |
| rs17171658 | 7 | 39,637,423 | 40,673,597 | C7orf10 CDC2L5 |
| rs17152739 | 7 | 78,803,891 | 78,947,358 | — |
| rs7802749 | 7 | 94,162,046 | 94,722,947 | PPP1R9A PON1 PON2 PON3 |
| rs3757759 | 7 | 126,534,572 | 127,377,349 | ZNF800 GCC1 ARF5 FSCN3 PAX4 NAG8 LRRC4 SND1 |
| rs6601569 | 8 | 10,791,891 | 11,126,489 | C8orf21 C8orf5 C8orf6 C8orf15 C8orf16 XKR6 |

TABLE 77

| Representative Single Nucleotide Polymorphism in the Region (Single Nucleotide Polymorphism with Lowest p-value) | Chromosome | Start Location | End Location | Genes in the Region |
|---|---|---|---|---|
| rs4316157 | 8 | 12,664,980 | 12,698,048 | — |
| rs10503907 | 8 | 31,616,810 | 32,720,310 | NRG1 AK127911 |
| rs9650336 | 8 | 38,606,462 | 38,689,512 | — |
| rs4394361 | 8 | 96,504,810 | 96,604,166 | — |
| rs4394361 | 8 | 97,343,317 | 97,558,505 | BC002376 AK126443 PTDSS1 |
| rs6995270 | 8 | 134,533,189 | 134,653,344 | ST3GAL1 |
| rs4142436 | 9 | 1,377,505 | 1,450,365 | — |
| rs12554461 | 9 | 4,777,149 | 4,866,435 | RCL1 |
| rs10815959 | 9 | 8,304,247 | 10,602,509 | PTPRD |
| rs2780197 | 9 | 16,976,415 | 17,493,915 | CNTLN C9orf39 |
| rs10967964 | 9 | 27,315,208 | 27,589,202 | MOBKL2B IFNK C9orf72 |
| rs10781440 | 9 | 68,550,170 | 69,099,672 | PIP5K1B TJP2 PRKACG FXN FAM122A |
| rs943509 | 9 | 75,083,939 | 75,297,469 | — |
| rs10869589 | 9 | 75,394,767 | 75,450,986 | — |
| rs10512277 | 9 | 100,256,889 | 100,625,025 | MURC MGC17337 BC090888 AL831919 TMEFF1 Corf30 |
| rs4979255 | 9 | 107,506,524 | 107,557,442 | — |
| rs2773395 | 9 | 125,999,689 | 126,067,452 | — |
| rs2151078 | 10 | 55,250,866 | 56,231,057 | PCDH15 |
| rs9416465 | 10 | 57,227,132 | 57,996,501 | ZWINT |

TABLE 78

| Representative Single Nucleotide Polymorphism in the Region (Single Nucleotide Polymorphism with Lowest p-value) | Chromosome | Start Location | End Location | Genes in the Region |
|---|---|---|---|---|
| rs1801041 | 10 | 69,539,256 | 70,125,600 | MYPN ATOH7 PBLD HNRPH3 MAWBP HNRPH3 RUFY2 SLC25A16 DNA2 CXXC6 |
| rs10823349 | 10 | 70,699,762 | 70,831,641 | HK1 |
| rs2395453 | 10 | 78,299,370 | 79,067,583 | KCNMA1 |
| rs7093891 | 10 | 111,370,433 | 111,673,192 | XPNPEP1 |
| rs7927545 | 11 | 11,249,002 | 11,600,128 | GALNTL4 |
| rs7112492 | 11 | 18,349,559 | 18,457,723 | LDHAL6A LDHA LDHC |
| rs12800710 | 11 | 57,713,408 | 58,200,377 | LPXN OR9Q2 OR1S2 OR1S1 OR10Q1 UNQ6469 LOC399898 OR5B17 OR5B3 OR5B2 OR5B12 ZFF91 |
| rs504105 | 11 | 82,583,199 | 84,312,113 | ANKRD42 DLG2 CCDC90B |
| rs10898459 | 11 | 85,583,115 | 85,745,023 | EED HSPC138 |
| rs161130 | 11 | 112,150,907 | 112,255,730 | — |

TABLE 79

| Representative Single Nucleotide Polymorphism in the Region (Single Nucleotide Polymorphism with Lowest p-value) | Chromosome | Start Location | End Location | Genes in the Region |
|---|---|---|---|---|
| rs4269933 | 11 | 119,110,064 | 119,202,392 | — |
| rs2322728 | 11 | 126,615,901 | 126,702,818 | — |
| rs10877835 | 12 | 38,306,287 | 39,318,456 | LOC283461 SLC2A13 BC047507 LRRK2 AK127729 AK093065 |
| rs2169856 | 12 | 53,730,141 | 53,972,700 | OR9K2 OR10A7 OR6C74 |
| rs11175627 | 12 | 63,667,042 | 63,801,383 | WIF1 |
| rs7959848 | 12 | 82,043,793 | 82,360,242 | — |
| rs11116586 | 12 | 83,546,501 | 83,667,628 | — |
| rs7296095 | 12 | 114,297,666 | 114,443,627 | — |
| rs11059862 | 12 | 127,746,927 | 127,761,568 | — |
| rs17640758 | 13 | 42,473,098 | 42,596,252 | DNAJD1 |
| rs4643164 | 13 | 106,618,880 | 107,317,084 | LOC728215 |
| rs10483416 | 14 | 31,868,274 | 32,372,018 | AKAP6 |
| rs8003168 | 14 | 71,294,225 | 72,102,991 | RGS6 AF130114 C14orf57 |
| rs1622029 | 14 | 83,422,711 | 84,117,961 | — |

TABLE 79-continued

| Representative Single Nucleotide Polymorphism in the Region (Single Nucleotide Polymorphism with Lowest p-value) | Chromosome | Start Location | End Location | Genes in the Region |
|---|---|---|---|---|
| rs1187627 | 14 | 94,607,134 | 94,855,955 | CLMN<br>DICER1<br>FLJ45244 |
| rs12900219 | 15 | 21,568,517 | 21,589,571 | — |

TABLE 80

| Representative Single Nucleotide Polymorphism in the Region (Single Nucleotide Polymorphism with Lowest p-value) | Chromosome | Start Location | End Location | Genes in the Region |
|---|---|---|---|---|
| rs16941388 | 15 | 57,215,856 | 57,465,385 | MYO1E |
| rs12591327 | 15 | 60,926,419 | 61,002,704 | — |
| rs2247154 | 15 | 67,997,515 | 68,083,355 | — |
| rs3863401 | 15 | 97,440,341 | 97,748,455 | AK127177<br>LRRC28<br>HCC-8<br>DMN<br>AK125000 |
| rs6500718 | 16 | 5,725,135 | 5,792,957 | — |
| rs12595990 | 16 | 12,053,556 | 12,575,647 | SNX29 |
| rs9302502 | 16 | 13,340,184 | 13,545,371 | — |
| rs1816581 | 16 | 47,722,996 | 47,860,850 | — |
| rs7198530 | 16 | 51,635,508 | 51,918,914 | CHD9 |
| rs1554401 | 16 | 63,494,458 | 63,713,420 | CDH11 |
| rs7212115 | 17 | 10,832,202 | 10,865,630 | — |
| rs295869 | 17 | 32,165,628 | 32,234,457 | — |
| rs8098925 | 18 | 69,240,762 | 69,384,770 | — |
| rs1828132 | 18 | 72,356,779 | 72,410,800 | — |
| rs12462868 | 19 | 41,159,572 | 41,215,615 | CLIP3<br>LOC644096<br>FLJ36445<br>BC052573<br>C19orf46<br>ALKBH6 |
| rs4802905 | 19 | 57,349,937 | 57,487,778 | FLJ16287<br>ZNF766<br>PPP2R1A |
| rs734380 | 19 | 63,548,356 | 63,597,982 | A1BG<br>RPS5<br>ZNF497 |
| rs517578 | 20 | 1,557,798 | 1,674,903 | SIRPB2 |
| rs6035140 | 20 | 1,822,813 | 1,926,301 | SIRPA<br>PTPNS1<br>PDYN |
| rs2050223 | 20 | 13,924,146 | 15,981,839 | MACROD2 |

TABLE 81

| Representative Single Nucleotide Polymorphism in the Region (Single Nucleotide Polymorphism with Lowest p-value) | Chromosome | Start Location | End Location | Genes in the Region |
|---|---|---|---|---|
| rs6083320 | 20 | 23,811,795 | 23,841,840 | — |
| rs6132862 | 20 | 24,988,884 | 25,706,656 | VSX1<br>ENTPD6<br>PYGB<br>ABHD12<br>GINS1<br>NLP<br>ZNF337<br>HDHD4 |
| rs926663 | 20 | 38,563,539 | 38,754,165 | MAFB |
| rs2076147 | 20 | 39,011,156 | 39,443,459 | TOP1<br>PLCG1<br>ZHX3<br>LPIN3 |

TABLE 81-continued

| Representative Single Nucleotide Polymorphism in the Region (Single Nucleotide Polymorphism with Lowest p-value) | Chromosome | Start Location | End Location | Genes in the Region |
|---|---|---|---|---|
| rs909882 | 20 | 39,456,460 | 39,703,552 | EMILIN3 AF090938 CHD6 AK124874 |
| rs4572656 | 20 | 40,018,906 | 41,251,971 | PTPRT |
| rs6017164 | 20 | 41,815,520 | 41,816,915 | — |
| rs1321001 | 20 | 44,235,783 | 44,313,741 | CDH22 |
| rs4812180 | 20 | 58,608,933 | 58,748,410 | — |
| rs6089908 | 20 | 61,470,599 | 61,628,090 | KCNQ2 AK127527 Ak127768 AY358189 EEF1A2 C20orf149 |
| rs369977 | 21 | 15,496,913 | 15,621,381 | — |
| rs7275647 | 21 | 21,292,504 | 21,833,085 | NCAM2 |
| rs94967 | 21 | 40,026,415 | 40,223,190 | PCP4 IGSF5 |
| rs5750009 | 22 | 33,671,179 | 33,694,293 | — |

The region listed in Tables 71 to 81 is a region or gene considered to be linked with a single nucleotide polymorphism associated with the progression of glaucoma in the present invention listed in Tables 53 to 70, and a single nucleotide polymorphism which exists in these regions or genes is considered to be linked with a single nucleotide polymorphism in the present invention. In other words, any single nucleotide polymorphisms which exist in these regions are linked with the single nucleotide polymorphism which exists in the region listed in Tables 53 to 70, and any of these single nucleotide polymorphisms can be used in the prediction of a progressive risk of glaucoma in the same manner.

Example 11

Logistic Regression Analysis

In the present invention, by combining any two or more single nucleotide polymorphisms determined to be involved in the progression of glaucoma, an extent to which the precision of the prediction of a risk of a disease improves is examined with logistic regression analysis, as compared to that where each of the single nucleotide polymorphisms is used alone. In the present analysis, any combinations of the single nucleotide polymorphisms determined to be significantly associated with the progression of glaucoma by statistically comparing allele or genotype frequencies can be used. In one example, 19 single nucleotide polymorphisms that showed a significant difference under the Bonferroni correction were subjected to the logistic regression analysis.

Out of 19 single nucleotide polymorphisms that had a significance under the Bonferroni correction, single nucleotide polymorphisms for use in the logistic regression analysis were further narrowed down according to a stepwise method. The value of 0.01 was adopted as a criterion of variable incorporation and variable exclusion in the stepwise method. Upon the application of a stepwise method, a single nucleotide polymorphism belonging to the same LD block (ones having the same description in the column of linkage disequilibrium in Table 52) is represented by any one of single nucleotide polymorphisms belonging to each of the LD blocks, and it is set so that any one of the single nucleotide polymorphisms is to be a subject to be incorporated. Each of the narrowed-down single nucleotide polymorphisms is defined as an independent variable (Π) (homozygote of one allele=0, heterozygote=1, homozygote of opposite allele=2), and a regression coefficient (λ) can be determined according to the logistic regression analysis, and the following formula (18) was obtained.

$$\Phi = 1/\{1+\exp[-(\lambda 0+\lambda 1\Pi 1+2\Pi 2+\lambda 3\Pi 3+\ldots)]\} \quad \text{formula (18)}$$

Next, in each sample, a value for risk prediction (Φ) was calculated by substituting a variable for each single nucleotide polymorphisms into this formula. When Φ is greater than 0.5, this sample donor was determined to be with a progressive risk. A concordance rate was calculated by comparing the determination results with the matter of whether the sample donor having a single nucleotide polymorphism was actually a progressive glaucoma case. Further, the concordance rate was determined as mentioned above for each of the incorporated single nucleotide polymorphisms alone, and all the combinations of any two or more single nucleotide polymorphisms, and means and standard deviations of the concordance rate were obtained for each of the number of single nucleotide polymorphisms used in combination. Table 82 shows the number of single nucleotide polymorphisms, alone or in a combination of arbitrary number, the number of combinations when arbitrary number of single nucleotide polymorphisms are combined, and the relationship between the mean and the standard deviation of the concordance rate. Here, all the calculations were performed using SAS 9.1.3, Windows (registered trademark) Edition, SAS Institute Japan Corporation.

As listed in Table 82, according to a stepwise method, the 19 single nucleotide polymorphisms (13 single nucleotide polymorphisms, if those belonging to the same LD block were each counted as one) were narrowed down to 10 single nucleotide polymorphisms (rs4316157, rs1358105, rs4076919, rs2395453, rs6132862, rs10483416, rs787433, rs4802905, rs12554461, and rs4927088). Therefore, it shows that similar results are obtained with the combination of 10 single nucleotide polymorphisms even when the remaining 3 single nucleotide polymorphisms are added. A value for risk prediction (Φ) of individual cases was calculated using a logistic regression formula, alone or in a combination of any two or more of these 10 single nucleotide polymorphisms. When a cut-off value for a value for risk prediction is defined as 0.5, mean±standard deviation of the concordance rate was 57.6±2.4% in a case that each of the single nucleotide polymorphisms was used alone. This concordance rate was elevated as an increase in the number of single nucleotide polymorphisms used in combination, and reached the maximum of 67.8% in a case that all the ten were combined.

TABLE 82

| The Number of SNP | The Number of Combination | Concordance Rate (Mean Value) | Standard Deviation |
|---|---|---|---|
| 1 | 10 | 57.6 | 2.4 |
| 2 | 45 | 59.0 | 1.7 |
| 3 | 120 | 60.6 | 1.8 |
| 4 | 210 | 62.1 | 1.9 |
| 5 | 252 | 63.1 | 1.8 |
| 6 | 210 | 64.1 | 1.5 |
| 7 | 120 | 64.9 | 1.7 |
| 8 | 45 | 65.7 | 1.5 |
| 9 | 10 | 66.6 | 1.4 |
| 10 | 1 | 67.8 | — |

As described above, it was evident that, in the determination of a progressive risk of glaucoma by a single nucleotide polymorphism, an excellent concordance rate can be obtained even in a case that each of the single nucleotide polymorphisms are used alone, and the diagnostic precision can be further enhanced by combining these single nucleotide polymorphisms.

As described above, an individual who has an allele or a genotype that is identified in a high frequency in the progressive glaucoma group disclosed in the present invention on the genome has a high progressive risk of glaucoma in future, and an individual who does not have an allele or a genotype that is identified in a high frequency in the progressive glaucoma group has a low progressive risk of glaucoma in future.

INDUSTRIAL APPLICABILITY

According to the method of the present invention, the level of a progressive risk of glaucoma of a sample donor can be determined by analyzing an allele or a genotype of a single nucleotide polymorphism in the present invention in a sample. A sample donor can take a preventive measure of glaucoma, or can receive appropriate treatments, on the basis of this risk. In addition, the method is useful because the period of a clinical trial for a glaucoma therapeutic drug can be shortened by selecting patients with a high progressive risk of glaucoma using a single nucleotide polymorphism associated with the progression of glaucoma in the present invention, and performing a clinical trial for a glaucoma therapeutic drug.

The invention claimed is:

1. A method of determining risk of glaucoma progression in a glaucoma patient, comprising:
   A. determining in vitro a sequence of a 31st base of SEQ ID NO:307, SEQ ID NO:308, or a full complement negative strand nucleotide sequence thereof in a sample from the glaucoma patient, and
   B. determining the risk of glaucoma progression in the glaucoma patient based on the presence of a G nucleotide instead of an A nucleotide at the $31^{st}$ base in SEQ ID NO:307 or SEQ ID NO: 308.

2. The method according to claim 1, wherein the glaucoma is primary open-angle glaucoma (POAG) or normal tension glaucoma (NTG).

3. The method according to claim 1, wherein the determining in vitro the sequence of the $31^{st}$ base comprises contacting the sample comprising nucleic acid with a nucleic acid probe comprising an A nucleotide at position 31 of SEQ ID NO:307, SEQ ID NO:308, or a full complement sequence thereof.

4. The method according to claim 1, wherein the determining in vitro the sequence of the $31^{st}$ base comprises contacting the sample comprising nucleic acid with a nucleic acid probe comprising a G nucleotide at position 31 of SEQ ID NO:307, SEQ ID NO:308, or a full complement sequence thereof.

5. The method according to claim 4, wherein the nucleic acid probe has 23 to 55 nucleotides.

6. The method according to claim 4, wherein the nucleic acid probe is immobilized.

7. The method according to claim 1, wherein the determining in vitro the sequence of the $31^{st}$ base comprises detecting the $31^{st}$ based of SEQ ID NO:307.

8. The method according to claim 1, wherein the determining in vitro the sequence of the $31^{st}$ base comprises detecting the $31^{st}$ base of SEQ ID NO:308.

9. The method according to claim 1, wherein the G nucleotide at the $31^{st}$ base is a homozygous genotype in the glaucoma patient.

10. The method according to claim 1, wherein the sample is a blood sample and the determining in vitro the sequence of the $31^{st}$ base comprises extracting nucleic acids from the blood sample of the glaucoma patient from which the sequence of the $31^{st}$ base is determined.

11. The method according to claim 1, wherein the determining in vitro the sequence of the $31^{st}$ base comprises extracting nucleic acids from the sample and applying the extracted nucleic acids to a microarray.

\* \* \* \* \*